US012514926B2

(12) United States Patent
Pazolli et al.

(10) Patent No.: US 12,514,926 B2
(45) Date of Patent: Jan. 6, 2026

(54) SPLICING MODULATOR ANTIBODY-DRUG CONJUGATES AND METHODS OF USE

(71) Applicant: EISAI R&D MANAGEMENT CO., LTD., Tokyo (JP)

(72) Inventors: Ermira Pazolli, Wayland, MA (US); Silvia Buonamici, Boston, MA (US); Thiwanka Samarakoon, Westwood, MA (US); Sudeep Prajapati, Somerville, MA (US); Nathan Fishkin, Weymouth, MA (US); James Palacino, Wellesley, MA (US); Michael Seiler, Belmont, MA (US); Ping Zhu, Acton, MA (US); Andrew Cook, Stow, MA (US); Peter Smith, Arlington, MA (US); Xiang Liu, Winchester, MA (US); Shelby Ellery, Boston, MA (US); Dominic Reynolds, Stoneham, MA (US); Lihua Yu, Acton, MA (US); Zhenhua Wu, Belmont, MA (US); Shouyong Peng, Belmont, MA (US); Nicholas Calandra, Boston, MA (US); Megan Sheehan, Allston, MA (US); Yonghong Xiao, Belmont, MA (US)

(73) Assignee: EISAI R&D MANAGEMENT CO., LTD., Tokyo (JP)

(*) Notice: Subject to any disclaimer, the term of this patent is extended or adjusted under 35 U.S.C. 154(b) by 0 days.

(21) Appl. No.: 18/581,307

(22) Filed: Feb. 19, 2024

(65) Prior Publication Data

US 2024/0360108 A1 Oct. 31, 2024

Related U.S. Application Data

(63) Continuation of application No. 17/661,909, filed on May 3, 2022, now Pat. No. 11,945,807, which is a continuation of application No. 17/247,117, filed on Nov. 30, 2020, now Pat. No. 11,352,348, which is a continuation of application No. PCT/US2019/035015, filed on May 31, 2019.

(Continued)

(51) Int. Cl.

| | |
|---|---|
| ***A61K 47/68*** | (2017.01) |
| ***A61K 9/127*** | (2025.01) |
| ***A61K 9/51*** | (2006.01) |
| ***A61K 31/365*** | (2006.01) |
| ***A61K 31/496*** | (2006.01) |
| ***A61K 39/00*** | (2006.01) |
| ***A61K 39/395*** | (2006.01) |
| ***A61K 45/06*** | (2006.01) |
| ***A61K 47/60*** | (2017.01) |

(Continued)

(52) U.S. Cl.

CPC .......... *A61K 47/6803* (2017.08); *A61K 9/127* (2013.01); *A61K 9/51* (2013.01); *A61K 31/365* (2013.01); *A61K 31/496* (2013.01); *A61K 39/0011* (2013.01); *A61K 39/3955* (2013.01); *A61K 39/39558* (2013.01); *A61K 45/06* (2013.01); *A61K 47/60* (2017.08); *A61K 47/6845* (2017.08); *A61K 47/6849* (2017.08); *A61K 47/6851* (2017.08); *A61K 47/6857* (2017.08); *A61K 47/6869* (2017.08); *A61K 47/6871* (2017.08); *A61K 47/6889* (2017.08); *A61P 35/00* (2018.01); *C07D 313/00* (2013.01); *C07D 405/06* (2013.01); *C07D 405/12* (2013.01); *C07K 16/24* (2013.01); *C07K 16/28* (2013.01); *C07K 16/2803* (2013.01); *C07K 16/2818* (2013.01); *C07K 16/2827* (2013.01); *C07K 16/2896* (2013.01); *C07K 16/3007* (2013.01); *C07K 16/3092* (2013.01); *C07K 16/32* (2013.01); *C07K 16/40* (2013.01); *C12Q 1/6886* (2013.01); *G01N 33/5011* (2013.01); *G01N 33/574* (2013.01); *A61K 39/00* (2013.01); *A61K 2039/505* (2013.01); *A61K 2039/53* (2013.01); *A61K 2039/545* (2013.01); *C07K 2317/565* (2013.01); *C07K 2317/76* (2013.01); *C12Q 2600/106* (2013.01); *G01N 2500/10* (2013.01)

(58) Field of Classification Search

None

See application file for complete search history.

(56) References Cited

U.S. PATENT DOCUMENTS

| | | | |
|---|---|---|---|
| 7,256,178 | B2 | 8/2007 | Kotake et al. |
| 7,550,503 | B2 | 6/2009 | Kotake et al. |

(Continued)

FOREIGN PATENT DOCUMENTS

| | | | |
|---|---|---|---|
| CN | 105188763 | A | 12/2015 |
| CN | 105669800 | A | 6/2016 |

(Continued)

OTHER PUBLICATIONS

Li et al., "Preclinical and Clinical Development of Neoantigen Vaccines," *Annals of Oncology*, vol. 28, No. Suppl. 12, Dec. 1, 2017, p. xii11-xii17.

(Continued)

*Primary Examiner* — Brian J Davis

(74) *Attorney, Agent, or Firm* — Finnegan, Henderson, Farabow, Garrett & Dunner, LLP

(57) ABSTRACT

Linker-drug compounds and antibody-drug conjugates that bind to human oncology targets are disclosed. The linker-drug compounds and antibody-drug conjugates comprise a splicing modulator drug moiety. The disclosure further relates to methods and compositions for use in the treatment of neoplastic disorders by administering the antibody-drug conjugates provided herein. In an embodiment, the splicing modulator comprises a pladienolide or a pladienolide derivative.

35 Claims, 35 Drawing Sheets

Specification includes a Sequence Listing.

Related U.S. Application Data

(60) Provisional application No. 62/779,324, filed on Dec. 13, 2018, provisional application No. 62/679,672, filed on Jun. 1, 2018, provisional application No. 62/679,631, filed on Jun. 1, 2018.

(51) Int. Cl.

| | |
|---|---|
| ***A61P 35/00*** | (2006.01) |
| ***C07D 313/00*** | (2006.01) |
| ***C07D 405/06*** | (2006.01) |
| ***C07D 405/12*** | (2006.01) |
| ***C07K 16/24*** | (2006.01) |
| ***C07K 16/28*** | (2006.01) |
| ***C07K 16/30*** | (2006.01) |
| ***C07K 16/32*** | (2006.01) |
| ***C07K 16/40*** | (2006.01) |
| ***C12Q 1/6886*** | (2018.01) |
| ***G01N 33/50*** | (2006.01) |
| ***G01N 33/574*** | (2006.01) |

(56) References Cited

U.S. PATENT DOCUMENTS

| | | | |
|---|---|---|---|
| 8,337,856 | B2 | 12/2012 | Blatattler et al. |
| 9,969,809 | B2 | 5/2018 | Kuo et al. |
| 10,155,821 | B2 | 12/2018 | Naito et al. |
| 10,221,242 | B2 | 3/2019 | Wong et al. |
| 10,322,192 | B2 | 6/2019 | Albone et al. |
| 10,548,986 | B2 | 2/2020 | Albone et al. |
| 10,689,458 | B2 | 6/2020 | Ma et al. |
| 11,352,348 | B2 | 6/2022 | Pazolli et al. |
| 11,572,414 | B2 | 2/2023 | Albone et al. |
| 11,679,107 | B2 | 6/2023 | Cook et al. |
| 11,926,619 | B2 | 3/2024 | Keaney et al. |
| 12,043,670 | B2 | 7/2024 | Henry et al. |
| 2006/0079572 | A1 | 4/2006 | Mizui et al. |
| 2006/0235002 | A1 | 10/2006 | Nagai et al. |
| 2008/0214564 | A1 | 9/2008 | Ishihara et al. |
| 2008/0280288 | A1 | 11/2008 | Uenaka et al. |
| 2010/0021918 | A1 | 1/2010 | Mizui et al. |
| 2014/0275010 | A1 | 9/2014 | Zheng et al. |
| 2016/0193356 | A1 | 7/2016 | Farias et al. |
| 2016/0297885 | A1 | 10/2016 | Kuo et al. |
| 2016/0333112 | A1 | 11/2016 | Naito et al. |
| 2017/0043033 | A1 | 2/2017 | Strop et al. |
| 2017/0151341 | A1 | 6/2017 | Ma et al. |
| 2017/0210812 | A1 | 7/2017 | Wong et al. |
| 2018/0140714 | A1 | 5/2018 | Dushin et al. |
| 2018/0318312 | A1 | 11/2018 | Yu et al. |
| 2019/0100513 | A1 | 4/2019 | Keaney et al. |
| 2020/0297860 | A1 | 9/2020 | Albone et al. |
| 2021/0238304 | A1 | 8/2021 | Albone et al. |
| 2022/0081486 | A1 | 3/2022 | Henry et al. |
| 2023/0301990 | A1 | 9/2023 | Cook et al. |
| 2024/0368140 | A1 | 11/2024 | Keaney et al. |

FOREIGN PATENT DOCUMENTS

| | | | |
|---|---|---|---|
| EP | 1 508 570 | A1 | 2/2005 |
| EP | 1712642 | A1 | 10/2006 |
| EP | 2136209 | A1 | 12/2009 |
| EP | 2168961 | A1 | 3/2010 |
| EP | 2478912 | A1 | 7/2012 |
| EP | 3538080 | A4 | 7/2020 |
| NC | 2016/0000187 | | 7/2016 |
| NC | 2016/0005345 | | 12/2016 |
| NC | 2018/0008667 | | 8/2018 |
| RU | 2006147264 | A | 7/2008 |
| RU | 2683780 | C2 | 4/2019 |
| WO | WO 2003/099813 | A1 | 12/2003 |
| WO | WO 2004/011661 | A1 | 2/2004 |
| WO | WO 2005/117986 | A2 | 12/2005 |
| WO | WO 2006/060533 | A2 | 6/2006 |
| WO | WO 2008/016187 | A1 | 2/2008 |
| WO | WO 2010/121226 | A2 | 10/2010 |
| WO | WO 2013/165940 | A1 | 11/2013 |
| WO | WO 2014/068443 | A1 | 5/2014 |
| WO | WO 2014/160160 | A2 | 10/2014 |
| WO | WO 2014/202775 | A1 | 12/2014 |
| WO | WO 2015/015401 | A2 | 2/2015 |
| WO | WO 2015/015448 | A2 | 2/2015 |
| WO | WO 2015175594 | A1 | 11/2015 |
| WO | WO 2016/030791 | A1 | 3/2016 |
| WO | WO 2017/087667 | A1 | 5/2017 |
| WO | WO 2017/151979 | A1 | 9/2017 |
| WO | WO 2018/086139 | A1 | 5/2018 |
| WO | WO 2019/075472 | A1 | 4/2019 |
| WO | WO 2019/199667 | A2 | 10/2019 |
| WO | WO 2019/200100 | A1 | 10/2019 |
| WO | WO 2019/232433 | A2 | 12/2019 |
| WO | WO 2019/232449 | A9 | 12/2019 |
| WO | WO 2020/123836 | A2 | 6/2020 |
| WO | WO 2021/090062 | A1 | 5/2021 |
| WO | WO 2021/148003 | A1 | 7/2021 |
| WO | WO 2021/248005 | A1 | 12/2021 |

OTHER PUBLICATIONS

Puthenveetil et al., "Multivalent Peptidic Linker Enables Identification of Preferred Sites of Conjunction for a Potent Thialanstatin Antibody Drug Conjugated," *Plos One*, May 30, 2017 (16 pages).

International Search Report for PCT/US2019/035015 dated Sep. 11, 2019 (6 pages).

Written Opinion of the International Search Authority for International Application No. PCT/US2019/035015 dated Sep. 11, 2019 (10 pages).

Beck et al., (2017) "Strategies and challenges for the next generation of antibody-drug conjugates" *Nat Rev Drug Discov*. 16(5):315-337.

Chilean Patent Application No. CL202102377, filed Sep. 10, 2021, by Eisai R&D Management, Co., Ltd., Substantive Report, dated Nov. 22, 2023 (30 pages with English translation).

Colombian Patent Application No. NC2020/0016137, filed May 30, 2019, by Eisai R&D Management Co., Ltd., Official Action No. 15694, dated Sep. 4, 2024 (20 pages with English translation).

Colombian Patent Application No. NC2024/0006782, filed May 2, 2024, by Eisai R&D Management Co., Ltd., Official Action No. 15695, dated Sep. 4, 2024 (17 pages with English translation).

Colombian Patent Application No. NC2024/0006784, filed May 2, 2024, by Eisai R&D Management Co., Ltd., Official Action No. 15696, dated Sep. 4, 2024 (15 pages with English translation).

Colombian Patent Application No. NC2024/0006785, filed May 2, 2024, by Eisai R&D Management Co., Ltd., Official Action No. 15697, dated Sep. 4, 2024 (10 pages with English translation).

Fu et al., (2018) "DNA damaging agent-based antibody-drug conjugates for cancer therapy" Antib Ther. 1(2):43- 53.

GCC Patent Application No. 2019/37676, filed May 30, 2019, by Eisai R&D Management Co., Ltd., Examination Report, dated Feb. 9, 2021 (9 pages).

Japanese Patent Application No. 2020-567044, filed May 31, 2019, by Eisai R&D Management Co., Ltd., Office Action, dated Jun. 13, 2023 (4 pages with English translation).

Manabe (2019) "Development and Current Status of Antibody-Drug Conjugate (ADC)" *Drug Delivery System* 34(1):10-21.

Mariuzza (1987) "The structural basis of antigen-antibody recognition" *Ann Rev Biophys Biophys Chem*. 16:139-159.

Puthenveetil et al., (2016) "Natural Product Splicing Inhibitors: A New Class of Antibody-Drug Conjugate (ADC) Payloads" *Bioconjug Chem*. 27(8):1880-1888.

Russian Patent Application No. 2020143425, filed May 31, 2019, by Eisai R&D Management Co., Ltd., Office Action, dated Dec. 22, 2022 (7 pages).

Russian Patent Application No. 2020143425, filed May 31, 2019, by Eisai R&D Management Co., Ltd., Search Report, dated Dec. 22, 2022 (2 pages).

U.S. Appl. No. 19/046,190, filed Feb. 5, 2025, by Keaney et al.

SPLICING MODULATOR ANTIBODY-DRUG CONJUGATES AND METHODS OF USE

This is a continuation of application Ser. No. 17/661,909, filed May 3, 2022, which is a continuation of application Ser. No. 17/247,117, filed Nov. 30, 2020, which is a continuation of PCT/US2019/035015, filed May 31, 2019, which claims the benefit of U.S. Provisional Application No. 62/679,672, filed Jun. 1, 2018; U.S. Provisional Application No. 62/679,631, filed Jun. 1, 2018; and U.S. Provisional Application No. 62/779,324, filed Dec. 13, 2018. All of the aforementioned applications are incorporated herein by reference in their entirety.

The instant application contains a Sequence Listing which has been submitted electronically in ST.26 XML format and is hereby incorporated by reference in its entirety. Said XML copy, created on May 23, 2024, is named 15647_0009-03000_SL.xml and is 175,695 bytes in size.

The present disclosure relates to antibody-drug conjugates (ADCs) comprising a splicing modulator and an antibody or antigen binding fragment thereof that binds a human oncology antigen target. The disclosure further relates to methods and compositions useful in the treatment or diagnosis of cancers that express a target antigen and/or are amenable to treatment by disruption of RNA splicing, as well as methods of making those compositions.

The majority of protein-coding genes in the human genome are composed of multiple exons (coding regions) that are separated by introns (non-coding regions). Gene expression results in a single precursor messenger RNA (pre-mRNA). The intron sequences are subsequently removed from the pre-mRNA by a process called splicing, which results in the mature messenger RNA (mRNA). By including different combinations of exons, alternative splicing gives rise to mRNAs encoding distinct protein isoforms.

RNA splicing is catalyzed by the spliceosome, a dynamic multiprotein-RNA complex composed of five small nuclear RNAs (snRNAs U1, U2, U4, U5, and U6) and associated proteins. The spliceosome assembles on pre-mRNAs to establish a dynamic cascade of multiple RNA and protein interactions that catalyze excision of the introns and ligation of exons (Matera and Wang (2014) Nat Rev Mol Cell Biol. 15(2):108-21). Accumulating evidence has linked human diseases to dysregulation in RNA splicing that impact many genes (Scotti and Swanson (2016) Nat Rev Genet. 17(1): 19-32).

The spliceosome is an important target in cancer biology. Several studies have now documented significant alterations in the splicing profile of cancer cells, as well as in the splicing factors themselves (Agrawal et al. (2018) Curr Opin Genet Dev. 48:67-74). Alternative splicing can lead to differential exon inclusion/exclusion, intron retention, or usage of cryptic splice sites (Seiler et al. (2018) Cell Rep. 23(1):282-296). Altogether, these events account for functional changes that may contribute to tumorigenesis or resistance to therapy (Siegfried and Karni (2018) Curr Opin Genet Dev. 48:16-21).

Certain natural products can bind the SF3b spliceosome complex. These small molecules modulate splicing by promoting intron retention and/or exon skipping (Teng et al. (2017) Nat Commun. 8:15522). A significant portion of the resulting transcripts contain premature stop codons triggering nonsense mediated mRNA decay (NMD).

Furthermore, because canonical splicing is impaired, canonical transcripts are considerably reduced, which can negatively impact cell function and viability. For this reason, splicing modulators have become a promising class of drugs for the treatment of cancer (Puthenveetil et al. (2016) Bioconjugate Chem. 27:1880-8).

The proto-oncogene human epidermal growth factor receptor 2 (HER2) encodes a transmembrane tyrosine kinase receptor that belongs to the human epidermal growth factor receptor (EGFR) family (King et al. (1985) Science 229: 974-6). Overexpression of HER2 enables constitutive activation of growth factor signaling pathways, such as the PI3K-AKT-mTOR pathway, and thereby serves as an oncogenic driver in several types of cancers, including approximately 20% of invasive breast carcinomas (Slamon et al. (1989) Science 244:707-12; Gajria and Chandarlapaty (2011) Expert Rev Anticancer Ther. 11:263-75). Given that HER2 amplification mediates the transformed phenotype, and because HER2 expression is largely restricted to malignant cells, HER2 is a promising antigen for targeting certain cancers and/or delivering novel cancer treatments (Parakh et al. (2017) Cancer Treat Rev. 59:1-21). Additional antigens for targeted delivery of cancer therapies include, but are not limited to, CD138 (also referred to as syndecan-1) and ephrin type-A receptor 2 (EPHA2).

CD138 is a cell surface heparan sulfate proteoglycan that is essential for maintaining cell morphology and interaction with the surrounding microenvironment (Akl et al. (2015) Oncotarget 6(30):28693-715; Szatmeri et al. (2015) Dis Markers 2015:796052). In general, the loss of CD138 expression in carcinoma cells reduces cell adhesion to the extracellular matrix and enhances cell motility and invasion (Teng et al. (2012) Matrix Biol. 31:3-16). Increased stromal CD138 expression also alters fibronectin production and extracellular matrix organization (Yang et al. (2011) Am J Pathol. 178:325-35). Additionally, increased expression of CD138 in stromal fibroblasts is associated with angiogenesis and cancer progression (Maeda et al. (2006) Oncogene 25:1408-12). CD138 expression increases during B cell development and its presence is a hallmark of plasma cells (Ribatti (2017) Immunol Lett. 188:64-7). CD138 expression is maintained in multiple myeloma, a malignancy of plasma cells. CD138 is therefore an attractive antigen for the targeted treatment of several cancers and other hematological malignancies (Sherbenou et al. (2015) Blood Rev. 29(2): 81-91; Wijdenes et al. (1996) Br J Haematol. 94(2):318-23).

EPHA2 is a transmembrane glycoprotein that is abundantly overexpressed in several malignant cancer-derived cell lines and in advanced forms of cancer (Wykosky and Debinski (2008) Mol Cancer Ref. 6(12):1795-1806). For instance, EPHA2 is strongly overexpressed in approximately 61% of GBM patient tumors (Wykosky et al. (2008) Clin Cancer Res. 14:199-208), 76% of ovarian cancers (Thaker et al. (2004) Clin Cancer Res. 10:5145-50), and 85% of prostate adenocarcinomas (Zeng et al. (2003) Am J Pathol. 163:2271-6). The EPHA2 protein is highly overexpressed with regard to percentage of patient tumors and percentage of cells within a tumor, and is a plasma membrane-localized receptor that can internalize on ligand binding (Walker-Daniels et al. (2002) Mol Cancer Res. 1:79-87). Moreover, expression of EPHA2 is associated with poor prognosis, increased metastasis, and decreased survival. Thus, due to its expression pattern, localization, and functional importance in the outcome of cancer patients, EPHA2 is another attractive antigen for the targeted delivery of novel anti-cancer therapies.

In various embodiments, the present disclosure provides, in part, novel compounds with biological activity against neoplastic cells. The compounds may slow, inhibit, and/or reverse tumor growth in mammals, and may be useful for treating human cancer patients. In various embodiments, the disclosure provides novel antibody-drug conjugates employing the novel compounds or other functional splice inhibitor molecules.

The present disclosure more specifically relates, in various embodiments, to antibody-drug conjugate (ADC) compounds that are capable of binding and killing neoplastic cells. In various embodiments, the ADC compounds disclosed herein comprise a linker that attaches a splicing modulator to a full-length antibody or an antigen binding fragment. In various embodiments, the ADC compounds are also capable of internalizing into a target cell after binding.

In various embodiments, ADC compounds may be represented by Formula (I):

$$Ab\text{-}(L\text{-}D)_p \quad (I)$$

wherein Ab is an antibody or an antigen binding fragment thereof which targets a neoplastic cell or another oncology-related target;

D is a splicing modulator;

L is a linker which covalently attaches Ab to D; and p is an integer from 1 to 15.

In various embodiments, ADC compounds may be represented by Formula (I):

$$Ab\text{-}(L\text{-}D)_p \quad (I)$$

wherein Ab is an antibody or an antigen binding fragment thereof which targets a neoplastic cell;

D is a splicing modulator of Formula (II):

(II)

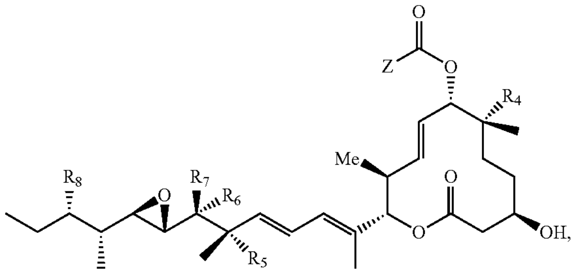

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$ alkyl groups, and —$NR^{15}R^{16}$;

$R^{15}$ and $R^{16}$ are each independently chosen from hydrogen, $R^{17}$, —C(═O)—$R^{17}$, and —C(═O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and Z is chosen from

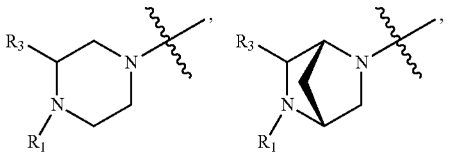

-continued

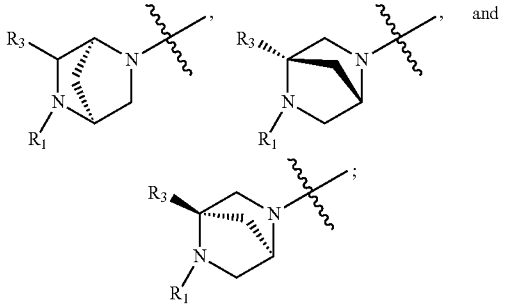

wherein $R^1$, $R^3$, $R^4$, $R^5$, $R^6$, $R^1$, $R^8$, $R^{1'}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator of Formula (II) ("L-D"), and L-D has a structure of Formula (II-A):

(II-A)

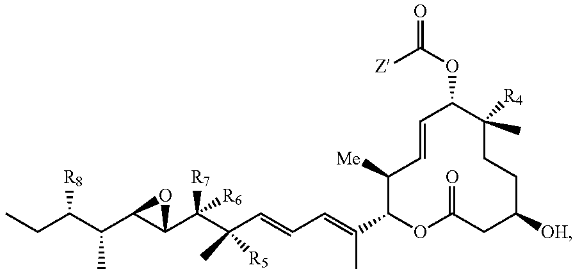

or a pharmaceutically acceptable salt thereof, wherein Z' is chosen from

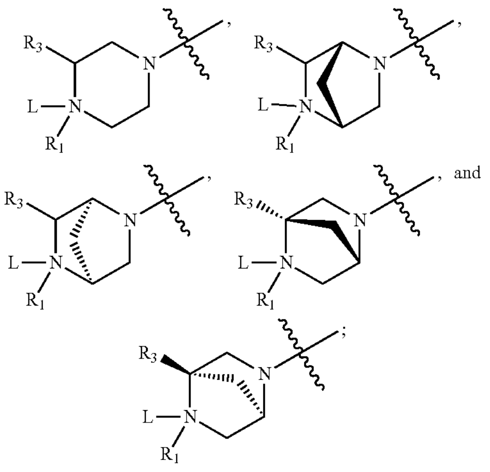

and wherein all other variables are as defined for Formula (II).

In various other embodiments, ADC compounds may be represented by of Formula (I):

$$\text{Ab-(L-D)}_p \qquad \text{(I)}$$

wherein Ab is an antibody or an antigen binding fragment thereof which targets a neoplastic cell;

D is a splicing modulator of Formula (IV):

(IV)

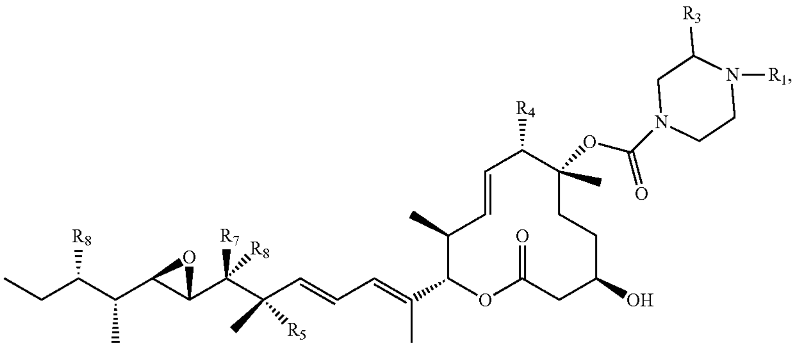

or a pharmaceutically acceptable salt thereof, wherein:

$R^1$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$—C alkyl groups, and —$NR^{15}R^{16}$;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator ("L-D"), and L-D has a structure of Formula (IV-A):

(IV-A)

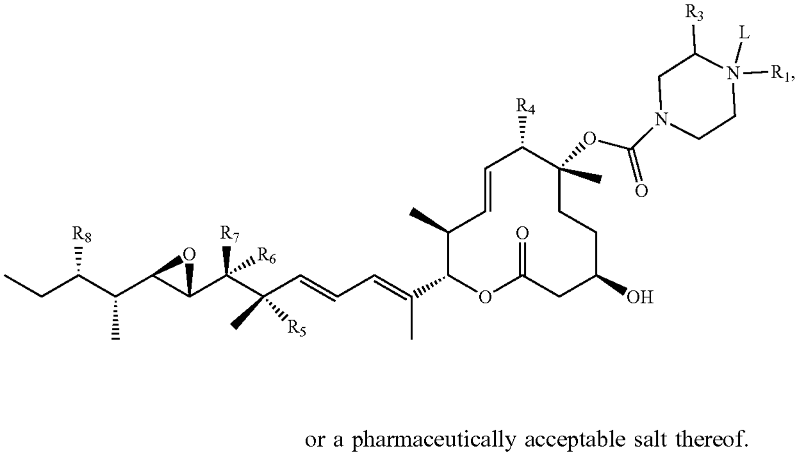

or a pharmaceutically acceptable salt thereof.

In various other embodiments, ADC compounds may be represented by Formula (I):

$$Ab\text{-}(L\text{-}D)_p \quad (I)$$

wherein Ab is an antibody or an antigen binding fragment thereof which targets a neoplastic cell;

D is a splicing modulator of Formula (VI):

(VI)

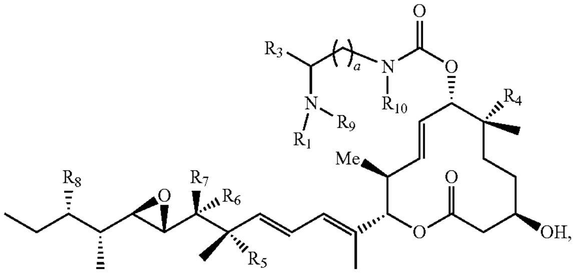

or a pharmaceutically acceptable salt thereof, wherein:

$R^1$ and $R^9$ are each independently chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$alkyl groups, —$NR^{15}R^{16}$, and a linker;

$R^{10}$ is chosen from hydrogen, $C_1$-$C_6$ alkyl groups, —C(═O)—($C_1$-$C_6$ alkyl) groups, and —CD3;

$R^{15}$ and $R^{16}$ are each independently chosen from hydrogen, $R^{17}$, —C(═O)—$R^{17}$, and —C(═O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and a is 1, 2, 3, 4, 5, 6, 7, 8, 9, or 10;

wherein $R^1$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein $R^1$ and $R^9$ cannot both be absent;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator ("L-D"), and L-D has a structure of Formula (VI-A):

(VI-A)

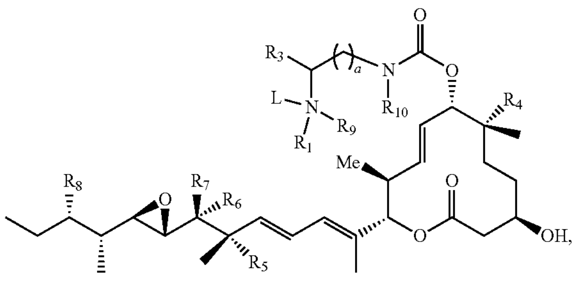

or a pharmaceutically acceptable salt thereof.

In various other embodiments, ADC compounds may be represented by Formula (I):

$$Ab\text{-}(L\text{-}D)_p \quad (I)$$

wherein Ab is an antibody or an antigen binding fragment thereof which targets a neoplastic cell;

D is a splicing modulator of Formula (VIII):

(VIII)

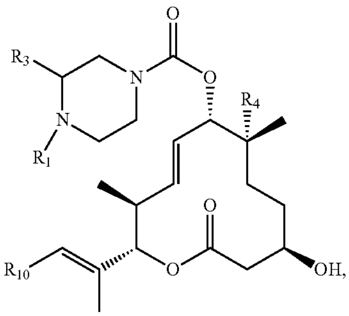

or a pharmaceutically acceptable salt thereof, wherein:

$R^1$ is chosen from absent, hydrogen, $C_1$-$C_6$alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$ is chosen from hydrogen, hydroxyl groups, —O—($C_1$-$C_6$ alkyl) groups, —O—C(═O)—($C_1$-$C_6$ alkyl) groups, and $C_1$-$C_6$alkyl groups; and $R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(═O)$_w$-(4 to 7 membered heterocycles), 4 to 7 membered carbocycles, and 4 to 7 membered heterocycles;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$alkyl groups, —(C═O)—($C_1$-$C_6$ alkyl) groups, —(C═O)—($C_1$-$C_6$ alkyl)-($C_3$-$C_{10}$ heterocyclyl groups), —S(═O)$_w$—($C_3$-$C_3$ heterocyclyl) groups, and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$alkyl groups; and w is 0, 1, or 2;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator ("L-D"), and L-D has a structure of Formula (VIII-A):

(VIII-A)

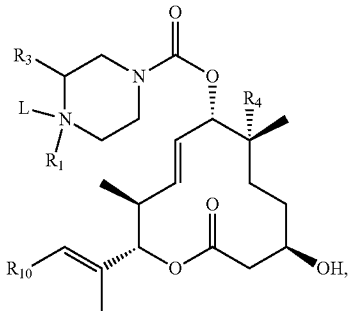

or a pharmaceutically acceptable salt thereof.

In some embodiments, the splicing modulator comprises a modulator of the SF3b complex.

In some embodiments, the splicing modulator comprises a pladienolide or a pladienolide derivative. In some embodiments, the splicing modulator comprises pladienolide D or a pladienolide D derivative. In some embodiments, the pladienolide D or derivative comprises D2, D1, D4, D8, D10, D11 (E7107), D20, D21, D22, D12, or D25. In some embodiments, the pladienolide D or derivative comprises D2. In some embodiments, the pladienolide D or derivative comprises D1. In some embodiments, the pladienolide D or derivative comprises D4. In some embodiments, the pladienolide D or derivative comprises D12.

In some embodiments, the pladienolide D or derivative is a zwitterionic pladienolide D or derivative. In some embodiments, the zwitterionic pladienolide D or derivative comprises D22 or D25.

In some other embodiments, the splicing modulator comprises pladienolide B or a pladienolide B derivative. In some embodiments, the pladienolide B or derivative comprises D9, D18, D19, or D13.

In some embodiments, the splicing modulator comprises an aryl pladienolide. In some embodiments, the aryl pladienolide comprises D15, D14, D16, D17, D26, or D33. In some embodiments, the aryl pladienolide comprises D15. In some embodiments, the aryl pladienolide is a zwitterionic aryl pladienolide. In some embodiments, the zwitterionic aryl pladienolide comprises D33.

In some embodiments, the splicing modulator comprises D1:

(D1)

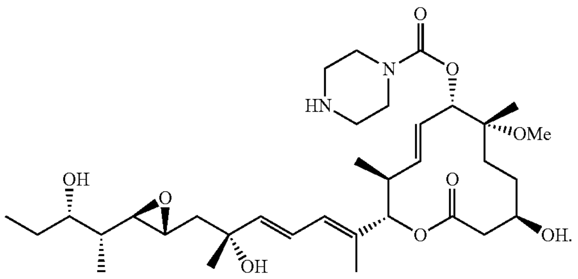

In some embodiments, the splicing modulator comprises D2:

(D2)

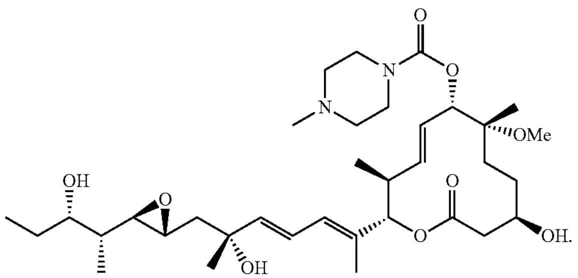

In some embodiments, the splicing modulator comprises D3:

(D3)

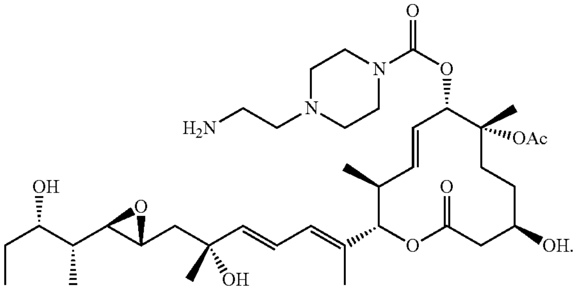

In some embodiments, the splicing modulator comprises D4:

(D4)

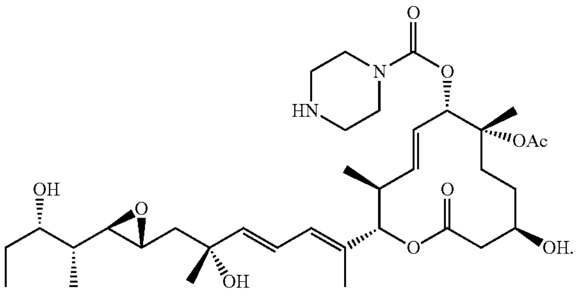

In some embodiments, the splicing modulator comprises D4':

(D4')

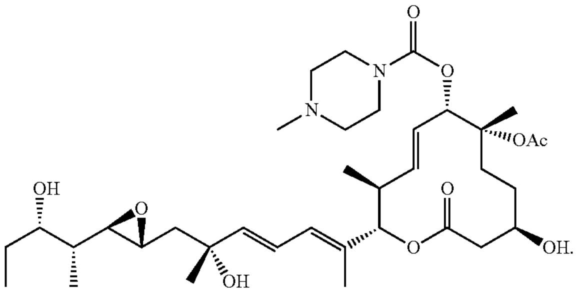

In some embodiments, the splicing modulator comprises D5:

(D5)

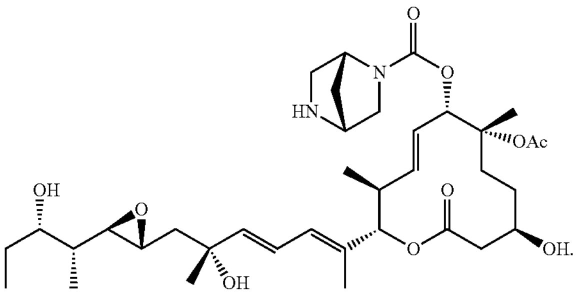

In some embodiments, the splicing modulator comprises D6:

(D6)

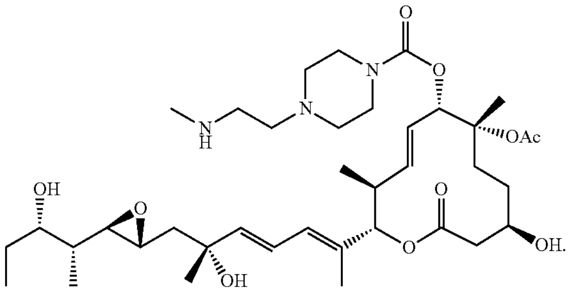

In some embodiments, the splicing modulator comprises D7:

(D7)

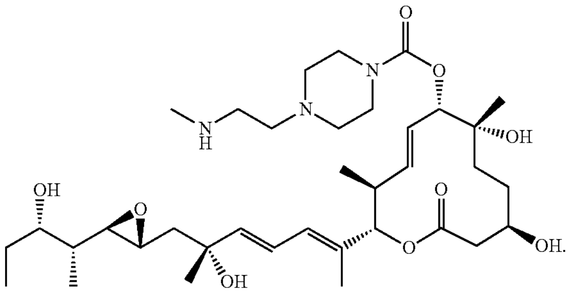

In some embodiments, the splicing modulator comprises D8:

(D8)

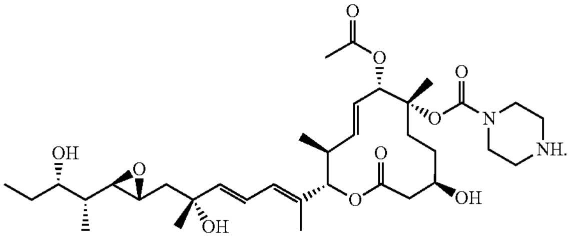

In some embodiments, the splicing modulator comprises D9:

(D9)

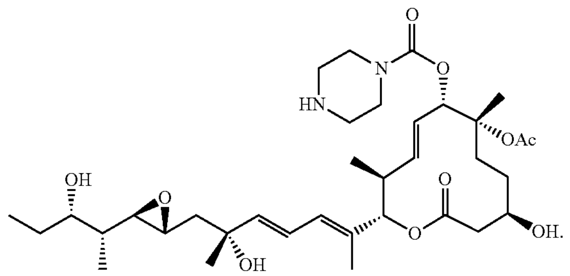

In some embodiments, the splicing modulator comprises D10:
(D10)
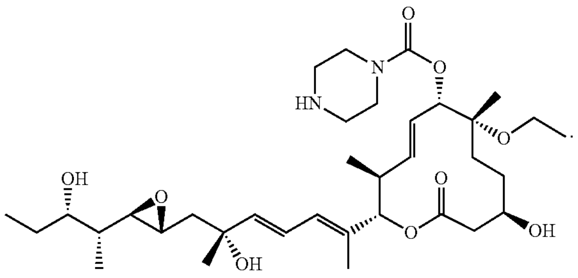
In some embodiments, the splicing modulator comprises D11:
(D11)
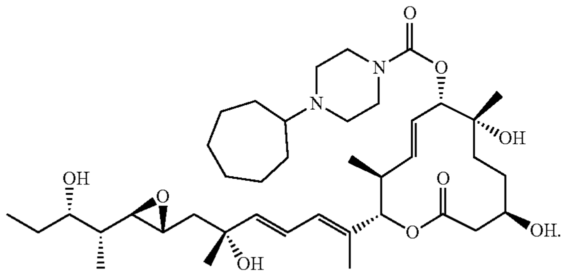
In some embodiments, the splicing modulator comprises D12:
(D12)
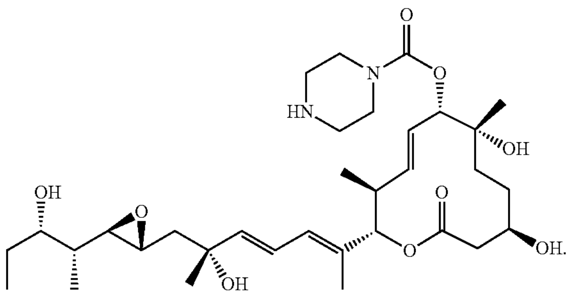
In some embodiments, the splicing modulator comprises D13:
(D13)
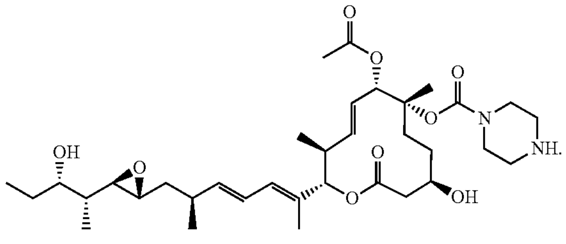
In some embodiments, the splicing modulator comprises D14:
(D14)
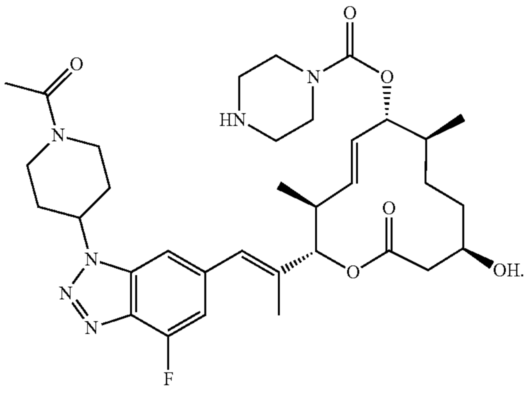
In some embodiments, the splicing modulator comprises D15:
(D15)
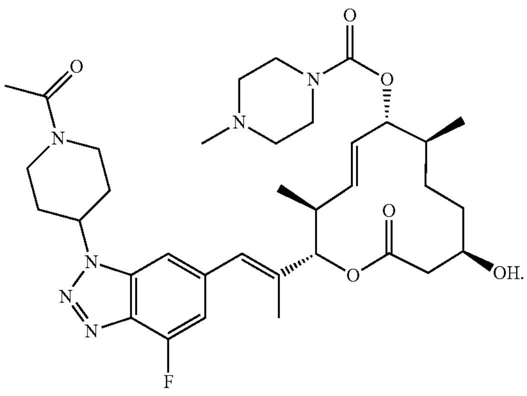

In some embodiments, the splicing modulator comprises D16:

(D16)

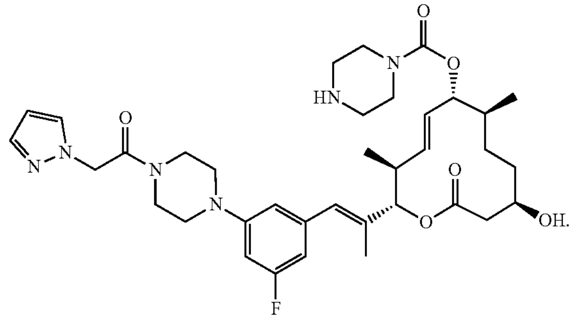

In some embodiments, the splicing modulator comprises D17:

(D17)

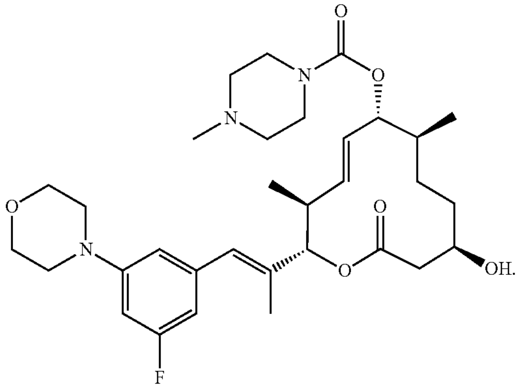

In some embodiments, the splicing modulator comprises D18:

(D18)

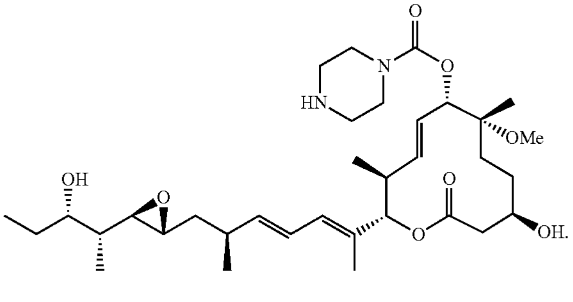

In some embodiments, the splicing modulator comprises D19:

(D19)

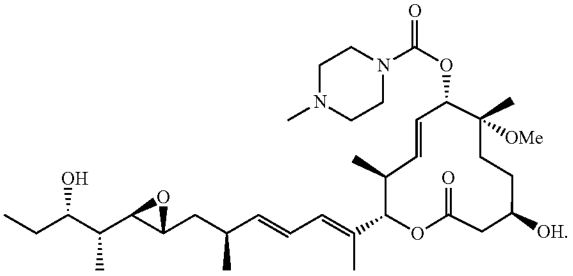

In some embodiments, the splicing modulator comprises D20:

(D20)

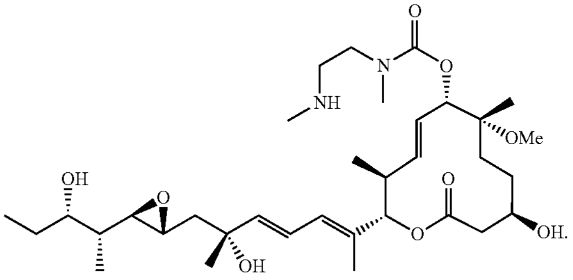

In some embodiments, the splicing modulator comprises D21:

(D21)

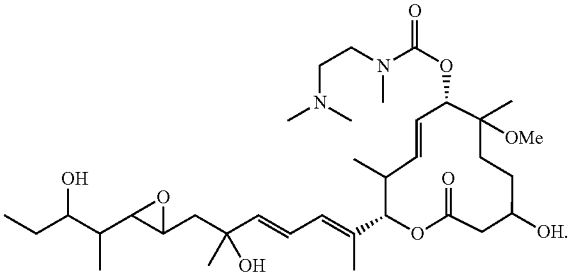

In some embodiments, the splicing modulator comprises D22:

(D22)

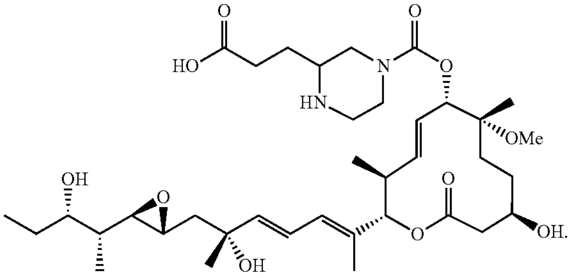

In some embodiments, the splicing modulator comprises D23:
(D23)
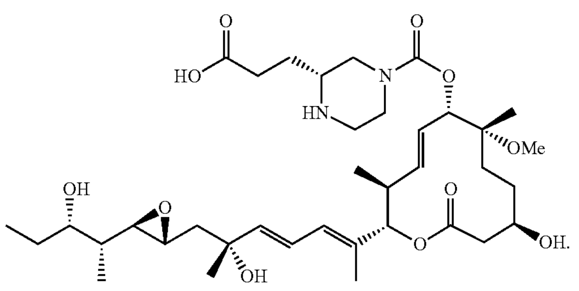
In some embodiments, the splicing modulator comprises D24:
(D24)
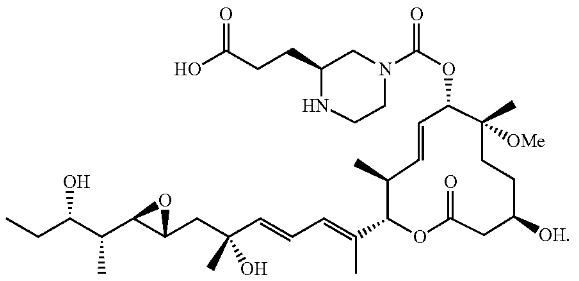
In some embodiments, the splicing modulator comprises D25:
(D25)
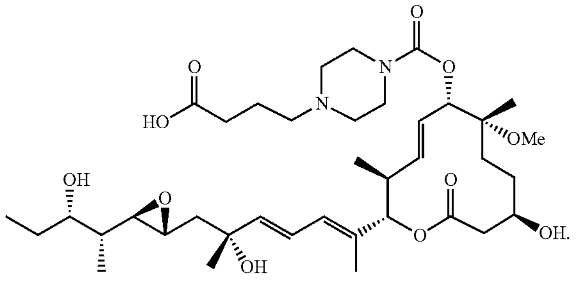
In some embodiments, the splicing modulator comprises D26:
(D26)
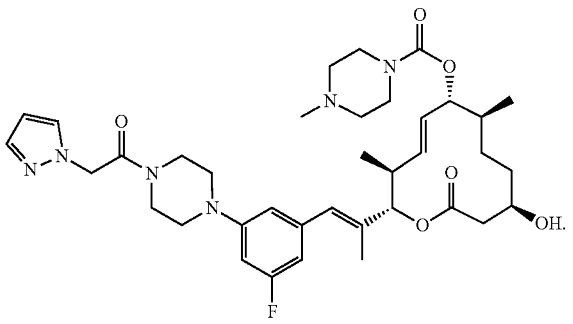
In some embodiments, the splicing modulator comprises D27:
(D27)
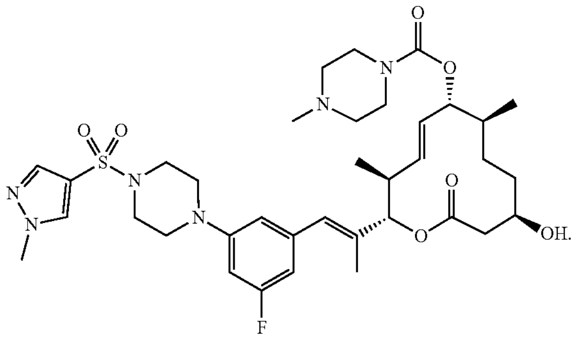
In some embodiments, the splicing modulator comprises D28:
(D28)
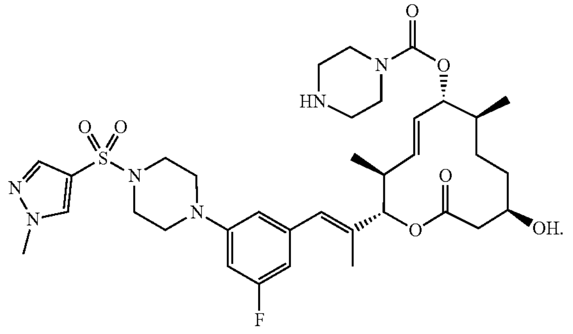

In some embodiments, the splicing modulator comprises D29:
(D29)
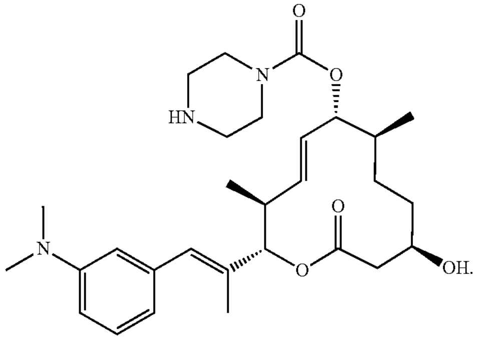
In some embodiments, the splicing modulator comprises D30:
(D30)
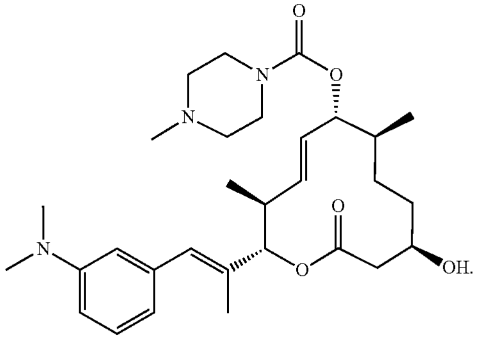
In some embodiments, the splicing modulator comprises D31:
(D31)
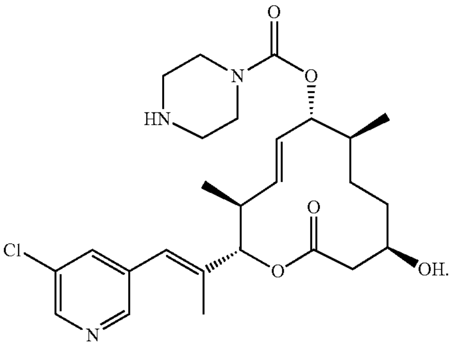
In some embodiments, the splicing modulator comprises D32:
(D32)
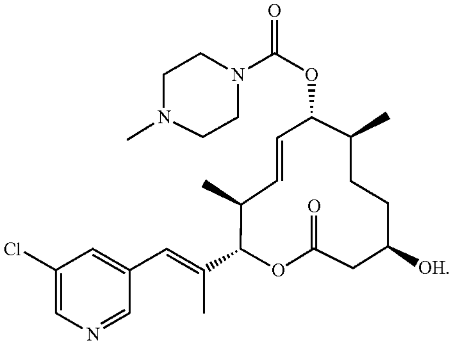
In some embodiments, the splicing modulator comprises D33:
(D33)
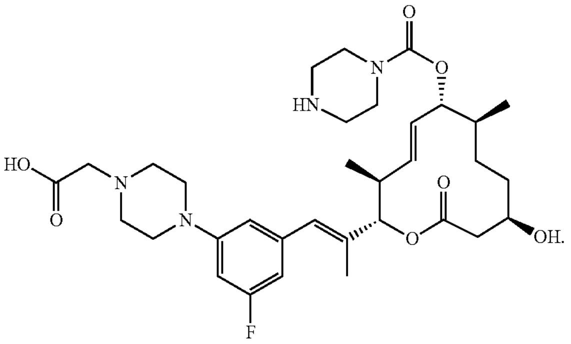
In some embodiments, the splicing modulator comprises D34:
(D34)
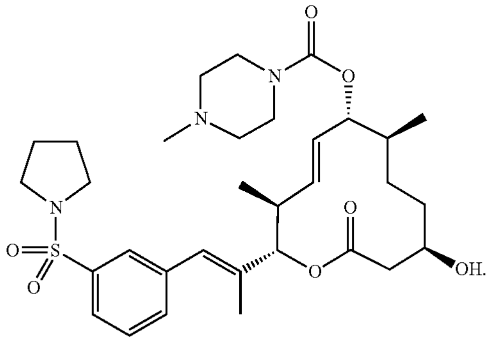

In some embodiments, the splicing modulator comprises D35:

(D35)

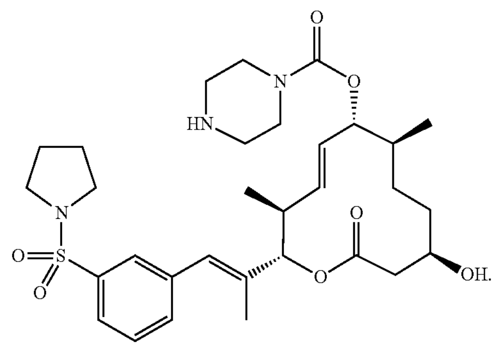

In some embodiments, the splicing modulator comprises one of the drug moieties listed in Table 7. In some embodiments, the splicing modulator comprises D1, D2, D3, D4, D4', D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, and/or D35.

In some embodiments, a splicing modulator is disclosed, as well as its use as a therapeutic alone or as part of an ADC. In some embodiments, the splicing modulator comprises D4, D4', D12, D15, D8, D9, D10, D13, D18, D19, D20, D21, D22, D25, or D33.

In some embodiments, the splicing modulator comprises D4 and the linker comprises MC-Val-Cit-pABC. In some embodiments, the splicing modulator comprises D4 and the linker comprises MC-β-glucuronide. In some embodiments, the splicing modulator comprises D12 and the linker comprises MC-Val-Cit-pABC. In some embodiments, the splicing modulator comprises D12 and the linker comprises MC-β-glucuronide. In some embodiments, the splicing modulator comprises D15 and the linker comprises MC-Val-Ala-pAB.

In various embodiments, the linker used in an ADC disclosed herein is stable outside a cell, such that the ADC remains intact when present in extracellular conditions, but is capable of being cleaved upon internalization into a cell, e.g., a tumor or cancer cell. In some embodiments, the splicing modulator is cleaved from the antibody or antigen binding fragment when the ADC enters a cell that expresses an antigen targeted by the antibody or antigen binding fragment of the ADC. In some embodiments, the linker is a cleavable linker.

In some embodiments, the linker comprises a cleavable peptide moiety. In some embodiments, the cleavable peptide moiety is cleavable by an enzyme. In some embodiments, the cleavable peptide moiety or linker comprises an amino acid unit. In some embodiments, the amino acid unit comprises valine-citrulline (“Val-Cit” or “VC”).

In some other embodiments, the amino acid unit comprises valine-alanine (“Val-Ala” or “VA”). In some other embodiments, the amino acid unit comprises glutamic acid-valine-citrulline (“Glu-Val-Cit” or “EVC”). In some other embodiments, the amino acid unit comprises alanine-alanine-asparagine (“Ala-Ala-Asn” or “AAN”).

In some embodiments, the linker comprises a cleavable glucuronide moiety. In some embodiments, the cleavable glucuronide moiety is cleavable by an enzyme. In some embodiments, the cleavable glucuronide moiety is cleavable by a glucuronidase. In some embodiments, the cleavable glucuronide moiety is cleavable by β-glucuronidase.

In some embodiments, the linker comprises at least one spacer unit. In some embodiments, the spacer unit or linker comprises a polyethylene glycol (PEG) moiety. In some embodiments, the PEG moiety comprises $-(PEG)_m-$ and m is an integer from 1 to 10. In some embodiments, m is 2. In some other embodiments, the spacer unit or linker comprises an alkyl moiety. In some embodiments, the alkyl moiety comprises $—(CH_2)_n—$ and n is an integer from 1 to 10. In some embodiments, n is 2. In some embodiments, n is 5. In some embodiments, n is 6.

In some embodiments, the spacer unit attaches to the antibody or antigen binding fragment via a maleimide (Mal) moiety (“Mal-spacer unit”). In some embodiments, the Mal-spacer unit is reactive with a cysteine residue on the antibody or antigen binding fragment. In some embodiments, the Mal-spacer unit is joined to the antibody or antigen binding fragment via a cysteine residue on the antibody or antigen binding fragment.

In some embodiments, the linker comprises the Mal-spacer unit and a cleavable peptide moiety. In some embodiments, the cleavable peptide moiety comprises an amino acid unit. In some embodiments, the cleavable peptide moiety or amino acid unit comprises Val-Cit. In some embodiments, the cleavable peptide moiety or amino acid unit comprises Val-Ala. In some embodiments, the cleavable peptide moiety or amino acid unit comprises Glu-Val-Cit. In some embodiments, the cleavable peptide moiety or amino acid unit comprises Ala-Ala-Asn. In some embodiments, the Mal-spacer unit comprises an alkyl moiety. In some embodiments, the Mal-spacer unit comprises a PEG moiety. In some embodiments, the Mal-spacer unit comprises a maleimidocaproyl (MC).

In some embodiments, the Mal-spacer unit attaches the antibody or antigen binding fragment to the cleavable moiety in the linker. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises MC-Val-Cit. In some embodiments, the linker comprises MC-Val-Ala. In some embodiments, the linker comprises MC-Glu-Val-Cit. In some embodiments, the linker comprises MC-Ala-Ala-Asn. In some embodiments, the Mal-spacer unit comprises an alkyl moiety. In some embodiments, the Mal-spacer unit comprises a PEG moiety. In some embodiments, the Mal-spacer unit comprises a maleimidocaproyl (MC).

In some embodiments, the cleavable moiety in the linker is directly joined to the splicing modulator, or a spacer unit attaches the cleavable moiety in the linker to the splicing modulator. In some embodiments, cleavage of the conjugate releases the splicing modulator from the antibody or antigen binding fragment and linker. In some embodiments, the spacer unit attaching the cleavable moiety in the linker to the splicing modulator is self-immolative.

In some embodiments, the spacer unit attaching the cleavable moiety in the linker to the splicing modulator comprises a p-aminobenzyloxycarbonyl (pABC). In some embodiments, the pABC attaches the cleavable moiety in the linker to the splicing modulator. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises Val-Cit-pABC. In some other embodiments, the linker comprises Val-Ala-pABC. In some embodiments, the linker comprises Glu-Val-Cit-pABC. In some embodiments, the linker comprises Ala-Ala-Asn-pABC.

In some embodiments, the spacer unit attaching the cleavable moiety in the linker to the splicing modulator comprises a p-aminobenzyl (pAB). In some embodiments, the pAB attaches the cleavable moiety in the linker to the splicing modulator. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises Val-Cit-pAB. In some other embodiments, the linker comprises Val-Ala-pAB. In some other embodiments, the linker comprises Glu-Val-Cit-pAB. In some other embodiments, the linker comprises Ala-Ala-Asn-pAB.

In various embodiments, the linker is a non-cleavable linker. In some embodiments, the splicing modulator of the ADC is released by degradation of the antibody or antigen binding fragment. In some embodiments, the linker remains covalently associated with at least one amino acid of the antibody and drug upon internalization by and degradation within the target cell.

In some embodiments, the linker is a non-cleavable linker comprising at least one spacer unit. In some embodiments, the spacer unit or linker comprises a polyethylene glycol (PEG) moiety. In some embodiments, the PEG moiety comprises $-(PEG)_m-$ and m is an integer from 1 to 10. In some embodiments, m is 2. In some other embodiments, the spacer unit or linker comprises an alkyl moiety. In some embodiments, the alkyl moiety comprises $—(CH_2)_n—$ or $—(CH_2)_n—O—(CH_2)_n$ and n is an integer from 1 to 10. In some embodiments, n is 2. In some embodiments, n is 5. In some embodiments, n is 6.

In some embodiments, the spacer unit in a non-cleavable linker attaches to the antibody or antigen binding fragment via a maleimide (Mal) moiety ("Mal-spacer unit"). In some embodiments, the Mal-spacer unit is reactive with a cysteine residue on the antibody or antigen binding fragment. In some embodiments, the Mal-spacer unit is joined to the antibody or antigen binding fragment via a cysteine residue on the antibody or antigen binding fragment. In some embodiments, the Mal-spacer unit comprises an alkyl moiety. In some embodiments, the Mal-spacer unit comprises a PEG moiety. In some embodiments, the linker or Mal-spacer unit comprises a maleimidocaproyl (MC). In some embodiments, the linker or Mal-spacer unit comprises a maleimidocaproyl (MC) and at least one additional spacer unit. In some embodiments, the linker or Mal-spacer unit comprises $MC-(PEG)_2$. In some embodiments, the linker or Mal-spacer unit comprises $MC-(PEG)_2$ and at least one additional spacer unit. In some embodiments, the linker or Mal-spacer unit comprises Mal-Hex. In some embodiments, the linker or Mal-spacer unit comprises Mal-Hex and at least one additional spacer unit. In some embodiments, the linker or Mal-spacer unit comprises Mal-Et. In some embodiments, the linker or Mal-spacer unit comprises Mal-Et and at least one additional spacer unit. In some embodiments, the linker or Mal-spacer unit comprises Mal-Et-O-Et. In some embodiments, the linker or Mal-spacer unit comprises Mal-Et-O-Et and at least one additional spacer unit. In some embodiments, the Mal-spacer unit attaches the antibody or antigen binding fragment to the splicing modulator.

In various embodiments, ADC compounds may be represented by Formula (I):

$$Ab-(L-D)_p \qquad (I)$$

wherein Ab is an antibody or an antigen binding fragment thereof which targets a neoplastic cell or another oncology-related target such as a cancer antigen (e.g., any of the antibody or binding domain sequences disclosed herein); D is any small molecule suitable for treating a cancer (e.g., a splicing modulator, e.g., any of the splicing modulators disclosed herein); L is a linker which covalently attaches Ab to D (e.g., any of the linkers disclosed herein); and p is an integer from 1 to 15.

In some embodiments, Ab is selected from any of the antibody or binding domain sequences disclosed herein. In some embodiments, Ab is an antibody or binding domain sequence which targets HER2 and/or a HER2-expressing neoplastic cell. In some embodiments, Ab is an antibody or binding domain sequence which targets CD138 and/or a CD138-expressing neoplastic cell. In some embodiments, Ab is an antibody or binding domain sequence which targets EPHA2 and/or an EPHA2-expressing neoplastic cell. In some embodiments, Ab is an antibody or binding domain sequence which targets MSLN and/or a MSLN-expressing neoplastic cell. In some embodiments, Ab is an antibody or binding domain sequence which targets FOLH1 and/or a FOLH1-expressing neoplastic cell. In some embodiments, Ab is an antibody or binding domain sequence which targets CDH6 and/or a CDH6-expressing neoplastic cell. In some embodiments, Ab is an antibody or binding domain sequence which targets CEACAM5 and/or a CEACAM5-expressing neoplastic cell. In some embodiments, Ab is an antibody or binding domain sequence which targets CFC1B and/or a CFC1B-expressing neoplastic cell. In some embodiments, Ab is an antibody or binding domain sequence which targets ENPP3 and/or an ENPP3-expressing neoplastic cell. In some embodiments, Ab is an antibody or binding domain sequence which targets FOLR1 and/or a FOLR1-expressing neoplastic cell. In some embodiments, Ab is an antibody or binding domain sequence which targets HAVCR1 and/or a HAVCR1-expressing neoplastic cell. In some embodiments, Ab is an antibody or binding domain sequence which targets KIT and/or a KIT-expressing neoplastic cell. In some embodiments, Ab is an antibody or binding domain sequence which targets MET and/or a MET-expressing neoplastic cell. In some embodiments, Ab is an antibody or binding domain sequence which targets MUC16 and/or a MUC16-expressing neoplastic cell. In some embodiments, Ab is an antibody or binding domain sequence which targets SLC39A6 and/or a SLC39A6-expressing neoplastic cell. In some embodiments, Ab is an antibody or binding domain sequence which targets SLC44A4 and/or a SLC44A4-expressing neoplastic cell. In some embodiments, Ab is an antibody or binding domain sequence which targets STEAP1 and/or a STEAP1-expressing neoplastic cell. In some embodiments, Ab is an antibody or binding domain sequence which targets another cancer antigen.

In some embodiments, D is a splicing modulator. In some embodiments, D is selected from any of the splicing modulators disclosed herein. In some embodiments, D is a splicing modulator selected from D2, D1, D4, D8, D10, D11 (E7107), D20, D21, D22, D12, D25, D9, D18, D19, D13, D15, D14, D16, D17, D26, and D33, or any derivative thereof. In some embodiments, D is a splicing modulator selected from D4, D12, D15, D8, D9, D10, D13, D18, D19, D20, D21, D22, D25, and D33, or any derivative thereof. In some embodiments, D is a splicing modulator comprising D2 or any derivative thereof. In some embodiments, D is a splicing modulator comprising D1 or any derivative thereof.

In some embodiments, L is selected from any of the linkers disclosed herein, or any combination of linker components disclosed herein. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL10, ADL12, ADL13, ADL14, ADL15, ADL21, ADL22, or ADL23 linker. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units. In some embodiments, L is an ADL1 linker and may optionally comprise one or more additional spacer units. In some embodiments, L is an ADL2 linker and may optionally comprise one or more additional spacer units. In some embodiments, L is an ADL5 linker and may optionally comprise one or more additional spacer units. In some embodiments, L is an ADL6 linker and may optionally comprise one or more additional spacer units. In some embodiments, L is an ADL7 linker and may optionally comprise one or more additional spacer units. In some embodiments, L is an ADL12 linker and may optionally comprise one or more additional spacer units. In some embodiments, L is an ADL14 linker and may optionally comprise one or more additional spacer units. In some embodiments, L is an ADL15 linker and may optionally comprise one or more additional spacer units. In various embodiments of the ADCs described herein, p is from 1 to 10. In various embodiments, p is from 2 to 8. In various embodiments, p is from 4 to 8. In some embodiments, p is 4. In some embodiments, p is 8.

In some embodiments, L-D of Formula (I) is ADL1-D1. In some embodiments, L-D of Formula (I) is ADL6-D1. In some embodiments, L-D of Formula (I) is ADL5-D2. In some embodiments, L-D of Formula (I) is ADL1-D18. In some embodiments, L-D of Formula (I) is ADL5-D19. In some embodiments, L-D of Formula (I) is ADL14-D1. In some embodiments, L-D of Formula (I) is ADL12-D1. In some embodiments, L-D of Formula (I) is ADL15-D1. In some embodiments, L-D of Formula (I) is ADL12-D20. In some embodiments, L-D of Formula (I) is ADL10-D1. In some embodiments, L-D of Formula (I) is ADL12-D2. In some embodiments, L-D of Formula (I) is ADL15-D2. In some embodiments, L-D of Formula (I) is ADL12-D21. In some embodiments, L-D of Formula (I) is ADL6-D9. In some embodiments, L-D of Formula (I) is ADL1-D4. In some embodiments, L-D of Formula (I) is ADL1-D3. In some embodiments, L-D of Formula (I) is ADL1-D12. In some embodiments, L-D of Formula (I) is ADL1-D7. In some embodiments, L-D of Formula (I) is ADL1-D6. In some embodiments, L-D of Formula (I) is ADL1-D5. In some embodiments, L-D of Formula (I) is ADL22-D4. In some embodiments, L-D of Formula (I) is ADL5-D10. In some embodiments, L-D of Formula (I) is ADL5-D11. In some embodiments, L-D of Formula (I) is ADL1-D13. In some embodiments, L-D of Formula (I) is ADL1-D8. In some embodiments, L-D of Formula (I) is ADL1-D22. In some embodiments, L-D of Formula (I) is ADL5-D25. In some embodiments, L-D of Formula (I) is ADL12-D22. In some embodiments, L-D of Formula (I) is ADL5-D15. In some embodiments, L-D of Formula (I) is ADL1-D14. In some embodiments, L-D of Formula (I) is ADL5-D26. In some embodiments, L-D of Formula (I) is ADL1-D16. In some embodiments, L-D of Formula (I) is ADL5-D17. In some embodiments, L-D of Formula (I) is ADL1-D33. In some embodiments, L-D of Formula (I) is ADL1-D28. In some embodiments, L-D of Formula (I) is ADL1-D31. In some embodiments, L-D of Formula (I) is ADL1-D29. In some embodiments, L-D of Formula (I) is ADL1-D35. In some embodiments, L-D of Formula (I) is ADL5-D32. In some embodiments, L-D of Formula (I) is ADL5-D27. In some embodiments, L-D of Formula (I) is ADL12-D35. In some embodiments, L-D of Formula (I) is ADL12-D28. In some embodiments, L-D of Formula (I) is ADL1-D23. In some embodiments, L-D of Formula (I) is ADL1-D24.

In some embodiments, a pool of ADCs is provided whereby random conjugation occurs, and the average p in the pool is between about 2 and about 8. In some embodiments, a pool of ADCs is provided whereby random conjugation occurs, and the average p in the pool is between about 4 and about 8. In some embodiments, a pool of ADCs is provided whereby random conjugation occurs, and the average p in the pool is about 4. In some embodiments, a pool of ADCs is provided whereby random conjugation occurs, and the average p in the pool is about 8. Compositions (e.g., pharmaceutical compositions) comprising multiple copies of any of the described ADCs, wherein the average drug loading (average p) of the ADCs in the composition is from about 3.5 to about 5.5 (e.g., about 4), or from about 7 to about 9 (e.g., about 8) are provided herein.

In some embodiments, the antibody or antigen binding fragment (Ab) of the ADC targets a neoplastic cell derived from a hematological malignancy or a solid tumor. In some embodiments, the antibody or antigen binding fragment targets a neoplastic cell derived from a hematological malignancy. In some embodiments, the hematological malignancy is selected from a B-cell malignancy, a leukemia (e.g., acute myeloid leukemia), a lymphoma, and a myeloma (e.g., multiple myeloma). In some embodiments, the hematological malignancy is selected from acute myeloid leukemia and multiple myeloma. In some embodiments, the antibody or antigen binding fragment targets a neoplastic cell derived from a solid tumor. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the antibody or antigen binding fragment (Ab) of the ADC is an anti-HER2 antibody or an antigen binding fragment thereof. In some embodiments, the antibody or antigen binding fragment binds to HER2 and targets HER2-expressing neoplastic cells (i.e., the ADC targets HER2-expressing neoplastic cells). In some embodiments, the antibody or antigen binding fragment of the ADC is an internalizing anti-HER2 antibody or internalizing antigen binding fragment thereof.

In some embodiments, the anti-HER2 antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3

(HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the anti-HER2 antibody or antigen binding fragment is an internalizing antibody or internalizing antigen binding fragment. In some embodiments, the anti-HER2 antibody or antigen binding fragment comprises human framework sequences. In some embodiments, the anti-HER2 antibody or antigen binding fragment comprises a heavy chain variable region comprising an amino acid sequence of SEQ ID NO:19, and a light chain variable region comprising an amino acid sequence of SEQ ID NO:20. In some embodiments, the anti-HER2 antibody or antigen binding fragment comprises a human IgG heavy chain constant region. In some embodiments, the anti-HER2 antibody or antigen binding fragment comprises a human IgG1 heavy chain constant region. In some embodiments, the anti-HER2 antibody or antigen binding fragment comprises a human Ig kappa or lambda light chain constant region. In some embodiments, the anti-HER2 antibody or antigen binding competes for binding and/or binds the same epitope as an antibody comprising a heavy chain variable domain of SEQ ID NO:19 and a light chain variable domain of SEQ ID NO:20.

In various embodiments, the antibody or antigen binding fragment (Ab) of the ADC is an anti-CD138 antibody or an antigen binding fragment thereof. In some embodiments, the antibody or antigen binding fragment binds to CD138 and targets CD138-expressing neoplastic cells (i.e., the ADC targets CD138-expressing neoplastic cells). In some embodiments, the antibody or antigen binding fragment of the ADC is an internalizing anti-CD138 antibody or internalizing antigen binding fragment thereof.

In some embodiments, the anti-CD138 antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the anti-CD138 antibody or antigen binding fragment is an internalizing antibody or internalizing antigen binding fragment. In some embodiments, the anti-CD138 antibody or antigen binding fragment comprises human framework sequences. In some embodiments, the anti-CD138 antibody or antigen binding fragment comprises a heavy chain variable region comprising an amino acid sequence of SEQ ID NO:21, and a light chain variable region comprising an amino acid sequence of SEQ ID NO:22. In some embodiments, the anti-CD138 antibody or antigen binding fragment comprises a murine IgG2a heavy chain constant region. In some embodiments, the anti-CD138 antibody or antigen binding fragment comprises a murine Ig kappa light chain constant region. In some embodiments, the anti-CD138 antibody or antigen binding fragment comprises a human IgG heavy chain constant region. In some embodiments, the anti-CD138 antibody or antigen binding fragment comprises a human IgG2a heavy chain constant region. In some embodiments, the anti-CD138 antibody or antigen binding fragment comprises a human Ig kappa or lambda light chain constant region. In some embodiments, the anti-CD138 antibody or antigen binding competes for binding and/or binds the same epitope as an antibody comprising a heavy chain variable domain of SEQ ID NO:21 and a light chain variable domain of SEQ ID NO:22.

In various embodiments, the antibody or antigen binding fragment (Ab) of the ADC is an anti-EPHA2 antibody or an antigen binding fragment thereof. In some embodiments, the antibody or antigen binding fragment binds to EPHA2 and targets EPHA2-expressing neoplastic cells (i.e., the ADC targets EPHA2-expressing neoplastic cells). In some embodiments, the antibody or antigen binding fragment of the ADC is an internalizing anti-EPHA2 antibody or internalizing antigen binding fragment thereof.

In some embodiments, the anti-EPHA2 antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the anti-EPHA2 antibody or antigen binding fragment is an internalizing antibody or internalizing antigen binding fragment. In some embodiments, the anti-EPHA2 antibody or antigen binding fragment comprises human framework sequences. In some embodiments, the anti-EPHA2 antibody or antigen binding fragment comprises a heavy chain variable region comprising an amino acid sequence of SEQ ID NO:23, and a light chain variable region comprising an amino acid sequence of SEQ ID NO:24. In some embodiments, the anti-EPHA2 antibody or antigen binding fragment comprises a human IgG heavy chain constant region. In some embodiments, the anti-EPHA2 antibody or antigen binding fragment comprises a human IgG1 heavy chain constant region. In some embodiments, the anti-EPHA2 antibody or antigen binding fragment comprises a human Ig kappa or lambda light chain constant region. In some embodiments, the anti-EPHA2 antibody or antigen binding competes for binding and/or binds the same epitope as an antibody comprising a heavy chain variable domain of SEQ ID NO:23 and a light chain variable domain of SEQ ID NO:24.

Also provided herein, in various embodiments, are compounds comprising a linker-drug defined by the generic formula: L-D, wherein L=a linker moiety, and D=a drug moiety (e.g., a splicing modulator drug moiety). In various embodiments, the linker-drug (L-D) compounds disclosed herein may attach to an antibody or antigen binding fragment and/or are suitable for use in the ADCs disclosed herein, e.g., in ADCs of Formula (I).

In various embodiments, the linker-drug (L-D) compounds disclosed herein comprise a linker-drug structure according to Formula (III). In various embodiments, the present disclosure provides a linker-drug (L-D) compound of Formula (III):

(III)

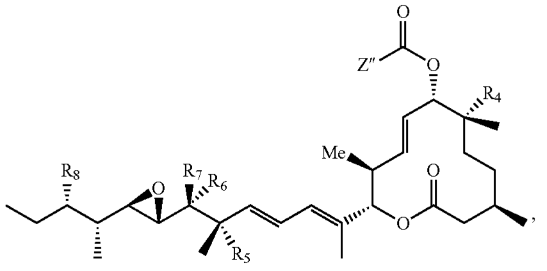

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and Z" is chosen from

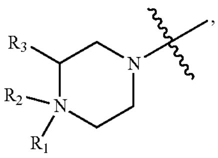
,
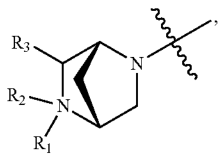
,
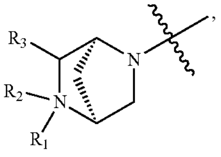
, and
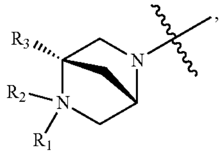
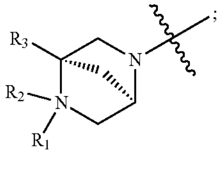
;

wherein $R^1$, $R^2$, $R^3$, $R^4$, $R^5$, $R^6$, $R^1$, $R^8$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In various other embodiments, the linker-drug (L-D) compounds disclosed herein comprise a linker-drug structure according to Formula (V). In various embodiments, the present disclosure provides a linker-drug (L-D) compound of Formula (V):

(V)

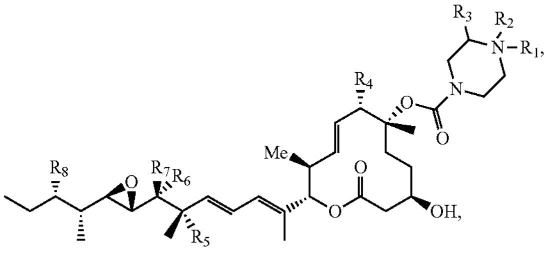

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In various other embodiments, the linker-drug (L-D) compounds disclosed herein comprise a linker-drug structure according to Formula (VII). In various embodiments, the present disclosure provides a linker-drug (L-D) compound of Formula (VII):

(VII)

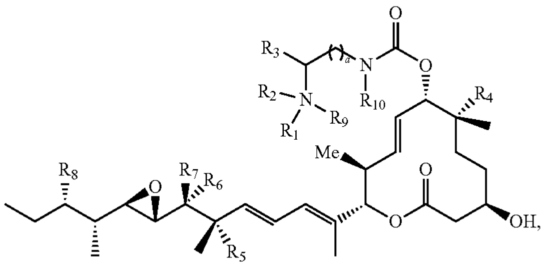

or a pharmaceutically acceptable salt thereof, wherein:

$R^1$ and $R^9$ are each independently chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$alkyl groups, —$NR^{15}R^{16}$, and a linker;

$R^{10}$ is chosen from hydrogen, $C_1$-$C_6$ alkyl groups, —C(═O)—($C_1$-$C_6$ alkyl) groups, and —CD3;

$R^{15}$ and $R^{16}$ are each independently chosen from hydrogen, $R^{17}$, —C(═O)—$R^{17}$, and —C(═O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and a is 1, 2, 3, 4, 5, 6, 7, 8, 9, or 10;

wherein $R^1$, $R^2$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen;

wherein if $R^2$ is a linker, then neither $R^6$ or $R^7$ is a linker, and if $R^6$ or $R^7$ is a linker, then $R^2$ is absent; and wherein $R^1$ and $R^9$ cannot both be absent.

In various other embodiments, the linker-drug (L-D) compounds disclosed herein comprise a linker-drug structure according to Formula (IX). In various embodiments, the present disclosure provides a linker-drug (L-D) compound of Formula (IX):

(IX)

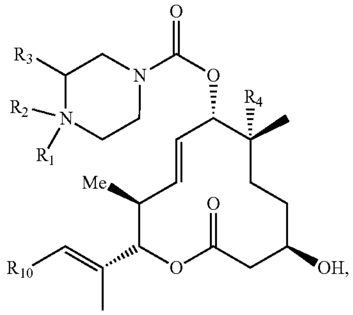

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^2$ is a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$ is chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(═O)$_w$-(4 to 7 membered heterocycles), 4 to 7 membered carbocycles, and 4 to 7 membered heterocycles;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^2$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$ alkyl groups, —(C═O)—($C_1$-$C_6$ alkyl) groups, —(C═O)—($C_1$-$C_6$ alkyl)-($C_3$-$C_{10}$ heterocyclyl)groups, and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$alkyl groups; and w is 0, 1, or 2.

Also, in various embodiments, provided herein are therapeutic uses for the described ADC compounds and compositions, e.g., in treating a neoplastic disorder, e.g., a cancer.

In certain aspects, the present disclosure provides methods of treating a neoplastic disorder, e.g., a cancer that expresses an antigen targeted by the antibody or antigen binding fragment of the ADC, such as HER2, CD138, EPHA2, MSLN, FOLH1, CDH6, CEACAM5, CFC1B, ENPP3, FOLR1, HAVCR1, KIT, MET, MUC16, SLC39A6, SLC44A4, or STEAP1.

In certain aspects, the present disclosure provides methods of treating a subject having or suspected of having a neoplastic disorder by administering to the subject a therapeutically effective amount and/or regimen of any one of the described ADCs or compositions. In some embodiments, the neoplastic disorder is a hematological malignancy or a solid tumor. In some embodiments, the neoplastic disorder is a hematological malignancy. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the neoplastic disorder is a solid tumor. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In some embodiments, treatment with the antibody-drug conjugate or composition induces bystander killing of neoplastic cells which do not express a target antigen but are adjacent to neoplastic cells which express a target antigen. In some embodiments, the subject has one or more neoplastic cells which express a target antigen.

In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In some embodiments, the subject is non-responsive or poorly responsive to treatment with (a) an anti-HER2 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CD138. In some embodiments, the one or more neoplastic cells are derived from a CD138-expressing multiple myeloma. In some embodiments, the subject is non-responsive or poorly responsive to treatment with (a) an anti-CD138 antibody when administered alone and/or (b) a splicing modulator when administered alone. In some embodiments, the subject is intolerant, non-responsive, or poorly responsive to treatment with a splicing modulator when administered alone.

In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the subject is non-responsive or poorly responsive to treatment with (a) an anti-EPHA2 antibody when administered alone and/or (b) a splicing modulator when administered alone. In some embodiments, the subject is intolerant, non-responsive, or poorly responsive to treatment with a splicing modulator when administered alone.

In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the subject is non-responsive or poorly responsive to treatment with (a) an anti-MSLN antibody when administered alone and/or (b) a splicing modulator when administered alone. In some embodiments, the subject is intolerant, non-responsive, or poorly responsive to treatment with a splicing modulator when administered alone.

In some embodiments, the target antigen is FOLH1. In some embodiments, the one or more neoplastic cells are derived from a FOLH1-expressing prostate cancer. In some embodiments, the subject is non-responsive or poorly responsive to treatment with (a) an anti-FOLH1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CDH6. In some embodiments, the one or more neoplastic cells are derived from a CDH6-expressing kidney cancer. In some embodiments, the subject is non-responsive or poorly responsive to treatment with (a) an anti-CDH6 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CEACAM5. In some embodiments, the one or more neoplastic cells are derived from a CEACAM5-expressing colorectal cancer. In some embodiments, the subject is non-responsive or poorly responsive to treatment with (a) an anti-CEACAM5 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CFC1B. In some embodiments, the one or more neoplastic cells are derived from a CFC1B-expressing pancreatic cancer. In some embodiments, the subject is non-responsive or poorly responsive to treatment with (a) an anti-CFC1B antibody when administered alone and/or (b) a splicing modulator when administered alone. In some embodiments, the subject is intolerant, non-responsive, or poorly responsive to treatment with a splicing modulator when administered alone.

In some embodiments, the target antigen is ENPP3. In some embodiments, the one or more neoplastic cells are derived from an ENPP3-expressing kidney cancer. In some embodiments, the subject is non-responsive or poorly responsive to treatment with (a) an anti-ENPP3 antibody when administered alone and/or (b) a splicing modulator when administered alone. In some embodiments, the subject is intolerant, non-responsive, or poorly responsive to treatment with a splicing modulator when administered alone.

In some embodiments, the target antigen is FOLR1. In some embodiments, the one or more neoplastic cells are derived from a FOLR1-expressing ovarian cancer. In some embodiments, the subject is non-responsive or poorly responsive to treatment with (a) an anti-FOLR1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is HAVCR1. In some embodiments, the one or more neoplastic cells are derived from a HAVCR1-expressing kidney cancer or esophageal cancer. In some embodiments, the subject is non-responsive or poorly responsive to treatment with (a) an anti-HAVCR1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is KIT. In some embodiments, the one or more neoplastic cells are derived from a KIT-expressing kidney cancer. In some embodiments, the subject is non-responsive or poorly responsive to treatment with (a) an anti-KIT antibody when administered alone and/or (b) a splicing modulator when administered alone. In some embodiments, the subject is intolerant, non-responsive, or poorly responsive to treatment with a splicing modulator when administered alone.

In some embodiments, the target antigen is MET. In some embodiments, the one or more neoplastic cells are derived from a MET-expressing kidney cancer or esophageal cancer. In some embodiments, the subject is non-responsive or poorly responsive to treatment with (a) an anti-MET antibody when administered alone and/or (b) a splicing modulator when administered alone. In some embodiments, the subject is intolerant, non-responsive, or poorly responsive to treatment with a splicing modulator when administered alone.

In some embodiments, the target antigen is MUC16. In some embodiments, the one or more neoplastic cells are derived from a MUC16-expressing ovarian cancer, cervical cancer, or breast cancer. In some embodiments, the subject is non-responsive or poorly responsive to treatment with (a) an anti-MUC16 antibody when administered alone and/or (b) a splicing modulator when administered alone. In some embodiments, the subject is intolerant, non-responsive, or poorly responsive to treatment with a splicing modulator when administered alone.

In some embodiments, the target antigen is SLC39A6. In some embodiments, the one or more neoplastic cells are derived from a SLC39A6-expressing breast cancer or prostate cancer. In some embodiments, the subject is non-responsive or poorly responsive to treatment with (a) an anti-SLC39A6 antibody when administered alone and/or (b) a splicing modulator when administered alone. In some embodiments, the subject is intolerant, non-responsive, or poorly responsive to treatment with a splicing modulator when administered alone.

In some embodiments, the target antigen is SLC44A4. In some embodiments, the one or more neoplastic cells are derived from a SLC44A4-expressing prostate cancer. In some embodiments, the subject is non-responsive or poorly responsive to treatment with (a) an anti-SLC44A4 antibody when administered alone and/or (b) a splicing modulator when administered alone. In some embodiments, the subject is intolerant, non-responsive, or poorly responsive to treatment with a splicing modulator when administered alone.

In some embodiments, the target antigen is STEAP1. In some embodiments, the one or more neoplastic cells are derived from a STEAP1-expressing prostate cancer. In some embodiments, the subject is non-responsive or poorly responsive to treatment with (a) an anti-STEAP1 antibody when administered alone and/or (b) a splicing modulator when administered alone. In some embodiments, the subject is intolerant, non-responsive, or poorly responsive to treatment with a splicing modulator when administered alone.

In certain other aspects, the present disclosure provides methods of reducing or inhibiting growth of a tumor in a subject having or suspected of having a neoplastic disorder by administering to the subject a therapeutically effective amount and/or regimen of any one of the described ADCs or compositions.

In some embodiments, treatment with the antibody-drug conjugate or composition induces bystander killing of neoplastic tumor cells which do not express a target antigen but are adjacent to neoplastic tumor cells which express a target antigen. In some embodiments, the tumor comprises one or more neoplastic cells which express a target antigen.

In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In some embodiments, the tumor is resistant or refractory to treatment with (a) an anti-HER2 antibody when administered alone and/or (b) a splicing modulator when administered alone.

In some embodiments, the target antigen is CD138. In some embodiments, the one or more neoplastic cells are derived from a CD138-expressing multiple myeloma. In some embodiments, the tumor is resistant or refractory to treatment with (a) an anti-CD138 antibody when administered alone and/or (b) a splicing modulator when administered alone.

In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the tumor is resistant or refractory to treatment with (a) an anti-EPHA2 antibody when administered alone and/or (b) a splicing modulator when administered alone.

In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the tumor is resistant or refractory to treatment with (a) an anti-MSLN antibody when administered alone and/or (b) a splicing modulator when administered alone.

In some embodiments, the target antigen is FOLH1. In some embodiments, the one or more neoplastic cells are derived from a FOLH1-expressing prostate cancer. In some embodiments, the tumor is resistant or refractory to treatment with (a) an anti-FOLH1 antibody when administered alone and/or (b) a splicing modulator when administered alone.

In some embodiments, the target antigen is CDH6. In some embodiments, the one or more neoplastic cells are derived from a CDH6-expressing kidney cancer. In some embodiments, the tumor is resistant or refractory to treatment with (a) an anti-CDH6 antibody when administered alone and/or (b) a splicing modulator when administered alone.

In some embodiments, the target antigen is CEACAM5. In some embodiments, the one or more neoplastic cells are derived from a CEACAM5-expressing colorectal cancer. In some embodiments, the tumor is resistant or refractory to treatment with (a) an anti-CEACAM5 antibody when administered alone and/or (b) a splicing modulator when administered alone.

In some embodiments, the target antigen is CFC1B. In some embodiments, the one or more neoplastic cells are derived from a CFC1B-expressing pancreatic cancer. In some embodiments, the tumor is resistant or refractory to treatment with (a) an anti-CFC1B antibody when administered alone and/or (b) a splicing modulator when administered alone.

In some embodiments, the target antigen is ENPP3. In some embodiments, the one or more neoplastic cells are derived from an ENPP3-expressing kidney cancer. In some embodiments, the tumor is resistant or refractory to treatment with (a) an anti-ENPP3 antibody when administered alone and/or (b) a splicing modulator when administered alone.

In some embodiments, the target antigen is FOLR1. In some embodiments, the one or more neoplastic cells are derived from a FOLR1-expressing ovarian cancer. In some embodiments, the tumor is resistant or refractory to treatment with (a) an anti-FOLR1 antibody when administered alone and/or (b) a splicing modulator when administered alone.

In some embodiments, the target antigen is HAVCR1. In some embodiments, the one or more neoplastic cells are derived from a HAVCR1-expressing kidney cancer or esophageal cancer. In some embodiments, the tumor is resistant or refractory to treatment with (a) an anti-HAVCR1 antibody when administered alone and/or (b) a splicing modulator when administered alone.

In some embodiments, the target antigen is KIT. In some embodiments, the one or more neoplastic cells are derived from a KIT-expressing kidney cancer. In some embodiments, the tumor is resistant or refractory to treatment with (a) an anti-KIT antibody when administered alone and/or (b) a splicing modulator when administered alone.

In some embodiments, the target antigen is MET. In some embodiments, the one or more neoplastic cells are derived from a MET-expressing kidney cancer or esophageal cancer. In some embodiments, the tumor is resistant or refractory to treatment with (a) an anti-MET antibody when administered alone and/or (b) a splicing modulator when administered alone.

In some embodiments, the target antigen is MUC16. In some embodiments, the one or more neoplastic cells are derived from a MUC16-expressing ovarian cancer, cervical cancer, or breast cancer. In some embodiments, the tumor is resistant or refractory to treatment with (a) an anti-MUC16 antibody when administered alone and/or (b) a splicing modulator when administered alone.

In some embodiments, the target antigen is SLC39A6. In some embodiments, the one or more neoplastic cells are derived from a SLC39A6-expressing breast cancer or prostate cancer. In some embodiments, the tumor is resistant or refractory to treatment with (a) an anti-SLC39A6 antibody when administered alone and/or (b) a splicing modulator when administered alone.

In some embodiments, the target antigen is SLC44A4. In some embodiments, the one or more neoplastic cells are derived from a SLC44A4-expressing prostate cancer. In some embodiments, the tumor is resistant or refractory to treatment with (a) an anti-SLC44A4 antibody when administered alone and/or (b) a splicing modulator when administered alone.

In some embodiments, the target antigen is STEAP1. In some embodiments, the one or more neoplastic cells are derived from a STEAP1-expressing prostate cancer. In some embodiments, the tumor is resistant or refractory to treatment with (a) an anti-STEAP1 antibody when administered alone and/or (b) a splicing modulator when administered alone.

In still other aspects, the present disclosure provides methods of determining whether a subject having or suspected of having a neoplastic disorder will be responsive to treatment with any one of the described ADCs or compositions by providing a biological sample from the subject and contacting the biological sample with the ADC or composition. In some embodiments, the biological sample is a tumor sample. In some embodiments, the tumor sample is a tumor biopsy or blood sample. In some embodiments, the blood sample is selected from blood, a blood fraction, or a cell obtained from the blood or blood fraction. In some embodiments, the subject has one or more neoplastic cells which express a target antigen. In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In some embodiments, the target antigen is CD138. In some embodiments, the one or more neoplastic cells are derived from a CD138-expressing multiple myeloma. In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the target antigen is FOLH1. In some embodiments, the one or more neoplastic cells are derived from a FOLH1-expressing prostate cancer. In some embodiments, the target antigen is CDH6. In some embodiments, the one or more neoplastic cells are derived from a CDH6-expressing kidney cancer. In some embodiments, the target antigen is CEACAM5. In some embodiments, the one or more neoplastic cells are derived from a CEACAM5-expressing colorectal cancer. In some embodiments, the target antigen is CFC1B. In some embodiments, the one or more neoplastic cells are derived from a CFC1B-expressing pancreatic cancer. In some embodiments, the target antigen is ENPP3. In some embodiments, the one or more neoplastic cells are derived from an ENPP3-expressing kidney cancer. In some embodiments, the target antigen is FOLR1. In some embodiments, the one or more neoplastic cells are derived from a FOLR1-expressing ovarian cancer. In some embodiments, the target antigen is HAVCR1. In some embodiments, the one or more neoplastic cells are derived from a HAVCR1-expressing kidney cancer or esophageal cancer. In some embodiments, the target antigen is KIT. In some embodiments, the one or more neoplastic cells are derived from a KIT-expressing kidney cancer. In some embodiments, the target antigen is MET. In some embodiments, the one or more neoplastic cells are derived from a MET-expressing kidney cancer or esophageal cancer. In some embodiments, the target antigen is MUC16. In some embodiments, the one or more neoplastic cells are derived from a MUC16-expressing ovarian cancer, cervical cancer, or breast cancer. In some embodiments, the target antigen is SLC39A6. In some embodiments, the one or more neoplastic cells are derived from a SLC39A6-expressing breast cancer or prostate cancer. In some embodiments, the target antigen is SLC44A4. In some embodiments, the one or more neoplastic cells are derived from a SLC44A4-expressing prostate cancer. In some embodiments, the target antigen is STEAP1. In some embodiments, the one or more neoplastic cells are derived from a STEAP1-expressing prostate cancer.

Further provided herein, in various embodiments, are pharmaceutical compositions comprising an ADC and a pharmaceutically acceptable diluent, carrier, and/or excipient. Methods of producing the described ADC compounds and compositions are also disclosed.

BRIEF DESCRIPTION OF THE DRAWINGS

FIG. 17A shows ELISpot plates indicating Neoantigen 1 priming of CD8+ T-cell activation. Stimulation of CD8+ T-cells was monitored by secretion of IFNγ. FIG. 17B shows quantification of IFNγ spots (spot number) in Neoantigen 1 ELISpot plates (FIG. 17A). FIG. 17C shows ELISpot plates indicating Neoantigen 3 priming of CD8+ T-cell activation. Stimulation of CD8+ T-cells was monitored by secretion of IFNγ. FIG. 17D shows quantification of IFNγ spots (fold change) in Neoantigen 3 ELISpot plates (FIG. 17C).

DETAILED DESCRIPTION OF ILLUSTRATIVE EMBODIMENTS

Figure 1:
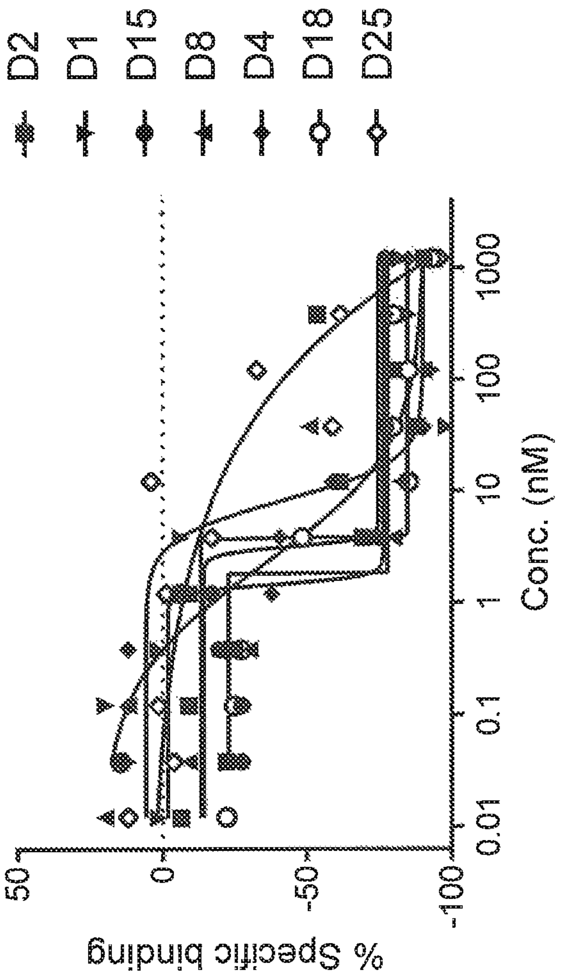
FIG. 1 shows dose response of exemplary payload compounds in a competitive binding assay. Nuclear extracts from 293F cells overexpressing wild type flag-tagged SF3B1 were immunoprecipitated with an anti-SF3B1 antibody and scintillation proximity assay (SPA) bead cocktail. Binding reactions contained the antibody-bead mixture and increasing concentrations of compound, followed by competition with an $^3H$-labelled pladienolide B (PB) probe. The y-axis represents the percent change (% response) of specific binding relative to the DMSO control (0%). Data are represented as mean±standard deviation (SD).

The disclosed compositions and methods may be understood more readily by reference to the following detailed description taken in connection with the accompanying figures, which form a part of this disclosure.

Throughout this text, the descriptions refer to compositions and methods of using the compositions. Where the disclosure describes or claims a feature or embodiment associated with a composition, such a feature or embodiment is equally applicable to the methods of using the composition. Likewise, where the disclosure describes or claims a feature or embodiment associated with a method of using a composition, such a feature or embodiment is equally applicable to the composition.

When a range of values is expressed, it includes embodiments using any particular value within the range. Further, reference to values stated in ranges includes each and every value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise. All references cited herein are incorporated by reference for any purpose. Where a reference and the specification conflict, the specification will control.

It is to be appreciated that certain features of the disclosed compositions and methods, which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly dictates otherwise.

The terms "about" or "approximately" in the context of numerical values and ranges refers to values or ranges that approximate or are close to the recited values or ranges such that the embodiment may perform as intended, such as having a desired amount of nucleic acids or polypeptides in a reaction mixture, as is apparent to the skilled person from the teachings contained herein. In some embodiments, about means plus or minus 10% of a numerical amount.

The terms "antibody-drug conjugate," "antibody conjugate," "conjugate," "immunoconjugate," and "ADC" are used interchangeably, and refer to one or more therapeutic compounds (e.g., a splicing modulator) that is linked to one or more antibodies or antigen binding fragments and is defined by the generic formula: $Ab-(L-D)_p$ (Formula I), wherein Ab= an antibody or antigen binding fragment, L=a linker moiety, D=a drug moiety (e.g., a splicing modulator drug moiety), and p=the number of drug moieties per antibody or antigen binding fragment. An ADC comprising a splicing modulator drug moiety may also be referred to herein more specifically as a "splicing modulator-loaded antibody" or a "SMLA." In ADCs comprising a splicing modulator drug moiety, "p" refers to the number of splicing modulator compounds linked to the antibody or antigen binding fragment. In some embodiments, the linker L can include a cleavable moiety between the antibody or antigen binding fragment and the therapeutic compound. In some embodiments, the linker L can include a cleavable moiety that can be attached to either or both the antibody or antigen binding fragment and therapeutic compound by spacer unit(s). In some embodiments, when a spacer unit attaches the cleavable moiety to the therapeutic compound, it is a self-immolative spacer unit. In other embodiments, the linker L does not include a cleavable moiety, and is a non-cleavable linker. In some embodiments, the linker L can include at least one spacer unit that can directly attach to the antibody or antigen binding fragment and to the therapeutic compound. Exemplary cleavable and non-cleavable linkers are described and exemplified herein.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain ($V_H$) and a heavy chain constant region ($C_H$). The light chain is composed of a light chain variable domain ($V_L$) and a light chain constant domain ($C_L$). For the purposes of this application, the mature heavy chain and light chain variable domains each comprise three complementarity determining regions (CDR1, CDR2 and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', $F(ab')_2$, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity (e.g., binds the target antigen, internalizes within a target-antigen expressing cell).

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see, e.g., U.S. Pat. No. 4,816,567). Monoclonal antibodies may also be isolated from phage antibody libraries using the techniques described in Clackson et al. (1991) Nature 352:624-8, and Marks et al. (1991) J Mol Biol. 222:581-97, for example.

The monoclonal antibodies described herein specifically include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity.

The term "human antibody," as used herein, refers an antibody produced by a human or an antibody having an amino acid sequence of an antibody produced by a human.

The term "chimeric antibody," as used herein, refers to antibodies wherein the amino acid sequence of the immunoglobulin molecule is derived from two or more species. In some instances, the variable regions of both heavy and light chains correspond to the variable regions of antibodies derived from one species with the desired specificity, affinity, and activity while the constant regions are homologous to antibodies derived from another species (e.g., human) to minimize an immune response in the latter species.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin. The humanized antibody can be further modified by the substitution of residues, either in the Fv framework region and/or within the replaced non-human residues to refine and optimize antibody specificity, affinity, and/or activity.

The term "antigen binding fragment" or "antigen binding portion" of an antibody, as used herein, refers to one or more fragments of an antibody or protein that retain the ability to specifically bind to an antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). Antigen binding fragments may also retain the ability to internalize into an antigen-expressing cell. In some embodiments, antigen binding fragments also retain immune effector activity. It has been shown that fragments of a full-length antibody can perform the antigen binding function of a full-length antibody. Examples of binding fragments encompassed within the term "antigen binding fragment" or "antigen binding portion" of an antibody include (i) a Fab fragment, a monovalent fragment consisting of the $V_L$, $V_H$, $C_L$, and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment, which comprises a single variable domain, e.g., a $V_H$ domain (see, e.g., Ward et al. (1989) Nature 341:544-6; and Intl. Pub. No. WO 1990/005144); and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). See, e.g., Bird et al. (1988) Science 242:423-6; and Huston et al. (1988) Proc Natl Acad Sci. USA 85:5879-83. Such single chain antibodies are also intended to be encompassed within the term "antigen binding fragment" or "antigen binding portion" of an antibody, and are known in the art as an exemplary type of binding fragment that can internalize into cells upon binding (see, e.g., Zhu et al. (2010) 9:2131-41; He et al. (2010) J Nucl Med. 51:427-32; and Fitting et al. (2015) MAbs 7:390-402). In certain embodiments, scFv molecules may be incorporated into a fusion protein. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc Natl Acad Sci. USA 90:6444-8; and Poljak et al. (1994) Structure 2:1121-3).

Antigen binding fragments are obtained using conventional techniques known to those of skill in the art, and the binding fragments are screened for utility (e.g., binding affinity, internalization) in the same manner as are intact antibodies. Antigen binding fragments may be prepared by cleavage of the intact protein, e.g., by protease or chemical cleavage.

"Internalizing" as used herein in reference to an antibody or antigen binding fragment refers to an antibody or antigen binding fragment that is capable of being taken through the cell's lipid bilayer membrane to an internal compartment (i.e., "internalized") upon binding to the cell, preferably into a degradative compartment in the cell. For example, an internalizing anti-HER2 antibody is one that is capable of being taken into the cell after binding to HER2 on the cell membrane. In some embodiments, the antibody or antigen binding fragment used in the ADCs disclosed herein targets a cell surface antigen (e.g., HER2) and is an internalizing antibody or internalizing antigen binding fragment (i.e., the ADC transfers through the cellular membrane after antigen binding). In some embodiments, the internalizing antibody or antigen binding fragment binds a receptor on the cell surface. An internalizing antibody or internalizing antigen binding fragment that targets a receptor on the cell membrane may induce receptor-mediated endocytosis. In some embodiments, the internalizing antibody or internalizing antigen binding fragment is taken into the cell via receptor-mediated endocytosis.

"Non-internalizing" as used herein in reference to an antibody or antigen binding fragment refers to an antibody or antigen binding fragment that remains at the cell surface upon binding to the cell. In some embodiments, the antibody or antigen binding fragment used in the ADCs disclosed herein targets a cell surface antigen and is a non-internalizing antibody or non-internalizing antigen binding fragment (i.e., the ADC remains at the cell surface and does not transfer through the cellular membrane after antigen binding). In some embodiments, the non-internalizing antibody or antigen binding fragment binds a non-internalizing receptor or other cell surface antigen. Exemplary non-internalizing cell surface antigens include but are not limited to CA125 and CEA, and antibodies that bind to non-internalizing antigen targets are also known in the art (see, e.g., Bast et al. (1981) J Clin Invest. 68(5):1331-7; Scholler and Urban (2007) Biomark Med. 1(4):513-23; and Boudousq et al. (2013) PLoS One 8(7):e69613).

The term "human epidermal growth factor receptor 2," "HER2," or "HER2/NEU," as used herein, refers to any native form of human HER2. The term encompasses full-length HER2 (e.g., UniProt Reference Sequence: P04626; SEQ ID NO:31), as well as any form of human HER2 that may result from cellular processing. The term also encompasses functional variants or fragments of human HER2, including but not limited to splice variants, allelic variants, and isoforms that retain one or more biologic functions of human HER2 (i.e., variants and fragments are encompassed unless the context indicates that the term is used to refer to the wild-type protein only). HER2 can be isolated from human, or may be produced recombinantly or by synthetic methods.

The term "anti-HER2 antibody" or "antibody that binds to HER2" refers to any form of antibody or fragment thereof that binds, e.g., specifically binds, to HER2, and encompasses monoclonal antibodies (including full-length monoclonal antibodies), polyclonal antibodies, and biologically functional antibody fragments so long as they bind, e.g., specifically bind, to HER2. U.S. Pat. No. 5,821,337 provides and is incorporated herein by reference for exemplary HER2-binding sequences, including exemplary anti-HER2 antibody sequences. In some embodiments, the anti-HER2 antibody used in the ADCs disclosed herein is an internalizing antibody or internalizing antibody fragment. Trastuzumab (U.S. Pat. No. 5,821,337; Molina et al. (2001) Cancer Res. 61(12):4744-9) is an exemplary anti-human HER2 antibody.

The term "syndecan-1," "SDC1," or "CD138," as used herein, refers to any native form of human CD138. The term encompasses full-length CD138 (e.g., UniProt Reference Sequence: P18827; SEQ ID NO:32), as well as any form of human CD138 that may result from cellular processing. The term also encompasses functional variants or fragments of human CD138, including but not limited to splice variants, allelic variants, and isoforms that retain one or more biologic functions of human CD138 (i.e., variants and fragments are encompassed unless the context indicates that the term is used to refer to the wild-type protein only). CD138 can be isolated from a human, or may be produced recombinantly or by synthetic methods.

The term "anti-CD138 antibody" or "antibody that binds to CD138" refers to any form of antibody or fragment thereof that binds, e.g., specifically binds, to CD138, and encompasses monoclonal antibodies (including full-length monoclonal antibodies), polyclonal antibodies, and biologically functional antibody fragments so long as they bind, e.g., specifically bind, to CD138. In some embodiments, the anti-CD138 antibody used in the ADCs disclosed herein is an internalizing antibody or internalizing antibody fragment. B-B4 (Tassone et al. (2004) Blood 104:3688-96) is an exemplary anti-human CD138 antibody.

The term "ephrin type-A receptor 2" or "EPHA2," as used herein, refers to any native form of human EPHA2. The term encompasses full-length EPHA2 (e.g., UniProt Reference Sequence: P29317; SEQ ID NO:33), as well as any form of human EPHA2 that may result from cellular processing. The term also encompasses functional variants or fragments of human EPHA2, including but not limited to splice variants, allelic variants, and isoforms that retain one or more biologic functions of human EPHA2 (i.e., variants and fragments are encompassed unless the context indicates that the term is used to refer to the wild-type protein only). EPHA2 can be isolated from a human, or may be produced recombinantly or by synthetic methods.

The term "anti-EPHA2 antibody" or "antibody that binds to EPHA2" refers to any form of antibody or fragment thereof that binds, e.g., specifically binds, to EPHA2, and encompasses monoclonal antibodies (including full-length monoclonal antibodies), polyclonal antibodies, and biologically functional antibody fragments so long as they bind, e.g., specifically bind, to EPHA2. WO 2007/030642 provides and is incorporated herein by reference for exemplary EPHA2-binding sequences, including exemplary anti-EPHA2 antibody sequences. In some embodiments, the anti-EPHA2 antibody used in the ADCs disclosed herein is an internalizing antibody or internalizing antibody fragment. 1C1 (WO 2007/030642; Jackson et al. (2008) Cancer Res. 68(22): 9367-74) is an exemplary anti-human EPHA2 antibody.

The term "mesothelin" or "MSLN," as used herein, refers to any native form of human MSLN. The term encompasses full-length MSLN (e.g., UniProt Reference Sequence: Q13421; SEQ ID NO:43), as well as any form of human MSLN that may result from cellular processing. The term also encompasses functional variants or fragments of human MSLN, including but not limited to splice variants, allelic variants, and isoforms that retain one or more biologic functions of human MSLN (i.e., variants and fragments are encompassed unless the context indicates that the term is used to refer to the wild-type protein only). MSLN can be isolated from a human, or may be produced recombinantly or by synthetic methods.

The term "anti-MSLN antibody" or "antibody that binds to MSLN" refers to any form of antibody or fragment thereof that binds, e.g., specifically binds, to MSLN, and encompasses monoclonal antibodies (including full-length monoclonal antibodies), polyclonal antibodies, and biologically functional antibody fragments so long as they bind, e.g., specifically bind, to MSLN. WO 2011/074621 provides and is incorporated herein by reference for exemplary MSLN-binding sequences, including exemplary anti-MSLN antibody sequences. In some embodiments, the anti-MSLN antibody used in the ADCs disclosed herein is an internalizing antibody or internalizing antibody fragment. 11-25, IC14-30, IC7-4, IC17-35 and 2-9 are exemplary anti-human MSLN antibodies.

The term "glutamate carboxypeptidase 2" or "FOLH1," as used herein, refers to any native form of human FOLH1. The term encompasses full-length FOLH1 (e.g., UniProt Reference Sequence: Q04609; SEQ ID NO:44), as well as any form of human FOLH1 that may result from cellular processing. The term also encompasses functional variants or fragments of human FOLH1, including but not limited to splice variants, allelic variants, and isoforms that retain one or more biologic functions of human FOLH1 (i.e., variants and fragments are encompassed unless the context indicates that the term is used to refer to the wild-type protein only). FOLH1 can be isolated from a human, or may be produced recombinantly or by synthetic methods.

The term "anti-FOLH1 antibody" or "antibody that binds to FOLH1" refers to any form of antibody or fragment thereof that binds, e.g., specifically binds, to FOLH1, and encompasses monoclonal antibodies (including full-length monoclonal antibodies), polyclonal antibodies, and biologically functional antibody fragments so long as they bind, e.g., specifically bind, to FOLH1. WO 2019/012260 and WO 2017/212250 provide and are incorporated herein by reference for exemplary FOLH1-binding sequences, including exemplary anti-FOLH1 antibody sequences. In some embodiments, the anti-FOLH1 antibody used in the ADCs disclosed herein is an internalizing antibody or internalizing antibody fragment. J591 (deimmunized) is an exemplary anti-human FOLH1 antibody.

The term "cadherin-6" or "CDH6," as used herein, refers to any native form of human CDH6. The term encompasses full-length CDH6 (e.g., UniProt Reference Sequence: P55285; SEQ ID NO:45), as well as any form of human CDH6 that may result from cellular processing. The term also encompasses functional variants or fragments of human CDH6, including but not limited to splice variants, allelic variants, and isoforms that retain one or more biologic functions of human CDH6 (i.e., variants and fragments are encompassed unless the context indicates that the term is used to refer to the wild-type protein only). CDH6 can be isolated from a human, or may be produced recombinantly or by synthetic methods.

The term "anti-CDH6 antibody" or "antibody that binds to CDH6" refers to any form of antibody or fragment thereof that binds, e.g., specifically binds, to CDH6, and encompasses monoclonal antibodies (including full-length monoclonal antibodies), polyclonal antibodies, and biologically functional antibody fragments so long as they bind, e.g., specifically bind, to CDH6. WO 2018/185618 provides and is incorporated herein by reference for exemplary CDH6-binding sequences, including exemplary anti-CDH6 antibody sequences. In some embodiments, the anti-CDH6 antibody used in the ADCs disclosed herein is an internalizing antibody or internalizing antibody fragment.

The term "carcinoembryonic antigen-related cell adhesion molecule 5" or "CEACAM5," as used herein, refers to any native form of human CEACAM5. The term encompasses full-length CEACAM5 (e.g., UniProt Reference Sequence: P06731; SEQ ID NO:46), as well as any form of human CEACAM5 that may result from cellular processing. The term also encompasses functional variants or fragments of human CEACAM5, including but not limited to splice variants, allelic variants, and isoforms that retain one or more biologic functions of human CEACAM5 (i.e., variants and fragments are encompassed unless the context indicates that the term is used to refer to the wild-type protein only). CEACAM5 can be isolated from a human, or may be produced recombinantly or by synthetic methods.

The term "anti-CEACAM5 antibody" or "antibody that binds to CEACAM5" refers to any form of antibody or fragment thereof that binds, e.g., specifically binds, to CEACAM5, and encompasses monoclonal antibodies (including full-length monoclonal antibodies), polyclonal antibodies, and biologically functional antibody fragments so long as they bind, e.g., specifically bind, to CEACAM5. US 2015/0125386 provides and is incorporated herein by reference for exemplary CEACAM5-binding sequences, including exemplary anti-CEACAM5 antibody sequences. In some embodiments, the anti-CEACAM5 antibody used in the ADCs disclosed herein is an internalizing antibody or internalizing antibody fragment. hMN14 is an exemplary anti-human CEACAM5 antibody.

The term "cryptic family protein 1B" or "CFC1B," as used herein, refers to any native form of human CFC1B. The term encompasses full-length CFC1B (e.g., UniProt Reference Sequence: POCG36; SEQ ID NO:47), as well as any form of human CFC1B that may result from cellular processing. The term also encompasses functional variants or fragments of human CFC1B, including but not limited to splice variants, allelic variants, and isoforms that retain one or more biologic functions of human CFC1B (i.e., variants and fragments are encompassed unless the context indicates that the term is used to refer to the wild-type protein only). CFC1B can be isolated from a human, or may be produced recombinantly or by synthetic methods.

The term "anti-CFC1B antibody" or "antibody that binds to CFC1B" refers to any form of antibody or fragment thereof that binds, e.g., specifically binds, to CFC1B, and encompasses monoclonal antibodies (including full-length monoclonal antibodies), polyclonal antibodies, and biologically functional antibody fragments so long as they bind, e.g., specifically bind, to CFC1B. WO 2002/088170 provides and is incorporated herein by reference for exemplary CFC1B-binding sequences, including exemplary anti-CFC1B antibody sequences. In some embodiments, the anti-CFC1B antibody used in the ADCs disclosed herein is an internalizing antibody or internalizing antibody fragment.

The term "ectonucleotide pyrophosphatase/phosphodiesterase family member 3" or "ENPP3," as used herein, refers to any native form of human ENPP3. The term encompasses full-length ENPP3 (e.g., UniProt Reference Sequence: 014638; SEQ ID NO:48), as well as any form of human ENPP3 that may result from cellular processing. The term also encompasses functional variants or fragments of human ENPP3, including but not limited to splice variants, allelic variants, and isoforms that retain one or more biologic functions of human ENPP3 (i.e., variants and fragments are encompassed unless the context indicates that the term is used to refer to the wild-type protein only). ENPP3 can be isolated from a human, or may be produced recombinantly or by synthetic methods.

The term "anti-ENPP3 antibody" or "antibody that binds to ENPP3" refers to any form of antibody or fragment thereof that binds, e.g., specifically binds, to ENPP3, and encompasses monoclonal antibodies (including full-length monoclonal antibodies), polyclonal antibodies, and biologically functional antibody fragments so long as they bind, e.g., specifically bind, to ENPP3. Donate et al. ((2016) Clin Cancer Res. 22(8):1989-99) provides and is incorporated herein by reference for exemplary ENPP3-binding sequences, including exemplary anti-ENPP3 antibody sequences. In some embodiments, the anti-ENPP3 antibody used in the ADCs disclosed herein is an internalizing antibody or internalizing antibody fragment.

The term "folate receptor alpha" or "FOLR1," as used herein, refers to any native form of human FOLR1. The term encompasses full-length FOLR1 (e.g., UniProt Reference Sequence: P15328; SEQ ID NO:49), as well as any form of human FOLR1 that may result from cellular processing. The term also encompasses functional variants or fragments of human FOLR1, including but not limited to splice variants, allelic variants, and isoforms that retain one or more biologic functions of human FOLR1 (i.e., variants and fragments are encompassed unless the context indicates that the term is used to refer to the wild-type protein only). FOLR1 can be isolated from a human, or may be produced recombinantly or by synthetic methods.

The term "anti-FOLR1 antibody" or "antibody that binds to FOLR1" refers to any form of antibody or fragment thereof that binds, e.g., specifically binds, to FOLR1, and encompasses monoclonal antibodies (including full-length monoclonal antibodies), polyclonal antibodies, and biologically functional antibody fragments so long as they bind, e.g., specifically bind, to FOLR1. WO 2005/080431 and Coney et al. ((1991) Cancer Res. 51(22):6125-32) provide and are incorporated herein by reference for exemplary FOLR1-binding sequences, including exemplary anti-FOLR1 antibody sequences. In some embodiments, the anti-FOLR1 antibody used in the ADCs disclosed herein is an internalizing antibody or internalizing antibody fragment. Farletuzumab and MOv19 are exemplary anti-human FOLR1 antibodies.

The term "hepatitis A virus cellular receptor 1" or "HAVCR1," as used herein, refers to any native form of human HAVCR1. The term encompasses full-length HAVCR1 (e.g., UniProt Reference Sequence: Q96D42; SEQ ID NO:50), as well as any form of human HAVCR1 that may result from cellular processing. The term also encompasses functional variants or fragments of human HAVCR1, including but not limited to splice variants, allelic variants, and isoforms that retain one or more biologic functions of human HAVCR1 (i.e., variants and fragments are encompassed unless the context indicates that the term is used to refer to the wild-type protein only). HAVCR1 can be isolated from a human, or may be produced recombinantly or by synthetic methods.

The term "anti-HAVCR1 antibody" or "antibody that binds to HAVCR1" refers to any form of antibody or fragment thereof that binds, e.g., specifically binds, to HAVCR1, and encompasses monoclonal antibodies (including full-length monoclonal antibodies), polyclonal antibodies, and biologically functional antibody fragments so long as they bind, e.g., specifically bind, to HAVCR1. Thomas et al. ((2016) Mol Cancer Ther. 15(12):2946-54) provides and is incorporated herein by reference for exemplary HAVCR1-binding sequences, including exemplary anti-HAVCR1 antibody sequences. In some embodiments, the anti-HAVCR1 antibody used in the ADCs disclosed herein is an internalizing antibody or internalizing antibody fragment.

The term "mast/stem cell growth factor receptor Kit" or "KIT," as used herein, refers to any native form of human KIT. The term encompasses full-length KIT (e.g., UniProt Reference Sequence: P10721; SEQ ID NO:51), as well as any form of human KIT that may result from cellular processing. The term also encompasses functional variants or fragments of human KIT, including but not limited to splice variants, allelic variants, and isoforms that retain one or more biologic functions of human KIT (i.e., variants and fragments are encompassed unless the context indicates that the term is used to refer to the wild-type protein only). KIT can be isolated from a human, or may be produced recombinantly or by synthetic methods.

The term "anti-KIT antibody" or "antibody that binds to KIT" refers to any form of antibody or fragment thereof that binds, e.g., specifically binds, to KIT, and encompasses monoclonal antibodies (including full-length monoclonal antibodies), polyclonal antibodies, and biologically functional antibody fragments so long as they bind, e.g., specifically bind, to KIT. Shi et al. ((2016) Proc Natl Acad Sci USA 113(33):E4784-93) and Abrams et al. ((2018) Clin Cancer Res. 24(17):4297-308) provide and are incorporated herein by reference for exemplary KIT-binding sequences, including exemplary anti-KIT antibody sequences. In some embodiments, the anti-KIT antibody used in the ADCs disclosed herein is an internalizing antibody or internalizing antibody fragment.

The term "hepatocyte growth factor receptor" or "MET," as used herein, refers to any native form of human MET. The term encompasses full-length MET (e.g., UniProt Reference Sequence: P08581; SEQ ID NO:52), as well as any form of human MET that may result from cellular processing. The term also encompasses functional variants or fragments of human MET, including but not limited to splice variants, allelic variants, and isoforms that retain one or more biologic functions of human MET (i.e., variants and fragments are encompassed unless the context indicates that the term is used to refer to the wild-type protein only). MET can be isolated from a human, or may be produced recombinantly or by synthetic methods.

The term "anti-MET antibody" or "antibody that binds to MET" refers to any form of antibody or fragment thereof that binds, e.g., specifically binds, to MET, and encompasses monoclonal antibodies (including full-length monoclonal antibodies), polyclonal antibodies, and biologically functional antibody fragments so long as they bind, e.g., specifically bind, to MET. Yang et al. ((2019) Acta Pharmacol Sin.) provides and is incorporated herein by reference for exemplary MET-binding sequences, including exemplary anti-MET antibody sequences. In some embodiments, the anti-MET antibody used in the ADCs disclosed herein is an internalizing antibody or internalizing antibody fragment.

The term "mucin-16" or "MUC16," as used herein, refers to any native form of human MUC16. The term encompasses full-length MUC16 (e.g., UniProt Reference Sequence: Q8WXI7; SEQ ID NO:53), as well as any form of human MUC16 that may result from cellular processing. The term also encompasses functional variants or fragments of human MUC16, including but not limited to splice variants, allelic variants, and isoforms that retain one or more biologic functions of human MUC16 (i.e., variants and fragments are encompassed unless the context indicates that the term is used to refer to the wild-type protein only). MUC16 can be isolated from a human, or may be produced recombinantly or by synthetic methods.

The term “anti-MUC16 antibody” or “antibody that binds to MUC16” refers to any form of antibody or fragment thereof that binds, e.g., specifically binds, to MUC16, and encompasses monoclonal antibodies (including full-length monoclonal antibodies), polyclonal antibodies, and biologically functional antibody fragments so long as they bind, e.g., specifically bind, to MUC16. Liu et al. ((2016) Ann Oncol. 27(11):2124-30) provides and is incorporated herein by reference for exemplary MUC16-binding sequences, including exemplary anti-MUC16 antibody sequences. In some embodiments, the anti-MUC16 antibody used in the ADCs disclosed herein is an internalizing antibody or internalizing antibody fragment.

The term “zinc transporter ZIP6” or “SLC39A6,” as used herein, refers to any native form of human SLC39A6. The term encompasses full-length SLC39A6 (e.g., UniProt Reference Sequence:Q13433; SEQ ID NO:54), as well as any form of human SLC39A6 that may result from cellular processing. The term also encompasses functional variants or fragments of human SLC39A6, including but not limited to splice variants, allelic variants, and isoforms that retain one or more biologic functions of human SLC39A6 (i.e., variants and fragments are encompassed unless the context indicates that the term is used to refer to the wild-type protein only). SLC39A6 can be isolated from a human, or may be produced recombinantly or by synthetic methods.

The term “anti-SLC39A6 antibody” or “antibody that binds to SLC39A6” refers to any form of antibody or fragment thereof that binds, e.g., specifically binds, to SLC39A6, and encompasses monoclonal antibodies (including full-length monoclonal antibodies), polyclonal antibodies, and biologically functional antibody fragments so long as they bind, e.g., specifically bind, to SLC39A6. Sussman et al. ((2014) Mol Cancer Ther. 13(12):2991-3000) provides and is incorporated herein by reference for exemplary SLC39A6-binding sequences, including exemplary anti-SLC39A6 antibody sequences. In some embodiments, the anti-SLC39A6 antibody used in the ADCs disclosed herein is an internalizing antibody or internalizing antibody fragment.

The term “choline transporter-like protein 4” or “SLC44A4,” as used herein, refers to any native form of human SLC44A4. The term encompasses full-length SLC44A4 (e.g., UniProt Reference Sequence: Q53GD3; SEQ ID NO:55), as well as any form of human SLC44A4 that may result from cellular processing. The term also encompasses functional variants or fragments of human SLC44A4, including but not limited to splice variants, allelic variants, and isoforms that retain one or more biologic functions of human SLC44A4 (i.e., variants and fragments are encompassed unless the context indicates that the term is used to refer to the wild-type protein only). SLC44A4 can be isolated from a human, or may be produced recombinantly or by synthetic methods.

The term “anti-SLC44A4 antibody” or “antibody that binds to SLC44A4” refers to any form of antibody or fragment thereof that binds, e.g., specifically binds, to SLC44A4, and encompasses monoclonal antibodies (including full-length monoclonal antibodies), polyclonal antibodies, and biologically functional antibody fragments so long as they bind, e.g., specifically bind, to SLC44A4. Mattie et al. ((2016) Mol Cancer Ther. 15(11):2679-87) provides and is incorporated herein by reference for exemplary SLC44A4-binding sequences, including exemplary anti-SLC44A4 antibody sequences. In some embodiments, the anti-SLC44A4 antibody used in the ADCs disclosed herein is an internalizing antibody or internalizing antibody fragment.

The term “metalloreductase STEAP1” or “STEAP1,” as used herein, refers to any native form of human STEAP1. The term encompasses full-length STEAP1 (e.g., UniProt Reference Sequence: Q9UHE8; SEQ ID NO:56), as well as any form of human STEAP1 that may result from cellular processing. The term also encompasses functional variants or fragments of human STEAP1, including but not limited to splice variants, allelic variants, and isoforms that retain one or more biologic functions of human STEAP1 (i.e., variants and fragments are encompassed unless the context indicates that the term is used to refer to the wild-type protein only). STEAP1 can be isolated from a human, or may be produced recombinantly or by synthetic methods.

The term “anti-STEAP1 antibody” or “antibody that binds to STEAP1” refers to any form of antibody or fragment thereof that binds, e.g., specifically binds, to STEAP1, and encompasses monoclonal antibodies (including full-length monoclonal antibodies), polyclonal antibodies, and biologically functional antibody fragments so long as they bind, e.g., specifically bind, to STEAP1. WO 2008/052187 provides and is incorporated herein by reference for exemplary STEAP1-binding sequences, including exemplary anti-STEAP1 antibody sequences. In some embodiments, the anti-STEAP1 antibody used in the ADCs disclosed herein is an internalizing antibody or internalizing antibody fragment.

As used herein, the term “specific,” “specifically binds,” and “binds specifically” refers to a binding reaction between an antibody or antigen binding fragment (e.g., an anti-HER2 antibody) and a target antigen (e.g., HER2) in a heterogeneous population of proteins and other biologics. Antibodies can be tested for specificity of binding by comparing binding to an appropriate antigen to binding to an irrelevant antigen or antigen mixture under a given set of conditions. If the antibody binds to the appropriate antigen with at least 2, 5, 7, and preferably 10 or more times more affinity than to the irrelevant antigen or antigen mixture, then it is considered to be specific. A “specific antibody” or a “target-specific antibody” is one that only binds the target antigen (e.g., HER2), but does not bind (or exhibits minimal binding) to other antigens. In certain embodiments, an antibody or antigen binding fragment that specifically binds a target antigen (e.g., HER2) has a $K_D$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In certain embodiments, the $K_D$ is 1 pM to 500 pM. In some embodiments, the $K_D$ is between 500 pM to 1 µM, 1 µM to 100 nM, or 100 mM to 10 nM.

The term “epitope” refers to the portion of an antigen capable of being recognized and specifically bound by an antibody. When the antigen is a polypeptide, epitopes can be formed from contiguous amino acids or noncontiguous amino acids juxtaposed by tertiary folding of the polypeptide. The epitope bound by an antibody may be identified using any epitope mapping technique known in the art, including X-ray crystallography for epitope identification by direct visualization of the antigen-antibody complex, as well as monitoring the binding of the antibody to fragments or mutated variations of the antigen, or monitoring solvent accessibility of different parts of the antibody and the antigen. Exemplary strategies used to map antibody epitopes include, but are not limited to, array-based oligo-peptide scanning, limited proteolysis, site-directed mutagenesis, high-throughput mutagenesis mapping, hydrogen-deuterium exchange, and mass spectrometry (see, e.g., Gershoni et al. (2007) 21:145-56; and Hager-Braun and Tomer (2005) Expert Rev Proteomics 2:745-56).

Competitive binding and epitope binning can also be used to determine antibodies sharing identical or overlapping epitopes. Competitive binding can be evaluated using a cross-blocking assay, such as the assay described in "Antibodies, A Laboratory Manual," Cold Spring Harbor Laboratory, Harlow and Lane ($1^{st}$ edition 1988, $2^{nd}$ edition 2014). In some embodiments, competitive binding is identified when a test antibody or binding protein reduces binding of a reference antibody or binding protein to a target antigen such as HER2 (e.g., a binding protein comprising CDRs and/or variable domains selected from those identified in Tables 2-4), by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes (see, e.g., Tzartos, Methods in Molecular Biology (Morris, ed. (1998) vol. 66, pp. 55-66)). In some embodiments, competitive binding can be used to sort groups of binding proteins that share similar epitopes. For example, binding proteins that compete for binding can be "binned" as a group of binding proteins that have overlapping or nearby epitopes, while those that do not compete are placed in a separate group of binding proteins that do not have overlapping or nearby epitopes.

The term "$k_{on}$" or "$k_a$" refers to the on-rate constant for association of an antibody to the antigen to form the antibody/antigen complex. The rate can be determined using standard assays, such as a surface plasmon resonance, biolayer inferometry, or ELISA assay.

The term "$k_{off}$" or "$k_d$" refers to the off-rate constant for dissociation of an antibody from the antibody/antigen complex. The rate can be determined using standard assays, such as a surface plasmon resonance, biolayer inferometry, or ELISA assay.

The term "$K_D$" refers to the equilibrium dissociation constant of a particular antibody-antigen interaction. $K_D$ is calculated by $k_a/k_d$. The rate can be determined using standard assays, such as a surface plasmon resonance, biolayer inferometry, or ELISA assay.

The term "p" or "drug loading" or "drug:antibody ratio" or "drug-to-antibody ratio" or "DAR" refers to the number of drug moieties per antibody or antigen binding fragment, i.e., drug loading, or the number of -L-D moieties per antibody or antigen binding fragment (Ab) in ADCs of Formula (I). In ADCs comprising a splicing modulator drug moiety, "p" refers to the number of splicing modulator compounds linked to the antibody or antigen binding fragment. For example, if two splicing modulator compounds (e.g., two compounds each having the structure of D1) are linked to an antibody or antigen binding fragment, p=2. In compositions comprising multiple copies of ADCs of Formula (I), "average p" refers to the average number of -L-D moieties per antibody or antigen binding fragment, also referred to as "average drug loading."

A "linker" or "linker moiety" is used herein to refer to any chemical moiety that is capable of covalently joining a compound, usually a drug moiety such as a splicing modulator drug moiety, to another moiety such as an antibody or antigen binding fragment. Linkers can be susceptible to or substantially resistant to acid-induced cleavage, peptidase-induced cleavage, light-based cleavage, esterase-induced cleavage, and/or disulfide bond cleavage, at conditions under which the compound or the antibody remains active.

The term "agent" is used herein to refer to a chemical compound, a mixture of chemical compounds, a biological macromolecule, or an extract made from biological materials. The term "therapeutic agent" or "drug" refers to an agent that is capable of modulating a biological process and/or has biological activity. The splicing modulator compounds described herein are exemplary therapeutic agents.

The term "chemotherapeutic agent" or "anti-cancer agent" is used herein to refer to all agents that are effective in treating cancer regardless of mechanism of action. Inhibition of metastasis or angiogenesis is frequently a property of a chemotherapeutic agent. Chemotherapeutic agents include antibodies, biological molecules, and small molecules, and encompass the splicing modulator compounds described herein. A chemotherapeutic agent may be a cytotoxic or cytostatic agent. The term "cytostatic agent" refers to an agent that inhibits or suppresses cell growth and/or multiplication of cells. The term "cytotoxic agent" refers to a substance that causes cell death primarily by interfering with a cell's expression activity and/or functioning.

As used herein, the terms "splicing modulator," "spliceosome modulator," or "splice modulator" refer to compounds that have anti-cancer activity by interacting with components of the spliceosome. In some embodiments, a splicing modulator alters the rate or form of splicing in a target cell. Splicing modulators that function as inhibitory agents, for example, are capable of decreasing uncontrolled cellular proliferation. In some embodiments, the splicing modulators may act by binding to the SF3b spliceosome complex. Such modulators may be natural compounds or synthetic compounds. Non-limiting examples of splicing modulators and categories of such modulators include pladienolide (e.g., pladienolide D or pladienolide B), pladienolide derivatives (e.g., pladienolide D or pladienolide B derivatives), herboxidiene, herboxidiene derivatives, spliceostatin, spliceostatin derivatives, sudemycin, or sudemycin derivatives. As used herein, the terms "derivative" and "analog" when referring to a splicing modulator, or the like, means any such compound that retains essentially the same, similar, or enhanced biological function or activity as the original compound but has an altered chemical or biological structure. In some embodiments, the splicing modulator is a pladienolide or pladienolide derivative.

As used herein, a "pladienolide derivative" refers to a compound which is structurally related to a member of the family of natural products known as the pladienolides and which retains one or more biological functions of the starting compound. Pladienolides were first identified in the bacteria *Streptomyces platensis* (Mizui et al. (2004) J Antibiot. 57:188-96) as being potently cytotoxic and resulting in cell cycle arrest in the G1 and G2/M phases of the cell cycle (e.g., Bonnal et al. (2012) Nat Rev Drug Dis 11:847-59). There are seven naturally occurring pladienolides, pladienolide A-G (Mizui et al. (2004) J Antibiot. 57:188-96; Sakai et al. (2004) J Antibiotics 57:180-7). U.S. Pat. Nos. 7,884,128 and 7,816,401 describe exemplary methods of synthesizing pladienolide B and D and are each incorporated herein by reference for such methods. Synthesis of pladienolide B and D may also be performed using the exemplary methods described in Kanada et al. ((2007) Angew Chem Int Ed. 46:4350-5). Kanada et al. and Intl. Pub. No. WO 2003/099813 describe exemplary methods for synthesizing E7107 (D11) (Compound 45 of WO 2003/099813) from Pladienolide D (11107D of WO 2003/099813). A corresponding U.S.

Pat. No. 7,550,503 to Kotake et al. Each of these references is incorporated herein for the described synthesis methods.

As used herein, a "splicing modulator drug moiety" refers to the component of an ADC or composition that provides the structure of a splicing modulator compound, e.g., the splicing modulator (D) component in an ADC of Formula (I), or in a composition comprising -L-D.

As used herein, a "spliceosome" refers to a ribonucleoprotein complex that removes introns from one or more RNA segments, such as pre-mRNA segments.

The term "homolog" refers to a molecule which exhibits homology to another molecule, by for example, having sequences of chemical residues that are the same or similar at corresponding positions.

The term "inhibit" or "inhibition of," as used herein, means to reduce by a measurable amount, and can include but does not require complete prevention or inhibition.

The term "target-negative," "target antigen-negative," or "antigen-negative" refers to the absence of target antigen expression by a cell or tissue. The term "target-positive," "target antigen-positive," or "antigen-positive" refers to the presence of target antigen expression. For example, a cell or a cell line that does not express a target antigen may be described as target-negative, whereas a cell or cell line that expresses a target antigen may be described as target-positive.

The term "bystander killing" or "bystander effect" refers to the killing of target-negative cells in the presence of target-positive cells, wherein killing of target-negative cells is not observed in the absence of target-positive cells. Cell-to-cell contact, or at least proximity between target-positive and target-negative cells, enables bystander killing. This type of killing is distinguishable from "off-target killing," which refers to the indiscriminate killing of target-negative cells. "Off-target killing" may be observed in the absence of target-positive cells.

The terms "neoplastic disorder" and "cancer" are used herein interchangeably to refer to the presence of cells possessing characteristics typical of cancer-causing cells, such as uncontrolled proliferation, immortality, metastatic potential, rapid growth and proliferation rate, and/or certain morphological features. Often, cancer cells can be in the form of a tumor or mass, but such cells may exist alone within a subject, or may circulate in the blood stream as independent cells, such as leukemic or lymphoma cells. The terms "neoplastic disorder" and "cancer" includes all types of cancers and cancer metastases, including hematological malignancy, solid tumors, sarcomas, carcinomas and other solid and non-solid tumor cancers. Hematological malignancies may include B-cell malignancies, cancers of the blood (leukemias), cancers of plasma cells (myelomas, e.g., multiple myeloma), or cancers of the lymph nodes (lymphomas). Exemplary B-cell malignancies include chronic lymphocytic leukemia (CLL), follicular lymphoma, mantle cell lymphoma, and diffuse large B-cell lymphoma. Leukemias may include acute lymphoblastic leukemia (ALL), acute myelogenous leukemia (AML), chronic lymphocytic leukemia (CLL), chronic myelogenous leukemia (CML), chronic myelomonocytic leukemia (CMML), acute monocytic leukemia (AMoL), etc. Lymphomas may include Hodgkin's lymphoma and non-Hodgkin's lymphoma. Other hematologic malignancies may include myelodysplasia syndrome (MDS). Solid tumors may include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

The terms "tumor" and "neoplasm" refer to any mass of tissue that results from excessive cell growth or proliferation, either benign or malignant, including precancerous lesions.

The terms "tumor cell" and "neoplastic cell" are used interchangeably and refer to individual cells or the total population of cells derived from a tumor or neoplasm, including both non-tumorigenic cells and cancer stem cells. As used herein, the term "tumor cell" will be modified by the term "non-tumorigenic" when referring solely to those tumor cells lacking the capacity to renew and differentiate to distinguish those tumor cells from cancer stem cells.

The terms "subject" and "patient" are used interchangeably herein to refer to any animal, such as any mammal, including but not limited to, humans, non-human primates, rodents, and the like. In some embodiments, the mammal is a mouse. In some embodiments, the mammal is a human. In some embodiments, the subject is a mouse. In some embodiments, the subject is a human.

The term "co-administration" or administration "in combination with" one or more therapeutic agents includes concurrent administration and consecutive administration in any order.

A "pharmaceutical composition" refers to a preparation which is in such form as to permit administration and subsequently provide the intended biological activity of the active ingredient(s) and/or to achieve a therapeutic effect, and which contains no additional components which are unacceptably toxic to a subject to which the formulation would be administered. The pharmaceutical composition may be sterile.

A "pharmaceutical excipient" comprises a material such as an adjuvant, a carrier, pH-adjusting and buffering agents, tonicity adjusting agents, wetting agents, preservative, and the like.

"Pharmaceutically acceptable" means approved or approvable by a regulatory agency of the Federal or a state government, or listed in the U.S. Pharmacopeia or other generally recognized pharmacopeia, for use in animals, and more particularly in humans A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al. "Commentary: Occurrence of Pharmaceutically Acceptable Anions and Cations in the Cambridge Structural Database," J Pharmaceutical Sciences, vol. 94, no. 10 (2005), and Berge et al. "Pharmaceutical Salts," J Pharmaceutical Sciences, vol. 66, no. 1 (1977), which are incorporated by reference herein.

The term "effective amount," as used herein, refers to the amount of a compound, ADC, or composition described herein (e.g., a splicing modulator or an ADC) that is sufficient to perform a specifically stated purpose, for example to produce a therapeutic effect after administration, such as a reduction in tumor growth rate or tumor volume, a reduction in a symptom of cancer, or some other indicia of treatment efficacy. An effective amount can be determined in a routine manner in relation to the stated purpose. The term "therapeutically effective amount" refers to an amount of a compound, an ADC, or composition described herein effective for detectable killing, reduction, and/or inhibition of the growth or spread of tumor cells, the size or number of tumors, and/or other measure of the level, stage, progression and/or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., inhibition of cell growth. The specific dose may vary depending on, for example, the particular pharmaceutical composition, the subject and their age and existing health conditions or risk for health conditions, the dosing regimen to be followed, the severity of the disease, whether it is administered in combination with other agents, timing of administration, the tissue to which it is administered, and the physical delivery system in which it is carried. In the case of cancer, a therapeutically effective amount of ADC can reduce the number of cancer cells, reduce tumor size, inhibit (e.g., slow or stop) tumor metastasis, inhibit (e.g., slow or stop) tumor growth, and/or relieve one or more symptoms.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "to treat" or "therapeutic" and grammatically related terms, refer to any improvement of any consequence of disease, such as prolonged survival, less morbidity, and/or a lessening of side effects which result from an alternative therapeutic modality. As is readily appreciated in the art, full eradication of disease is encompassed but not required for a treatment act. "Treatment" or "treat," as used herein, refers to the administration of a described ADC or composition to a subject, e.g., a patient. The treatment can be to cure, heal, alleviate, relieve, alter, remedy, ameliorate, palliate, improve or affect the disorder, the symptoms of the disorder or the predisposition toward the disorder, e.g., a cancer. In some embodiments, in addition to treating a subject with a condition, a composition disclosed herein can also be provided prophylactically to prevent or reduce the likelihood of developing that condition.

In some embodiments, a labeled ADC is used. Suitable "labels" include radionuclides, enzymes, substrates, cofactors, inhibitors, fluorescent moieties, chemiluminescent moieties, magnetic particles, and the like.

By "protein," as used herein, is meant at least two covalently attached amino acids. The term encompasses polypeptides, oligopeptides, and peptides. In some embodiments, the two or more covalently attached amino acids are attached by a peptide bond. The protein may be made up of naturally occurring amino acids and peptide bonds, for example when the protein is made recombinantly using expression systems and host cells. Alternatively, the protein may include synthetic amino acids (e.g., homophenylalanine, citrulline, ornithine, and norleucine), or peptidomimetic structures, i.e., "peptide or protein analogs," such as peptoids. Peptoids are an exemplary class of peptidomimetics whose side chains are appended to the nitrogen atom of the peptide backbone, rather than to the α-carbons (as they are in amino acids), and have different hydrogen bonding and conformational characteristics in comparison to peptides (see, e.g., Simon et al. (1992) Proc Natl Acad Sci. USA 89:9367). As such, peptoids can be resistant to proteolysis or other physiological or storage conditions, and effective at permeating cell membranes. Such synthetic amino acids may be incorporated in particular when the antibody is synthesized in vitro by conventional methods well known in the art. In addition, any combination of peptidomimetic, synthetic and naturally occurring residues/structures can be used. "Amino acid" also includes imino acid residues, such as proline and hydroxyproline. The amino acid "R group" or "side chain" may be in either the (L)- or the (S)-configuration. In a specific embodiment, the amino acids are in the (L)- or (S)-configuration.

A "recombinant protein" is a protein made using recombinant techniques using any techniques and methods known in the art, i.e., through the expression of a recombinant nucleic acid. Methods and techniques for the production of recombinant proteins are well known in the art.

An "isolated" protein is unaccompanied by at least some of the material with which it is normally associated in its natural state, for example constituting at least about 5%, or at least about 50% by weight of the total protein in a given sample. It is understood that the isolated protein may constitute from 5% to 99.9% by weight of the total protein content depending on the circumstances. For example, the protein may be made at a significantly higher concentration through the use of an inducible promoter or high expression promoter, such that the protein is made at increased concentration levels. The definition includes the production of an antibody in a wide variety of organisms and/or host cells that are known in the art.

For amino acid sequences, sequence identity and/or similarity may be determined using standard techniques known in the art, including, but not limited to, the local sequence identity algorithm of Smith and Waterman (1981) Adv Appl Math. 2:482, the sequence identity alignment algorithm of Needleman and Wunsch (1970) J Mol Biol. 48:443, the search for similarity method of Pearson and Lipman (1988) Proc Nat Acad Sci. USA 85:2444, computerized implementations of these algorithms (GAP, BESTFIT, FASTA, and TFASTA in the Wisconsin Genetics Software Package, Genetics Computer Group, 575 Science Drive, Madison, Wisconsin), the Best Fit sequence program described by Devereux et al. (1984) Nucl Acid Res. 12:387-95, preferably using the default settings, or by inspection. Preferably, percent identity is calculated by FastDB based upon the following parameters: mismatch penalty of 1; gap penalty of 1; gap size penalty of 0.33; and joining penalty of 30 ("Current Methods in Sequence Comparison and Analysis," Macromolecule Sequencing and Synthesis, Selected Methods and Applications, pp. 127-149 (1988), Alan R. Liss, Inc).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J Mol Evol. 35:351-60; the method is similar to that described by Higgins and Sharp (1989) CABIOS 5:151-3. Useful PILEUP parameters including a default gap weight of 3.00, a default gap length weight of 0.10, and weighted end gaps.

Another example of a useful algorithm is the BLAST algorithm, described in: Altschul et al. (1990) J Mol Biol.

215:403-10; Altschul et al. (1997) Nucl Acid Res. 25:3389-402; and Karin et al. (1993) Proc Natl Acad Sci. USA 90:5873-87. A particularly useful BLAST program is the WU-BLAST-2 program which was obtained from Altschul et al. (1996) Methods in Enzymology 266:460-80. WU-BLAST-2 uses several search parameters, most of which are set to the default values. The adjustable parameters are set with the following values: overlap span=I, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. (1997) Nucl Acid Res. 25:3389-402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between proteins disclosed herein and variants thereof, including variants of target antigens (such as HER2, CD138, EPHA2, MSLN, FOLH1, CDH6, CEACAM5, CFC1B, ENPP3, FOLR1, HAVCR1, KIT, MET, MUC16, SLC39A6, SLC44A4, or STEAP1) and variants of antibody variable domains (including individual variant CDRs), are at least 80% to the sequences depicted herein, e.g., homologies or identities of at least 85%, 90%, 91%, 92%, 93%, 94%, 95%, 96%, 97%, 98%, 99%, almost 100%, or 100%.

In a similar manner, "percent (%) nucleic acid sequence identity" with respect to the nucleic acid sequence of the antibodies and other proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, MI3 primer mutagenesis and PCR mutagenesis "Alkyl" or "alkyl group," as used herein, means a straight-chain, branched, or cyclic hydrocarbon chain that is completely saturated. In certain embodiments, alkyl groups may contain 1-8 carbon atoms ("$C_1$-$C_8$alkyl"). In certain embodiments, alkyl groups may contain 1-6 carbon atoms ("$C_1$-$C_8$alkyl"). In certain embodiments, alkyl groups contain 1-3 carbon atoms. In still other embodiments, alkyl groups contain 2-3 carbon atoms, and in yet other embodiments alkyl groups contain 1-2 carbon atoms.

"Alkylalkoxy," as used herein, means an alkyl group substituted with an alkoxy group. "Alkoxy", as used herein, refers to an alkyl group, as previously defined, attached to the principal carbon chain through an oxygen ("alkoxy") atom.

"Alkylamino," as used herein, means an alkyl group substituted with an amino group. "Amino," as used herein, refers to —$NH_2$, —NH(alkyl), or —N(alkyl)(alkyl).

"Alkylhydroxy," as used herein, means an alkyl group substituted with an amino group. "Hydroxy" or "hydroxyl," as used herein, refers to —OH.

"Alkylene" refers to a divalent radical of an alkyl group. For example, —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$— refer to methylene, ethylene, n-propylene, n-butylene, n-pentylene, and n-hexylene, respectively.

"Carbocycle," as used herein, includes both aromatic (e.g., aryl) and non-aromatic (e.g., cycloalkyl) groups. In certain embodiments, carbocycle groups contain 3-10 carbon atoms ("3 to 10 membered carbocycle"). In certain embodiments, carbocycle groups contain 3-8 carbon atoms ("3 to 8 membered carbocycle"). In certain embodiments, carbocycle groups contain 3-6 carbon atoms ("3 to 6 membered carbocycle"). In certain embodiments, carbocycle groups contain 3-5 carbon atoms ("3 to 5 membered carbocycle").

"Halogen" refers to a radical of any halogen, e.g., —F, —Cl, —Br, or —I.

The terms "heterocycle", "heterocyclyl", and "heterocyclic" as used herein, mean a monocyclic heterocycle, a bicyclic heterocycle, or a tricyclic heterocycle containing at least one heteroatom in the ring.

The monocyclic heterocycle is a 3-, 4-, 5-, 6-, 7, or 8-membered ring containing at least one heteroatom independently chosen from O, N, and S. In some embodiments, the heterocycle is a 3- or 4-membered ring containing one heteroatom chosen from O, N and S. In some embodiments, the heterocycle is a 5-membered ring containing zero or one double bond and one, two or three heteroatoms chosen from O, N and S. In some embodiments, the heterocycle is a 6-, 7-, or 8-membered ring containing zero, one or two double bonds and one, two or three heteroatoms chosen from O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present disclosure may include a monocyclic heterocycle fused to an aryl group, or a monocyclic heterocycle fused to a monocyclic cycloalkyl, or a monocyclic heterocycle fused to a monocyclic cycloalkenyl, or a monocyclic heterocycle fused to a monocyclic heterocycle having a total of 5 to 12 ring atoms. Examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The terms "heterocycle", "heterocyclyl", and "heterocyclic" encompass heteroaryls. "Heteroaryl" refers to a cyclic moiety having one or more closed rings, with one or more heteroatoms (oxygen, nitrogen or sulfur) in at least one of the rings, wherein at least one of the rings is aromatic, and wherein the ring or rings may independently be fused, and/or bridged. Examples include without limitation phenyl, thiophenyl, triazolyl, pyridinyl, pyrimidinyl, pyridazinyl, and pyrazinyl.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Combinations of substituents envisioned under this disclosure are preferably those that result in the formation of stable or chemically feasible compounds.

One skilled in the art will be understand that "substitution" or "substituted with" or "absent" includes the implicit proviso that such substitution or absence is in accordance with permitted valence of the substituted atom and the substituent, and that the substitution or absence results in a stable compound, e.g., which does not spontaneously undergo transformation such as by rearrangement, cyclization, elimination, etc. For purposes of this disclosure, the heteroatoms such as nitrogen may have hydrogen substituents, and/or any permissible substituents of organic compounds described herein which satisfy the valences of the heteroatoms.

"Stable" refers to compounds that are not substantially altered chemically and/or physically when subjected to conditions to allow for their production, detection, and, in certain embodiments, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. In some embodiments, the compounds disclosed herein are stable.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

The compounds described herein may also contain unnatural proportions of atomic isotopes at one or more of the atoms that constitute such compounds. For example, the compounds may be radiolabeled with radioactive isotopes, such as, for example, deuterium ($^{2}H$), tritium ($^{3}H$), carbon-13 ($^{13}C$), or carbon-14 ($^{14}C$). All isotopic variations of the compounds disclosed herein, whether radioactive or not, are intended to be encompassed within the scope of the present disclosure. In addition, all tautomeric forms of the compounds described herein are intended to be within the scope of the claimed disclosure.

Antibody-Drug Conjugates

The antibody-drug conjugate (ADC) compounds of the present disclosure include those with anti-cancer activity. In particular, the ADC compounds include an antibody or antigen binding fragment (including an antigen binding fragment thereof) conjugated (i.e., covalently attached by a linker) to a drug moiety (e.g., a splicing modulator), wherein the drug moiety when not conjugated to an antibody or antigen binding fragment has a cytotoxic or cytostatic effect. In various embodiments, the drug moiety when not conjugated to an antibody or antigen binding fragment is capable of binding to and/or interacting with the SF3b spliceosome complex. In various embodiments, the drug moiety when not conjugated to an antibody or antigen binding fragment is capable of modulating in vitro and/or in vivo RNA splicing. By targeting RNA splicing, in various embodiments, the drug moieties and ADCs disclosed herein are potent antiproliferative agents. In various embodiments, the drug moieties and ADCs disclosed herein can target both actively dividing and quiescent cells.

In various embodiments, the present disclosure is based, at least in part, on the discovery that certain biologically active splicing modulators may provide improved properties when used in ADCs. While a splicing modulator may show desirably improved features (e.g., robust SF3b spliceosome complex binding, potent modulation of RNA splicing) when used on its own, in various embodiments, the splicing modulator may exhibit fewer of the same desirably improved features when conjugated to an antibody or antigen binding fragment. Thus, the development and production of an ADC for use as a human therapeutic agent, e.g., as an oncologic agent, may require more than the identification of an antibody capable of binding to a desired target or targets and attaching to a drug used on its own to treat cancer. Linking the antibody to the drug may have significant effects on the activity of one or both of the antibody and the drug, effects which will vary depending on the type of linker and/or drug chosen. In some embodiments, therefore, the components of the ADC are selected to (i) retain one or more therapeutic properties exhibited by the antibody and drug moieties in isolation, (ii) maintain the specific binding properties of the antibody or antigen binding fragment; (iii) optimize drug loading and drug-to-antibody ratios; (iv) allow delivery, e.g., intracellular delivery, of the drug moiety via stable attachment to the antibody or antigen binding fragment; (v) retain ADC stability as an intact conjugate until transport or delivery to a target site; (vi) minimize aggregation of the ADC prior to or after administration; (vii) allow for the therapeutic effect, e.g., cytotoxic effect, of the drug moiety after cleavage or other release mechanism in the cellular environment; (viii) exhibit in vivo anti-cancer treatment efficacy comparable to or superior to that of the antibody and drug moieties in isolation; (ix) minimize off-target killing by the drug moiety; and/or (x) exhibit desirable pharmacokinetic and pharmacodynamics properties, formulatability, and toxicologic/immunologic profiles. Each of these properties may be needed to identify an improved ADC for therapeutic use (Ab et al. (2015) Mol Cancer Ther. 14:1605-13).

In various embodiments, the ADCs disclosed herein exhibit unexpectedly favorable properties in some or each of the categories listed above. For instance, in some embodiments, the ADC constructs disclosed herein exhibit surprisingly favorable drug loading, aggregation, and/or stability profiles, and/or preserve antibody binding function, drug activity, and/or improved bystander killing, while reducing off-target killing, as compared to ADCs comprising an alternate linker and/or drug moiety (e.g., an alternate splicing modulator). In some embodiments, ADC constructs disclosed herein demonstrate superior stability, activity, potency, or other effect (measured in vivo or in vitro) as compared to ADCs using an alternate linker and/or drug moiety (e.g., an alternate splicing modulator). In some embodiments, the ADC constructs disclosed herein exhibit in vivo treatment efficacy when administered as a single dose. In some embodiments, the ADC constructs disclosed herein are surprisingly stable as compared to ADCs using an alternate linker and/or drug moiety (e.g., an alternate splicing modulator).

The ADC compounds of the present disclosure may selectively deliver an effective dose of a cytotoxic or cytostatic agent to cancer cells or to tumor tissue. It has been discovered that the disclosed ADCs have potent cytotoxic and/or cytostatic activity against cells expressing the respective target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). In some embodiments, the cytotoxic and/or cytostatic activity of the ADC is dependent on target antigen expression in a cell. In some embodiments, the disclosed ADCs are particularly effective at killing cancer cells expressing a target antigen while minimizing off-target killing. In some embodiments, the disclosed ADCs do not exhibit a cytotoxic and/or cytostatic effect on cancer cells that do not express a target antigen.

Exemplary HER2-expressing cancers include but are not limited to breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer (English et al. (2013) Mol Diagn Ther. 17:85-99).

Exemplary CD138-expressing cancers include but are not limited to intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), hematological malignancies (e.g., myeloma such as multiple myeloma, B-cell malignancies, Hodgkin's lymphoma), and thyroid cancer (Szatmári et al. (2015) Dis Markers 2015: 796052).

Exemplary EPHA2-expressing cancers include breast cancer, brain cancer, ovarian cancer, bladder cancer, pancreatic cancer, esophageal cancer, lung cancer, prostate cancer, melanoma, esophageal cancer, and gastric cancer (Tandon et al. (2011) Expert Opin Ther Targets 15(1):31-51).

In some embodiments, cleavage of an ADC releases the splicing modulator from the antibody or antigen binding fragment and linker. In some embodiments, the linker and/or splicing modulator is designed to facilitate bystander killing (the killing of neighboring cells). In some embodiments, the linker and/or splicing modulator is designed to facilitate bystander killing through cleavage after cellular internalization and diffusion of the linker-drug moiety and/or the drug moiety alone to neighboring cells. In some embodiments, the linker promotes cellular internalization. In some embodiments, the linker is designed to minimize cleavage in the extracellular environment and thereby reduce toxicity to off-target tissue (e.g., non-cancerous tissue), while preserving ADC binding to target tissue and bystander killing of cancerous tissue that does not express an antigen targeted by the antibody or antigen binding fragment of an ADC, but surrounds target cancer tissue expressing that antigen. In some embodiments, the drug moiety, or the catabolite of the drug moiety produced by cleavage of an ADC, is designed to facilitate uptake by target cells or by neighboring cells (i.e., cell permeable). Such drug moieties and catabolites may be referred to herein as "bystander active," whereas drug moieties or catabolites with reduced cell permeability may be referred to as "bystander inactive."

In some embodiments, the disclosed ADCs also demonstrate bystander killing activity, but low off-target cytotoxicity. Without being bound by theory, the bystander killing activity of an ADC may be particularly beneficial where its penetration into a solid tumor is limited and/or target antigen expression among tumor cells is heterogeneous. In some embodiments, an ADC comprising a cleavable linker is particularly effective at bystander killing and/or demonstrates improved bystander killing activity, relative to comparable treatment with an ADC comprising a non-cleavable linker. In some embodiments, the ADCs disclosed herein exhibit improved solubility and target cell penetrance over the drug moieties on their own. In some embodiments, the ADCs disclosed herein exhibit improved cytotoxicity over that of the drug moiety on its own. In some embodiments, ADCs disclosed herein use drug moieties that exhibit lower cytotoxicity, when evaluated as a stand-alone drug, yet are surprisingly better than ADCs comprising other drug moieties which have higher cytotoxicity when evaluated as a stand-alone drug. In some embodiments, cleavage and release of the splicing modulator improves cytotoxicity of the ADC, relative to comparable treatment with an ADC comprising a non-cleavable linker. In other embodiments, cleavage and release of the splicing modulator is not required for an ADC to possess a desirable biological activity. In some embodiments, an ADC comprising a non-cleavable linker having increased spacer length (e.g., ADL12) provides the same or similar cytotoxicity relative to comparable treatment with an ADC comprising a cleavable linker (e.g., ADL1, ADL5) and surprisingly superior cytotoxicity relative to comparable treatment with an ADC comprising a shorter non-cleavable linker. In some embodiments, an ADC comprising a non-cleavable linker having increased spacer length without a carbonyl group (e.g., ADL12) provides the same or similar cytotoxicity relative to comparable treatment with an ADC comprising a cleavable linker (e.g., ADL1, ADL5) and surprisingly superior cytotoxicity relative to comparable treatment with an ADC comprising a non-cleavable linker having the same or similar spacer length with a carbonyl group (e.g., ADL10). In some embodiments, the removal of a carbonyl group from a non-cleavable MC linker (e.g., ADL12) can result in a greater than 50-fold, greater than 75-fold, greater than 100-fold, greater than 150-fold, or greater than 200-fold increase in cytotoxicity, relative to comparable treatment with an ADC comprising an unmodified non-cleavable MC linker (e.g., ADL10). In some embodiments, the removal of a carbonyl group from a non-cleavable MC linker (e.g., ADL12) and increased spacer length (e.g., the addition of at least one spacer unit) can result in a greater than 50-fold, greater than 75-fold, greater than 100-fold, greater than 150-fold, or greater than 200-fold increase in cytotoxicity, relative to comparable treatment with an ADC comprising an unmodified non-cleavable MC linker (e.g., ADL10).

Provided herein are ADC compounds comprising an antibody or antigen binding fragment thereof (Ab) which targets a tumor cell, a splicing modulator drug moiety (D), and a linker moiety (L) that covalently attaches Ab to D. In certain aspects, the antibody or antigen binding fragment is able to bind to a tumor-associated antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1) with high specificity and high affinity. In certain embodiments, the antibody or antigen binding fragment is internalized into a target cell upon binding, e.g., into a degradative compartment in the cell. In various embodiments, ADCs that internalize upon binding to a target cell, undergo degradation, and release the splicing modulator drug moiety to kill cancer cells may be used. The splicing modulator drug moiety may be released from the antibody and/or the linker moiety of the ADC by enzymatic action, hydrolysis, oxidation, or any other mechanism.

An exemplary ADC has Formula (I):

$$\text{Ab-(L-D)}_p \tag{I}$$

wherein Ab= an antibody or antigen binding fragment, L=a linker moiety, D=a splicing modulator drug moiety, and p=the number of splicing modulator drug moieties per antibody or antigen binding fragment.

In certain preferred embodiments, the drug-targeting moiety for use in the described ADCs and compositions is an antibody or antigen binding fragment. Other exemplary drug-targeting moieties for use in the described ADCs and compositions are also provided and described herein. In some embodiments, a drug-targeting moiety can be any one of a variety of cell-binding agents and non-antibody scaffolds. In some embodiments, the drug-targeting moiety is a cell-binding agent. As used herein, the term "cell-binding agent" refers to any agent that is capable of binding to an animal (e.g., human) cell and delivering a drug moiety (e.g., a splicing modulator drug moiety as disclosed herein). The term encompasses the exemplary antibodies and antigen binding fragments disclosed herein (e.g., monoclonal antibodies and fragments thereof such as Fabs and scFVs). The term further encompasses exemplary cell-binding agents such as DARPins, duobodies, bicyclic peptides, nanobodies, centyrins, MSH (melanocyte-stimulating hormone), receptor-Fc fusion molecules, T-cell receptor structures, steroid hormones such as androgens and estrogens, growth factors, colony-stimulating factors such as EGF, and other non-antibody scaffolds. In various embodiments, non-antibody scaffolds can broadly fall into two structural classes, namely domain-sized compounds (approximately 6-20 kDa) and constrained peptides (approximately 2-4 kDa). Exemplary domain-sized scaffolds include but are not limited to affibodies, affilins, anticalins, atrimers, DARPins, FN3 scaffolds (e.g., adnectins and centyrins), fynomers, Kunitz domains, pronectins, O-bodies, and receptor-Fc fusion proteins, whereas exemplary constrained peptides include avimers, bicyclic peptides, and Cys-knots. In some embodiments, the drug-targeting moiety used in the described ADCs and compositions is selected from an affibody, an affilin, an anticalin, an atrimer, a DARPin, a FN3 scaffold such as an adnectin or a centyrin, a fynomer, a Kunitz domain, a pronectin, an O-body, an avimer, a bicyclic peptide, and a Cys-knot. In some embodiments, the drug-targeting moiety used in the described ADCs and compositions is a receptor-Fc fusion protein, e.g., a HER2-Fc chimeric fusion protein. Non-antibody scaffolds are reviewed, e.g., in Vazquez-Lombardi et al. (2015) Drug Dis Today 20(10):1271-83.

Antibodies

The antibody or antigen binding fragment (Ab) of Formula (I) includes within its scope any antibody or antigen binding fragment that specifically binds to a target antigen on a cancer cell. The antibody or antigen binding fragment may bind to a target antigen with a dissociation constant ($K_D$) of ≤1 mM, 5100 nM or ≤10 nM, or any amount in between, as measured by, e.g., BIAcore® analysis. In certain embodiments, the $K_D$ is 1 pM to 500 pM. In some embodiments, the $K_D$ is between 500 pM to 1 μM, 1 μM to 100 nM, or 100 mM to 10 nM.

In some embodiments, the antibody or antigen binding fragment is a four-chain antibody (also referred to as an immunoglobulin or a full-length or intact antibody), comprising two heavy chains and two light chains. In some embodiments, the antibody or antigen binding fragment is a two-chain half body (one light chain and one heavy chain), or an antigen binding fragment of an immunoglobulin. In some embodiments, the antibody or antigen binding fragment is an antigen binding fragment of an immunoglobulin that retains the ability to bind a target cancer antigen and/or provide a function of an immunoglobulin.

In some embodiments, the antibody or antigen binding fragment is an antibody or antigen binding fragment thereof. In some embodiments, the antibody or antigen binding fragment is an internalizing antibody or internalizing antigen binding fragment thereof. In some embodiments, the internalizing antibody or internalizing antigen binding fragment thereof binds to a target cancer antigen expressed on the surface of a cell and enters the cell upon binding. In some embodiments, the splicing modulator drug moiety of the ADC is released from the antibody or antigen binding fragment of the ADC after the ADC enters and is present in a cell expressing the target cancer antigen (i.e., after the ADC has been internalized), e.g., by cleavage, by degradation of the antibody or antigen binding fragment, or by any other suitable release mechanism.

Amino acid sequences of exemplary antibodies of the present disclosure are set forth in Tables 2-4.

TABLE 1

Antibodies

| mAb | Type | Target |
|---|---|---|
| trastuzumab (AB185) | humanized | HER2/NEU |
| B-B4 (AB205) | murine | CD138 (syndecan-1) |
| 1C1 (AB206) | humanized | EPHA2 |

TABLE 2

Amino acid sequences of mAb variable regions

| mAb | IgG chain | SEQ ID NO | Amino acid sequence |
|---|---|---|---|
| trastuzumab (AB185) | Heavy chain | 19 | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| trastuzumab (AB185) | Light chain | 20 | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRT |
| B-B4 (AB205) | Heavy chain | 21 | QVQLQQSGSELMMPGASVKISCKATGYTFSNYWIQRPGHGLEWIGEILPGTGRTIYNEKFKGKATFTADISSNTVQMQLSSLTSEDSAVYYCARRDYYGNFYYAMDYWGQGTSVTVSS |
| B-B4 (AB205) | Light chain | 22 | DIQMTQSTSSLSASLGDRVTISCSASQGINNYLNWYQQKPDGTVELLIYYTSTLQSGVPSRFSGSGSGTDYSLTISNLEPEDIGTYYCQQYSKLPRTFGGGTKLEIK |
| 1C1 (AB206) | Heavy chain | 23 | EVQLLESGGGLVQPGGSLRLSCAASGFTFSHYMMAWVRQAPGKGLEWVSRIGPS |

TABLE 2-continued

Amino acid sequences of mAb variable regions

| mAb | IgG chain | SEQ ID NO | Amino acid sequence |
|---|---|---|---|
| | | | GGPTHYADSVKGRFTISRDNSKNTLYL QMNSLRAEDTAVYYCAGYDSGYDYVAV AGPAE-YFQHWGQGTLVTVSS |
| 1C1 (AB206) | Light chain | 24 | DIQMTQSPSSLSASVGDRVTITCRASQ SISTWLAWYQQKPGKAPKLLIYKASNL HTGVPSRFSGSGSGTEFSLTISGLQPD DFATYYCQQYNSYS-RTFGQGTKVEIK |

TABLE 3

Amino acid sequences of mAb CDRs

| mAb | IgG chain | SEQ ID NO | Amino acid sequence |
|---|---|---|---|
| trastuzumab (AB185) | HCDR1 | 1 | GFNIKDTYIH |
| trastuzumab (AB185) | HCDR2 | 2 | RIYPTNGYTRYADSVKG |
| trastuzumab (AB185) | HCDR3 | 3 | WGGDGFYAMDV |
| trastuzumab (AB185) | LCDR1 | 4 | RASQDVNTAVAW |
| trastuzumab (AB185) | LCDR2 | 5 | SASFLES |
| trastuzumab (AB185) | LCDR3 | 6 | QQHYTTPPT |

TABLE 3-continued

Amino acid sequences of mAb CDRs

| mAb | IgG chain | SEQ ID NO | Amino acid sequence |
|---|---|---|---|
| B-B4 (AB205) | HCDR1 | 7 | NYWIE |
| B-B4 (AB205) | HCDR2 | 8 | ILPGTGRTIYNEKFKGKA |
| B-B4 (AB205) | HCDR3 | 9 | RDYYGNFYYAMDY |
| B-B4 (AB205) | LCDR1 | 10 | ASQGINNYLN |
| B-B4 (AB205) | LCDR2 | 11 | TSTLQS |
| B-B4 (AB205) | LCDR3 | 12 | QQYSKLPRT |
| 1C1 (AB206) | HCDR1 | 13 | HYMMA |
| 1C1 (AB206) | HCDR2 | 14 | RIGPSGGPTHYADSVKG |
| 1C1 (AB206) | HCDR3 | 15 | YDSGYDYVAVAGPAE-YFQH |
| 1C1 (AB206) | LCDR1 | 16 | RASWSISTWLA |
| 1C1 (AB206) | LCDR2 | 17 | KASNLHT |
| 1C1 (AB206) | LCDR3 | 18 | QQYNSYS-RT |

TABLE 4

Amino acid sequences of full-length mAb ig chains

| mAb | IgG chain | Class | SEQ ID NO | Amino acid sequence |
|---|---|---|---|---|
| trastuzumab (AB185) | Heavy chain | IgG1 | 25 | EVQLVESGGGLVQPGGSLRLSCAA SGFNIKDTYIHWVRQAPGKGLEWV ARIYPTNGYTRYADSVKGRFTISA DTSKNTAYLQMNSLRAEDTAVYYC SRWGGDGFYAMDYWGQGTLVTVSS ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPPKSCDKTHTCPPCPAPELLG GPSVFLFPPKPKDTLMISRTPEVT CVVVDVSHEDPEVKFNWYVDGVEV HNAKTKPREEQYNSTYRVVSVLTV LHQDWLNGKEYKCKVSNKALPAPI EKTISKAKGQPREPQVYTLPPSRD ELTKNQVSLTCLVKGFYPSDIAVE WESNGQPENNYKTTPPVLDSDGSF FLYSKLTVDKSRWQQGNVFSCSVM HEALHNHYTQKSLSLSPGK |
| trastuzumab (AB185) | Light chain | kappa | 26 | DIQMTQSPSSLSASVGDRVTITCR ASQDVNTAVAWYQQKPGKAPKLLI YSASFLYSGVPSRFSGSRSGTDFT LTISSLQPEDFATYYCQQHYTTPP TFGQGTKVEIKRTVAAPSVFIFPP SDEQLKSGTASVVCLLNNFYPREA KVQWKVDNALQSGNSQESVTEQDS KDSTYSLSSTLTLSKADYEKHKVY ACEVTHQGLSSPVTKSFNRGEC |

TABLE 4-continued

| Amino acid sequences of full-length mAb ig chains | | | | |
|---|---|---|---|---|
| mAb | IgG chain | Class | SEQ ID NO | Amino acid sequence |
| B-B4 (AB205) | Heavy chain | IgG2a | 27 | QVQLQQSGSELMMPGASVKISCKA<br>TGYTFSNYWIQRPGHGLEWIGEIL<br>PGTGRTIYNEKFKGKATFTADISS<br>NTVQMQLSSLTSEDSAVYYCARRD<br>YYGNFYYAMDYWGQGTSVTVSSAK<br>TTPPSVYPLAPGSAAQTNSMVTLG<br>CLVKGYFPEPVTVTWNSGSLSSGV<br>HTFPAVLQSDLYTLSSSVTVPSST<br>WPSETVTCNVAHPASSTKVDKKIV<br>PRDCGCKPCICTVPEVSSVFIFPP<br>KPKDVLTITLTPKVTCVVVDISKD<br>DPEVQFSWFVDDVEVHTAQTQPRE<br>EQFNSTFRSVSELPIMHQDWLNGK<br>EFKCRVNSAAFPAPIEKTISKTKG<br>RPKAPQVYTIPPPKEQMAKDKVSL<br>TCMITDFFPEDITVEWQWNGQPAE<br>NYKNTQPIMDTDGSYFVYSKLNVQ<br>KSNWEAGNTFTCSVLHEGLHNHHT<br>EKSLSHSPG |
| B-B4 (AB205) | Light chain | kappa | 28 | DIQMTQSTSSLSASLGDRVTISCS<br>ASQGINNYLNWYQQKPDGTVELLI<br>YYTSTLQSGVPSRFSGSGSGTDYS<br>LTISNLEPEDIGTYYCQQYSKLPR<br>TFGGGTKLEIKRADAAPTVSIFPP<br>SSEQLTSGGASWCFLNNFYPKDI<br>NVKWKIDGSERQNGVLNSWTDQDS<br>KDSTYSMSSTLTLTKDEYERHNSY<br>TCEATHKTSTSPIVKSFNRNEC |
| 1C1 (AB206) | Heavy chain | IgG1 | 29 | EVQLLESGGGLVQPGGSLRLSCAA<br>SGFTFSHYMMAWVRQAPGKGLEWV<br>SRIGPSGGPTHYADSVKGRFTISR<br>DNSKNTLYLQMNSLRAEDTAVYYC<br>AGYDSGYDYVAVAGPAEYFQHWGQ<br>GTLVTVSSASTKGPSVFPLAPSSK<br>STSGGTAALGCLVKDYFPEPVTVS<br>WNSGALTSGVHTFPAVLQSSGLYS<br>LSSVVTVPSSSLGTQTYICNVNHK<br>PSNTKVDKKVEPKSCDKTHTCPPC<br>PAPELLGGPSVFLFPPKPKDTLMI<br>SRTPEVTCVVVDVSHEDPEVKFNW<br>YVDGVEVHNAKTKPREEQYNSTYR<br>VVSVLTVLHQDWLNGKEYKCKVSN<br>KALPAPIEKTISKAKGQPREPQVY<br>TLPPSRDELTKNQVSLTCLVKGFY<br>PSDIAVEWESNGQPENNYKTTPPV<br>LDSDGSFFLYSKLTVDKSRWQQGN<br>VFSCSVMHEALHNHYTQKSLSLSP<br>G |
| 1C1 (AB206) | Light chain | kappa | 30 | DIQMTQSPSSLSASVGDRVTITCR<br>ASQSISTWLAWYQQKPGKAPKLLI<br>YKASNLHTGVPSRFSGSGSGTEFS<br>LTISGLQPDDFATYYCQQYNSYSR<br>TFGQGTKVEIKRTVAAPSVFIFPP<br>SDEQLKSGTASVVCLLNNFYPREA<br>KVQWKVDNALQSGNSQESVTEQDS<br>KDSTYSLSSTLTLSKADYEKHKVY<br>ACEVTHQGLSSPVTKSFNRGEC |

TABLE 5

| Exemplary target antigen amino acid sequences | | |
|---|---|---|
| Antigen | SEQ ID NO | Amino acid sequence |
| HER2/NEU | 31 | MELAALCRWGLLLALLPPGAASTQVCTGTDMKLRLPASPETHLDM<br>LRHLYQGCQVVQGNLELTYLPTNASLSFLQDIQEVQGYVLIAHNQ<br>VRQVPLQRLRIVRGTQLFEDNYALAVLDNGDPLNNTTPVTGASPG<br>GLRELQLRSLTEILKGGVLIQRNPQLCYQDTILWKDIFHKNNQLA<br>LTLIDTNRSRACHPCSPMCKGSRCWGESSEDCQSLTRTVCAGGCA |

TABLE 5-continued

Exemplary target antigen amino acid sequences

| Antigen | SEQ ID NO | Amino acid sequence |
|---|---|---|
| | | RCKGPLPTDCCHEQCAAGCTGPKHSDCLACLHFNHSGICELHCPA<br>LVTYNTDTFESMPNPEGRYTFGASCVTACPYNYLSTDVGSCTLVC<br>PLHNQEVTAEDGTQRCEKCSKPCARVCYGLGMEHLREVRAVTSAN<br>IQEFAGCKKIFGSLAFLPESFDGDPASNTAPLQPEQLQVFETLEE<br>ITGYLYISAWPDSLPDLSVFQNLQVIRGRILHNGAYSLTLQGLGI<br>SWLGLRSLRELGSGLALIHHNTHLCFVHTVPWDQLFRNPHQALLH<br>TANRPEDECVGEGLACHQLCARGHCWGPGPTQCVNCSQFLRGQEC<br>VEECRVLQGLPREYVNARHCLPCHPECQPQNGSVTCFGPEADQCV<br>ACAHYKDPPFCVARCPSGVKPDLSYMPIWKFPDEEGACQPCPINC<br>THSCVDLDDKGCPAEQRASPLTSIISAVVGILLVVVLGVVFGILI<br>KRRQQKIRKYTMRRLLQETELVEPLTPSGAMPNQAQMRILKETEL<br>RKVKVLGSGAFGTVYKGIWIPDGENVKIPVAIKVLRENTSPKANK<br>EILDEAYVMAGVGSPYVSRLLGICLTSTVQLVTQLMPYGCLLDHV<br>RENRGRLGSQDLLNWCMQIAKGMSYLEDVRLVHRDLAARNVLVKS<br>PNHVKITDFGLARLLDIDETEYHADGGKVPIKWMALESILRRRFT<br>HQSDVWSYGVTVWELMTFGAKPYDGIPAREIPDLLEKGERLPQPP<br>ICTIDVYMIMVKCWMIDSECRPRFRELVSEFSRMARDPQRFVVIQ<br>NEDLGPASPLDSTFYRSLLEDDDMGDLVDAEEYLVPQQGFFCPDP<br>APGAGGMVHHRHRSSSTRSGGGDLTLGLEPSEEEAPRSPLAPSEG<br>AGSDVFDGDLGMGAAKGLQSLPTHDPSPLQRYSEDPTVPLPSETD<br>GYVAPLTCSPQPEYVNQPDVRPQPPSPREGPLPAARPAGATLERP<br>KTLSPGKNGVVKDVFAFGGAVENPEYLTPQGGAAPQPHPPPAFSP<br>AFDNLYYWDQDPPERGAPPSTFKGTPTAENPEYLGLDVPV |
| CD138 | 32 | MRRAALWLWLCALALSLQPALPQIVATNLPPEDQDGSGDDSDNFS<br>GSGAGALQDITLSQQTPSTWKDTQLLTAIPTSPEPTGLEATAAST<br>STLPAGEGPKEGEAVVLPEVEPGLTAREQEATPRPRETTQLPTTH<br>LASTTTATTAQEPATSHPHRDMQPGHHETSTPAGPSQADLHTPHT<br>EDGGPSATERAAEDGASSQLPAAEGSGEQDFTFETSGENTAVVAV<br>EPDRRNQSPVDQGATGASQGLLDRKEVLGGVIAGGLVGLIFAVCL<br>VGFMLYRMKKKDEGSYSLEEPKQANGGAYQKPTKQEEFYA |
| EPHA2 | 33 | MELQAARACFALLWGCALAAAAAAQGKEVVLLDFAAAGGELGWLT<br>HPYGKGWDLMQNIMNDMPIYMYSVCNVMSGDQDNWLRTNWVYRGE<br>AERIFIELKFTVRDCNSFPGGASSCKETFNLYYAESDLDYGTNFQ<br>KRLFTKIDTIAPDEITVSSDFEARHVKLNVEERSVGPLTRKGFYL<br>AFQDIGACVALLSVRVYYKKCPELLQGLAHFPETIAGSDAPSLAT<br>VAGTCVDHAVVPPGGEEPRMHCAVDGEWLVPIGQCLCQAGYEKVE<br>DACQACSPGFFKFEASESPCLECPEHTLPSPEGATSCECEEGFFR<br>APQDPASMPCTRPPSAPHYLTAVGMGAKVELRWTPPQDSGGREDI<br>VYSVTCEQCWPESGECGPCEASVRYSEPPHGLTRTSVTVSDLEPH<br>MNYTFTVEARNGVSGLVTSRSFRTASVSINQTEPPKVRLEGRSTT<br>SLSVSWSIPPPQQSRVWKYEVTYRKKGDSNSYNVRRTEGFSVTLD<br>DLAPDTTYLVQVQALTQEGQGAGSKVHEFQTLSPEGSGNLAVIGG<br>VAVGVVLLLVLAGVGFFIHRRRKNQRARQSPEDVYFSKSEQLKPL<br>KTYVDPHTYEDPNQAVLKFTTEIHPSCVTRQKVIGAGEFGEVYKG<br>MLKTSSGKKEVPVAIKTLKAGYTEKQRVDFLGEAGIMGQFSHHNI<br>IRLEGVISKYKPMMIITEYMENGALDKFLREKDGEFSVLQLVGML<br>RGIAAGMKYLANMNYVHRDLAARNILVNSNLVCKVSDFGLSRVLE<br>DDPEATYTTSGGKIPIRWTAPEAISYRKFTSASDVWSFGIVMWEV<br>MTYGERPYWELSNHEVMKAINDGFRLPTPMDCPSAIYQLMMQCWQ<br>QERARRPKFADIVSILDKLIRAPDSLKTLADFDPRVSIRLPSTSG<br>SEGVPFRTVSEWLESIKMQQYTEHFMAAGYTAIEKVVQMTNDDIK<br>RIGVRLPGHQKRIAYSLLGLKDQVNTVGIPI |
| MSLN | 43 | MALPTARPLLGSCGTPALGSLLFLLFSLGWVQPSRTLAGETGQEA<br>APLDGVLANPPNISSLSPRQLLGFPCAEVSGLSTERVRELAVALA<br>QKNVKLSTEQLRCLAHRLSEPPEDLDALPLDLLLFLNPDAFSGPQ<br>ACTRFFSRITKANVDLLPRGAPERQRLLPAALACWGVRGSLLSEA<br>DVRALGGLACDLPGRFVAESAEVLLPRLVSCPGPLDQDQQEAARA<br>ALQGGGPPYGPPSTWSVSTMDALRGLLPVLGQPIIRSIPQGIVAA<br>WRQRSSRDPSWRQPERTILRPRFRREVEKTACPSGKKAREIDESL<br>IFYKKWELEACVDAALLATQMDRVNAIPFTYEQLDVLKHKLDELY<br>PQGYPESVIQHLGYLFLKMSPEDIRKWNVTSLETLKALLEVNKGH<br>EMSPQAPRRPLPQVATLIDRFVKGRGQLDKDTLDTLTAFYPGYLC<br>SLSPEELSSVPPSSIWAVRPQDLDTCDPRQLDVLYPKARLAFQNM<br>NGSEYFVKIQSFLGGAPTEDLKALSQQNVSMDLATFMKLRTDAVL<br>PLTVAEVQKLLGPHVEGLKAEERHRPVRDWILRQRQDDLDTLGLG<br>LQGGIPNGYLVLDLSMQEALSGTPCLLGPGPVLTVLALLLASTLA |
| FOLH1 | 44 | MWNLLHETDSAVATARRPRWLCAGALVLAGGFFLLGFLFGWFIKS<br>SNEATNITPKHNMKAFLDELKAENIKKFLYNFTQIPHLAGTEQNF<br>QLAKQIQSQWKEFGLDSVELAHYDVLLSYPNKTHPNYISIINEDG<br>NEIFNTSLFEPPPPGYENVSDIVPPFSAFSPQGMPEGDLVYVNYA<br>RTEDFFKLERDMKINCSGKIVIARYGKVFRGNKVKNAQLAGAKGV<br>ILYSDPADYFAPGVKSYPDGWNLPGGGVQRGNILNLNGAGDPLTP |

TABLE 5-continued

| Antigen | SEQ ID NO | Amino acid sequence |
|---|---|---|
| | | GYPANEYAYRRGIAEAVGLPSIPVHPIGYYDAQKLLEKMGGSAPP DSSWRGSLKVPYNVGPGFTGNFSTQKVKMHIHSTNEVTRIYNVIG TLRGAVEPDRYVILGGHRDSWVFGGIDPQSGAAVVHEIVRSFGTL KKEGWRPRRTILFASWDAEEFGLLGSTEWAEENSRLLQERGVAYI NADSSIEGNYTLRVDCTPLMYSLVHNLTKELKSPDEGFEGKSLYE SWTKKSPSPEFSGMPRISKLGSGNDFEVFFQRLGIASGRARYTKN WETNKFSGYPLYHSVYETYELVEKFYDPMFKYHLTVAQVRGGMVF ELANSIVLPFDCRDYAVVLRKYADKIYSISMKHPQEMKTYSVSFD SLFSAVKNFTEIASKFSERLQDFDKSNPIVLRMMNDQLMFLERAF IDPLGLPDRPFYRHVIYAPSSHNKYAGESFPGIYDALFDIESKVD PSKAWGEVKRQIYVAAFTVQAAAETLSEVA |
| CDH6 | 45 | MRTYRYFLLLFWVGQPYPTLSTPLSKRTSGFPAKKRALELSGNSK NELNRSKRSWMWNQFFLLEEYTGSDYQYVGKLHSDQDRGDGSLKY ILSGDGAGDLFIINENTGDIQATKRLDREEKPVYILRAQAINRRT GRPVEPESEFIIKIHDINDNEPIFTKEVYTATVPEMSDVGTFVVQ VTATDADDPTYGNSAKVVYSILQGQPYFSVESETGIIKTALLNMD RENREQYQVVIQAKDMGGQMGGLSGTTTVNITLTDVNDNPPRFPQ STYQFKTPESSPPGTPIGRIKASDADVGENAEIEYSITDGEGLDM FDVITDQETQEGIITVKKLLDFEKKKVYTLKVEASNPYVEPRFLY LGPFKDSATVRIVVEDVDEPPVFSKLAYILQIREDAQINTTIGSV TAQDPDAARNPVKYSVDRHTDMDRIFNIDSGNGSIFTSKLLDRET LLWHNITVIATEINNPKQSSRVPLYIKVLDVNDNAPEFAEFYETF VCEKAKADQLIQTLHAVDKDDPYSGHQFSFSLAPEAASGSNFTIQ DNKDNTAGILTRKNGYNRHEMSTYLLPVVISDNDYPVQSSTGTVT VRVCACDHHGNMQSCHAEALIHPTGLSTGALVAILLCIVILLVTV VLFAALRRQRKKEPLIISKEDIRDNIVSYNDEGGGEEDTQAFDIG TLRNPEAIEDNKLRRDIVPEALFLPRRTPTARDNTDVRDFINQRL KENDTDPTAPPYDSLATYAYEGTGSVADSLSSLESVTTDADQDYD YLSDWGPRFKKLADMYGGVDSDKDS |
| CEACAM5 | 46 | MESPSAPPHRWCIPWQRLLLTASLLTFWNPPTTAKLTIESTPFNV AEGKEVLLLVHNLPQHLFGYSWYKGERVDGNRQIIGYVIGTQQAT PGPAYSGREIIYPNASLLIQNIIQNDTGFYTLHVIKSDLVNEEAT GQFRVYPELPKPSISSNNSKPVEDKDAVAFTCEPETQDATYLWWV NNQSLPVSPRLQLSNGNRTLTLFNVTRNDTASYKCETQNPVSARR SDSVILNVLYGPDAPTISPLNTSYRSGENLNLSCHAASNPPAQYS WFVNGTFQQSTQELFIPNITVNNSGSYTCQAHNSDTGLNRTTVTT ITVYAEPPKPFITSNNSNPVEDEDAVALTCEPEIQNTTYLWWVNN QSLPVSPRLQLSNDNRTLTLLSVTRNDVGPYECGIQNKLSVDHSD PVILNVLYGPDDPTISPSYTYYRPGVNLSLSCHAASNPPAQYSWL IDGNIQQHTQELFISNITEKNSGLYTCQANNSASGHSRTTVKTIT VSAELPKPSISSNNSKPVEDKDAVAFTCEPEAQNTTYLWWVNGQS LPVSPRLQLSNGNRTLTLFNVTRNDARAYVCGIQNSVSANRSDPV TLDVLYGPDTPIISPPDSSYLSGANLNLSCHSASNPSPQYSWRIN GIPQQHTQVLFIAKITPNNNGTYACFVSNLATGRNNSIVKSITVS ASGTSPGLSAGATVGIMIGVLVGVALI |
| CFC1B | 47 | MTWRHHVRLLFTVSLALQIINLGNSYQREKHNGGREEVTKVATQK HRQSPLNWTSSHFGEVTGSAEGWGPEEPLPYSWAFGEGASARPRC CRNGGTCVLGSFCVCPAHFTGRYCEHDQRRSECGALEHGAWTLRA CHLCRCIFGALHCLPLQTPDRCDPKDFLASHAHGPSAGGAPSLLL LLPCALLHRLLRPDAPAHPRSLVPSVLQRERRPCGRPGLGHRL |
| ENPP3 | 48 | MESTLTLATEQPVKKNTLKKYKIACIVLLALLVIMSLGLGLGLGL RKLEKQGSCRKKCFDASFRGLENCRCDVACKDRGDCCWDFEDTCV ESTRIWMCNKFRCGETRLEASLCSCSDDCLQRKDCCADYKSVCQG ETSWLEENCDTAQQSQCPEGFDLPPVILFSMDGFRAEYLYTWDTL MPNINKLKTCGIHSKYMRAMYPTKTFPNHYTIVTGLYPESHGIID NNMYDVNLNKNFSLSSKEQNNPAWWHGQPMWLTAMYQGLKAATYF WPGSEVAINGSFPSIYMPYNGSVPFEERISTLLKWLDLPKAERPR FYTMYFEEPDSSGHAGGPVSARVIKALQVVDHAFGMLMEGLKQRN LHNCVNIILLADHGMDQTYCNKMEYMTDYFPRINFFYMYEGPAPR IRAHNIPHDFFSFNSEEIVRNLSCRKPDQHFKPYLTPDLPKRLHY AKNVRIDKVHLFVDQQWLAVRSKSNTNCGGGNHGYNNEFRSMEAI FLAHGPSFKEKTEVEPFENIEVYNLMCDLLRIQPAPNNGTHGSLN HLLKVPFYEPSHAEEVSKFSVCGFANPLPTESLDCFCPHLQNSTQ LEQVNQMLNLTQEEITATVKVNLPFGRPRVLQKNVDHCLLYHREY VSGFGKAMRMPMWSSYTVPQLGDTSPLPPTVPDCLRADVRVPPSE SQKCSFYLADKNITHGFLYPPASNRTSDSQYDALITSNLVPMYEE FRKMWDYFHSVLLIKHATERNGVNVVSGPIFDYNYDGHFDAPDEI TKHLANTDVPIPTHYFVVLTSCKNKSHTPENCPGWLDVLPFIIPH RPTNVESCPEGKPEALWVEERFTAHIARVRDVELLTGLDFYQDKV QPVSEILQLKTYLPTFETTI |

TABLE 5-continued

Exemplary target antigen amino acid sequences

| Antigen | SEQ ID NO | Amino acid sequence |
|---|---|---|
| FOLR1 | 49 | MAQRMTTQLLLLLVWVAVVGEAQTRIAWARTELLNVCMNAKHHKE<br>KPGPEDKLHEQCRPWRKNACCSTNTSQEAHKDVSYLYRFNWNHCG<br>EMAPACKRHFIQDTCLYECSPNLGPWIQQVDQSWRKERVLNVPLC<br>KEDCEQWWEDCRTSYTCKSNWHKGWNWTSGFNKCAVGAACQPFHF<br>YFPTPTVLCNEIWTHSYKVSNYSRGSGRCIQMWFDPAQGNPNEEV<br>ARFYAAAMSGAGPWAAWPFLLSLALMLLWLLS |
| HAVCR1 | 50 | MHPQVVILSLILHLADSVAGSVKVGGEAGPSVTLPCHYSGAVTSM<br>CWNRGSCSLFTCQNGIVWTNGTHVTYRKDTRYKLLGDLSRRDVSL<br>TIENTAVSDSGVYCCRVEHRGWFNDMKITVSLEIVPPKVTTTPIV<br>TTVPTVTTVRTSTTVPTTTTVPMTTVPTTTVPTTMSIPTTTTVLT<br>TMTVSTTTSVPTTTSIPTTTSVPVTTTVSTFVPPMPLPRQNHEPV<br>ATSPSSPQPAETHPTTLQGAIRREPTSSPLYSYTTDGNDTVTESS<br>DGLWNNNQTQLFLEHSLLTANTTKGIYAGVCISVLVLLALLGVII<br>AKKYFFKKEVQQLSVSFSSLQIKALQNAVEKEVQAEDNIYIENSL<br>YATD |
| KIT | 51 | MRGARGAWDFLCVLLLLLRVQTGSSQPSVSPGEPSPPSIHPGKSD<br>LIVRVGDEIRLLCTDPGFVKWTFEILDETNENKQNEWITEKAEAT<br>NTGKYTCTNKHGLSNSIYVFVRDPAKLFLVDRSLYGKEDNDTLVR<br>CPLTDPEVTNYSLKGCQGKPLPKDLRFIPDPKAGIMIKSVKRAYH<br>RLCLHCSVDQEGKSVLSEKFILKVRPAFKAVPVVSVSKASYLLRE<br>GEEFTVTCTIKDVSSSVYSTWKRENSQTKLQEKYNSWHHGDFNYE<br>RQATLTISSARVNDSGVFMCYANNTFGSANVTTTLEVVDKGFINI<br>FPMINTTVFVNDGENVDLIVEYEAFPKPEHQQWIYMNRTFTDKWE<br>DYPKSENESNIRYVSELHLTRLKGTEGGTYTFLVSNSDVNAAIAF<br>NVYVNTKPEILTYDRLVNGMLQCVAAGFPEPTIDWYFCPGTEQRC<br>SASVLPVDVQTLNSSGPPFGKLVVQSSIDSSAFKHNGTVECKAYN<br>DVGKTSAYFNFAFKGNNKEQIHPHTLFTPLLIGFVIVAGMMCIIV<br>MILTYKYLQKPMYEVQWKVVEEINGNNYVYIDPTQLPYDHKWEFP<br>RNRLSFGKTLGAGAFGKVVEATAYGLIKSDAAMTVAVKMLKPSAH<br>LTEREALMSELKVLSYLGNHMNIVNLLGACTIGGPTLVITEYCCY<br>GDLLNFLRRKRDSFICSKQEDHAEAALYKNLLHSKESSCSDSTNE<br>YMDMKPGVSYVVPTKADKRRSVRIGSYIERDVTPAIMEDDELALD<br>LEDLLSFSYQVAKGMAFLASKNCIHRDLAARNILLTHGRITKICD<br>FGLARDIKNDSNYVVKGNARLPVKWMAPESIFNCVYTFESDVWSY<br>GIFLWELFSLGSSPYPGMPVDSKFYKMIKEGFRMLSPEHAPAEMY<br>DIMKTCWDADPLKRPTFKQIVQLIEKQISESTNHIYSNLANCSPN<br>RQKPVVDHSVRINSVGSTASSSQPLLVHDDV |
| MET | 52 | MKAPAVLAPGILVLLFTLVQRSNGECKEALAKSEMNVNMKYQLPN<br>FTAETPIQNVILHEHHIFLGATNYIYVLNEEDLQKVAEYKTGPVL<br>EHPDCFPCQDCSSKANLSGGVWKDNINMALVVDTYYDDQLISCGS<br>VNRGTCQRHVFPHNHTADIQSEVHCIFSPQIEEPSQCPDCVVSAL<br>GAKVLSSVKDRFINFFVGNTINSSYFPDHPLHSISVRRLKETKDG<br>FMFLTDQSYIDVLPEFRDSYPIKYVHAFESNNFIYFLTVQRETLD<br>AQTFHTRIIRFCSINSGLHSYMEMPLECILTEKRKKRSTKKEVFN<br>ILQAAYVSKPGAQLARQIGASLNDDILFGVFAQSKPDSAEPMDRS<br>AMCAFPIKYVNDFFNKIVNKNNVRCLQHFYGPNHEHCFNRTLLRN<br>SSGCEARRDEYRTEFTTALQRVDLFMGQFSEVLLTSISTFIKGDL<br>TIANLGTSEGRFMQVVVSRSGPSTPHVNFLLDSHPVSPEVIVEHT<br>LNQNGYTLVITGKKITKIPLNGLGCRHFQSCSQCLSAPPFVQCGW<br>CHDKCVRSEECLSGTWTQQICLPAIYKVFPNSAPLEGGTRLTICG<br>WDFGFRRNNKFDLKKTRVLLGNESCTLTLSESTMNTLKCTVGPAM<br>NKHFNMSIIISNGHGTTQYSTFSYVDPVITSISPKYGPMAGGTLL<br>TLTGNYLNSGNSRHISIGGKTCTLKSVSNSILECYTPAQTISTEF<br>AVKLKIDLANRETSIFSYREDPIVYEIHPTKSFISGGSTITGVGK<br>NLNSVSVPRMVINVHEAGRNFTVACQHRSNSEIICCTTPSLQQLN<br>LQLPLKTKAFFMLDGILSKYFDLIYVHNPVFKPFEKPVMISMGNE<br>NVLEIKGNDIDPEAVKGEVLKVGNKSCENIHLHSEAVLCTVPNDL<br>LKLNSELNIEWKQAISSTVLGKVIVQPDQNFTGLIAGVVSISTAL<br>LLLLGFFLWLKKRKQIKDLGSELVRYDARVHTPHLDRLVSARSVS<br>PTTEMVSNESVDYRATFPEDQFPNSSQNGSCRQVQYPLTDMSPIL<br>TSGDSDISSPLLQNTVHIDLSALNPELVQAVQHVVIGPSSLIVHF<br>NEVIGRGHFGCVYHGTLLDNDGKKIHCAVKSLNRITDIGEVSQFL<br>TEGIIMKDFSHPNVLSLLGICLRSEGSPLVVLPYMKHGDLRNFIR<br>NETHNPTVKDLIGFGLQVAKGMKYLASKKFVHRDLAARNCMLDEK<br>FTVKVADFGLARDMYDKEYYSVHNKTGAKLPVKWMALESLQTQKF<br>TTKSDVWSFGVLLWELMTRGAPPYPDVNTFDITVYLLQGRRLLQP<br>EYCPDPLYEVMLKCWHPKAEMRPSFSELVSRISAIFSTFIGEHYV<br>HVNATYVNVKCVAPYPSLLSSEDNADDEVDTRPASFWETS |
| MUC16 | 53 | MLKPSGLPGSSSPTRSLMTGSRSTKATPEMDSGLTGATLSPKTST<br>GAIVVTEHTLPFTSPDKTLASPTSSVVGRTTQSLGVMSSALPEST<br>SRGMTHSEQRTSPSLSPQVNGTPSRNYPATSMVSGLSSPRTRTSS<br>TEGNFTKEASTYTLTVETTSGPVTEKYTVPTETSTTEGDSTETPW |

TABLE 5-continued

Exemplary target antigen amino acid sequences

| Antigen | SEQ ID NO | Amino acid sequence |
|---|---|---|
| | | DTRYIPVKITSPMKTFADSTASKENAPVSMTPAETTVTDSHTPGR |
| | | TNPSFGTLYSSFLDLSPKGTPNSRGETSLELILSTTGYPFSSPEP |
| | | GSAGHSRISTSAPLSSSASVLDNKISETSIFSGQSLTSPLSPGVP |
| | | EARASTMPNSAIPFSMTLSNAETSAERVRSTISSLGTPSISTKQT |
| | | AETILTFHAFAETMDIPSTHIAKTLASEWLGSPGTLGGTSTSALT |
| | | TTSPSTTLVSEETNTHHSTSGKETEGTLNTSMTPLETSAPGEESE |
| | | MTATLVPTLGFTTLDSKIRSPSQVSSSHPTRELRTTGSTSGRQSS |
| | | STAAHGSSDILRATTSSTSKASSWTSESTAQQFSEPQHTQWVETS |
| | | PSMKTERPPASTSVAAPITTSVPSVVSGFTTLKTSSTKGIWLEET |
| | | SADTLIGESTAGPTTHQFAVPTGISMTGGSSTRGSQGTTHLLTRA |
| | | TASSETSADLTLATNGVPVSVSPAVSKTAAGSSPPGGTKPSYTMV |
| | | SSVIPETSSLQSSAFREGTSLGLTPLNTRHPFSSPEPDSAGHTKI |
| | | STSIPLLSSASVLEDKVSATSTFSHHKATSSITTGTPEISTKTKP |
| | | SSAVLSSMTLSNAATSPERVRNATSPLTHPSPSGEETAGSVLTLS |
| | | TSAETTDSPNIHPTGTLTSESSESPSTLSLPSVSGVKTTFSSSTP |
| | | STHLFTSGEETEETSNPSVSQPETSVSRVRTTLASTSVPTPVFPT |
| | | MDTWPTRSAQFSSSHLVSELRATSSTSVTNSTGSALPKISHLTGT |
| | | ATMSQTNRDTFNDSAAPQSTTWPETSPRFKTGLPSATTTVSTSAT |
| | | SLSATVMVSKFTSPATSSMEATSIREPSTTILTTETTNGPGSMAV |
| | | ASTNIPIGKGYITEGRLDTSHLPIGTTASSETSMDFTMAKESVSM |
| | | SVSPSQSMDAAGSSTPGRTSQFVDTFSDDVYHLTSREITIPRDGT |
| | | SSALTPQMTATHPPSPDPGSARSTWLGILSSSPSSPTPKVTMSST |
| | | FSTQRVTTSMIMDTVETSRWNMPNLPSTTSLTPSNIPTSGAIGKS |
| | | TLVPLDTPSPATSLEASEGGLPTLSTYPESTNTPSIHLGAHASSE |
| | | SPSTIKLTMASVVKPGSYTPLTFPSIETHIHVSTARMAYSSGSSP |
| | | EMTAPGETNTGSTWDPTTYITTTDPKDTSSAQVSTPHSVRTLRTT |
| | | ENHPKTESATPAAYSGSPKISSSPNLTSPATKAWTITDTTEHSTQ |
| | | LHYTKLAEKSSGFETQSAPGPVSVVIPTSPTIGSSTLELTSDVPG |
| | | EPLVLAPSEQTTITLPMATWLSTSLTEEMASTDLDISSPSSPMST |
| | | FAIFPPMSTPSHELSKSEADTSAIRNTDSTTLDQHLGIRSLGRTG |
| | | DLTTVPITPLTTTWTSVIEHSTQAQDTLSATMSPTHVTQSLKDQT |
| | | SIPASASPSHLTEVYPELGTQGRSSSEATTFWKPSTDTLSREIET |
| | | GPTNIQSTPPMDNTTTGSSSSGVTLGIAHLPIGTSSPAETSTNMA |
| | | LERRSSTATVSMAGTMGLLVTSAPGRSISQSLGRVSSVLSESTTE |
| | | GVTDSSKGSSPRLNTQGNTALSSSLEPSYAEGSQMSTSIPLTSSP |
| | | TTPDVEFIGGSTFWTKEVTTVMTSDISKSSARTESSSATLMSTAL |
| | | GSTENTGKEKLRTASMDLPSPTPSMEVTPWISLTLSNAPNTTDSL |
| | | DLSHGVHTSSAGTLATDRSLNTGVTRASRLENGSDTSSKSLSMGN |
| | | STHTSMTYTEKSEVSSSIHPRPETSAPGAETTLTSTPGNRAISLT |
| | | LPFSSIPVEEVISTGITSGPDINSAPMTHSPITPPTIVWTSTGTI |
| | | EQSTQPLHAVSSEKVSVQTQSTPYVNSVAVSASPTHENSVSSGSS |
| | | TSSPYSSASLESLDSTISRRNAITSWLWDLTTSLPTTTWPSTSLS |
| | | EALSSGHSGVSNPSSTTTEFPLFSAASTSAAKQRNPETETHGPQN |
| | | TAASTLNTDASSVTGLSETPVGASISSEVPLPMAITSRSDVSGLT |
| | | SESTANPSLGTASSAGTKLTRTISLPTSESLVSFRMNKDPWTVSI |
| | | PLGSHPTTNTETSIPVNSAGPPGLSTVASDVIDTPSDGAESIPTV |
| | | SFSPSPDTEVTTISHFPEKTTHSFRTISSLTHELTSRVTPIPGDW |
| | | MSSAMSTKPTGASPSITLGERRTITSAAPTTSPIVLTASFTETST |
| | | VSLDNETTVKTSDILDARKTNELPSDSSSSSDLINTSIASSTMDV |
| | | TKTASISPTSISGMTASSSPSLFSSDRPQVPTSTTETNTATSPSV |
| | | SSNTYSLDGGSNVGGTPSTLPPFTITHPVETSSALLAWSRPVRTF |
| | | STMVSTDTASGENPTSSNSVVTSVPAPGTWTSVGSTTDLPAMGFL |
| | | KTSPAGEAHSLLASTIEPATAFTPHLSAAVVTGSSATSEASLLTT |
| | | SESKAIHSSPQTPTTPTSGANWETSATPESLLVVTETSDTTLTSK |
| | | ILVTDTILFSTVSTPPSKFPSTGTLSGASFPTLLPDTPAIPLTAT |
| | | EPTSSLATSFDSTPLVTIASDSLGTVPETTLTMSETSNGDALVLK |
| | | TVSNPDRSIPGITIQGVTESPLHPSSTSPSKIVAPRNTTYEGSIT |
| | | VALSTLPAGTTGSLVFSQSSENSETTALVDSSAGLERASVMPLTT |
| | | GSQGMASSGGIRSGSTHSTGTKTFSSLPLTMNPGEVTAMSEITTN |
| | | RLTATQSTAPKGIPVKPTSAESGLLTPVSASSSPSKAFASLTTAP |
| | | PTWGIPQSTLTFEFSEVPSLDTKSASLPTPGQSLNTIPDSDASTA |
| | | SSSLSKSPEKNPRARMMTSTKAISASSFQSTGFTETPEGSASPSM |
| | | AGHEPRVPTSGTGDPRYASESMSYPDPSKASSAMTSTSLASKLTT |
| | | LFSTGQAARSGSSSSPISLSTEKETSFLSPTASTSRKTSLFLGPS |
| | | MARQPNILVHLQTSALTLSPTSTLNMSQEEPPELTSSQTIAEEEG |
| | | TTAETQTLTFTPSETPTSLLPVSSPTEPTARRKSSPETWASSISV |
| | | PAKTSLVETTDGTLVTTIKMSSQAAQGNSTWPAPAEETGSSPAGT |
| | | SPGSPEMSTTLKIMSSKEPSISPEIRSTVRNSPWKTPETTVPMET |
| | | TVEPVTLQSTALGSGSTSISHLPTGTTSPTKSPTENMLATERVSL |
| | | SPSPPEAWTNLYSGTPGGTRQSLATMSSVSLESPTARSITGTGQQ |
| | | SSPELVSKTTGMEFSMWHGSTGGTTGDTHVSLSTSSNILEDPVTS |
| | | PNSVSSLTDKSKHKTETWVSTTAIPSTVLNNKIMAAEQQTSRSVD |
| | | EAYSSTSSWSDQTSGSDITLGASPDVTNTLYITSTAQTTSLVSLP |
| | | SGDQGITSLTNPSGGKTSSASSVTSPSIGLETLRANVSAVKSDIA |
| | | PTAGHLSQTSSPAEVSILDVTTAPTPGISTTITTMGTNSISTTTP |
| | | NPEVGMSTMDSTPATERRTTSTEHPSTWSSTAASDSWTVTDMTSN |

TABLE 5-continued

Exemplary target antigen amino acid sequences

| Antigen | SEQ ID NO | Amino acid sequence |
|---|---|---|
| | | LKVARSPGTISTMHTTSFLASSTELDSMSTPHGRITVIGTSLVTP |
| | | SSDASAVKTETSTSERTLSPSDTTASTPISTFSRVQRMSISVPDI |
| | | LSTSWTPSSTEAEDVPVSMVSTDHASTKTDPNTPLSTFLFDSLST |
| | | LDWDTGRSLSSATATTSAPQGATTPQELTLETMISPATSQLPFSI |
| | | GHITSAVTPAAMARSSGVTFSRPDPTSKKAEQTSTQLPTTTSAHP |
| | | GQVPRSAATTLDVIPHTAKTPDATFQRQGQTALTTEARATSDSWN |
| | | EKEKSTPSAPWITEMMNSVSEDTIKEVTSSSSVLRTLNTLDINLE |
| | | SGTTSSPSWKSSPYERIAPSESTTDKEAIHPSTNTVETTGWVTSS |
| | | EHASHSTIPAHSASSKLTSPVVTTSTREQAIVSMSTTTWPESTRA |
| | | RTEPNSFLTIELRDVSPYMDTSSTTQTSIISSPGSTAITKGPRTE |
| | | ITSSKRISSSFLAQSMRSSDSPSEAITRLSNFPAMTESGGMILAM |
| | | QTSPPGATSLSAPTLDTSATASWTGTPLATTQRFTYSEKTTLFSK |
| | | GPEDTSQPSPPSVEETSSSSSLVPIHATTSPSNILLTSQGHSPSS |
| | | TPPVTSVFLSETSGLGKTTDMSRISLEPGTSLPPNLSSTAGEALS |
| | | TYEASRDTKAIHHSADTAVTNMEATSSEYSPIPGHTKPSKATSPL |
| | | VTSHIMGDITSSTSVFGSSETTEIETVSSVNQGLQERSTSQVASS |
| | | ATETSTVITHVSSGDATTHVTKTQATFSSGTSISSPHQFITSTNT |
| | | FTDVSTNPSTSLIMTESSGVTITTQTGPTGAATQGPYLLDTSTMP |
| | | YLTETPLAVTPDFMQSEKTTLISKGPKDVSWTSPPSVAETSYPSS |
| | | LTPFLVTTIPPATSTLQGQHTSSPVSATSVLTSGLVKTTDMLNTS |
| | | MEPVTNSPQNLNNPSNEILATLAATTDIETIHPSINKAVTNMGTA |
| | | SSAHVLHSTLPVSSEPSTATSPMVPASSMGDALASISIPGSETTD |
| | | IEGEPTSSLTAGRKENSTLQEMNSTTESNIILSNVSVGAITEATK |
| | | MEVPSFDATFIPTPAQSTKFPDIFSVASSRLSNSPPMTISTHMTT |
| | | TQTGSSGATSKIPLALDTSTLETSAGTPSVVTEGFAHSKITTAMN |
| | | NDVKDVSQTNPPFQDEASSPSSQAPVLVTTLPSSVAFTPQWHSTS |
| | | SPVSMSSVLTSSLVKTAGKVDTSLETVTSSPQSMSNTLDDISVTS |
| | | AATTDIETTHPSINTVVTNVGTTGSAFESHSTVSAYPEPSKVTSP |
| | | NVTTSTMEDTTISRSIPKSSKTTRTETETTSSLTPKLRETSISQE |
| | | ITSSTETSTVPYKELTGATTEVSRTDVTSSSSTSFPGPDQSTVSL |
| | | DISTETNTRLSTSPIMTESAEITITTQTGPHGATSQDTFTMDPSN |
| | | TTPQAGIHSAMTHGFSQLDVTTLMSRIPQDVSWTSPPSVDKTSSP |
| | | SSFLSSPAMTTPSLISSTLPEDKLSSPMTSLLTSGLVKITDILRT |
| | | RLEPVTSSLPNFSSTSDKILATSKDSKDTKEIFPSINTEETNVKA |
| | | NNSGHESHSPALADSETPKATTQMVITTTVGDPAPSTSMPVHGSS |
| | | ETTNIKREPTYFLTPRLRETSTSQESSFPTDTSFLLSKVPTGTIT |
| | | EVSSTGVNSSSKISTPDHDKSTVPPDTFTGEIPRVFTSSIKTKSA |
| | | EMTITTQASPPESASHSTLPLDTSTTLSQGGTHSTVTQGFPYSEV |
| | | TTLMGMGPGNVSWMTTPPVEETSSVSSLMSSPAMTSPSPVSSTSP |
| | | QSIPSSPLPVTALPTSVLVTTTDVLGTTSPESVTSSPPNLSSITH |
| | | ERPATYKDTAHTEAAMHHSTNTAVTNVGTSGSGHKSQSSVLADSE |
| | | TSKATPLMSTTSTLGDTSVSTSTPNISQTNQIQTEPTASLSPRLR |
| | | ESSTSEKTSSTTETNTAFSYVPTGAITQASRTEISSSRTSISDLD |
| | | RPTIAPDISTGMITRLFTSPIMTKSAEMTVTTQTTTPGATSQGIL |
| | | PWDTSTTLFQGGTHSTVSQGFPHSEITTLRSRTPGDVSWMTTPPV |
| | | EETSSGFSLMSPSMTSPSPVSSTSPESIPSSPLPVTALLTSVLVT |
| | | TTNVLGTTSPEPVTSSPPNLSSPTQERLTTYKDTAHTEAMHASMH |
| | | TNTAVANVGTSISGHESQSSVPADSHTSKATSPMGITFAMGDTSV |
| | | STSTPAFFETRIQTESTSSLIPGLRDTRTSEEINTVTETSTVLSE |
| | | VPTTTTTEVSRTEVITSSRTTISGPDHSKMSPYISTETITRLSTF |
| | | PFVTGSTEMAITNQTGPIGTISQATLTLDTSSTASWEGTHSPVTQ |
| | | RFPHSEETTTMSRSTKGVSWQSPPSVEETSSPSSPVPLPAITSHS |
| | | SLYSAVSGSSPTSALPVTSLLTSGRRKTIDMLDTHSELVTSSLPS |
| | | ASSFSGEILTSEASTNTETIHFSENTAETNMGTTNSMHKLHSSVS |
| | | IHSQPSGHTPPKVTGSMMEDAIVSTSTPGSPETKNVDRDSTSPLT |
| | | PELKEDSTALVMNSTTESNTVFSSVSLDAATEVSRAEVTYYDPTF |
| | | MPASAQSTKSPDISPEASSSHSNSPPLTISTHKTIATQTGPSGVT |
| | | SLGQLTLDTSTIATSAGTPSARTQDFVDSETTSVMNNDLNDVLKT |
| | | SPFSAEEANSLSSQAPLLVTTSPSPVTSTLQEHSTSSLVSVTSVP |
| | | TPTLAKITDMDTNLEPVTRSPQNLRNTLATSEATTDTHTMHPSIN |
| | | TAVANVGTTSSPNEFYFTVSPDSDPYKATSAVVITSTSGDSIVST |
| | | SMPRSSAMKKIESETTFSLIFRLRETSTSQKIGSSSDTSTVFDKA |
| | | FTAATTEVSRTELTSSSRTSIQGTEKPTMSPDTSTRSVTMLSTFA |
| | | GLTKSEERTIATQTGPHRATSQGTLTWDTSITTSQAGTHSAMTHG |
| | | FSQLDLSTLTSRVPEYISGTSPPSVEKTSSSSSLLSLPAITSPSP |
| | | VPTTLPESRPSSPVHLTSLPTSGLVKTTDMLASVASLPPNLGSTS |
| | | HKIPTTSEDIKDTEKMYPSTNIAVTNVGTTTSEKESYSSVPAYSE |
| | | PPKVTSPMVTSFNIRDTIVSTSMPGSSEITRIEMESTFSLAHGLK |
| | | GTSTSQDPIVSTEKSAVLHKLTTGATETSRTEVASSRRTSIPGPD |
| | | HSTESPDISTEVIPSLPISLGITESSNMTIITRTGPPLGSTSQGT |
| | | FTLDTPTTSSRAGTHSMATQEFPHSEMTTVMNKDPEILSWTIPPS |
| | | IEKTSFSSSLMPSPAMTSPPVSSTLPKTIHTTPSPMTSLLTPSLV |
| | | MTTDTLGTSPEPTTSSPPNLSSTSHEILTTDEDTTAIEAMHPSTS |
| | | TAATNVETTSSGHGSQSSVLADSEKTKATAPMDTTSTMGHTTVST |
| | | SMSVSSETTKIKRESTYSLTPGLRETSISQNASFSTDTSIVLSEV |
| | | PTGTTAEVSRTEVTSSGRTSIPGPSQSTVLPEISTRTMTRLFASP |

TABLE 5-continued

Exemplary target antigen amino acid sequences

| Antigen | SEQ ID NO | Amino acid sequence |
|---|---|---|
| | | TMTESAEMTIPTQTGPSGSTSQDTLTLDTSTTKSQAKTHSTLTQR<br>FPHSEMTTLMSRGPGDMSWQSSPSLENPSSLPSLLSLPATTSPPP<br>ISSTLPVTISSSPLPVTSLLTSSPVTTTDMLHTSPELVTSSPPKL<br>SHTSDERLTTGKDTTNTEAVHPSTNTAASNVEIPSSGHESPSSAL<br>ADSETSKATSPMFITSTQEDTTVAISTPHFLETSRIQKESISSLS<br>PKLRETGSSVETSSAIETSAVLSEVSIGATTEISRTEVTSSSRTS<br>ISGSAESTMLPEISTTRKIIKFPTSPILAESSEMTIKTQTSPPGS<br>TSESTFTLDTSTTPSLVITHSTMTQRLPHSEITTLVSRGAGDVPR<br>PSSLPVEETSPPSSQLSLSAMISPSPVSSTLPASSHSSSASVTSL<br>LTPGQVKTTEVLDASAEPETSSPPSLSSTSVEILATSEVTTDTEK<br>IHPFSNTAVTKVGTSSSGHESPSSVLPDSETTKATSAMGTISIMG<br>DTSVSTLTPALSNTRKIQSEPASSLTTRLRETSTSEETSLATEAN<br>TVLSKVSTGATTEVSRTEAISFSRTSMSGPEQSTMSQDISIGTIP<br>RISASSVLTESAKMTITTQTGPSESTLESTLNLNTATTPSWVETH<br>SIVIQGFPHPEMTTSMGRGPGGVSWPSPPFVKETSPPSSPLSLPA<br>VTSPHPVSTTFLAHIPPSPLPVTSLLTSGPATTTDILGTSTEPGT<br>SSSSSLSTTSHERLTTYKDTAHTEAVHPSTNTGGTNVATTSSGYK<br>SQSSVLADSSPMCTTSTMGDTSVLTSTPAFLETRRIQTELASSLT<br>PGLRESSGSEGTSSGTKMSTVLSKVPTGATTEISKEDVTSIPGPA<br>QSTISPDISTRTVSWFSTSPVMTESAEITMNTHTSPLGATTQGTS<br>TLDTSSTTSLTMTHSTISQGFSHSQMSTLMRRGPEDVSWMSPPLL<br>EKTRPSFSLMSSPATTSPSPVSSTLPESISSSPLPVTSLLTSGLA<br>KTTDMLHKSSEPVTNSPANLSSTSVEILATSEVTTDTEKTHPSSN<br>RTVTDVGTSSSGHESTSFVLADSQTSKVTSPMVITSTMEDTSVST<br>STPGFFETSRIQTEPTSSLTLGLRKTSSSEGTSLATEMSTVLSGV<br>PTGATAEVSRTEVTSSSRTSISGFAQLTVSPETSTETITRLPTSS<br>IMTESAEMMIKTQTDPPGSTPESTHTVDISTTPNWVETHSTVTQR<br>FSHSEMTTLVSRSPGDMLWPSQSSVEETSSASSLLSLPATTSPSP<br>VSSTLVEDFPSASLPVTSLLNPGLVITTDRMGISREPGTSSTSNL<br>SSTSHERLTTLEDTVDTEDMQPSTHTAVTNVRTSISGHESQSSVL<br>SDSETPKATSPMGTTYTMGETSVSISTSDFFETSRIQIEPTSSLT<br>SGLRETSSSERISSATEGSTVLSEVPSGATTEVSRTEVISSRGTS<br>MSGPDQFTISPDISTEAITRLSTSPIMTESAESAITIETGSPGAT<br>SEGTLTLDTSTTTFWSGTHSTASPGFSHSEMTTLMSRTPGDVPWP<br>SLPSVEEASSVSSSLSSPAMTSTSFFSTLPESISSSPHPVTALLT<br>LGPVKTTDMLRTSSEPETSSPPNLSSTSAEILATSEVTKDREKIH<br>PSSNTPVVNVGTVIYKHLSPSSVLADLVTTKPTSPMATTSTLGNT<br>SVSTSTPAFPETMMTQPTSSLTSGLREISTSQETSSATERSASLS<br>GMPTGATTKVSRTEALSLGRTSTPGPAQSTISPEISTETITRIST<br>PLTTTGSAEMTITPKTGHSGASSQGTFTLDTSSRASWPGTHSAAT<br>HRSPHSGMTTPMSRGPEDVSWPSRPSVEKTSPPSSLVSLSAVTSP<br>SPLYSTPSESSHSSPLRVTSLFTPVMMKTTDMLDTSLEPVTTSPP<br>SMNITSDESLATSKATMETEAIQLSENTAVTQMGTISARQEFYSS<br>YPGLPEPSKVTSPVVTSSTIKDIVSTTIPASSEITRIEMESTSTL<br>TPTPRETSTSQEIHSATKPSTVPYKALTSATIEDSMTQVMSSSRG<br>PSPDQSTMSQDISTEVITRLSTSPIKTESTEMTITTQTGSPGATS<br>RGTLTLDTSTTFMSGTHSTASQGFSHSQMTALMSRTPGDVPWLSH<br>PSVEEASSASFSLSSPVMTSSSPVSSTLPDSIHSSSLPVTSLLTS<br>GLVKTTELLGTSSEPETSSPPNLSSTSAEILAITEVTTDTEKLEM<br>TNVVTSGYTHESPSSVLADSVTTKATSSMGITYPTGDTNVLTSTP<br>AFSDTSRIQTKSKLSLTPGLMETSISEETSSATEKSTVLSSVPTG<br>ATTEVSRTEAISSSRTSIPGPAQSTMSSDTSMETITRISTPLTRK<br>ESTDMAITPKTGPSGATSQGTFTLDSSSTASWPGTHSATTQRFPQ<br>SVVTTPMSRGPEDVSWPSPLSVEKNSPPSSLVSSSSVTSPSPLYS<br>TPSGSSHSSPVPVTSLFTSIMMKATDMLDASLEPETTSAPNMNIT<br>SDESLAASKATTETEAIHVFENTAASHVETTSATEELYSSSPGFS<br>EPTKVISPVVTSSSIRDNMVSTTMPGSSGITRIEIESMSSLTPGL<br>RETRTSQDITSSTETSTVLYKMPSGATPEVSRTEVMPSSRTSIPG<br>PAQSTMSLDISDEVVTRLSTSPIMTESAEITITTQTGYSLATSQV<br>TLPLGTSMTFLSGTHSTMSQGLSHSEMTNLMSRGPESLSWTSPRE<br>VETTRSSSSLTSLPLTTSLSPVSSTLLDSSPSSPLPVTSLILPGL<br>VKTTEVLDTSSEPKTSSSPNLSSTSVEIPATSEIMTDTEKIHPSS<br>NTAVAKVRTSSSVHESHSSVLADSETTITIPSMGITSAVDDTTVF<br>TSNPAFSETRRIPTEPTFSLTPGFRETSTSEETTSITETSAVLYG<br>VPTSATTEVSMTEIMSSNRIHIPDSDQSTMSPDIITEVITRLSSS<br>SMMSESTQMTITTQKSSPGATAQSTLTLATTTAPLARTHSTVPPR<br>FLHSEMTTLMSRSPENPSWKSSLFVEKTSSSSSLLSLPVTTSPSV<br>SSTLPQSIPSSSFSVTSLLTPGMVKTTDTSTEPGTSLSPNLSGTS<br>VEILAASEVTTDTEKIHPSSSMAVTNVGTTSSGHELYSSVSIHSE<br>PSKATYPVGTPSSMAETSISTSMPANFETTGFEAEPFSHLTSGFR<br>KTNMSLDTSSVTPTNTPSSPGSTHLLQSSKTDFTSSAKTSSPDWP<br>PASQYTEIPVDIITPFNASPSITESTGITSFPESRFTMSVTESTH<br>HLSTDLLPSAETISTGTVMPSLSEAMTSFATTGVPRAISGSGSPF<br>SRTESGPGDATLSTIAESLPSSTPVPFSSSTFTTTDSSTIPALHE<br>ITSSSATPYRVDTSLGTESSTTEGRLVMVSTLDTSSQPGRTSSSP<br>ILDTRMTESVELGTVTSAYQVPSLSTRLTRTDGIMEHITKIPNEA |

TABLE 5-continued

Exemplary target antigen amino acid sequences

| Antigen | SEQ ID NO | Amino acid sequence |
|---|---|---|
| | | AHRGTIRPVKGPQTSTSPASPKGLHTGGTKRMETTTTALKTTTTA |
| | | LKTTSRATLTTSVYTPTLGTLTPLNASMQMASTIPTEMMITTPYV |
| | | FPDVPETTSSLATSLGAETSTALPRTTPSVFNRESETTASLVSRS |
| | | GAERSPVIQTLDVSSSEPDTTASWVIHPAETIPTVSKTTPNFFHS |
| | | ELDTVSSTATSHGADVSSAIPTNISPSELDALTPLVTISGTDTST |
| | | TFPTLTKSPHETETRTTWLTHPAETSSTIPRTIPNFSHHESDATP |
| | | SIATSPGAETSSAIPIMTVSPGAEDLVTSQVTSSGTDRNMTIPTL |
| | | TLSPGEPKTIASLVTHPEAQTSSAIPTSTISPAVSRLVTSMVTSL |
| | | AAKTSTTNRALTNSPGEPATTVSLVTHPAQTSPTVPWTTSIFFHS |
| | | KSDTTPSMTTSHGAESSSAVPTPTVSTEVPGVVTPLVTSSRAVIS |
| | | TTIPILTLSPGEPETTPSMATSHGEEASSAIPTPTVSPGVPGVVT |
| | | SLVTSSRAVTSTTIPILTFSLGEPETTPSMATSHGTEAGSAVPTV |
| | | LPEVPGMVTSLVASSRAVTSTTLPTLTLSPGEPETTPSMATSHGA |
| | | EASSTVPTVSPEVPGVVTSLVTSSSGVNSTSIPTLILSPGELETT |
| | | PSMATSHGAEASSAVPTPTVSPGVSGVVTPLVTSSRAVTSTTIPI |
| | | LTLSSSEPETTPSMATSHGVEASSAVLTVSPEVPGMVTSLVTSSR |
| | | AVTSTTIPTLTISSDEPETTTSLVTHSEAKMISAIPTLAVSPTVQ |
| | | GLVTSLVTSSGSETSAFSNLTVASSQPETIDSWVAHPGTEASSVV |
| | | PTLTVSTGEPFTNISLVTHPAESSSTLPRTTSRFSHSELDTMPST |
| | | VTSPEAESSSAISTTISPGIPGVLTSLVTSSGRDISATFPTVPES |
| | | PHESEATASWVTHPAVTSTTVPRTTPNYSHSEPDTTPSIATSPGA |
| | | EATSDFPTITVSPDVPDMVTSQVTSSGTDTSITIPTLTLSSGEPE |
| | | TTTSFITYSETHTSSAIPTLPVSPGASKMLTSLVISSGTDSTTTF |
| | | PTLTETPYEPETTAIQLIHPAETNTMVPRTTPKFSHSKSDTTLPV |
| | | AITSPGPEASSAVSTTTISPDMSDLVTSLVPSSGTDTSTTFPTLS |
| | | ETPYEPETTATWLTHPAETSTTVSGTIPNFSHRGSDTAPSMVTSP |
| | | GVDTRSGVPTTTIPPSIPGVVTSQVTSSATDTSTAIPTLTPSPGE |
| | | PETTASSATHPGTQTGFTVPIRTVPSSEPDTMASWVTHPPQTSTP |
| | | VSRTTSSFSHSSPDATPVMATSPRTEASSAVLTTISPGAPEMVTS |
| | | QITSSGAATSTTVPTLTHSPGMPETTALLSTHPRTETSKTFPAST |
| | | VFPQVSETTASLTIRPGAETSTALPTQTTSSLFTLLVTGTSRVDL |
| | | SPTASPGVSAKTAPLSTHPGTETSTMIPTSTLSLGLLETTGLLAT |
| | | SSSAETSTSTLTLTVSPAVSGLSSASITTDKPQTVTSWNTETSPS |
| | | VTSVGPPEFSRTVTGTTMTLIPSEMPTPPKTSHGEGVSPTTILRT |
| | | TMVEATNLATTGSSPTVAKTTTTFNTLAGSLFTPLTTPGMSTLAS |
| | | ESVTSRTSYNHRSWISTTSSYNRRYWTPATSTPVTSTFSPGISTS |
| | | SIPSSTAATVPFMVPFTLNFTITNLQYEEDMRHPGSRKFNATERE |
| | | LQGLLKPLFRNSSLEYLYSGCRLASLRPEKDSSATAVDAICTHRP |
| | | DPEDLGLDRERLYWELSNLTNGIQELGPYTLDRNSLYVNGFTHRS |
| | | SMPTTSTPGTSTVDVGTSGTPSSSPSPTTAGPLLMPFTLNFTITN |
| | | LQYEEDMRRTGSRKFNTMESVLQGLLKPLFKNTSVGPLYSGCRLT |
| | | LLRPEKDGAATGVDAICTHRLDPKSPGLNREQLYWELSKLTNDIE |
| | | ELGPYTLDRNSLYVNGFTHQSSVSTTSTPGTSTVDLRTSGTPSSL |
| | | SSPTIMAAGPLLVPFTLNFTITNLQYGEDMGHPGSRKFNTTERVL |
| | | QGLLGPIFKNTSVGPLYSGCRLTSLRSEKDGAATGVDAICIHHLD |
| | | PKSPGLNRERLYWELSQLTNGIKELGPYTLDRNSLYVNGFTHRTS |
| | | VPTSSTPGTSTVDLGTSGTPFSLPSPATAGPLLVLFTLNFTITNL |
| | | KYEEDMHRPGSRKFNTTERVLQTLLGPMFKNTSVGLLYSGCRLTL |
| | | LRSEKDGAATGVDAICTHRLDPKSPGVDREQLYWELSQLTNGIKE |
| | | LGPYTLDRNSLYVNGFTHWIPVPTSSTPGTSTVDLGSGTPSSLPS |
| | | PTTAGPLLVPFTLNFTITNLKYEEDMHCPGSRKFNTTERVLQSLL |
| | | GPMFKNTSVGPLYSGCRLTLLRSEKDGAATGVDAICTHRLDPKSP |
| | | GVDREQLYWELSQLTNGIKELGPYTLDRNSLYVNGFTHQTSAPNT |
| | | STPGTSTVDLGTSGTPSSLPSPTSAGPLLVPFTLNFTITNLQYEE |
| | | DMHHPGSRKFNTTERVLQGLLGPMFKNTSVGLLYSGCRLTLLRPE |
| | | KNGAATGMDAICSHRLDPKSPGLNREQLYWELSQLTHGIKELGPY |
| | | TLDRNSLYVNGFTHRSSVAPTSTPGTSTVDLGTSGTPSSLPSPTT |
| | | AVPLLVPFTLNFTITNLQYGEDMRHPGSRKFNTTERVLQGLLGPL |
| | | FKNSSVGPLYSGCRLISLRSEKDGAATGVDAICTHHLNPQSPGLD |
| | | REQLYWQLSQMTNGIKELGPYTLDRNSLYVNGFTHRSSGLTTSTP |
| | | WTSTVDLGTSGTPSPVPSPTTTGPLLVPFTLNFTITNLQYEENMG |
| | | HPGSRKFNITESVLQGLLKPLFKSTSVGPLYSGCRLTLLRPEKDG |
| | | VATRVDAICTHRPDPKIPGLDRQQLYWELSQLTHSITELGPYTLD |
| | | RDSLYVNGFTQRSSVPTTSTPGTFTVQPETSETPSSLPGPTATGP |
| | | VLLPFTLNFTITNLQYEEDMRRPGSRKFNTTERVLQGLLMPLFKN |
| | | TSVSSLYSGCRLTLLRPEKDGAATRVDAVCTHRPDPKSPGLDRER |
| | | LYWKLSQLTHGITELGPYTLDRHSLYVNGFTHQSSMTTTRTPDTS |
| | | TMHLATSRTPASLSGPMTASPLLVLFTINFTITNLRYEENMHHPG |
| | | SRKFNTTERVLQGLLRPVFKNTSVGPLYSGCRLTLLRPKKDGAAT |
| | | KVDAICTYRPDPKSPGLDREQLYWELSQLTHSITELGPYTLDRDS |
| | | LYVNGFTQRSSVPTTSIPGTPTVDLGTSGTPVSKPGPSAASPLLV |
| | | LFTLNFTITNLRYEENMQHPGSRKFNTTERVLQGLLRSLFKSTSV |
| | | GPLYSGCRLTLLRPEKDGTATGVDAICTHHPDPKSPRLDREQLYW |
| | | ELSQLTHNITELGPYALDNDSLFVNGFTHRSSVSTTSTPGTPTVY |
| | | LGASKTPASIFGPSAASHLLILFTLNFTITNLRYEENMWPGSRKF |
| | | NTTERVLQGLLRPLFKNTSVGPLYSGCRLTLLRPEKDGEATGVDA |

TABLE 5-continued

Exemplary target antigen amino acid sequences

| Antigen | SEQ ID NO | Amino acid sequence |
|---|---|---|
| | | ICTHRPDPTGPGLDREQLYLELSQLTHSITELGPYTLDRDSLYVN GFTHRSSVPTTSTGVVSEEPFTLNFTINNLRYMADMGQPGSLKFN ITDNVMQHLLSPLFQRSSLGARYTGCRVIALRSVKNGAETRVDLL CTYLQPLSGPGLPIKQVFHELSQQTHGITRLGPYSLDKDSLYLNG YNEPGPDEPPTTPKPATTFLPPLSEATTAMGYHLKTLTLNFTISN LQYSPDMGKGSATFNSTEGVLQHLLRPLFQKSSMGPFYLGCQLIS LRPEKDGAATGVDTTCTYHPDPVGPGLDIQQLYWELSQLTHGVTQ LGFYVLDRDSLFINGYAPQNLSIRGEYQINFHIVNWNLSNPDPTS SEYITLLRDIQDKVTTLYKGSQLHDTFRFCLVTNLTMDSVLVTVK ALFSSNLDPSLVEQVFLDKTLNASFHWLGSTYQLVDIHVTEMESS VYQPTSSSSTQHFYLNFTITNLPYSQDKAQPGTTNYQRNKRNIED ALNQLFRNSSIKSYFSDCQVSTFRSVPNRHHTGVDSLCNFSPLAR RVDRVAIYEEFLRMTRNGTQLQNFTLDRSSVLVDGYSPNRNEPLT GNSDLPFWAVILIGLAGLLGVITCLICGVLVTTRRRKKEGEYNVQ QQCPGYYQSHLDLEDLQ |
| SLC39A6 | 54 | MARKLSVILILTFALSVTNPLHELKAAAFPQTTEKISPNWESGIN VDLAISTRQYHLQQLFYRYGENNSLSVEGFRKLLQNIGIDKIKRI HIHHDHDHHSDHEHHSDHERHSDHEHHSEHEHHSDHDHHSHHNHA ASGKNKRKALCPDHDSDSSGKDPRNSQGKGAHRPEHASGRRNVKD SVSASEVTSTVYNTVSEGTHFLETIETPRPGKLFPKDVSSSTPPS VTSKSRVSRLAGRKTNESVSEPRKGFMYSRNTNENPQECFNASKL LTSHGMGIQVPLNATEFNYLCPAIINQIDARSCLIHTSEKKAEIP PKTYSLQIAWVGGFIAISIISFLSLLGVILVPLMNRVFFKFLLSF LVALAVGTLSGDAFLHLLPHSHASHHHSHSHEEPAMEMKRGPLFS HLSSQNIEESAYFDSTWKGLTALGGLYFMFLVEHVLTLIKQFKDK KKKNQKKPENDDDVEIKKQLSKYESQLSTNEEKVDTDDRTEGYLR ADSQEPSHFDSQQPAVLEEEEVMIAHAHPQEVYNEYVPRGCKNKC HSHFHDTLGQSDDLIHHHHDYHHILHHHHHQNHHPHSHSQRYSRE ELKDAGVATLAWMVIMGDGLHNFSDGLAIGAAFTEGLSSGLSTSV AVFCHELPHELGDFAVLLKAGMTVKQAVLYNALSAMLAYLGMATG IFIGHYAENVSMWIFALTAGLFMYVALVDMVPEMLHNDASDHGCS RWGYFFLQNAGMLLGFGIMLLISIFEHKIVFRINF |
| SLC44A4 | 55 | MGGKQRDEDDEAYGKPVKYDPSFRGPIKNRSCTDVICCVLFLLFI LGYIVVGIVAWLYGDPRQVLYPRNSTGAYCGMGENKDKPYLLYFN IFSCILSSNIISVAENGLQCPTPQVCVSSCPEDPWTVGKNEFSQT VGEVFYTKNRNFCLPGVPWNMTVITSLQQELCPSFLLPSAPALGR CFPWTNVTPPALPGITNDTTIQQGISGLIDSLNARDISVKIFEDF AQSWYWILVALGVALVLSLLFILLLRLVAGPLVLVLILGVLGVLA YGIYYCWEEYRVLRDKGASISQLGFTTNLSAYQSVQETWLAALIV LAVLEAILLLMLIFLRQRIRIAIALLKEASKAVGQMMSTMFYPLV TFVLLLICIAYWAMTALYLATSGQPQYVLWASNISSPGCEKVPIN TSCNPTAHLVNSSCPGLMCVFQGYSSKGLIQRSVFNLQIYGVLGL FWTLNWVLALGQCVLAGAFASFYWAFHKPQDIPTFPLISAFIRTL RYHTGSLAFGALILTLVQIARVILEYIDHKLRGVQNPVARCIMCC FKCCLWCLEKFIKFLNRNAYIMIAIYGKNFCVSAKNAFMLLMRNI VRVVVLDKVTDLLLFFGKLLVVGGVGVLSFFFFSGRIPGLGKDFK SPHLNYYWLPIMTSILGAYVIASGFFSVFGMCVDTLFLCFLEDLE RNNGSLDRPYYMSKSLLKILGKKNEAPPDNKKRKK |
| STEAP1 | 56 | MESRKDITNQEELWKMKPRRNLEEDDYLHKDTGETSMLKRPVLLH LHQTAHADEFDCPSELQHTQELFPQWHLPIKIAAIIASLTFLYTL LREVIHPLATSHQQYFYKIPILVINKVLPMVSITLLALVYLPGVI AAIVQLHNGTKYKKFPHWLDKWMLTRKQFGLLSFFFAVLHAIYSL SYPMRRSYRYKLLNWAYQQVQQNKEDAWIEHDVWRMEIYVSLGIV GLAILALLAVTSIPSVSDSLTWREFHYIQSKLGIVSLLLGTIHAL IFAWNKWIDIKQFVWYTPPTFMIAVFLPIVVLIFKSILFLPCLRK KILKIRHGWEDVTKINKTEICSQL |

In various embodiments, an ADC disclosed herein may comprise any set of heavy and light chain variable domains listed in the tables above, or the set of six CDR sequences from the heavy and light chain set, e.g., by transplanting the six CDRs into a chosen human donor antibody framework. In various embodiments, an ADC disclosed herein may comprise amino acid sequences that are homologous to the sequences listed in the tables above, so long as the ADC retains the ability to bind to its target cancer antigen (e.g., with a $K_D$ of less than $1\times10^{-8}$ M) and retains one or more functional properties of the ADCs disclosed herein (e.g., ability to internalize, modulate RNA splicing, inhibit cell growth, etc.).

In some embodiments, the ADC further comprises human heavy and light chain constant domains or fragments thereof. For instance, the ADC may comprise a human IgG heavy chain constant domain (such as an IgG1) and a human kappa or lambda light chain constant domain. In various embodiments, the antibody or antigen binding fragment of the described ADCs comprises a human immunoglobulin G subtype 1 (IgG1) heavy chain constant domain with a human Ig kappa light chain constant domain.

In various other embodiments, the target cancer antigen for an ADC is human epidermal growth factor receptor 2 (HER2).

In various embodiments, the anti-HER2 antibody or antigen binding fragment thereof comprises three heavy chain CDRs and three light chain CDRs as follows: heavy chain CDR1 (HCDR1) consisting of SEQ ID NO:1, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:4, light chain CDR2 (LCDR2) consisting of SEQ ID NO:5, and light chain CDR3 (LCDR3) consisting of SEQ ID NO:6, as defined by the Kabat numbering system.

In various embodiments, the anti-HER2 antibody or antigen binding fragment thereof comprises a heavy chain variable region comprising the amino acid sequence of SEQ ID NO:19, and a light chain variable region comprising the amino acid sequence of SEQ ID NO:20. In some embodiments, the anti-HER2 antibody or antigen binding fragment thereof comprises the heavy chain variable region amino acid sequence of SEQ ID NO:19 and the light chain variable region amino acid sequence of SEQ ID NO:20, or sequences that are at least 95% identical to the disclosed sequences. In some embodiments, the anti-HER2 antibody or antigen binding fragment thereof has a heavy chain variable region amino acid sequence that is at least 96%, at least 97%, at least 98%, or at least 99% identical to SEQ ID NO:19 and/or a light chain variable region amino acid sequence that is at least 96%, at least 97%, at least 98%, or at least 99% identical to SEQ ID NO:20.

In various embodiments, the anti-HER2 antibody or antigen binding fragment thereof is an internalizing antibody or internalizing antigen binding fragment. In various embodiments, the anti-HER2 antibody comprises a human IgG1 heavy chain constant domain and a human Ig kappa light chain constant domain.

In various embodiments, the anti-HER2 antibody comprises the heavy chain amino acid sequence of SEQ ID NO:19 or a sequence that is at least 95% identical to SEQ ID NO:19, and the light chain amino acid sequence of SEQ ID NO:20 or a sequence that is at least 95% identical to SEQ ID NO:20. In particular embodiments, the anti-HER2 antibody comprises the heavy chain amino acid sequence of SEQ ID NO:19 and the light chain amino acid sequence of SEQ ID NO:20, or sequences that are at least 95% identical to the disclosed sequences. In some embodiments, the anti-HER2 antibody has a heavy chain amino acid sequence that is at least 96%, at least 97%, at least 98%, or at least 99% identical to SEQ ID NO:19 and a light chain amino acid sequence that is at least 96%, at least 97%, at least 98%, or at least 99% identical to SEQ ID NO:20. In various embodiments, the anti-HER2 antibody is trastuzumab, or an antigen binding fragment thereof.

In various embodiments, the anti-HER2 antibody or antigen binding fragment thereof comprises the three heavy chain CDRs and three light chain CDRs of trastuzumab or wherein the CDRs include no more than one, two, three, four, five, or six amino acid additions, deletions or substitutions of HCDR1 (SEQ ID NO:1), HCDR2 (SEQ ID NO:2), HCDR3 (SEQ ID NO:3); LCDR1 (SEQ ID NO:4), LCDR2 (SEQ ID NO:5), and LCDR3 (SEQ ID NO:6).

In various other embodiments, the target cancer antigen for an ADC is human syndecan-1 (CD138).

In various embodiments, the anti-CD138 antibody or antigen binding fragment thereof comprises three heavy chain CDRs and three light chain CDRs as follows: heavy chain CDR1 (HCDR1) consisting of SEQ ID NO:7, heavy chain CDR2 (HCDR2) consisting of SEQ ID NO:8, heavy chain CDR3 (HCDR3) consisting of SEQ ID NO:9; light chain CDR1 (LCDR1) consisting of SEQ ID NO:10, light chain CDR2 (LCDR2) consisting of SEQ ID NO:11, and light chain CDR3 (LCDR3) consisting of SEQ ID NO:12, as defined by the Kabat numbering system.

In various embodiments, the anti-CD138 antibody or antigen binding fragment thereof comprises a heavy chain variable region comprising the amino acid sequence of SEQ ID NO:21, and a light chain variable region comprising the amino acid sequence of SEQ ID NO:22. In some embodiments, the anti-CD138 antibody or antigen binding fragment thereof comprises the heavy chain variable region amino acid sequence of SEQ ID NO:21 and the light chain variable region amino acid sequence of SEQ ID NO:22, or sequences that are at least 95% identical to the disclosed sequences. In some embodiments, the anti-CD138 antibody or antigen binding fragment thereof has a heavy chain variable region amino acid sequence that is at least 96%, at least 97%, at least 98%, or at least 99% identical to SEQ ID NO:21 and/or a light chain variable region amino acid sequence that is at least 96%, at least 97%, at least 98%, or at least 99% identical to SEQ ID NO:22.

In various embodiments, the anti-CD138 antibody or antigen binding fragment thereof is an internalizing antibody or internalizing antigen binding fragment. In various embodiments, the anti-CD138 antibody comprises a murine IgG2a heavy chain constant domain and a murine Ig kappa light chain constant domain. In various embodiments, the anti-CD138 antibody comprises a human IgG2a heavy chain constant domain and a human Ig kappa light chain constant domain.

In various embodiments, the anti-CD138 antibody comprises the heavy chain amino acid sequence of SEQ ID NO:21 or a sequence that is at least 95% identical to SEQ ID NO:21, and the light chain amino acid sequence of SEQ ID NO:22 or a sequence that is at least 95% identical to SEQ ID NO:22. In particular embodiments, the anti-CD138 antibody comprises the heavy chain amino acid sequence of SEQ ID NO:21 and the light chain amino acid sequence of SEQ ID NO:22, or sequences that are at least 95% identical to the disclosed sequences. In some embodiments, the anti-CD138 antibody has a heavy chain amino acid sequence that is at least 96%, at least 97%, at least 98%, or at least 99% identical to SEQ ID NO:21 and a light chain amino acid sequence that is at least 96%, at least 97%, at least 98%, or at least 99% identical to SEQ ID NO:22. In various embodiments, the anti-CD138 antibody is B-B4, or an antigen binding fragment thereof.

In various embodiments, the anti-CD138 antibody or antigen binding fragment thereof comprises the three heavy chain CDRs and three light chain CDRs of B-B4 or wherein the CDRs include no more than one, two, three, four, five, or six amino acid additions, deletions or substitutions of HCDR1 (SEQ ID NO:7), HCDR2 (SEQ ID NO:8), HCDR3 (SEQ ID NO:9); LCDR1 (SEQ ID NO:10), LCDR2 (SEQ ID NO:11), and LCDR3 (SEQ ID NO:12).

In various other embodiments, the target cancer antigen for an ADC is human ephrin type-A receptor 2 (EPHA2).

In various embodiments, the anti-EPHA2 antibody or antigen binding fragment thereof comprises three heavy chain CDRs and three light chain CDRs as follows: heavy chain CDR1 (HCDR1) consisting of SEQ ID NO:13, heavy chain CDR2 (HCDR2) consisting of SEQ ID NO:14, heavy chain CDR3 (HCDR3) consisting of SEQ ID NO:15; light chain CDR1 (LCDR1) consisting of SEQ ID NO: 16, light chain CDR2 (LCDR2) consisting of SEQ ID NO:17, and light chain CDR3 (LCDR3) consisting of SEQ ID NO:18, as defined by the Kabat numbering system.

In various embodiments, the anti-EPHA2 antibody or antigen binding fragment thereof comprises a heavy chain variable region comprising the amino acid sequence of SEQ ID NO:23, and a light chain variable region comprising the amino acid sequence of SEQ ID NO:24. In some embodiments, the anti-EPHA2 antibody or antigen binding fragment thereof comprises the heavy chain variable region amino acid sequence of SEQ ID NO:23 and the light chain variable region amino acid sequence of SEQ ID NO:24, or sequences that are at least 95% identical to the disclosed sequences. In some embodiments, the anti-EPHA2 antibody or antigen binding fragment thereof has a heavy chain variable region amino acid sequence that is at least 96%, at least 97%, at least 98%, or at least 99% identical to SEQ ID NO:23 and/or a light chain variable region amino acid sequence that is at least 96%, at least 97%, at least 98%, or at least 99% identical to SEQ ID NO:24.

In various embodiments, the anti-EPHA2 antibody or antigen binding fragment thereof is an internalizing antibody or internalizing antigen binding fragment. In various embodiments, the anti-EPHA2 antibody comprises a human IgG1 heavy chain constant domain and a human Ig kappa light chain constant domain.

In various embodiments, the anti-EPHA2 antibody comprises the heavy chain amino acid sequence of SEQ ID NO:23 or a sequence that is at least 95% identical to SEQ ID NO:23, and the light chain amino acid sequence of SEQ ID NO:24 or a sequence that is at least 95% identical to SEQ ID NO:24. In particular embodiments, the anti-EPHA2 antibody comprises the heavy chain amino acid sequence of SEQ ID NO:23 and the light chain amino acid sequence of SEQ ID NO:24, or sequences that are at least 95% identical to the disclosed sequences. In some embodiments, the anti-EPHA2 antibody has a heavy chain amino acid sequence that is at least 96%, at least 97%, at least 98%, or at least 99% identical to SEQ ID NO:23 and a light chain amino acid sequence that is at least 96%, at least 97%, at least 98%, or at least 99% identical to SEQ ID NO:24. In some embodiments, the anti-EPHA2 antibody comprises a heavy chain encoded by the nucleotide sequence of SEQ ID NO:23; and a light chain encoded by the nucleotide sequence of SEQ ID NO:24. In various embodiments, the anti-EPHA2 antibody is 1C1, or an antigen binding fragment thereof.

In various embodiments, the anti-EPHA2 antibody or antigen binding fragment thereof comprises the three heavy chain CDRs and three light chain CDRs of 1C1 or wherein the CDRs include no more than one, two, three, four, five, or six amino acid additions, deletions or substitutions of HCDR1 (SEQ ID NO:13), HCDR2 (SEQ ID NO:14), HCDR3 (SEQ ID NO:15); LCDR1 (SEQ ID NO:16), LCDR2 (SEQ ID NO:17), and LCDR3 (SEQ ID NO:18).

In various embodiments, amino acid substitutions are of single residues. Insertions usually will be on the order of from about 1 to about 20 amino acid residues, although considerably larger insertions may be tolerated as long as biological function is retained (e.g., binding to a target antigen). Deletions usually range from about 1 to about 20 amino acid residues, although in some cases deletions may be much larger. Substitutions, deletions, insertions, or any combination thereof may be used to arrive at a final derivative or variant. Generally, these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as Table 6.

TABLE 6

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 6. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general may produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

In various embodiments where variant antibody sequences are used in an ADC, the variants typically exhibit the same qualitative biological activity and will elicit the same immune response, although variants may also be selected to modify the characteristics of the antigen binding proteins as needed. Alternatively, the variant may be designed such that the biological activity of the antigen binding protein is altered. For example, glycosylation sites may be altered or removed.

Various antibodies may be used with the ADCs used herein to target cancer cells. As shown below, the linker-payloads in the ADCs disclosed herein are surprisingly effective with different tumor antigen-targeting antibodies. Suitable antigens expressed on tumor cells but not healthy cells, or expressed on tumor cells at a higher level than on healthy cells, are known in the art, as are antibodies directed against them. These antibodies may be used with the linkers and splicing modulator payloads disclosed herein. In some embodiments, the antibody or antigen binding fragment targets HER2, and the HER2-targeting antibody or antigen binding fragment is trastuzumab. In some embodiments, the antibody or antigen binding fragment targets CD138, and the CD138-targeting antibody or antigen binding fragment is B-B4. In some embodiments, the antibody or antigen binding fragment targets EPHA2, and the EPHA2-targeting antibody or antigen binding fragment is 1C1. In some embodiments, while the disclosed linkers and splicing modulator payloads are surprisingly effective with several different tumor-targeting antibodies, HER2-targeting antibodies such as trastuzumab, CD138-targeting antibodies such as B-B4, and EPHA2-targeting antibodies such as 1C1 provided particularly improved drug:antibody ratio, aggregation level, stability (i.e., in vitro and in vivo stability), tumor targeting (i.e., cytotoxicity, potency), and/or treatment efficacy. Improved treatment efficacy can be measured in vitro or in vivo, and may include reduced tumor growth rate and/or reduced tumor volume.

In certain embodiments, alternate antibodies to the same targets or antibodies to different antigen targets are used and provide at least some of the favorable functional properties described above (e.g., improved stability, improved tumor targeting, improved treatment efficacy, etc.). In some embodiments, some or all of these favorable functional properties are observed when the disclosed linkers and splicing modulator payloads are conjugated to an alternate HER2-, CD138-, or EPHA2-targeting antibody or antigen binding fragment. In some other embodiments, some or all of these favorable functional properties are observed when the disclosed linkers and splicing modulator payloads are conjugated to a HER2-targeting antibody or antigen binding fragment. In some embodiments, the antibody or antigen binding fragment targets HER2. In some embodiments, the HER2-targeting antibody or antigen binding fragment is trastuzumab. In some other embodiments, some or all of these favorable functional properties are observed when the disclosed linkers and splicing modulator payloads are conjugated to a CD138-targeting antibody or antigen binding fragment. In some embodiments, the antibody or antigen binding fragment targets CD138. In some embodiments, the CD138-targeting antibody or antigen binding fragment is B-B4. In some other embodiments, some or all of these favorable functional properties are observed when the disclosed linkers and splicing modulator payloads are conjugated to an EPHA2-targeting antibody or antigen binding fragment. In some embodiments, the antibody or antigen binding fragment targets EPHA2. In some embodiments, the EPHA2-targeting antibody or antigen binding fragment is 1C1.

Linkers

In various embodiments, the linker in an ADC is stable extracellularly in a sufficient manner to be therapeutically effective. In some embodiments, the linker is stable outside a cell, such that the ADC remains intact when present in extracellular conditions (e.g., prior to transport or delivery into a cell). The term "intact," used in the context of an ADC, means that the antibody or antigen binding fragment remains attached to the drug moiety (e.g., the splicing modulator). As used herein, "stable," in the context of a linker or ADC comprising a linker, means that no more than 20%, no more than about 15%, no more than about 10%, no more than about 5%, no more than about 3%, or no more than about 1% of the linkers (or any percentage in between) in a sample of ADC are cleaved (or in the case of an overall ADC are otherwise not intact) when the ADC is present in extracellular conditions. In some embodiments, the linkers and/or ADCs disclosed herein are surprisingly stable compared to alternate linkers and/or ADCs with alternate linkers and/or splicing modulator payloads. In some embodiments, the ADCs disclosed herein can remain intact for more than about 48 hours, more than 60 hours, more than about 72 hours, more than about 84 hours, or more than about 96 hours.

Whether a linker is stable extracellularly can be determined, for example, by including an ADC in plasma for a predetermined time period (e.g., 2, 4, 6, 8, 16, 24, 48, or 72 hours) and then quantifying the amount of free drug moiety present in the plasma. Stability may allow the ADC time to localize to target tumor cells and prevent the premature release of the drug moiety, which could lower the therapeutic index of the ADC by indiscriminately damaging both normal and tumor tissues. In some embodiments, the linker is stable outside of a target cell and releases the drug moiety from the ADC once inside of the cell, such that the drug can bind to its target (e.g., to the SF3b spliceosome complex). Thus, an effective linker will: (i) maintain the specific binding properties of the antibody or antigen binding fragment; (ii) allow delivery, e.g., intracellular delivery, of the drug moiety via stable attachment to the antibody or antigen binding fragment; (iii) remain stable and intact until the ADC has been transported or delivered to its target site; and (iv) allow for the therapeutic effect, e.g., cytotoxic effect, of the drug moiety after cleavage or alternate release mechanism.

Linkers may impact the physico-chemical properties of an ADC. As many cytotoxic agents are hydrophobic in nature, linking them to the antibody with an additional hydrophobic moiety may lead to aggregation. ADC aggregates are insoluble and often limit achievable drug loading onto the antibody, which can negatively affect the potency of the ADC. Protein aggregates of biologics, in general, have also been linked to increased immunogenicity. As shown below, linkers disclosed herein result in ADCs with low aggregation levels and desirable levels of drug loading.

A linker may be "cleavable" or "non-cleavable" (Ducry and Stump (2010) Bioconjugate Chem. 21:5-13). Cleavable linkers are designed to release the drug moiety (e.g., the splicing modulator) when subjected to certain environment factors, e.g., when internalized into the target cell, whereas non-cleavable linkers generally rely on the degradation of the antibody or antigen binding fragment itself.

In some embodiments, the linker is a non-cleavable linker. In some embodiments, the splicing modulator drug moiety of the ADC is released by degradation of the antibody or antigen binding fragment. Non-cleavable linkers tend to remain covalently associated with at least one amino acid of the antibody and the drug upon internalization by and degradation within the target cell. Numerous exemplary non-cleavable linkers are described herein, and others are known in the art. Exemplary non-cleavable linkers may comprise thioether, cyclohexyl, N-succinimidyl 4-(N-maleimidomethyl) cyclohexane-1 carboxylate (SMCC), or N-hydroxysuccinimide (NHS), one or more polyethylene glycol (PEG) moieties, e.g., 1, 2, 3, 4, 5, or 6 PEG moieties, or one or more alkyl moieties.

In some embodiments, the linker is a cleavable linker. A cleavable linker refers to any linker that comprises a cleavable moiety. As used herein, the term "cleavable moiety" refers to any chemical bond that can be cleaved. Suitable cleavable chemical bonds are well known in the art and include, but are not limited to, acid labile bonds, protease/peptidase labile bonds, photolabile bonds, disulfide bonds, and esterase labile bonds. Linkers comprising a cleavable moiety can allow for the release of the splicing modulator drug moiety from the ADC via cleavage at a particular site in the linker.

In some embodiments, the linker is cleavable under intracellular conditions, such that cleavage of the linker sufficiently releases the splicing modulator drug moiety from the antibody or antigen binding fragment in the intracellular environment to activate the drug and/or render the drug therapeutically effective. In some embodiments, the splicing modulator drug moiety is not cleaved from the antibody or antigen binding fragment until the ADC enters a cell that expresses an antigen specific for the antibody or antigen binding fragment of the ADC, and the splicing modulator drug moiety is cleaved from the antibody or antigen binding fragment upon entering the cell. In some embodiments, the linker comprises a cleavable moiety that is positioned such that no part of the linker or the antibody or antigen binding fragment remains bound to the splicing modulator drug moiety upon cleavage. Exemplary cleavable linkers include acid labile linkers, protease/peptidase-sensitive linkers, photolabile linkers, dimethyl-, disulfide-, or sulfonamide-containing linkers.

In some embodiments, the linker is a pH-sensitive linker, and is sensitive to hydrolysis at certain pH values. Typically, the pH-sensitive linker is cleavable under acidic conditions. This cleavage strategy generally takes advantage of the lower pH in the endosomal (pH~5-6) and lysosomal (pH~4.8) intracellular compartments, as compared to the cytosol (pH~7.4), to trigger hydrolysis of an acid labile group in the linker, such as a hydrazone (Jain et al. (2015) Pharm Res 32:3526-40). In some embodiments, the linker is an acid labile and/or hydrolyzable linker. For example, an acid labile linker that is hydrolyzable in the lysosome, and contains an acid labile group (e.g., a hydrazone, a semicarbazone, a thiosemicarbazone, a cis-aconitic amide, an orthoester, an acetal, a ketal, or the like) can be used. See, e.g., U.S. Pat. Nos. 5,122,368; 5,824,805; 5,622,929; Dubowchik and Walker (1999) Pharm Therapeutics 83:67-123; Neville et al. (1989) Biol Chem. 264:14653-61. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond) (see, e.g., U.S. Pat. No. 5,622,929).

In some embodiments, the linker is cleavable under reducing conditions. In some embodiments, the linker is cleavable in the presence of a reducing agent, such as glutathione or dithiothreitol. In some embodiments, the linker is a cleavable disulfide linker or a cleavable sulfonamide linker.

In some embodiments, the linker is a cleavable disulfide linker. A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio) toluene), SPDB and SMPT. See, e.g., Thorpe et al. (1987) Cancer Res. 47:5924-31; Wawrzynczak et al., In Immunoconjugates: Antibody Conjugates in Radioimagery and Therapy of Cancer (C. W. Vogel ed., Oxford U. Press, 1987). See also U.S. Pat. No. 4,880,935. Disulfide linkers are typically used to exploit the abundance of intracellular thiols, which can facilitate the cleavage of their disulfide bonds. The intracellular concentrations of the most abundance intracellular thiol, reduced glutathione, are generally in the range of 1-10 nM, which is about 1,000-fold higher than that of the most abundant low-molecular thiol in the blood (i.e., cysteine) at about 5 μM (Goldmacher et al., In Cancer Drug Discovery and Development: Antibody-Drug Conjugates and Immunotoxins (G. L. Phillips ed., Springer, 2013)). The intracellular enzymes of the protein disulfide isomerase family may also contribute to the intracellular cleavage of a disulfide linker. As used herein, a cleavable disulfide linker refers to any linker that comprises a cleavable disulfide moiety. The term "cleavable disulfide moiety" refers to a disulfide bond that can be cleaved and/or reduced, e.g., by a thiol or enzyme.

In some embodiments, the linker is a cleavable sulfonamide linker. As used herein, a cleavable sulfonamide linker refers to any linker that comprises a cleavable sulfonamide moiety. The term "cleavable sulfonamide moiety" refers to a sulfonamide group, i.e., sulfonyl group connected to an amine group, wherein the sulfur-nitrogen bond can be cleaved.

In some embodiments, the linker may be a dendritic type linker for covalent attachment of more than one drug moiety to an antibody or antigen binding fragment through a branching, multifunctional linker moiety. See, e.g., Sun et al. (2002) Bioorg Med Chem Lett. 12:2213-5; Sun et al. (2003) Bioorg Med Chem. 11:1761-8. Dendritic linkers can increase the molar ratio of drug to antibody, i.e., drug loading, which is related to the potency of the ADC. Thus, where an antibody or antigen binding fragment bears only one reactive cysteine thiol group, for example, a multitude of splicing modulator drug moieties may be attached through a dendritic linker. In some embodiments, the linker moiety or linker-drug moiety may be attached to the antibody or antigen binding fragment via reduced disulfide bridging chemistry or limited lysine utilization technology. See, e.g., Intl. Publ. Nos. WO 2013/173391 and WO 2013/173393.

In some embodiments, the linker is cleavable by a cleaving agent, e.g., an enzyme, that is present in the intracellular environment (e.g., within a lysosome or endosome or caveola). The linker can be, e.g., a peptide linker that is cleaved by an intracellular peptidase or protease enzyme, including, but not limited to, a lysosomal or endosomal protease.

In some embodiments, the linker is a cleavable peptide linker. As used herein, a cleavable peptide linker refers to any linker that comprises a cleavable peptide moiety. The term "cleavable peptide moiety" refers to any chemical bond linking amino acids (natural or synthetic amino acid derivatives) that can be cleaved by an agent that is present in the intracellular environment. For instance, a linker may comprise a valine-alanine (Val-Ala) sequence, or a valine-citrulline (Val-Cit) sequence that is cleavable by a peptidase such as cathepsin, e.g., cathepsin B. In some embodiments, a linker may comprise a glutamic acid-valine-citrulline (Glu-Val-Cit) sequence. In some embodiments, the linker is an enzyme-cleavable linker and a cleavable peptide moiety in the linker is cleavable by the enzyme. In some embodiments, the cleavable peptide moiety is cleavable by a lysosomal enzyme, e.g., cathepsin. In some embodiments, the linker is a cathepsin-cleavable linker. In some embodiments, the cleavable peptide moiety in the linker is cleavable by a lysosomal cysteine cathepsin, such as cathepsin B, C, F, H, K, L, O, S, V, X, or W. In some embodiments, the cleavable peptide moiety is cleavable by cathepsin B. An exemplary dipeptide that may be cleaved by cathepsin B is valine-citrulline (Val-Cit) (Dubowchik et al. (2002) Bioconjugate Chem. 13:855-69).

In some embodiments, the linker or the cleavable peptide moiety in the linker comprises an amino acid unit. In some embodiments, the amino acid unit allows for cleavage of the linker by a protease, thereby facilitating release of the splicing modulator drug moiety from the ADC upon exposure to one or more intracellular proteases, such as one or more lysosomal enzymes (Doronina et al. (2003) Nat Biotechnol. 21:778-84; Dubowchik and Walker (1999) Pharm Therapeutics 83:67-123). Exemplary amino acid units include, but are not limited to, dipeptides, tripeptides, tetrapeptides, and pentapeptides. Exemplary dipeptides include, but are not limited to, valine-alanine (Val-Ala), valine-citrulline (Val-Cit), alanine-asparagine (Ala-Asn), alanine-phenylalanine (Ala-Phe), phenylalanine-lysine (Phe-Lys), alanine-lysine (Ala-Lys), alanine-valine (Ala-Val), valine-lysine (Val-Lys), lysine-lysine (Lys-Lys), phenylalanine-citrulline (Phe-Cit), leucine-citrulline (Leu-Cit), isoleucine-citrulline (Ile-Cit), tryptophan-citrulline (Trp-Cit), and phenylalanine-alanine (Phe-Ala). Exemplary tripeptides include, but are not limited to, alanine-alanine-asparagine (Ala-Ala-Asn), glycine-valine-citrulline (Gly-Val-Cit), glycine-glycine-glycine (Gly-Gly-Gly), phenylalanine-phenylalanine-lysine (Phe-Phe-Lys), glutamic acid-valine-citrulline (Glu-Val-Cit) (see, e.g., Anami et al. (2018) Nat Comm. 9:2512, which is incorporated herein by reference for exemplary linkers comprising Glu-Val-Cit), and glycine-phenylalanine-lysine (Gly-Phe-Lys). Other exemplary amino acid units include, but are not limited to, Gly-Phe-Gly-Gly (SEQ ID NO:34), Gly-Phe-Leu-Gly (SEQ ID NO:35), Ala-Leu-Ala-Leu (SEQ ID NO:36), Phe-$N^9$-tosyl-Arg, and Phe-$N^9$-Nitro-Arg, as described in, e.g., U.S. Pat. No. 6,214,345. In some embodiments, the amino acid unit in the linker comprises Val-Ala. In some embodiments, the amino acid unit in the linker comprises Val-Cit. In some embodiments, the amino acid unit in the linker comprises Glu-Val-Cit. An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, a lysosomal protease such as cathepsin B, C, D, or S, or a plasmin protease.

In some embodiments, the linker is a cleavable β-glucuronide linker. As used herein, a cleavable β-glucuronide linker refers to any linker that comprises a cleavable β-glucuronide moiety. An exemplary cleavable β-glucuronide linker comprises the structure:

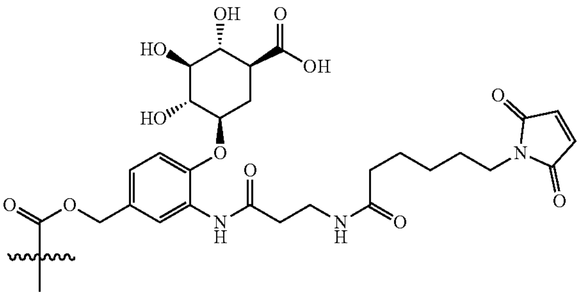 [SMILES: *C(=O)OCc1ccc(O[C@@H]2C[C@H](C(=O)O)[C@@H](O)[C@H](O)[C@H]2O)c(NC(=O)CCNC(=O)CCCCCN2C(=O)C=CC2=O)c1]

The term "cleavable β-glucuronide moiety" refers to a glycosidic bond that can be cleaved by an agent having β-glucuronidase activity. In some embodiments, the linker comprises a glycosidic bond that can be cleaved by a β-glucuronidase. A β-glucuronidase is a UDP-glucuronosyl transferase that catalyzes the hydrolysis of the glycosidic bond of glucuronides with β-configuration.

In some embodiments, an ADC disclosed herein comprises a cleavable β-glucuronide moiety in the linker that is cleavable by the enzyme. In some embodiments, the cleavable β-glucuronide moiety in the linker is cleavable by a lysosomal enzyme, e.g., a β-glucuronidase. In some embodiments, the linker is a β-glucuronidase-cleavable linker. In some embodiments, the cleavable β-glucuronide moiety in the linker allows for cleavage of the linker by a β-glucuronidase after internalization of the ADC, thereby facilitating release of the drug moiety from the ADC in the cellular environment.

In some embodiments, the linker in any of the ADCs disclosed herein may comprise at least one spacer unit joining the antibody or antigen binding fragment to the drug moiety (e.g., the splicing modulator drug moiety). In some embodiments, a spacer unit between the antibody or antigen binding fragment and cleavable moiety, when present, joins a cleavage site (e.g., a cleavable peptide moiety) in the linker to the antibody or antigen binding fragment. In some embodiments, a spacer unit between the drug moiety and cleavable moiety, when present, joins a cleavage site (e.g., a cleavable peptide moiety) in the linker to the drug moiety. In some embodiments, no cleavage site is present, and the spacer unit is used to link the antibody or antigen binding fragment to the drug moiety.

In some embodiments, the linker, and/or spacer unit in the linker, is substantially hydrophilic. A hydrophilic linker may be used to reduce the extent to which the drug may be pumped out of resistant cancer cells through multiple drug resistance (MDR) or functionally similar transporters. In some embodiments, a hydrophilic linker may include one or more polyethylene glycol (PEG) moieties, e.g., 1, 2, 3, 4, 5, or 6 PEG moieties. In some embodiments, the linker comprises 2 PEG moieties.

In some embodiments, the spacer unit in the linker comprises one or more PEG moieties. In some embodiments, the spacer unit comprises one or more $-(PEG)_m-$, and m is an integer from 1 to 10 (i.e., m may be 1, 2, 3, 4, 5, 6, 7, 8, 9, or 10). In some embodiments, m ranges from 1 to 10; from 2 to 8; from 2 to 6; from 2 to 5; from 2 to 4; or from 2 to 3. In some embodiments, m is 2. In some embodiments, the spacer unit comprises $(PEG)_2$, $(PEG)_3$, $(PEG)_4$, $(PEG)_5$, $(PEG)_6$, $(PEG)_7$, $(PEG)_8$, $(PEG)_9$, or $(PEG)_{10}$. In some embodiments, the spacer unit comprises $(PEG)_2$.

In some embodiments, the spacer unit in the linker comprises an alkyl moiety. In some embodiments, the spacer unit comprises one or more $—(CH_2)_n—$, and n is an integer from 1 to 10 (i.e., n may be 1, 2, 3, 4, 5, 6, 7, 8, 9, or 10). In some embodiments, n ranges from 1 to 10; from 2 to 8; from 2 to 6; from 2 to 5; from 2 to 4; or from 2 to 3. In some embodiments, n is 2. In some embodiments, n is 5. In some embodiments, n is 6. In some embodiments, the spacer unit comprises $(CH_2)_2$, $(CH_2)_3$, $(CH_2)_4$, $(CH_2)_5$, $(CH_2)_6$, $(CH_2)_7$, $(CH_2)_8$, $(CH_2)_9$, or $(CH_2)_{10}$. In some embodiments, the spacer unit comprises $(CH_2)_2$ ("Et"). In some embodiments, the spacer unit comprises $(CH_2)_6$ ("Hex"). In some embodiments, the spacer unit comprises $(CH_2)_2—O—(CH_2)_2$ ("Et-O-Et").

A spacer unit may be used, for example, to link the antibody or antigen binding fragment to the drug moiety, either directly or indirectly. In some embodiments, the spacer unit links the antibody or antigen binding fragment to the splicing modulator drug moiety directly. In some embodiments, the antibody or antigen binding fragment and the splicing modulator drug moiety are attached via a spacer unit comprising one or more PEG moieties (e.g., $(PEG)_2$), or one or more alkyl moieties (e.g., $(CH_2)_2$, $(CH_2)_6$, or $(CH_2)$ $_2$—O—$(CH_2)_2$). In some embodiments, the spacer unit links the antibody or antigen binding fragment to the splicing modulator drug moiety indirectly. In some embodiments, the spacer unit links the antibody or antigen binding fragment to the splicing modulator drug moiety indirectly through a cleavable moiety (e.g., a cleavable peptide or a cleavable β-glucuronide) and/or an attachment moiety to join the spacer unit to the antibody or antigen binding fragment, e.g., a maleimide moiety.

The spacer unit, in various embodiments, attaches to the antibody or antigen binding fragment (i.e., the antibody or antigen binding fragment) via a maleimide (Mal) moiety.

A spacer unit that attaches to the antibody or antigen binding fragment via a Mal is referred to herein as a "Mal-spacer unit." The term "Mal" or "maleimide moiety," as used herein, means a compound that contains a maleimide group and that is reactive with a sulfhydryl group, e.g., a sulfhydryl group of a cysteine residue on the antibody or antigen binding fragment. Other functional groups that are reactive with sulfhydryl groups (thiols) include, but are not limited to, iodoacetamide, bromoacetamide, vinyl pyridine, disulfide, pyridyl disulfide, isocyanate, and isothiocyanate. In some embodiments, the Mal-spacer unit is reactive with a cysteine residue on the antibody or antigen binding fragment. In some embodiments, the Mal-spacer unit is joined to the antibody or antigen binding fragment via the cysteine residue. In some embodiments, the Mal-spacer unit comprises a PEG moiety. In some embodiments, the Mal-spacer unit comprises an alkyl moiety.

In certain embodiments, the linker comprises the Mal-spacer unit and a cleavable peptide moiety. In some embodiments, the cleavable peptide moiety comprises an amino acid unit. In some embodiments, the amino acid unit comprises Val-Cit. In some embodiments, the amino acid unit comprises Val-Ala. In some embodiments, the amino acid unit comprises Glu-Val-Cit. In some embodiments, the linker comprises the Mal-spacer unit and Val-Cit. In some embodiments, the linker comprises the Mal-spacer unit and Val-Ala. In some embodiments, the linker comprises the Mal-spacer unit and Val-Cit, wherein the Mal-spacer unit comprises a maleimidocaproyl (MC). In some embodiments, the linker comprises the Mal-spacer unit and Val-Ala, wherein the Mal-spacer unit comprises a maleimidocaproyl (MC). In some embodiments, the linker comprises the Mal-spacer unit and a cleavable β-glucuronide moiety.

In some embodiments, the linker comprises the structure: Mal-spacer unit. In some embodiments, the Mal-spacer unit comprises a maleimidocaproyl (MC). In some embodiments, the linker comprises the structure: MC. In some embodiments, the linker comprises the structure: Mal-$(CH_2)_2$ ("Mal-Et"). In some embodiments, the linker comprises the structure: Mal-$(CH_2)_6$ ("Mal-Hex"). In some embodiments, the linker comprises the structure: Mal-$(CH_2)_2$—O—$(CH_2)_2$ ("Mal-Et-O-Et"). In some embodiments, the linker comprises the structure: Mal-$(PEG)_2$. In some embodiments, the linker comprises the structure: Mal-$(PEG)_2$-CO.

In various embodiments, the Mal-spacer unit attaches the antibody or antigen binding fragment to a cleavable peptide moiety. In some embodiments, the linker comprises Mal-spacer unit-peptide. In some embodiments, the linker comprises the structure: Mal-spacer unit-Val-Cit. In some embodiments, the Mal-spacer unit comprises a maleimidocaproyl (MC). In some embodiments, the linker comprises the structure: MC-Val-Cit.

In some embodiments, the linker comprises the structure: Mal-spacer unit-Val-Ala. In some embodiments, the Mal-spacer unit comprises a maleimidocaproyl (MC). In some embodiments, the linker comprises the structure: MC-Val-Ala.

In various embodiments, the Mal-spacer unit attaches the antibody or antigen binding fragment to a cleavable β-glucuronide moiety. In some embodiments, the linker comprises Mal-spacer unit-β-glucuronide. In some embodiments, the linker comprises MC-β-glucuronide.

In various embodiments, the cleavable moiety in the linker is joined directly to the splicing modulator drug moiety. In other embodiments, a spacer unit is used to attach the cleavable moiety in the linker to the splicing modulator drug moiety. In various embodiments, the splicing modulator is attached to the cleavable moiety in the linker by a spacer unit.

A spacer unit may be "self-immolative" or "non-self-immolative." A "non-self-immolative" spacer unit is one in which part or all of the spacer unit remains bound to the splicing modulator drug moiety upon cleavage of the linker. Examples of non-self-immolative spacer units include, but are not limited to, a glycine spacer unit and a glycine-glycine spacer unit. Non-self-immolative spacer units may eventually degrade over time but do not readily release a linked native drug moiety entirely under cellular conditions. A "self-immolative" spacer unit allows for release of the native drug moiety under intracellular conditions. A "native drug" or "native drug moiety" is one where no part of the spacer unit or other chemical modification remains after cleavage/degradation of the spacer unit.

Self-immolation chemistry is known in the art and could be readily selected for the disclosed ADCs. In various embodiments, the spacer unit attaching the cleavable moiety in the linker to the splicing modulator drug moiety is self-immolative, and undergoes self-immolation concurrently with or shortly before/after cleavage of the cleavable moiety under intracellular conditions. In some embodiments, the splicing modulator is attached to the cleavable moiety in the linker by a self-immolative spacer unit. In certain embodiments, the splicing modulator is attached to the cleavable moiety in the linker by a self-immolative spacer unit, the cleavable moiety comprises Val-Cit, and a maleimidocaproyl (MC) joins the cleavable moiety to the antibody or antigen binding fragment. In certain embodiments, the splicing modulator is attached to the cleavable moiety in the linker by a self-immolative spacer unit, the cleavable moiety comprises Val-Ala, and a maleimidocaproyl (MC) joins the cleavable moiety to the antibody or antigen binding fragment. In certain embodiments, the splicing modulator is attached to the cleavable moiety in the linker by a self-immolative spacer unit, the cleavable moiety comprises Glu-Val-Cit, and a maleimidocaproyl (MC) joins the cleavable moiety to the antibody or antigen binding fragment. In certain embodiments, the splicing modulator is joined to the antibody or antigen binding fragment via a Mal-spacer unit (e.g., MC) in the linker joined to a Val-Cit cleavable moiety and a pABC or pAB self-immolative spacer unit. In certain other embodiments, the splicing modulator is joined to the antibody or antigen binding fragment via a Mal-spacer unit (e.g., MC) in the linker joined to a Val-Ala cleavable moiety and a pABC or pAB self-immolative spacer unit. In certain other embodiments, the splicing modulator is joined to the antibody or antigen binding fragment via a Mal-spacer unit (e.g., MC) in the linker joined to a Glu-Val-Cit cleavable moiety and a pABC or pAB self-immolative spacer unit.

In certain embodiments, the self-immolative spacer unit in the linker comprises a p-aminobenzyl unit. In some embodiments, a p-aminobenzyl alcohol (pABOH) is attached to an amino acid unit or other cleavable moiety in the linker via an amide bond, and a carbamate, methylcarbamate, or carbonate is made between the pABOH and the drug moiety (Hamann et al. (2005) Expert Opin Ther Patents 15:1087-103). In some embodiments, the self-immolative spacer unit is or comprises p-aminobenzyloxycarbonyl (pABC). Without being bound by theory, it is thought that the self-immolation of pABC involves a spontaneous 1,6-elimination reaction (Jain et al. (2015) Pharm Res. 32:3526-40).

In various embodiments, the structure of the p-aminobenzyloxycarbonyl (pABC) used in the disclosed ADCs is shown below:

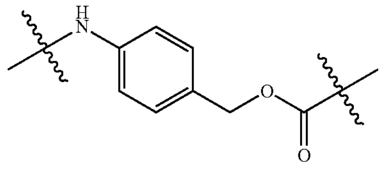 [SMILES: *Nc1ccc(COC(*)=O)cc1]

In various embodiments, the self-immolative spacer unit attaches the cleavable moiety in the linker to the splicing modulator. In some embodiments, the self-immolative spacer unit is pABC. In some embodiments, the pABC attaches the cleavable moiety in the linker to the splicing modulator. In some embodiments, the pABC undergoes self-immolation upon cleavage of the cleavable moiety, and the splicing modulator is released from the ADC in its native, active form.

In some embodiments, an anti-HER2 antibody or antigen binding fragment is joined to the splicing modulator by a linker comprising MC-Val-Cit-pABC. In other embodiments, an anti-HER2 antibody or antigen binding fragment is joined to the splicing modulator by a linker comprising MC-Val-Ala-pABC.

In some embodiments, an anti-CD138 antibody or antigen binding fragment is joined to the splicing modulator by a linker comprising MC-Val-Cit-pABC. In other embodiments, an anti-CD138 antibody or antigen binding fragment is joined to the splicing modulator by a linker comprising MC-Val-Ala-pABC.

In some embodiments, an anti-EPHA2 antibody or antigen binding fragment is joined to the splicing modulator by a linker comprising MC-Val-Cit-pABC. In other embodiments, an anti-EPHA2 antibody or antigen binding fragment is joined to the splicing modulator by a linker comprising MC-Val-Ala-pABC.

In some embodiments, the pABC undergoes self-immolation upon cleavage of a cleavable peptide moiety in the linker. In some embodiments, the cleavable peptide moiety comprises an amino acid unit. In some embodiments, the linker comprises amino acid unit-pABC. In some embodiments, the amino acid unit is Val-Cit. In some embodiments, the linker comprises Val-Cit-pABC. In some embodiments, the amino acid unit is Val-Ala. In some embodiments, the linker comprises Val-Ala-pABC. In some embodiments, the amino acid unit is Glu-Val-Cit. In some embodiments, the linker comprises Glu-Val-Cit-pABC. In some embodiments, the amino acid unit is Ala-Ala-Asn. In some embodiments, the linker comprises Ala-Ala-Asn-pABC.

In some embodiments, the pABC undergoes self-immolation upon cleavage of a cleavable β-glucuronide moiety in the linker. In some embodiments, the linker comprises β-glucuronide-pABC.

In certain embodiments, the self-immolative spacer unit in the linker comprises a p-aminobenzyl unit. In some embodiments, the self-immolative spacer unit in the linker comprises a p-aminobenzyl (pAB). In some embodiments, the self-immolation of pAB involves a spontaneous 1,6-elimination reaction.

In various embodiments, the structure of the p-aminobenzyl (pAB) used in the disclosed ADCs is shown below:

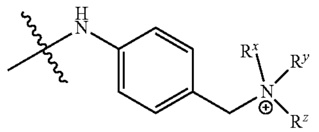

In various embodiments, the self-immolative spacer unit attaches the cleavable moiety in the linker to the splicing modulator. In some embodiments, the self-immolative spacer unit is pAB. In some embodiments, the pAB attaches the cleavable moiety in the linker to the splicing modulator. In some embodiments, the pAB undergoes self-immolation upon cleavage of the cleavable moiety, and the splicing modulator is released from the ADC in its native, active form.

In some embodiments, an anti-HER2 antibody or antigen binding fragment is joined to the splicing modulator by a linker comprising MC-Val-Cit-pAB. In other embodiments, an anti-HER2 antibody or antigen binding fragment is joined to the splicing modulator by a linker comprising MC-Val-Ala-pAB.

In some embodiments, an anti-CD138 antibody or antigen binding fragment is joined to the splicing modulator by a linker comprising MC-Val-Cit-pAB. In other embodiments, an anti-CD138 antibody or antigen binding fragment is joined to the splicing modulator by a linker comprising MC-Val-Ala-pAB.

In some embodiments, an anti-EPHA2 antibody or antigen binding fragment is joined to the splicing modulator by a linker comprising MC-Val-Cit-pAB. In other embodiments, an anti-EPHA2 antibody or antigen binding fragment is joined to the splicing modulator by a linker comprising MC-Val-Ala-pAB.

In some embodiments, the pAB undergoes self-immolation upon cleavage of a cleavable peptide moiety in the linker. In some embodiments, the cleavable peptide moiety comprises an amino acid unit. In some embodiments, the linker comprises amino acid unit-pAB. In some embodiments, the amino acid unit is Val-Cit. In some embodiments, the linker comprises Val-Cit-pAB. In some embodiments, the amino acid unit is Val-Ala. In some embodiments, the linker comprises Val-Ala-pAB. In some embodiments, the amino acid unit is Glu-Val-Cit. In some embodiments, the linker comprises Glu-Val-Cit-pAB. In some embodiments, the amino acid unit is Ala-Ala-Asn. In some embodiments, the linker comprises Ala-Ala-Asn-pAB.

In some embodiments, the pAB undergoes self-immolation upon cleavage of a cleavable β-glucuronide moiety in the linker. In some embodiments, the linker comprises β-glucuronide-pAB.

In some other embodiments, the splicing modulator is attached to the cleavable moiety in the linker by a non-self-immolative spacer unit. In certain embodiments, the splicing modulator is attached to the cleavable moiety in the linker by a non-self-immolative spacer unit, the cleavable moiety comprises Val-Cit, and a maleimidocaproyl (MC) joins the cleavable moiety to the antibody or antigen binding fragment. In certain embodiments, the splicing modulator is attached to the cleavable moiety in the linker by a non-self-immolative spacer unit, the cleavable moiety comprises Val-Ala, and a maleimidocaproyl (MC) joins the cleavable moiety to the antibody or antigen binding fragment.

In various aspects, the antibody or antigen binding fragment of the ADC is conjugated to the splicing modulator drug moiety via a linker, wherein the linker comprises a Mal-spacer unit (e.g., MC), a cleavable amino acid unit, and a pABC. In some embodiments, the spacer unit comprises an alkyl moiety. In some embodiments, the Mal-spacer unit comprises a maleimidocaproyl (MC). In some embodiments, the linker comprises Mal-spacer unit-amino acid unit-pABC. In some embodiments, the linker comprises MC-amino acid unit-pABC. In some embodiments, the linker comprises MC-Val-Cit-pABC. In some embodiments, the linker comprises MC-Val-Ala-pABC. In some embodiments, the linker comprises MC-Glu-Val-Cit-pABC. In some embodiments, the linker comprises MC-Ala-Ala-Asn-pABC.

In various other aspects, the antibody or antigen binding fragment of the ADC is conjugated to the splicing modulator drug moiety via a linker, wherein the linker comprises a Mal-spacer unit (e.g., MC), a cleavable amino acid unit, and a pAB. In some embodiments, the spacer unit comprises an alkyl moiety. In some embodiments, the Mal-spacer unit comprises a maleimidocaproyl (MC). In some embodiments, the linker comprises Mal-spacer unit-amino acid unit-pAB. In some embodiments, the linker comprises MC-amino acid unit-pAB. In some embodiments, the linker comprises MC-Val-Cit-pAB. In some embodiments, the linker comprises MC-Val-Ala-pAB. In some embodiments, the linker comprises MC-Glu-Val-Cit-pAB. In some embodiments, the linker comprises MC-Ala-Ala-Asn-pAB.

In various other aspects, the antibody or antigen binding fragment of the ADC is conjugated to the splicing modulator drug moiety via a linker, wherein the linker comprises a Mal-spacer unit (e.g., MC), a cleavable β-glucuronide, and a pABC. In some embodiments, the linker comprises Mal-spacer unit-β-glucuronide-pABC. In some embodiments, the linker comprises MC-β-glucuronide-pABC.

In still other aspects, the antibody or antigen binding fragment of the ADC is conjugated to the splicing modulator drug moiety via a linker, wherein the linker comprises a Mal-spacer unit (e.g., MC), a cleavable β-glucuronide, and a pAB. In some embodiments, the linker comprises Mal-spacer unit-β-glucuronide-pAB. In some embodiments, the linker comprises MC-β-glucuronide-pAB.

In various embodiments, the ADC compound has Formula (I):

$$\text{Ab-(L-D)}_p \qquad \text{(I)}$$

wherein Ab is an antibody or antigen binding fragment which targets a neoplastic cell;

D is a splicing modulator;

L is a linker that covalently attaches Ab to D; and p is an integer from 1 to 15.

In some embodiments, the antibody or antigen binding fragment (Ab) of the ADC is conjugated to the splicing modulator drug moiety via a linker, wherein the linker is any of the linkers disclosed or incorporated by reference herein, or comprises one or more components of any of the linkers disclosed or incorporated by reference herein.

In some embodiments, the linker comprises a cleavable moiety that is positioned such that no part of the linker or the antibody or antigen binding fragment remains bound to the splicing modulator after cleavage. In some embodiments, the cleavable moiety is a cleavable peptide moiety, e.g., an amino acid unit such as Val-Cit or Val-Ala.

In some embodiments, the amino acid unit or linker comprises Val-Cit. In some embodiments, the amino acid unit or linker comprises Val-Ala. In some embodiments, the amino acid unit or linker comprises Glu-Val-Cit.

In some embodiments, the linker comprises at least one spacer unit joining the antibody or antigen binding fragment to the cleavable moiety. In some embodiments, the linker comprises at least one spacer unit joining the antibody or antigen binding fragment to the drug moiety. In some embodiments, the spacer unit or linker comprises at least one alkyl moiety.

In some embodiments, a spacer unit in the linker attaches to the antibody or antigen binding fragment via a Mal moiety ("Mal-spacer unit"). In some embodiments, the Mal-spacer unit comprises at least one alkyl moiety. In some embodiments, the linker comprises a maleimidocaproyl (MC). In some embodiments, the linker comprises Mal-$(CH_2)_2$ ("Mal-Et"). In some embodiments, the linker comprises Mal-$(CH_2)_6$ ("Mal-Hex"). In some embodiments, the linker comprises Mal-$(CH_2)_2$—O—$(CH_2)_2$ ("Mal-Et-O-Et"). In some embodiments, the linker comprises Mal-$(PEG)_2$-CO. In some embodiments, the Mal-spacer unit attaches the antibody or antigen binding fragment to the drug moiety.

In some embodiments, the Mal-spacer unit or linker comprises Mal-$(PEG)_2$, Mal-$(PEG)_3$, Mal-$(PEG)_4$, Mal-$(PEG)_5$, Mal-$(PEG)_6$, Mal-$(PEG)_7$, or Mal-$(PEG)_3$. In some embodiments, the Mal-spacer unit or linker comprises Mal-$(PEG)_2$. In some embodiments, the Mal-spacer unit or linker comprises Mal-$(PEG)_2$-CO, Mal-$(PEG)_3$-CO, Mal-$(PEG)_4$-CO, Mal-$(PEG)_5$-CO, Mal-$(PEG)_6$-CO, Mal-$(PEG)_7$-CO, or Mal-$(PEG)_3$-CO. In some embodiments, the Mal-spacer unit or linker comprises Mal-$(PEG)_2$-CO. In some embodiments, the Mal-spacer unit or linker comprises Mal-$(PEG)_2$-CO and at least one additional spacer unit. In some embodiments, the Mal-$(PEG)_2$-CO attaches the antibody or antigen binding fragment to the drug moiety. In some embodiments, linker comprises or consists of Mal-$(PEG)_2$-CO. An example of a "Mal-$(PEG)_2$-CO" linker is also referred to herein as "ADL2" or an "ADL2" linker.

In some embodiments, the Mal-spacer unit or linker comprises MC. In some embodiments, the Mal-spacer unit or linker comprises MC and at least one additional spacer unit. In some embodiments, the MC attaches the antibody or antigen binding fragment to the drug moiety. In some embodiments, the linker comprises or consists of MC. An example of an "MC" linker is also referred to herein as "ADL10" or an "ADL10" linker.

In some embodiments, the Mal-spacer unit or linker comprises Mal-$(CH_2)_6$ ("Mal-Hex"). In some embodiments, the Mal-spacer unit or linker comprises Mal-Hex and at least one additional spacer unit. In some embodiments, the Mal-Hex attaches the antibody or antigen binding fragment to the drug moiety. In some embodiments, the linker comprises Mal-Hex. An example of a "Mal-Hex" linker is also referred to herein as "ADL12" or an "ADL12" linker.

In some embodiments, the Mal-spacer unit or linker comprises Mal-$(CH_2)_2$ ("Mal-Et"). In some embodiments, the Mal-spacer unit or linker comprises Mal-Et and at least one additional spacer unit. In some embodiments, the Mal-Et attaches the antibody or antigen binding fragment to the drug moiety. In some embodiments, the linker comprises Mal-Et. An example of a "Mal-Et" linker is also referred to herein as "ADL14" or an "ADL14" linker.

In some embodiments, the Mal-spacer unit or linker comprises Mal-$(CH_2)_2$—O—$(CH_2)_2$ ("Mal-Et-O-Et"). In some embodiments, the Mal-spacer unit or linker comprises Mal-Et-O-Et and at least one additional spacer unit. In some embodiments, the Mal-Et-O-Et attaches the antibody or antigen binding fragment to the drug moiety. In some embodiments, the linker comprises Mal-Et-O-Et. An example of a "Mal-Et-O-Et" linker is also referred to herein as "ADL15" or an "ADL15" linker.

In some other embodiments, the Mal-spacer unit attaches the antibody or antigen binding fragment to the cleavable moiety in the linker. In some embodiments, the cleavable moiety in the linker is a cleavable peptide moiety, e.g., an amino acid unit. In some embodiments, the cleavable peptide moiety is Val-Cit or Val-Ala. In some embodiments, the Mal-spacer unit or linker comprises MC. In some embodiments, the linker comprises MC-Val-Cit. In some embodiments, the linker comprises MC-Val-Ala. In some embodiments, the linker comprises MC-Glu-Val-Cit. In some embodiments, the linker comprises MC-Ala-Ala-Asn.

In some embodiments, a spacer unit attaches the cleavable moiety in the linker to the splicing modulator. In some embodiments, the spacer unit that attaches the cleavable moiety to the splicing modulator is self-immolative.

In some embodiments, the spacer unit comprises pABC. In some embodiments, the pABC attaches the cleavable moiety to the splicing modulator. In some embodiments, the cleavable moiety is a cleavable peptide moiety, e.g., an amino acid unit. In some embodiments, the linker comprises amino acid unit-pABC.

In some embodiments, the linker comprises Val-Cit-pABC. In some embodiments, the linker comprises Val-Cit-pABC and a MC Mal-spacer unit joining the linker to the antibody or antigen binding fragment. In some embodiments, the linker comprises MC-Val-Cit-pABC. In some embodiments, the linker comprises MC-Val-Cit-pABC and at least one additional spacer unit. An example of an MC-Val-Cit-pABC linker is also referred to herein as "ADL1" or an "ADL1" linker.

In some embodiments, the linker comprises Val-Ala-pABC. In some embodiments, the linker comprises Val-Ala-pABC and a MC Mal-spacer unit joining the linker to the antibody or antigen binding fragment. In some embodiments, the linker comprises MC-Val-Ala-pABC. In some embodiments, the linker comprises MC-Val-Ala-pABC and at least one additional spacer unit. An example of an MC-Val-Ala-pABC linker is also referred to herein as "ADL6" or an "ADL6" linker.

In some embodiments, the linker comprises Glu-Val-Cit-pABC. In some embodiments, the linker comprises Glu-Val-Cit-pABC and a MC Mal-spacer unit joining the linker to the antibody or antigen binding fragment. In some embodiments, the linker comprises MC-Glu-Val-Cit-pABC. In some embodiments, the linker comprises MC-Glu-Val-Cit-pABC and at least one additional spacer unit. An example of an MC-Glu-Val-Cit-pABC linker is also referred to herein as "ADL23" or an "ADL23" linker.

In some embodiments, the linker comprises Ala-Ala-Asn-pABC. In some embodiments, the linker comprises Ala-Ala-Asn-pABC and a MC Mal-spacer unit joining the linker to the antibody or antigen binding fragment. In some embodiments, the linker comprises MC-Ala-Ala-Asn-pABC. In some embodiments, the linker comprises MC-Ala-Ala-Asn-pABC and at least one additional spacer unit. An example of an MC-Ala-Ala-Asn-pABC linker is also referred to herein as "ADL21" or an "ADL21" linker.

In some other embodiments, the spacer unit comprises pAB. In some embodiments, the pAB attaches the cleavable moiety to the splicing modulator. In some embodiments, the cleavable moiety is a cleavable peptide moiety, e.g., an amino acid unit. In some embodiments, the linker comprises amino acid unit-pAB.

In some embodiments, the linker comprises Val-Ala-pAB. In some embodiments, the linker comprises Val-Ala-pAB and an MC Mal-spacer unit joining the linker to the antibody or antigen binding fragment. In some embodiments, the linker comprises MC-Val-Ala-pAB. In some embodiments, the linker comprises MC-Val-Ala-pAB and at least one additional spacer unit. An example of an MC-Val-Ala-pAB linker is also referred to herein as "ADL5" or an "ADL5" linker.

In some embodiments, the linker comprises Val-Cit-pAB. In some embodiments, the linker comprises Val-Cit-pAB and an MC Mal-spacer unit joining the linker to the antibody or antigen binding fragment. In some embodiments, the linker comprises MC-Val-Cit-pAB. In some embodiments, the linker comprises MC-Val-Cit-pAB and at least one additional spacer unit. An example of an MC-Val-Cit-pAB linker is also referred to herein as "ADL7" or an "ADL7" linker.

In some embodiments, the linker comprises β-glucuronide-pABC. In some embodiments, the linker comprises β-glucuronide-pABC and an MC Mal-spacer unit joining the linker to the antibody or antigen binding fragment. In some embodiments, the linker comprises MC-β-glucuronide-pABC. In some embodiments, the linker comprises MC-β-glucuronide-pABC and at least one additional spacer unit. An example of an MC-β-glucuronide-pABC is also referred to herein as "ADL13" or an "ADL13" linker.

In some embodiments, the linker comprises β-glucuronide-pAB. In some embodiments, the linker comprises β-glucuronide-pAB and an MC Mal-spacer unit joining the linker to the antibody or antigen binding fragment. In some embodiments, the linker comprises MC-β-glucuronide-pAB.

In some embodiments, the antibody or antigen binding fragment is conjugated to the splicing modulator drug moiety via an ADL1, ADL2, ADL5, ADL6, ADL7, ADL12, ADL13, ADL14, ADL21, ADL23, or ADL15 linker. It has been discovered, in various embodiments, that ADCs comprising an ADL1, ADL2, ADL5, ADL6, ADL7, ADL12, ADL13, ADL14, ADL21, ADL23, or ADL15 linker and a splicing modulator drug moiety disclosed herein demonstrate desirable properties for a therapeutic ADC. In various embodiments, these properties include, but are not limited to, effective levels of drug loading, low aggregation levels, stability under storage conditions or when in circulation in the body (e.g., serum stability), retained affinity for target-expressing cells comparable to unconjugated antibody, potent cytotoxicity against target-expressing cells, low levels of off-target cell killing, high levels of bystander killing, and/or effective in vivo anti-cancer activity, all as compared to ADCs using other linker-payloads. For instance, in various embodiments, ADCs comprising an ADL1, ADL2, ADL5, ADL6, ADL7, ADL12, ADL13, ADL14, ADL21, ADL23, or ADL15 linker and a splicing modulator drug moiety disclosed herein exhibit an increased ability to inhibit growth and/or proliferation in target-expressing cells, as compared to ADCs using other linker-payloads (e.g., an ADL10 linker and a splicing modulator drug moiety). In various embodiments, ADCs comprising an ADL1, ADL2, ADL5, ADL6, ADL7, ADL12, ADL13, ADL14, ADL21, ADL23, or ADL15 linker and a splicing modulator drug moiety disclosed herein exhibit surprisingly increased in vivo stability (e.g., plasma stability), as compared to other splicing modulator-based ADCs (e.g., a thailanstatin A-based ADC, for example, as reported in Puthenveetil et al. Bioconjugate Chem. (2016) 27:1880-8).

In some embodiments, the good or superior functional properties provided by the particular combination of an ADL1, ADL2, ADL5, ADL6, ADL7, ADL12, ADL13, ADL14, ADL21, ADL23, or ADL15 linker and a splicing modulator drug moiety disclosed herein may be observed with the linker-payload conjugated to, e.g., an anti-HER2 antibody such as trastuzumab; an anti-CD138 antibody such as B-B4; or an anti-EPHA2 antibody such as 1C1.

In some embodiments, the ADC comprises ADL1-splicing modulator and an antibody or antigen binding fragment comprising an antibody or an antigen binding fragment thereof that retains the ability to target and internalize in a neoplastic cell. In some embodiments, the ADC comprises ADL2-splicing modulator and an antibody or antigen binding fragment comprising an antibody or an antigen binding fragment thereof that retains the ability to target and internalize in a neoplastic cell. In some embodiments, the ADC comprises ADL5-splicing modulator and an antibody or antigen binding fragment comprising an antibody or an antigen binding fragment thereof that retains the ability to target and internalize in a neoplastic cell. In some embodiments, the ADC comprises ADL6-splicing modulator and an antibody or antigen binding fragment comprising an antibody or an antigen binding fragment thereof that retains the ability to target and internalize in a neoplastic cell. In some embodiments, the ADC comprises ADL7-splicing modulator and an antibody or antigen binding fragment comprising an antibody or an antigen binding fragment thereof that retains the ability to target and internalize in a neoplastic cell. In some embodiments, the ADC comprises ADL12-splicing modulator and an antibody or antigen binding fragment comprising an antibody or an antigen binding fragment thereof that retains the ability to target and internalize in a neoplastic cell. In some embodiments, the ADC comprises ADL13-splicing modulator and an antibody or antigen binding fragment comprising an antibody or an antigen binding fragment thereof that retains the ability to target and internalize in a neoplastic cell. In some embodiments, the ADC comprises ADL14-splicing modulator and an antibody or antigen binding fragment comprising an antibody or an antigen binding fragment thereof that retains the ability to target and internalize in a neoplastic cell. In some embodiments, the ADC comprises ADL15-splicing modulator and an antibody or antigen binding fragment comprising an antibody or an antigen binding fragment thereof that retains the ability to target and internalize in a neoplastic cell.

In some embodiments, the ADC comprises ADL1-splicing modulator and an antibody or antigen binding fragment thereof that targets a HER2-expressing neoplastic cell. In some embodiments, the ADC comprises ADL2-splicing modulator and an antibody or antigen binding fragment thereof that targets a HER2-expressing neoplastic cell. In some embodiments, the ADC comprises ADL5-splicing modulator and an antibody or antigen binding fragment thereof that targets a HER2-expressing neoplastic cell. In some embodiments, the ADC comprises ADL6-splicing modulator and an antibody or antigen binding fragment thereof that targets a HER2-expressing neoplastic cell. In some embodiments, the ADC comprises ADL7-splicing modulator and an antibody or antigen binding fragment thereof that targets a HER2-expressing neoplastic cell. In some embodiments, the ADC comprises ADL12-splicing modulator and an antibody or antigen binding fragment thereof that targets a HER2-expressing neoplastic cell. In some embodiments, the ADC comprises ADL13-splicing modulator and an antibody or antigen binding fragment thereof that targets a HER2-expressing neoplastic cell. In some embodiments, the ADC comprises ADL14-splicing modulator and an antibody or antigen binding fragment thereof that targets a HER2-expressing neoplastic cell. In some embodiments, the ADC comprises ADL15-splicing modulator and an antibody or antigen binding fragment thereof that targets a HER2-expressing neoplastic cell.

In some embodiments, the antibody or antigen binding fragment thereof that targets a HER2-expressing neoplastic cell is an internalizing antibody or internalizing antigen binding fragment. In some embodiments, the antibody or antigen binding fragment thereof that targets a HER2-expressing neoplastic cell comprises three heavy chain complementarity determining regions (HCDRs) comprising amino acid sequences of SEQ ID NO:1 (HCDR1), SEQ ID NO:2 (HCDR2), and SEQ ID NO:3 (HCDR3); and three light chain complementarity determining regions (LCDRs) comprising amino acid sequences of SEQ ID NO:4 (LCDR1), SEQ ID NO:5 (LCDR2), and SEQ ID NO:6 (LCDR3).

In some embodiments, the ADC has Formula (I):

$$Ab\text{-}(L\text{-}D)_p \quad (I)$$

wherein:

(i) Ab is an anti-HER2 antibody or antigen binding fragment thereof comprising three heavy chain complementarity determining regions (HCDRs) comprising amino acid sequences of SEQ ID NO:1 (HCDR1), SEQ ID NO:2 (HCDR2), and SEQ ID NO:3 (HCDR3); and three light chain complementarity determining regions (LCDRs) comprising amino acid sequences of SEQ ID NO:4 (LCDR1), SEQ ID NO:5 (LCDR2), and SEQ ID NO:6 (LCDR3);

(ii) D is a splicing modulator;

(iii) L is a linker comprising ADL1, ADL2, ADL5, ADL6, ADL7, ADL12, ADL13, ADL14, ADL21, ADL23, or ADL15; and (iv) p is an integer from 1 to 15.

In some embodiments, the antibody or antigen binding fragment thereof that targets a HER2-expressing neoplastic cell comprises a heavy chain variable region comprising an amino acid sequence of SEQ ID NO: 19, and a light chain variable region comprising an amino acid sequence of SEQ ID NO:20. In some embodiments, the antibody or antigen binding fragment thereof that targets a HER2-expressing neoplastic cell comprises a human IgG1 heavy chain constant domain and a human Ig kappa light chain constant domain. In some embodiments, the antibody is trastuzumab. In some embodiments, p is an integer from 1 to 10, from 2 to 8, or from 4 to 8. In some embodiments, p is 4. In some embodiments, p is 8.

In some embodiments, the ADC comprises ADL1-splicing modulator and an antibody or antigen binding fragment thereof that targets a CD138-expressing neoplastic cell. In some embodiments, the ADC comprises ADL2-splicing modulator and an antibody or antigen binding fragment thereof that targets a CD138-expressing neoplastic cell. In some embodiments, the ADC comprises ADL5-splicing modulator and an antibody or antigen binding fragment thereof that targets a CD138-expressing neoplastic cell. In some embodiments, the ADC comprises ADL6-splicing modulator and an antibody or antigen binding fragment thereof that targets a CD138-expressing neoplastic cell. In some embodiments, the ADC comprises ADL7-splicing modulator and an antibody or antigen binding fragment thereof that targets a CD138-expressing neoplastic cell. In some embodiments, the ADC comprises ADL12-splicing modulator and an antibody or antigen binding fragment thereof that targets a CD138-expressing neoplastic cell. In some embodiments, the ADC comprises ADL13-splicing modulator and an antibody or antigen binding fragment thereof that targets a CD138-expressing neoplastic cell. In some embodiments, the ADC comprises ADL14-splicing modulator and an antibody or antigen binding fragment thereof that targets a CD138-expressing neoplastic cell. In some embodiments, the ADC comprises ADL15-splicing modulator and an antibody or antigen binding fragment thereof that targets a CD138-expressing neoplastic cell.

In some embodiments, the antibody or antigen binding fragment thereof that targets a CD138-expressing neoplastic cell is an internalizing antibody or internalizing antigen binding fragment. In some embodiments, the antibody or antigen binding fragment thereof that targets a CD138-expressing neoplastic cell comprises three heavy chain complementarity determining regions (HCDRs) comprising amino acid sequences of SEQ ID NO:7 (HCDR1), SEQ ID NO:8 (HCDR2), and SEQ ID NO:9 (HCDR3); and three light chain complementarity determining regions (LCDRs) comprising amino acid sequences of SEQ ID NO:10 (LCDR1), SEQ ID NO:11 (LCDR2), and SEQ ID NO:12 (LCDR3).

In some embodiments, the ADC has Formula (I):

$$Ab\text{-}(L\text{-}D)_p \qquad (I)$$

wherein:

(i) Ab is an anti-CD138 antibody or antigen binding fragment thereof comprising three heavy chain complementarity determining regions (HCDRs) comprising amino acid sequences of SEQ ID NO:7 (HCDR1), SEQ ID NO:8 (HCDR2), and SEQ ID NO:9 (HCDR3); and three light chain complementarity determining regions (LCDRs) comprising amino acid sequences of SEQ ID NO:10 (LCDR1), SEQ ID NO:11 (LCDR2), and SEQ ID NO:12 (LCDR3);

(ii) D is a splicing modulator;

(iii) L is a linker comprising ADL1, ADL2, ADL5, ADL6, ADL7, ADL12, ADL13, ADL14, ADL21, ADL23, or ADL15; and (iv) p is an integer from 1 to 15.

In some embodiments, the antibody or antigen binding fragment thereof that targets a CD138-expressing neoplastic cell comprises a heavy chain variable region comprising an amino acid sequence of SEQ ID NO:21, and a light chain variable region comprising an amino acid sequence of SEQ ID NO:22. In some embodiments, the antibody or antigen binding fragment thereof that targets a CD138-expressing neoplastic cell comprises a murine IgG2a heavy chain constant domain and a murine Ig kappa light chain constant domain. In some embodiments, the antibody or antigen binding fragment thereof that targets a CD138-expressing neoplastic cell comprises a human IgG2a heavy chain constant domain and a human Ig kappa light chain constant domain. In some embodiments, the antibody is B-B4. In some embodiments, p is an integer from 1 to 10, from 2 to 8, or from 4 to 8. In some embodiments, p is 4. In some embodiments, p is 8.

In some embodiments, the ADC comprises ADL1-splicing modulator and an antibody or antigen binding fragment thereof that targets an EPHA2-expressing neoplastic cell. In some embodiments, the ADC comprises ADL2-splicing modulator and an antibody or antigen binding fragment thereof that targets an EPHA2-expressing neoplastic cell. In some embodiments, the ADC comprises ADL5-splicing modulator and an antibody or antigen binding fragment thereof that targets an EPHA2-expressing neoplastic cell. In some embodiments, the ADC comprises ADL6-splicing modulator and an antibody or antigen binding fragment thereof that targets an EPHA2-expressing neoplastic cell. In some embodiments, the ADC comprises ADL7-splicing modulator and an antibody or antigen binding fragment thereof that targets an EPHA2-expressing neoplastic cell. In some embodiments, the ADC comprises ADL12-splicing modulator and an antibody or antigen binding fragment thereof that targets an EPHA2-expressing neoplastic cell. In some embodiments, the ADC comprises ADL13-splicing modulator and an antibody or antigen binding fragment thereof that targets an EPHA2-expressing neoplastic cell. In some embodiments, the ADC comprises ADL14-splicing modulator and an antibody or antigen binding fragment thereof that targets an EPHA2-expressing neoplastic cell. In some embodiments, the ADC comprises ADL15-splicing modulator and an antibody or antigen binding fragment thereof that targets an EPHA2-expressing neoplastic cell.

In some embodiments, the antibody or antigen binding fragment thereof that targets an EPHA2-expressing neoplastic cell is an internalizing antibody or internalizing antigen binding fragment. In some embodiments, the antibody or antigen binding fragment thereof that targets an EPHA2-expressing neoplastic cell comprises three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3).

In some embodiments, the ADC has Formula (I):

$$Ab\text{-}(L\text{-}D)_p \qquad (I)$$

wherein:

(i) Ab is an anti-EPHA2 antibody or antigen binding fragment thereof comprising three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO: 16 (LCDR1), SEQ ID NO:17 (LCDR2), and SEQ ID NO:18 (LCDR3);

(ii) D is a splicing modulator;

(iii) L is a linker comprising ADL1, ADL2, ADL5, ADL6, ADL7, ADL12, ADL13, ADL14, ADL21, ADL23, or ADL15; and (iv) p is an integer from 1 to 15.

In some embodiments, the antibody or antigen binding fragment thereof that targets an EPHA2-expressing neoplastic cell comprises a heavy chain variable region comprising an amino acid sequence of SEQ ID NO:23, and a light chain variable region comprising an amino acid sequence of SEQ ID NO:24. In some embodiments, the antibody or antigen binding fragment thereof that targets an EPHA2-expressing neoplastic cell comprises a human IgG1 heavy chain constant domain and a human Ig kappa light chain constant domain. In some embodiments, the antibody is 1C1. In some embodiments, p is an integer from 1 to 10, from 2 to 8, or from 4 to 8. In some embodiments, p is 4. In some embodiments, p is 8.

Drug Moieties

The drug moiety (D) of the ADCs described herein can be any chemotherapeutic agent. Useful classes of chemotherapeutic agents include, for example, modulators of RNA splicing. In certain preferred embodiments, the drug moiety is a splicing modulator. Exemplary splicing modulator compounds are described and exemplified herein.

In various embodiments, the drug moiety is a splicing modulator compound of Formula (II):

(II)

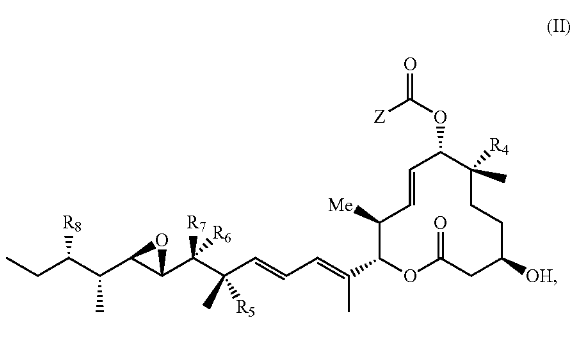

or a pharmaceutically acceptable salt thereof, wherein:

- $R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;
- $R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and
- $R^4$, $R^5$, and $R^8$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;
- $R^6$ and $R^7$ are each independently chosen from hydrogen, —O—$R^{17}$, —O—C(═O)—$R^{17}$, —O—C(═O)—$NR^{15}R^{16}$, $C_1$-$C_6$ alkyl groups, and —$NR^{15}R^{16}$;
- $R^{15}$ and $R^{16}$ are each independently chosen from hydrogen, $R^{17}$, —C(═O)—$R^{17}$, and —C(═O)—O—$R^{17}$;
- $R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and
- Z is is chosen from

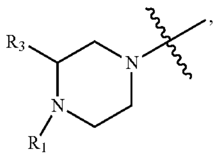
,
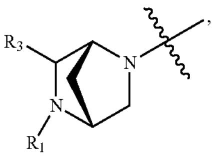
,
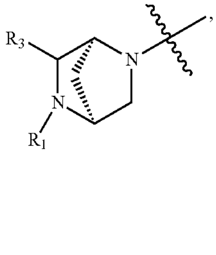
,
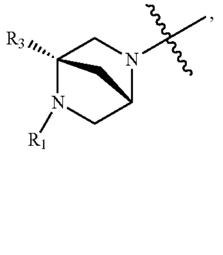
, and

-continued

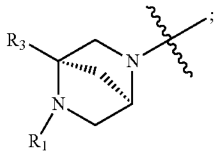
;

wherein $R^1$, $R^3$, $R^4$, $R^5$, $R^6$, $R^1$, $R^3$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen.

In some embodiments, $R^1$ is chosen from hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(═O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(═O)—($C_1$-$C_4$ alkyl) group. In some embodiments, $R^4$ is —O—C(═O)—$CH_3$. In some embodiments, $R^4$ is —O—C(═O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$, and wherein $R^{17}$ is chosen from hydrogen, $C_1$-$C_6$ alkyl groups, $C_3$-$C_8$ cycloalkyl groups, and $C_3$-$C_3$ heterocyclyl groups. In some embodiments, $R^6$ is —O—$R^{17}$. In some embodiments, $R^6$ is —O—C(═O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$. In some embodiments, $R^7$ is —O—$R^{17}$. In some embodiments, $R^7$ is —O—C(═O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, Z is

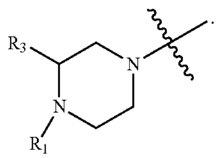

In some embodiments, Z is

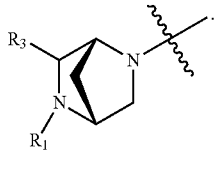

In some embodiments, Z is

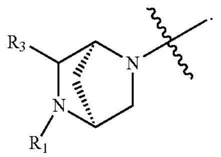

In some embodiments, Z is

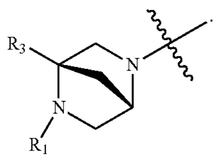

In some embodiments, Z is

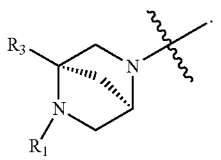

In some embodiments, the splicing modulator compound of Formula (II) attaches to the linker L, e.g., in an ADC of Formula (I), as shown in Formula (II-A):

(II-A)

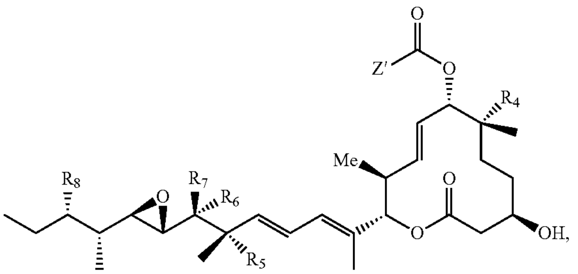

wherein Z' is chosen from

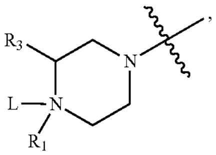

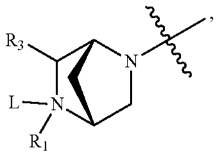

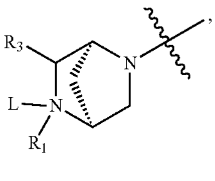

and

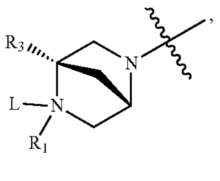

-continued

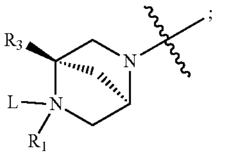

and wherein all other variables are as defined for Formula (II).

In various other embodiments, the drug moiety is a splicing modulator compound of Formula (IV):

$C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups.

(IV)

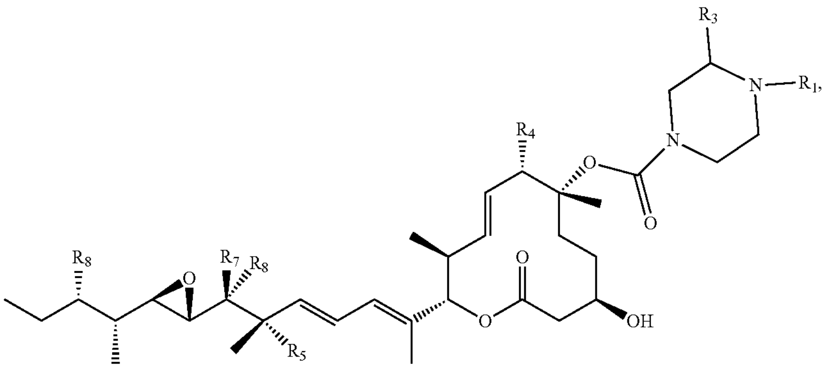

or a pharmaceutically acceptable salt thereof, wherein:

$R^1$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$—C alkyl groups, and —$NR^{15}R^{16}$;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen.

In some embodiments, $R^1$ is chosen from hydrogen, $C_1$-$C_4$ alkyl groups, $C_1$-$C_4$ alkylcarboxylic acid groups, and In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(═O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(═O)—($C_1$-$C_4$ alkyl) group. In some embodiments, $R^4$ is —O—C(═O)—$CH_3$. In some embodiments, $R^4$ is —O—C(═O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C_1$-$C^4$ alkyl groups.

In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C_1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$.

In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$, and wherein $R^{17}$ is chosen from hydrogen, $C_1$-$C_6$ alkyl groups, $C_3$-$C_8$ cycloalkyl groups, and $C_3$-$C_3$ heterocyclyl groups. In some embodiments, $R^6$ is —O—$R^{17}$.

In some embodiments, $R^6$ is —O—C(═O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(═O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^8$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, the splicing modulator compound of Formula (IV) attaches to the linker L, e.g., in an ADC of Formula (I), as shown in Formula (IV-A):

In various other embodiments, the drug moiety is a splicing modulator compound of Formula (VI):

(VI)

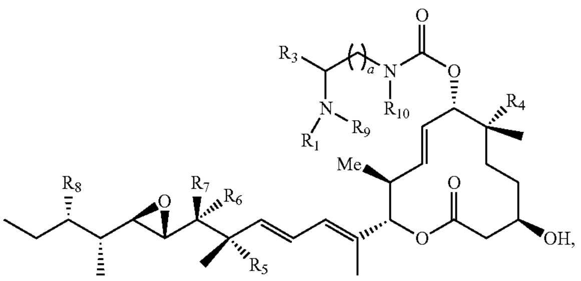

or a pharmaceutically acceptable salt thereof, wherein:

$R^1$ and $R^9$ are each independently chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$alkyl groups, —$NR^{15}R^{16}$, and a linker;

$R^{10}$ is chosen from hydrogen, $C_1$-$C_6$ alkyl groups, —C(═O)—($C_1$-$C_6$ alkyl) groups, and —CD3;

$R^{15}$ and $R^{16}$ are each independently chosen from hydrogen, $R^{17}$, —C(═O)—$R^{17}$, and —C(═O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and a is 1, 2, 3, 4, 5, 6, 7, 8, 9, or 10;

wherein $R^1$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3

(IV-A)

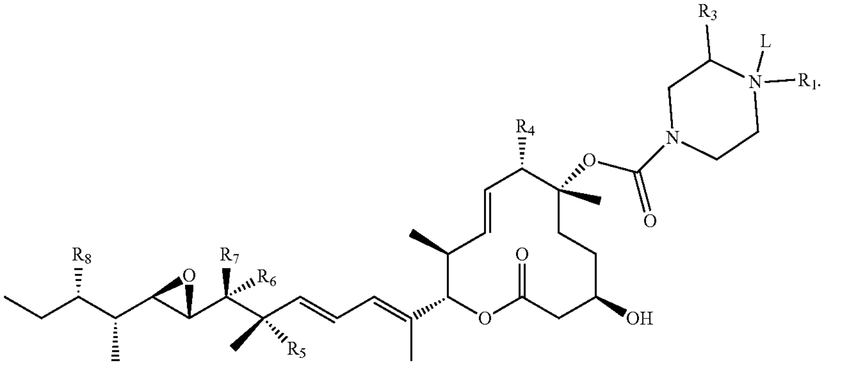

groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein $R^1$ and $R^9$ cannot both be absent.

In some embodiments, $R^1$ is chosen from hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups.

In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^9$ is chosen from absent, hydrogen, $C_1$-$C_4$alkyl groups, —(C=O)—($C_1$-$C_4$ alkyl) groups, and —$CD_3$. In some embodiments, $R^9$ is absent. In some embodiments, $R^9$ is hydrogen. In some embodiments, $R^9$ is a $C_1$-$C_4$alkyl group. In some embodiments, the $C_1$-$C_4$alkyl group is methyl. In some embodiments, the $C_1$-$C_4$ alkyl group is ethyl. In some embodiments, $R^9$ is a —(C=O)—($C_1$-$C_4$ alkyl) group. In some embodiments, the —(C=O)—($C_1$-$C_4$ alkyl) group is —(C=O)-methyl. In some embodiments, $R^9$ is —CD3.

In some embodiments, $R^{10}$ is chosen from hydrogen, $C_1$-$C_4$alkyl groups, —(C=O)—($C_1$-$C_4$alkyl) groups, and —$CD_3$. In some embodiments, $R^{10}$ is hydrogen. In some embodiments, $R^{10}$ is a $C_1$-$C_4$ alkyl group. In some embodiments, the $C_1$-$C_4$ alkyl group is methyl. In some embodiments, the $C_1$-$C_4$alkyl group is ethyl. In some embodiments, $R^{10}$ is a —(C=O)—($C_1$-$C_4$ alkyl) group. In some embodiments, the —(C=O)—($C_1$-$C_4$ alkyl) group is —(C=O)-methyl. In some embodiments, $R^{10}$ is —$CD_3$.

In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_8$ cycloalkyl groups, and $C_3$-$C_3$ heterocyclyl groups. In some embodiments, $R^6$ is —O—$R^{17}$. In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{18}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, a is 1, 2, 3, 4, 5, 6, 7, 8, 9, or 10. In some embodiments, a is 1, 2, 3, 4, 5, or 6. In some embodiments, a is 1, 2, 3, 4, or 5. In some embodiments, a is 1, 2, 3, or 4. In some embodiments, a is 1, 2, or 3. In some embodiments, a is 1 or 2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10.

In some embodiments, the splicing modulator compound of Formula (VI) attaches to the linker L, e.g., in an ADC of Formula (I), as shown in Formula (VI-A):

(VI-A)

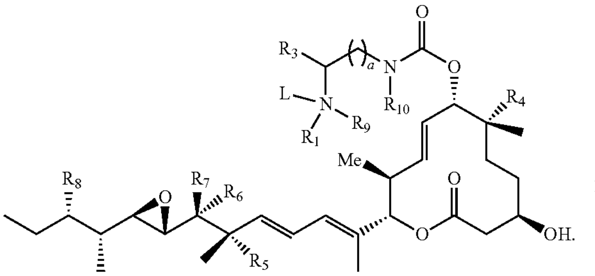

In various other embodiments, the drug moiety is a splicing modulator compound of Formula (VIII):

(VIII)

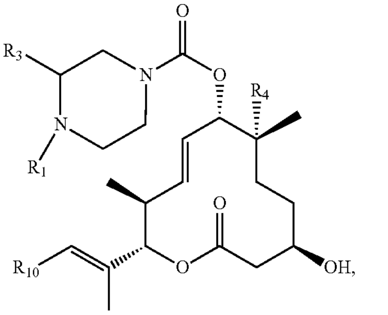

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$ is chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups; and $R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(=O)$_w$-(4 to 7 membered heterocycles), 4 to 7 membered carbocycles, and 4 to 7 membered heterocycles;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$ alkyl groups, —(C=O)—($C_1$-$C_6$ alkyl) groups, —(C=O)—($C_1$-$C_6$ alkyl)-($C_3$-$C_{10}$ heterocyclyl groups), and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$alkyl groups; and w is 0, 1, or 2.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$alkyl group. In some embodiments, $R^4$ is methyl. In some embodiments, $R^4$ is ethyl.

In some embodiments, $R^{10}$ is chosen from 6 to 9 membered carbocycles and 6 to 9 membered heterocycles, each of which is substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$ alkylcarboxylic acid groups.

In some embodiments, the carbocycle is a phenyl substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$ alkylcarboxylic acid groups. In some embodiments, the phenyl is substituted with 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$alkylcarboxylic acid groups. In some embodiments, the phenyl is

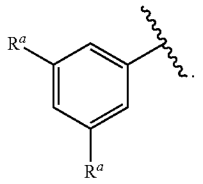

In some embodiments, the heterocycle is a 9 membered heterocycle substituted with 0 to 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups. In some embodiments, the 9 membered heterocycle is

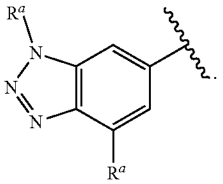

In some embodiments, $R^a$ is chosen from halogens, 3 to 10 membered carbocycles, and 3 to 10 membered heterocycles, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$alkylcarboxylic acid groups. In some embodiments, $R^a$ is chosen from halogens,

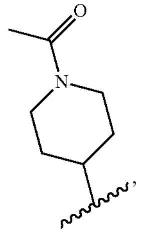
,
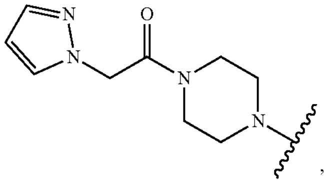
,
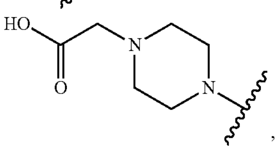
, and
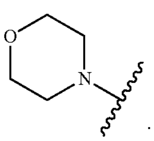
.

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a C heterocyclyl group.

In some embodiments, the splicing modulator compound of Formula (VIII) attaches to the linker L, e.g., in an ADC of Formula (I), as shown in Formula (VIII-A):

(VIII-A)

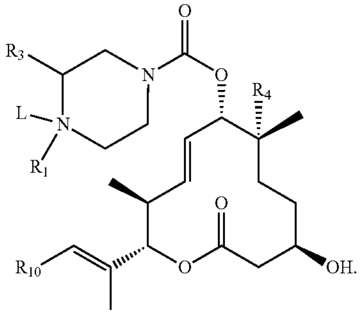

In various embodiments, the drug moiety is a splicing modulator selected from D2 and D1.

In various embodiments, the drug moiety is D2. In various embodiments, the structure of the D2 drug moiety used in the disclosed ADCs is shown below:

D2

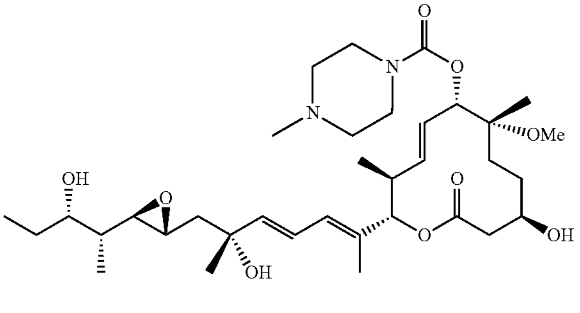

In various embodiments, the linker in the ADCs (e.g., ADCs of Formula (I)) described herein covalently attaches to the D2 drug moiety via an amine on the piperazine group. In various embodiments, the drug moiety is a derivative of D2. In various embodiments, the D2 derivative retains at least one biological function or activity as D2 (e.g., SF3b complex binding, in vitro splicing activity, cytotoxicity) but has an altered chemical structure.

In various embodiments, the drug moiety is D1 or a pharmaceutically acceptable salt thereof. In various embodiments, the structure of the D1 drug moiety used in the disclosed ADCs is shown below:

D1

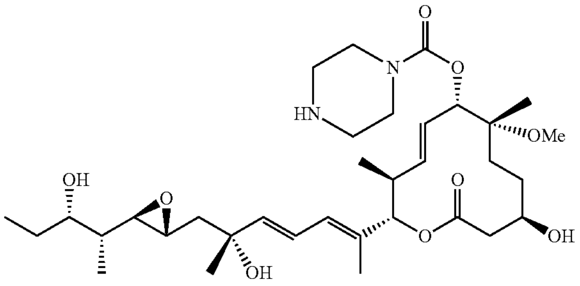

In various embodiments, the linker in the ADCs (e.g., ADCs of Formula (I)) described herein covalently attaches to the D1 drug moiety via an amine on the piperazine group. In various embodiments, the drug moiety is a derivative of D1. In various embodiments, the D1 derivative retains at least one biological function or activity as D1 (e.g., SF3b complex binding, in vitro splicing activity, cytotoxicity) but has an altered chemical structure.

In some embodiments, the splicing modulator comprises D1:

(D1)

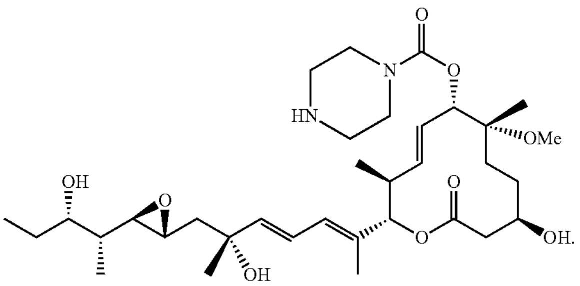

In some embodiments, the splicing modulator comprises D2:

(D2)

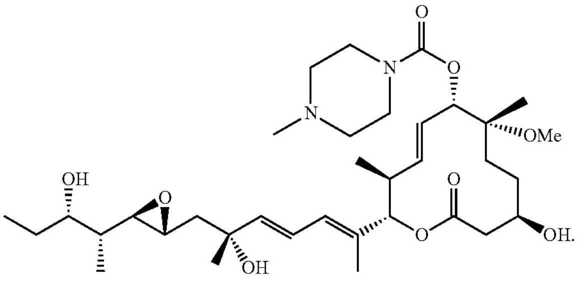

In some embodiments, the splicing modulator comprises D3:

(D3)

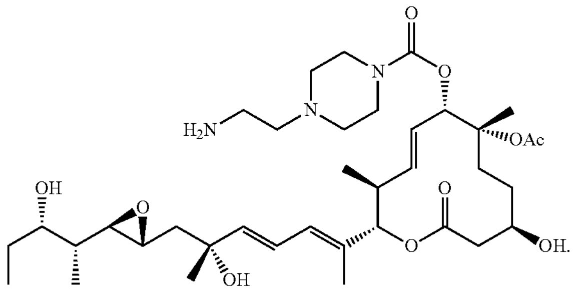

In some embodiments, the splicing modulator comprises D4:

(D4)

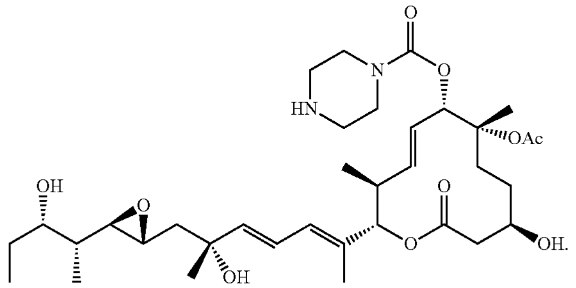

In some embodiments, the splicing modulator comprises D4':

(D4')

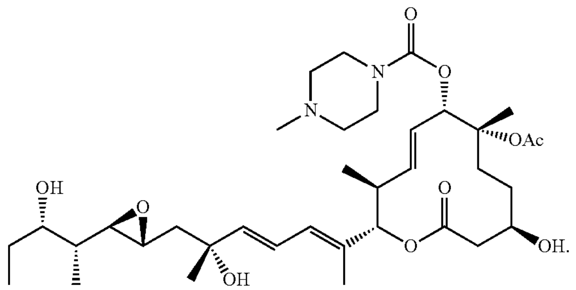

In some embodiments, the splicing modulator comprises D5:
(D5)
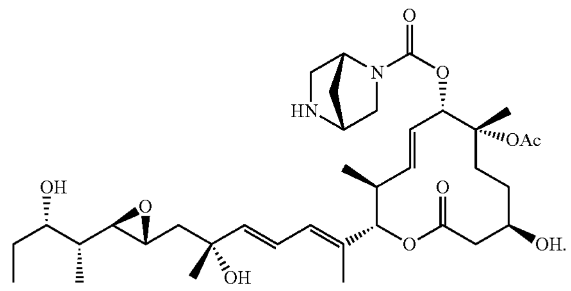
In some embodiments, the splicing modulator comprises D6:
(D6)
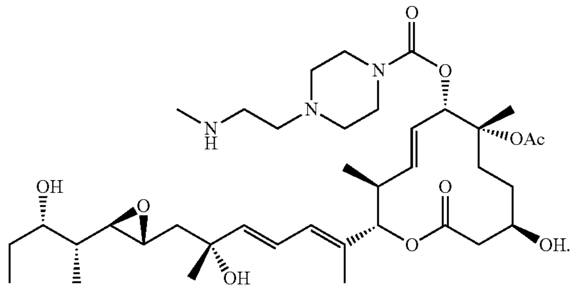
In some embodiments, the splicing modulator comprises D7:
(D7)
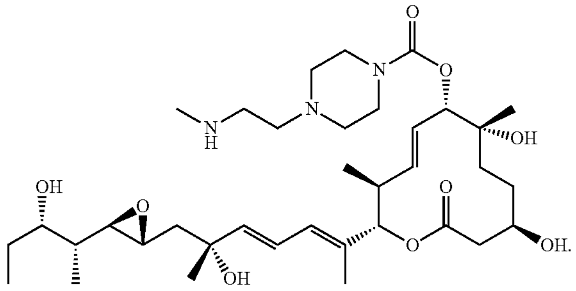
In some embodiments, the splicing modulator comprises D8:
(D8)
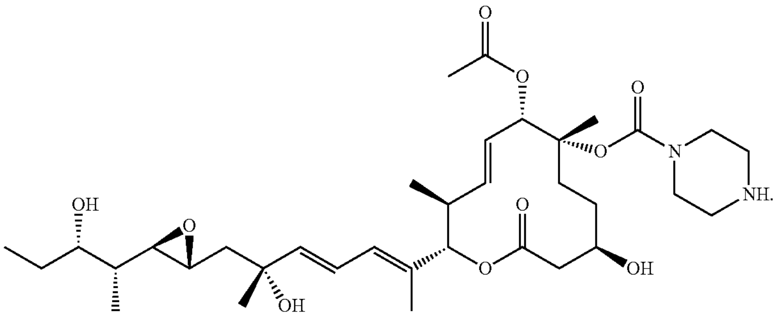

In some embodiments, the splicing modulator comprises D9:
(D9)
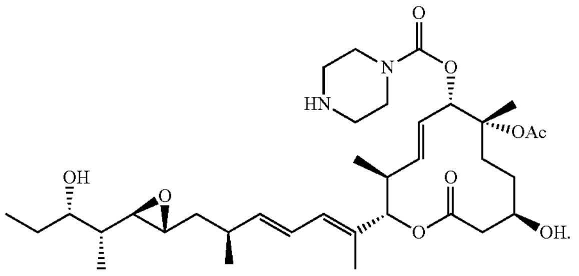
In some embodiments, the splicing modulator comprises D10:
(D10)
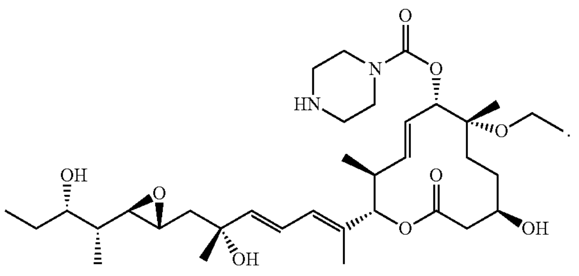
In some embodiments, the splicing modulator comprises D11:
(D11)
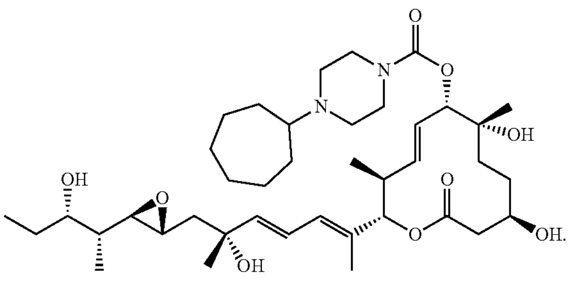
In some embodiments, the splicing modulator comprises D12:
(D12)
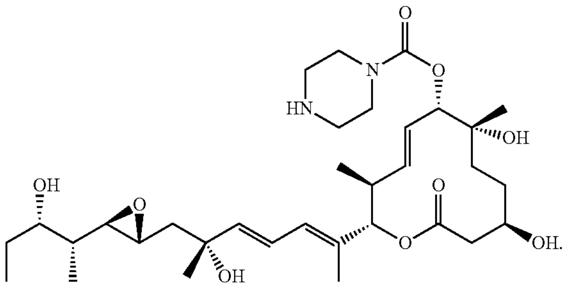
In some embodiments, the splicing modulator comprises D13:
(D13)
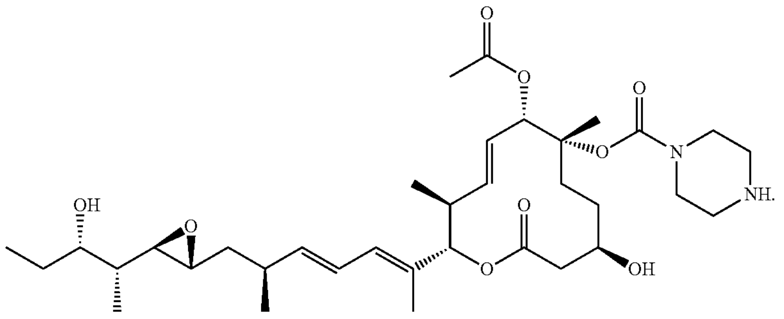

In some embodiments, the splicing modulator comprises D14:
(D14)
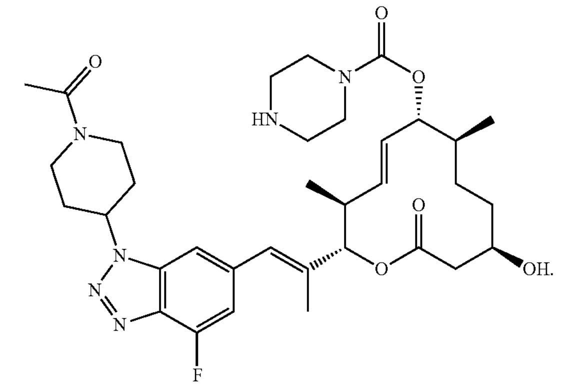
In some embodiments, the splicing modulator comprises D15:
(D15)
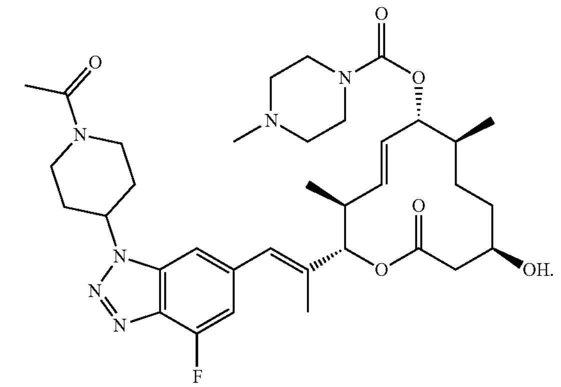
In some embodiments, the splicing modulator comprises D16:
(D16)
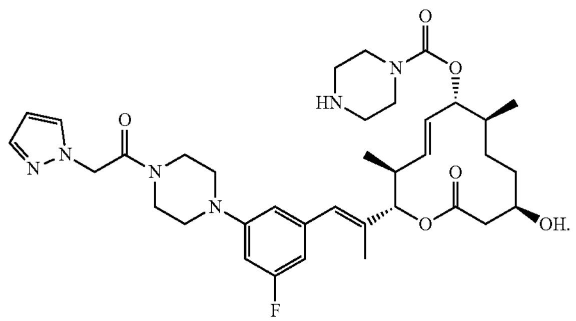
In some embodiments, the splicing modulator comprises D17:
(D17)
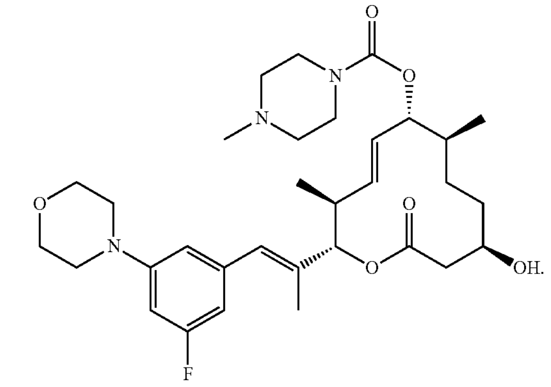
In some embodiments, the splicing modulator comprises D18:
(D18)
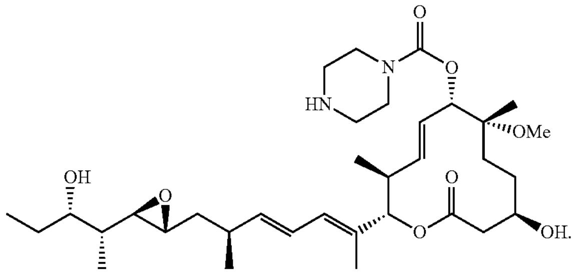
In some embodiments, the splicing modulator comprises D19:
(D19)
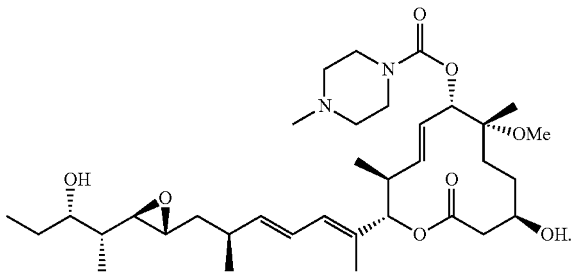

In some embodiments, the splicing modulator comprises D20:

(D20)

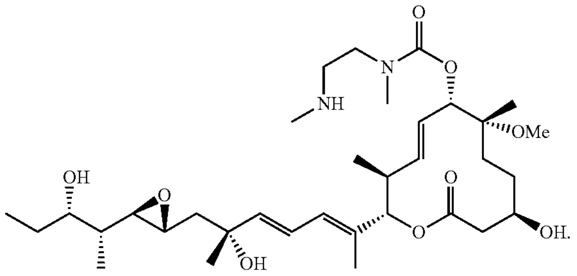

In some embodiments, the splicing modulator comprises D21:

(D21)

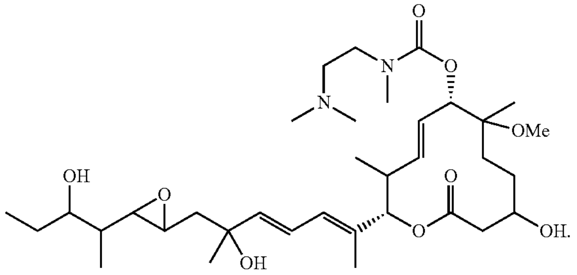

In some embodiments, the splicing modulator comprises D22:

(D22)

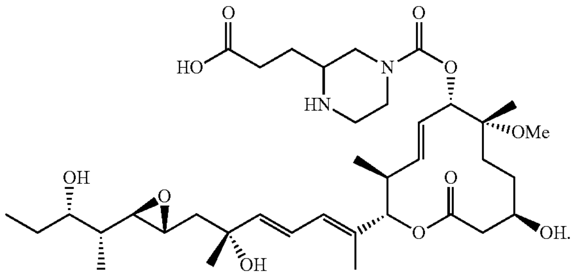

In some embodiments, the splicing modulator comprises D23:

(D23)

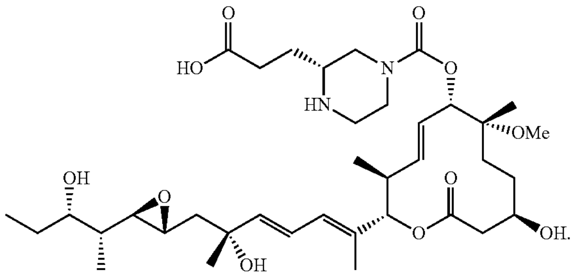

In some embodiments, the splicing modulator comprises D24:

(D24)

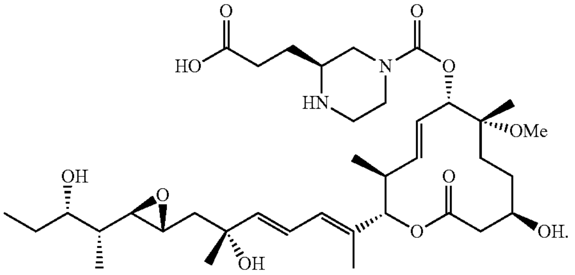

In some embodiments, the splicing modulator comprises D25:

(D25)

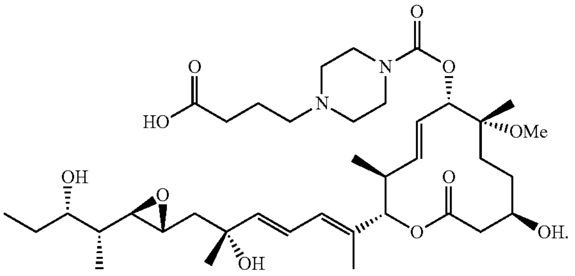

In some embodiments, the splicing modulator comprises D26:

(D26)

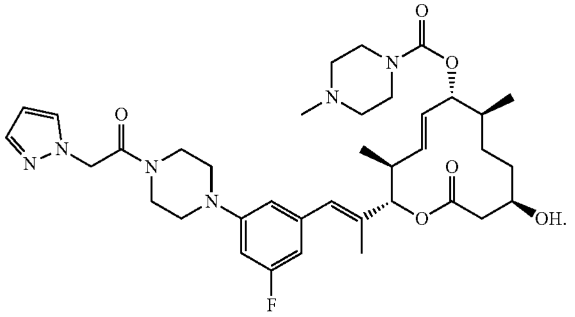

In some embodiments, the splicing modulator comprises D27:

(D27)

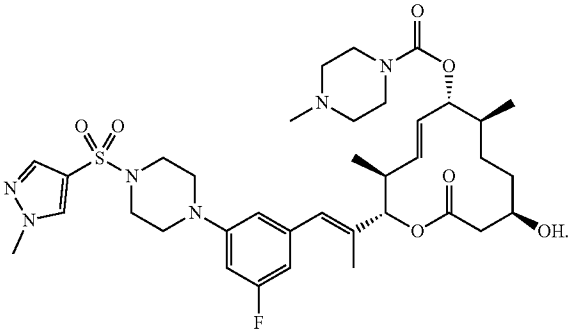

In some embodiments, the splicing modulator comprises D28:
(D28)
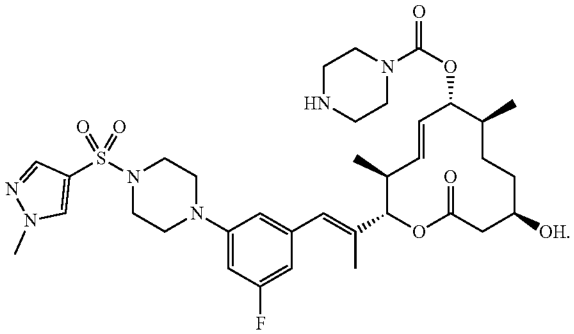
In some embodiments, the splicing modulator comprises D29:
(D29)
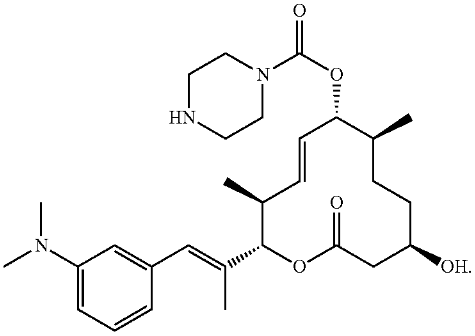
In some embodiments, the splicing modulator comprises D30:
(D30)
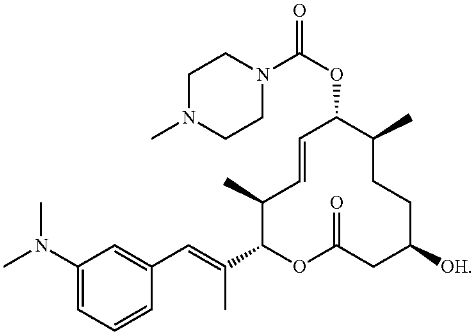
In some embodiments, the splicing modulator comprises D31:
(D31)
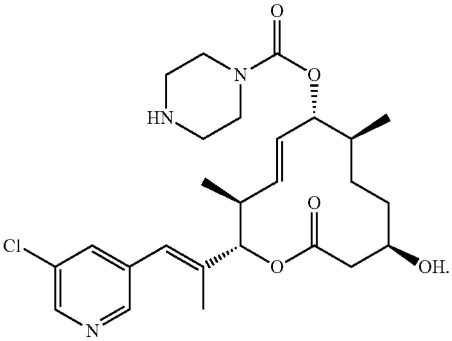
In some embodiments, the splicing modulator comprises D32:
(D32)
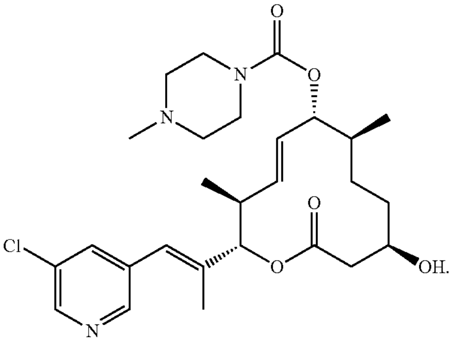
In some embodiments, the splicing modulator comprises D33:
(D33)
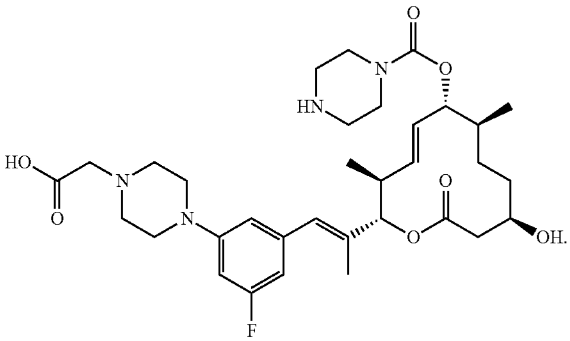

In some embodiments, the splicing modulator comprises D34:

(D34)

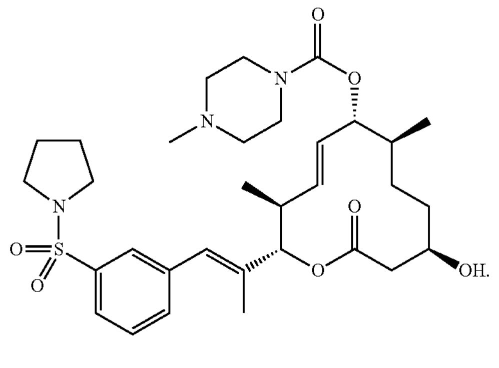

In some embodiments, the splicing modulator comprises D35:

(D35)

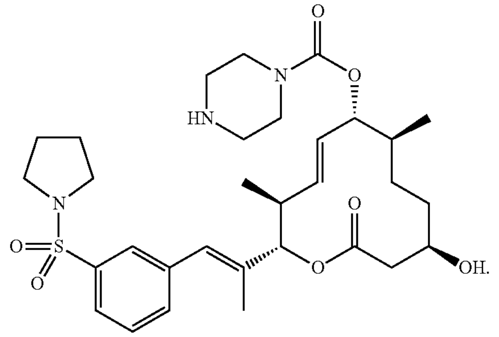

An exemplary ADC has Formula (I):

$$Ab\text{-}(L\text{-}D)_p \quad (I)$$

wherein

Ab is an antibody or antigen binding fragment which targets a neoplastic cell;

D is D2;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO: 16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets an ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

In some embodiments, L is selected from any of the linkers disclosed herein, or any combination of linker components disclosed herein. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab\text{-}(L\text{-}D)_p \qquad (I)$$

wherein

Ab is an antibody or antigen binding fragment which targets a neoplastic cell;

D is D1;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO: 16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets an ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab\text{-}(L\text{-}D)_p \quad (I)$$

wherein

Ab is an antibody or antigen binding fragment which targets a neoplastic cell;

D is D4;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab\text{-}(L\text{-}D)_p \quad (I)$$

wherein

Ab is an antibody or antigen binding fragment which targets a neoplastic cell;

D is D12;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab\text{-}(L\text{-}D)_p \quad (I)$$

wherein

Ab is an antibody or antigen binding fragment which targets a neoplastic cell;

D is D15;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

In some embodiments, L is selected from any of the linkers disclosed herein, or any combination of linker components disclosed herein. In some embodiments, L is a cleavable linker. In some embodiments, L is a non-cleavable linker. In some embodiments, L is a linker comprising MC-Val-Cit-pABC, MC-Val-Ala-pABC, MC-Val-Ala-pAB, MC-Glu-Val-Cit-pABC, Ala-Ala-Asn-pABC, or β-glucuronide. In some embodiments, L is a linker comprising Mal-Hex, Mal-Et, or Mal-Et-O-Et. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

In some embodiments, p is from 1 to 10. In some embodiments, p is from 2 to 8. In some embodiments, p is from 4 to 8. In some embodiments, p is 4. In some embodiments, p is 8.

Another exemplary ADC has Formula (I):

$$Ab\text{-}(L\text{-}D)_p \quad (I)$$

wherein Ab is an anti-HER2 antibody or antigen binding fragment comprising three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:19, and a light chain variable region comprising an amino acid sequence of SEQ ID NO:20.

In some embodiments, L is selected from any of the linkers disclosed herein, or any combination of linker components disclosed herein. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab\text{-}(L\text{-}D)_p \quad (I)$$

wherein Ab is an anti-CD138 antibody or antigen binding fragment comprising three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:21, and a light chain variable region comprising an amino acid sequence of SEQ ID NO:22.

In some embodiments, L is selected from any of the linkers disclosed herein, or any combination of linker components disclosed herein. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab\text{-}(L\text{-}D)_p \quad (I)$$

wherein Ab is an anti-EPHA2 antibody or antigen binding fragment comprising three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:23, and a light chain variable region comprising an amino acid sequence of SEQ ID NO:24.

In some embodiments, L is selected from any of the linkers disclosed herein, or any combination of linker components disclosed herein. In some embodiments, L is a linker comprising MC-Val-Cit-pABC, Mal-$(PEG)_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

In various embodiments, ADCs comprising a D2 or D1 drug moiety can include a cleavable or non-cleavable linker.

In various embodiments, the linker is a cleavable linker. In various embodiments, the cleavable linker comprises MC-Val-Cit-pABC. In various embodiments, the cleavable linker comprises MC-Val-Ala-pABC. In various embodiments, the cleavable linker comprises MC-Val-Ala-pAB. In various embodiments, the cleavable linker comprises MC-Glu-Val-Cit-pABC. In various embodiments, the cleavable linker comprises MC-Ala-Ala-Asn-pABC.

In various other embodiments, the linker is a non-cleavable linker. In various embodiments, the non-cleavable linker comprises MC, alone or in combination with at least one additional spacer unit. In various embodiments, the non-cleavable linker comprises Mal-Hex, alone or in combination with at least one additional spacer unit. In various embodiments, the non-cleavable linker comprises Mal-Et, alone or in combination with at least one additional spacer unit. In various embodiments, the non-cleavable linker comprises Mal-Et-O-Et, alone or in combination with at least one additional spacer unit.

In various embodiments, in ADCs comprising a D2 or D1 drug moiety, p is from 1 to 10. In various embodiments, p is from 2 to 8. In various embodiments, p is from 4 to 8. In various embodiments, p is 4. In various embodiments, p is 8.

In various embodiments, an ADC comprising a D2 or D1 drug moiety as disclosed herein demonstrates improved drug:antibody ratio, lower aggregation levels, increased stability, increased on-target killing of cancer cells, decreased off-target killing of non-cancer cells, and/or increased cytotoxicity and/or potency relative to an ADC comprising an alternate drug moiety (e.g., an alternate splicing modulator drug moiety). In some embodiments, an ADC comprising a D2 or D1 drug moiety as disclosed herein provides good or superior properties in one or more of the categories listed above, or across a spectrum of functional properties for a therapeutic ADC. In some embodiments, an ADC comprising a D2 or D1 drug moiety exhibits surprisingly effective potency and increased inhibition of cell growth and/or proliferation in cells that express the antigen targeted by the ADC, as compared to an ADC comprising an alternate drug moiety (e.g., an alternate splicing modulator drug moiety). In some embodiments, potency can be measured in terms of the concentration of compound to cause 50% reduction in cell proliferation ($GI_{50}$). In various embodiments, ADCs comprising a D2 or D1 drug moiety exhibit surprisingly increased in vivo stability (e.g., plasma stability), as compared to an ADC with an alternate drug moiety (e.g., an alternate splicing modulator drug moiety, e.g., thailanstatin A). See, e.g., the ADC described in Puthenveetil et al. (Bioconjugate Chem. (2016) 27:1880-8), which shows complete bioconversion of payload by 72 hours (i.e., acetate is completely hydrolyzed).

In certain embodiments, an intermediate, which is the precursor of the linker moiety, is reacted with the drug moiety (e.g., the splicing modulator) under appropriate conditions. In certain embodiments, reactive groups are used on the drug and/or the intermediate or linker. The product of the reaction between the drug and the intermediate, or the derivatized drug (drug plus linker), is subsequently reacted with the antibody or antigen binding fragment under appropriate conditions. Alternatively, the intermediate or linker may first be reacted with the antibody or antigen binding fragment, or a derivatized antibody or antigen binding fragment, and then reacted with the drug or derivatized drug.

A number of different reactions are available for covalent attachment of the drug moiety and/or linker moiety to the antibody or antigen binding fragment. This is often accomplished by reaction of one or more amino acid residues of the antibody or antigen binding fragment, including the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a drug moiety to an amino (or carboxy) group on an antibody or antigen binding fragment. Additionally, bifunctional agents such as dialdehydes or imidoesters may also be used to link the amino group on a drug moiety to an amino group on an antibody or antigen binding fragment. Also available for attachment of drugs (e.g., a splicing modulator) to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure. Examples of drug moieties that can be generated and linked to an antibody or antigen binding fragment using various chemistries known to in the art include splicing modulators, e.g., the splicing modulators described and exemplified herein.

Linker-Drug/Drug Compounds

Further disclosed herein are exemplary linker-drug (L-D) compounds, as well as compositions comprising multiple copies of such compounds. In various embodiments, the linker-drug compounds disclosed herein can be defined by the generic formula: L-D, wherein L=a linker moiety, and D=a drug moiety (e.g., a splicing modulator drug moiety). In certain embodiments, the disclosed L-D compounds are suitable for use in the ADCs described herein, e.g., in ADCs of Formula (I).

In various embodiments, the linker-drug (L-D) compounds disclosed herein comprise a linker-drug structure according to Formula (III). In various embodiments, the present disclosure provides a linker-drug (L-D) compound of Formula (III):

(III)

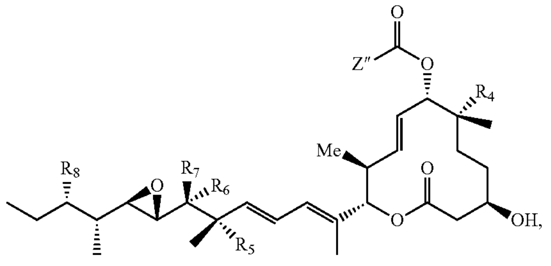

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$alkyl groups, —$NR^{15}R^{16}$, and a linker;

$R^{15}$ and $R^{16}$ are each independently chosen from hydrogen, $R^{17}$, —C(═O)—$R^{17}$, and —C(═O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and Z" is chosen from

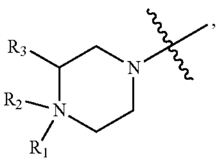,

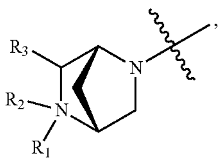,

-continued

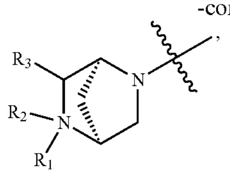,

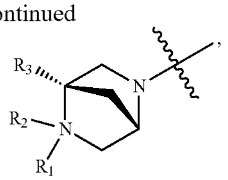, and

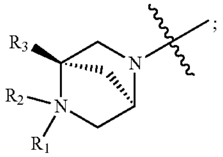;

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl.

In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(═O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(═O)—($C_1$-$C_4$ alkyl) group. In some embodiments, $R^4$ is —O—C(═O)—$CH_3$. In some embodiments, $R^4$ is —O—C(═O)—$CH_2CH_3$. In some embodiments, $R^4$ is a $C_1$-$C_4$alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^2$ is absent and $R^6$ is a linker. In some embodiments, $R^2$ is absent and $R^7$ is a linker. In some embodiments, $R^2$ is a linker. In some embodiments, $R^6$ is hydrogen. In some embodiments, $R^7$ is hydrogen.

In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$, and wherein $R^{17}$ is chosen from hydrogen, $C_1$-$C_6$ alkyl groups, $C_3$-$C_3$ cycloalkyl groups, and $C_3$-$C_3$ heterocyclyl groups. In some embodiments, $R^6$ is —O—$R^{17}$. In some embodiments, $R^6$ is —O—C(═O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(═O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^8$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a C heterocyclyl group.

In some embodiments, Z' is

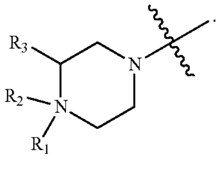.

In some embodiments, Z' is

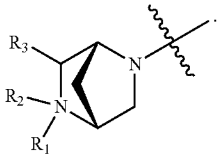

In some embodiments, Z' is

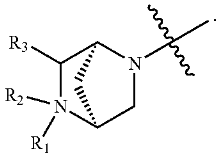

In some embodiments, Z' is

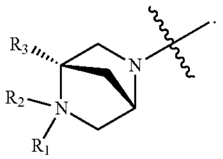

In some embodiments, Z' is

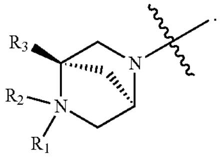

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises $-(PEG)_m-$, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from p-aminobenzyloxycarbonyl (pABC) and p-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises $-(PEG)_m-$, wherein m is an integer from 1 to 6.

In various other embodiments, the linker-drug (L-D) compounds disclosed herein comprise a linker-drug structure according to Formula (V). In various embodiments, the present disclosure provides a linker-drug (L-D) compound of Formula (V):

(V)

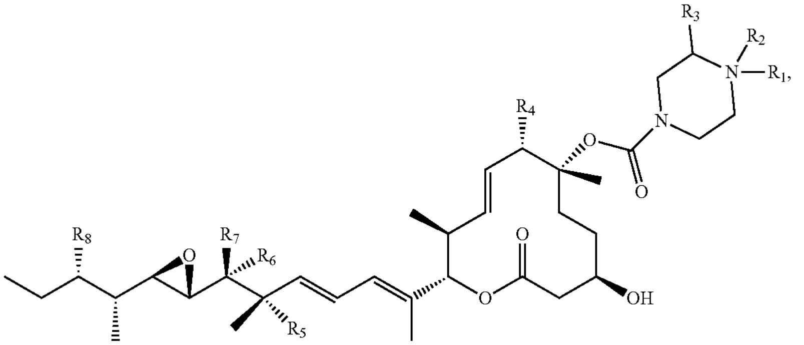

or a pharmaceutically acceptable salt thereof, wherein:

$R^1$ is chosen from absent, hydrogen, $C_1$-$C_6$alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(═O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups; and $R^4$, $R^5$, and $R^3$ are each independently chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^6$ and $R^7$ are each independently chosen from hydrogen, —O—$R^{17}$, —O—C(═O)—$R^{17}$, —O—C(═O)—$NR^{15}R^{16}$, $C_1$-$C_6$alkyl groups, —$NR^{15}R^{16}$, and a linker;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(═O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(═O)—($C_1$-$C_4$ alkyl) group. In some embodiments, $R^4$ is —O—C(═O)—$CH_3$. In some embodiments, $R^4$ is —O—C(═O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^2$ is absent and $R^6$ is a linker. In some embodiments, $R^2$ is absent and $R^7$ is a linker. In some embodiments, $R^2$ is a linker. In some embodiments, $R^6$ is hydrogen. In some embodiments, $R^7$ is hydrogen.

In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(═O)—$R^{17}$, and —C(═O)—O—$R^{17}$, and wherein $R^{17}$ is chosen from hydrogen, $C_1$-$C_6$ alkyl groups, $C_3$-$C_3$ cycloalkyl groups, and $C_3$-$C_3$ heterocyclyl groups. In some embodiments, $R^6$ is —O—$R^{17}$. In some embodiments, $R^6$ is —O—C(═O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(═O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^8$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{16}$ is $R^{17}$. In some embodiments, $R^{15}$ is —C(═O)—$R^{17}$. In some embodiments, $R^{16}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises -$(PEG)_m$-, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from p-aminobenzyloxycarbonyl (pABC) and p-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises -$(PEG)_m$-, wherein m is an integer from 1 to 6.

In various other embodiments, the linker-drug (L-D) compounds disclosed herein comprise a linker-drug structure according to Formula (VII). In various embodiments, the present disclosure provides a linker-drug (L-D) compound of Formula (VII):

(VII)

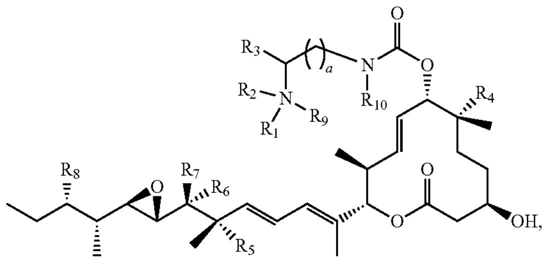

or a pharmaceutically acceptable salt thereof, wherein:

- $R^1$ and $R^9$ are each independently chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;

$R^{10}$ is chosen from hydrogen, $C_1$-$C_6$ alkyl groups, —C(=O)—($C_1$-$C_6$ alkyl) groups, and —CD3;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_3$ cycloalkyl groups, benzyl groups, and $C_3$-$C_8$ heterocyclyl groups; and a is 1, 2, 3, 4, 5, 6, 7, 8, 9, or 10;

wherein $R^1$, $R^2$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen;

wherein if $R^2$ is a linker, then neither $R^6$ or $R^7$ is a linker, and if $R^6$ or $R^7$ is a linker, then $R^2$ is absent; and wherein $R^1$ and $R^9$ cannot both be absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl.

In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^9$ is chosen from absent, hydrogen, $C_1$-$C_4$alkyl groups, —(C=O)—($C_1$-$C_4$ alkyl) groups, and —$CD_3$. In some embodiments, $R^9$ is absent. In some embodiments, $R^9$ is hydrogen. In some embodiments, $R^9$ is a $C_1$-$C_4$alkyl group. In some embodiments, the $C_1$-$C_4$alkyl group is methyl. In some embodiments, the $C_1$-$C_4$ alkyl group is ethyl. In some embodiments, $R^9$ is a —(C=O)—($C_1$-$C_4$ alkyl) group. In some embodiments, the —(C=O)—($C_1$-$C_4$ alkyl) group is —(C=O)-methyl. In some embodiments, $R^9$ is —CD3.

In some embodiments, $R^{10}$ is chosen from hydrogen, $C_1$-$C_4$alkyl groups, —(C=O)—($C_1$-$C_4$alkyl) groups, and —$CD_3$. In some embodiments, $R^{10}$ is hydrogen. In some embodiments, $R^{10}$ is a $C_1$-$C_4$ alkyl group. In some embodiments, the $C_1$-$C_4$ alkyl group is methyl. In some embodiments, the $C_1$-$C_4$alkyl group is ethyl. In some embodiments, $R^{10}$ is a —(C=O)—($C_1$-$C_4$ alkyl) group. In some embodiments, the —(C=O)—($C_1$-$C_4$ alkyl) group is —(C=O)-methyl. In some embodiments, $R^{10}$ is —$CD_3$.

In some embodiments, $R^2$ is absent and $R^6$ is a linker. In some embodiments, $R^2$ is absent and $R^7$ is a linker. In some embodiments, $R^2$ is a linker. In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_8$ cycloalkyl groups, and $C_3$-$C_3$ heterocyclyl groups. In some embodiments, $R^6$ is —O—$R^{17}$. In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, a is 1, 2, 3, 4, 5, 6, 7, 8, 9, or 10. In some embodiments, a is 1, 2, 3, 4, 5, or 6. In some embodiments, a is 1, 2, 3, 4, or 5. In some embodiments, a is 1, 2, 3, or 4. In some embodiments, a is 1, 2, or 3. In some embodiments, a is 1 or 2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10.

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises $-(PEG)_m-$, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from p-aminobenzyloxycarbonyl (pABC) and p-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises $-(PEG)_m-$, wherein m is an integer from 1 to 6.

In various other embodiments, the linker-drug (L-D) compounds disclosed herein comprise a linker-drug structure according to Formula (IX). In various embodiments, the present disclosure provides a linker-drug (L-D) compound of Formula (IX):

(IX)

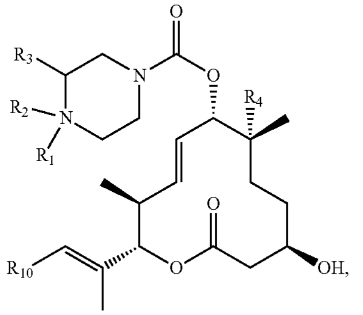

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$—C cycloalkyl groups, benzyl groups, $C_3$-$C_8$ heterocyclyl groups, —O—C(=O)—($C_1$-$C_6$ alkyl) groups, and —$CD_3$;

$R^2$ is a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(═O)—($C_1$-$C_6$ alkyl) groups;

$R^4$ is chosen from hydrogen, hydroxyl groups, —O—($C_1$-$C_6$ alkyl) groups, —O—C(═O)—($C_1$-$C_6$ alkyl) groups, and $C_1$-$C_6$ alkyl groups;

$R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(═O)$_w$-(4 to 7 membered heterocycles), 4 to 7 membered carbocycles, and 4 to 7 membered heterocycles;

$R^{15}$ and $R^{16}$ are each independently chosen from hydrogen, $R^{17}$, —C(═O)—$R^{17}$, and —C(═O)—O—$R^{17}$; and $R^{17}$ is chosen from hydrogen, $C_1$-$C_6$ alkyl groups, $C_3$-$C_3$ cycloalkyl groups, benzyl groups, and $C_3$-$C_8$ heterocyclyl groups;

wherein $R^1$, $R^2$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$—C cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$ alkyl groups, —(C═O)—($C_1$-$C_6$ alkyl) groups, —(C═O)—($C_1$-$C_6$ alkyl)-($C_3$-$C_{10}$ heterocyclyl groups), and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$alkyl groups; and w is 0, 1, or 2.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(═O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(═O)—($C_1$-$C_4$ alkyl) group. In some embodiments, $R^4$ is —O—C(═O)—$CH_3$. In some embodiments, $R^4$ is —O—C(═O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^{10}$ is chosen from 6 to 9 membered carbocycles and 6 to 9 membered heterocycles, each of which is substituted with 0 to 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups.

In some embodiments, the carbocycle is a phenyl substituted with 0 to 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups. In some embodiments, the phenyl is substituted with 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$alkylcarboxylic acid groups. In some embodiments, the phenyl is

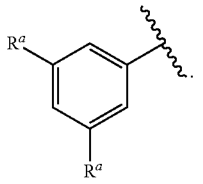

In some embodiments, the heterocycle is a 9 membered heterocycle substituted with 0 to 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups. In some embodiments, the 9 membered heterocycle is

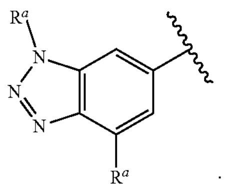

In some embodiments, $R^a$ is chosen from halogens, 3 to 10 membered carbocycles, and 3 to 10 membered heterocycles, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$alkylcarboxylic acid groups. In some embodiments, $R^a$ is chosen from halogens,

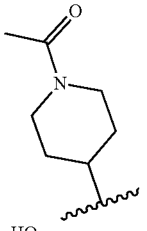,
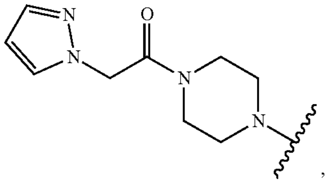,
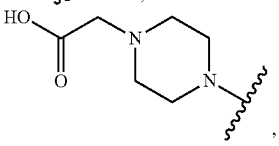, and
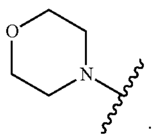.

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a C heterocyclyl group.

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises $-(PEG)_m-$, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from p-aminobenzyloxycarbonyl (pABC) and p-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises $-(PEG)_m-$, wherein m is an integer from 1 to 6.

In some embodiments, the drug moiety is a splicing modulator chosen from D1, D2, D3, D4, D4', D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, and D35.

In various embodiments, the drug moiety is a splicing modulator selected from D2 and D1.

In various embodiments, the drug moiety is D2. In various embodiments, the structure of the D2 drug moiety used in the disclosed linker-drug (L-D) compounds is shown below:

D2

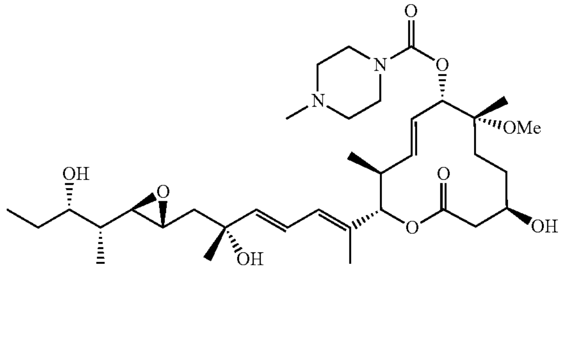

In various embodiments, the linker in the linker-drug (L-D) compounds described herein covalently attaches to the D2 drug moiety via an amine on the piperazine group. In various embodiments, the drug moiety is a derivative of D2. In various embodiments, the D2 derivative retains at least one biological function or activity as D2 (e.g., SF3b complex binding, in vitro splicing activity, cytotoxicity) but has an altered chemical structure.

In various embodiments, the drug moiety is D1. In various embodiments, the structure of the D1 drug moiety used in the disclosed linker-drug (L-D) compounds is shown below:

D1

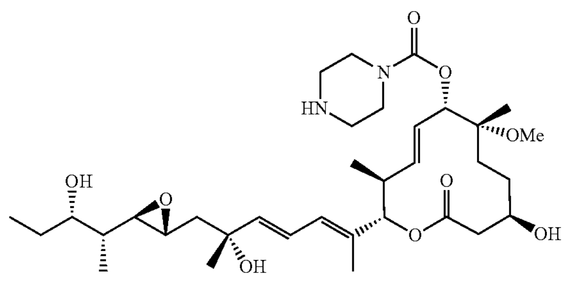

In various embodiments, the linker in the linker-drug (L-D) compounds described herein covalently attaches to the D1 drug moiety via an amine on the piperazine group. In various embodiments, the drug moiety is a derivative of D1. In various embodiments, the D1 derivative retains at least one biological function or activity as D1 (e.g., SF3b complex binding, in vitro splicing activity, cytotoxicity) but has an altered chemical structure Also disclosed herein are exemplary splicing modulator drug compounds, for use on their own or as drug moieties in the ADCs disclosed herein. The present disclosure, in various embodiments, further provides compositions comprising multiple copies of such compounds, e.g., pharmaceutical compositions comprising a splicing modulator drug compound and a pharmaceutically acceptable carrier.

In various embodiments, the present disclosure provides a compound chosen from a compound of formula (D4)

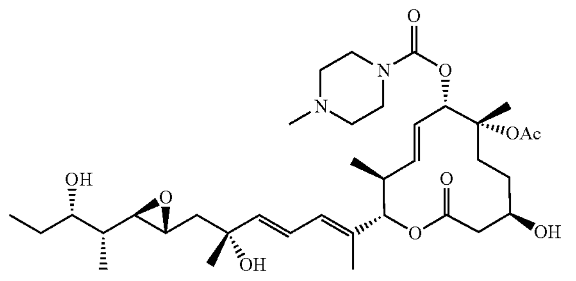

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D8)

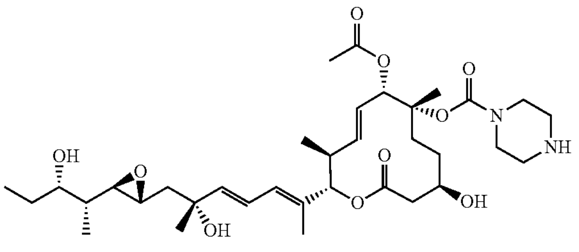

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D9)

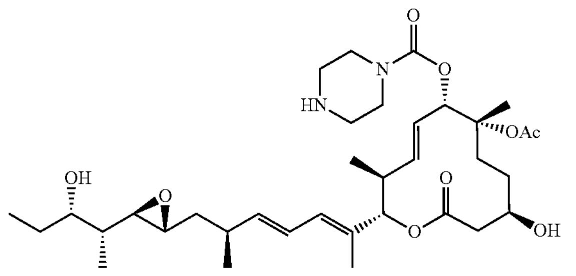

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D10)

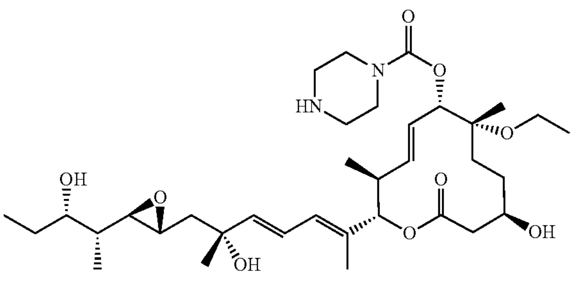

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D13)

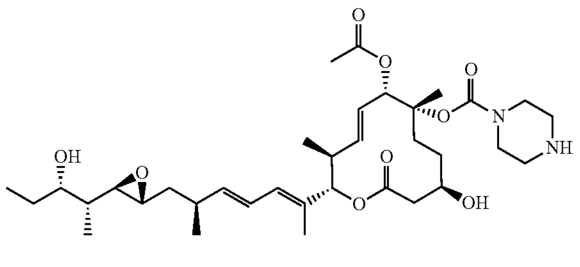

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D18)

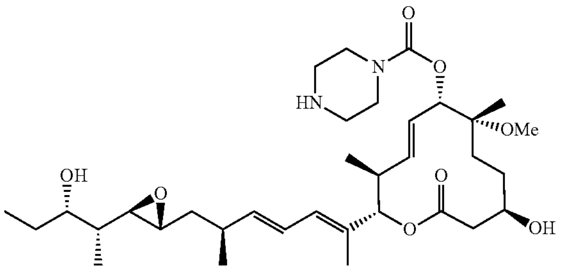

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D19)

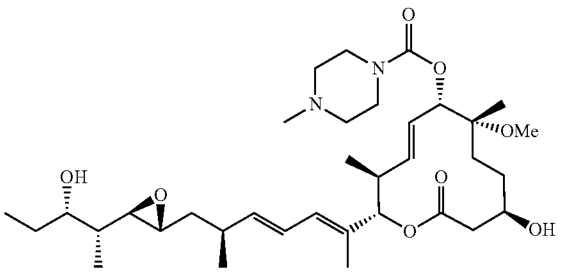

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D20)

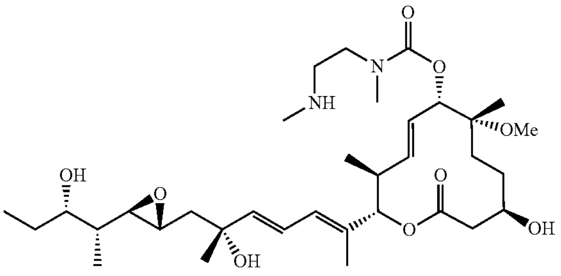

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D21)

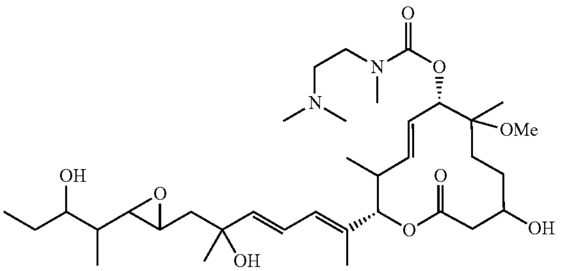

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D22)

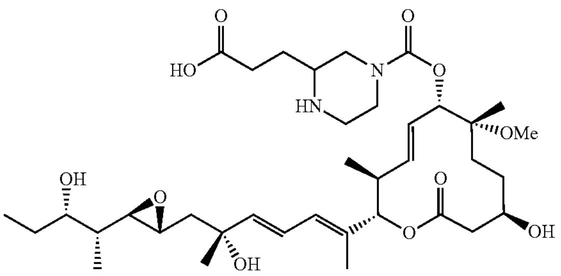

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D25)

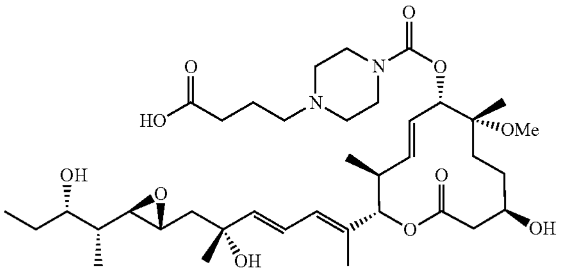

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D33)

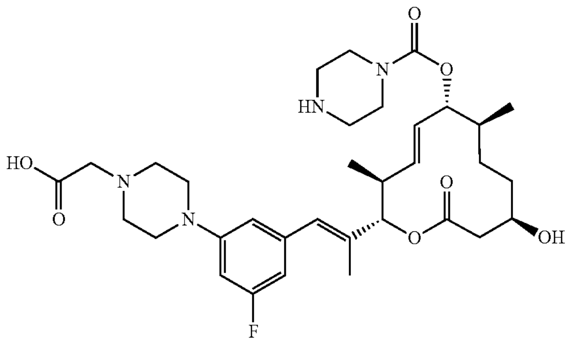

and pharmaceutically acceptable salts thereof. In various embodiments, the present disclosure further provides a pharmaceutical composition comprising the compound, or a pharmaceutically acceptable salt thereof, and a pharmaceutically acceptable carrier.

Bioconjugation

Figure 26:
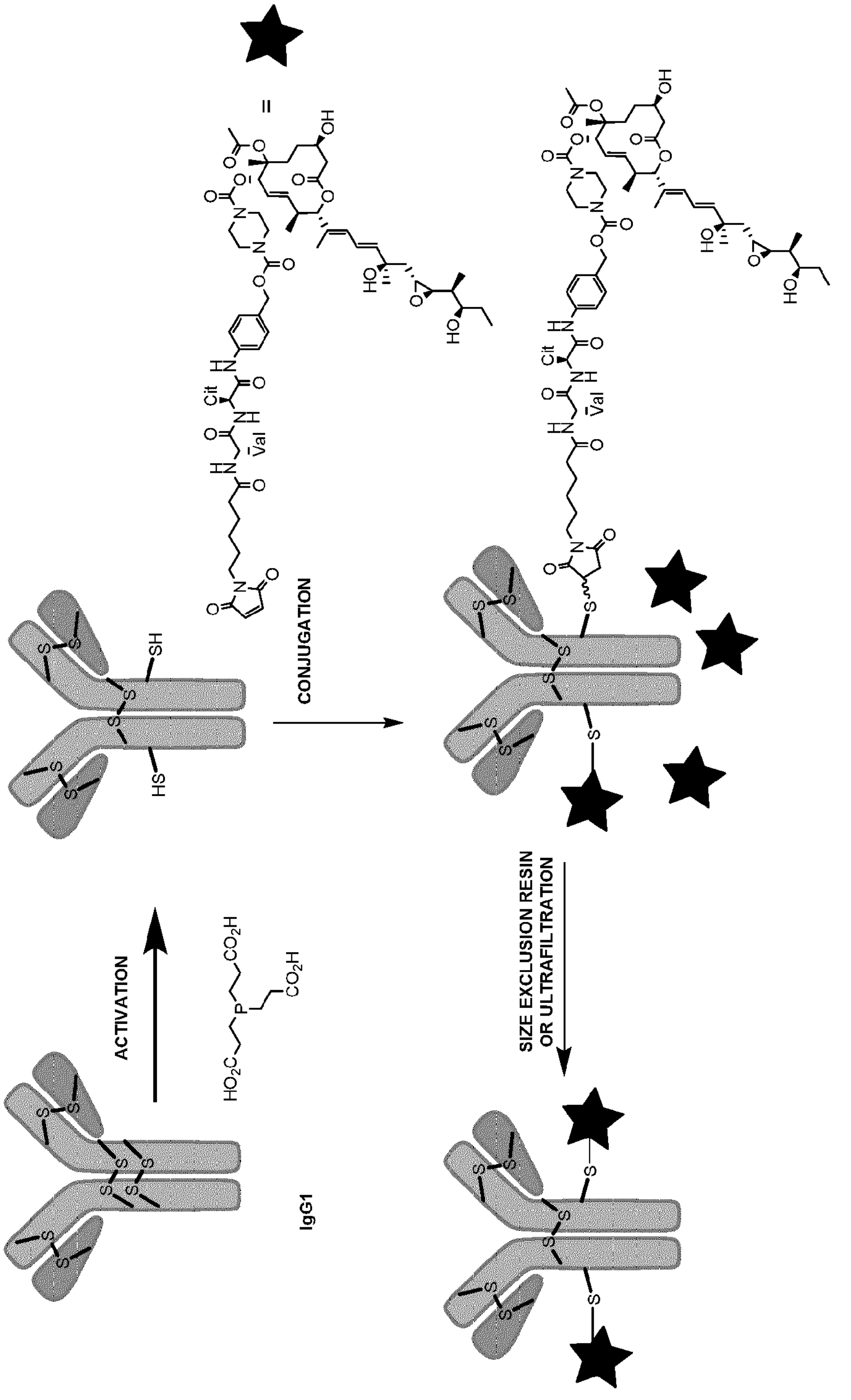
FIG. 26 shows an exemplary bioconjugation scheme for preparation of ADCs using splicing modulators.

In some embodiments, a linker-drug compound may be conjugated to an antibody or antigen binding fragment according to the exemplary scheme depicted in FIG. 26. Briefly, in some embodiments, an antibody or antigen binding fragment may be treated with a reagent, e.g., a reducing agent, e.g., tris(2-carboxyethyl)phosphine, to activate the antibody or antigen binding fragment by reducing one or more disulfide bonds. In some embodiments, the activated antibody or antigen binding fragment is then treated with a linker-drug compound at a predetermined stoichiometry. Subsequently, in some embodiments, the mixture is then subjected to a purification technique, e.g., size exclusion resin or ultrafiltration to afford the desired antibody-drug conjugate.

In some embodiments, provided herein is an antibody-drug conjugate having the structure (Ab-ADL1-D1)

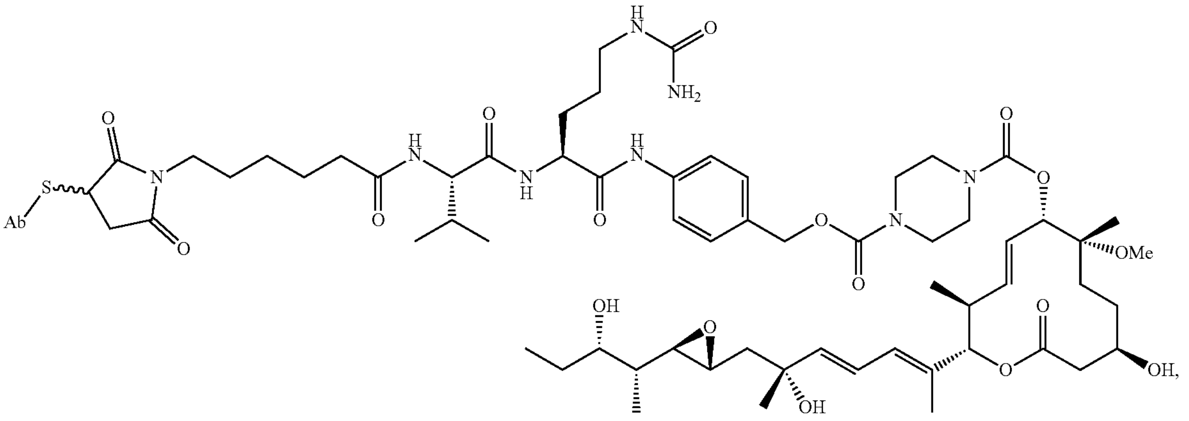

wherein Ab is an antibody or antigen binding fragment covalently bound to a maleimide group of the linker-drug compound (ADL1-D1) through the sulfur atom of a thiol group on the antibody or antigen binding fragment.

In some embodiments, provided herein is an antibody-drug conjugate having the structure (Ab-ADL1-D4)

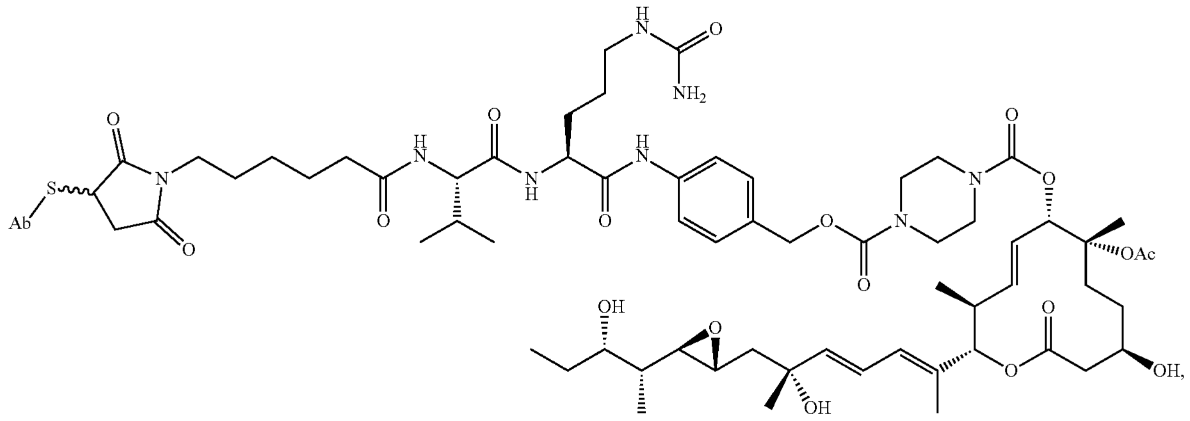

wherein Ab is an antibody or antigen binding fragment covalently bound to a maleimide group of the linker-drug compound (ADL1-D4) through the sulfur atom of a thiol group on the antibody or antigen binding fragment.

In some embodiments, provided herein is an antibody-drug conjugate having the structure (Ab-ADL1-D12)

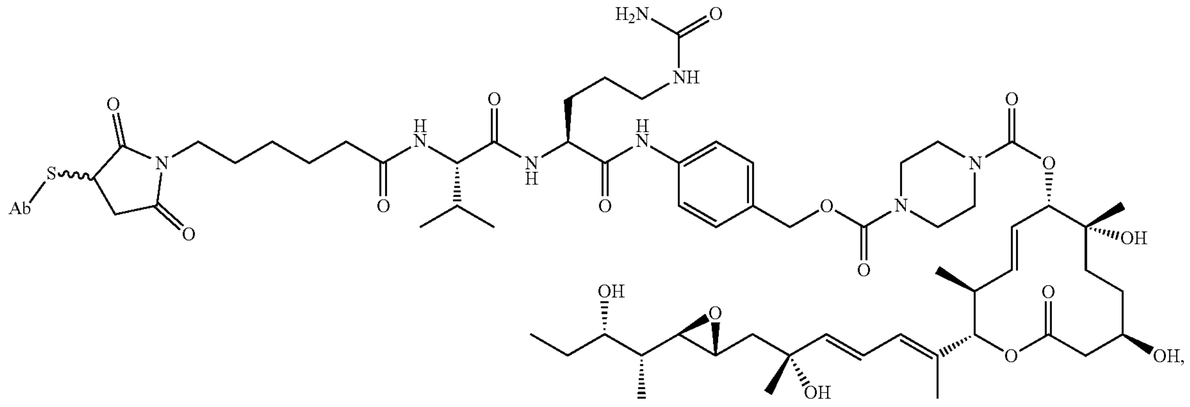

wherein Ab is an antibody or antigen binding fragment covalently bound to a maleimide group of the linker-drug compound (ADL1-D12) through the sulfur atom of a thiol group on the antibody or antigen binding fragment.

In some embodiments, provided herein is an antibody-drug conjugate having the structure (Ab-ADL5-D2)

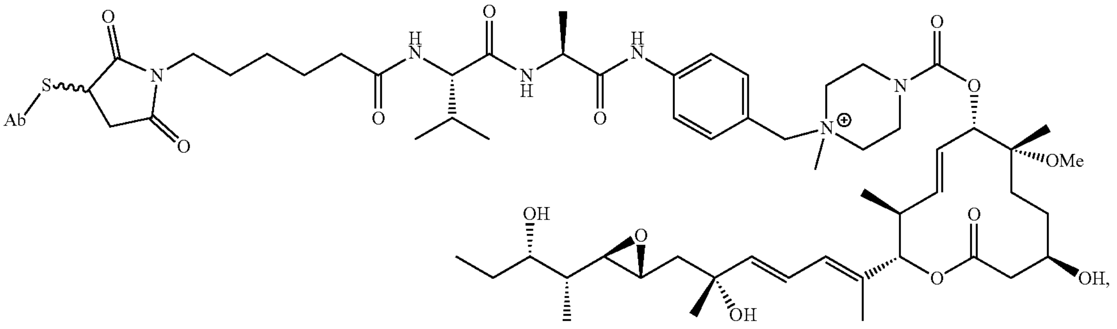

wherein Ab is an antibody or antigen binding fragment covalently bound to a maleimide group of the linker-drug compound (ADL5-D2) through the sulfur atom of a thiol group on the antibody or antigen binding fragment.

In some embodiments, provided herein is an antibody-drug conjugate having the structure (Ab-ADL5-D15)

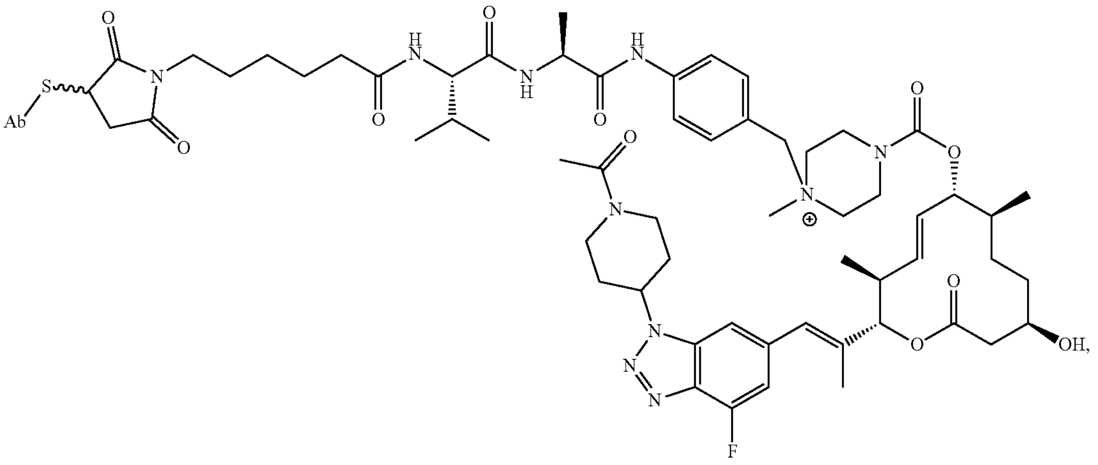

wherein Ab is an antibody or antigen binding fragment covalently bound to a maleimide group of the linker-drug compound (ADL5-D15) through the sulfur atom of a thiol group on the antibody or antigen binding fragment.

In some embodiments, provided herein is an antibody-drug conjugate having the structure (Ab-ADL13-D4)

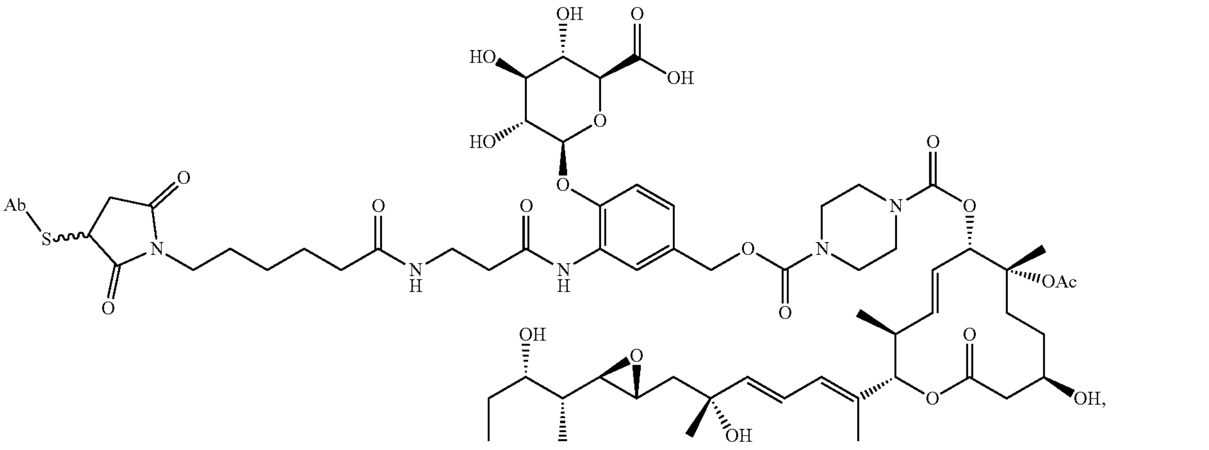

wherein Ab is an antibody or antigen binding fragment covalently bound to a maleimide group of the linker-drug compound (ADL13-D4) through the sulfur atom of a thiol group on the antibody or antigen binding fragment.

In some embodiments, the Ab is an anti-HER2 antibody or an antigen binding fragment thereof. In some embodiments, the Ab binds to HER2 and targets HER2-expressing neoplastic cells (i.e., the ADC targets HER2-expressing neoplastic cells). In some embodiments, the Ab is an internalizing anti-HER2 antibody or internalizing antigen binding fragment thereof.

In some embodiments, the anti-HER2 antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the anti-HER2 antibody or antigen binding fragment is an internalizing antibody or internalizing antigen binding fragment. In some embodiments, the anti-HER2 antibody or antigen binding fragment comprises human framework sequences. In some embodiments, the anti-HER2 antibody or antigen binding fragment comprises a heavy chain variable region comprising an amino acid sequence of SEQ ID NO:19, and a light chain variable region comprising an amino acid sequence of SEQ ID NO:20. In some embodiments, the anti-HER2 antibody or antigen binding fragment comprises a human IgG1 heavy chain constant region. In some embodiments, the anti-HER2 antibody or antigen binding fragment comprises a human Ig kappa light chain constant region.

Drug Loading

Drug loading is represented by p, and is also referred to herein as the drug-to-antibody ratio (DAR). Drug loading may range from 1 to 10 drug moieties per antibody or antigen binding fragment. In some embodiments, p is an integer from 1 to 10. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 1 to 8. In some embodiments, p is an integer from 2 to 4. In other embodiments, p is an integer from 4 to 8. In other embodiments, p is 1, 2, 3, 4, 5, 6, 7, or 8, preferably 4 or 8.

Drug loading may be limited by the number of attachment sites on the antibody or antigen binding fragment. In some embodiments, the linker moiety (L) of the ADC attaches to the antibody or antigen binding fragment through a chemically active group on one or more amino acid residues on the antibody or antigen binding fragment. For example, the linker may be attached to the antibody or antigen binding fragment via a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, or to the sulfhydryl group of one or more cysteine residues). The site to which the linker is attached can be a natural residue in the amino acid sequence of the antibody or antigen binding fragment, or it can be introduced into the antibody or antigen binding fragment, e.g., by DNA recombinant technology (e.g., by introducing a cysteine residue into the amino acid sequence) or by protein biochemistry (e.g., by reduction, pH adjustment, or hydrolysis).

In some embodiments, the number of drug moieties that can be conjugated to an antibody or antigen binding fragment is limited by the number of free cysteine residues. For example, where the attachment is a cysteine thiol group, an antibody may have only one or a few cysteine thiol groups, or may have only one or a few sufficiently reactive thiol groups through which a linker may be attached. Generally, antibodies do not contain many free and reactive cysteine thiol groups that may be linked to a drug moiety. Indeed, most cysteine thiol residues in antibodies are involved in either interchain or intrachain disulfide bonds. Conjugation to cysteines can, in some embodiments, therefore require at least partial reduction of the antibody. Over-attachment of linker-toxin to an antibody may destabilize the antibody by reducing the cysteine residues available to form disulfide bonds. Therefore, an optimal drug:antibody ratio should increase potency of the ADC (by increasing the number of attached drug moieties per antibody) without destabilizing the antibody or antigen binding fragment. In some embodiments, an optimal ratio may be 2, 4, 6, or 8.

In some embodiments, an antibody or antigen binding fragment is exposed to reducing conditions prior to conjugation in order to generate one or more free cysteine residues. An antibody, in some embodiments, may be reduced with a reducing agent such as dithiothreitol (DTT) or tris(2-carboxyethyl)phosphine (TCEP), under partial or total reducing conditions, to generate reactive cysteine thiol groups. Unpaired cysteines may be generated through partial reduction with limited molar equivalents of TCEP, which can reduce the interchain disulfide bonds which link the light chain and heavy chain (one pair per H-L pairing) and the two heavy chains in the hinge region (two pairs per H—H pairing in the case of human IgG1) while leaving the intrachain disulfide bonds intact (Stefano et al. (2013) Methods Mol Biol. 1045:145-71). In embodiments, disulfide bonds within the antibodies are reduced electrochemically, e.g., by employing a working electrode that applies an alternating reducing and oxidizing voltage. This approach can allow for on-line coupling of disulfide bond reduction to an analytical device (e.g., an electrochemical detection device, an NMR spectrometer, or a mass spectrometer) or a chemical separation device (e.g., a liquid chromatograph (e.g., an HPLC) or an electrophoresis device (see, e.g., U.S. Publ. No. 20140069822)). In certain embodiments, an antibody is subjected to denaturing conditions to reveal reactive nucleophilic groups on amino acid residues, such as cysteine.

The drug loading of an ADC may be controlled in different ways, e.g., by: (i) limiting the molar excess of drug-linker intermediate or linker reagent relative to antibody; (ii) limiting the conjugation reaction time or temperature; (iii) partial or limiting reductive conditions for cysteine thiol modification; and/or (iv) engineering by recombinant techniques the amino acid sequence of the antibody such that the number and position of cysteine residues is modified for control of the number and/or position of linker-drug attachments.

In some embodiments, free cysteine residues are introduced into the amino acid sequence of the antibody or antigen binding fragment. For example, cysteine engineered antibodies can be prepared wherein one or more amino acids of a parent antibody are replaced with a cysteine amino acid. Any form of antibody may be so engineered, i.e. mutated. For example, a parent Fab antibody fragment may be engineered to form a cysteine engineered Fab referred to as a “ThioFab.” Similarly, a parent monoclonal antibody may be engineered to form a “ThioMab.” A single site mutation yields a single engineered cysteine residue in a ThioFab, whereas a single site mutation yields two engineered cysteine residues in a ThioMab, due to the dimeric nature of the IgG antibody. DNA encoding an amino acid sequence variant of the parent polypeptide can be prepared by a variety of methods known in the art (see, e.g., the methods described in Intl. Pub. No. WO 2006/034488). These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may also be constructed by restriction fragment manipulation or by overlap extension PCR with synthetic oligonucleotides. ADCs of Formula (I) include, but are not limited to, antibodies that have 1, 2, 3, or 4 engineered cysteine amino acids (Lyon et al. (2012) Methods Enzymol. 502:123-38). In some embodiments, one or more free cysteine residues are already present in an antibody or antigen binding fragment, without the use of engineering, in which case the existing free cysteine residues may be used to conjugate the antibody or antigen binding fragment to a drug moiety.

Where more than one nucleophilic group reacts with a drug-linker intermediate or a linker moiety reagent followed by drug moiety reagent, in a reaction mixture comprising multiple copies of the antibody or antigen binding fragment and linker moiety, then the resulting product can be a mixture of ADC compounds with a distribution of one or more drug moieties attached to each copy of the antibody or antigen binding fragment in the mixture. In some embodiments, the drug loading in a mixture of ADCs resulting from a conjugation reaction ranges from 1 to 10 drug moieties attached per antibody or antigen binding fragment. The average number of drug moieties per antibody or antigen binding fragment (i.e., the average drug loading, or average p) may be calculated by any conventional method known in the art, e.g., by mass spectrometry (e.g., reverse-phase LC-MS), and/or high-performance liquid chromatography (e.g., HIC-HPLC). In some embodiments, the average number of drug moieties per antibody or antigen binding fragment is determined by hydrophobic interaction chromatography-high performance liquid chromatography (HIC-HPLC). In some embodiments, the average number of drug moieties per antibody or antigen binding fragment is determined by reverse-phase liquid chromatography-mass spectrometry (LC-MS). In some embodiments, the average number of drug moieties per antibody or antigen binding fragment is from about 1.5 to about 3.5, about 2.5 to about 4.5, about 3.5 to about 5.5, about 4.5 to about 6.5, about 5.5 to about 7.5, about 6.5 to about 8.5, or about 7.5 to about 9.5. In some embodiments, the average number of drug moieties per antibody or antigen binding fragment is from about 2 to about 4, about 3 to about 5, about 4 to about 6, about 5 to about 7, about 6 to about 8, about 7 to about 9, about 2 to about 8, or about 4 to about 8.

In some embodiments, the average number of drug moieties per antibody or antigen binding fragment is about 2. In some embodiments, the average number of drug moieties per antibody or antigen binding fragment is about 1.5, about 1.6, about 1.7, about 1.8, about 1.9, about 2, about 2.1, about 2.2, about 2.3, about 2.4, or about 2.5. In some embodiments, the average number of drug moieties per antibody or antigen binding fragment is 2.

In some embodiments, the average number of drug moieties per antibody or antigen binding fragment is about 4. In some embodiments, the average number of drug moieties per antibody or antigen binding fragment is about 3.5, about 3.6, about 3.7, about 3.8, about 3.9, about 4, about 4.1, about 4.2, about 4.3, about 4.4, or about 4.5. In some embodiments, the average number of drug moieties per antibody or antigen binding fragment is 4.

In some embodiments, the average number of drug moieties per antibody or antigen binding fragment is about 8. In some embodiments, the average number of drug moieties per antibody or antigen binding fragment is about 7.5, about 7.6, about 7.7, about 7.8, about 7.9, about 8, about 8.1, about 8.2, about 8.3, about 8.4, or about 8.5. In some embodiments, the average number of drug moieties per antibody or antigen binding fragment is 8.

In various embodiments, the term “about,” as used with respect to the average number of drug moieties per antibody or antigen binding fragment, means plus or minus 10%.

Individual ADC compounds, or “species,” may be identified in the mixture by mass spectroscopy and separated by UPLC or HPLC, e.g. hydrophobic interaction chromatography (HIC-HPLC). In certain embodiments, a homogeneous or nearly homogenous ADC product with a single loading value may be isolated from the conjugation mixture, e.g., by electrophoresis or chromatography.

In some embodiments, higher drug loading (e.g., p>8) may cause aggregation, insolubility, toxicity, or loss of cellular permeability of certain antibody-drug conjugates. Higher drug loading may also negatively affect the pharmacokinetics (e.g., clearance) of certain ADCs. In some embodiments, lower drug loading (e.g., p<2) may reduce the potency of certain ADCs against target-expressing cells and/or bystander cells. In some embodiments, the drug loading for an ADC of the present disclosure ranges from about 2 to about 8; from about 2 to about 6; from about 2 to about 5; from about 3 to about 5; from about 2 to about 4; or from about 4 to about 8.

In some embodiments, a drug loading and/or an average drug loading of about 2 is achieved, e.g., using partial reduction of intrachain disulfides on the antibody or antigen binding fragment, and provides beneficial properties. In some embodiments, a drug loading and/or an average drug loading of about 4 is achieved, e.g., using partial reduction of intrachain disulfides on the antibody or antigen binding fragment, and provides beneficial properties. In some embodiments, a drug loading and/or an average drug loading of about 8 is achieved, e.g., using partial reduction of intrachain disulfides on the antibody or antigen binding fragment, and provides beneficial properties. In some embodiments, a drug loading and/or an average drug loading of less than about 2 may result in an unacceptably high level of unconjugated antibody species, which can compete with the ADC for binding to a target antigen and/or provide for reduced treatment efficacy. In some embodiments, a drug loading and/or average drug loading of more than about 8 may result in an unacceptably high level of product heterogeneity and/or ADC aggregation. A drug loading and/or an average drug loading of more than about 8 may also affect stability of the ADC, due to loss of one or more chemical bonds required to stabilize the antibody or antigen binding fragment.

The present disclosure includes methods of producing the described ADCs. Briefly, the ADCs comprise an antibody or antigen binding fragment as the antibody or antigen binding fragment, a drug moiety (e.g., a splicing modulator), and a linker that joins the drug moiety and the antibody or antigen binding fragment. In some embodiments, the ADCs can be prepared using a linker having reactive functionalities for covalently attaching to the drug moiety and to the antibody or antigen binding fragment. For example, in some embodiments, a cysteine thiol of an antibody or antigen binding fragment can form a bond with a reactive functional group of a linker or a drug-linker intermediate (e.g., a maleimide moiety) to make an ADC. The generation of the ADCs can be accomplished by any technique known to the skilled artisan.

In some embodiments, an ADC is produced by contacting an antibody or antigen binding fragment with a linker and a drug moiety (e.g., a splicing modulator) in a sequential manner, such that the antibody or antigen binding fragment is covalently linked to the linker first, and then the pre-formed antibody-linker intermediate reacts with the drug moiety. The antibody-linker intermediate may or may not be subjected to a purification step prior to contacting the drug moiety. In other embodiments, an ADC is produced by contacting an antibody or antigen binding fragment with a linker-drug compound pre-formed by reacting a linker with a drug moiety. The pre-formed linker-drug compound may or may not be subjected to a purification step prior to contacting the antibody or antigen binding fragment. In other embodiments, the antibody or antigen binding fragment contacts the linker and the drug moiety in one reaction mixture, allowing simultaneous formation of the covalent bonds between the antibody or antigen binding fragment and the linker, and between the linker and the drug moiety. This method of producing ADCs may include a reaction, wherein the antibody or antigen binding fragment contacts the antibody or antigen binding fragment prior to the addition of the linker to the reaction mixture, and vice versa. In certain embodiments, an ADC is produced by reacting an antibody or antigen binding fragment with a linker joined to a drug moiety, such as ADL1-splicing modulator (e.g., ADL1-D1) or ADL5-splicing modulator (e.g., ADL5-D2), under conditions that allow conjugation.

The ADCs prepared according to the methods described above may be subjected to a purification step. The purification step may involve any biochemical methods known in the art for purifying proteins, or any combination of methods thereof. These include, but are not limited to, tangential flow filtration (TFF), affinity chromatography, ion exchange chromatography, any charge or isoelectric point-based chromatography, mixed mode chromatography, e.g., CHT (ceramic hydroxyapatite), hydrophobic interaction chromatography, size exclusion chromatography, dialysis, filtration, selective precipitation, or any combination thereof.

Therapeutic Uses and Compositions

Disclosed herein are methods of using the disclosed ADCs and compositions in treating a subject for a disorder, e.g., a neoplastic disorder. ADCs may be administered alone or in combination with a second therapeutic agent, and may be administered in any pharmaceutically acceptable formulation, dosage, and dosing regimen. ADC treatment efficacy may be evaluated for toxicity as well as indicators of efficacy and adjusted accordingly. Efficacy measures include, but are not limited to, a cytostatic and/or cytotoxic effect observed in vitro or in vivo, reduced tumor volume, tumor growth inhibition, and/or prolonged survival.

Methods of determining whether an ADC exerts a cytostatic and/or cytotoxic effect on a cell are known. For example, the cytotoxic or cytostatic activity of an ADC can be measured by: exposing mammalian cells expressing a target protein of the ADC in a cell culture medium; culturing the cells for a period from about 6 hours to about 6 days; and measuring cell viability. Cell-based in vitro assays may also be used to measure viability (proliferation), cytotoxicity, and induction of apoptosis (caspase activation) of the ADC.

For determining whether an ADC exerts a cytostatic effect, a thymidine incorporation assay may be used. For example, cancer cells expressing a target antigen at a density of 5,000 cells/well of a 96-well plated can be cultured for a 72-hour period and exposed to 0.5 μCi of $^3$H-thymidine during the final 8 hours of the 72-hour period. The incorporation of $^3$H-thymidine into cells of the culture is measured in the presence and absence of the ADC.

For determining cytotoxicity, necrosis or apoptosis (programmed cell death) may be measured. Necrosis is typically accompanied by increased permeability of the plasma membrane; swelling of the cell, and rupture of the plasma membrane. Apoptosis can be quantitated, for example, by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica (1999) No. 2, pp. 34-37 (Roche Molecular Biochemicals).

Apoptosis may also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al., eds. (1992) pp. 3.17.1-3.17.16). Cells also can be labeled with a DNA dye (e.g., acridine orange, ethidium bromide, or propidium iodide) and the cells observed for chromatin condensation and margination along the inner nuclear membrane. Apoptosis may also be determined, in some embodiments, by screening for caspase activity. In some embodiments, a Caspase-Glo® Assay can be used to measure activity of caspase-3 and caspase-7. In some embodiments, the assay provides a luminogenic caspase-3/7 substrate in a reagent optimized for caspase activity, luciferase activity, and cell lysis. In some embodiments, adding Caspase-Glo® 3/7 Reagent in an "add-mix-measure" format may result in cell lysis, followed by caspase cleavage of the substrate and generation of a "glow-type" luminescent signal, produced by luciferase. In some embodiments, luminescence may be proportional to the amount of caspase activity present, and can serve as an indicator of apoptosis. Other morphological changes that can be measured to determine apoptosis include, e.g., cytoplasmic condensation, increased membrane blebbing, and cellular shrinkage. Determination of any of these effects on cancer cells indicates that an ADC is useful in the treatment of cancers.

Cell viability may be measured, e.g., by determining in a cell the uptake of a dye such as neutral red, trypan blue, Crystal Violet, or ALAMAR™ blue (see, e.g., Page et al. (1993) Intl J Oncology 3:473-6). In such an assay, the cells are incubated in media containing the dye, the cells are washed, and the remaining dye, reflecting cellular uptake of the dye, is measured spectrophotometrically. Cell viability may also be measured, e.g., by quantifying ATP, an indicator of metabolically active cells. In certain embodiments, in vitro potency and/or cell viability of prepared ADCs or splicing modulator compounds may be assessed using a CellTiter-Glo® Luminescent Cell Viability Assay, as described in the examples provided herein. In this assay, in certain embodiments, the single reagent (CellTiter-Glo® Reagent) is added directly to cells cultured in serum-supplemented medium. The addition of reagent results in cell lysis and generation of a luminescent signal proportional to the amount of ATP present. The amount of ATP is directly proportional to the number of cells present in culture. The protein-binding dye sulforhodamine B (SRB) can also be used to measure cytotoxicity (Skehan et al. (1990) J Natl Cancer Inst. 82:1107-12).

The disclosed ADCs may also be evaluated for bystander killing activity. Bystander killing activity may be determined, e.g., by an assay employing two cell lines, one positive for a target antigen and one negative for a target antigen. In certain embodiments, the design of the assay allows tracking of only target negative cells. In certain embodiments, cells are plated under three conditions: (i) target negative cells alone (tagged or labeled); (ii) target positive cells alone; and (iii) co-culture of target negative cells and target positive cells. Cells are then treated with an ADC followed by monitoring of cytotoxicity. When plates are read with CellTiter-Glo® Reagent, viability of all cell populations can be monitored. When plates are read with OneGlo® Reagent, only the tagged or labeled target negative cells produce a signal. Killing of the target-negative cells when mixed with target-positive cells is indicative of bystander killing, whereas killing of the target-negative cells in the absence of the target-positive cells is indicative of off-target killing.

In certain aspects, the present disclosure features a method of killing, inhibiting or modulating the growth of, or interfering with the metabolism of, a cancer cell or tissue by disrupting RNA splicing. The method may be used with any subject where disruption of RNA splicing provides a therapeutic benefit. Subjects that may benefit from disrupting RNA splicing include, but are not limited to, those having or at risk of having a neoplastic disorder such as a hematological malignancy or a solid tumor. In certain embodiments, the hematological malignancy is a B-cell malignancy, a cancer of the blood (leukemia), a cancer of plasma cells (myeloma, e.g., multiple myeloma), or a cancer of the lymph nodes (lymphoma). In certain embodiments, the hematological malignancy is acute myelogenous leukemia or multiple myeloma. In certain embodiments, the leukemia is acute lymphoblastic leukemia (ALL), acute myelogenous leukemia (AML), chronic lymphocytic leukemia (CLL), chronic myelogenous leukemia (CML), chronic myelomonocytic leukemia (CMML), or acute monocytic leukemia (AMoL). In certain embodiments, the lymphoma is Hodgkin's lymphoma or non-Hodgkin's lymphoma. In certain embodiments, the hematological malignancy is myelodysplasia syndrome (MDS). In certain embodiments, the solid tumor is a carcinoma such as breast cancer, pancreatic cancer, prostate cancer, colon or colorectal cancer, lung cancer, gastric cancer, cervical cancer, endometrial cancer, ovarian cancer, cholangiocarcinoma, glioma, or melanoma. In certain embodiments, the solid tumor is breast cancer, gastric cancer, prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In certain embodiments, the lung cancer is lung adenocarcinoma. In certain embodiments, the uterine cancer is uterine serous endometrial carcinoma.

In various embodiments, the disclosed ADCs may be administered in any cell or tissue that expresses HER2, such as a HER2-expressing neoplastic cell or tissue. An exemplary embodiment includes a method of inhibiting HER2-mediated cell signaling or a method of killing a cell. The method may be used with any cell or tissue that expresses HER2, such as a cancerous cell or a metastatic lesion. Non-limiting examples of HER2-expressing cancers include breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer (English et al. (2013) Mol Diagn Ther. 17:85-99). Non-limiting examples of HER2-expressing cells include HCC1954 and SKBR3 human breast ductal carcinoma cells, N87 human gastric carcinoma cells, and cells comprising a recombinant nucleic acid encoding HER2 or a portion thereof.

In various embodiments, the disclosed ADCs may be administered in any cell or tissue that expresses CD138, such as a CD138-expressing neoplastic cell or tissue. An exemplary embodiment includes a method of inhibiting CD138-mediated cell signaling or a method of killing a cell. The method may be used with any cell or tissue that expresses CD138, such as a cancerous cell or a metastatic lesion. Non-limiting examples of CD138-expressing cancers include intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), hematological malignancies (e.g., myeloma such as multiple myeloma, Hodgkin's lymphoma), and thyroid cancer (Szatmeri et al. (2015) Dis Markers 2015:796052). Non-limiting examples of CD138-expressing cells include MOLP8 human multiple myeloma cells, and cells comprising a recombinant nucleic acid encoding CD138 or a portion thereof.

In various embodiments, the disclosed ADCs may be administered in any cell or tissue that expresses EPHA2, such as an EPHA2-expressing neoplastic cell or tissue. An exemplary embodiment includes a method of inhibiting EPHA2-mediated cell signaling or a method of killing a cell. The method may be used with any cell or tissue that expresses EPHA2, such as a cancerous cell or a metastatic lesion. Non-limiting examples of EPHA2-expressing cancers include breast cancer, brain cancer, ovarian cancer, bladder cancer, pancreatic cancer, esophageal cancer, lung cancer, prostate cancer, melanoma, esophageal cancer, and gastric cancer (Tandon et al. (2011) Expert Opin Ther Targets 15(1):31-51. Non-limiting examples of EPHA2-expressing cells include PC3 human prostate cancer cells, and cells comprising a recombinant nucleic acid encoding EPHA2 or a portion thereof.

Exemplary methods include the steps of contacting a cell with an ADC, as described herein, in an effective amount, i.e., amount sufficient to kill the cell. The method can be used on cells in culture, e.g. in vitro, in vivo, ex vivo, or in situ. For example, cells that express HER2 (e.g., cells collected by biopsy of a tumor or metastatic lesion; cells from an established cancer cell line; or recombinant cells), can be cultured in vitro in culture medium and the contacting step can be affected by adding the ADC to the culture medium. The method will result in killing of cells expressing HER2, including in particular tumor cells expressing HER2. Alternatively, the ADC can be administered to a subject by any suitable administration route (e.g., intravenous, subcutaneous, or direct contact with a tumor tissue) to have an effect in vivo. This approach can be used for antibodies targeting other cell surface antigens (e.g., CD138, EPHA2).

The in vivo effect of a disclosed ADC therapeutic composition can be evaluated in a suitable animal model. For example, xenogeneic cancer models can be used, wherein cancer explants or passaged xenograft tissues are introduced into immune compromised animals, such as nude or SCID mice (Klein et al. (1997) Nature Med. 3:402-8). Efficacy may be predicted using assays that measure inhibition of tumor formation, tumor regression or metastasis, and the like.

In vivo assays that evaluate the promotion of tumor death by mechanisms such as apoptosis may also be used. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

Further provided herein are methods of treating a neoplastic disorder, e.g., a cancer. The ADCs disclosed herein can be administered to a non-human mammal or human subject for therapeutic purposes. The therapeutic methods entail administering to a subject having or suspected of having a neoplastic disorder a therapeutically effective amount of an ADC or composition comprising a splicing modulator linked to a targeting antibody that binds to an antigen expressed, is accessible to binding, or is localized on a cancer cell surface. In some embodiments, treatment with the antibody-drug conjugate or composition induces bystander killing of neoplastic cells which do not express a target antigen but are adjacent to neoplastic cells which express a target antigen.

An exemplary embodiment is a method of delivering a splicing modulator to a cell expressing HER2, comprising conjugating the splicing modulator to an antibody that immunospecifically binds to a HER2 epitope and exposing the cell to the ADC. Exemplary tumor cells that express HER2 for which the ADCs of the present disclosure are indicated include gastric carcinoma cells and breast ductal carcinoma cells.

Another exemplary embodiment is a method of delivering a splicing modulator to a cell expressing CD138, comprising conjugating the splicing modulator to an antibody that immunospecifically binds to a CD138 epitope and exposing the cell to the ADC. Exemplary tumor cells that express CD138 for which the ADCs of the present disclosure are indicated include multiple myeloma cells.

Another exemplary embodiment is a method of delivering a splicing modulator to a cell expressing EPHA2, comprising conjugating the splicing modulator to an antibody that immunospecifically binds to an EPHA2 epitope and exposing the cell to the ADC. Exemplary tumor cells that express EPHA2 for which the ADCs of the present disclosure are indicated include prostate cancer cells.

Another exemplary embodiment is a method of reducing or inhibiting growth of a tumor (e.g., a HER2-expressing tumor, a CD138-expressing tumor, an EPHA2-expressing tumor), comprising administering a therapeutically effective amount of an ADC or composition comprising an ADC. In some embodiments, the treatment is sufficient to reduce or inhibit the growth of the patient's tumor, reduce the number or size of metastatic lesions, reduce tumor load, reduce primary tumor load, reduce invasiveness, prolong survival time, and/or maintain or improve the quality of life. In some embodiments, the tumor is resistant or refractory to treatment with the antibody or antigen binding fragment of the ADC (e.g., an anti-HER2 antibody, an anti-CD138 antibody, an anti-EPHA2 antibody) when administered alone, and/or the tumor is resistant or refractory to treatment with the splicing modulator drug moiety when administered alone In certain aspects, the present disclosure provides a method of reducing or inhibiting growth of a HER2-expressing tumor. In certain embodiments, treatment with the antibody-drug conjugate or composition induces bystander killing of tumor cells which do not express HER2 but that are adjacent to neoplastic tumor cells which do express HER2. Exemplary HER2-expressing tumor types include but are not limited to tumors derived from a HER2-expressing breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer. In certain embodiments, the HER2-expressing tumor is a tumor derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In certain embodiments, the HER2-expressing tumor is a lung adenocarcinoma or uterine serous endometrial carcinoma.

In certain aspects, the present disclosure provides a method of reducing or inhibiting growth of a CD138-expressing tumor. In certain embodiments, treatment with the antibody-drug conjugate or composition induces bystander killing of tumor cells which do not express CD138 but that are adjacent to neoplastic tumor cells which do express CD138. Exemplary CD138-expressing tumor types include but are not limited to tumors derived from a CD138-expressing intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), and thyroid cancer.

In certain aspects, the present disclosure provides a method of reducing or inhibiting growth of an EPHA2-expressing tumor. In certain embodiments, treatment with the antibody-drug conjugate or composition induces bystander killing of tumor cells which do not express EPHA2 but that are adjacent to neoplastic tumor cells which do express EPHA2. Exemplary EPHA2-expressing tumor types include but are not limited to tumors derived from an EPHA2-expressing breast cancer, brain cancer, ovarian cancer, bladder cancer, pancreatic cancer, esophageal cancer, lung cancer, prostate cancer, melanoma, esophageal cancer, and gastric cancer. In certain embodiments, the EPHA2-expressing tumor is a tumor derived from an EPHA2-expressing breast cancer, prostate cancer, ovarian cancer, lung cancer, melanoma, colon cancer, or esophageal cancer.

Moreover, antibodies of the present disclosure may be administered to a non-human mammal expressing an antigen with which the ADC is capable of binding for veterinary purposes or as an animal model of human disease. Regarding the latter, such animal models may be useful for evaluating the therapeutic efficacy of the disclosed ADCs (e.g., testing of dosages and time courses of administration).

Further provided herein are therapeutic uses of the disclosed ADCs and compositions. An exemplary embodiment is the use of an ADC in the treatment of a neoplastic disorder (e.g., a HER2-expressing cancer, a CD138-expressing cancer, an EPHA2-expressing cancer). Another exemplary embodiment is an ADC for use in the treatment of a neoplastic disorder (e.g., a HER2-expressing cancer, a CD138-expressing cancer, an EPHA2-expressing cancer). Methods for identifying subjects having cancers that express a target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1) are known in the art and may be used to identify suitable patients for treatment with a disclosed ADC.

Another exemplary embodiment is the use of an ADC in a method of manufacturing a medicament for the treatment of a neoplastic disorder (e.g., a HER2-expressing cancer, a CD138-expressing cancer, an EPHA2-expressing cancer).

The therapeutic compositions used in the practice of the foregoing methods may be formulated into pharmaceutical compositions comprising a pharmaceutically acceptable carrier suitable for the desired delivery method. An exemplary embodiment is a pharmaceutical composition comprising an ADC of the present disclosure and a pharmaceutically acceptable carrier. Suitable carriers include any material that, when combined with the therapeutic composition, retains the anti-tumor function of the therapeutic composition and is generally non-reactive with the patient's immune system. Pharmaceutically acceptable carriers include any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, mesylate salt, and the like, as well as combinations thereof. In many cases, isotonic agents are included, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the ADC.

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. Therapeutic protein preparations can be lyophilized and stored as sterile powders, e.g., under vacuum, and then reconstituted in bacteriostatic water (containing for example, benzyl alcohol preservative) or in sterile water prior to injection. Therapeutic formulations may comprise an ADC or a pharmaceutically acceptable salt thereof, e.g., a mesylate salt.

In some embodiments, the ADC is administered to the patient daily, bimonthly, or any time period in between. Dosages and administration protocols for the treatment of cancers using the foregoing methods will vary with the method and the target cancer, and will generally depend on a number of other factors appreciated in the art.

Various delivery systems are known and may be used to administer one or more ADCs of the present disclosure. Methods of administering the ADCs include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration may be employed, e.g., by use of an inhaler or nebulizer, and formulation with an aerosolizing agent. See, e.g., the compositions and methods for pulmonary administration described in U.S. Pat. Nos. 6,019,968, 5,985,320, 5,985,309, 5,934,272, 5,874,064, 5,855,913, 5,290,540, and 4,880,078; and Intl. Publ. Nos. WO 1992/019244, WO 1997/032572, WO 1997/044013, WO 1998/031346, and WO 1999/066903. The ADCs may be administered by any convenient route, for example, by infusion or bolus injection, or by absorption through epithelial or mucocutaneous linings (e.g., oral mucosa, rectal and intestinal mucosa, etc.). Administration can be either systemic or local.

Therapeutic compositions disclosed herein may be sterile and stable under the conditions of manufacture and storage. In some embodiments, one or more of the ADCs, or pharmaceutical compositions, is supplied as a dry sterilized lyophilized powder or water free concentrate in a hermetically sealed container and can be reconstituted (e.g., with water or saline) to the appropriate concentration for administration to a subject. In some embodiments, one or more of the prophylactic or therapeutic agents or pharmaceutical compositions is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg, or any amount in between. In some embodiments, the lyophilized ADCs or pharmaceutical compositions is stored at between 2° C. and 8° C. in the original container. In some embodiments, one or more of the ADCs or pharmaceutical compositions described herein is supplied in liquid form in a hermetically sealed container, e.g., a container indicating the quantity and concentration of the agent. In some embodiments, the liquid form of the administered composition is supplied in a hermetically sealed container of at least 0.25 mg/mL, at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL, or at least 100 mg/mL ADC. The liquid form may be stored at between 2° C. and 8° C. in the original container.

In some embodiments, the disclosed ADCs can be incorporated into a pharmaceutical composition suitable for parenteral administration. The injectable solution may be composed of either a liquid or lyophilized dosage form in a flint or amber vial, ampule, or pre-filled syringe, or other known delivery or storage device.

The compositions described herein may be in a variety of forms. These include, for example, liquid, semi-solid, and solid dosage forms, such as liquid solutions (e.g., injectable and infusible solutions), dispersions or suspensions, tablets, pills, powders, liposomes, and suppositories. The preferred form depends on the intended mode of administration and therapeutic application.

In various embodiments, treatment involves single bolus or repeated administration of the ADC preparation via an acceptable route of administration.

Patients may be evaluated for the levels of target antigen in a given sample (e.g. the levels of target antigen expressing cells) in order to assist in determining the most effective dosing regimen, etc. An exemplary embodiment is a method of determining whether a patient will be responsive to treatment with an ADC of the present disclosure, comprising providing a biological sample from the patient and contacting the biological sample with the ADC. Exemplary biological samples include tissue or body fluid, such as an inflammatory exudate, blood, serum, bowel fluid, stool sample, or tumor biopsy (e.g., a tumor biopsy derived from a patient having or at risk of a target antigen-expressing cancer, e.g., a HER2-expressing cancer, a CD138-expressing cancer, an EPHA2-expressing cancer). In some embodiments, a sample (e.g., a tissue and/or body fluid) can be obtained from a subject, and a suitable immunological method can be used to detect and/or measure protein expression of the target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). Such evaluations are also used for monitoring purposes throughout therapy, and are useful to gauge therapeutic success in combination with the evaluation of other parameters.

In some embodiments, the efficacy of an ADC may be evaluated by contacting a tumor sample from a subject with the ADC and evaluating tumor growth rate or volume. In some embodiments, when an ADC has been determined to be effective, it may be administered to the subject.

The above therapeutic approaches can be combined with any one of a wide variety of additional surgical, chemotherapy, or radiation therapy regimens. In some embodiments, the ADCs or compositions disclosed herein are co-formulated and/or co-administered with one or more additional therapeutic agents, e.g., one or more chemotherapeutic agents. Non-limiting examples of chemotherapeutic agents include alkylating agents, for example, nitrogen mustards, ethyleneimine compounds, and alkyl sulphonates; antimetabolites, for example, folic acid, purine or pyrimidine antagonists; anti-mitotic agents, for example, anti-tubulin agents such as eribulin or eribulin mesylate (Halaven™), vinca alkaloids, and auristatins; cytotoxic antibiotics; compounds that damage or interfere with DNA expression or replication, for example, DNA minor groove binders; and growth factor receptor antagonists. In some embodiments, a chemotherapeutic agent may be a cytotoxic or cytostatic agent. Examples of cytotoxic agents include, but are not limited to, anti-mitotic agents, such as eribulin or eribulin mesylate (Halaven™), auristatins (e.g., monomethyl auristatin E (MMAE), monomethyl auristatin F (MMAF)), maytansinoids (e.g., maytansine), dolastatins, duostatins, cryptophycins, vinca alkaloids (e.g., vincristine, vinblastine), taxanes, taxols, and colchicines; anthracyclines (e.g., daunorubicin, doxorubicin, dihydroxyanthracindione); cytotoxic antibiotics (e.g., mitomycins, actinomycins, duocarmycins (e.g., CC-1065), auromycins, duomycins, calicheamicins, endomycins, phenomycins); alkylating agents (e.g., cisplatin); intercalating agents (e.g., ethidium bromide); topoisomerase inhibitors (e.g., etoposide, tenoposide); radioisotopes, such as $At^{211}$, $I^{131}$, $I^{125}$, $Y^{90}$, $Re^{186}$, $Re^{188}$, $Sm^{153}$, $Bi^{212 \text{ or } 213}$, $P^{32}$, and radioactive isotopes of lutetium (e.g., $Lu^{177}$); and toxins of bacterial, fungal, plant or animal origin (e.g., ricin (e.g., ricin A-chain), diphtheria toxin, *Pseudomonas* exotoxin A (e.g., PE40), endotoxin, mitogellin, combrestatin, restrictocin, gelonin, alpha-sarcin, abrin (e.g., abrin A-chain), modeccin (e.g., modeccin A-chain), curicin, crotin, *Sapaonaria officinalis* inhibitor, glucocorticoid).

Also disclosed herein are uses of one or more of the disclosed ADCs in the manufacture of a medicament for treating cancer, e.g., according to the methods described above. In some embodiments, the ADCs disclosed herein are used for treating cancer, e.g., according to the methods described above.

In various embodiments, kits for use in the laboratory and therapeutic applications described herein are within the scope of the present disclosure. Such kits may comprise a carrier, package, or container that is compartmentalized to receive one or more containers such as vials, tubes, and the like, each of the container(s) comprising one of the separate elements to be used in a method disclosed herein, along with a label or insert comprising instructions for use, such as a use described herein. Kits may comprise a container comprising a drug moiety. The present disclosure also provides one or more of the ADCs, or pharmaceutical compositions thereof, packaged in a hermetically sealed container, such as an ampoule or sachette, indicating the quantity of the agent.

Kits may comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label may be present on or with the container to indicate that the composition is used for a specific therapy or non-therapeutic application, such as a prognostic, prophylactic, diagnostic, or laboratory application. A label may also indicate directions for either in vivo or in vitro use, such as those described herein. Directions and or other information may also be included on an insert(s) or label(s), which is included with or on the kit. The label may be on or associated with the container. A label may be on a container when letters, numbers, or other characters forming the label are molded or etched into the container itself. A label may be associated with a container when it is present within a receptacle or carrier that also holds the container, e.g., as a package insert. The label may indicate that the composition is used for diagnosing or treating a condition, such as a cancer a described herein.

Neoantigens and Methods of Use

Also disclosed herein, in various embodiments, are methods of treating a patient by inducing neoantigens in tumor cells that can be targeted by the patient's immune system for clearance. Without being bound by theory, in various embodiments, administering a splicing modulator, alone and/or as part of an ADC or composition, may produce neoantigens that induce an immune response, induce a double-stranded RNA immune response, e.g., as a result of re-expressed intron-resident endogenous retroviruses, and/or produce neoantigens that induce immunogenic cell death.

As used herein, the term "neoantigen" refers to any antigen to which the immune system has not previously been exposed that arises from one or more tumor-specific mutations and/or from exposing a tumor to a drug (e.g., any one or more of the splicing modulators disclosed herein, alone and/or as part of an ADC or composition). Tumor-specific mutations can include missense mutations, frameshifts, translocations, and mRNA splicing variants, as well as mutations that influence posttranslational processing, such as phosphorylation and glycosylation. These exemplary mutations, in various embodiments, can be derived from non-synonymous coding changes and/or mutations that alter mRNA processing (e.g., splicing). All of these exemplary mutations, in various embodiments, can result in molecular changes that can be discriminated by an appropriate T-cell receptor. In various preferred embodiments, an exemplary neoantigen is a neoantigen induced by delivery of a splicing modulator, alone and/or as part of an ADC or composition. In various embodiments, delivery of a splicing modulator (e.g., any one or more of the splicing modulators disclosed herein) can induce novel mRNA splicing that results in the translation of proteins containing one or more novel peptide domains to which the immune system has not previously been exposed. In various embodiments, tumor-specific mutations may be mRNA splicing variants resulting from delivery or administration of a splicing modulator, ADC, or composition comprising a splicing modulator or ADC.

Without being bound by theory, in various embodiments, the delivery of splicing modulators, alone and as part of an ADC or composition, may induce novel mRNA splicing (e.g., exon skipping, intron retention) that results in the alteration of the open reading frames and/or coding sequences of various genes. In various embodiments, these altered genes are translated into proteins containing one or more novel peptide domains recognized by the immune system as foreign. In various embodiments, the one or more novel peptide domains do not exist in the proteins or in any other part of the human proteome in the absence of splicing modulator treatment. In various embodiments, the proteins containing the one or more novel peptide domains can be degraded by the proteasome to create novel peptide fragments that act as substrates for the immunopeptide presentation machinery, e.g., via MHC presentation. In various embodiments, the novel peptide fragments representing neoantigens can be presented in the MHC1-bound peptidome, e.g., on tumor cells.

In various embodiments, the delivery of splicing modulators, alone and as part of an ADC or composition, may lead to one or more tumor cell-intrinsic events (e.g., cell growth arrest). In various embodiments, the tumor cell-intrinsic event(s) may lead to (1) enhanced engagement by phagocytic cells (Bracci et al. (2014) Cell Death Differ. 21(1):15-25); (2) the transport of novel peptide fragments to a tumor draining lymph node to engage with antigen-presenting cells; (3) antigen-presenting cells processing novel peptide fragments from a phagocytosed tumor cell and presenting the fragments as neoantigens to circulating naïve T-cell populations; (4) novel peptide fragments interacting with T-cells expressing receptors that recognize the fragments as neoantigens; (5) maturation and activation of effector T-cell responses (e.g., CD4+ and/or CD8+ T-cells; and/or (6) engagement of T-cells with additional tumor cells exposed to the splicing modulator treatment and presenting novel peptide fragments representing neoantigens on their surface MHC1 complexes. In various embodiments, the tumor cell-intrinsic event(s) may result, either directly or indirectly, in T-cell engagement of effector function and/or killing of neoantigen-presenting tumor cells.

Also, without being bound by theory, in various embodiments, the delivery of splicing modulators, alone and as part of an ADC or composition, may cause the re-expression of intron-resident endogenous retroviruses, leading to a double-stranded RNA immune response.

Further, without being bound by theory, in various embodiments, the delivery of splicing modulators, alone and as part of an ADC or composition, may lead to immunogenic cell death triggered by splice modulator-induced release of mutationally-derived neoantigens. In various embodiments, the delivery of splicing modulators, alone and as part of an ADC or composition, may induce a double-stranded RNA immune response. In various embodiments, the double-stranded RNA immune response can result from the re-expression of intron-resident endogenous retroviruses. In various embodiments, the double-stranded RNA immune response can result in tumor cell death. In various embodiments, the delivery of splicing modulators, alone and as part of an ADC or composition, may induce immunogenic cell death. In various embodiments, the immunogenic cell death can result from release of mutational-derived neoantigens and/or a host immune response against tumor cells.

Accordingly, in various embodiments, methods of treatment are disclosed comprising inducing neoantigens by administering one or more splicing modulators and/or ADCs and/or compositions comprising a splicing modulator or ADC, e.g., any splicing modulator, ADC, or composition disclosed herein. In various embodiments, the method comprises administering a reduced dosage of the splicing modulator, ADC, or composition than would be needed absent the induction of neoantigens. In some embodiments, the method comprises administering one or more initial induction doses to produce neoantigens and induce an immune response (e.g., converting naïve T-cells to memory cells), followed by a reduced dosage or administration frequency (i.e., because of the combinatorial effect of the splicing modulator, ADC, or composition and of immune targeting of the neoantigens). In some embodiments, treatment can comprise a combination of administering the splicing modulator, ADC, or composition to induce a neoantigen-based immune response and at least one additional therapy (e.g., a second anti-cancer therapy). For example, in some embodiments, treatment can comprise a combination of administering the splicing modulator, ADC, or composition to induce a neoantigen-based immune response and one or more checkpoint inhibitors. In some embodiments, treatment can comprise a combination of administering the splicing modulator, ADC, or composition to induce a neoantigen-based immune response and one or more cytokines or cytokine analogs. In some embodiments, treatment can comprise a combination of administering the splicing modulator, ADC, or composition to induce a neoantigen-based immune response and one or more neoantigen vaccines. In some other embodiments, treatment can comprise a combination of administering the splicing modulator, ADC, or composition to induce a neoantigen-based immune response and one or more engineered tumor-targeting T-cells (e.g., CAR-T).

In some embodiments, neoantigens can be used to monitor the effectiveness of treatment with a splicing modulator, ADC, or composition. For instance, after administration of a splicing modulator, ADC, or composition, a patient sample (e.g., a tumor biopsy) can be obtained and screened for neoantigens or for identifiers of an immune or inflammatory response. Further treatment can be provided, e.g., at reduced dosage, if a neoantigen and/or immune response is detected.

In various embodiments, methods of treatment are disclosed comprising inducing a double-stranded RNA immune response by administering one or more splicing modulators and/or ADCs and/or compositions comprising a splicing modulator or ADC, e.g., any splicing modulator, ADC, or composition disclosed herein.

In various embodiments, methods of treatment are disclosed comprising inducing immunogenic cell death by administering one or more splicing modulators and/or ADCs and/or compositions comprising a splicing modulator or ADC, e.g., any splicing modulator, ADC, or composition disclosed herein.

In various embodiments, administration of a splicing modulator, ADC, or composition comprising a splicing modulator can be combined with any known anti-cancer therapy. Examples of current immune activating strategies available for oncology treatment include, but are not limited to, treatment with immune checkpoint inhibitor (ICI) molecules, treatment with cytokines or cytokine analogs, vaccination with tumor-associated vaccines, and engineering tumor-targeting T-cells (e.g., expansion of tumor-infiltrating lymphocytes or CAR-T). These technologies are predominantly focused on enhancing or inducing an immune response to already existing tumor antigens (either mutations or aberrant expression of cell-surface proteins). One or more of these strategies may involve one or more mutations that are capable of inducing an antigenic T-cell response. For example, patient responses to checkpoint inhibition may correlate with non-synonymous mutational burden. In addition, cancer vaccine approaches may be used that rely on pre-existing mutations and the antigenicity of these mutations.

Splicing modulators and/or ADCs comprising such modulators may induce broad-ranging changes in the transcriptome that occur in multiple lineages. Translation of these mRNA changes may produce robust and reproducible protein changes that produce MHC1-bound neopeptides with high affinity across multiple HLA isotypes. Without being bound by theory, due to the large number of changes to the transcriptome and proteome, treatment with splicing modulators and/or ADCs may enrich the number of potentially reactive neoantigens for enhanced engagement of the adaptive immune response.

As described herein, the terms “splicing modulator,” “spliceosome modulator,” or “splice modulator” refer to compounds that have anti-cancer activity by interacting with components of the spliceosome. In some embodiments, a splicing modulator alters the rate or form of splicing in a target cell. Splicing modulators that function as inhibitory agents, for example, are capable of decreasing uncontrolled cellular proliferation. In particular, in some embodiments, the splicing modulators may act by inhibiting the SF3b spliceosome complex. In some embodiments, a splicing modulator is chosen from any one or more of the splicing modulators disclosed herein. In some embodiments, a splicing modulator is used, delivered to a cell, and/or administered to a subject as a stand-alone agent. In some other embodiments, a splicing modulator is used, delivered to a cell, and/or administered to a subject as part of an ADC (e.g., an ADC chosen from any of the exemplary ADCs disclosed herein). In some other embodiments, a splicing modulator is used, delivered to a cell, and/or administered to a subject as part of a composition comprising multiple copies of the splicing modulator or multiple copies of an ADC carrying the splicing modulator. Such compositions are disclosed herein.

In some embodiments, a splicing modulator used, delivered to a cell, and/or administered to a subject as part of an ADC (e.g., an ADC chosen from any of the exemplary ADCs disclosed herein) provides added therapeutic benefits over a splicing modulator used, delivered to a cell, and/or administered to a subject as a stand-alone agent. For example, in some embodiments, a splicing modulator used, delivered to a cell, and/or administered to a subject as part of an ADC provides targeted delivery of the splicing modulator to a neoplastic cell expressing the target antigen (i.e., the antigen targeted by the antibody moiety of the ADC). In some embodiments, such targeted delivery of the splicing modulator reduces off-target treatment and/or off-target cytotoxicity. In some embodiments, such targeted delivery promotes tumor-selective neoantigen presentation on neoplastic cells, but not on healthy cells that do not express the target antigen. In some embodiments, such targeted delivery leads to, e.g., at least 75%, 80%, 85%, 90%, 95%, or 99%, of the alternative splicing and induction of novel mRNAs and MHC-associated peptides representing neoantigens in targeted neoplastic cells rather than off-target cells. Thus, without being bound by theory, in some embodiments, following effector T-cell priming and/or expansion (e.g., using a neoantigen vaccine), the immune system may preferentially attack neoantigen-presenting neoplastic cells rather than healthy cells due to the preferential expression of neoantigens on tumor cells after treatment with an ADC as disclosed herein.

Immune Induction and Treatment Regimen:

In various embodiments, the present disclosure provides a method of inducing at least one neoantigen by contacting a neoplastic cell with an effective amount of a splicing modulator, a splicing modulator-based antibody-drug conjugate (ADC), or a composition comprising a splicing modulator or ADC. In various embodiments, the present disclosure provides a method of inducing a double-stranded RNA immune response by contacting a neoplastic cell with an effective amount of a splicing modulator, a splicing modulator-based antibody-drug conjugate (ADC), or a composition comprising a splicing modulator or ADC. In various embodiments, the present disclosure provides a method of inducing immunogenic cell death by contacting a neoplastic cell with an effective amount of a splicing modulator, a splicing modulator-based antibody-drug conjugate (ADC), or a composition comprising a splicing modulator or ADC.

In some embodiments, the at least one neoantigen comprises an amino acid sequence of any one of SEQ ID NOs: 37-65. In some embodiments, the at least one neoantigen comprises an amino acid sequence of SEQ ID NO: 37. In some embodiments, the at least one neoantigen comprises an amino acid sequence of SEQ ID NO: 39. In some embodiments, the at least one neoantigen comprises an amino acid sequence of any one of SEQ ID NOs: 46-49.

In some embodiments, the neoplastic cell is present in an in vitro cell culture. In some embodiments, the neoplastic cell is obtained from a subject. In some embodiments, the neoplastic cell is present in a subject. In some embodiments, the neoplastic cell is derived from a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the present disclosure further provides a method of inducing at least one neoantigen and/or a T-cell response in a subject having or suspected of having a neoplastic disorder by administering to the subject an effective amount of a splicing modulator, an ADC, or a composition comprising a splicing modulator or ADC. Also provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces at least one neoantigen and/or a T-cell response.

In various other embodiments, the present disclosure provides a method of inducing a double-stranded RNA immune response in a subject having or suspected of having a neoplastic disorder by administering to the subject an effective amount of a splicing modulator, an ADC, or a composition comprising a splicing modulator or ADC. Also provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces a double-stranded RNA immune response.

In still other embodiments, the present disclosure provides a method of inducing immunogenic cell death in a subject having or suspected of having a neoplastic disorder by administering to the subject an effective amount of a splicing modulator, an ADC, or a composition comprising a splicing modulator or ADC. Further provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces immunogenic cell death.

In some embodiments of the therapeutic methods described herein, the at least one neoantigen comprises an amino acid sequence of any one of SEQ ID NOs: 37-65. In some embodiments, the at least one neoantigen comprises an amino acid sequence of SEQ ID NO: 37. In some embodiments, the at least one neoantigen comprises an amino acid sequence of SEQ ID NO: 39. In some embodiments, the at least one neoantigen comprises an amino acid sequence of any one of SEQ ID NOs: 46-49.

In some embodiments, the present disclosure further provides a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces immunogenic cell death, in combination with one or more additional therapies comprising a second agent.

In some embodiments of the therapeutic methods described herein, the amount of the splicing modulator, antibody-drug conjugate, composition, or second agent administered is reduced due to induction of at least one neoantigen and/or a T-cell response, as compared to a standard dosage of the splicing modulator, antibody-drug conjugate, composition, or second agent. In some embodiments, the administered amount of the splicing modulator, antibody-drug conjugate, composition, or second agent is reduced by 10%, 15%, 20%, 25%, 30%, 35%, 40%, 45%, 50%, 75%, or 90%, as compared to a standard dosage of the splicing modulator, antibody-drug conjugate, composition, or second agent. In some embodiments, the splicing modulator, antibody-drug conjugate, composition, or second agent is administered at least 10%, 15%, 20%, 25%, 30%, 35%, 40%, 45%, 50%, 75%, or 90% less frequently, as compared to a standard dosing regimen of the splicing modulator, antibody-drug conjugate, composition, or second agent. In some embodiments, the administered amount and/or dosage of the splicing modulator, antibody-drug conjugate, composition, or second agent results in lower systemic toxicity and/or improved tolerance.

As used herein, the term “standard dosage” or “standard dosing regimen” refers to any usual or routine dosing regimen for a therapeutic agent, e.g., a regimen proposed by the manufacturer, approved by regulatory authorities, or otherwise tested in human subjects to meet the average patient’s needs. In some embodiments, the therapeutic agent is a splicing modulator, an antibody, or an antibody-drug conjugate with anti-cancer activity.

For instance, a standard dosing regimen for trastuzumab, an exemplary anti-HER2 antibody disclosed herein, may be 8 mg/kg administered intravenously over 90 min (week 1) followed by 6 mg/kg administered intravenously over 30-90 min every 3 weeks (week 4 through the end of the therapy cycle) (Herceptin® (trastuzumab) FDA Label Supplement, 2017).

As another example, a standard dosing regimen for ipilimumab, an exemplary anti-CTLA4 checkpoint inhibitor antibody, may be 3 mg/kg administered intravenously over 90 min every 3 weeks for 4 doses (Yervoy® (ipilimumab) FDA Label Supplement, 2018). Another standard dosing regimen for ipilimumab may be 10 mg/kg administered intravenously over 90 min every 3 weeks for 4 doses, followed by 10 mg/kg every 12 weeks for up to 3 years (Yervoy® (ipilimumab) FDA Label Supplement, 2018).

As another example, a standard dosing regimen for nivolumab, an exemplary anti-PD1 checkpoint inhibitor antibody, may be 3 mg/kg administered intravenously over 60 min every 2 weeks (Opdivo® (nivolumab) FDA Label, 2015).

As another example, a standard dosing regimen for atezolizumab, an exemplary anti-PDL1 checkpoint inhibitor antibody, may be 1200 mg administered intravenously over 60 min every 3 weeks (Tecentriq® (atezolizumab) FDA Label Supplement, 2018).

As yet another example, a standard dosing regimen for T-DM1, an exemplary anti-HER2 antibody-drug conjugate, may be 3.6 mg/kg administered intravenously over 90 min every 3 weeks (Kadcyla® (T-DM1) FDA Label Supplement, 2016).

In some embodiments, the methods described herein may further comprise administering at least one additional therapy (e.g., a checkpoint inhibitor, a neoantigen vaccine, a cytokine or cytokine analog, CAR-T, etc.). In some embodiments, the amount of the splicing modulator, antibody-drug conjugate, composition, and/or the at least one additional therapy administered is reduced due to induction of at least one neoantigen and/or a T-cell response, as compared to a standard dosage of the splicing modulator, antibody-drug conjugate, composition, and/or the at least one additional therapy. In some embodiments, the amount of the splicing modulator, antibody-drug conjugate, composition, and/or the at least one additional therapy administered is reduced due to induction of a double-stranded RNA immune response, as compared to a standard dosage of the splicing modulator, antibody-drug conjugate, composition, and/or the at least one additional therapy. In some embodiments, the amount of the splicing modulator, antibody-drug conjugate, composition, and/or the at least one additional therapy administered is reduced due to induction of immunogenic cell death, as compared to a standard dosage of the splicing modulator, antibody-drug conjugate, composition, and/or the at least one additional therapy. In some embodiments, the administered amount of the splicing modulator, antibody-drug conjugate, composition, and/or the at least one additional therapy is reduced by 10%, 15%, 20%, 25%, 30%, 35%, 40%, 45%, 50%, 75%, or 90%, as compared to a standard dosage of the splicing modulator, antibody-drug conjugate, composition, and/or the at least one additional therapy. In some embodiments, the splicing modulator, antibody-drug conjugate, composition, and/or the at least one additional therapy is administered at least 10%, 15%, 20%, 25%, 30%, 35%, 40%, 45%, 50%, 75%, or 90% less frequently, as compared to a standard dosing regimen of the splicing modulator, antibody-drug conjugate, composition, and/or the at least one additional therapy. In some embodiments, the administered amount and/or dosage of the splicing modulator, antibody-drug conjugate, composition, and/or the at least one additional therapy results in lower systemic toxicity and/or improved tolerance.

In some embodiments, administration of the splicing modulator, antibody-drug conjugate, or composition is initiated before administration of the at least one additional therapy. In other embodiments, administration of the splicing modulator, antibody-drug conjugate, or composition is initiated after administration of the at least one additional therapy. In still other embodiments, administration of the splicing modulator, antibody-drug conjugate, or composition is initiated concurrently with administration of the at least one additional therapy.

In some embodiments, administration of the splicing modulator, antibody-drug conjugate, or composition is repeated at least once after initial administration. In some embodiments, the amount of the splicing modulator, antibody-drug conjugate, or composition used for repeated administration is reduced as compared to the amount used for initial administration. In some embodiments, the amount of the splicing modulator, antibody-drug conjugate, or composition used for repeated administration is reduced as compared to a standard dosage of the splicing modulator, antibody-drug conjugate, or composition. In some embodiments, the amount of the splicing modulator, antibody-drug conjugate, or composition used for repeated administration is reduced by 10%, 15%, 20%, 25%, 30%, 35%, 40%, 45%, 50%, 75%, or 90%, as compared to a standard dosage or initial dosage of the splicing modulator, antibody-drug conjugate, or composition.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage or initial dosage of the at least one additional therapy.

In some embodiments, repeated administration of the splicing modulator, antibody-drug conjugate, or composition is concurrent with repeated administration of the at least one additional therapy. In some embodiments, administration of the splicing modulator, antibody-drug conjugate, or composition is sequential or staggered with repeated administration of the at least one additional therapy.

In some embodiments, the at least one additional therapy comprises administering a checkpoint inhibitor, e.g., any checkpoint inhibitor disclosed herein. In some embodiments, the subject is intolerant, non-responsive, or poorly responsive to the checkpoint inhibitor when administered alone. In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule.

In some other embodiments, the at least one additional therapy comprises administering a neoantigen vaccine, e.g., any neoantigen vaccine disclosed herein. In some embodiments, the splicing modulator, ADC, or composition is administered before administration of the neoantigen vaccine. In some embodiments, the splicing modulator, ADC, or composition is administered after administration of the neoantigen vaccine. In some embodiments, the splicing modulator, ADC, or composition is administered concurrently with administration of the neoantigen vaccine. In some embodiments, administration of the splicing modulator, ADC, or composition is repeated at least once after initial administration. In some embodiments, the amount of the splicing modulator, ADC, or composition used for repeated administration is reduced as compared to the amount used for initial administration.

In some embodiments, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length. In some embodiments, the at least one neoantigen peptide comprises one or more than one neoantigen sequence.

In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

The term "antigenic portion" or "antigenic fragment" of a neoantigen sequence, as used herein, refers to one or more fragments of a neoantigen sequence that retain the ability to induce a T-cell response (e.g., antigen-specific expansion and/or maturation of effector T-cell population(s)). An antigenic portion, in some embodiments, may also retain the ability to be internalized, processed, and/or presented by antigen-presenting cells (e.g., dendritic cells). In some embodiments, an antigenic portion also retains T-cell priming function. In some embodiments, an antigenic portion of a neoantigen sequence ranges from about 10 to about 50 amino acids in length. In some embodiments, an antigenic portion of a neoantigen sequence ranges from about 10 to about 35 amino acids in length. In some embodiments, an antigenic portion of a neoantigen sequence ranges from about 15 to about 25 amino acids in length. In some embodiments, an antigenic portion of a neoantigen sequence ranges from about 10 to about 20 amino acids in length. In some embodiments, an antigenic portion of a neoantigen sequence (e.g., an antigenic portion of any one of SEQ ID NOs: 66-93), or its encoding mRNA, is formulated as a neoantigen vaccine.

An exemplary embodiment of an antigenic portion is the region(s) flanking amino acids 45-53 of SEQ ID NO: 66. Another exemplary embodiment of an antigenic portion is the region(s) flanking amino acids 82-90 of SEQ ID NO: 66. In some embodiments, the antigenic portion is capable of binding to at least one HLA allele expressed in a subject (e.g., HLA-A*02:01). In some other embodiments, the antigenic portion is capable of binding to at least one HLA allele expressed in at least 10%, at least 15%, at least 20%, at least 25%, at least 30%, at least 35%, at least 40%, or at least 45% of subjects in a population of subjects suffering from a neoplastic disorder. In some embodiments, the antigenic portion is capable of eliciting a T-cell response against a tumor present in at least 1%, at least 5%, or at least 10% of a population of subjects suffering from a neoplastic disorder.

In some embodiments, an antigenic portion does not exclusively overlap or consist of a canonical peptide sequence. The term "canonical peptide sequence," as used herein, refers to any contiguous peptide sequence present in the human proteome in the absence of contact with a splicing modulator (e.g., in the absence of contact with a splicing modulator alone and/or as part of an ADC or composition), and/or to which the immune has previously been exposed. In some embodiments, the canonical peptide sequence is derived from and/or encoded by the canonical transcript open reading frame. Exemplary canonical peptide sequences are underlined in Table 21.

In some embodiments, when a splicing modulator is administered (e.g., alone and/or as part of an ADC or composition), a canonical peptide sequence may be derived from and/or encoded by the immediate 5' in-frame 24 nucleotides preceding an aberrant splicing event induced by the splicing modulator. Thus, in some embodiments, the canonical peptide sequence comprises or consists of the 8 amino acids immediately N-terminal to the neoantigen sequence induced by the splicing modulator. In some embodiments, when a 5' exon sequence terminates with a terminal nucleotide of a codon, the canonical peptide sequence terminates at the end of the exon. In some other embodiments, when a 5' exon sequence terminates with one or two of the three nucleotides of a codon, the canonical peptide sequence is derived from and/or encoded by the 24 nucleotides preceding the incomplete codon. In some embodiments, mRNA sequences 3' of the aberrant splicing event may be translated in the same open reading frame derived from the 5' exon until reaching a stop codon, whereupon translation may terminate. In some embodiments, when the aberrant splicing event (e.g., exon skipping) results in a conservation of the canonical transcript open reading frame, the C-terminal sequence may be translated for an additional 24 nucleotides, encoding 8 C-terminal amino acids. In this context, in some embodiments, only the region across the aberrant exon junction may encode a neoantigen sequence. In some embodiments, when the open reading frame is shifted (e.g., intron retention), the complete C-terminal sequence (encoded by the 3' mRNA) may encode a neoantigen sequence.

In some embodiments, an antigenic portion of a neoantigen sequence is chosen by comparing the neoantigen sequence to the canonical peptide sequence; and selecting a portion of the neoantigen sequence that does not exclusively overlap, consist of, and/or align with the canonical peptide sequence. An antigenic portion of a neoantigen sequence, in some embodiments, can be screened for antigenicity and/or T-cell priming function in the same manner as are full-length neoantigen sequences (e.g., the neoantigen sequence from which the antigenic portion is derived). In some embodiments, an antigenic portion of a neoantigen sequence is evaluated for antigenicity and/or T-cell priming function using a T-cell priming assay, such as the exemplary T-cell priming experiments described herein.

In some embodiments, the neoantigen sequence is a neoantigen sequence specific to the subject. In some embodiments, the neoantigen sequence is a personalized neoantigen vaccine for the subject. In some embodiments, the neoantigen sequence used to create a personalized neoantigen vaccine for a subject is capable of binding to at least one HLA allele expressed in the subject. In some embodiments, a personalized neoantigen vaccine is selected by identifying neoantigens expressed in a subject's tumor, e.g., after administration of a splicing modulator or ADC, and selecting a vaccine comprising a neoantigen sequence observed in the patient's tumor, e.g., a vaccine comprising an amino acid sequence of any one of SEQ ID NOs: 37-65 that is observed in the tumor.

The term "personalized" when used to describe a neoantigen vaccine refers to a vaccine created by identifying one or more neoantigens produced in a patient, preferably one identified in the patient after an exposure to a splicing modulator, ADC, or composition, and then using one or more of those neoantigens as the basis of the vaccine for the same patient. Accordingly, in some embodiments, a patient is given a splicing modulator, ADC, or composition and screened for neoantigens produced by the treatment. In some embodiments, the selected neoantigen vaccine comprises a neoantigen peptide or mRNA disclosed herein and confirmed to be present in the patient after exposure to the splicing modulator, ADC, or composition. In some embodiments, the splicing modulator, ADC, or composition and/or peptide or mRNA vaccine may be administered to the patient once or repeatedly. Subsequently, in some embodiments, one or more of those neoantigens are used to create a personalized vaccine that is given to the patient. In some embodiments, the one or more neoantigens used to create a personalized vaccine possess binding affinity for one or more patient-specific HLA alleles. In some embodiments, the patient expresses one or more MHC1 alleles that bind to the one or more neoantigens. The prediction of whether a given neoantigen will bind to a specific MHC1 allele can be determined using any computational prediction method known in the art. Exemplary computational prediction methods are disclosed, e.g., in Meydan et al. (2013) BMC Bioinformatics 14(Suppl. 2):S13, which is incorporated herein by reference for such methods.

In some other embodiments, the neoantigen sequence is a universal neoantigen sequence. In some embodiments, the neoantigen sequence is a universal neoantigen vaccine.

The term "universal" when used to describe a neoantigen vaccine refers to a vaccine having a peptide or mRNA sequence that is based on common or known neoantigen(s) observed by sequencing neoantigens produced in multiple patients and/or patient tissue samples, preferably after an exposure to a splicing modulator, ADC, or composition. The peptide or mRNA sequence used in the vaccine need not be present in every patient but rather be observed in at least several patients or patient tissue samples. In some embodiments, the splicing modulator, ADC, or composition and/or peptide or mRNA vaccine may be administered to the patient once or repeatedly.

Subsequently, in some embodiments, that peptide or mRNA sequence is used for vaccinating further patients. In some embodiments, a patient is given a splicing modulator, ADC, or composition, and then given a peptide or mRNA vaccine of known neoantigen to enhance immune response to the neoantigens produced by the splicing modulator, ADC, or composition. In some embodiments, a patient is given a universal peptide or mRNA vaccine and then given a splicing modulator, ADC, or composition once or repeatedly. In some embodiments, the neoantigen sequence (or sequences) used to create a universal neoantigen vaccine is selected based on overall MHC1 allele frequency in a given patient population (Maiers et al. (2007) Hum. Immunol. 68(9):779-88).

In some embodiments, the neoantigen (e.g., a universal neoantigen) sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide, or its encoding mRNA, induced in the subject by administering an effective amount of the splicing modulator, antibody-drug conjugate, or composition. In some embodiments, the at least one neoantigen peptide comprises a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier (e.g., any of the exemplary carriers described herein). In some embodiments, the at least one neoantigen peptide is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen peptide and the pharmaceutically acceptable carrier are covalently attached via a linker. In some embodiments, the neoantigen peptide and the pharmaceutically acceptable carrier are expressed as a fusion protein. In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant.

In some embodiments, the neoantigen vaccine comprises at least one neoantigen mRNA. In some embodiments, the at least one neoantigen mRNA encodes one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing the protein sequence of at least one neoantigen. In some embodiments, the neoantigen sequence has been identified by sequencing at least one mRNA encoding a neoantigen induced in the subject by administering an effective amount of the splicing modulator, antibody-drug conjugate, or composition. In some embodiments, the at least one neoantigen mRNA encodes a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier (e.g., any of the exemplary carriers described herein). In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant. In some embodiments, the neoantigen mRNA is encapsulated by an encapsulating agent. In some embodiments, the encapsulating agent is a liposome. In some embodiments, the encapsulating agent is a nanoparticle.

In some embodiments, the at least one additional therapy comprises administering a cytokine or cytokine analog, e.g., any cytokine or cytokine analog disclosed herein. In some embodiments, the subject is intolerant, non-responsive, or poorly responsive to the cytokine or cytokine analog when administered alone. In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a splicing modulator, antibody-drug conjugate, or composition due to the induction and presentation of neoantigens.

In some embodiments, the at least one additional therapy comprises administering engineered tumor-targeting T-cells (i.e., CAR-T), e.g., any CAR-T therapy disclosed herein.

In some embodiments, the methods described herein may further comprise detecting one or more neoantigens and/or a T-cell response in the subject after administration of the splicing modulator, antibody-drug conjugate, or composition, and, optionally, continuing administration of the splicing modulator, antibody-drug conjugate, or composition if one or more neoantigens and/or a T-cell response is detected. In some embodiments, detecting one or more neoantigens and/or a T-cell response in the subject indicates efficacy of treatment with the splicing modulator, antibody-drug conjugate, or composition. In some embodiments, treatment with the additional therapy, along with splicing modulator, antibody-drug conjugate, or composition, is continued if one or more neoantigens and/or a T-cell response is detected. In some embodiments, treatment is continued at a reduced dosage and/or frequency if one or more neoantigens and/or a T-cell response is detected.

In some embodiments, the methods described herein may further comprise detecting a double-stranded RNA immune response in the subject after administration of the splicing modulator, antibody-drug conjugate, or composition, and, optionally, continuing administration of the splicing modulator, antibody-drug conjugate, or composition if a double-stranded RNA immune response is detected. In some embodiments, detecting a double-stranded RNA immune response in the subject indicates efficacy of treatment with the splicing modulator, antibody-drug conjugate, or composition. In some embodiments, treatment with the additional therapy, along with splicing modulator, antibody-drug conjugate, or composition, is continued if a double-stranded RNA immune response is detected. In some embodiments, treatment is continued at a reduced dosage and/or frequency if a double-stranded RNA immune response is detected.

In some embodiments, the methods described herein may further comprise detecting immunogenic cell death in the subject after administration of the splicing modulator, antibody-drug conjugate, or composition, and, optionally, continuing administration of the splicing modulator, antibody-drug conjugate, or composition if immunogenic cell death is detected. In some embodiments, detecting immunogenic cell death in the subject indicates efficacy of treatment with the splicing modulator, antibody-drug conjugate, or composition. In some embodiments, treatment with the additional therapy, along with splicing modulator, antibody-drug conjugate, or composition, is continued if immunogenic cell death is detected. In some embodiments, treatment is continued at a reduced dosage and/or frequency if immunogenic cell death is detected.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the present disclosure further provides a method of treating a subject having or suspected of having a neoplastic disorder, comprising: (a) administering to the subject an effective amount of a splicing modulator, an ADC, or composition comprising a splicing modulator or ADC, wherein administration of the splicing modulator, antibody-drug conjugate, or composition induces at least one neoantigen and/or a T-cell response; (b) detecting one or more neoantigens and/or a T-cell response in the subject after administration of the splicing modulator, antibody-drug conjugate, or composition; and (c) continuing administration of the splicing modulator, antibody-drug conjugate, or composition if one or more neoantigens and/or a T-cell response is detected. In some embodiments, detecting one or more neoantigens and/or a T-cell response in the subject indicates efficacy of treatment with the splicing modulator, antibody-drug conjugate, or composition. In some embodiments, the one or more neoantigens comprise an amino acid sequence of any one of SEQ ID NOs: 37-65. In some embodiments, the one or more neoantigens comprise an amino acid sequence of SEQ ID NO: 37. In some embodiments, the one or more neoantigens comprise an amino acid sequence of SEQ ID NO: 39. In some embodiments, the one or more neoantigens comprise an amino acid sequence of any one of SEQ ID NOs: 46-49.

Combination of Splicing Modulator/ADC and Immune Checkpoint Inhibition:

In various embodiments, a patient having a cancer as described herein can be treated with a combination of a splicing modulator, ADC, or composition and a checkpoint inhibitor therapy. Immune checkpoints are inhibitory pathways that slow down or stop immune reactions and prevent excessive tissue damage from uncontrolled activity of immune cells. As used herein, the term "checkpoint inhibitor" is meant to refer to any therapeutic agent, including any small molecule chemical compound, antibody, nucleic acid molecule, or polypeptide, or any fragments thereof, that inhibits one or more of the inhibitory pathways, thereby allowing more extensive immune activity.

Treatment of patients with immune checkpoint inhibition has been shown to have robust efficacy in certain clinical indications. Recently, the FDA approved use of a checkpoint inhibitor in patients with tumors exhibiting high microsatellite instability, agnostic to the tissue lineage. This approval was based, in part, on the observation that response rates correlate positively with mutational burden (Rizvi et al. (2015) Science 348(6230):124-8; Hellmann et al. (2018) Cancer Cell 33(5):853-861). Estimates from the literature vary in absolute numbers and by lineage, but generally support that above a threshold of ~150-250 mutations, the probability of response rises. Analysis of TCGA data shows that a large percentage of adult-onset tumor lineages have comparatively low non-synonymous mutational burden (Vogelstein et al. (2013) Science 339:1549-58). Most lineages have median non-synonymous mutational rates of ~30-80 per patient, well below the thresholds for improved odds of response to checkpoint inhibitors.

For instance, HER2-positive breast cancer has been shown to have a median of ~60 non-synonymous mutations present per patient sample. However, the threshold for checkpoint inhibitor treatment efficacy, as mentioned above, is estimated to be in the range of ~150-250 non-synonymous mutations, i.e., patients above this threshold are more likely to show complete remission, partial remission, and/or stable disease, whereas patients below this threshold are more likely to exhibit progressive disease. Strategies to enhance the apparent number of non-synonymous mutations and/or neoantigens being presented on tumor cells are therefore desirable, and may enhance the overall probability of response, e.g., to checkpoint inhibitor therapies. As cytokines (and analogs thereof) act via a similar mechanism of action, such strategies may also enhance the overall probability of response to cytokine-based therapies.

Current response rates in HER2-positive breast cancer are ~15-25% (CTI NCT02129556). In various embodiments disclosed herein, treatment with a splicing modulator, ADC, or composition in combination with a checkpoint inhibitor and/or cytokine therapy may improve such response rates. In various embodiments, treatment with a splicing modulator, ADC, or composition in combination with a checkpoint inhibitor and/or cytokine therapy may apply to any adult-onset tumor, particularly those in which the median non-synonymous mutational rate is below the estimated ~150 mutations threshold. In various embodiments, exemplary cancer types suitable for treatment with a splicing modulator, ADC, or composition of the present disclosure, alone or in combination with an additional therapy (e.g., a checkpoint inhibitor therapy, a cytokine therapy) include but are not limited to esophageal cancer, non-Hodgkin's lymphoma, colorectal cancer, head and neck cancer, gastric cancer, endometrial cancer, pancreatic adenocarcinoma, ovarian cancer, prostate cancer, hepatocellular cancer, glioblastoma, breast cancer (e.g., HER2-positive breast cancer), lung cancer (e.g., non-small cell lung cancer), chronic lymphocytic leukemia, and acute myeloid leukemia. Other exemplary suitable cancer types are identified, e.g., in Vogelstein et al. (2013) Science 339:1549-58, which is incorporated herein by reference in its entirety.

As many checkpoint inhibitor therapies are based on chronic expression of tumor-associated antigens, regular treatment boosts are required for efficacy and for "re-boosting" reactive T-cell populations. The inducible nature of splicing modulator or ADC-derived neoantigens described herein provide for therapeutic dosing regimens that may be designed to enhance the immune response of neoantigen-reactive T-cells, while limiting T-cell exhaustion often caused by chronic antigen stimulation. For instance, in some embodiments, an initial dose of a splicing modulator, ADC, or composition is administered to a subject to trigger aberrant splicing and production of neoantigen peptides. After a period of time to allow for protein production and antigen presentation, in some embodiments, the subject is then administered an initial dose of a checkpoint inhibitor to boost and/or enhance effector T-cell priming and expansion. In some embodiments, the wait period between doses of splicing modulator, ADC, or composition and checkpoint inhibitor is about 2, about 3, about 4, about 5, about 6, or about 7 days. In some embodiments, the wait period is between about 3 days and about 5 days. In some embodiments, the checkpoint inhibitor is targeted at CTLA4, OX40, CD40, and/or GITR. In some embodiments, the combination therapeutic benefit of a splicing modulator, ADC, or composition and a checkpoint inhibitor may be additive or superadditive.

In some embodiments, after a period to allow for T-cell priming and expansion, the subject is then administered a second or subsequent dose of the splicing modulator, ADC, or composition to trigger re-presentation of neoantigen peptides. In some embodiments, the wait period between an initial dose of a checkpoint inhibitor and a second or subsequent dose of a splicing modulator, ADC, or composition is about 2, about 3, about 4, or about 5 weeks. In some embodiments, the wait period is about 3 weeks. Following a second or subsequent dose of the splicing modulator, ADC, or composition, in some embodiments, the immune system may engage with the neoantigen-presenting tumor cells and/or elicit tumor cell killing. In some embodiments, the subject is then administered a second or subsequent dose of the checkpoint inhibitor to further expand the memory effector T-cell population, after allowing for secondary T-cell priming and expansion.

In some embodiments, dosing of the splicing modulator, ADC, or composition following this exemplary initial treatment regimen can be pulsatile, i.e., the splicing modulator, ADC, or composition may be dosed at prolonged intervals (e.g., about every 4 weeks, about every 5 weeks, about every 6 weeks) to allow for antigen presentation, T-cell engagement and/or tumor cell killing, and/or recovery of the memory T-cell population. At later timepoints, in some embodiments, the splicing modulator, ADC, or composition treatment may be combined with one or more checkpoint inhibitors targeted to restore effector functionality to exhausted T-cell populations. For example, in some embodiments, at later timepoints, the splicing modulator, ADC, or composition treatment may be combined with one or more checkpoint inhibitors targeted at PD1/PDL1, LAG3, and/or TIM3. In some embodiments, the pulsed nature of neoantigen presentation and priming may allow a checkpoint inhibitor and/or a splicing modulator, ADC, or composition to be administered less frequently and/or at lower doses. In some embodiments, the pulsed nature of neoantigen presentation may provide one or more treatment benefits for a checkpoint inhibitor (e.g., an anti-CTLA4 antibody such as ipilimumab), as compared to the checkpoint inhibitor when administered without concurrent splicing modulator, ADC, or composition treatment, for example, by lowering the potential risk of adverse reactions often observed with the checkpoint inhibitor's standard dosing regimen.

In certain embodiments, the checkpoint inhibitor is an inhibitor of the cytotoxic T-lymphocyte-associated antigen (CTLA4) pathway. CTLA4, also known as CD152, is a protein receptor that downregulates immune responses. CTLA4 is constitutively expressed in regulatory T-cells, but only upregulated in conventional T-cells after activation. As used herein, the term "CTLA4 inhibitor" is meant to refer to any inhibitor of CTLA4 and/or the CTLA4 pathway. Exemplary CTLA4 inhibitors include but are not limited to anti-CTLA4 antibodies. CTLA4 blocking antibodies for use in humans were developed based on the pre-clinical activity seen in mouse models of anti-tumor immunity. Exemplary anti-CTLA4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the anti-CTLA4 antibody is ipilimumab.

In certain embodiments, the checkpoint inhibitor is an inhibitor of the programmed death-1 (PD1) pathway. The programmed cell death 1 (PD1) pathway represents a major immune control switch which may be engaged by tumor cells to overcome active T-cell immune surveillance. The ligands for PD1 (PDL1 and PDL2) are constitutively expressed or can be induced in various tumors. High expression of PDL1 on tumor cells (and to a lesser extent of PDL2) has been found to correlate with poor prognosis and survival in various other solid tumor types. Furthermore, PD1 has been suggested to regulate tumor-specific T-cell expansion in patients with malignant melanoma. These observations suggest that the PD1/PDL1 pathway plays a critical role in the tumor immune evasion and may be considered an attractive target for therapeutic intervention. As used herein, the term "PD1 inhibitor" is meant to refer to any inhibitor of PD1 and/or the PD1 pathway. Exemplary PD1 inhibitors include but are not limited to anti-PD1 and anti-PDL1 antibodies. In certain embodiments, the checkpoint inhibitor is an anti-PD1 antibody. Exemplary anti-PD1 antibodies include but are not limited to nivolumab and pembrolizumab (MK-3475). Nivolumab, for example, is a fully human immunoglobulin G4 (IgG4) PD1 immune checkpoint inhibitor antibody that disrupts the interaction of the PD1 receptor with its ligands PDL1 and PDL2, thereby inhibiting the cellular immune response (Guo et al. (2017) J Cancer 8(3):410-6). In some embodiments, the anti-PD1 antibody is nivolumab. Pembrolizumab, for example, is a potent and highly-selective humanized mAb of the IgG4/kappa isotype designed to directly block the interaction between PD1 and its ligands, PDL1 and PDL2. Pembrolizumab strongly enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFNγ), and other cytokines. Exemplary anti-PDL1 antibodies include but are not limited to atezolizumab, avelumab, and durvalumab. Atezolizumab, for example, is an IgG1 humanized mAb that is reported to block the PD1/PDL1 interaction, by targeting the expressed PDL1 on numerous kinds of malignant cells. This blockage of the PD1/PDL1 pathway may stimulate the immune defense mechanisms against tumors (Abdin et al. (2018) Cancers (Basel) 10(2):32). In some embodiments, the anti-PDL1 antibody is atezolizumab.

In certain embodiments, the checkpoint inhibitor is targeted at PD1/PDL1, CTLA4, OX40, CD40, LAG3, TIM3, GITR, and/or KIR. In certain embodiments, the checkpoint inhibitor is targeted at CTLA4, OX40, CD40, and/or GITR. In certain embodiments, a checkpoint inhibitor is targeted with an inhibitory antibody or other similar inhibitory molecule (e.g., an inhibitory anti-CTLA4 or anti-PD1/PDL1 antibody). In certain other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T-cell suppression, while enhancing effector T-cell functions. Agonist anti-GITR antibodies have also been shown to make effector T-cells more resistant to the inhibition induced by regulatory T-cells (Karaki et al. (2016) Vaccines (Basel) 4(4):37). Likewise, agonist CD40 antibodies demonstrate T-cell-dependent anti-tumor activity. Activation of CD40 on dendritic cells increases cross-presentation of tumor antigens and consequently the number of activated tumor-directed effector T-cells (Ellmark et al. (2015) Oncoimmunol. 4(7): e1011484).

In certain embodiments, the checkpoint inhibitor is targeted at CTLA4 (e.g., an anti-CTLA4 antibody). In certain embodiments, targeting CTLA4 facilitates priming and activation of naïve T-cells. In certain embodiments, the checkpoint inhibitor is targeted at OX40 (e.g., an anti-OX40 antibody). In certain embodiments, targeting OX40 enhances expansion of effector T-cells. In certain embodiments, the checkpoint inhibitor is targeted at CD40 (e.g., an anti-CD40 antibody). In certain embodiments, targeting CD40 inhibits "tolerogenic" priming of T-cells and/or formation of regulatory T-cells. In certain embodiments, the checkpoint inhibitor is targeted at GITR (e.g., an anti-GITR antibody). In certain embodiments, targeting GITR inhibits activity of regulatory T-cells. In certain embodiments, the benefit of combination therapy (e.g., the effect on at least one symptom or the risk/rate of disease progression) with a splicing modulator, ADC, or composition and a CTLA4-, OX40-, CD40-, and/or GITR-targeted agent is additive. In some embodiments, the benefit of combination therapy with a splicing modulator, ADC, or composition and a CTLA4-, OX40-, CD40-, and/or GITR-targeted agent is superadditive (i.e., synergistic).

Checkpoint inhibitor treatment strategies are based on the hypothesis that treatment facilitates and/or enhances priming of T-cell responses to weakly or poorly antigenic tumors (e.g., CTLA4) or that treatment restores and/or reinvigorates T-cells that respond to tumor antigens, but have become "exhausted" due to the chronic nature of the antigen presentation (e.g., PD1, PDL1) (Chen and Mellman (2013) Immunity 39(1):1-10). Examples of suitable checkpoint inhibition therapies and agents, e.g., anti-PD1, anti-PDL1, or anti-CTLA4 antibodies, are known in the art. See, e.g., WO 2001/014424 WO 2013/173223, WO 2016/007235.

Combining these primed T-cell responses following checkpoint inhibitor therapy with treatment to induce neoantigens in tumor cells to which the primed immune system can react may provide beneficial synergy. As the splicing modulator or ADC-derived neoantigens have not yet been presented for T-cell priming, combination with a CTLA4 inhibitor may be particularly beneficial. In some embodiments, treatment comprises administering one or more splicing modulator, ADC, or composition to induce the production of neoantigens, followed before, concurrently, or thereafter by an initial administration of a CTLA4 inhibitor to stimulate CD8 T-cell priming. In some embodiments, additional administrations of an CTLA4 inhibitor are provided to the patient, e.g., to further stimulate priming and/or activation of neoantigen-reactive CD8 populations. In some embodiments, additional administrations of splicing modulator, ADC, or composition can be given to the patient to increase neoantigen presentation by the tumor. Repeat administrations of splicing modulator, ADC, or composition and checkpoint inhibitor therapy can occur concurrently or in staggered intervals. In some embodiments, treatment further comprises administering a PD1/PDL1 inhibitor co-treatment, e.g., to restore effector function of exhausted neoantigen-targeted T-cells within the tumor microenvironment.

The terms "combination" or "combination therapy," as used herein, refer to the administration of one or more splicing modulator, ADC, or composition together with an additional agent or therapy (e.g., a checkpoint inhibitor, a cytokine or cytokine analog, a neoantigen vaccine, CAR-T), as part of a treatment regimen intended to provide a beneficial (i.e., additive or synergistic) effect from the co-action of one or more of the administered agents. In some embodiments, the combination may also include one or more additional agents, including but not limited to chemotherapeutic agents, anti-angiogenesis agents, and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a medical condition (e.g., a neoplastic disorder). For example, in some embodiments, the two or more treatments are delivered after the subject has been diagnosed with a disease or disorder, and before the disease or disorder has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., a splicing modulator, ADC, or composition and a checkpoint inhibitor) are comprised in the same composition. Such compositions may be administered in any appropriate form and by any suitable route. In other embodiments, the two treatments (e.g., a splicing modulator, ADC, or composition and a checkpoint inhibitor) are administered in separate compositions, in any appropriate form and by any suitable route. For example, in some embodiments, a composition comprising a splicing modulator or ADC and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease or disorder, is greater than what would be observed with the first treatment delivered in the absence of the second treatment. In other embodiments, an analogous situation is observed with the second treatment. In some embodiments, the benefit of combination therapy (e.g., the effect on at least one symptom or the risk/rate of disease progression) is additive. In some embodiments, the benefit of combination therapy is superadditive.

In various embodiments, the present disclosure provides a method of treating a subject having or suspected of having a neoplastic disorder by administering to the subject an effective amount of a splicing modulator, an ADC, or a composition comprising a splicing modulator or ADC; and at least one additional therapy (e.g., a checkpoint inhibitor therapy, a cytokine or cytokine analog, a neoantigen vaccine, CAR-T). In some embodiments, administration of the splicing modulator, ADC, or composition induces at least one neoantigen and/or a T-cell response. In some embodiments, administration of the splicing modulator, ADC, or composition induces a double-stranded RNA immune response. In some embodiments, administration of the splicing modulator, ADC, or composition induces immunogenic cell death. In some embodiments, the at least one additional therapy may comprise at least one, at least two, at least three, at least four, or at least five additional therapies. For example, in some embodiments, a splicing modulator, ADC, or composition may be administered in combination with two checkpoint therapies, i.e., using two different checkpoint inhibitors. In some other embodiments, a splicing modulator, ADC, or composition may be administered in combination with a checkpoint inhibitor therapy and a neoantigen vaccine.

In some embodiments of combination therapy, the administered amount of the splicing modulator, antibody-drug conjugate, or composition and/or the at least one additional therapy is reduced by 10%, 15%, 20%, 25%, 30%, 35%, 40%, 45%, 50%, 75%, or 90%, as compared to a standard dosage of the splicing modulator, antibody-drug conjugate, or composition and/or the at least one additional therapy. In some embodiments, the splicing modulator, antibody-drug conjugate, or composition and/or the at least one additional therapy is administered at least 10%, 15%, 20%, 25%, 30%, 35%, 40%, 45%, 50%, 75%, or 90% less frequently, as compared to a standard dosing regimen of the splicing modulator, antibody-drug conjugate, or composition and/or the at least one additional therapy. In some embodiments, the administered amount and/or dosage of the splicing modulator, antibody-drug conjugate, or composition and/or the at least one additional therapy results in lower systemic toxicity and/or improved tolerance.

In some embodiments, administration of the splicing modulator, antibody-drug conjugate, or composition is initiated before administration of the at least one additional therapy. In some embodiments, administration of the splicing modulator, antibody-drug conjugate, or composition is initiated after administration of the at least one additional therapy. In some embodiments, administration of the splicing modulator, antibody-drug conjugate, or composition is initiated concurrently with administration of the at least one additional therapy.

In some embodiments, administration of the splicing modulator, antibody-drug conjugate, or composition is repeated at least once after initial administration. In some embodiments, the amount of the splicing modulator, antibody-drug conjugate, or composition used for repeated administration is reduced as compared to the amount used for initial administration. In some embodiments, the amount of the splicing modulator, antibody-drug conjugate, or composition used for repeated administration is reduced as compared to a standard dosage of the splicing modulator, antibody-drug conjugate, or composition. In some embodiments, the amount of the splicing modulator, antibody-drug conjugate, or composition used for repeated administration is reduced by 10%, 15%, 20%, 25%, 30%, 35%, 40%, 45%, 50%, 75%, or 90%, as compared to a standard dosage of the splicing modulator, antibody-drug conjugate, or composition.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage of the at least one additional therapy.

In some embodiments, repeated administration of the splicing modulator, antibody-drug conjugate, or composition is concurrent with repeated administration of the at least one additional therapy. In some embodiments, repeated administration of the splicing modulator, antibody-drug conjugate, or composition is sequential or staggered with repeated administration of the at least one additional therapy.

In various embodiments, the present disclosure provides a method of treating a subject having or suspected of having a neoplastic disorder by administering to the subject an effective amount of a splicing modulator, an ADC, or a composition comprising a splicing modulator or ADC; and a checkpoint inhibitor therapy. In some embodiments, the checkpoint inhibitor therapy comprises administering at least one checkpoint inhibitor. In some embodiments, the subject is intolerant, non-responsive, or poorly responsive to the at least one checkpoint inhibitor when administered alone. In some embodiments, a subject may be considered non-responsive or poorly responsive to the at least one checkpoint inhibitor as determined using, e.g., the immune-related Response Criteria (irRC) and/or the immune-related Response Evaluation Criteria in Solid Tumors (irRECIST). See, e.g., Wolchok et al. (2009) Clin Cancer Res. 15(23): 7412-20; Bohnsack et al. "Adaptation of the Immune-Related Response Criteria:irRECIST" (Abstract 4958) ESMO 2014. Exemplary criteria may include those used in the art to define when tumors in cancer patients improve ("respond"), remain the same ("stabilize"), or worsen ("progress") during treatment, when the treatment being evaluated is an immune-oncology drug (e.g., a checkpoint inhibitor). In some embodiments, a subject may be considered intolerant to the at least one checkpoint inhibitor if the subject presents with one or more than one adverse (grade 2+) event identified for the respective checkpoint inhibitor (e.g., ipilimumab). In some embodiments, for example, a subject may be considered intolerant to ipilimumab treatment if the subject presents with one or more adverse events selected from enterocolitis, hepatitis, dermatitis (including toxic epidermal necrolysis), neuropathy, and endocrinopathy (Yervoy® (ipilimumab) FDA Label Supplement, 2018).

In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is targeted with an inhibitory antibody or other similar inhibitory molecule. In some other embodiments, the checkpoint inhibitor is targeted with an agonist antibody or other similar agonist molecule. In some embodiments, the checkpoint inhibitor comprises a cytotoxic T-lymphocyte-associated antigen 4 pathway (CTLA4) inhibitor. In some embodiments, the CTLA4 inhibitor is an anti-CTLA4 antibody. In some embodiments, the anti-CTLA4 antibody is ipilimumab. In some embodiments, the checkpoint inhibitor comprises a programmed death-1 pathway (PD1) inhibitor. In some embodiments, the PD1 inhibitor is an anti-PD1 antibody. In some embodiments, the anti-PD1 antibody is nivolumab. In some embodiments, the PD1 inhibitor is an anti-PDL1 antibody. In some embodiments, the anti-PDL1 antibody is atezolizumab. In some embodiments, the checkpoint inhibitor comprises a CTLA4 inhibitor and a PD1 inhibitor. In some embodiments, the checkpoint inhibitor is targeted at OX40. In some embodiments, the checkpoint inhibitor is targeted at CD40. In some embodiments, the checkpoint inhibitor is targeted at GITR. In some embodiments, the benefit of combination therapy (e.g., the effect on at least one symptom or the risk/rate of disease progression) with a splicing modulator, ADC, or composition and a checkpoint inhibitor (e.g., a CTLA4-, PD1/PDL1-, OX40-, CD40-, and/or GITR-targeted antibody or molecule) is additive. In some embodiments, the benefit of combination therapy with a splicing modulator, ADC, or composition and a checkpoint inhibitor (e.g., a CTLA4-, PD1/PDL1, OX40-, CD40-, and/or GITR-targeted antibody or molecule) is superadditive (i.e., synergistic).

In various embodiments, the present disclosure provides a method of treating a subject having or suspected of having a neoplastic disorder by administering to the subject an effective amount of a splicing modulator, an ADC, or a composition comprising a splicing modulator or ADC; and a cytokine or cytokine analog therapy. In some embodiments, the cytokine or cytokine analog therapy comprises administering at least one cytokine or cytokine analog. In some embodiments, the subject is intolerant, non-responsive, or poorly responsive to the at least one cytokine or cytokine analog when administered alone.

In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a splicing modulator, antibody-drug conjugate, or composition due to induction and presentation of neoantigens.

In some embodiments, the cytokine or cytokine analog comprises IL-2. In some embodiments, IL-2 boosts signals to effector cells promoting their expansion (Rosenberg (2014) J Immunol. 192(12):5451-8). In some embodiments, the cytokine or cytokine analog comprises IL-10. In some embodiments, IL-10 boosts CD8+ T-cell priming and activation (Mumm et al. (2011) Cancer Cell 20(6):781-96). In some embodiments, the cytokine or cytokine analog comprises IL-12. In some embodiments, IL-12 links the innate and adaptive immune responses to boost antigen-specific priming and targeting (Tugues et al. (2015) Cell Death Differ. 22(2):237-46). In some embodiments, the cytokine or cytokine analog comprises IL-15. In some embodiments, IL-15 boosts T-effector (CD8) cell priming and/or activation. In some embodiments, the cytokine or cytokine analog comprises IFNγ. In some embodiments, IFNγ supplements T-effector cell secretion of IFNγ. In some embodiments, the cytokine or cytokine analog comprises TNFα. In some embodiments, TNFα supplements T-effector cell secretion of TNFα.

In some embodiments, an initial dose of a splicing modulator, ADC, or composition is administered to a subject to trigger aberrant splicing and production of neoantigen peptides. After a period to allow for protein production and antigen presentation, in some embodiments, the subject is then administered an initial dose of a cytokine or cytokine analog to boost and/or enhance effector T-cell priming and expansion. In some embodiments, the wait period between doses of splicing modulator, ADC, or composition and cytokine or cytokine analog is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of a splicing modulator, ADC, or composition and a cytokine or cytokine analog may be additive or superadditive.

In some other embodiments, an initial dose of a cytokine or cytokine analog is administered to a subject to boost and/or enhance effector T-cell priming and expansion. After a wait period, in some embodiments, the subject is then administered an initial dose of a splicing modulator, ADC, or composition to trigger aberrant splicing and production of neoantigen peptides. In some embodiments, the wait period between doses of cytokine or cytokine analog and splicing modulator, ADC, or composition is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of a cytokine or cytokine analog and a splicing modulator, ADC, or composition may be additive or superadditive.

In some embodiments, after a period to allow for T-cell priming and expansion, the subject is then administered a second or subsequent dose of the splicing modulator, ADC, or composition to trigger re-presentation of neoantigen peptides. In some embodiments, the wait period between an initial dose of a cytokine or cytokine analog and a second or subsequent dose of a splicing modulator, ADC, or composition is about 2, about 3, about 4, or about 5 weeks. In some embodiments, the wait period is about 3 weeks. In some embodiments, subsequent doses of the cytokine or cytokine analog may be administered, e.g., interspersed between subsequent doses of the splicing modulator, ADC, or composition. Following a second or subsequent dose of the splicing modulator, ADC, or composition, in some embodiments, the immune system may engage with the neoantigen-presenting tumor cells and/or elicit tumor cell killing. In some embodiments, dosing of the splicing modulator, ADC, or composition following this exemplary initial treatment regimen can be pulsatile, i.e., the splicing modulator, ADC, or composition may be dosed at prolonged intervals (e.g., about every 4 weeks, about every 5 weeks, about every 6 weeks) to allow for antigen presentation, T-cell engagement and/or tumor cell killing, and/or recovery of the memory T-cell population.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

Combination of Splicing Modulator/ADC and Neoantigen Vaccine:

In various embodiments, a patient having a cancer as described herein can be treated with a combination of a splicing modulator, ADC, or composition and a neoantigen vaccine. Without being bound by theory, vaccines, used alone or in combination with immune checkpoint inhibitor (ICI) molecules, have shown promise in early trials (Ott et al. (2017) Nature 547(7662):217-21; Sahin et al. (2017) Nature 547(7662):222-6), but generally require sequencing of patient tumor mutations (Ott et al. (2017) Nature 547 (7662):217-21; Aldous and Dong (2018) Bioorg. Med. Chem. 26(10):2842-9). As such, vaccines are often dependent on sufficient numbers of non-synonymous mutations that are antigenic. In general, tumors with very low mutation burden provide few candidate antigens, and those with rapid growth provide limited time to identify and produce patient-specific vaccines.

To date, attempts to develop vaccines that would be broadly immunogenic across a large percentage of patients have focused on proteins that are either frequently mutated, ectopically overexpressed, or amplified, and/or that exist as "self" proteins within the organism. In addition, these proteins are often expressed in immunologically restricted tissues (e.g., neuronal markers expressed in neuroendocrine tumor types), while others may be normally expressed during embryogenesis (e.g., oncofetal antigens). Thus, utility of vaccines using such proteins as antigens is often limited to specific tumor lineages or subsets where one or more of the antigens are presented. Vaccine utility would also need to be confirmed by sequencing of patient tumor samples, which can be time-consuming.

Moreover, if these antigens exist as "self" proteins, the immune system would likely be primed to recognize these as "self" and thus, not respond. Or, alternatively, if the immune system is able to mount an effector response to these antigens, it may lead to on-target side effects in tissues where the antigen may be expressed. In both of these cases, one of the key challenges is that most antigenic peptides are derived from "passenger" genes (i.e., genes that are mutated or amplified in the course of tumorigenesis, but that do not play a critical role in the continued survival or proliferation of the tumor itself). As such, these genes may be silenced without significant consequence to the tumor progression, and thus would allow a tumor to "escape" an immune response against these antigens. Without wishing to be bound by theory, this mechanism may play a role in tumor evolution, where random mutations that are strongly antigenic are often "selected against" by the tumor during the early stages of tumorigenesis (Dunn et al. (2004) Annu. Rev. Immunol. 22:329-60).

In addition, certain evidence also indicates that chronic antigen presentation and immune stimulation may lead to immune cell anergy and exhaustion (Pardoll (2012) Nat. Rev. Cancer 12(4):252-64). These phenotypes underlie the therapeutic rationale behind current ICI treatments, as ICI has been shown to either repress the exhausted immune cell phenotype (α-PD1/PD-L1) or to facilitate additional immune cell responses (α-CTLA4). Notably, with α-CTLA4 therapy, a certain subset of patients have been reported to exhibit severe immune-related adverse events that may be ascribed to the promotion of T-cell activation and a break of the immune tolerance mechanisms that restrain self-reactive immune responses.

Both of these approaches (i.e., triggering or enhancing de novo immune responses to neoantigens or derepressing the anergy or exhaustion of existing immune responses) are linked to a chronic immune activation. As such, these approaches are sensitive to anergy, editing, and other tumor-mediated mechanisms designed to suppress immune engagement.

In contrast, treatment with a splicing modulator, ADC, or composition disclosed herein may induce an immune response to novel sequences representing neoantigens. In some embodiments, presentation of neoantigens provides the adaptive immune system with more divergent targets with which to engage and activate. In some embodiments, the ability of a splicing modulator, ADC, or composition to acutely induce alternative splicing and the resulting neoantigens may reduce the risk of immune system fatigue due to chronic exposure to mutation-driven neoantigens and/or limit the ability of tumor cells to adapt to evade therapy. In some embodiments, administering a splicing modulator, ADC, or composition in combination with a neoantigen vaccine enhances the immune response to the neoantigens produced by the splicing modulator, ADC, or composition. In some embodiments, the splicing modulator, ADC, or composition is administered before, during, or after vaccination. In some embodiments, the splicing modulator, ADC, or composition and/or vaccine may be administered once or more than once during the course of treatment. In some embodiments, the vaccine is administered once and the splicing modulator, ADC, or composition is administered more than once during the course of treatment. In some embodiments, the vaccine is administered once and then one or more boosters are administered during the course of treatment.

As used herein, the term "neoantigen vaccine" refers to a pooled sample of one or more immunogenic neoantigen peptides or mRNAs, for example at least two, at least three, at least four, at least five, or more neoantigen peptides. The term "vaccine" refers to a composition for generating immunity for the prophylaxis and/or treatment of a disease (e.g., a neoplastic disorder, e.g., a hematological malignancy or solid tumor). Accordingly, vaccines are medicaments which comprise immunogenic agents and are intended to be used in humans or animals for generating specific immune defenses and protective substances after vaccination. A neoantigen vaccine can additionally include a pharmaceutically acceptable carrier, diluent, excipient, and/or adjuvant.

As used herein, the term "immunogenic" refers to any agent or composition that can elicit an immune response, e.g., a T-cell response. The immune response can be antibody- or cell-mediated, or both.

In some embodiments, a patient is given a splicing modulator, ADC, or composition and then given a peptide or mRNA vaccine of known neoantigen to enhance immune response to the neoantigens produced by the splicing modulator, ADC, or composition. In some other embodiments, a patient is given a splicing modulator, ADC, or composition and screened for neoantigens produced by the treatment. Subsequently, one or more of those neoantigens are used to create a personalized vaccine that is given to the patient. In either of these embodiments, the splicing modulator, ADC, or composition and/or peptide or mRNA vaccine may be administered to the patient once or repeatedly.

In various embodiments, a suitable neoantigen for a vaccine can be identified by screening a panel of transcripts with altered splicing and robust expression from one or more tissue samples in a patient (e.g., from a tumor biopsy). In some embodiments, variant protein sequences are identified in the screened sample based on translation across the aberrantly spliced mRNA junction while retaining portions of the protein sequence (up to 12 amino acids) flanking the junction-spanning amino acid changes. In some embodiments, these junction-spanning peptide fragments are scanned for high affinity binding to MHC1 alleles, e.g., using a tool such as NetMHC1 (Nielsen et al. (2003) Protein Sci 12(5):1007-17; Andreatta and Neilsen (2016) Bioinformatics 32(4):511-7). These results allow for filtering of the neopeptides to those that are predicted high affinity binders for a unique patient HLA allele makeup as well as assembly of pools of neopeptides predicted to be broadly binding to HLA alleles that are present with high frequencies in different populations (Maiers et al. (2007) Hum Immunol 68(9):779-88). In various embodiments, the identified neopeptides are then formulated as a vaccine, e.g., by conjugation to a suitable carrier or adjuvant (Ott et al. (2017) Nature 547(7662):217-21), or for delivery as an mRNA (Sahin et al. (2017) Nature 547(7662):222-6).

In some embodiments, the selected neoantigen is based on a screen of an individual patent's tumor response to the splicing modulator, ADC, or composition to identify one or more neoantigens resulting from treatment to use in subsequent vaccination. In other embodiments, a neoantigen is chosen, e.g., based on screening a panel of samples from different patients to identify common neoantigens produced by the splicing modulator, ADC, or composition and then used as a universal vaccine for future patients.

Without being bound by theory, in some embodiments, use of a universal neoantigen vaccine would avoid the need to sequence and analyze the unique mutation status of each patient's tumor because the chosen neoantigens are not dependent on tumor mutation but rather mimic a neoantigen produced by a splicing modulator, ADC, or composition and generally recognized by the body as foreign. In addition, in some embodiments, use of a neoantigen vaccine may be particularly effective since a patient's tumor cells may be more likely to mutate away from producing one or more neoantigens that are dependent on tumor mutation, as compared to those that mimic a neoantigen produced by a splicing modulator, ADC, or composition. This may allow for the formulation of a bulk vaccine that would be broadly immunogenic across a large percentage of patients, expediting the initiation of a treatment regime. Patients may be vaccinated according to the schedules outlined herein and, prior to following completion of the vaccination, could be further treated with a splicing modulator, ADC, or composition, e.g., to induce expression of the neoantigen peptides. In some embodiments, patients may be administered a splicing modulator, ADC, or composition before, at the same time as, or after vaccination. In some embodiments, patients are administered a splicing modulator, ADC, or composition, screened for one or more neoantigens found in a panel of universal neoantigens, and vaccinated with a universal neoantigen vaccine comprising at least one universal neoantigen identified in the subject. In some embodiments, patients may be administered a splicing modulator, ADC, or composition once or more than once after vaccination. Splicing modulator or ADC or composition and/or vaccine may be administered once or more than once during the course of treatment.

In various embodiments, a vaccine may comprise one or more than one neoantigen peptide or mRNA. In various embodiments, a vaccine may comprise one or more than one long neoantigen peptide. Such "long" neoantigen peptides, in various embodiments, undergo efficient internalization, processing, and cross-presentation in professional antigen-presenting cells such as dendritic cells. Similarly, long vaccine peptides have been shown, in other contexts, to induce cytotoxic T-cells in humans (Melief and van der Burg (2008) Nat Rev Cancer 8(5):351-60). In various embodiments, a neoantigen peptide is extended to comprise the neoantigen peptide sequence itself in addition to flanking amino acid sequences. In various embodiments, the extended peptide sequence facilitates the uptake of protein by antigen-presenting cells, e.g., dendritic cells. In various embodiments, the extended peptide sequence enables efficient antigen presentation and T-cell priming in models with different HLA isotypes. In various embodiments, a longer neoantigen peptide and/or extended peptide sequence exhibits increased uptake by antigen-presenting cells (e.g., dendritic cells), increased antigen presentation, and/or increased T-cell priming, as compared to a shorter neoantigen peptide and/or shorter peptide sequence (e.g., a peptide sequence less than about 10 or less than about 5 amino acids in length). In some embodiments, a long neoantigen peptide ranges from about 5 to about 50 amino acids in length. In some embodiments, a long neoantigen peptide ranges from about 10 to about 50 amino acids in length. In some embodiments, a long neoantigen peptide ranges from about 10 to about 35 amino acids in length. In some embodiments, a long neoantigen peptide ranges from about 15 to about 25 amino acids in length. Amino acid sequences of exemplary long neoantigen peptides are set forth in Table 21.

As used herein, a neoantigen peptide or mRNA vaccine encompasses using a fragment of a neoantigen peptide or its encoding mRNA, so long as that fragment retains immunogenic potential.

In some embodiments, a neoantigen vaccine comprises at least one neoantigen peptide. In some embodiments, a neoantigen vaccine comprises at least 2, at least 3, at least 4, at least 5, at least 6, at least 7, at least 8, at least 9, at least 10, at least 12, at least 15, or at least 20 neoantigen peptides. In some embodiments, the neoantigen peptide(s) range from about 5 to about 50 amino acids in length. In some embodiments, the neoantigen peptide(s) range from about 10 to about 50 amino acids in length. In some embodiments, the neoantigen peptide(s) range from about 10 to about 35 amino acids in length. In some embodiments, the neoantigen peptide(s) range from about 15 to about 25 amino acids in length.

In various embodiments, the present disclosure provides a method of treating a subject having or suspected of having a neoplastic disorder by administering to the subject an effective amount of a splicing modulator, an ADC, or a composition comprising a splicing modulator or ADC; and a neoantigen vaccine. A neoantigen vaccine may be, e.g., a peptide or mRNA neoantigen vaccine. In some embodiments, the splicing modulator, ADC, or composition is administered before administration of the neoantigen vaccine. In some embodiments, the splicing modulator, ADC, or composition is administered after administration of the neoantigen vaccine. In some embodiments, the splicing modulator, ADC, or composition is administered concurrently with administration of the neoantigen vaccine. In some embodiments, administration of the splicing modulator, ADC, or composition is repeated at least once after initial administration. In some embodiments, the amount of the splicing modulator, ADC, or composition used for repeated administration is reduced as compared to the amount used for initial administration.

In various embodiments, the present disclosure further provides a combination comprising a splicing modulator, an ADC, or a composition comprising a splicing modulator or ADC; and a neoantigen vaccine (e.g., a universal neoantigen vaccine) for use in treating a subject having or suspected of having a neoplastic disorder. In some embodiments, the neoantigen vaccine is a peptide or mRNA neoantigen vaccine. In some embodiments, the combination further comprises at least one additional therapy. In some embodiments, the at least one additional therapy comprises at least one, at least two, at least three, at least four, or at least five additional therapies.

In various embodiments, the present disclosure further provides a method of treating a subject having or suspected of having a neoplastic disorder by (a) administering to the subject an effective amount of a splicing modulator, an ADC, or a composition comprising a splicing modulator or ADC; (b) detecting one or more neoantigens in the subject after administration of the splicing modulator, ADC, or composition; (c) comparing the one or more neoantigens to a panel of universal neoantigens; and (d) administering to the subject a universal neoantigen vaccine comprising at least one universal neoantigen present in the subject. In some embodiments, the universal neoantigen vaccine is administered alone or in combination with at least one additional therapy. In some embodiments, the at least one additional therapy comprises at least one, at least two, at least three, at least four, or at least five additional therapies.

In some embodiments, the at least one additional therapy comprises repeated administration of the splicing modulator, ADC, or composition. In some embodiments, repeated administration of the splicing modulator, ADC, or composition is initiated before administration of the universal neoantigen vaccine. In some embodiments, repeated of the splicing modulator, ADC, or composition is initiated after administration of the universal neoantigen vaccine. In some embodiments, repeated administration of the splicing modulator, ADC, or composition is initiated concurrently with administration of the universal neoantigen vaccine. In some embodiments, the amount of the splicing modulator, ADC, or composition used for repeated administration is reduced as compared to the amount used for initial administration. In some embodiments, the amount of the splicing modulator, ADC, or composition used for the initial and/or repeated administration is reduced as compared to a standard dosage of the splicing modulator, ADC, or composition when used without a vaccine treatment. In some embodiments, the amount of the splicing modulator, ADC, or composition used for initial and/or repeated administration is reduced by 10%, 15%, 20%, 25%, 30%, 35%, 40%, 45%, 50%, 75%, or 90%, as compared to a standard dosage of the splicing modulator, ADC, or composition.

In some embodiments, the at least one additional therapy comprises administering a checkpoint inhibitor (e.g., any of the exemplary checkpoint inhibitors described herein). In some embodiments, administration of the checkpoint inhibitor is initiated before administration of the universal neoantigen vaccine and/or repeated administration of the splicing modulator, ADC, or composition. In some embodiments, administration of the checkpoint inhibitor is initiated after administration of the universal neoantigen vaccine and/or repeated of the splicing modulator, ADC, or composition. In some embodiments, administration of the checkpoint inhibitor is initiated concurrently with administration of the universal neoantigen vaccine and/or repeated administration of the splicing modulator, ADC, or composition. In some embodiments, administration of the checkpoint inhibitor is repeated at least once after initial administration. In some embodiments, the amount of the checkpoint inhibitor used for repeated administration is reduced as compared to the amount used for initial administration. In some embodiments, the amount of the checkpoint inhibitor used for repeated administration is reduced as compared to a standard dosage of the checkpoint inhibitor. In some embodiments, the amount of the checkpoint inhibitor used for repeated administration is reduced by 10%, 15%, 20%, 25%, 30%, 35%, 40%, 45%, 50%, 75%, or 90%, as compared to a standard dosage of the checkpoint inhibitor. In some embodiments, the subject is intolerant, non-responsive, or poorly responsive to the checkpoint inhibitor when administered alone.

Also provided herein, in various embodiments, are neoantigen vaccines comprising at least one neoantigen peptide or at least one neoantigen mRNA. In some embodiments, a neoantigen vaccine comprises at least one neoantigen peptide. In some other embodiments, a neoantigen vaccine comprises at least one neoantigen mRNA.

Also provided herein, in various embodiments, are kits comprising a splicing modulator, an ADC, or a composition comprising a splicing modulator or ADC; and a neoantigen vaccine (e.g., a universal neoantigen vaccine). In some embodiments, the neoantigen vaccine is a peptide or mRNA neoantigen vaccine. In some embodiments, the kit further comprises one or more additional components, including but not limited to: instructions for use; other agents, e.g., one or more additional therapeutic agents; devices, containers, or other materials for preparing the splicing modulator, ADC, composition, and/or neoantigen vaccine for therapeutic administration; pharmaceutically acceptable carriers; and devices, containers, or other materials for administering the splicing modulator, ADC, composition, and/or neoantigen vaccine to a patient. Instructions for use can include guidance for therapeutic applications including suggested dosages and/or modes of administration, e.g., in a patient having or suspected of having a neoplastic disorder. In various embodiments, the kit further contains instructions for therapeutic use, e.g., use of the splicing modulator, ADC, or composition, and the neoantigen vaccine to treat or prevent a neoplastic disorder in a patient. In various embodiments, the kit further contains at least one additional therapeutic agent (e.g., for administering together with the splicing modulator, ADC, or composition, and the neoantigen vaccine, e.g., a checkpoint inhibitor). In various embodiments, the splicing modulator, ADC, composition, and/or neoantigen vaccine is formulated as a pharmaceutical composition.

In some embodiments of the methods and compositions disclosed herein, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length.

In some embodiments, the at least one neoantigen peptide comprises one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide induced in the subject by administering an effective amount of the splicing modulator, antibody-drug conjugate, or composition. In some embodiments, the at least one neoantigen peptide comprises a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide or mRNA and a pharmaceutically acceptable carrier. In various embodiments, a neoantigen peptide or mRNA can be linked to a suitable carrier to help elicit an immune response. Exemplary carriers for linking to immunogenic agents (e.g., a neoantigen peptide or mRNA) include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1α and β peptides, IL-2, γINF, IL-10, GM-CSF, and chemokines, such as M1P1α and β and RANTES. Immunogenic agents can also be linked to peptides that enhance transport across tissues, as described, e.g., in WO 97/17613 and WO 97/17614. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen peptide or mRNA may be linked to the pharmaceutically acceptable carrier. Immunogenic agents can be linked to carriers by chemical crosslinking. Techniques for linking an immunogenic peptide to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described in Jansen et al. ((1982) Immun Rev. 62:185). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt. In some embodiments, the neoantigen peptide and the pharmaceutically acceptable carrier are covalently attached via a linker.

Neoantigen and other such immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein. In some embodiments, the neoantigen peptide and the pharmaceutically acceptable carrier are expressed as a fusion protein.

In some embodiments, the neoantigen vaccine comprises at least one neoantigen peptide or its encoding mRNA and a pharmaceutically acceptable diluent. In some embodiments, the neoantigen vaccine comprises at least one neoantigen peptide or its encoding mRNA and a pharmaceutically acceptable adjuvant (e.g., an adjuvant as described herein).

In some embodiments of the methods and compositions disclosed herein, the neoantigen vaccine comprises at least one neoantigen mRNA. In some embodiments, the at least one neoantigen mRNA encodes one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen mRNA induced in the subject by administering an effective amount of the splicing modulator, antibody-drug conjugate, or composition. In some embodiments, the at least one neoantigen mRNA encodes a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier. In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant (e.g., an adjuvant as described herein).

In some embodiments, the neoantigen mRNA is encapsulated by an encapsulating agent. In some embodiments, the encapsulating agent protects the neoantigen mRNA from degradation and improves vaccine delivery (McNamara et al. (2015) J Immunol Res. 2015:794528). In some embodiments, the encapsulating agent is a liposome. In some embodiments, the liposome is a cationic liposome such as N-[1-(2,3-dioleoloxy)propyl]-N,N,N-trimethyl ammonium chloride 1 (DOTAP). In some embodiments, the encapsulating agent is a nanoparticle. In some embodiments, the nanoparticle protects the neoantigen mRNA from nuclease degradation and/or enhances cell uptake and/or delivery efficiency. In some embodiments, the nanoparticle may be engineered to be fully degradable. In some embodiments, the nanoparticle is a biodegradable core-shell structured nanoparticle with a pH responsive poly-(b-amino ester) (PBAE) core enveloped by a phospholipid shell (Su et al. (2011) Mol Pharm. 8(3):774-87). In some embodiments, such nanoparticles are particularly efficient in delivering mRNA in vivo and eliciting an anti-tumor immune response.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

As used herein, "adjuvant" refers to a substance that is capable of increasing, amplifying, or modulating an immune response to an accompanying immunogenic agent, e.g., a neoantigen peptide or mRNA. In certain embodiments, a neoantigen of the present disclosure can be administered in combination with adjuvants, i.e., substances that do not themselves cause adaptive immune responses, but amplify or modulate the response to an accompanying neoantigen. A variety of adjuvants can be used in combination with the disclosed neoantigens, in order to elicit an immune response. In some embodiments, the adjuvant(s) are chosen to augment the intrinsic response to the neoantigen without causing conformational changes in the neoantigen that would affect the qualitative form of the response. In some embodiments, the adjuvant(s) are chosen to enhance T-effector (e.g., CD8) cell priming and/or activation.

In certain embodiments, the adjuvant is an aluminum salt (alum), such as aluminum hydroxide, aluminum phosphate, and aluminum sulphate. Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-AI-D-isoglu-L-Ala-dipalmitoxy propylamide (DTP-DPP)), or other bacterial cell wall components. Other adjuvants are oil-in-water emulsions and include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem) containing 2% squalene, 0.2% Tween 80, and one or more bacterial cell wall components from the group consisting of monophosphoryllipid A (MPL), trehalose dimycolate (TDM), and cell wall skeleton (CWS), for example MPL-FCWS (Detox™). In some embodiments, the adjuvant is a saponin, such as Stimulon™ (QS21) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

An adjuvant can be administered with an immunogenic agent (e.g., a neoantigen peptide or mRNA) as a single composition, or can be administered before, concurrent with, or after administration of the immunogenic agent. In some embodiments, the immunogenic agent and adjuvant can be packaged and supplied in the same vial or can be packaged in separate vials and mixed before use. In some embodiments, the immunogenic agent and adjuvant can be packaged with a label, indicating the intended therapeutic application. In some embodiments, if the immunogenic agent and adjuvant are packaged separately, the packaging can include instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al. (1998) Adv Drug Deliv Rev. 32:173-186) alone or optionally in combination with any of alum, QS21, and MPL and all combinations thereof are suitable for human administration.

In various embodiments, the present disclosure further provides methods of screening for and identifying at least one neoantigen. More specifically, in various embodiments, the present disclosure provides a method of identifying at least one neoantigen by (a) contacting a neoplastic cell with an effective amount of a splicing modulator, an ADC, or a composition comprising a splicing modulator or ADC; (b) detecting at least one alternatively-spliced mRNA transcript after contacting the neoplastic cell with the splicing modulator, ADC, or composition; (c) predicting translation of the at least one alternatively-spliced mRNA transcript into at least one peptide; and (d) comparing the at least one peptide to a reference proteome, wherein at least one neoantigen is identified if the at least one peptide does not match any peptides in the reference proteome. In various embodiments, the method further comprises contacting one or more additional neoplastic cells to identify at least one universal neoantigen. In various embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In various other embodiments, the present disclosure provides a method of identifying at least one neoantigen by (a) contacting a neoplastic cell with an effective amount of a splicing modulator, an ADC, or a composition comprising a splicing modulator or ADC; (b) detecting at least one peptide comprising a potential neoantigen sequence after contacting the neoplastic cell with the splicing modulator, ADC, or composition; and (c) comparing the at least one peptide to a reference proteome, wherein at least one neoantigen is identified if the at least one peptide does not match any peptides in the reference proteome. In various embodiments, the method further comprises contacting one or more additional neoplastic cells to identify at least one universal neoantigen. In various embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In some embodiments of the neoantigen identification methods described herein, detecting at least one alternatively-spliced mRNA transcript comprises RNAseq. In some embodiments, predicting translation of the at least one alternatively-spliced mRNA transcript comprises quantifying the change in percent spliced in (dPSI) value for the at least one transcript. In some embodiments, predicting translation of the at least one alternatively-spliced mRNA transcript comprises RiboSeq and/or ribosomal profiling.

In some embodiments of the neoantigen identification methods described herein, the methods further comprise evaluating the at least one peptide for predicted major histocompatibility complex (MHC) binding. In some embodiments, predicted MHC binding is determined by measuring raw affinity predicted binding strength of the at least one peptide. In some embodiments, a raw affinity predicted binding strength of about 500 nM or higher indicates MHC binding. In some embodiments, predicted MHC binding is determined by identifying a distribution of predicted binding strengths for a series of random peptides; and comparing predicted binding strength of the at least one peptide to the distribution. In some embodiments, a predicted binding strength in the top 2.0% of the distribution indicates weak MHC binding. In some embodiments, a predicted binding strength in the top 0.5% of the distribution indicates strong MHC binding.

In some embodiments of the neoantigen identification methods described herein, the neoplastic cell is present in an in vitro cell culture. In some embodiments, the neoplastic cell is obtained from the subject. In some embodiments, the neoplastic cell is present in the subject.

Also provided herein, in various embodiments, are methods of making a neoantigen vaccine by (a) identifying at least one neoantigen (e.g., at least one neoantigen peptide or its encoding mRNA) using any of the exemplary identification methods disclosed herein; and (b) formulating the at least one neoantigen together with a pharmaceutically acceptable carrier, diluent, or adjuvant (e.g., any of the pharmaceutically acceptable carriers, diluents, or adjuvants described herein). In some embodiments, the at least one neoantigen used in the vaccine comprises an amino acid sequence of any one of SEQ ID NOs: 37-65. In some embodiments, the at least one neoantigen used in the vaccine comprises an amino acid sequence of SEQ ID NO: 37. In some embodiments, the at least one neoantigen used in the vaccine comprises an amino acid sequence of SEQ ID NO: 39. In some embodiments, the at least one neoantigen used in the vaccine comprises an amino acid sequence of any one of SEQ ID NOs: 46-49.

In some other embodiments, the at least one neoantigen used in the vaccine comprises an amino acid sequence of any one of SEQ ID NOs: 66-93, or an antigenic portion of any one of SEQ ID NOs: 66-93. In some embodiments, the at least one neoantigen used in the vaccine comprises an amino acid sequence of SEQ ID NO: 66, or an antigenic portion of SEQ ID NO: 66. In some embodiments, the at least one neoantigen used in the vaccine comprises an amino acid sequence of any one of SEQ ID NOs: 74-77, or an antigenic portion of any one of SEQ ID NOs: 74-77. In some embodiments, the at least one neoantigen and/or antigenic portion ranges from about 10 to about 50 amino acids in length. In some embodiments, the at least one neoantigen and/or antigenic portion ranges from about 10 to about 35 amino acids in length. In some embodiments, the at least one neoantigen and/or antigenic portion ranges from about 15 to about 25 amino acids in length. In some embodiments, the at least one neoantigen and/or antigenic portion ranges from about 10 to about 20 amino acids in length. In some embodiments, the at least one neoantigen and/or antigenic portion does not exclusively overlap or consist of the canonical peptide sequence (e.g., any of the exemplary canonical peptide sequences underlined in Table 21).

In some embodiments, the at least one neoantigen used in the vaccine is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

Combination of Splicing Modulator/ADC and Engineered T-Cells (CAR-T):

In various embodiments, a patient having a cancer as described herein can be treated with a combination of a splicing modulator, ADC, or composition and one or more engineered tumor-targeting T-cells (i.e., CAR-T). Thus, in various embodiments, the present disclosure provides a method of treating a subject having or suspected of having a neoplastic disorder by administering to the subject an effective amount of a splicing modulator, an ADC, or a composition comprising a splicing modulator or ADC; and engineered tumor-targeting T-cells (i.e., CAR-T). In various embodiments, a chimeric T-cell receptor can be engineered using antigen recognition sequences that are reactive with an identified neoantigen.

For instance, in various embodiments, in order to target splicing modulator- or ADC-induced changes in the extracellular domains of cell surface proteins, a chimeric antigen-reactive T-cell receptor (CAR) may be engineered by first identifying antibodies that recognize a cell surface-expressed neoantigen protein domain. The antigen recognition sequences of such antibodies can then be fused to a T-cell receptor domain for selective targeting and activation.

In various other embodiments, a strategy integrating the antigen presentation machinery of tumor cells together with splicing modulator- or ADC-derived neoantigens is employed. In some embodiments, cells containing known and frequently represented HLA alleles (e.g., HLA-A*02:01) can be treated with a splicing modulator, ADC, or composition and MHC1-bound neoantigens are identified by ligandomics. In some embodiments, these peptides can be used to prime and/or expand T-cells from healthy donors expressing the same HLA allele. Such T-cells, in some embodiments, can be isolated and the T-cell receptor (TCR) α and β chains sequenced to identify the cognate antigen recognition/variable regions. In some embodiments, a cognate CAR can then be engineered.

In some embodiments, the CAR sequences are cloned into patient-derived T-cell populations and expanded using currently available protocols. In some embodiments, the engineered T-cells are then transfused back into the patient's circulation, following treatment with a splicing modulator, ADC, or composition. After treatment with the splicing modulator, ADC, or composition, in some embodiments, the tumor cells may begin to present antigen. In some embodiments, the engineered T-cell population can engage with and kill antigen presenting tumor cells.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the disclosure in detail, the same will be more clearly understood by reference to the following examples, which are included for purposes of illustration only and are not intended to be limiting.

EXAMPLES

Example 1

Synthesis methods for payloads, linkers, and conjugatable linker-payload (linker-drug, L-D) compounds, having the structures shown in Tables 7-9, are described. Conjugatable linker-payloads were used in the preparation of antibody-drug conjugates (ADCs). Exemplary ADCs are described in Examples 3-5.

1.1 Reagents and Materials

The starting materials used in the following synthesis methods are either commercially available or can be readily prepared by standard methods from known materials. The disclosed conjugatable linker-payloads can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated herein.

Preparative liquid chromatography-mass spectrometry (LC/MS) was conducted using a Waters AutoPurification System and an XTerra MS C18 column (5 μm, 19 mm×100 mm) under acidic mobile phase conditions. Nuclear magnetic resonance (NMR) spectra were recorded at 400 MHz using a Varian instrument (Agilent Technologies). Microwave heating was performed using a Biotage Emrys Liberator or Initiator microwave. Column chromatography was carried out using a Teledyne Isco Combiflash Rf200d. Solvent removal was carried out using either a BQchi rotary evaporator or a Genevac centrifugal evaporator.

Terms/Abbreviations: As used herein, the term "inerted" refers to replacement of the air in a reactor (e.g., a reaction vessel, a flask, a glass reactor) with an essentially moisture-free, inert gas, such as nitrogen or argon. The following abbreviations are used herein: DCM=dichloromethane, DMF=dimethylformamide, HPLC=high performance liquid chromatography, KHMDS=potassium bis(trimethylsilyl) amide, LC/MS=liquid chromatography-mass spectrometry, MeOH=methanol, RT=room temperature, TBSCl=tert-butyldimethylsilyl chloride, THF=tetrahydrofuran, TLC=thin-layer chromatography. Multiplicities are indicated using the following abbreviations: s=singlet, d=doublet, t=triplet, q=quartet, quint=quintet, sxt=sextet, m=multiplet, dd=doublet of doublets, ddd=doublet of doublets of doublets, dt=doublet of triplets, br s=a broad singlet.

LC/MS: Mobile phases=A (0.1% formic acid in $H_2O$) and B (0.1% formic acid in acetonitrile). Gradient=B 5% to 95% in 1.8 min. Column=Waters Acquity BEH 018 column (1.7 μm, 2.1×50 mm).

References: U.S. Pat. Nos. 7,884,128 and 7,816,401 describe exemplary methods of synthesizing pladienolide B and D and are each incorporated herein by reference for such methods. Synthesis of pladienolide B and D may also be performed using the exemplary methods described in Kanada et al. ((2007) Angew Chem Int Ed. 46:4350-5). Kanada et al. and Intl. Pub. No. WO 2003/099813 describe exemplary methods for synthesizing E7107 (D11) (Compound 45 of WO 2003/099813) from Pladienolide 0 (111070 of WO 2003/099813). A corresponding U.S. Pat. No. 7,550,503 to Kotake et al. Each of these references is incorporated herein for the described synthesis methods.

TABLE 7

| Structures of exemplary drug moieties (payloads) Payload Structure/ID (Payload Series) |
|---|
| 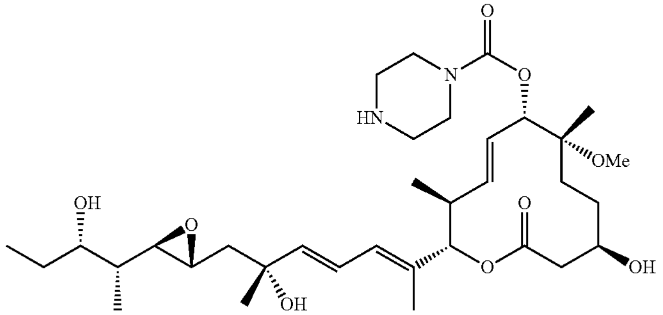 |
| D1 (Pladienolide D) |
| 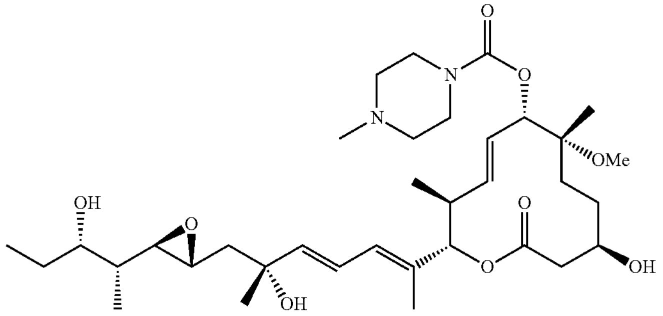 |
| D2 (Pladienolide D) |
| 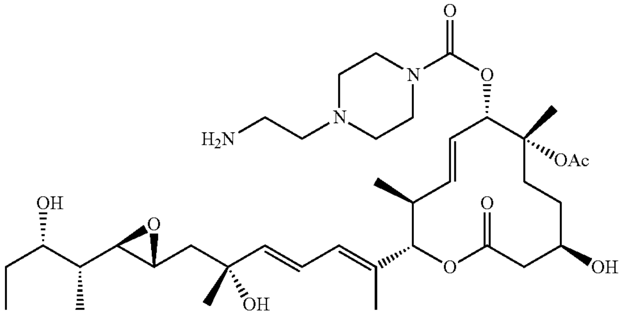 |
| D3 (Pladienolide D) |

TABLE 7-continued
| Structures of exemplary drug moieties (payloads) Payload Structure/ID (Payload Series) |
|---|
| 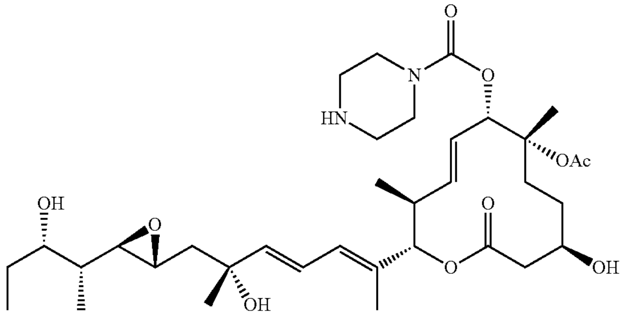 D4 (Pladienolide D) |
| 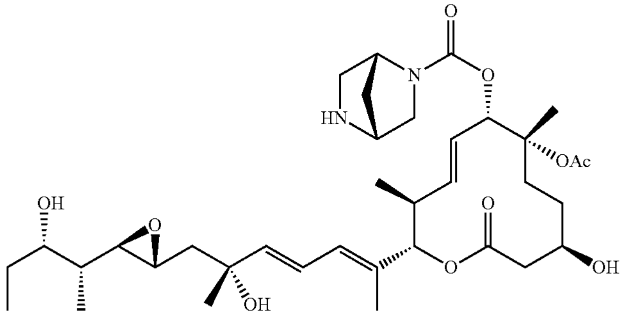 D5 (Pladienolide D) |
| 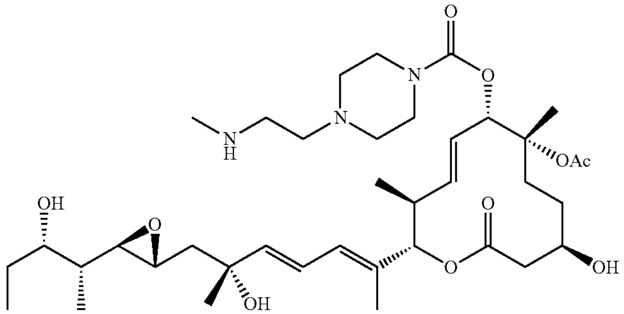 D6 (Pladienolide D) |
| 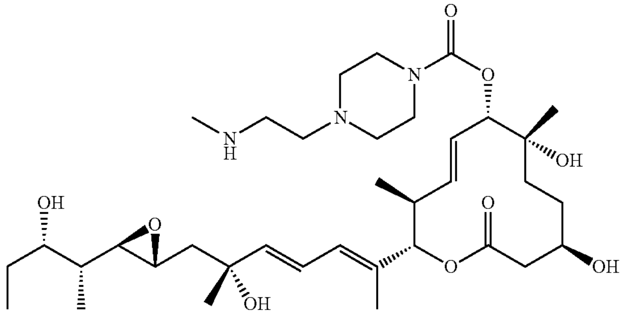 D7 (Pladienolide D) |

TABLE 7-continued
| Structures of exemplary drug moieties (payloads) Payload Structure/ID (Payload Series) |
|---|
| 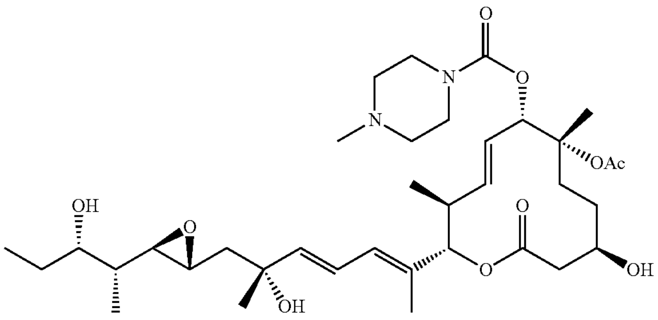 D4′ (Pladienolide D) |
| 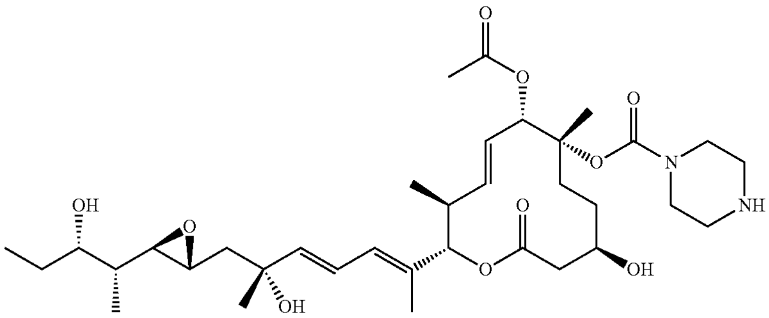 D8 (Pladienolide D) |
| 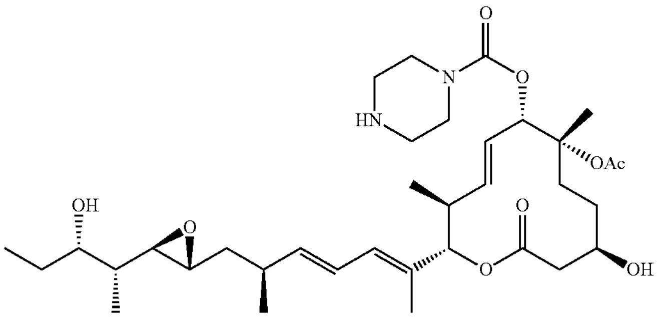 D9 (Pladienolide B) |
| 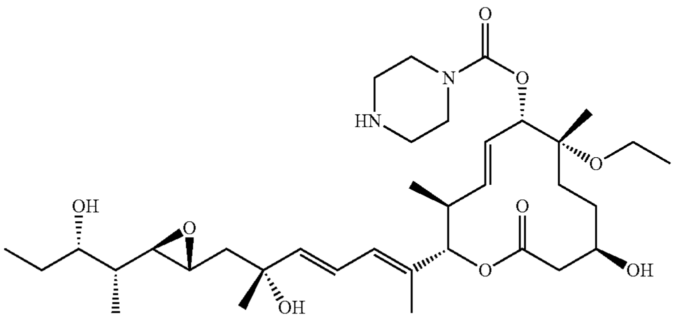 D10 (Pladienolide D) |

TABLE 7-continued
| Structures of exemplary drug moieties (payloads) Payload Structure/ID (Payload Series) |
| --- |
| 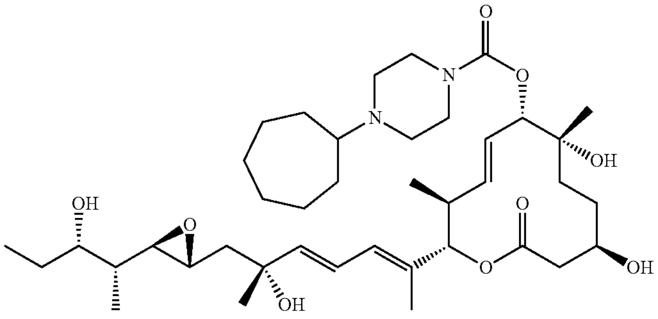 |
| D11 (E7107) (Pladienolide D) |
| 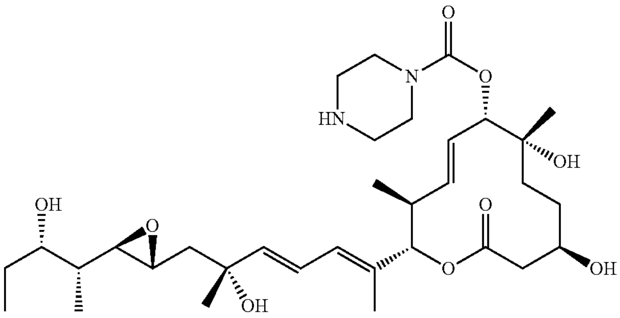 |
| D12 (Pladienolide D) |
| 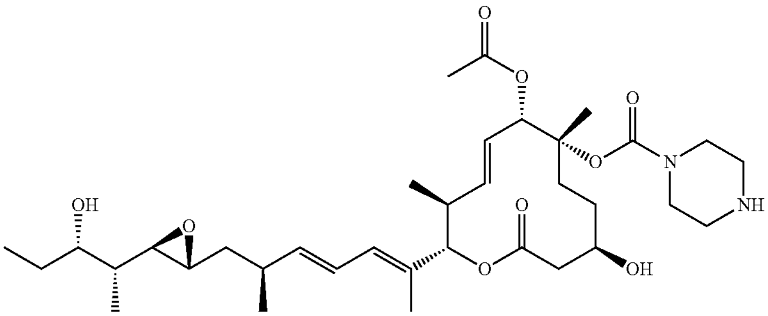 |
| D13 (Pladienolide B) |

TABLE 7-continued
| Structures of exemplary drug moieties (payloads) Payload Structure/ID (Payload Series) |
| --- |
| 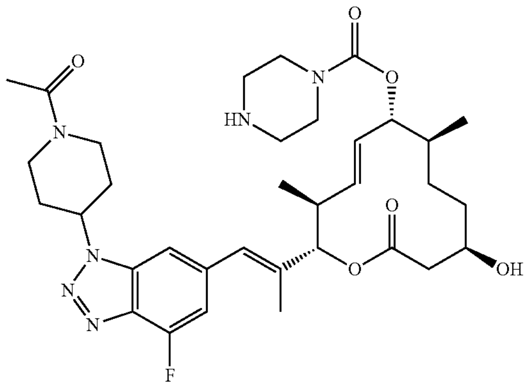 |
| D14 (Aryl Pladienolide) |
| 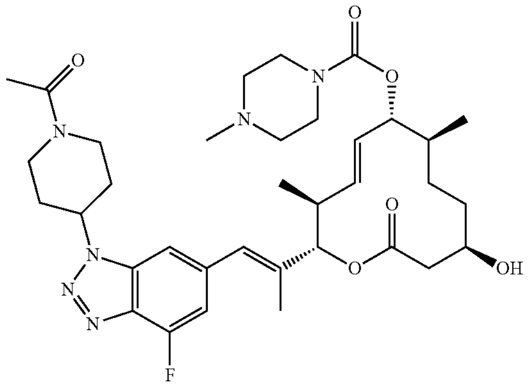 |
| D15 (Aryl Pladienolide) |
| 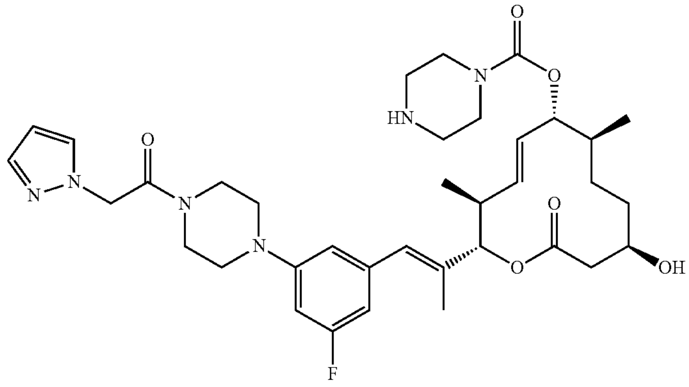 |
| D16 (Aryl Pladienolide) |

TABLE 7-continued
| Structures of exemplary drug moieties (payloads) Payload Structure/ID (Payload Series) |
|---|
| 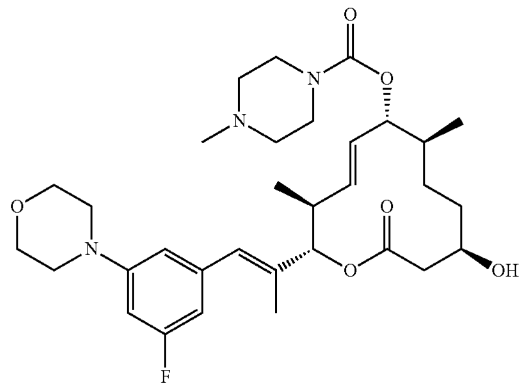 D17 (Aryl Pladienolide) |
| 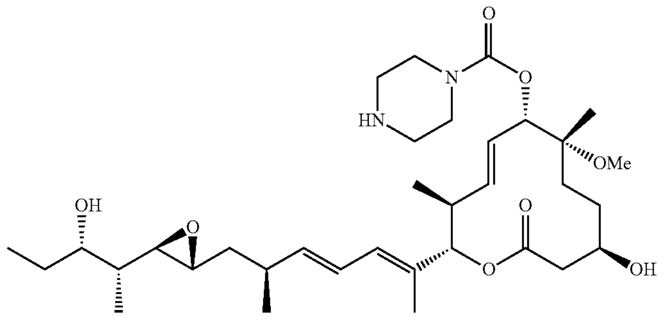 D18 (Pladienolide B) |
| 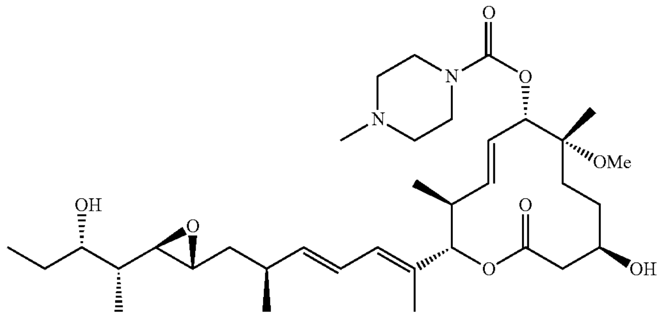 D19 (Pladienolide B) |

TABLE 7-continued
| Structures of exemplary drug moieties (payloads) Payload Structure/ID (Payload Series) |
|---|
| 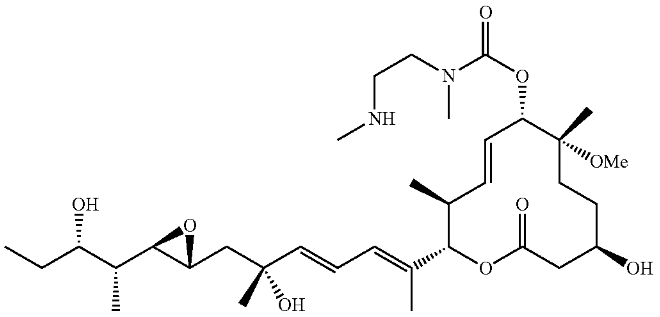 D20 (Pladienolide D) |
| 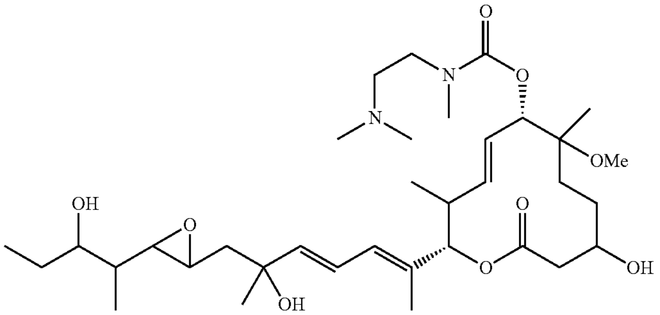 D21 (Pladienolide D) |
| 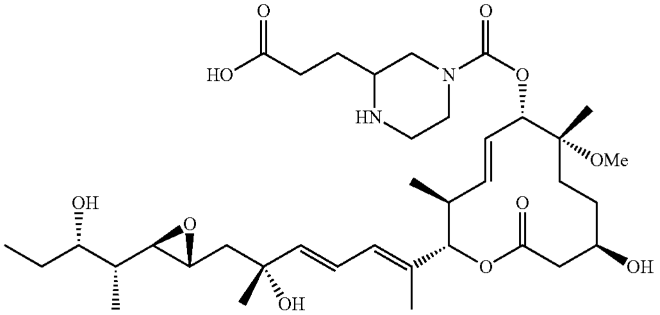 D22 (Pladienolide D Zwitt) |
| 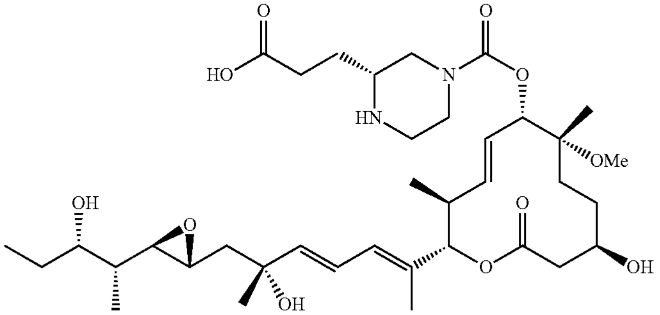 D23 (Pladienolide D Zwitt) |

TABLE 7-continued
| Structures of exemplary drug moieties (payloads) Payload Structure/ID (Payload Series) |
|---|
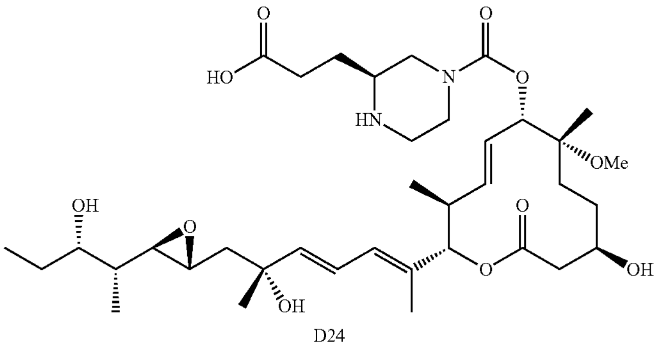
D24
(Pladienolide D Zwitt)
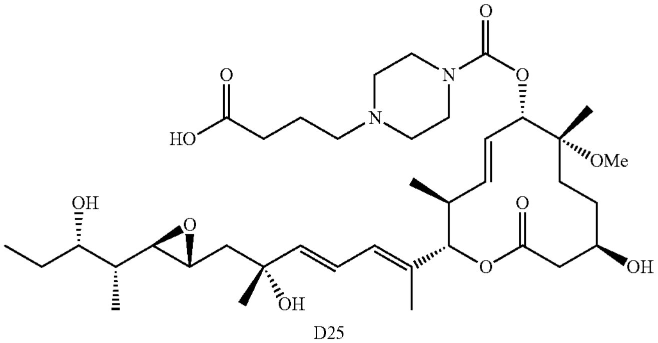
D25
(Pladienolide D Zwitt)
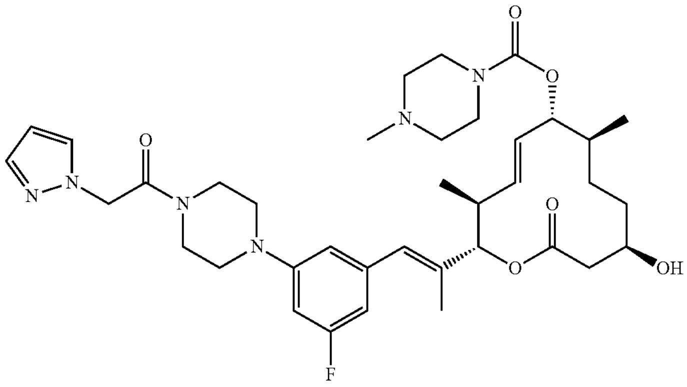
D26
(Aryl Pladienolide)

TABLE 7-continued
| Structures of exemplary drug moieties (payloads) Payload Structure/ID (Payload Series) |
|---|
| 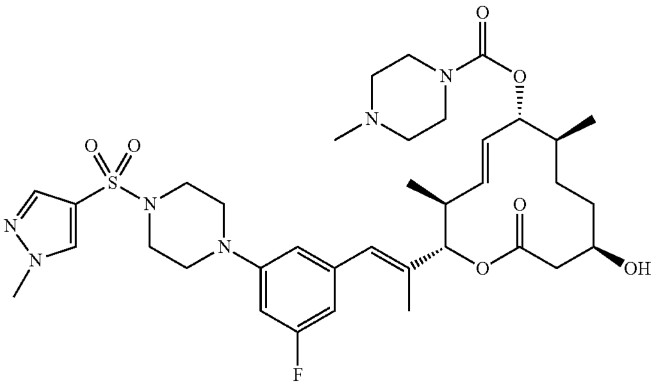 D27 (Aryl Pladienolide) |
| 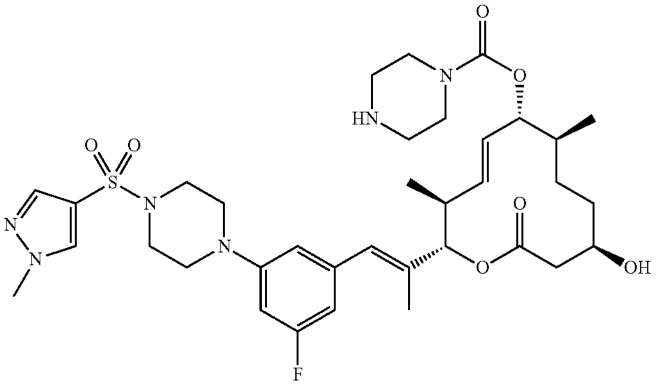 D28 (Aryl Pladienolide) |
| 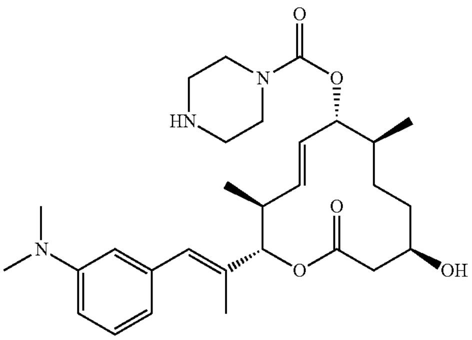 D29 (Aryl Pladienolide) |

TABLE 7-continued
| Structures of exemplary drug moieties (payloads) Payload Structure/ID (Payload Series) |
| --- |
| 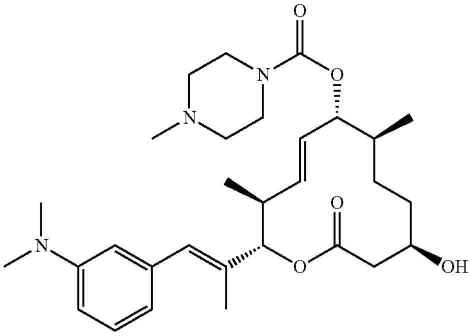 D30 (Aryl Pladienolide) |
| 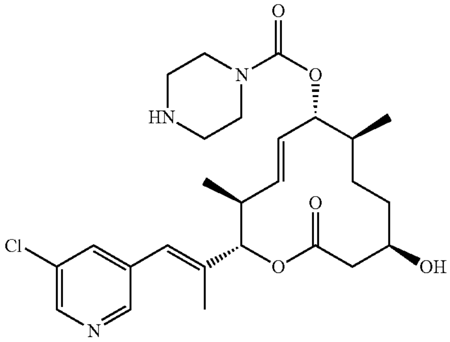 D31 (Aryl Pladienolide) |
| 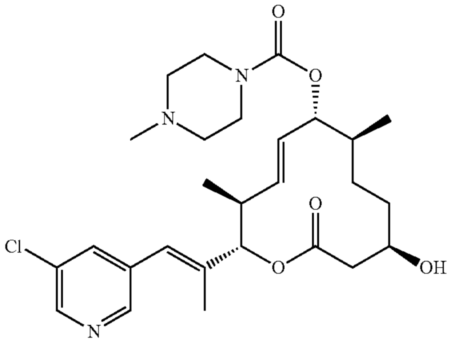 D32 (Aryl Pladienolide) |

TABLE 7-continued
| Structures of exemplary drug moieties (payloads) Payload Structure/ID (Payload Series) |
| --- |
| 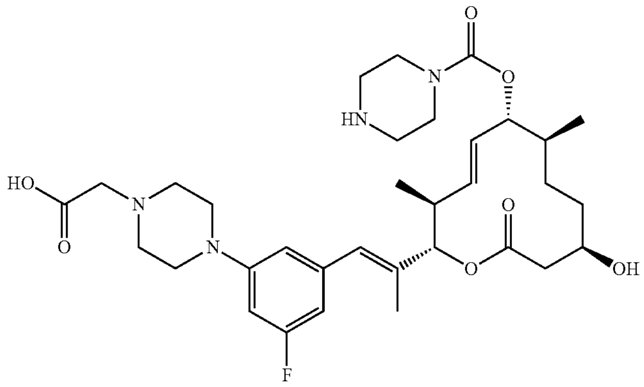 D33 (Aryl Pladienolide Zwitt) |
| 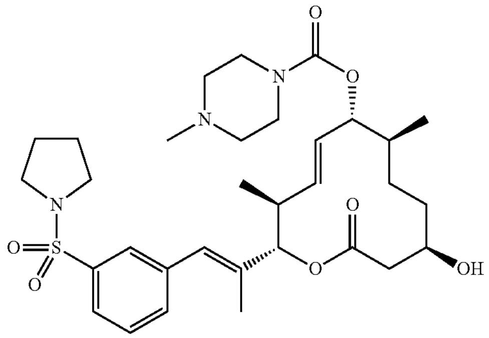 D34 (Aryl Pladienolide Zwitt) |
| 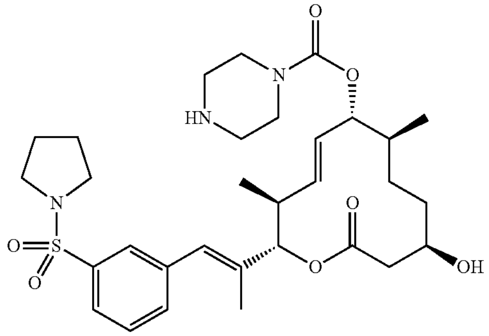 D35 (Aryl Pladienolide Zwitt) |

TABLE 8

| Structures of exemplary linkers<br>Linker Structure/ID<br>(IUPAC Name) |
|---|

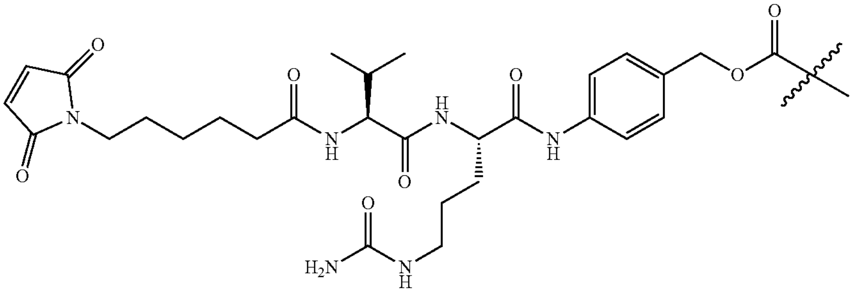 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

ADL1 - "MC-Val-Cit-pABC"
({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methyl formate)

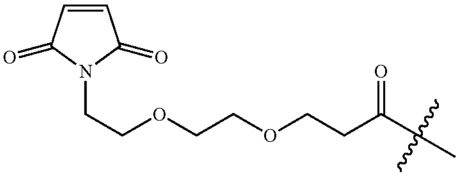 [SMILES: *C(=O)CCOCCOCCN1C(=O)C=CC1=O]

ADL2 - "MC-(PEG)$_2$-CO"
(3-{2-[2-(2,5-dioxo-2,5-dihydro-1H-pyrrol-1-yl)ethoxy]ethoxy}propanal)

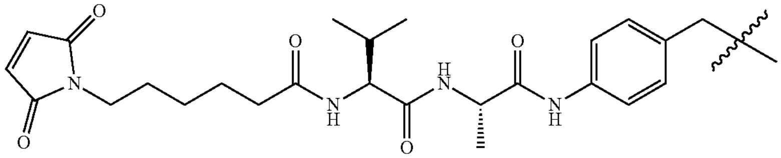 [SMILES: *Cc1ccc(NC(=O)[C@H](C)NC(=O)[C@@H](NC(=O)CCCCCN2C(=O)C=CC2=O)C(C)C)cc1]

ADL5 - "MC-Val-Ala-pAB"
(6-(2,5-dioxo-2,5-dihydro-1H-pyrrol-1-yl)-N-[(1S)-2-methyl-1-{[(1S)-1-[(4-methylphenyl)carbamoyl]ethyl]carbamoyl}propyl]hexanamide)

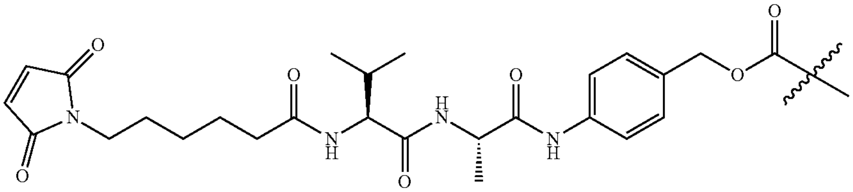 [SMILES: *C(=O)OCc1ccc(NC(=O)[C@H](C)NC(=O)[C@@H](NC(=O)CCCCCN2C(=O)C=CC2=O)C(C)C)cc1]

ADL6 - "MC-Val-Ala-pABC"
({4-[(2S)-2-[(2S)-2-[6-(2,5-dioxo-2,5-dihydro-1H-pyrrol-1-yl)hexanamido]-3-methylbutanamido]propanamido]phenyl}methyl formate)

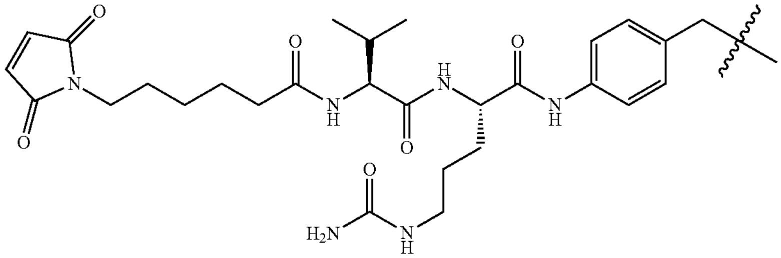 [SMILES: *Cc1ccc(NC(=O)[C@H](CCCNC(N)=O)NC(=O)[C@@H](NC(=O)CCCCCN2C(=O)C=CC2=O)C(C)C)cc1]

ADL7 - "MC-Val-Cit-pAB"
(N-[(1S)-1-{[(1S)-4-(carbamoylamino)-1-[(4-methylphenyl)carbamoyl]butyl]carbamoyl}-2-methylpropyl]-6-(2,5-dioxo-2,5-dihydro-1H-pyrrol-1-yl)hexanamide)

TABLE 8-continued

| Structures of exemplary linkers<br>Linker Structure/ID<br>(IUPAC Name) |
|---|
| 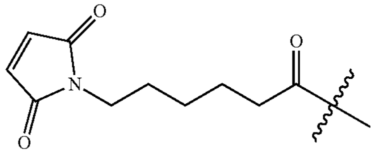 [SMILES: *C(=O)CCCCCN1C(=O)C=CC1=O] |
| ADL10 - "MC"<br>(6-(2,5-dioxo-2,5-dihydro-1H-pyrrol-1-yl)hexanal) |
| 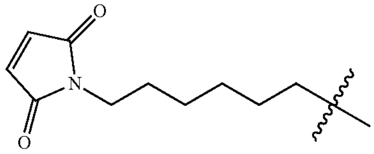 [SMILES: *CCCCCCN1C(=O)C=CC1=O] |
| ADL12 - "Mal-Hex"<br>(1-hexyl-2,5-dihydro-1H-pyrrole-2,5-dione) |
| 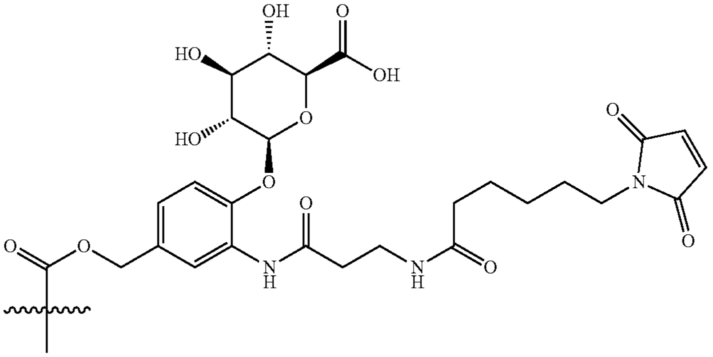 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1] |
| ADL13 - "MC-β-glucuronide"<br>((2S,3S,4S,5R,6S)-6-(2-{3-[6-(2,5-dioxo-2,5-dihydro-1H-pyrrol-1-yl)hexanamido]propanamido}-4-[(formyloxy)methyl]phenoxy)-3,4,5-trihydroxyoxane-2-carboxylic acid) |
| 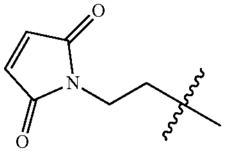 [SMILES: *CCN1C(=O)C=CC1=O] |
| ADL14 - "Mal-Et"<br>(1-ethyl-2,5-dihydro-1H-pyrrole-2,5-dione) |
| 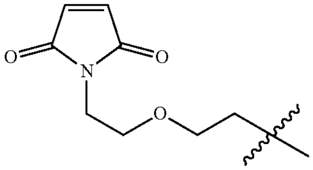 [SMILES: *CCOCCN1C(=O)C=CC1=O] |
| ADL15 - "Mal-Et-O-Et"<br>(1-(2-ethoxyethyl)-2,5-dihydro-1H-pyrrole-2,5-dione) |

TABLE 8-continued
| Structures of exemplary linkers<br>Linker Structure/ID<br>(IUPAC Name) |
|---|
| 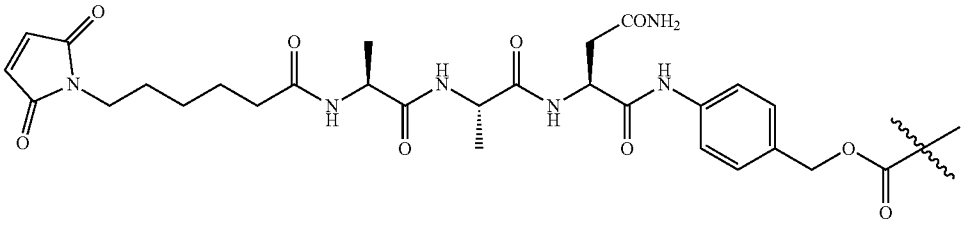 [SMILES: *C(=O)OCc1ccc(NC(=O)[C@H](CC(N)=O)NC(=O)[C@H](C)NC(=O)[C@H](C)NC(=O)CCCCCN2C(=O)C=CC2=O)cc1]<br>ADL21 - "MC-Ala-Ala-Asp-pABC" |
| 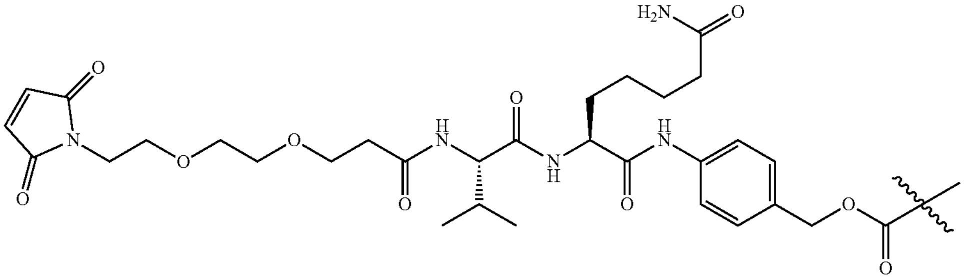 [SMILES: *C(=O)OCc1ccc(NC(=O)[C@H](CCCCC(N)=O)NC(=O)[C@@H](NC(=O)CCOCCOCCN2C(=O)C=CC2=O)C(C)C)cc1]<br>ADL22 - "Mc-PEG2-Val-Cit-pABC" |
| 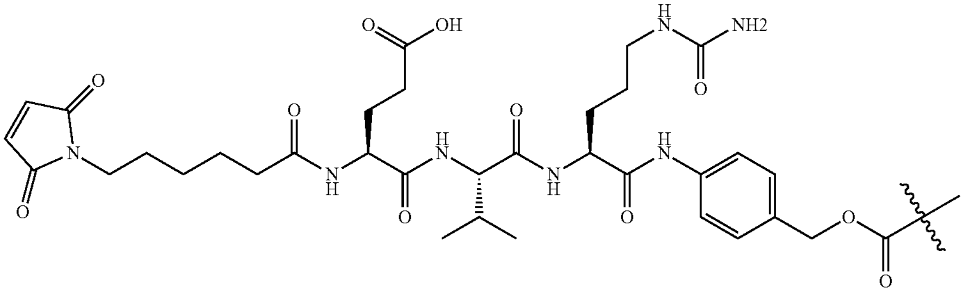 [SMILES: *C(=O)OCc1ccc(NC(=O)[C@H](CCCNC(N)=O)NC(=O)[C@@H](NC(=O)[C@H](CCC(=O)O)NC(=O)CCCCCN2C(=O)C=CC2=O)C(C)C)cc1]<br>ADL23 - "MC-Glu-Val-Cit-pABC" |
TABLE 9
| Structures of exemplary conjugatable linker-payload (L-D) compounds |
|---|
| ADL1-D1<br>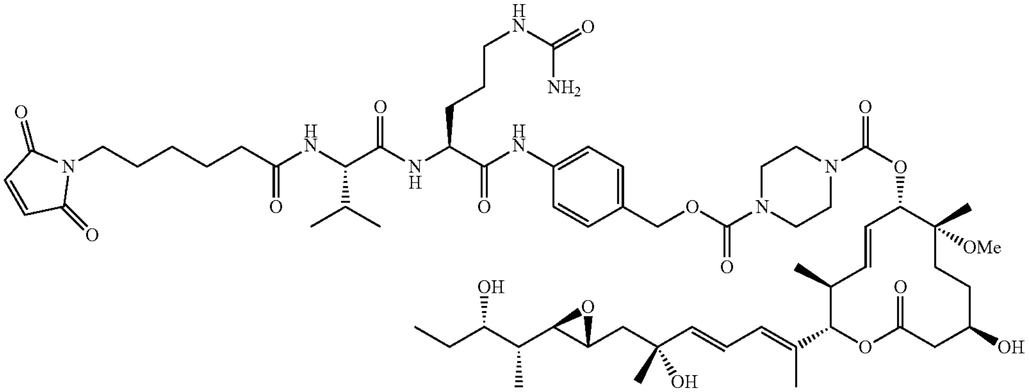 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]<br>Chemical Formula: $C_{63}H_{94}N_8O_{17}$<br>Exact Mass: 1234.67<br>Molecular Weight: 1235.48 |

TABLE 9-continued
Structures of exemplary conjugatable linker-payload (L-D) compounds
ADL6-D1
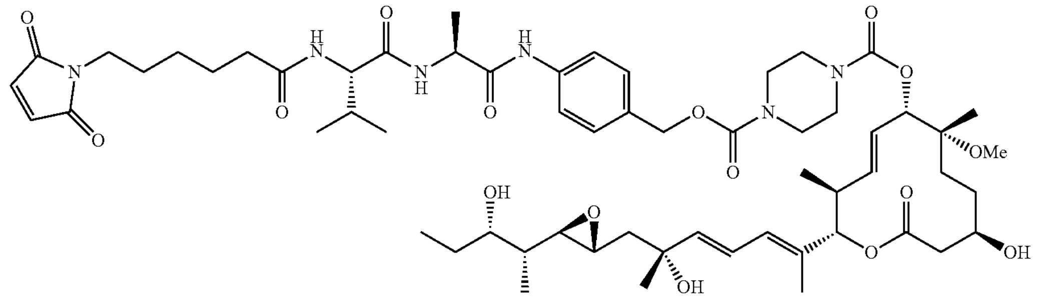 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{60}H_{88}N_6O_{16}$
Exact Mass: 1148.63
Molecular Weight: 1149.39
ADL5-D2
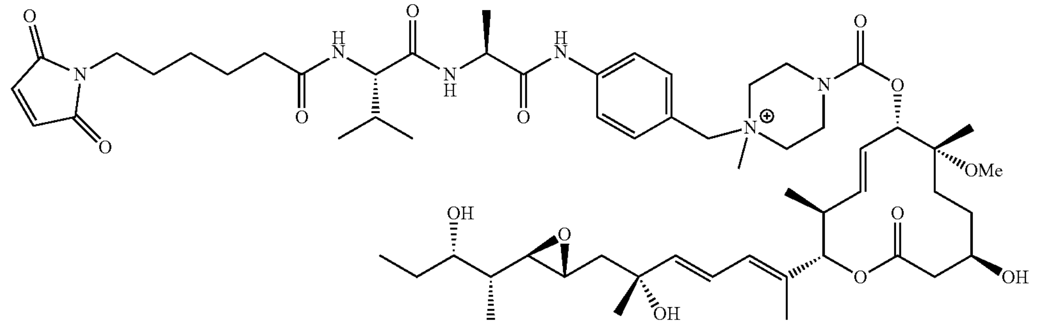 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{60}H_{91}N_6O_{14}^+$
Exact Mass: 1119.66
Molecular Weight: 1120.42
ADL1-D18
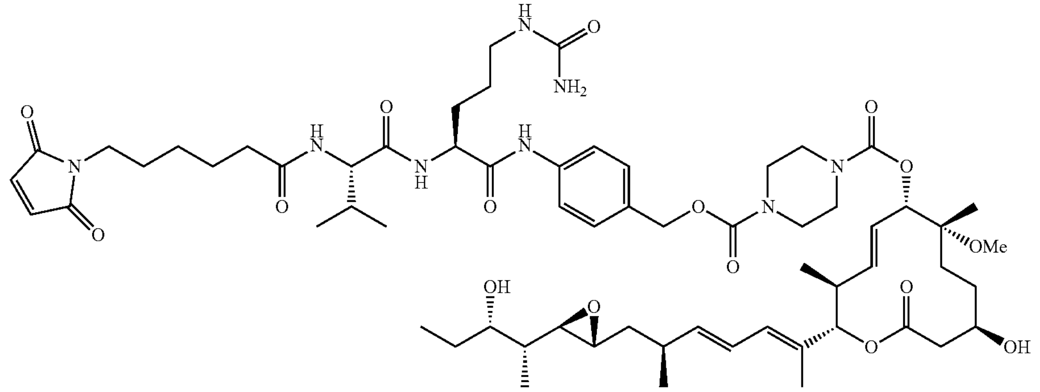 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{63}H_{94}N_8O_{16}$
Exact Mass: 1218.68
Molecular Weight: 1219.49
ADL5-D19
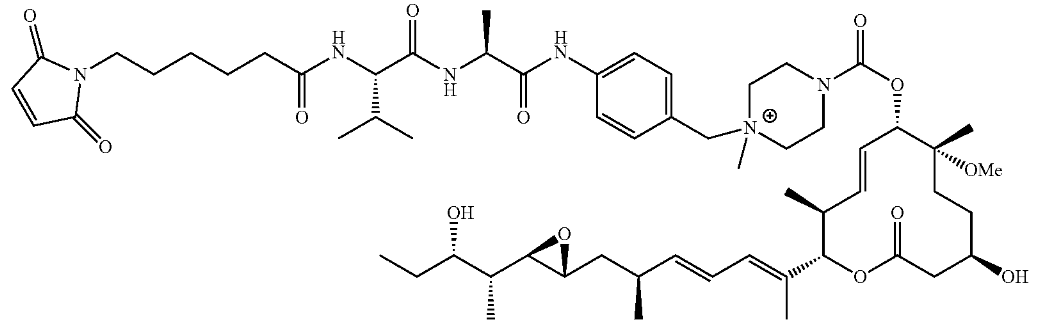 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

TABLE 9-continued
| Structures of exemplary conjugatable linker-payload (L-D) compounds |
| --- |
| Chemical Formula: $C_{60}H_{91}N_6O_{13}^+$<br>Exact Mass: 1103.66<br>Molecular Weight: 1104.42 |
| 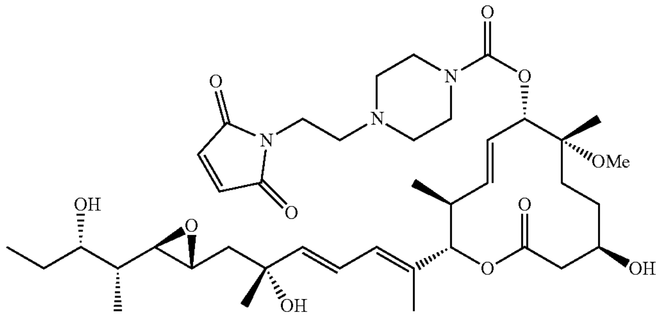 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCN3C(=O)C=CC3=O)CC2)/C=C/[C@@H]1C] ADL14-D1 |
| Chemical Formula: $C_{40}H_{61}N_3O_{11}$<br>Exact Mass: 759.43<br>Molecular Weight: 759.94 |
| 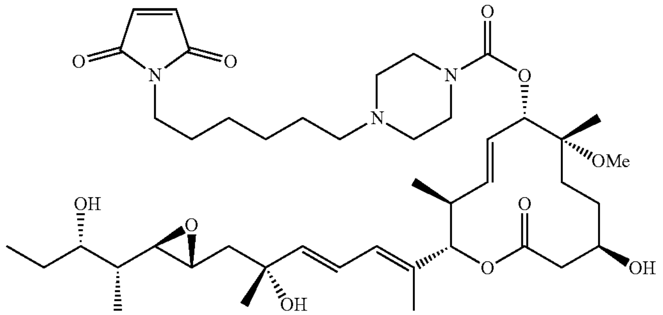 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)CC2)/C=C/[C@@H]1C] ADL12-D1 |
| Chemical Formula: $C_{44}H_{69}N_3O_{11}$<br>Exact Mass: 815.49<br>Molecular Weight: 816.05 |
| ADL15-D1<br>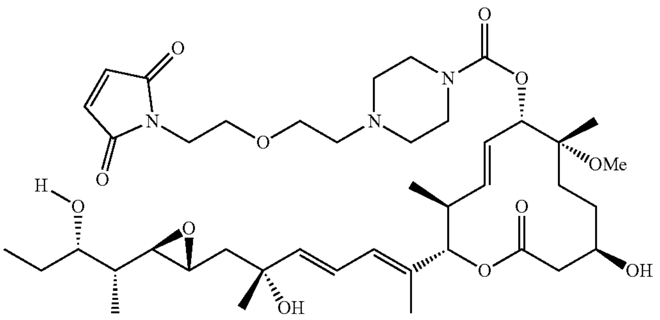 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCOCCN3C(=O)C=CC3=O)CC2)/C=C/[C@@H]1C] |
| Chemical Formula: $C_{42}H_{65}N_3O_{12}$<br>Exact Mass: 803.46<br>Molecular Weight: 803.99 |

TABLE 9-continued
Structures of exemplary conjugatable linker-payload (L-D) compounds
ADL12-D20
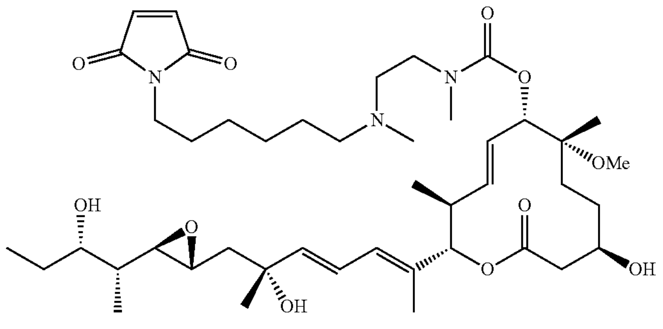 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N(C)CCN(C)CCCCCCN2C(=O)C=CC2=O)/C=C/[C@@H]1C]
Chemical Formula: $C_{44}H_{71}N_3O_{11}$
Exact Mass: 817.51
Molecular Weight: 818.06
ADL10-D1
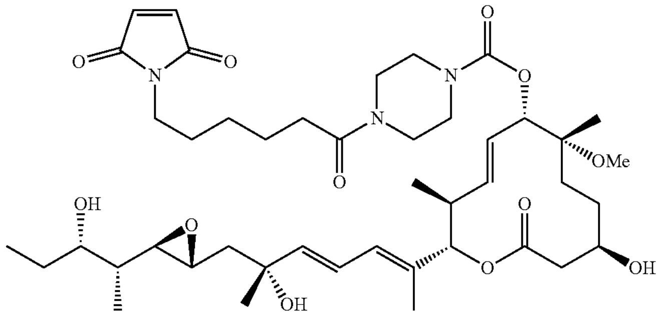 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)CCCCCN3C(=O)C=CC3=O)CC2)/C=C/[C@@H]1C]
Chemical Formula: $C_{44}H_{67}N_3O_{12}$
Exact Mass: 829.47
Molecular Weight: 830.03
ADL12-D2
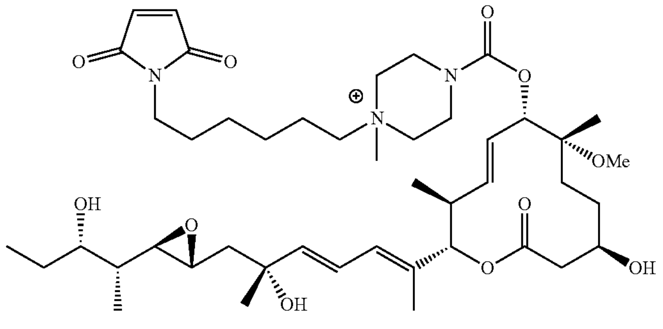
Chemical Formula: $C_{45}H_{72}N_3O_{11}^+$
Exact Mass: 830.52
Molecular Weight: 831.08
ADL15-D2
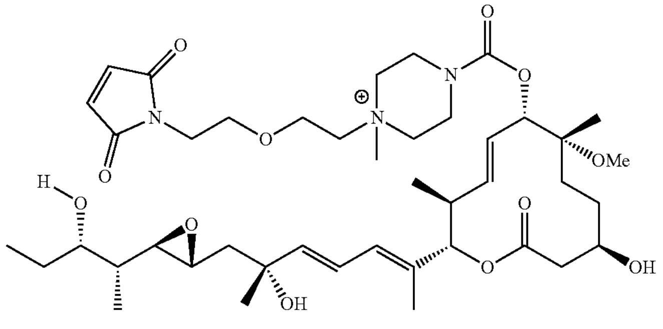 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCOCCN3C(=O)C=CC3=O)CC2)/C=C/[C@@H]1C]
Chemical Formula: $C_{43}H_{68}N_3O_{12}^+$
Exact Mass: 818.48
Molecular Weight: 819.03

TABLE 9-continued
| Structures of exemplary conjugatable linker-payload (L-D) compounds |
| --- |
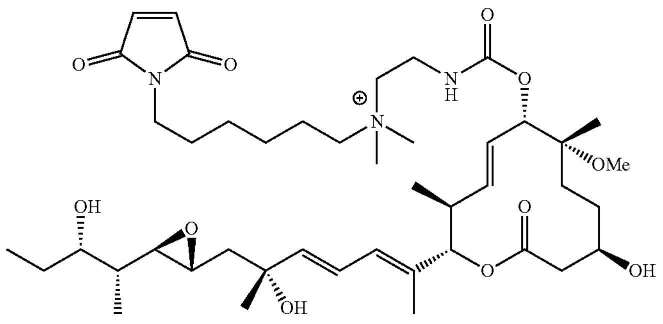 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)NCC[N+](C)(C)CCCCCCN2C(=O)C=CC2=O)/C=C/[C@@H]1C]
ADL12-D21
Chemical Formula: $C_{44}H_{72}N_3O_{11}^+$
Exact Mass: 818.52
Molecular Weight: 819.07
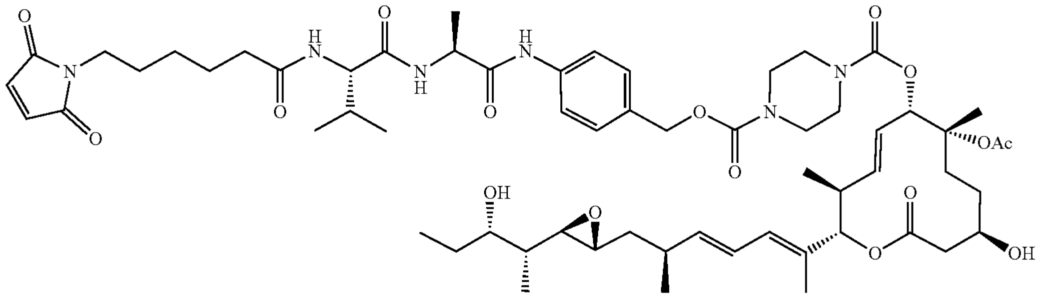 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]
ADL6-D9
Chemical Formula: $C_{61}H_{88}N_6O_{16}$
Exact Mass: 1160.63
Molecular Weight: 1161.40
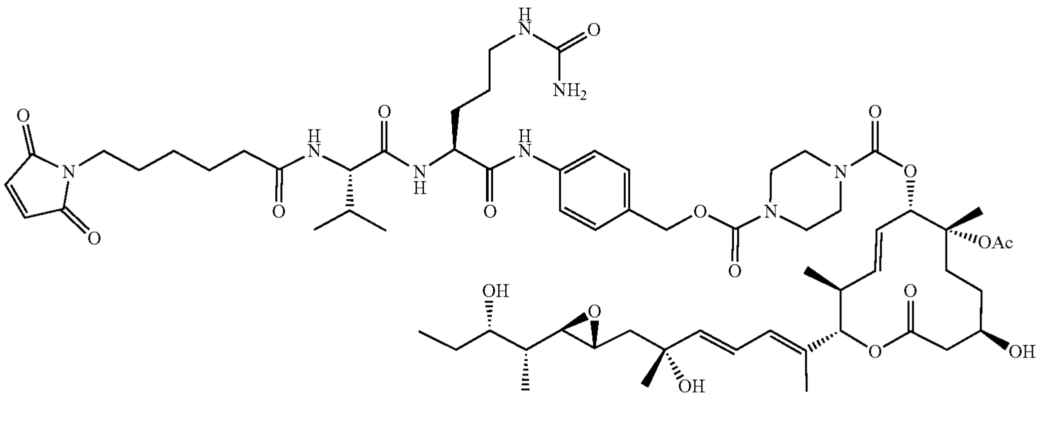 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
ADL1-D4
Chemical Formula: $C_{64}H_{94}N_8O_{18}$
Exact Mass: 1262.67
Molecular Weight: 1263.49

TABLE 9-continued
Structures of exemplary conjugatable linker-payload (L-D) compounds
ADL1-D3
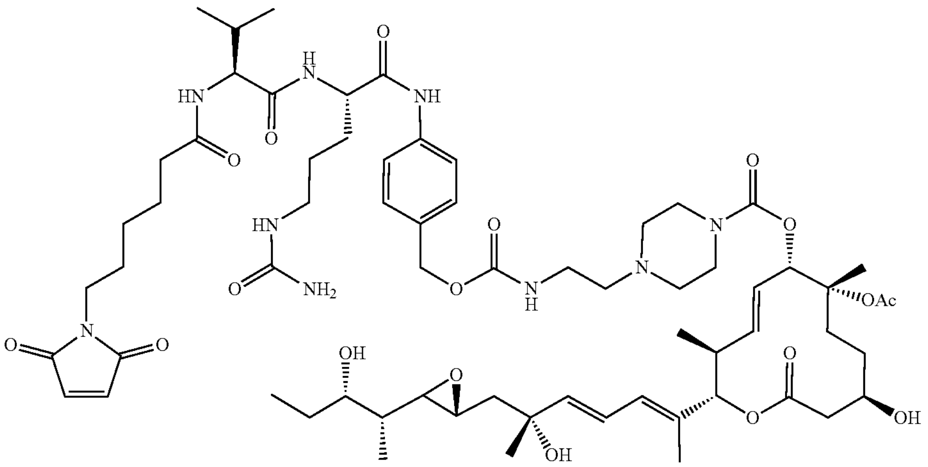
Chemical Formula: $C_{66}H_{99}N_9O_{18}$
Molecular Weight: 1306.56
ADL1-D12
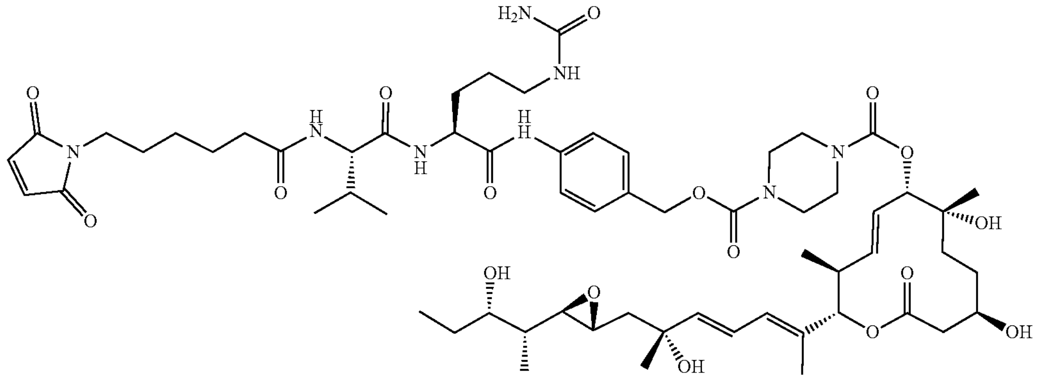
Chemical Formula: $C_{62}H_{92}N_8O_{17}$
Molecular Weight: 1221.46
ADL1-D7
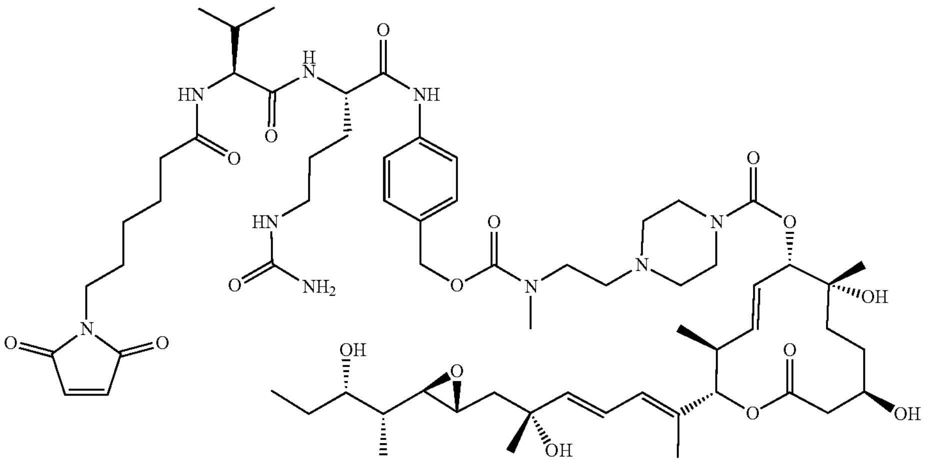 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(CCN(C)C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{65}H_{99}N_9O_{17}$
Molecular Weight: 1278.55

TABLE 9-continued
Structures of exemplary conjugatable linker-payload (L-D) compounds
ADL1-D6
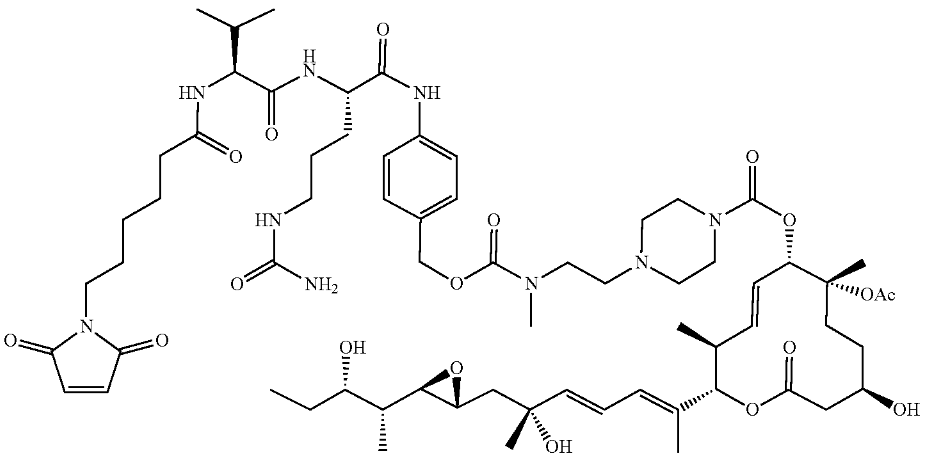 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCN(C)C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{67}H_{101}N_9O_{18}$
Molecular Weight: 1320.59
ADL1-D5
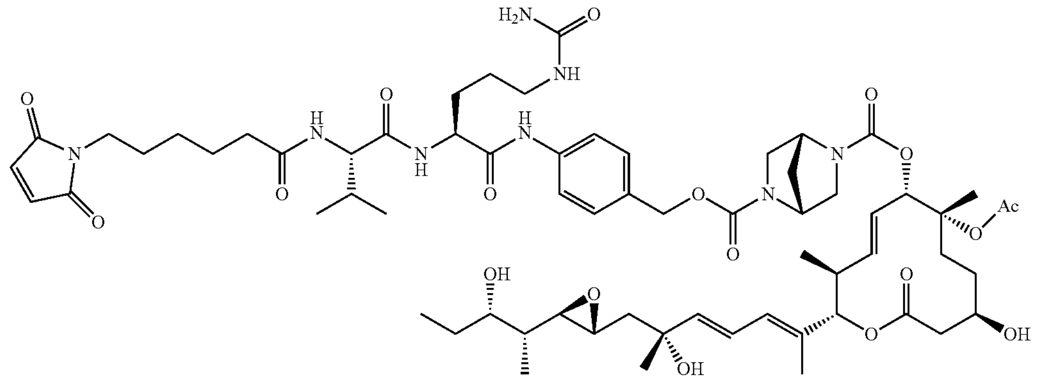 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2C[C@H]3C[C@@H]2CN3C(=O)OCc2ccc(NC(=O)[C@H](CCCNC(N)=O)NC(=O)[C@@H](NC(=O)CCCCCN3C(=O)C=CC3=O)C(C)C)cc2)/C=C/[C@@H]1C]
Chemical Formula: $C_{65}H_{94}N_8O_{18}$
Molecular Weight: 1275.51
ADL22-D4
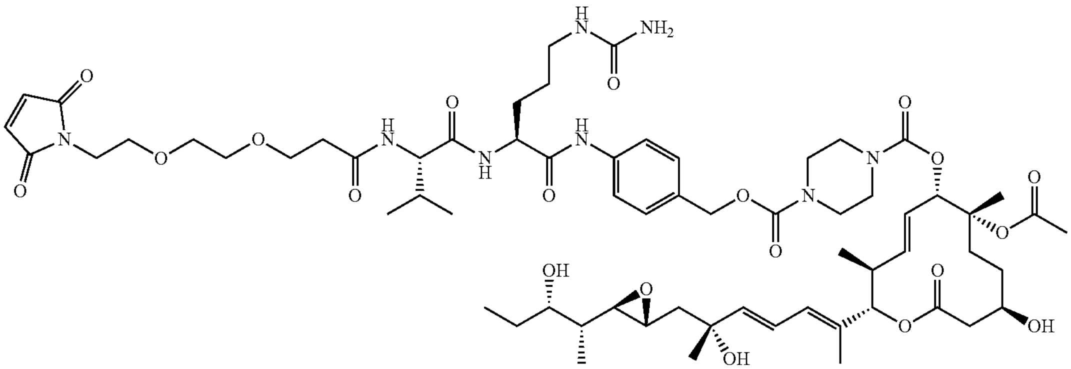 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCOCCOCCN4C(=O)C=CC4=O)C(C)C)cc3)CC2)/C=C/[C@@H]1C]
Chemical Formula: $C_{65}H_{96}N_8O_{20}$
Molecular Weight: 1309.52

TABLE 9-continued
Structures of exemplary conjugatable linker-payload (L-D) compounds
ADL5-D10
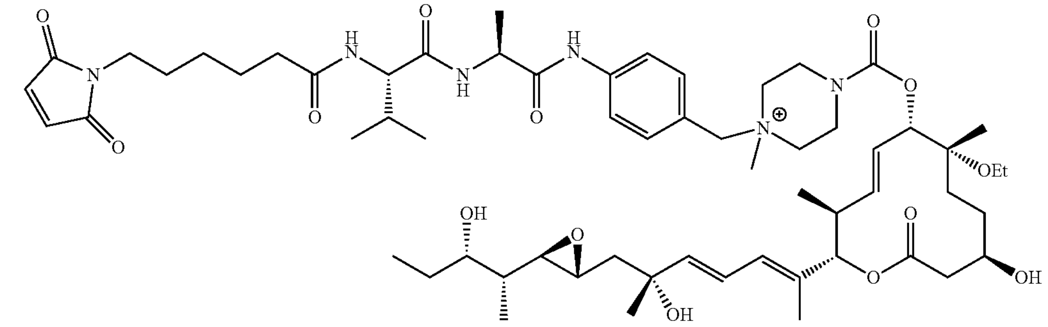 [SMILES: CCO[C@]1(C)CC[C@@H](O)CC(=O)O[C@H](/C(C)=C/C=C/[C@](C)(O)C[C@H]2O[C@@H]2[C@H](C)[C@@H](O)CC)[C@@H](C)/C=C/[C@@H]1OC(=O)N1CC[N+](C)(Cc2ccc(NC(=O)[C@H](C)NC(=O)[C@@H](NC(=O)CCCCCN3C(=O)C=CC3=O)C(C)C)cc2)CC1]
Chemical Formula: $C_{61}H_{93}N_6O_{14}^+$
Exact Mass: 1133.67
Molecular Weight: 1134.44
ADL5-D11
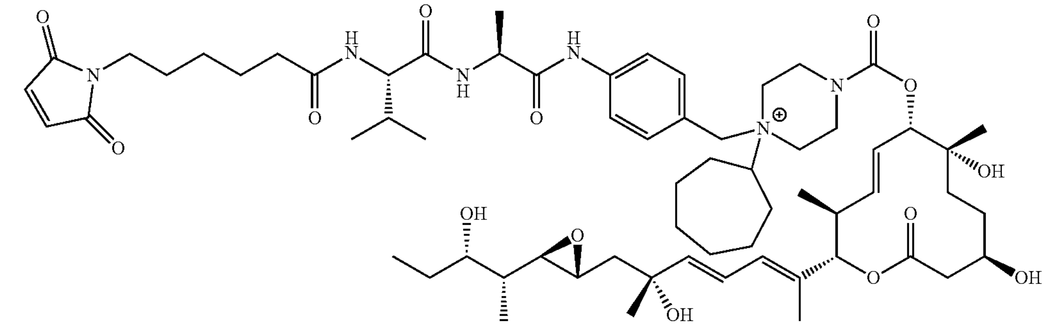 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CC[N+](Cc3ccc(NC(=O)[C@H](C)NC(=O)[C@@H](NC(=O)CCCCCN4C(=O)C=CC4=O)C(C)C)cc3)(C3CCCCCC3)CC2)/C=C/[C@@H]1C]
Chemical Formula: $C_{65}H_{99}N_6O_{14}^+$
Exact Mass: 1187.72
Molecular Weight: 1188.53
ADL1-D13
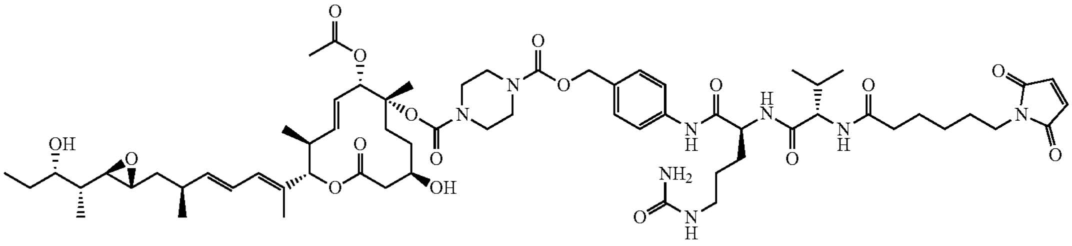 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]
Chemical Formula: $C_{64}H_{94}N_8O_{17}$
Exact Mass: 1246.67
Molecular Weight: 1247.50
ADL1-D8
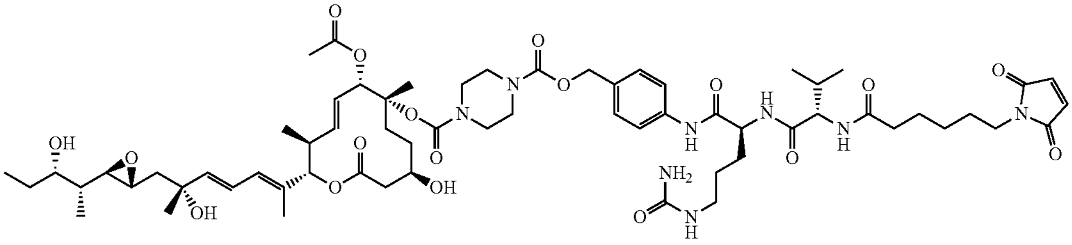 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]
ADL1-110978
Chemical Formula: $C_{64}H_{94}N_8O_{18}$
Exact Mass: 1262.67
Molecular Weight: 1263.49

TABLE 9-continued
| Structures of exemplary conjugatable linker-payload (L-D) compounds |
| --- |
ADL1-D22
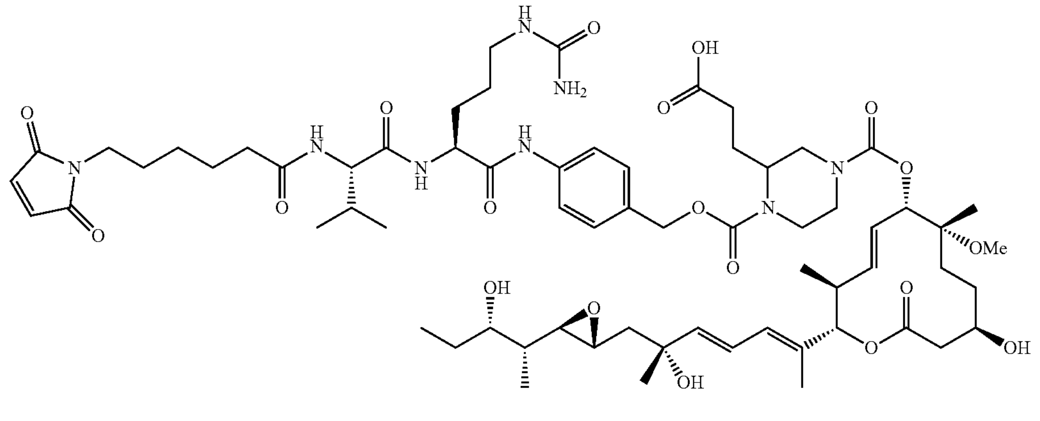 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)C(CCC(=O)O)C2)/C=C/[C@@H]1C]
Chemical Formula: $C_{66}H_{98}N_8O_{19}$
Exact Mass: 1306.69
Molecular Weight: 1307.55
ADL5-D25
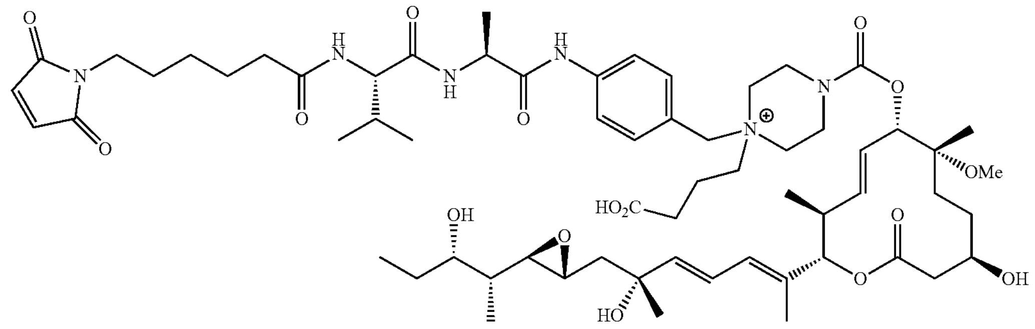 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](CCCC(=O)O)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{63}H_{95}N_6O_{16}^{+}$
Exact Mass: 1191.68
Molecular Weight: 1192.48
ADL12-D22
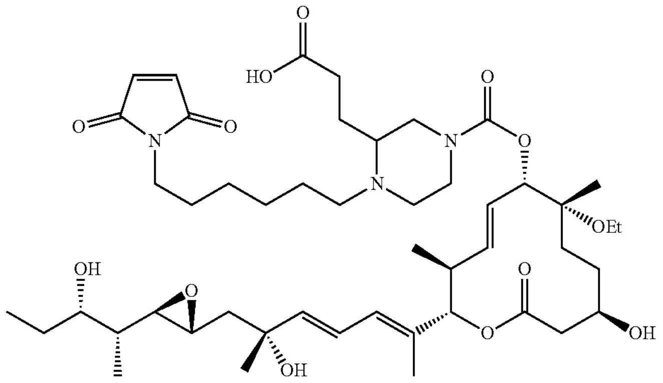 [SMILES: CCO[C@]1(C)CC[C@@H](O)CC(=O)O[C@H](/C(C)=C/C=C/[C@](C)(O)C[C@H]2O[C@@H]2[C@H](C)[C@@H](O)CC)[C@@H](C)/C=C/[C@@H]1OC(=O)N1CCN(CCCCCCN2C(=O)C=CC2=O)C(CCC(=O)O)C1]
Chemical Formula: $C_{47}H_{73}N_3O_{13}$
Exact Mass: 887.51
Molecular Weight: 888.11

TABLE 9-continued
Structures of exemplary conjugatable linker-payload (L-D) compounds
ADL5-D15
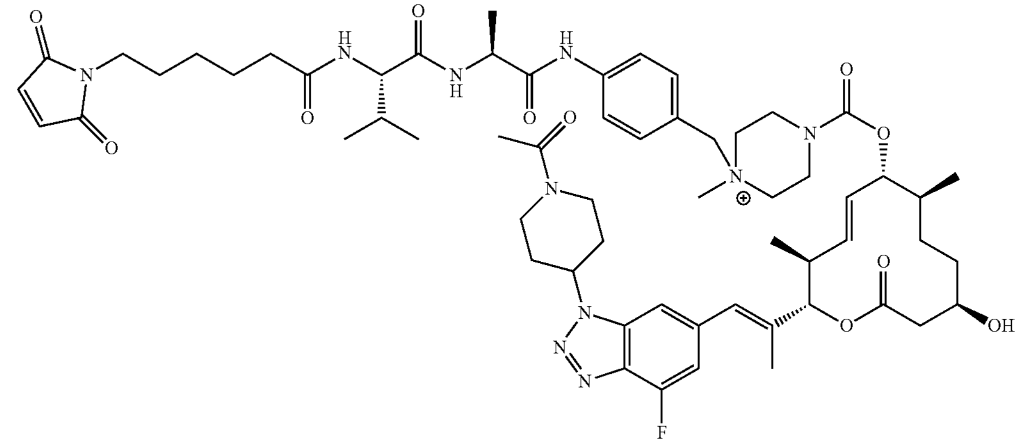 [SMILES: CC(=O)N1CCC(n2nnc3c(F)cc(/C=C(\C)[C@H]4OC(=O)C[C@H](O)CC[C@H](C)[C@@H](OC(=O)N5CC[N+](C)(Cc6ccc(NC(=O)[C@H](C)NC(=O)[C@@H](NC(=O)CCCCCN7C(=O)C=CC7=O)C(C)C)cc6)CC5)/C=C/[C@@H]4C)cc32)CC1]
Chemical Formula: $C_{60}H_{82}FN_{10}O_{11}^{+}$
Exact Mass: 1137.61
Molecular Weight: 1138.37
ADL1-D14
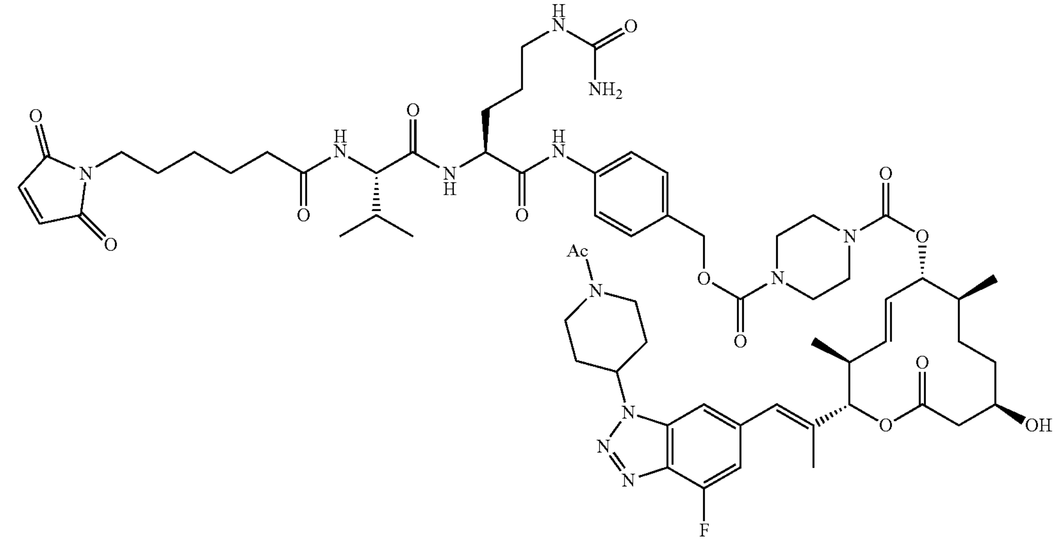 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]
Chemical Formula: $C_{63}H_{85}FN_{12}O_{14}$
Exact Mass: 1252.63
Molecular Weight: 1253.44
ADL5-D26
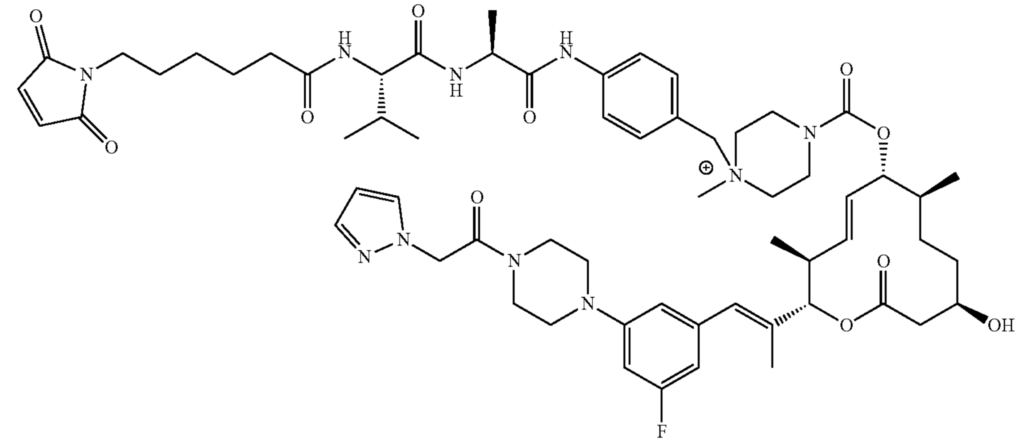

TABLE 9-continued
Structures of exemplary conjugatable linker-payload (L-D) compounds
Chemical Formula: $C_{62}H_{84}FN_{10}O_{11}^{+}$
Exact Mass: 1163.63
Molecular Weight: 1164.41
ADL1-D16
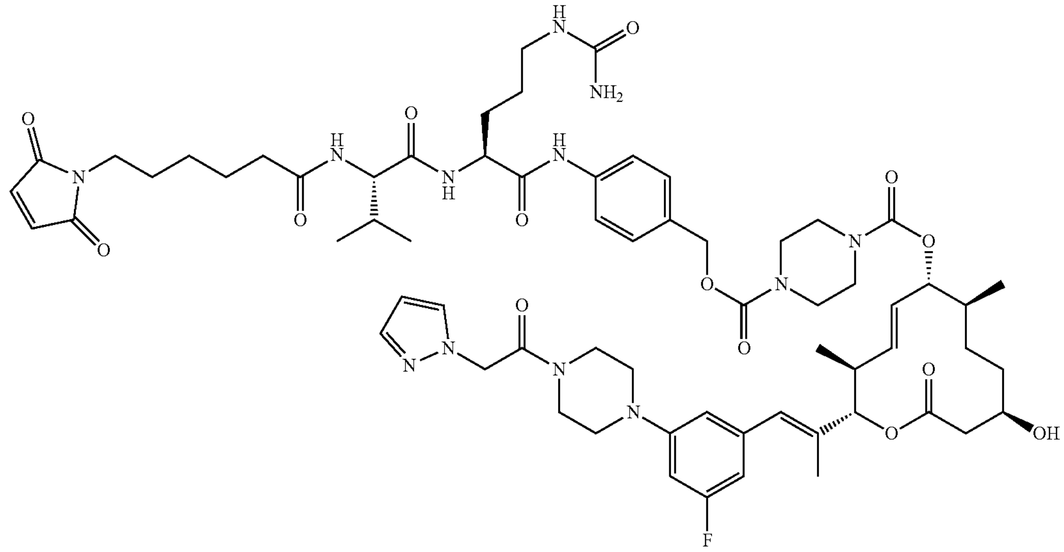 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{65}H_{87}FN_{12}O_{14}$
Exact Mass: 1278.64
Molecular Weight: 1279.48
ADL5-D17
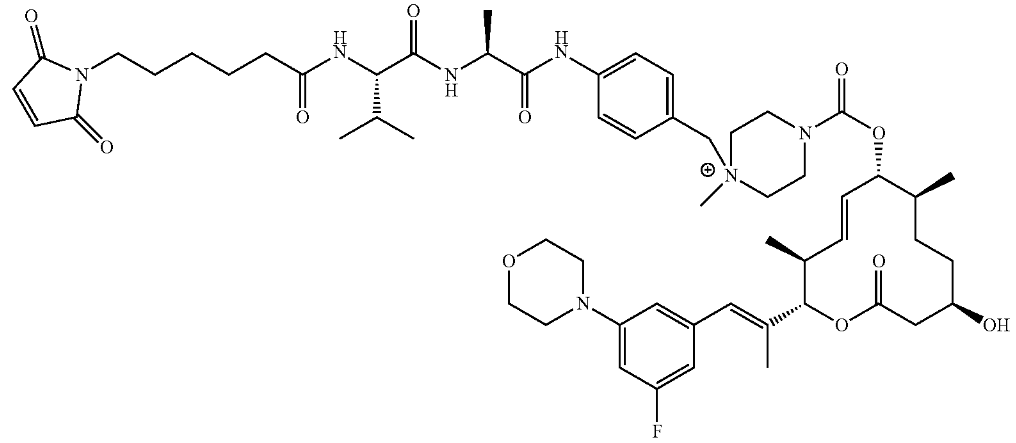 [SMILES: C/C(=C\c1cc(F)cc(N2CCOCC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{57}H_{79}FN_{7}O_{11}^{+}$
Exact Mass: 1056.58
Molecular Weight: 1057.29

TABLE 9-continued
Structures of exemplary conjugatable linker-payload (L-D) compounds
ADL1-D33
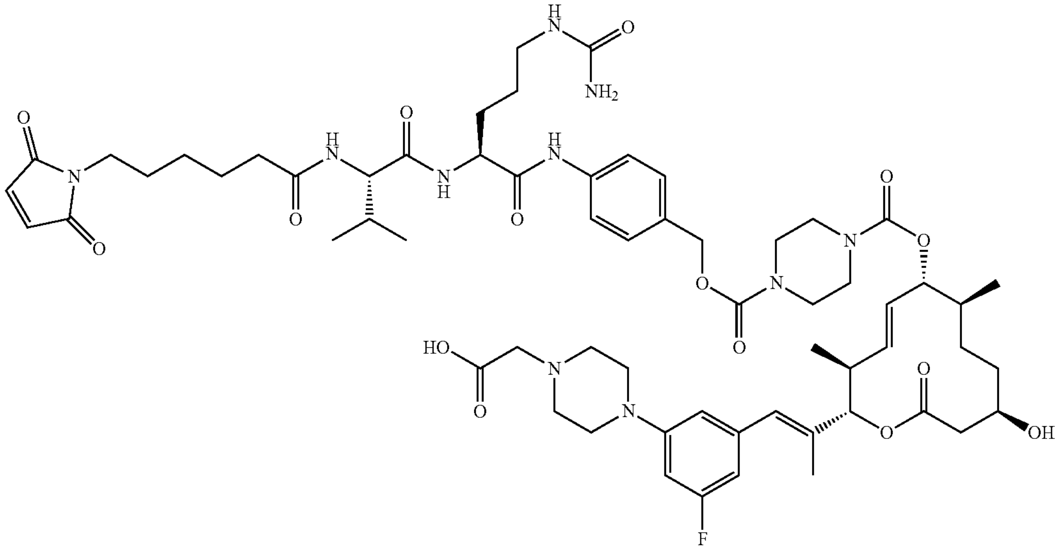 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{62}H_{85}FN_{10}O_{15}$
Exact Mass: 1228.62
Molecular Weight: 1229.42
ADL1-D28
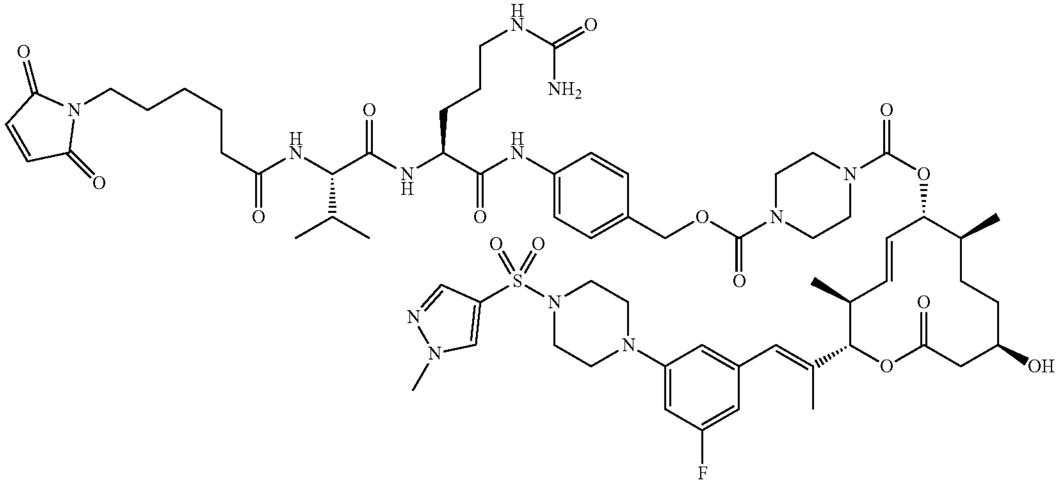 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{64}H_{87}FN_{12}O_{15}S$
Molecular Weight: 1315.53
ADL1-D31
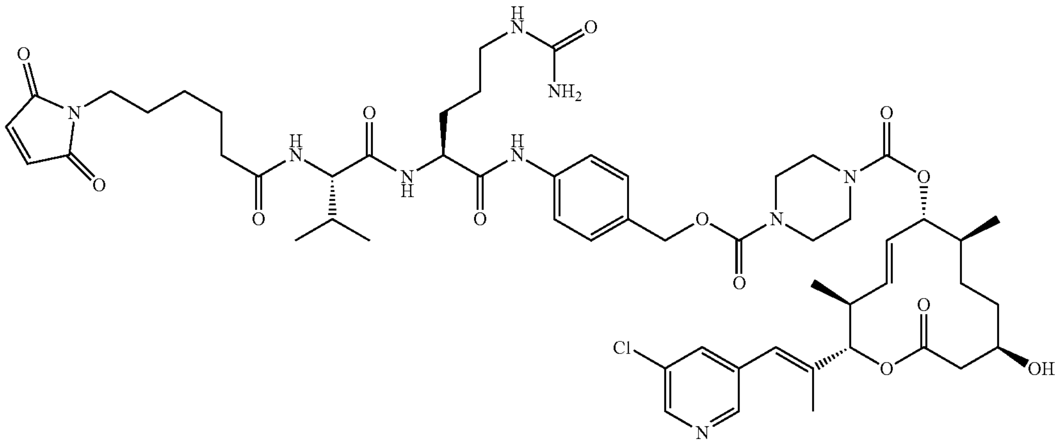 [SMILES: C/C(=C\c1cncc(Cl)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

TABLE 9-continued
Structures of exemplary conjugatable linker-payload (L-D) compounds
Chemical Formula: $C_{55}H_{74}ClN_9O_{13}$
Molecular Weight: 1104.70
ADL1-D29
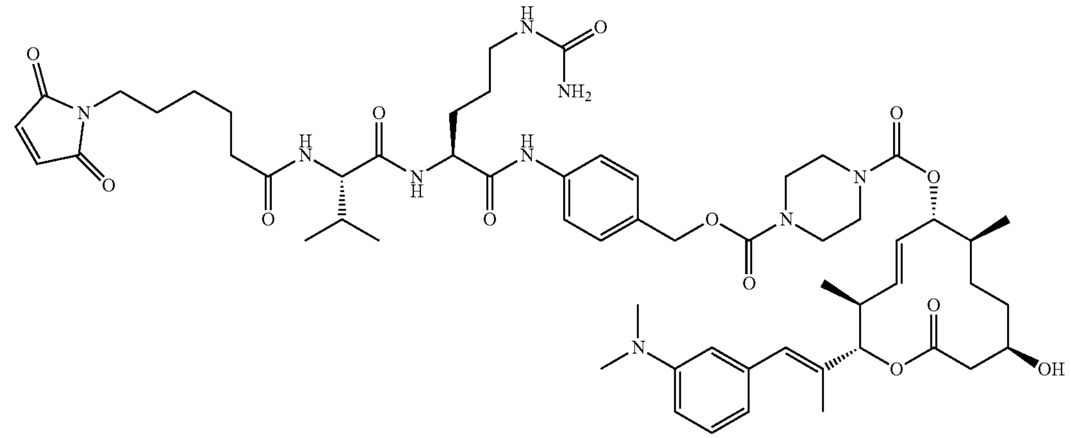 [SMILES: C/C(=C\c1cccc(N(C)C)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{58}H_{81}N_9O_{13}$
Molecular Weight: 1112.34
ADL1-D35
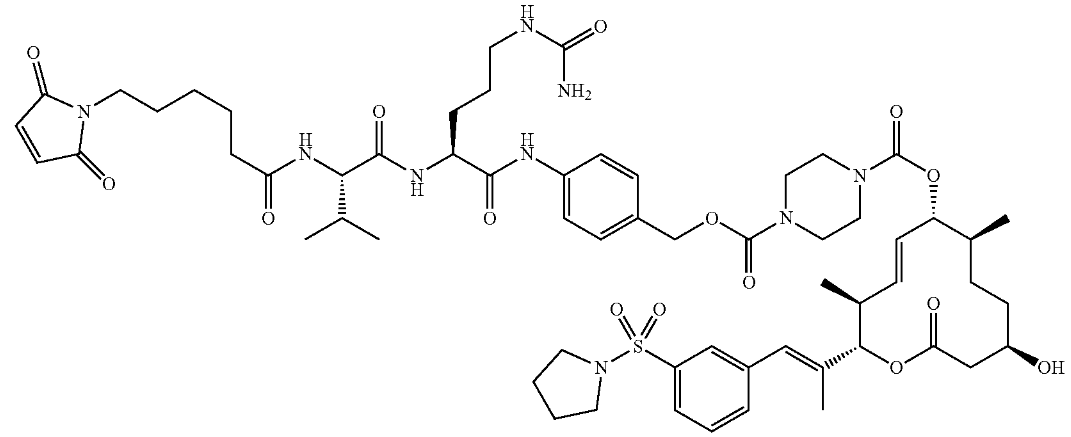 [SMILES: C/C(=C\c1cccc(S(=O)(=O)N2CCCC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{60}H_{83}N_9O_{15}S$
Molecular Weight: 1202.43
ADL5-D32
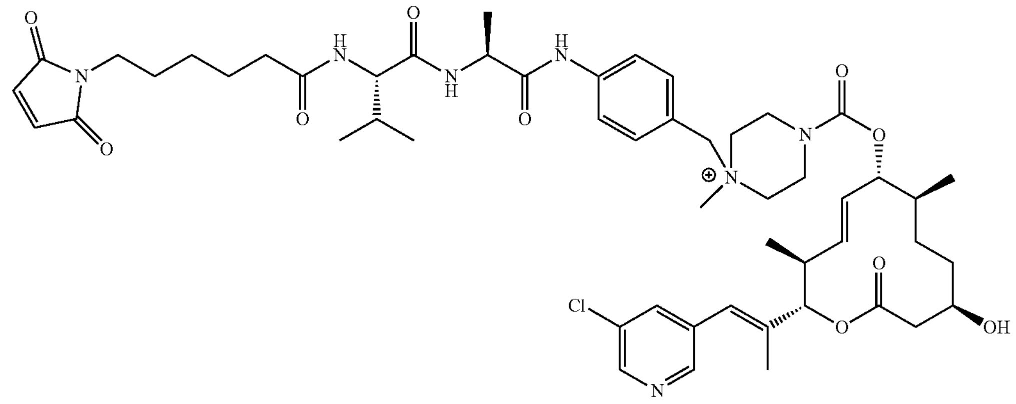 [SMILES: C/C(=C\c1cncc(Cl)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{52}H_{71}ClN_7O_{10}^+$
Molecular Weight: 989.63

TABLE 9-continued
| Structures of exemplary conjugatable linker-payload (L-D) compounds |
| --- |
ADL5-D27
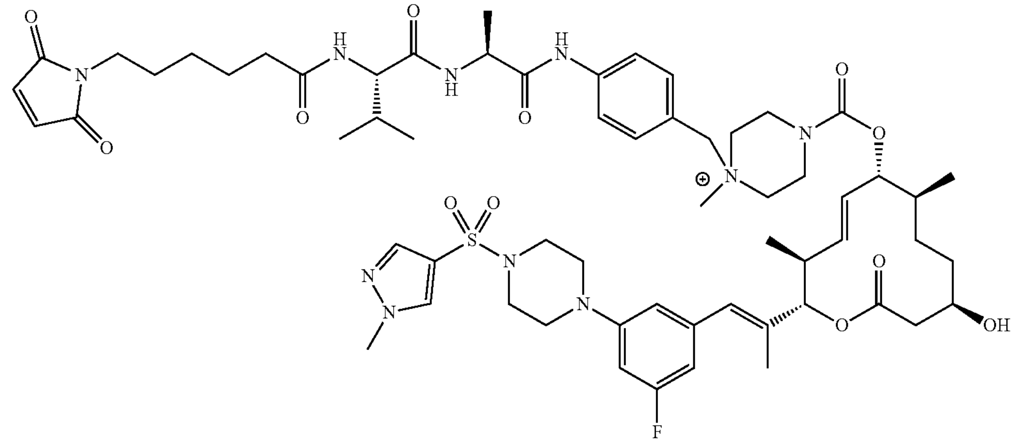
Chemical Formula: $C_{61}H_{84}FN_{10}O_{12}S^{+}$
Molecular Weight: 1200.46
ADL12-D35
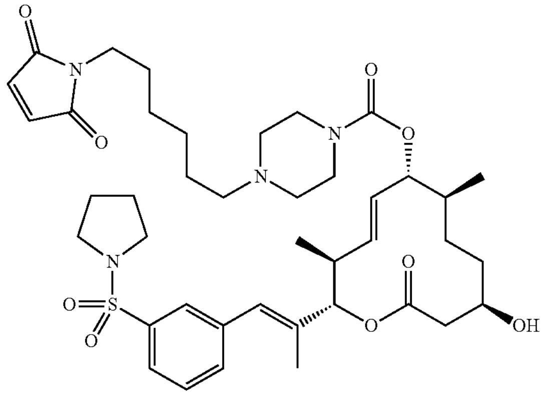 [SMILES: C/C(=C\c1cccc(S(=O)(=O)N2CCCC2)c1)[C@H]1OC(=O)C[C@H](O)CC[C@H](C)[C@@H](OC(=O)N2CCN(CCCCCCN3C(=O)C=CC3=O)CC2)/C=C/[C@@H]1C]
Chemical Formula: $C_{41}H_{58}N_{4}O_{9}S$
Molecular Weight: 782.99
ADL12-D28
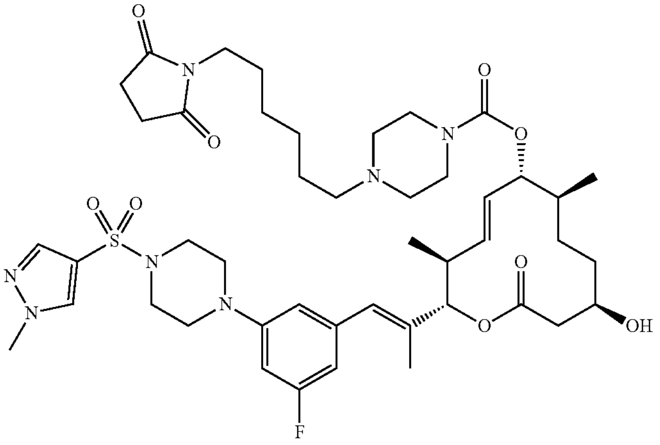 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(CCCCCCN3C(=O)CCC3=O)CC2)/C=C/[C@@H]1C]
Chemical Formula: $C_{45}H_{64}FN_{7}O_{9}S$
Molecular Weight: 898.11

TABLE 9-continued
Structures of exemplary conjugatable linker-payload (L-D) compounds
ADL1-D23
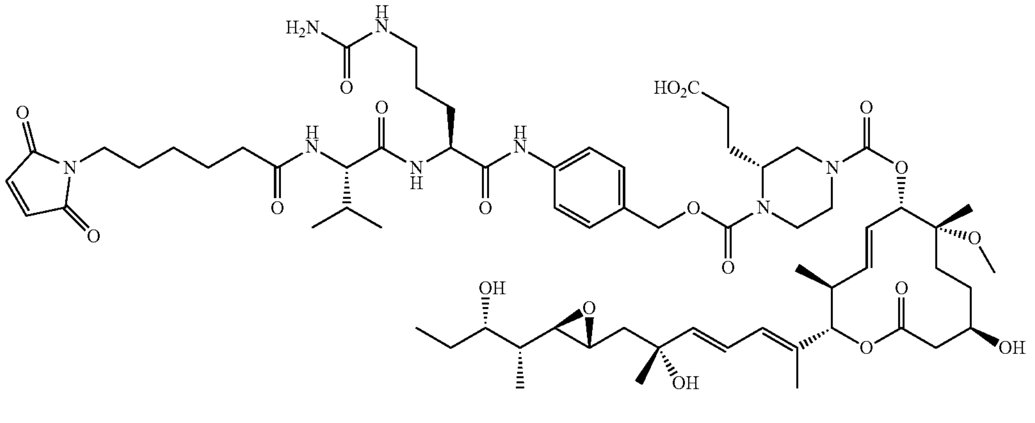 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)[C@H](CCC(=O)O)C2)/C=C/[C@@H]1C]
Chemical Formula: $C_{66}H_{98}N_8O_{19}$
Molecular Weight: 1307.55
ADL1-D24
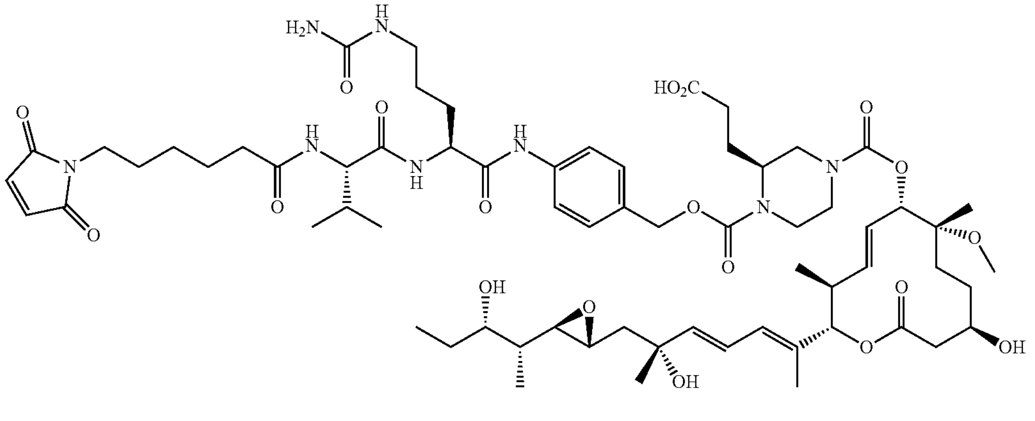 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)[C@@H](CCC(=O)O)C2)/C=C/[C@@H]1C]
Chemical Formula: $C_{66}H_{98}N_8O_{19}$
Molecular Weight: 1307.55
ADL5-D30
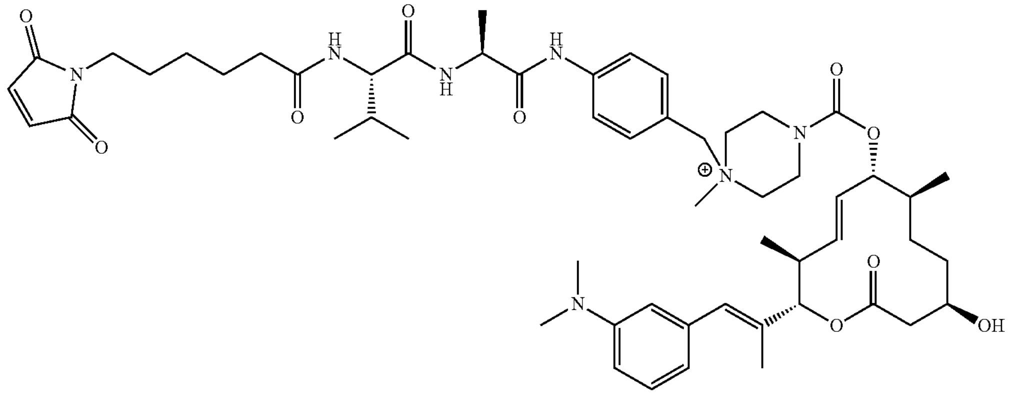 [SMILES: C/C(=C\c1cccc(N(C)C)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

TABLE 9-continued
| Structures of exemplary conjugatable linker-payload (L-D) compounds |
| --- |
| 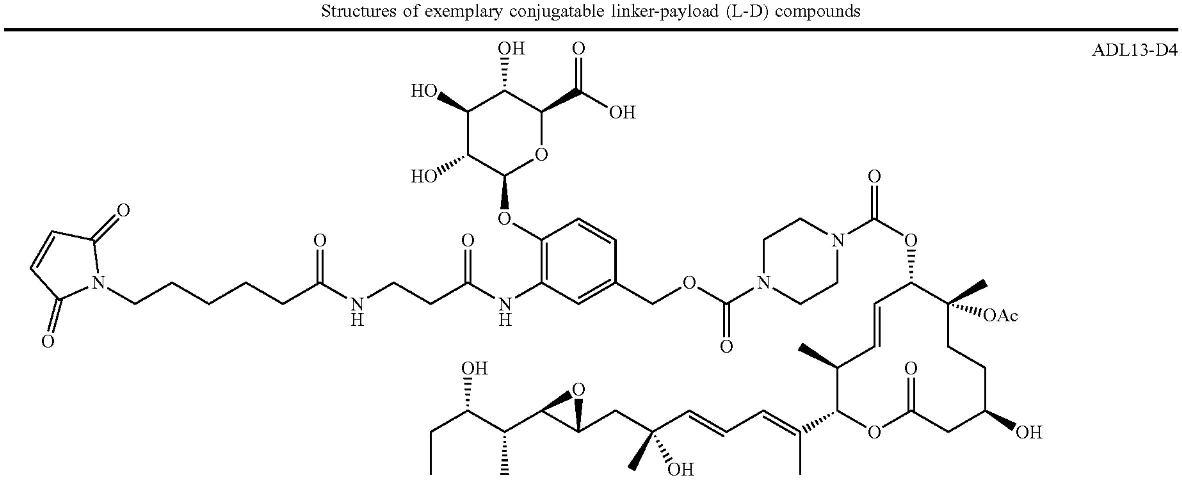 ADL13-D4 |
1.2 Preparation of Pladienolide-Based Payloads
1.2.1 Overview—General Procedure 1

Scheme 1
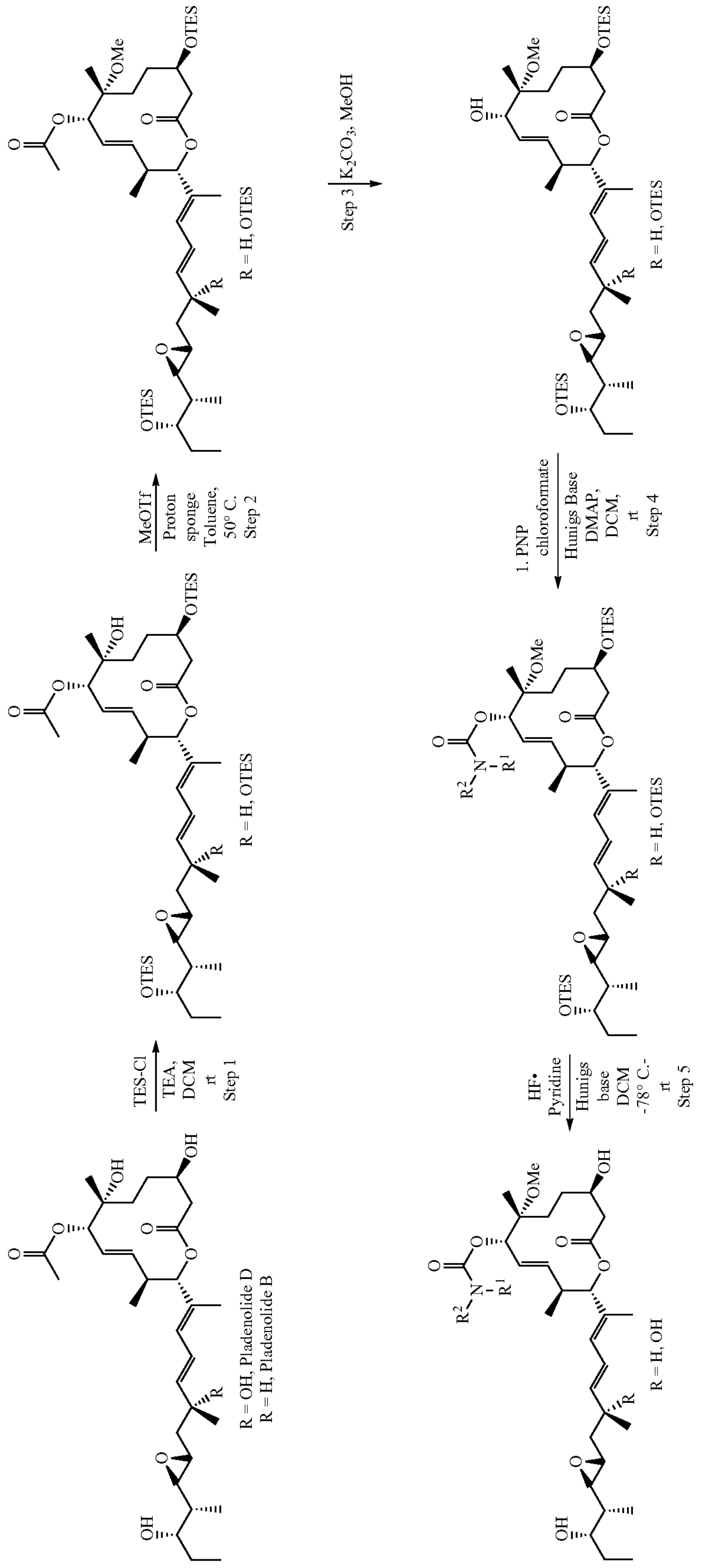

Step 1: (2S,3S,6S,7R,10R,E)-7,10-dihydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl acetate (1.7 g, 3.154 mmol), triethylamine (4.40 mL, 31.536 mmol), 1,2-dichloroethane (31.5 mL, 3.154 mmol) were combined and stirred at RT. Chlorotriethylsilane (2.1 mL, 12.615 mmol) was added and stirred overnight. Brine was poured into the reaction mix and stirred for 30 min and the organic layer separated. The aqueous layer was back extracted with DCM (3×). The organic layers were combined, dried (an. $Na_2SO_4$), concentrated to dryness, and chromatographed to afford (2S,3S,6S,7R,10R,E)-7-hydroxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (1.274 g, 1.423 mmol, 45.1% yield).

$^1$H-NMR (400 MHz, DMSO-d6): δ ppm 0.51-0.64 (m, 18H) 0.74-0.84 (m, 9H) 0.90-0.97 (m, 26H) 1.04 (s, 3H) 1.18 (s, 4H) 1.37 (s, 3H) 1.41-1.57 (m, 4H) 1.69 (s, 3H) 1.84-1.93 (m, 1H) 2.00-2.05 (m, 3H) 2.24-2.35 (m, 1H) 2.38-2.45 (m, 1H) 2.72-2.80 (m, 1H) 3.28-3.30 (m, 1H) 3.62-3.70 (m, 1H) 3.80-3.90 (m, 1H) 4.56 (s, 1H) 4.81-4.93 (m, 2H) 5.41-5.52 (m, 1H) 5.63-5.73 (m, 1H) 5.77-5.87 (m, 1H) 6.01-6.12 (m, 1H) 6.42 (dd, J=15.12, 11.11 Hz, 1H).

Step 2: To a solution of (2S,3S,6S,7R,10R,E)-7-hydroxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (0.7 g, 0.782 mmol) in toluene (4.16 mL, 39.085 mmol) was added 1,8-Naphthalenediamine, N,N,N',N'-tetramethyl-(1.173 g, 5.472 mmol), followed by methyl trifluoromethanesulfonate (0.354 mL, 3.127 mmol) at 0° C. The reaction mixture was then warmed up to 50° C. and heated for 3 hours. Solvent was evaporated. Purification by column chromatography afforded (2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (467 mg, 0.513 mmol, 65.7% yield) as a colorless oil.

$^1$H-NMR (400 MHz, MeOH-d4): δ ppm 0.62-0.70 (m, 18H) 0.83-0.95 (m, 13H) 0.99-1.07 (m, 27H) 1.22 (s, 3H) 1.24-1.36 (m, 2H), 1.28-1.28 (m, 1H) 1.45 (s, 3H) 1.47-1.65 (m, 8H) 1.78 (d, J=0.88 Hz, 3H) 1.91-2.00 (m, 1H) 2.07 (s, 3H) 2.37-2.45 (m, 1H) 2.51-2.68, (m, 3H) 2.88-2.92 (m, 1H) 3.20-3.24 (m, 1H) 3.35 (s, 3H) 3.74-3.82 (m, 1H) 3.93-4.02 (m, 1H) 4.94-4.99 (m, 1H) 5.08-5.14 (m, 1H), 5.53-5.64 (m, 1H) 5.70-5.79 (m, 1H) 5.81-5.88 (m, 1H) 6.12-6.18 (m, 1H) 6.47-6.58 (m, 1H).

Step 3: (2S,3S,6S,7R,10R,E)-7-hydroxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (500 mg, 0.558 mmol) was dissolved in MeOH (6009 μL, 148.524 mmol) and potassium carbonate (232 mg, 1.675 mmol) was added. The reaction mixture was stirred at RT for 1 hour and showed the reaction complete. The reaction mixture was diluted with water and extracted with EtOAc (3×). The combined organics were washed with brine, dried over sodium sulfate, filtered, and concentrated. Purification by column chromatography afforded (4R,7R,8S,11S,12S,E)-7,8-dihydroxy-7,11-dimethyl-12-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (305 mg, 0.357 mmol, 64.0% yield).

$^1$H-NMR (400 MHz, MeOH-d4): δ ppm 0.61-0.72 (m, 18H) 0.82-0.92 (m, 7H) 0.92-1.06 (m, 30H) 1.19-1.40 (m, 7H) 1.42-1.66 (m, 8H) 1.51-1.52 (m, 1H) 1.75-1.81 (m, 3H) 1.91-2.01 (m, 1H) 2.34-2.45 (m, 1H) 2.51-2.61 (m, 2H) 2.61-2.69 (m, 1H) 2.86-2.94 (m, 1H) 3.67-3.73 (m, 1H) 3.73-3.80 (m, 1H) 3.89-3.96 (m, 1H) 4.08-4.17 (m, 1H) 4.93-4.99 (m, 1H) 5.36-5.47 (m, 1H) 5.67-5.78 (m, 1H) 5.80-5.88 (m, 1H) 6.10-6.19 (m, 1H) 6.47-6.58 (m, 1H).

Step 4: (4R,7R,8S,11S,12S,E)-8-hydroxy-7-methoxy-7,11-dimethyl-12-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (0.386 g, 0.445 mmol), DCM (0.1 M), DMAP (1.0 equiv.), Hunig's base (5.0 equiv.), 4-Nitrophenyl chloroformate (1.8 equiv.) were combined and stirred overnight. The reaction mixture was then extracted with 1N NaOH. The organic layer was dried (an. $Na_2SO_4$) and concentrated to dryness. The residue was mixed with DCM (0.1 M), Hunig's base (5.0 equiv.), amine (2.0 equiv.), which were combined and stirred for 1 hour. The reaction mixture was concentrated and chromatographed to afford the triTES-Pladienolide carbamate.

Step 5: triTES-Pladienolide carbamate (1 equiv.), DCM (0.04 M), and DIPEA (191 equiv.) were combined and cooled to −78° C. Hydrogen fluoride-pyridine (6.2 equiv.) was added and the reaction was allowed to warm to RT and stirred overnight. The reaction mixture was cooled in an ice bath, then sat. $NaHCO_3$ was added, stirred, and extracted with DCM. The organic layers were combined, dried over an. $Na_2SO_4$, concentrated, and chromatographed to afford the pladienolide carbamate.

1.2.1.1 D1

General procedure 1 (outlined in section 1.2.1) was employed to synthesize D1.

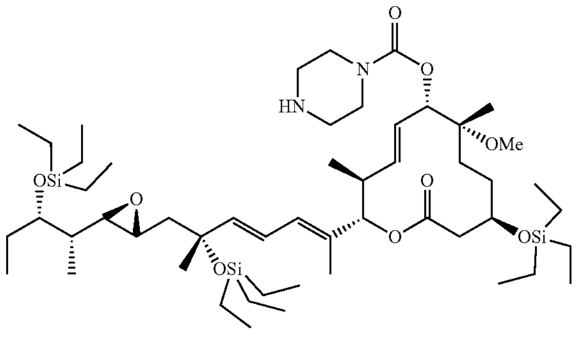

(2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (240 mg, 0.245 mmol, 55.1% yield). LC/MS (ESI, m/z), 980.4 [M+H]+.

$^1$H-NMR (400 MHz, $CDCl_3$-d): δ ppm 0.56-0.66 (m, 18H) 0.78-0.91 (m, 9H) 0.96 (t, J=7.91 Hz, 27H) 1.18-1.22 (m, 3H) 1.23-1.28 (m, 1H) 1.37-1.41 (m, 3H) 1.41-1.63 (m, 7H) 1.69-1.74 (m, 3H) 1.89 (dd, J=13.87, 4.96 Hz, 1H) 2.33-2.62 (m, 4H) 2.78-2.89 (m, 5H), 3.35 (s, 3H) 3.43-3.52 (m, 4H) 3.73 (td, J=6.40, 3.51 Hz, 1H) 3.86 (br dd, J=7.84, 3.95 Hz, 1H) 4.94-5.13 (m, 2H) 5.58-5.76 (m, 3H) 6.12, (br d, J=0.75 Hz, 1H) 6.41 (dd, J=15.06, 11.04 Hz, 1H).

D1

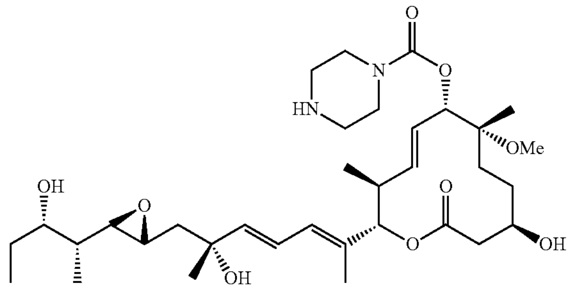

(2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (240 mg, 0.245 mmol, 55.1% yield). LC/MS (ESI, m/z), 637.6 [M+H]+.

$^1$H-NMR (400 MHz, MeOH-d4): δ ppm 0.83-1.01 (m, 10H) 1.23 (s, 3H) 1.25-1.32 (m, 1H) 1.35 (s, 3H) 1.40-1.61 (m, 6H) 1.61-1.71 (m, 2H) 1.79 (d, J=0.75 Hz, 3H) 1.84-1.93 (m, 1H) 2.45-2.63 (m, 3H) 2.63-2.72 (m, 1H) 2.77-2.85 (m, 4H) 2.86-2.94 (m, 1H) 3.33-3.37 (m, 3H) 3.40-3.57 (m, 5H) 3.77-3.89 (m, 1H) 4.38-4.42 (m, 1H) 5.01-5.12 (m, 2H) 5.52-5.65 (m, 1H) 5.69-5.80 (m, 1H) 5.84-5.92 (m, 1H) 6.09-6.18 (m, 1H) 6.49-6.60 (m, 1H).

1.2.1.2 D2

General procedure 1 (outlined in section 1.2.1) was employed to synthesize D2.

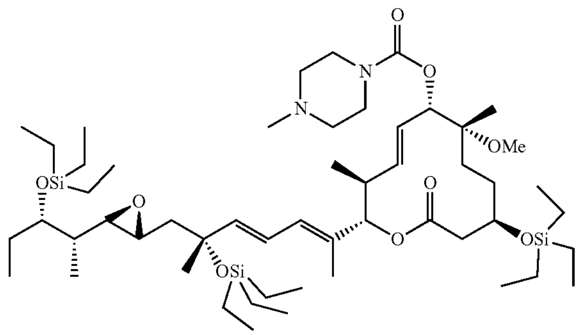

(2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 4-methylpiperazine-1-carboxylate (413 mg, 0.416 mmol, 90% yield). LC/MS (ESI, m/z), 994 [M+H]+.

$^1$H-NMR (400 MHz, MeOH-d4): δ ppm 0.61-0.71 (m, 18H) 0.83-0.94 (m, 9H) 0.98-1.07 (m, 28H) 1.23 (s, 3H) 1.41-1.48 (m, 3H) 1.48-1.65 (m, 7H) 1.72-1.81 (m, 3H) 1.93-1.99 (m, 1H) 2.03 (s, 3H) 2.32 (s, 3H) 2.38-2.48 (m, 5H) 2.52-2.67 (m, 3H) 2.87-2.93 (m, 1H) 3.47-3.61 (m, 4H) 3.72-3.81 (m, 1H) 3.96-4.04 (m, 1H) 4.53-4.62 (m, 1H) 4.93-5.07 (m, 2H) 5.51-5.64 (m, 1H) 5.69-5.79 (m, 1H) 5.81-5.92 (m, 1H) 6.09-6.21 (m, 1H) 6.46-6.60 (m, 1H).

D2

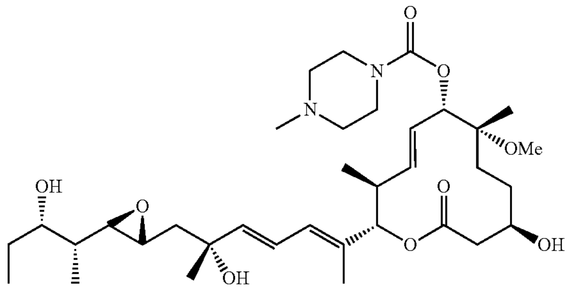

(2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-methylpiperazine-1-carboxylate (37.8 mg, 0.058 mmol, 24.05% yield). LC/MS (ESI, m/z), 651.69 [M+H]+.

$^1$H-NMR (400 MHz, DMSO-d6): δ ppm 0.76-0.89 (m, 9H) 1.10 (s, 3H) 1.20-1.26 (m, 3H) 1.30-1.42 (m, 4H) 1.42-1.55 (m, 2H) 1.66-1.75 (m, 3H) 1.75-1.82 (m, 1H) 2.13-2.21 (m, 3H) 2.25 (br s, 4H) 2.31-2.41 (m, 2H) 2.54-2.60 (m, 2H) 2.72-2.82 (m, 1H) 3.22 (s, 3H) 3.36-3.40 (m, 3H) 3.66-3.76 (m, 1H) 4.36-4.46 (m, 1H) 4.53-4.60 (m, 1H) 4.78-4.85 (m, 1H) 4.86-4.96 (m, 2H) 5.36-5.50 (m, 1H) 5.60-5.74 (m, 1H) 5.80-5.92 (m, 1H) 6.02-6.11 (m, 1H) 6.34-6.46 (m, 1H).

1.3 Preparation of MC-Val-Cit-pABC Linker-Payloads 1.3.1 Overview—General Procedure 1

Scheme 2

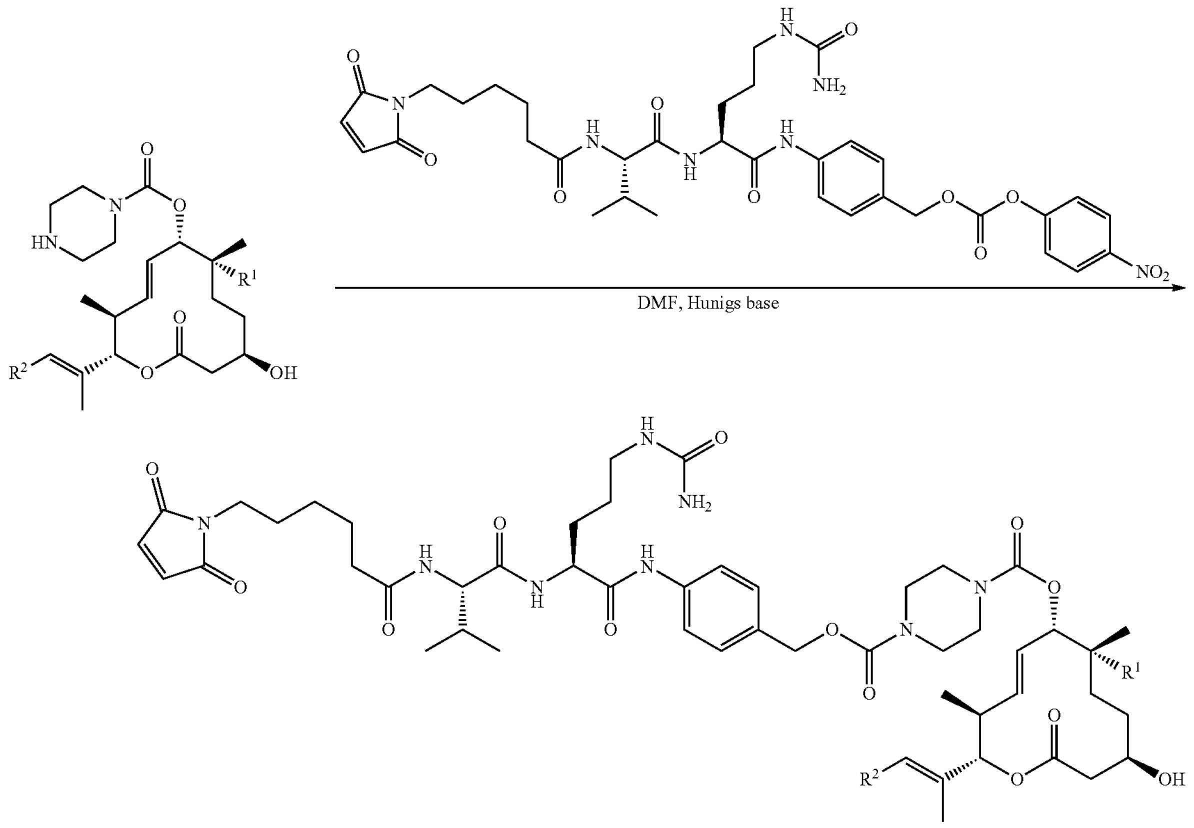

Payload (1.0 equiv.), Hunig's base (3.0 equiv.), DMF (0.1 M), and 4-((S)-2-((S)-2-(6-(2,5-dioxo-2,5-dihydro-1H-pyrrol-1-yl)hexanamido)-5-ureidopentanamido)-3-methylbutanamido)benzyl (4-nitrophenyl) carbonate (1.2 equiv.) were combined and stirred at RT overnight. The reaction mixture was then concentrated and purified via column chromatography (MeOH in DCM) or reverse-phase HPLC to afford the product.

1.3.1.1 ADL1-D1

Linker-Payload (ADL1-D1): General procedure 1 (outlined in section 1.3.1) was employed to synthesize 1-(4-((S)-2-((S)-2-((((9H-fluoren-9-yl)methoxy)carbonyl)amino)-3-methylbutanamido)-5-ureidopentanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate

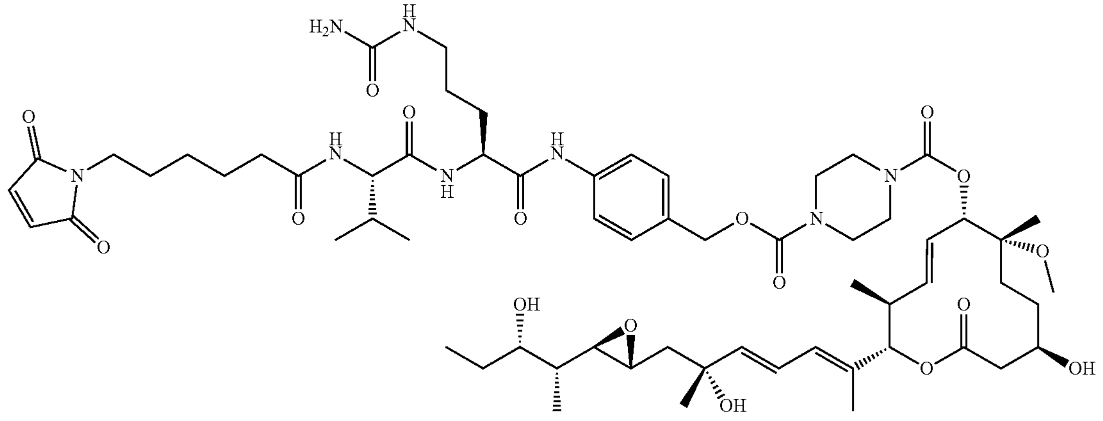 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

(50 mg, 0.040 mmol, 42% yield). LC/MS (ESI, m/z), 1258.5 $[M+Na]^+$.

$^1$H-NMR (400 MHz, MeOH-d4): δ ppm 0.85-1.04 (m, 16H) 1.18-1.26 (m, 3H) 1.26-1.38 (m, 6H) 1.40-1.71 (m, 14H) 1.80 (s, 3H) 1.85-1.98 (m, 2H) 2.02-2.15 (m, 1H) 2.24-2.34 (m, 2H) 2.44-2.64 (m, 3H) 2.65-2.72 (m, 1H) 2.87-2.96 (m, 1H) 3.06-3.27 (m, 2H) 3.37 (s, 6H) 3.43-3.61 (m, 12H) 3.79-3.90 (m, 1H) 4.12-4.21 (m, 1H) 4.48-4.55 (m, 1H) 5.02-5.14 (m, 4H) 5.55-5.65 (m, 1H), 5.69-5.81 (m, 1H) 5.85-5.93 (m, 1H) 6.12-6.19 (m, 1H) 6.49-6.60 (m, 1H) 6.81 (s, 2H) 7.29-7.38 (m, 2H) 7.57-7.65 (m, 2H).

1.3.1.2 ADL1-D18

The payload D18 was prepared using procedures outlined in section 1.2.1, employing pladienolide B as the starting material (SM) (R=H; Scheme 1).

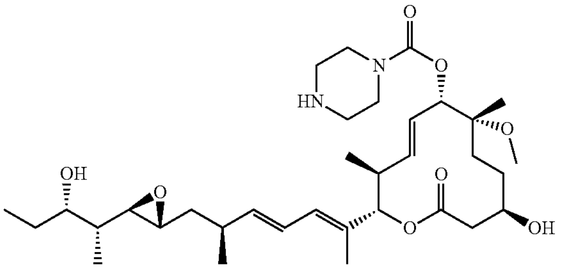 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CCNCC2)/C=C/[C@@H]1C]

(2S,3S,6S,7R,10R,E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (205 mg, 0.330 mmol, 77% yield). LC/MS (ESI, m/z), 621.6 $[M+H]^+$.

$^1$H-NMR (400 MHz, MeOH-d4): δ ppm 0.88-0.99 (m, 9H) 1.10 (d, J=6.78 Hz, 3H) 1.24 (s, 4H) 1.42-1.69 (m, 8H) 1.77 (d, J=0.88 Hz, 3H) 2.43-2.63 (m, 4H) 2.64-2.70 (m, 1H) 2.71-2.82 (m, 5H) 3.34 (br s, 3H) 3.37 (s, 2H) 3.42-3.57 (m, 5H) 3.79-3.89 (m, 1H) 5.06 (s, 2H), 5.54-5.63 (m, 1H) 5.64-5.80 (m, 2H) 6.07-6.16 (m, 1H) 6.29-6.40 (m, 1H).

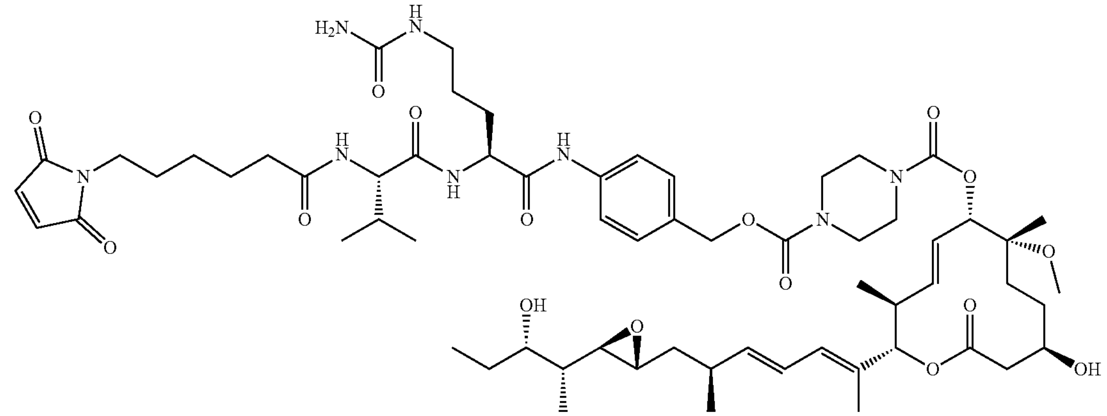 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

-

Linker-Payload (ADL1-D18): General procedure 1 (outlined in section 1.3.1) was employed to synthesize 1-(4-((S)-2-((S)-2-(6-(2,5-dioxo-2,5-dihydro-1H-pyrrol-1-yl)hexanamido)-5-ureidopentanamido)-3-methylbutanamido)benzyl) 4-((2S,3S,6S,7R,10R,E)-10-hydroxy-2-((S,2E,4E)-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (72 mg, 0.059 mmol, 54.7% yield). LC/MS (ESI, m/z), 1220.08 $[M+H]^+$.

$^1$H-NMR (400 MHz, MeOH-d4): δ ppm 0.87-1.02 (m, 15H) 1.10 (d, J=6.78 Hz, 3H) 1.23 (s, 4H) 1.29-1.38 (m, 2H) 1.44-1.68 (m, 13H), 1.54-1.55 (m, 1H) 1.77 (d, J=0.75 Hz, 4H) 1.87-1.95 (m, 1H) 2.05-2.15 (m, 1H) 2.24-2.32 (m, 2H) 2.45-2.62 (m, 4H) 2.65-2.70 (m, 1H), 2.71-2.78 (m, 1H) 3.13-3.18 (m, 2H) 3.46-3.58 (m, 11H) 3.79-3.90 (m, 1H) 4.13-4.21 (m, 1H) 4.47-4.56 (m, 1H) 5.11 (s, 4H) 5.53-5.81 (m, 3H) 6.06-6.16 (m, 1H) 6.29-6.40 (m, 1H) 6.81 (s, 2H) 7.34 (d, J=8.53 Hz, 2H) 7.60 (d, J=8.53 Hz, 2H).

1.3.1.3 ADL1-D8 & ADL6-D8

The payload D8 was synthesized according to the procedure outlined below:

Scheme 3

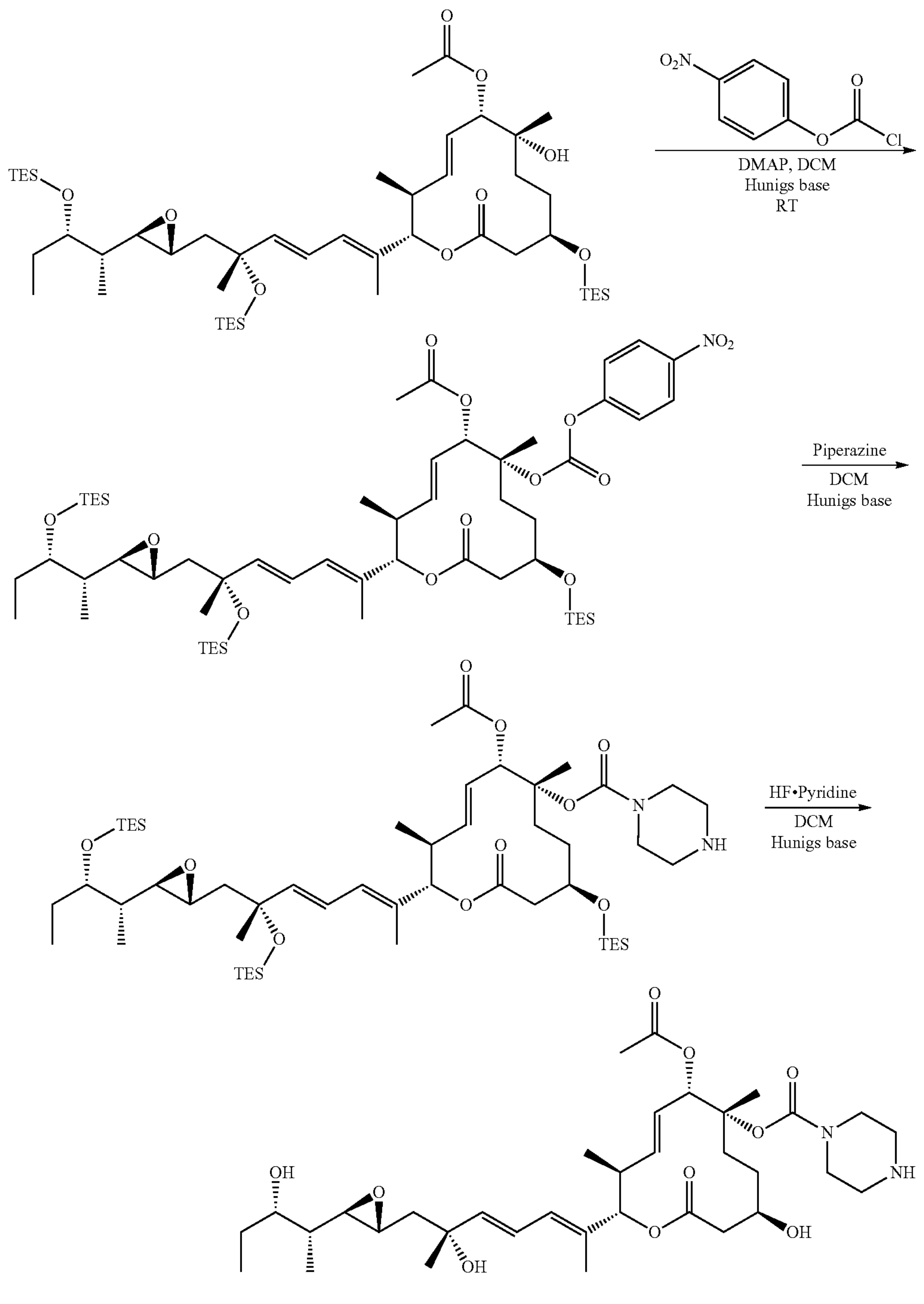

Step 1: To a solution of tri-TES-Pladienolide 0 (200 mg, 0.223 mmol) in dichloromethane (2 mL) at 000 was added DMAP (409 mg, 3.35 mmol) and 4-nitrophenyl chloroformate (338 mg, 1.675 mmol). The reaction mixture was stirred at RT for 7 days, diluted with EtOAc and water, then the layers were separated. The aqueous layer was extracted with EtOAc (2×), and the combined organic extracts were washed with brine. The combined organic layers were dried over $Na_2SO_4$, filtered and concentrated in vacuo. Flash chromatography afforded (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-7-(((4-nitrophenoxy)carbonyl)oxy)-12-oxo-10-((triethylsilyl)oxy)oxacyclododec-4-en-6-yl acetate. (170 mg, 72% yield).

$^1$H-NMR (400 MHz, $CHCl_3$-d): δ ppm 0.54-0.67 (m, 18H) 0.78-1.03 (m, 36H) 1.19-1.32 (m, 1H) 1.39 (s, 3H)

1.43-1.52 (m, 3H) 1.55-1.63 (m, 3H) 1.64 (s, 3H) 1.74 (s, 3H) 1.88 (dd, J=13.80, 5.02 Hz, 1H) 2.13 (s, 3H) 2.23-2.37 (m, 1H) 2.39-2.48 (m, 2H) 2.51-2.63 (m, 2H) 2.84 (s, 1H) 3.69-3.77 (m, 1H) 3.82-4.00 (m, 1H) 5.04 (d, J=10.79 Hz, 1H) 5.24 (d, J=9.03 Hz, 1H) 5.67-5.84 (m, 3H) 6.12 (d, J=10.16 Hz, 1H) 6.42 (dd, J=15.06, 11.04 Hz, 1H) 7.42 (d, J=9.29 Hz, 2H) 8.29 (d, J=9.16 Hz, 2H).

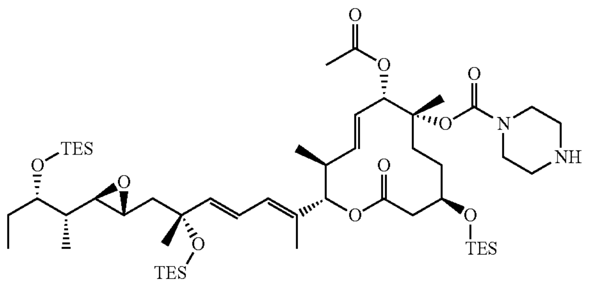

Step 2: To a solution of (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-7-(((4-nitrophenoxy)carbonyl)oxy)-12-oxo-10-((triethylsilyl)oxy)oxacyclododec-4-en-6-yl acetate (100 mg, 0.094 mmol) in DCM was added piperazine and DMAP. The resulting yellowish suspension was stirred for 6 hours. The reaction mixture was concentrated to give the crude product. Flash chromatography afforded (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate (95 mg, 100%). LC/MS (ESI, m/z), 1008.8 $[M+H]^+$.

$^1$H-NMR (400 MHz, $CHCl_3$-d): δ ppm 0.42-0.70 (m, 22H) 0.79-0.84 (m, 7H) 0.86-0.91 (m, 4H) 0.92-1.03 (m, 30H) 1.15-1.30 (m, 2H) 1.37-1.42 (m, 3H) 1.44-1.52 (m, 3H) 1.56-1.62 (m, 2H) 1.62-1.68 (m, 1H) 1.71-1.76 (m, 3H) 1.83-1.93 (m, 1H) 2.03-2.11 (m, 4H) 2.36-2.45 (m, 2H) 2.45-2.53 (m, 2H) 2.54-2.64 (m, 1H) 2.78-2.86 (m, 1H) 2.86-3.07 (m, 4H) 3.32-3.45 (m, 1H) 3.45-3.64 (m, 3H) 3.69-3.78 (m, 1H) 3.79-3.94 (m, 1H) 5.00 (d, J=10.54 Hz, 1H) 5.18 (s, 1H) 5.54-5.79 (m, 3H) 5.98-6.21 (m, 1H) 6.33-6.57 (m, 1H) 6.84-6.96 (m, 3H) 8.02-8.35 (m, 2H) 8.06-8.08 (m, 1H).

Step 3: To a solution of (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate in (95 mg, 0.094 mmol) in THF (3 mL) was added TBAF (0.424 mL, 1 M, 0.424 mmol) and stirred at RT for 10 hours. The mixture as concentrated and diluted with EtOAc, washed with water and brine. The organic layer was separated and dried with $Na_2SO_4$, filtered and concentrated in vacuo. HPLC purification afforded (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate (16 mg, 26%). LC/MS (ESI, m/z), 665.6 $[M+H]^+$.

$^1$H-NMR (400 MHz, $CHCl_3$-d): δ ppm 0.90 (dd, J=6.84, 2.20 Hz, 6H) 0.94 (t, J=7.40 Hz, 3H) 1.20-1.30 (m, 1H) 1.34 (s, 3H) 1.39-1.54 (m, 3H) 1.55 (s, 3H) 1.59-1.73 (m, 3H) 1.78 (d, J=0.88 Hz, 3H) 1.86 (dd, J=13.99, 5.46 Hz, 1H) 2.05 (s, 3H) 2.39-2.53 (m, 3H) 2.55-2.65 (m, 1H) 2.67 (dd, J=8.03, 2.26 Hz, 1H) 2.89 (s, 1H) 3.22 (br s, 4H) 3.50-3.57 (m, 1H) 3.58-3.90 (m, 5H) 5.08 (d, J=10.67 Hz, 1H) 5.18 (d, J=9.03 Hz, 1H) 5.58-5.78 (m, 2H) 5.88 (d, J=15.31 Hz, 1H) 6.10-6.23 (m, 1H) 6.53 (dd, J=15.25, 10.98 Hz, 1H).

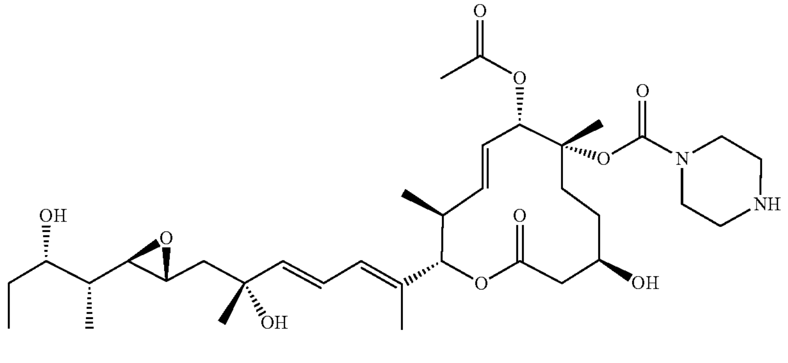 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCNCC2)[C@@H](OC(C)=O)/C=C/[C@@H]1C]

Step 4

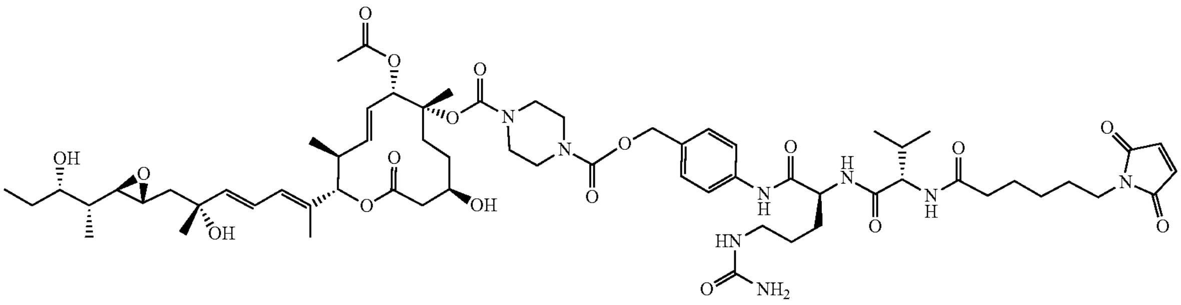 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]

Linker-Payload (ADL1-D8): 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (7.5 mg, 10.166 μmol) in DMF (315 μL, 4.066 mmol) was added Hunig's base (5.33 μL, 0.03 mmol). The reaction was cooled to 0° C., and added (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate (7.50 mg, 0.011 mmol). The reaction mixture was stirred at RT until consumption of starting material. The reaction mixture was concentrated in vacuo. Flash chromatography afforded ADL1-D8 (7.2 mg, 5.70 μmol, 56.1% yield). LC/MS (ESI, m/z), 1263.8 $[M+H]^+$. General procedure 1 (1.3.1) can also be employed for the preparation of ADL1-110987.

$^1$H-NMR (400 MHz, CHLOROFORM-d): δ ppm 0.80-1.02 (m, 16H) 1.20-1.35 (m, 6H) 1.38-1.48 (m, 2H) 1.57-1.69 (m, 7H) 1.74-1.81 (m, 4H) 1.86-1.96 (m, 2H) 2.00-2.11 (m, 4H) 2.31 (br d, J=6.02 Hz, 2H) 2.45-2.55 (m, 2H) 2.59-2.74 (m, 2H) 2.85-2.96 (m, 1H) 3.05-3.25 (m, 5H) 3.40-3.59 (m, 9H) 3.62-3.88 (m, 1H) 4.15 (d, J=7.53 Hz, 1H) 5.05-5.22 (m, 5H) 5.56-5.77 (m, 2H) 5.84-5.98 (m, 1H) 6.11-6.22 (m, 1H) 6.47-6.61 (m, 1H) 7.31-7.40 (m, 2H) 7.56-7.65 (m, 2H).

Linker-Payload (ADL6-D8): 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (5 mg, 7.673 μmol) in DMF (238 μL, 3.069 mmol) was added Hunig's base (4.02 μL, 0.023 mmol). The reaction mixture was cooled to 0° C., and added (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate. The reaction mixture was stirred at RT until consumption of starting material. The reaction mixture was concentrated in vacuo. HPLC purification afforded ADL6-D8 (1.2 mg, 1.019 μmol, 13.28% yield). LC/MS (ESI, m/z), 1199.9 $[M+Na]^+$.

$^1$H NMR (400 MHz, $CHCl_3$-d): δ ppm 0.78-1.04 (m, 18H) 1.15-1.52 (m, 58H) 1.64-1.72 (m, 3H) 1.78 (d, J=6.53 Hz, 4H) 2.04-2.19 (m, 3H) 2.21-2.30 (m, 1H) 2.44-2.67 (m, 4H) 2.76 (dd, J=6.09, 2.95 Hz, 1H) 2.90-3.02 (m, 1H) 3.42-3.57 (m, 8H) 3.61-3.70 (m, 1H) 3.77 (br s, 1H) 4.10-4.27 (m, 1H) 4.58 (br d, J=6.65 Hz, 1H) 5.01-5.26 (m, 4H) 5.52-5.70 (m, 2H) 5.88 (s, 1H) 5.93-6.02 (m, 1H) 6.08-6.18 (m, 1H) 6.47-6.58 (m, 1H) 7.29-7.35 (m, 2H) 7.55 (d, J=8.66 Hz, 1H).

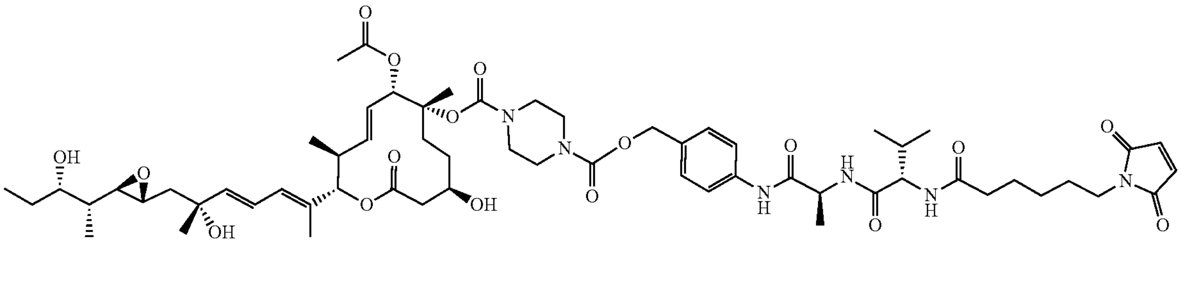 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)[C@@H](OC(C)=O)/C=C/[C@@H]1C]

1.3.1.4 ADL1-D4
ADL1-D4 was synthesized using the procedures outlined below.
Scheme 4
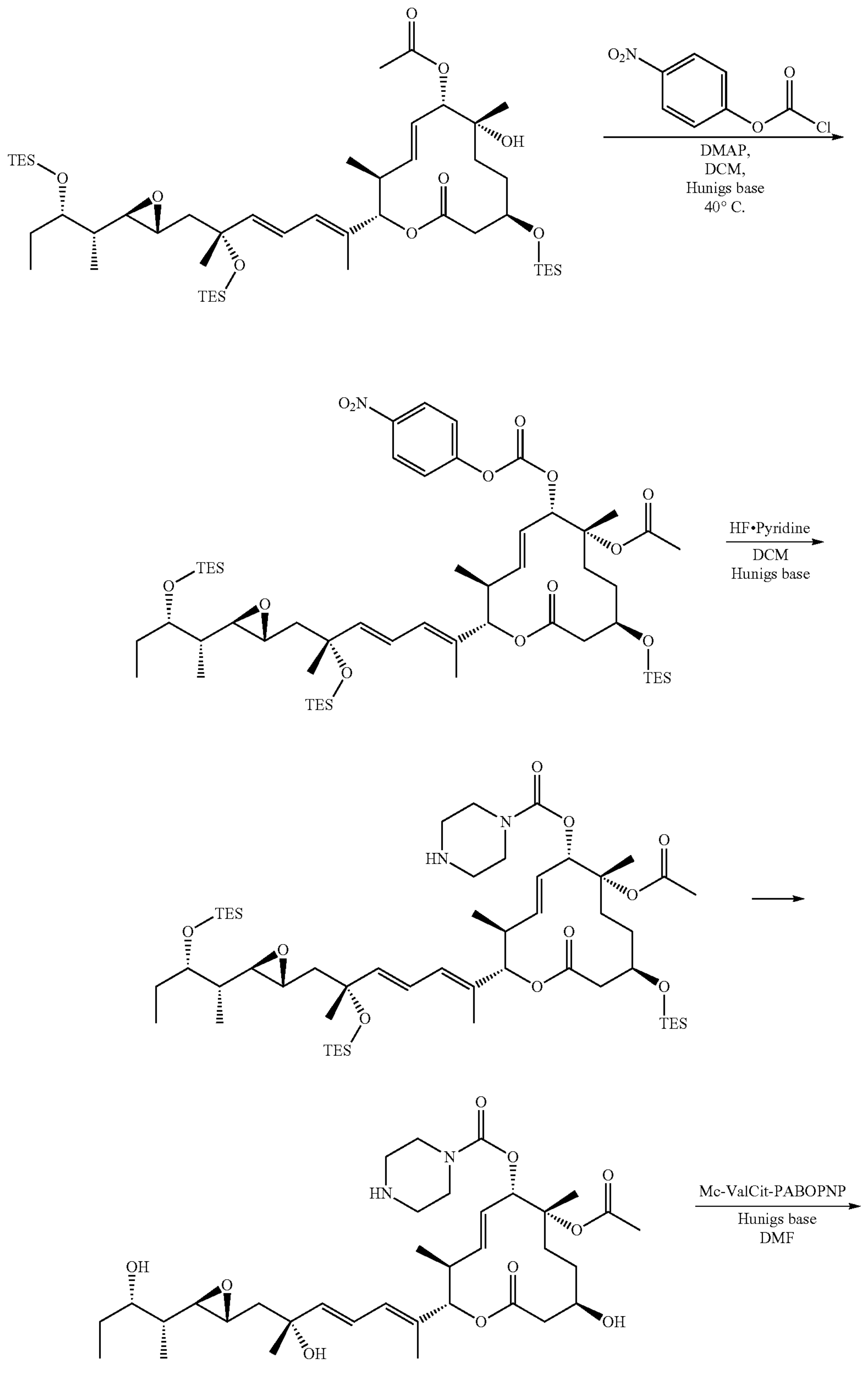

-continued

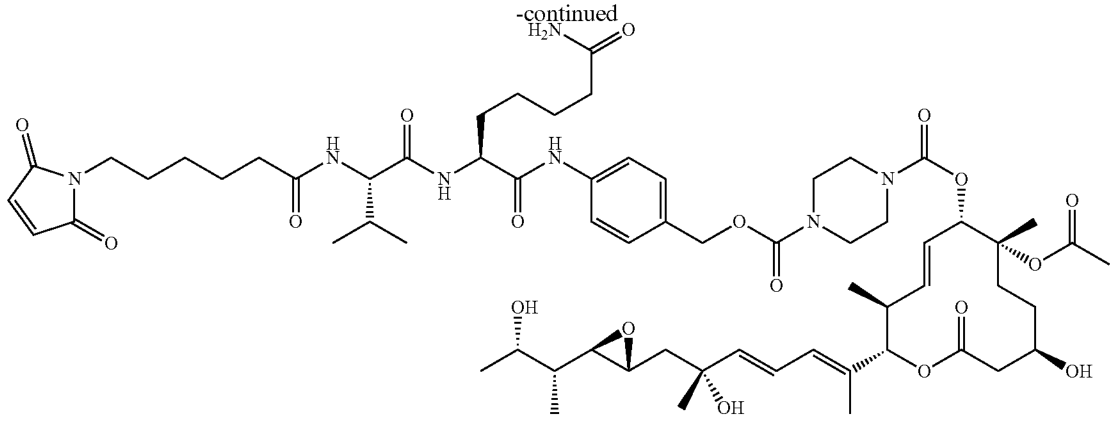

Step 1: (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-6-(((4-nitrophenoxy)carbonyl)oxy)-12-oxo-10-((triethylsilyl)oxy)oxacyclododec-4-en-7-yl acetate

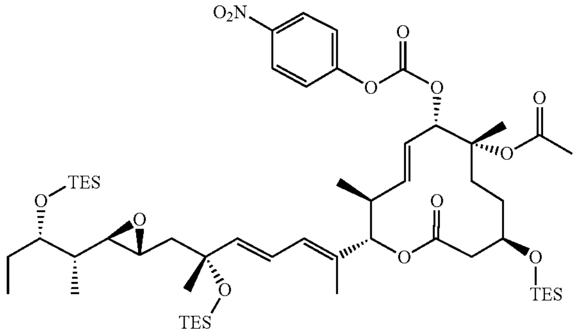

To a solution of tri-TES Pladienolide D (160 mg, 0.179 mmol) in 1,2-dichloroethane (5 mL) at 20° C. was added DMAP (32.7 mg, 0.268 mmol), triethyl amine (0.75 mL, 5.36 mmol) and 4-nitrophenyl chloroformate (360 mg, 1.787 mmol). The reaction mixture was stirred at 40° C. for 4 days, and at 60° C. for 2 hours. The reaction mixture was diluted with EtOAc and washed with water, then the layers were separated. The aqueous layer was extracted with EtOAc (2×). The combined organic extracts were successively washed with water and brine, dried over $MgSO_4$, filtered, and concentrated in vacuo. Flash chromatography afforded (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (150 mg, 79% yield).

$^1$H-NMR (400 MHz, $CHCl_3$-d): δ ppm 0.48-0.71 (m, 24H) 0.78-0.85 (m, 7H) 0.86-0.93 (m, 5H) 0.94-1.03 (m, 34H) 1.18-1.22 (m, 2H) 1.22-1.26 (m, 2H) 1.35-1.43 (m, 4H) 1.43-1.52 (m, 4H) 1.54 (s, 4H) 1.56-1.65 (m, 3H) 1.68-1.72 (m, 3H) 1.75 (br d, J=0.75 Hz, 2H) 1.84-1.95 (m, 1H) 2.01-2.06 (m, 2H) 2.09 (s, 2H) 2.11 (s, 2H) 2.33-2.52 (m, 4H) 2.57 (dd, J=8.09, 2.07 Hz, 2H) 2.80-2.90 (m, 1H) 3.66-3.80 (m, 1H) 3.82-3.93 (m, 2H) 4.92-5.13 (m, 2H) 5.63-5.68 (m, 1H) 5.69-5.74 (m, 1H) 5.75-5.83 (m, 2H) 6.12 (br d, J=10.67 Hz, 1H) 6.41 (ddd, J=15.15, 11.01, 5.08 Hz, 1H) 7.50 (d, J=9.41 Hz, 2H) 8.35 (d, J=9.29 Hz, 2H).

Step 2: (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate

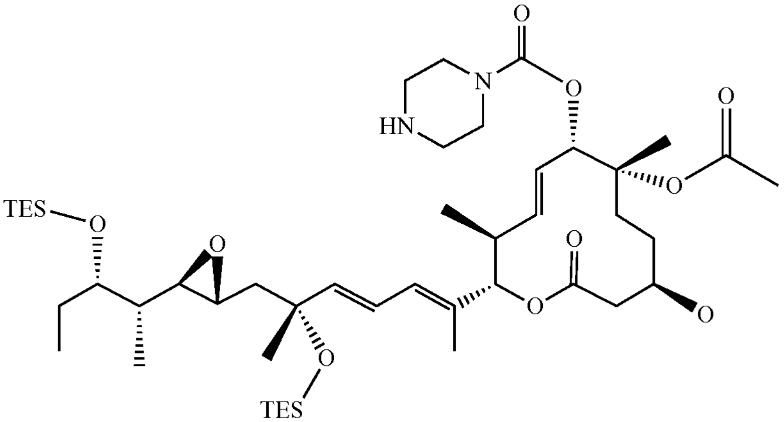

To a solution of (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-6-(((4-nitrophenoxy)carbonyl)oxy)-12-oxo-10-((triethylsilyl)oxy)oxacyclododec-4-en-7-yl acetate in DCM (1 mL) was added piperazine (0.447 g, 5.195 mmol) and Hunig's base (0.9 mL, 5.195 mmol). The resulting yellowish suspension was stirred for 6 hours. Reaction mixture was concentrated and chromatographed over silica gel to afford (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.0 g, 0.844 mmol, 81% yield). LC/MS (ESI, m/z), 1008.1 $[M+H]^+$.

7-acetoxy-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (225 mg, 36.8%). LC/MS (ESI, m/z), 665.6 $[M+H]^+$.

$^1$H-NMR (400 MHz, $CHCl_3$-d): δ ppm 0.87-0.92 (m, 6H) 0.94 (t, J=7.40 Hz, 3H) 1.16-1.31 (m, 1H) 1.35 (s, 3H) 1.40-1.56 (m, 4H) 1.59 (s, 3H) 1.66 (br dd, J=14.68, 7.03 Hz, 3H) 1.76-1.80 (m, 3H) 1.87 (dd, J=14.12, 5.46 Hz, 1H) 2.05 (s, 3H) 2.30-2.41 (m, 1H) 2.50 (d, J=3.76 Hz, 2H) 2.56-2.72 (m, 2H) 2.90 (br d, J=2.01 Hz, 1H) 3.19 (br t, J=5.14 Hz, 4H) 3.50-3.59 (m, 1H) 3.71 (br s, 4H) 3.77-3.89 (m, 1H) 5.01-5.13 (m, 2H) 5.58-5.71 (m, 1H) 5.71-5.81 (m, 1H) 5.88 (d, J=15.31 Hz, 1H) 6.15 (br d, J=10.79 Hz, 1H) 6.53 (dd, J=15.18, 10.92 Hz, 1H).

AD1-D4

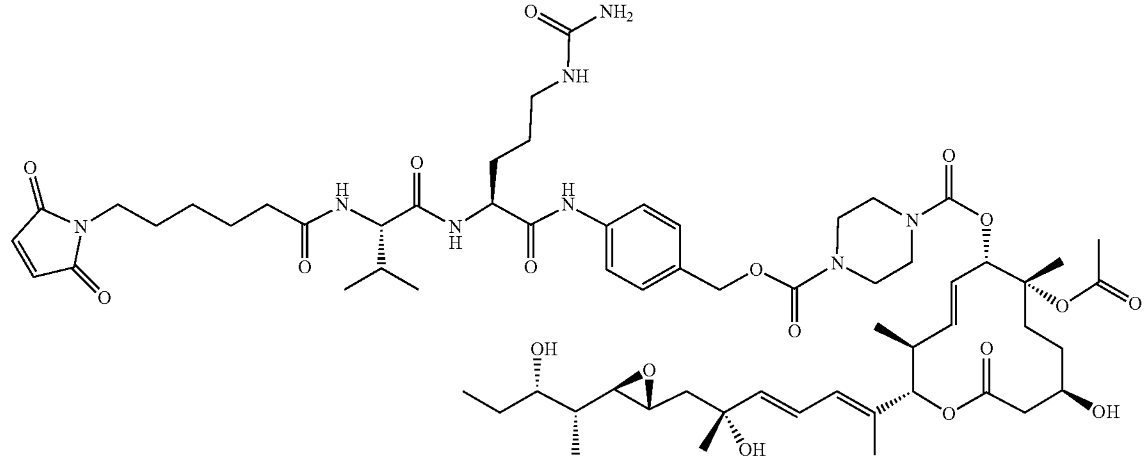

D4

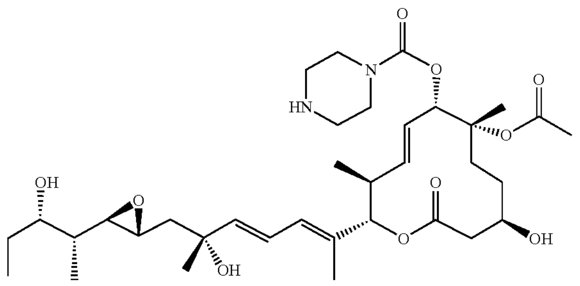 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCNCC2)/C=C/[C@@H]1C]

Step 3: (2S, 3S,6S,7R,10R,E)-7-acetoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.09 g, 0.92 mmol), DCM (20.71 mL, 321.826 mmol), and DIPEA (19.91 mL, 114.018 mmol) were combined and cooled to −78° C. Hydrogen fluoride-pyridine (0.518 g, 5.232 mmol) was added and the reaction allowed to warm to RT and stirred overnight. LC/MS suggested desilylation. The reaction mixture was cooled in an ice bath. Saturated $NaHCO_3$ was added and stirred and extracted with DCM. The organic layers were combined, dried over an. $Na_2SO_4$ and concentrated and chromatographed to afford (2S,3S,6S,7R,10R,E)-

To 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (23 mg, 0.031 mmol) in DMF (966 μL) in a round-bottom flask was added Hunig's base (16.33 μL, 0.094 mmol). The reaction mixture was cooled to 0° C., and D4 (22.80 mg, 0.034 mmol) was added and stirred at RT. The reaction mixture was concentrated in vacuo. Flash chromatography afforded ADL1-D4 (30.5 mg, 0.024 mmol, 77% yield). LC/MS (ESI, m/z), 1263.8 $[M+H]^+$.

$^1$H-NMR (400 MHz, MeOH-$d_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

1.3.1.5 ADL1-D9, ADL6-D9, & ADL1-D13

D9 & D13

D9 and D13 were synthesized as a 3:1 mixture of isomers employing procedures outlined in the synthesis of D4 (Scheme 4) utilizing tri-TES Pladienolide B.

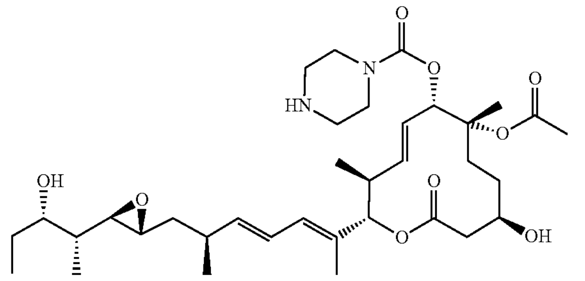
Payload (D9): LC/MS (ESI, m/z), 649.7 [M+H]$^+$.
$^1$H-NMR (400 MHz, $CHCl_3$-d): δ ppm 0.87-1.01 (m, 10H) 1.08 (d, J=6.78 Hz, 3H) 1.27-1.63 (m, 12H) 1.66-1.74 (m, 1H) 1.76 (s, 3H) 1.97-2.10 (m, 3H) 2.35-2.57 (m, 5H) 2.58-2.65 (m, 1H) 2.65-2.71 (m, 1H) 2.77 (td, J=5.93, 2.32 Hz, 1H) 2.89-3.05 (m, 4H) 3.07-3.34 (m, 8H) 3.50-3.68 (m, 5H) 3.72-3.88 (m, 1H) 4.88-5.09 (m, 1H) 5.18 (d, J=10.67 Hz, 1H) 5.50-5.84 (m, 3H) 6.01-6.13 (m, 1H) 6.19-6.36 (m, 1H).
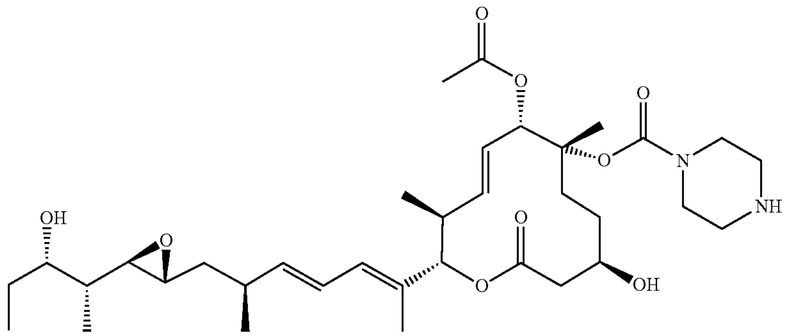
Payload (D13): LC/MS (ESI, m/z), 649.6 [M+H]$^+$.
$^1$H NMR (400 MHz, $CHCl_3$-d) δ ppm 0.84-1.01 (m, 11H) 1.08 (d, J=6.78 Hz, 3H) 1.29-1.64 (m, 10H) 1.63-1.73 (m, 1H) 1.76 (s, 3H) 1.94-2.12 (m, 4H) 2.37-2.58 (m, 4H) 2.59-2.65 (m, 1H) 2.68 (dd, J=7.40, 2.26 Hz, 1H) 2.77 (td, J=5.93, 2.32 Hz, 1H) 3.01-3.30 (m, 4H) 3.49 (s, 1H) 3.54-3.67 (m, 2H) 3.69-3.92 (m, 5H) 4.13-4.78 (m, 11H) 5.13-5.24 (m, 2H) 5.48-5.61 (m, 1H) 5.62-5.74 (m, 2H) 6.04-6.13 (m, 1H) 6.18-6.32 (m, 1H).
ADL1-D9
General procedure 1 (outlined in section 1.3.1) was employed to synthesize ADL1-D9.
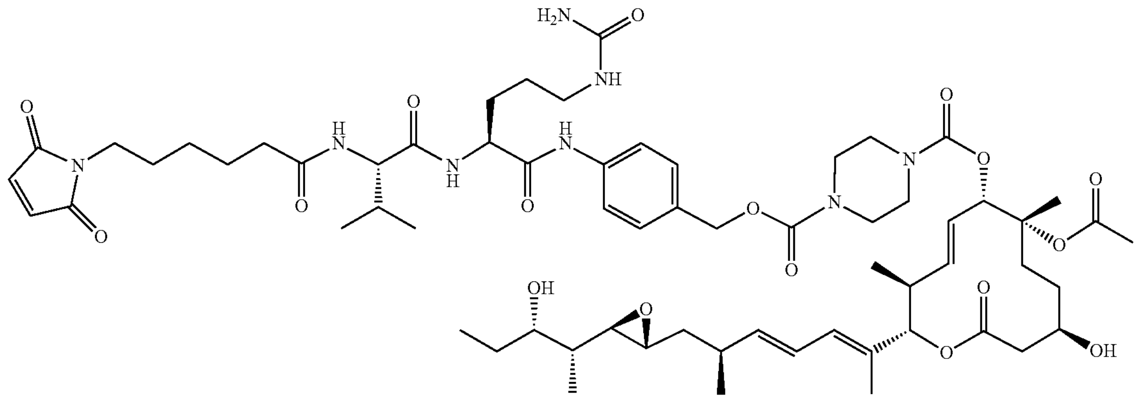 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

2Linker-Payload (ADL1-D9): (30.5 mg, 0.024 mmol, 77% yield). LC/MS (ESI, m/z), 1263.8 $[M+H]^+$.

$^1$H-NMR (400 MHz, MeOH-$d_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

ADL6-D9

General procedure 1 (outlined in section 1.3.1) was employed to synthesize ADL6-D9.

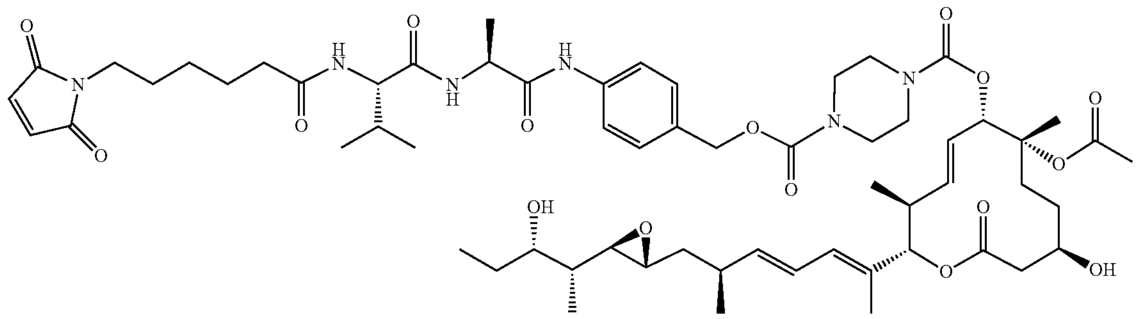 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Linker-Payload (ADL6-D9): To diluted 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (16.5 mg, 0.025 mmol) in DMF (784 μL) was added Hunig's Base (13.27 μL, 0.076 mmol). The reaction mixture was cooled to 0° C., and D9 was added. The reaction mixture was stirred at RT until LC/MS showed the reaction complete. The reaction mixture was concentrated in vacuo. Flash chromatography of the residue on silica gel with DCM/MeOH gave the titled compound (16.7 mg, 57% yield). LC/MS (ESI, m/z), 1184.6 $[M+Na]^+$.

$^1$H-NMR (400 MHz, MeOH-$d_4$): δ ppm 0.80-1.02 (m, 16H) 1.05-1.12 (m, 4H) 1.13-1.34 (m, 5H) 1.38-1.51 (m, 7H) 1.53-1.68 (m, 11H) 1.71-1.80 (m, 4H) 1.97-2.16 (m, 4H) 2.24-2.32 (m, 2H) 2.32-2.42 (m, 1H) 2.43-2.55 (m, 3H) 2.56-2.69 (m, 3H) 2.73 (br d, J=2.13 Hz, 1H) 3.07-3.18 (m, 1H) 3.42-3.61 (m, 17H) 3.75-3.91 (m, 1H) 4.11-4.24 (m, 1H) 4.43 (s, 2H) 5.59-5.88 (m, 4H) 6.06-6.17 (m, 1H) 6.29-6.39 (m, 1H) 7.24-7.39 (m, 2H) 7.52-7.64 (m, 2H).

ADL1-D13

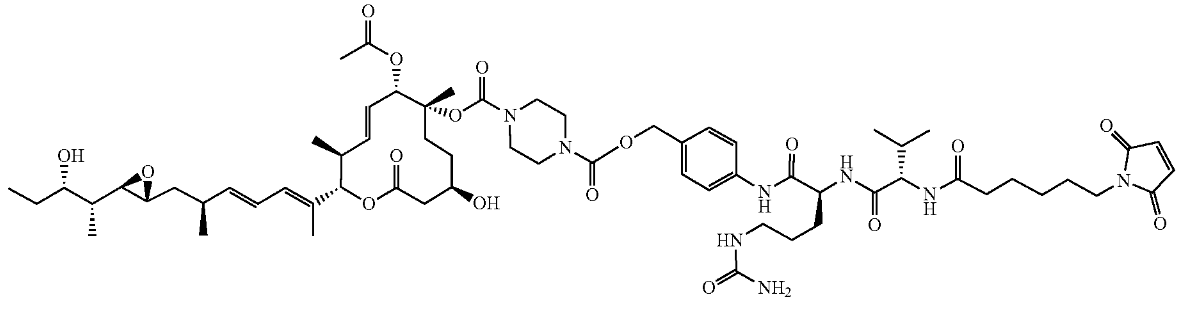 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]

Linker-Payload (AD1-D13): 4-((S)-2-((S)-2-(6-(2,5-dioxo-2,5-dihydro-1H-pyrrol-1-yl)hexanamido)-3-methylbutanamido)-5ureidopentanamido)benzyl (4-nitrophenyl) carbonate (4.2 mg, 5.693 μmol) in DMF (176 μL, 2.277 mmol) was added Hunig's base (2.98 μL, 0.017 mmol). The reaction mixture was cooled to 0° C., and D13 was added (4.06 mg, 6.262 μmol). The reaction mixture was stirred at RT until LC/MS showed the reaction complete. The reaction mixture was concentrated in vacuo. Flash chromatography of the residue on silica gel with DCM/MeOH gave the title compound (4.8 mg, 68% yield). LC/MS (ESI, m/z), 1248.0 $[M+H]^+$.

$^1$H-NMR (400 MHz, $CHCl_3$-d): δ ppm 0.58-0.98 (m, 10H) 0.99-1.06 (m, 2H) 1.11-1.31 (m, 6H) 1.57-1.75 (m, 3H) 2.11-2.26 (m, 1H) 2.30-2.73 (m, 2H) 3.28-3.80 (m, 7H) 4.14-4.33 (m, 1H) 4.44-4.55 (m, 1H) 4.63-4.81 (m, 1H) 4.92-5.06 (m, 1H) 5.09 (s, 1H) 5.49-5.74 (m, 1H) 5.88-6.09 (m, 1H) 6.14-6.36 (m, 1H) 6.99-7.08 (m, 1H) 7.21-7.38 (m, 2H) 7.53-7.67 (m, 1H) 7.95 (s, 1H).

1.3.1.6 ADL1-D14

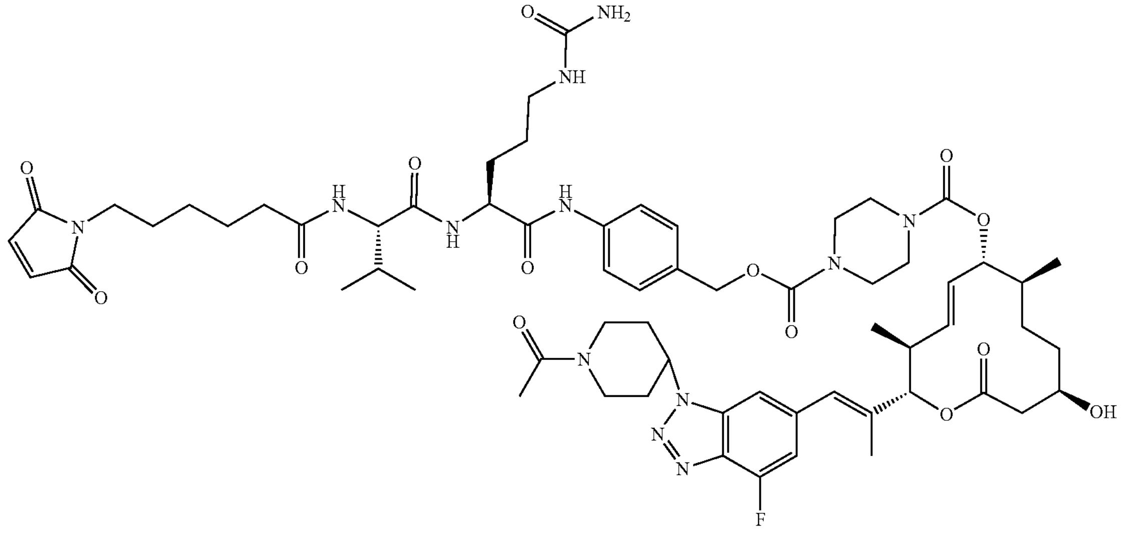 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]

General procedure 1 (outlined in section 1.3.1) was employed to synthesize 1-((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)-5-ureidopentanamido)benzyl) piperazine-1,4-dicarboxylate (30 mg, 0.024 mmol, 39.2% yield). LC/MS (ESI, m/z), 1254.5 $[M+H]^+$.

$^1$H-NMR (400 MHz, DMSO-d6): δ ppm 0.75-1.00 (m, 12H), 1.06-1.26 (m, 4H), 1.26-1.77 (m, 13H), 1.75-2.02 (m, 7H), 2.08 (s, 8H), 2.23-2.35 (m, 2H), 2.54-2.70 (m, 2H), 2.78-3.10 (m, 4H), 3.36 (br s, 13H), 3.66-3.79 (m, 1H), 3.95-4.08 (m, 1H), 4.11-4.25 (m, 1H), 4.28-4.46 (m, 1H), 4.46-4.58 (m, 1H), 4.58-4.66 (m, 1H), 4.66-4.77 (m, 1H), 5.01 (s, 3H), 5.14-5.27 (m, 1H), 5.39 (s, 4H), 5.71-5.79 (m, 1H), 5.87-6.00 (m, 1H), 6.63-6.75 (m, 1H), 6.99 (s, 2H), 7.13-7.24 (m, 1H), 7.24-7.34 (m, 2H), 7.52-7.62 (m, 2H), 7.65-7.74 (m, 1H), 7.75-7.82 (m, 1H), 7.98-8.13 (m, 1H).

1.3.1.7 ADL1-D33

D33

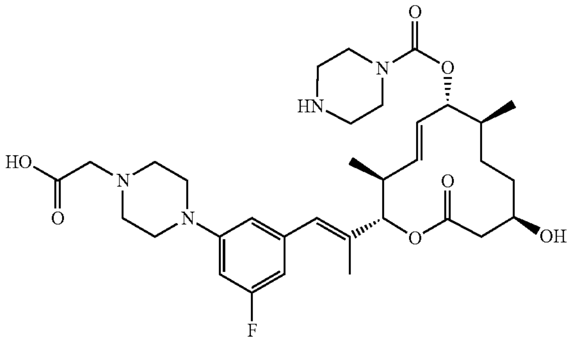 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCNCC2)/C=C/[C@@H]1C]

To a stirred solution of (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate (27 mg, 0.042 mmol) in $THF/H_2O$ (3 mL/1 mL) at 0° C. was added LiOH, and the reaction mixture was allowed to slowly warm to 25° C. (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate was synthesized using procedures outlined in International Application No. PCT/US2019/026992 (see, e.g., Procedures 17 and 19), which is incorporated herein by reference. After 6 hours, the reaction mixture was neutralized with phosphate buffer ($NaH_2PO_4$, 1.0 M, 3 mL) and the phases were separated. The aqueous layer was extracted with ethyl acetate (3×2 mL), and the combined organic layers were dried with anhydrous sodium sulfate and concentrated in vacuo. Reversed phase column chromatography afforded the titled compound (19.4 mg, 0.031 mmol, 73.4% yield). LC/MS (ESI, m/z), 631.4 $[M+H]^+$.

$^1$H-NMR (400 MHz, $CHCl_3$-d): δ ppm 0.85-1.16 (m, 2H) 1.23-1.52 (m, 1H) 1.57-1.77 (m, 1H) 1.87 (s, 1H) 1.92-2.13 (m, 1H) 2.35-2.55 (m, 1H) 2.50-2.74 (m, 1H) 3.11 (br s, 1H) 3.36-3.54 (m, 2H) 3.64 (br d, J=10.42 Hz, 2H) 3.77-3.90 (m, 1H) 4.76 (br s, 4H) 5.07-5.19 (m, 1H) 5.38-5.68 (m, 1H) 6.40-6.76 (m, 1H) 8.02-8.66 (m, 1H).

ADL1-D33

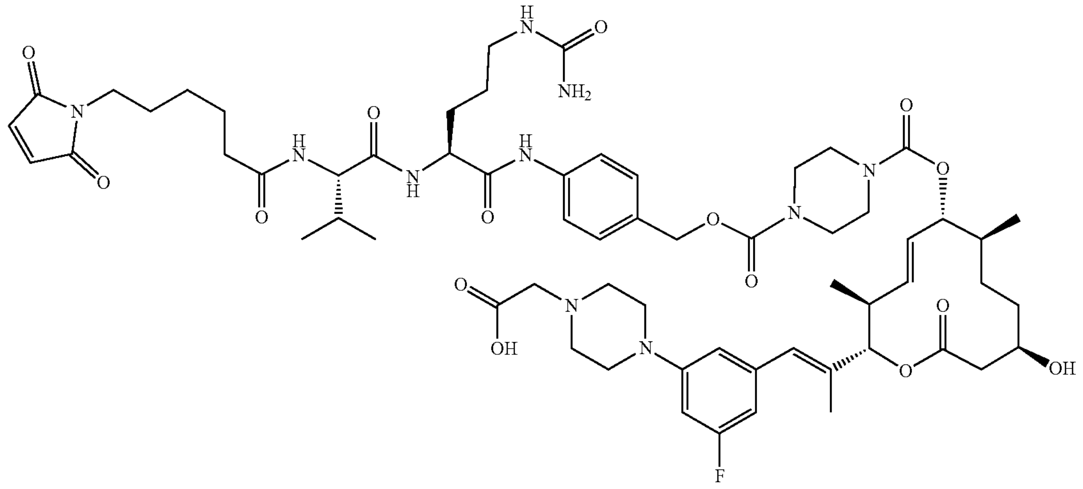 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

Linker-Payload (ADL1-D33): To 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (17 mg, 0.023 mmol) in DMF (714 μL, 9.217 mmol) was added Hunig's base (12.07 μL, 0.069 mmol). The reaction mixture was cooled to 0° C., and added 2-(4-(3-fluoro-5-((E)-2-((2S,3S,6R,7S,10R,E)-10-hydroxy-3,7-dimethyl-12-oxo-6-((piperazine-1-carbonyl)oxy)oxacyclododec-4-en-2-yl)prop-1-en-1-yl)phenyl)piperazin-1-yl) acetic acid (16.71 mg, 0.026 mmol). The reaction mixture was stirred at RT until LC/MS showed the reaction complete. The reaction mixture was concentrated in vacuo. Flash chromatography on silica gel and further HPLC purification gave the titled compound (13.5 mg, 10.98 μmol, 47.7% yield). LC/MS (ESI, m/z), 1229.5 $[M+H]^+$.

$^1$H-NMR (400 MHz, MeOH-$d_4$): δ ppm 0.92-0.99 (m, 10H) 1.01 (d, J=6.78 Hz, 3H) 1.24-1.46 (m, 9H) 1.52-1.70 (m, 10H) 1.70-1.82 (m, 1H) 1.87 (d, J=1.00 Hz, 4H) 1.89-2.00 (m, 2H) 2.01-2.23 (m, 2H) 2.27 (t, J=7.40 Hz, 2H) 2.46 (dd, J=14.31, 5.27 Hz, 1H) 2.57-2.71 (m, 2H) 2.86 (d, J=0.63 Hz, 1H) 3.00 (s, 1H) 3.06-3.27 (m, 4H) 3.35 (s, 5H) 3.41-3.53 (m, 19H) 3.66 (s, 2H) 3.76-3.90 (m, 1H) 4.07-4.21 (m, 1H) 4.39-4.69 (m, 37H) 5.09 (s, 3H) 5.13 (d, J=10.54 Hz, 1H) 5.52 (dd, J=14.56, 9.03 Hz, 2H) 6.55 (br s, 2H) 6.69 (d, J=1.38 Hz, 2H) 7.33 (d, J=8.66 Hz, 2H) 7.59 (d, J=8.53 Hz, 2H) 7.88-8.04 (m, 1H) 8.16-8.33 (m, 1H).

1.3.2 ADL1-D4, ADL1-D5, ADL21-D4, ADL22-D4, ADL23-D4, ADL13-D4

1.3.2.1 General Procedure for Preparation of D4 and D5

The 4-step procedure outlined below was employed to synthesize the title compounds.

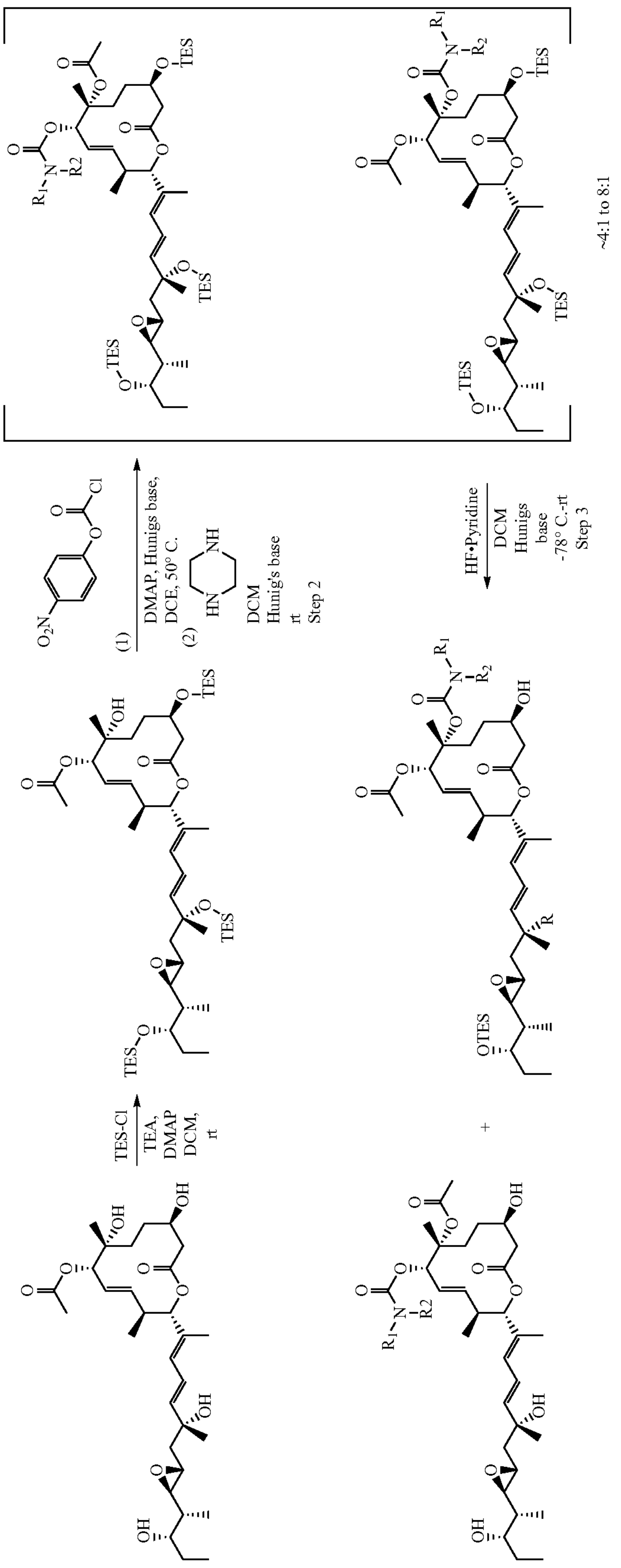
TES-Cl
TEA, DMAP DCM, rt
(1)
DMAP, Hunigs base, DCE, 50° C.
(2)
DCM Hunig's base rt Step 2
HF•Pyridine DCM Hunigs base -78° C.-rt Step 3
+
~4:1 to 8:1

Step 2

To a solution of tri-TES Pladenolide D (1.0 equiv.) in 1,2-dichloroethane (0.2 M) at 20° C. was added DMAP (1.5 equiv.), triethylamine (30 equiv.) and 4-Nitrophenyl chloroformate (10 equiv.). The mixture was stirred at 40° C. for 4 days, and then for 2 h at 60° C. The reaction mixture was diluted with EtOAc and washed with water, then the layers were separated, and the aqueous layer was extracted with EtOAc (2×). The combined organic extracts were successively washed with water and brine, dried over magnesium sulfate, filtered and concentrated in vacuo. The resulting residue was purified by silica gel chromatography (EtOAc in Hexane) to afford the intermediate carbonate. Carbonate (1.0 equiv.), DCM (0.2M), triethylamine (3.0 equiv.), and amine (2.0 equiv.) were combined and stirred at RT for 1 hour. The resulting mixture was concentrated in vacuo and chromatographed (DCM/MeOH) to afford the carbamate intermediate as a mixture of regioisomers.

Step 3

The mixture of regioisomeric carbamates obtained in Step 2 (1.0 equiv.) was dissolved in DCM (0.04 M). Hunig's base (124 equiv.) was added and the resulting mixture was cooled to −78° C. HF·Pyridine (30 equiv.) was added dropwise and the mixture was warmed to rt and stirred overnight at rt. The mixture was then cooled to −78° C. and saturated sodium bicarbonate was added dropwise to the reaction mixture and the mixture was warmed to rt. The organic layers were partioned and the aqueous layer was extracted with DCM (3×). The combined organic layers were dried over anhydrous sodium sulfate, filtered, and concentrated in vacuo. The resulting residue was subjected to reverse-phase HPLC purification to afford each of desired regioisomeric products.

D5

The title compound was prepared using 2,5-diazabicyclo[2.2.1]heptane in step 2 via the general procedure 1.3.2.1 step 2 & 3

Step 2

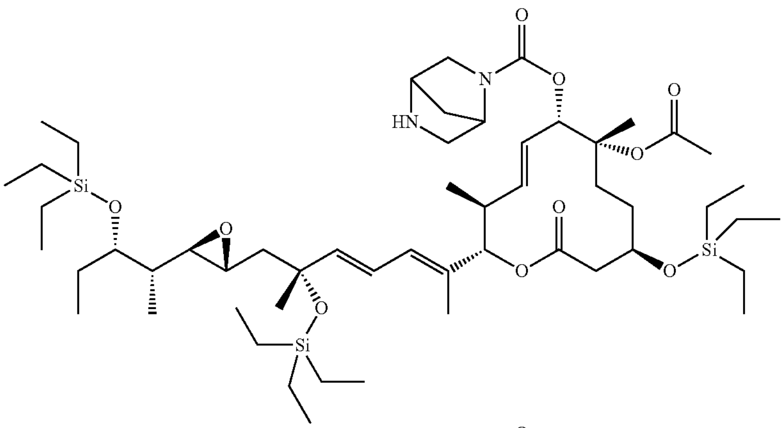

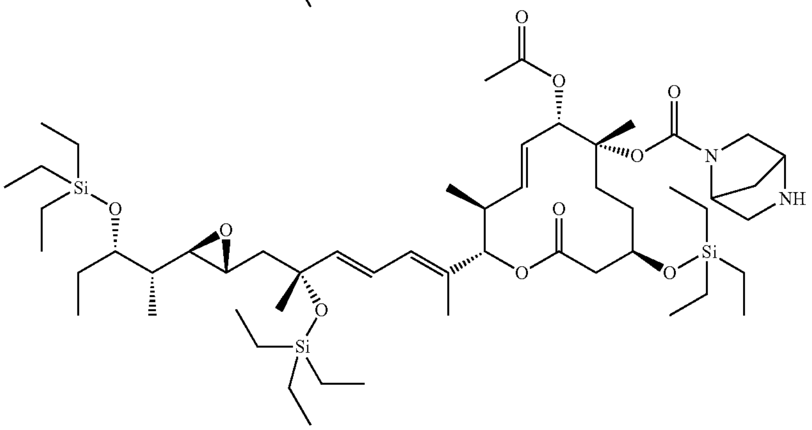

A mixture of (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 2,5-diazabicyclo[2.2.1]heptane-2-carboxylate and (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl 2,5-diazabicyclo[2.2.1]heptane-2-carboxylate was obtained (21.7 mg, 45.1%) as a Colorless oil. LCMS (ESI, m/z), $[M+H]^+$ 1020.6

$^1$H NMR (400 MHz, METHANOL-d) δ ppm 0.61-0.70 (m, 19H) 0.82-0.95 (m, 10H) 0.95-1.04 (m, 29H) 1.23 (br dd, J=7.15, 4.64 Hz, 1H)1.30 (s, 1H) 1.42-1.64 (m, 12H) 1.78 (s, 4H) 1.88-2.01 (m, 2H) 2.06 (br d, J=10.92 Hz, 3H) 2.14 (br s, 1H) 2.43 (br d, J=4.64 Hz, 2H) 2.49 (br s, 1H) 2.63 (dd, J=8.16, 2.13 Hz, 2H) 2.86-2.91 (m, 1H) 3.47-3.66

(m, 2H) 3.76 (td, J=6.37, 3.33 Hz, 1H) 3.95 (br d, J=4.27 Hz, 1H) 4.34 (br s, 1H) 6.15 (br d, J=10.92 Hz, 1H) 6.52 (dd, J=15.12, 10.98 Hz, 1H)

Step 3

D5

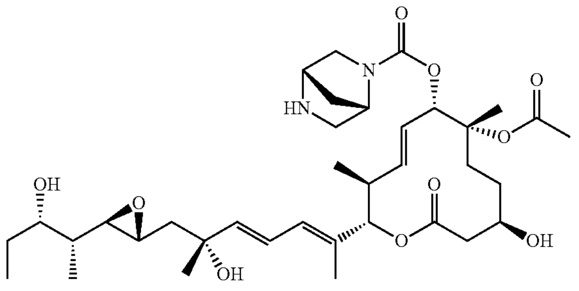 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2C[C@@H]3C[C@H]2CN3)/C=C/[C@@H]1C]

HPLC purification afforded (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl (1S,4S)-2,5-diazabicyclo[2.2.1]heptane-2-carboxylate (5 mg, 34.7%) as a white solid. LCMS (ESI, m/z), $[M+H]^+$ 677.6

$^1$H NMR (400 MHz, METHANOL-d4) δ ppm 0.85-0.98 (m, 9H) 1.25 (td, J=7.40, 4.14 Hz, 1H) 1.34 (s, 3H) 1.42-1.69 (m, 9H) 1.79 (s, 4H) 1.82-1.96 (m, 2H) 2.04 (d, J=9.29 Hz, 3H) 2.33 (br d, J=10.04 Hz, 1H) 2.47-2.54 (m, 2H) 2.57-2.72 (m, 2H) 2.87-2.92 (m, 1H) 3.03 (br s, 2H) 3.33-3.43 (m, 2H) 3.43-3.57 (m, 2H) 3.77-3.84 (m, 1H) 3.86-3.94 (m, 1H) 4.50 (br s, 1H) 4.97-5.11 (m, 2H) 5.60-5.68 (m, 1H) 5.73-5.82 (m, 1H) 5.88 (d, J=15.31 Hz, 1H) 6.15 (br d, J=11.04 Hz, 1H) 6.53 (dd, J=15.25, 10.98 Hz, 1H) 8.54 (s, 1H)

D4

The title compound was prepared using piperazine in step 2 via the general procedure 1.3.2.1 step 2 & 3

Step 2

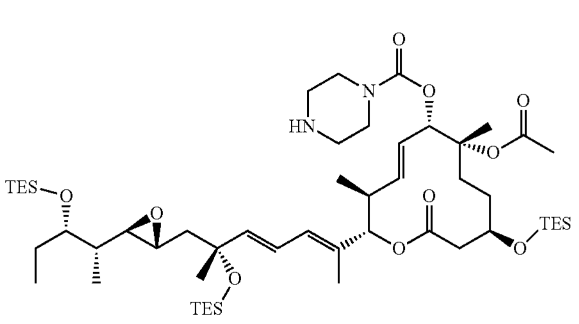

General procedure 1.3.2.1, step 2 employing piperazine afforded (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.0 g, 0.844 mmol, 81% yield). LC/MS (ESI, m/z), 1008.1 $[M+H]^+$.

Step 3: D4

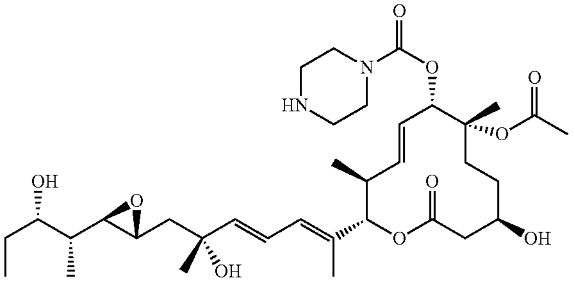 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCNCC2)/C=C/[C@@H]1C]

HPLC purification afforded (2S,3S,6S,7R,10R,E)-7-acetoxy-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (225 mg, 36.8%). LC/MS (ESI, m/z), 665.6 $[M+H]^+$.

$^1$H-NMR (400 MHz, $CHCl_3$-d): δ ppm 0.87-0.92 (m, 6H) 0.94 (t, J=7.40 Hz, 3H) 1.16-1.31 (m, 1H) 1.35 (s, 3H) 1.40-1.56 (m, 4H) 1.59 (s, 3H) 1.66 (br dd, J=14.68, 7.03 Hz, 3H) 1.76-1.80 (m, 3H) 1.87 (dd, J=14.12, 5.46 Hz, 1H) 2.05 (s, 3H) 2.30-2.41 (m, 1H) 2.50 (d, J=3.76 Hz, 2H) 2.56-2.72 (m, 2H) 2.90 (br d, J=2.01 Hz, 1H) 3.19 (br t, J=5.14 Hz, 4H) 3.50-3.59 (m, 1H) 3.71 (br s, 4H) 3.77-3.89 (m, 1H) 5.01-5.13 (m, 2H) 5.58-5.71 (m, 1H) 5.71-5.81 (m, 1H) 5.88 (d, J=15.31 Hz, 1H) 6.15 (br d, J=10.79 Hz, 1H) 6.53 (dd, J=15.18, 10.92 Hz, 1H).

ADL1-D4

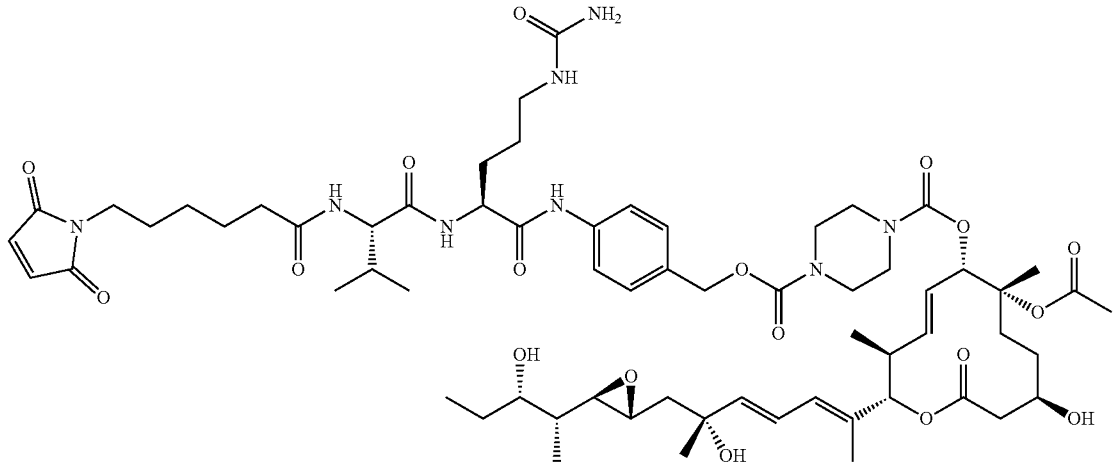 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

General procedure 1 (1.3.1) was employed for the preparation of ADL1-D4. Flash chromatography afforded ADL1-D4 (30.5 mg, 0.024 mmol, 77% yield).

LC/MS (ESI, m/z), 1263.8 $[M+H]^+$.

$^1$H-NMR (400 MHz, MeOH-$d_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

ADL1-D5

General procedure 1 (1.3.1) was employed for the preparation of ADL1-D5 using D5. Flash chromatography afforded (14 mg, 51.6% yield). LCMS (ESI, m/z), 1276.43 $[M+H]^+$ $^1$H NMR (400 MHz, METHANOL-d4) δ ppm 0.86-1.00 (m, 16H) 1.23-1.40 (m, 7H) 1.42-1.69 (m, 16H) 1.73-1.80 (m, 4H) 1.84-1.96 (m, 4H) 1.98-2.10 (m, 4H) 2.27 (t, J=7.40 Hz, 2H) 2.31-2.41 (m, 1H) 2.50 (br d, J=3.39 Hz, 2H) 2.56-2.64 (m, 1H) 2.64-2.72 (m, 1H) 2.80-2.93 (m, 1H) 3.12 (br d, J=6.90 Hz, 1H) 3.16-3.26 (m, 1H) 3.35-3.56 (m, 7H) 3.76-3.86 (m, 1H) 4.16 (d, J=7.40 Hz, 1H) 4.48-4.58 (m, 3H) 4.93-5.16 (m, 4H) 5.65 (br d, J=9.91 Hz, 1H) 5.70-5.82 (m, 1H) 5.88 (d, J=15.18 Hz, 1H) 6.14 (br d, J=11.04 Hz, 1H) 6.50-6.58 (m, 1H), 6.79 (s, 2H) 7.26-7.36 (m, 2H) 7.56-7.63 (m, 2H)

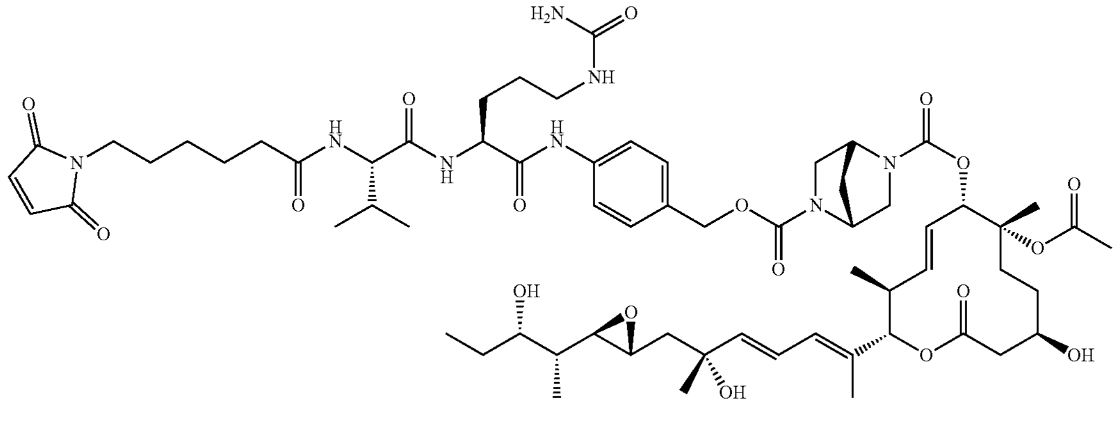

1.3.3 Synthesis of ADL22-D4

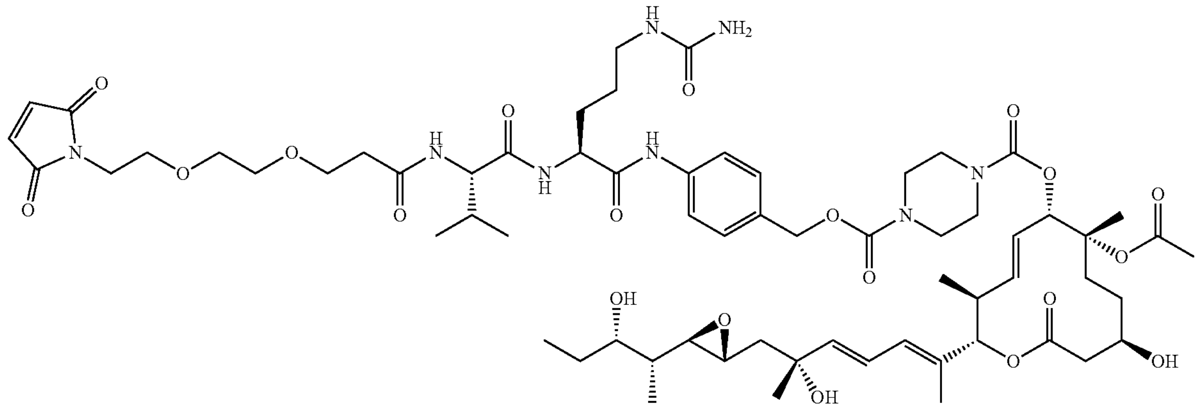 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCOCCOCCN4C(=O)C=CC4=O)C(C)C)cc3)CC2)/C=C/[C@@H]1C]

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (12 mg, 0.018 mmol) in DMF (2 mL) was added 4-((2S,5S)-15-(2,5-dioxo-2,5-dihydro-1H-pyrrol-1-yl)-5-isopropyl-4,7-dioxo-2-(3-ureidopropyl)-10,13-dioxa-3,6-diazapentadecanamido)benzyl (4-nitrophenyl) carbonate (16.98 mg, 0.022 mmol) and Hunig's base (7.00 mg, 0.054 mmol). The mixture was stirred for 1 h at 20° C. The mixture was concentrated in vacuo directly on to silica gel and purified by column chromatography (MeOH/DCM 0-20%) to provide 1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((2S,5S)-15-(2,5-dioxo-2,5-dihydro-1H-pyrrol-1-yl)-5-isopropyl-4,7-dioxo-2-(3-ureidopropyl)-10,13-dioxa-3,6-diazapentadecanamido)benzyl) piperazine-1,4-dicarboxylate (12 mg, 9.16 μmol, 50.8% yield) as a white solid. LCMS (ESI, m/z), 1310.2 $[M+H]^+$ Chemical Formula: C65H96N8O20 Molecular Weight: 1309.52

$^1H$ NMR (400 MHz, DMSO-d6) δ ppm 0.73-0.89 (m, 17H) 1.03-1.13 (m, 1H) 1.21-1.25 (m, 4H) 1.25-1.40 (m, 5H) 1.42-1.47 (m, 4H) 1.48, (br s, 3H) 1.69 (s, 4H) 1.73-1.83 (m, 1H) 1.99 (s, 2H) 2.10-2.25 (m, 1H) 2.36 (br s, 3H) 2.40-2.48 (m, 2H) 2.54-2.66 (m, 2H) 2.72-2.80, (m, 1H) 2.88-3.08 (m, 2H) 3.34-3.44 (m, 9H) 3.44-3.48 (m, 3H) 3.48-3.52 (m, 2H) 3.52-3.59 (m, 3H) 3.64-3.75 (m, 1H) 4.24 (s, 1H), 4.40 (br d, J=5.65 Hz, 2H) 4.62 (d, J=5.02 Hz, 1H) 4.80-4.85 (m, 1H) 4.90 (br d, J=9.03 Hz, 2H) 5.01 (s, 2H) 5.40 (s, 2H) 5.48-5.57 (m, 1H), 5.66-5.76 (m, 1H) 5.81-5.91 (m, 1H) 5.94-6.01 (m, 1H) 6.02-6.11 (m, 1H) 6.36-6.45 (m, 1H) 7.02 (s, 2H) 7.27-7.33 (m, 2H) 7.58 (s, 2H) 7.81-7.89 (m, 1H) 8.11 (br d, J=7.40 Hz, 1H) 9.96-10.02 (m, 1H)

1.3.4 General Procedure for Synthesis of ADL21-D12, ADL21-D1, ADL21-D4

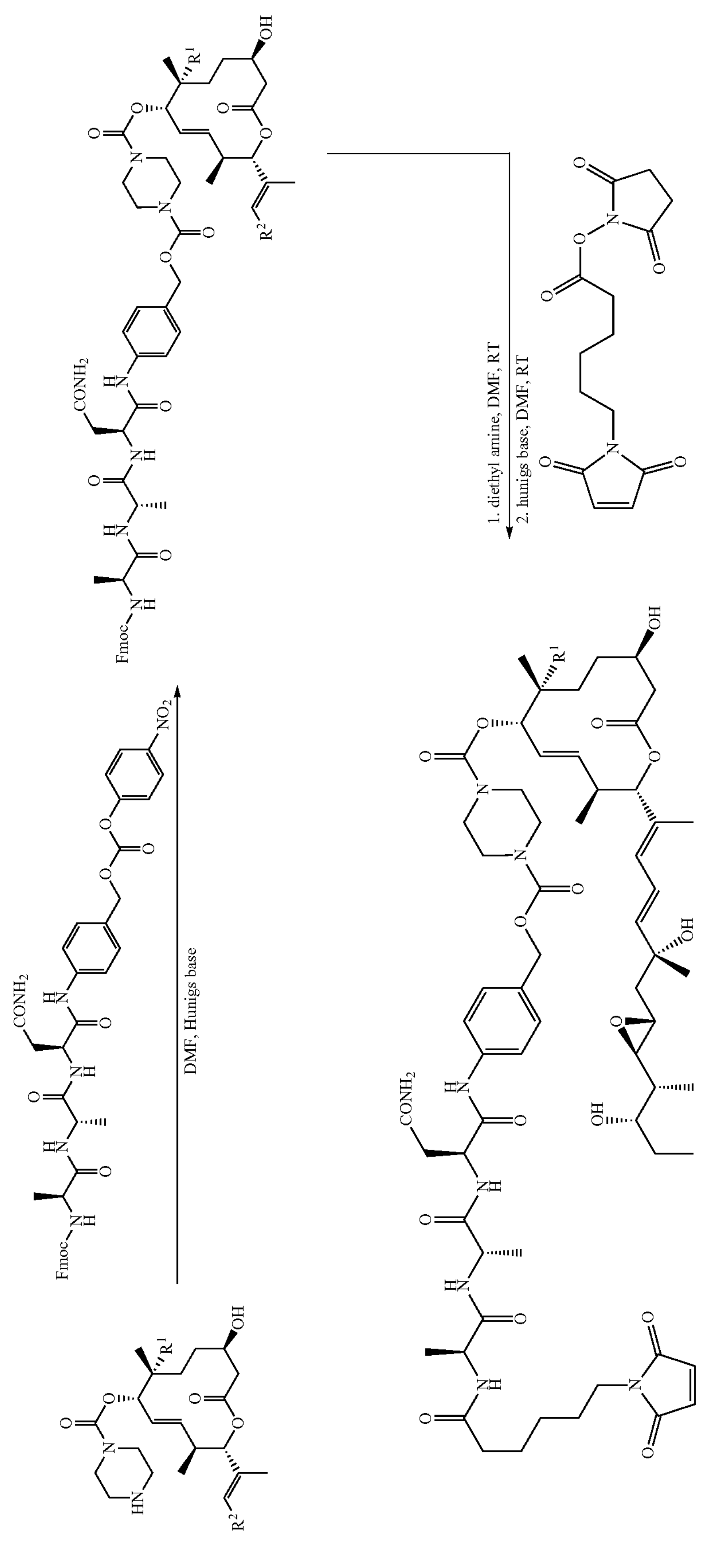
DMF, Hunigs base
1. diethyl amine, DMF, RT
2. hunigs base, DMF, RT

Step 1

The Payload (1.0 equiv) and (9H-fluoren-9-yl)methyl ((S)-1-(((S)-1-(((S)-4-amino-1-((4-((((4-nitrophenoxy)carbonyl)oxy)methyl)phenyl)amino)-1,4-dioxobutan-2-yl)amino)-1-oxopropan-2-yl)amino)-1-oxopropan-2-yl)carbamate (1.0 equiv.) were dissolved in DMF (0.1M) and Hunig's Base (3.0 equiv.) was added. The reaction mixture was stirred at RT for 30 minutes after which the reaction was concentrated to in vacuo and the resulting residue was chromatographed (MeOH/DCM) to afford the desired product.

Step 2 and 3 fmoc-Ala-Ala-Aspargine PABC payload (1.0 equiv.), was dissolved in N,N-dimethylformamide (0.05 M), then diethylamine (6.0 equiv.) was added. The reaction was stirred at RT for 1 hour and the mixture evaporated to dryness. The crude product was diluted with N,N-dimethylformamide (0.05 M). 2,5-dioxopyrrolidin-1-yl 6-(2,5-dioxo-2,5-dihydro-1H-pyrrol-1-yl)hexanoate (1.2 equiv.) and Hunig's base (2.5 equiv.) were added to the mixture and stirred at RT for 1 ixture was then concentrated in vacuo and the resulting residue was purified via reverse-phour. The mhase HPLC to afford the desired Maleimidocaprolyl Ala-Ala-Aspargine PABC linker payload.

1.3.4.1 ADL21-D1

Step 1

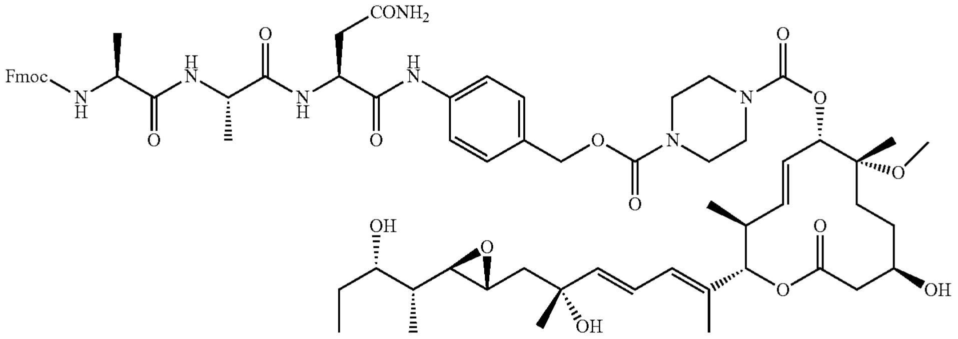

1-(4-((5S,8S,11S)-11-(2-amino-2-oxoethyl)-1-(9H-fluoren-9-yl)-5,8-dimethyl-3,6,9-trioxo-2-oxa-4,7,10-triazadodecan-12-amido)benzyl) 4-((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (140.2 mg, 71.9%) LCMS (ESI, m/z) 1265.6 $[M+H]^+$ Chemical Formula: $C_{67}H_{89}N_7O_{17}$ Molecular Weight: 1264.48

Steps 2 and 3

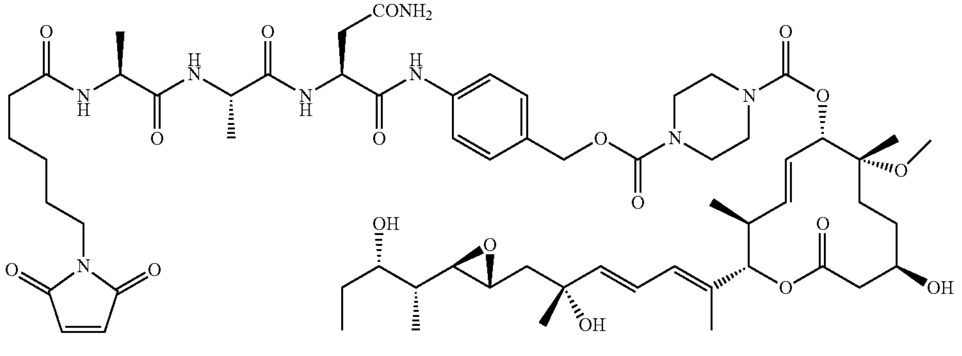 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)/C=C/[C@@H]1C]

1-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) 4-((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (49.1 mg, 35.8%) LCMS (ESI, m/z) 1258.19 $[M+Na]^+$ $^1$H NMR (400 MHz, METHANOL-d4) δ ppm 0.85-0.98 (m, 10H) 1.22 (s, 4H) 1.26-1.45 (m, 14H) 1.45-1.69 (m, 12H) 1.79 (s, 3H) 1.90 (s, 2H) 2.20-2.27 (m, 2H) 2.52 (br dd, J=10.10, 3.70 Hz, 3H) 2.67 (br d, J=2.13 Hz, 1H) 2.85 (t, J=6.15 Hz, 3H) 3.14 (t, J=1.57 Hz, 1H) 3.41-3.57, (m, 14H) 3.78-3.88 (m, 1H) 4.27 (dd, J=12.36, 7.09 Hz, 2H) 4.77 (s, 1H) 4.97-5.13 (m, 6H) 5.51-5.64 (m, 1H) 5.72 (br d, J=9.66 Hz, 1H), 5.88 (d, J=15.43 Hz, 1H) 6.12-6.17 (m, 1H) 6.47-6.61 (m, 1H) 6.79 (s, 2H) 7.33 (m, J=8.66 Hz, 2H), 7.68 (m, J=8.66 Hz, 2H)

1.3.4.2 ADL21-D4

Step 1

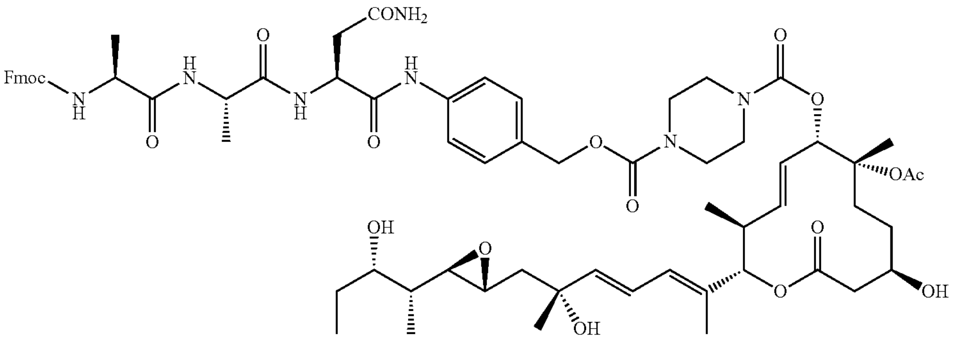

1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((5S,8S,11S)-11-(2-amino-2-oxoethyl)-1-(9H-fluoren-9-yl)-5,8-dimethyl-3,6,9-trioxo-2-oxa-4,7,10-triazadodecan-12-amido)benzyl) piperazine-1,4-dicarboxylate (125 mg, 85.6%) LCMS (ESI, m/z) 1293.4 $[M+H]^+$ Steps 2 and 3

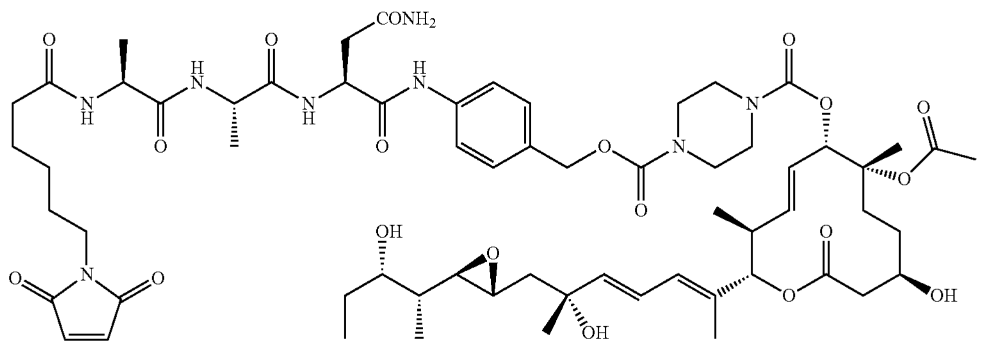 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)/C=C/[C@@H]1C]

1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) piperazine-1,4-dicarboxylate (35 mg, 80%) LCMS (ESI, m/z) 1285.0 $[M+Na]^+$ $^1$H NMR (400 MHz, DMSO-d6) δ ppm 0.71-0.87 (m, 9H) 1.04-1.12 (m, 1H) 1.14-1.26 (m, 13H) 1.27-1.40 (m, 3H) 1.40-1.52 (m, 9H) 1.52-1.62 (m, 1H) 1.69 (s, 3H) 1.74-1.83 (m, 1H) 1.99 (d, J=4.27 Hz, 4H) 2.03-2.14 (m, 2H) 2.15-2.26 (m, 1H) 2.31-2.41 (m, 2H) 2.54-2.65 (m, 4H) 2.72-2.80 (m, 1H) 3.17 (d, J=5.27 Hz, 3H) 3.36 (br s, 9H) 3.63-3.74 (m, 1H) 3.99-4.12 (m, 2H) 4.14-4.22 (m, 1H) 4.23-4.30 (m, 1H) 4.40 (d, J=5.65 Hz, 1H) 4.55-4.65 (m, 2H) 4.82 (s, 1H) 4.87-4.93 (m, 2H) 5.01 (s, 2H) 5.47-5.57 (m, 1H) 5.66-5.77 (m, 1H) 6.01-6.09 (m, 1H) 6.35-6.45 (m, 1H) 6.89-6.96 (m, 1H) 6.99 (s, 2H) 7.30 (d, J=8.66 Hz, 2H) 7.36-7.42 (m, 1H) 7.62 (s, 2H) 7.97-8.21 (m, 3H), 9.62-9.72 (m, 1H).

1.3.5 ADL21-D12

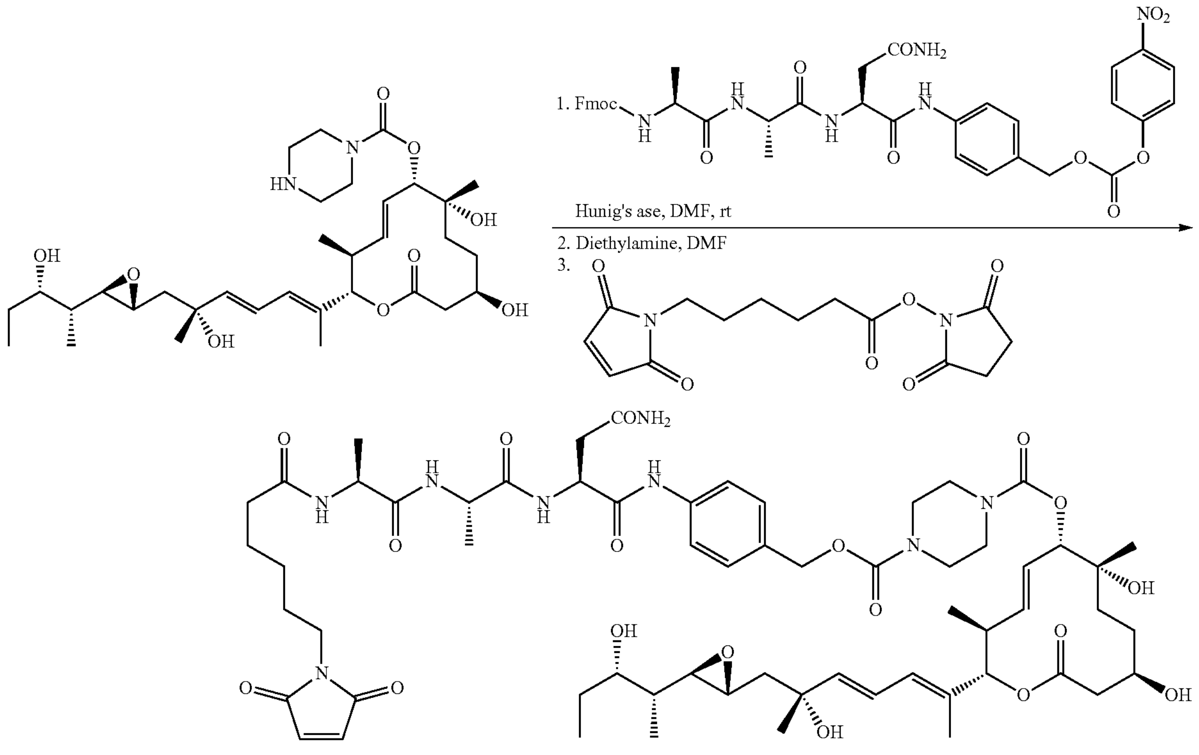

To a solution of (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (50 mg, 0.08 mmol) in DMF (1 mL) was added (9H-fluoren-9-yl)methyl ((S)-1-(((S)-1-(((S)-4-amino-1-((4-((((4-nitrophenoxy)carbonyl)oxy)methyl)phenyl)amino)-1,4-dioxobutan-2-yl)amino)-1-oxopropan-2-yl)amino)-1-oxopropan-2-yl)carbamate (73.9 mg, 0.096 mmol) followed by N-ethyl-N-isopropylpropan-2-amine (104 mg, 0.803 mmol). The reaction mixture was stirred for 1 h. The reaction mixture was concentrated to dryness and purified by silica gel column chromatography. The fractions containing the desired compound were concentrated to provide a clear oil that was carried on directly to the following step assuming 100% yield. The oil obtained was then dissolved in DMF (2 mL) and charged with diethylamine (58.7 mg, 0.803 mmol). The resulting mixture was stirred 1 h at 20° C. and concentrated in vacuo. The residue residue was re-dissolved in DMF (1 mL) and then 2,5-dioxopyrrolidin-1-yl 6-(2,5-dioxo-2,5-dihydro-1H-pyrrol-1-yl)hexanoate (32.2 mg, 0.104 mmol) and N-ethyl-N-isopropylpropan-2-amine (104 mg, 0.803 mmol) were added. The resulting mixture was stirred for 1 h. The reaction mixture was concentrated to dryness and purified under reverse-phase HPLC to furnish 1-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) 4-((2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) piperazine-1,4-dicarboxylate (7.5 mg, 6.14 μmol, 7.65% yield) as a white solid. LCMS (ESI, m/z) 1222.28 $[M+H]^+$ 1.3.6 ADL21-D8

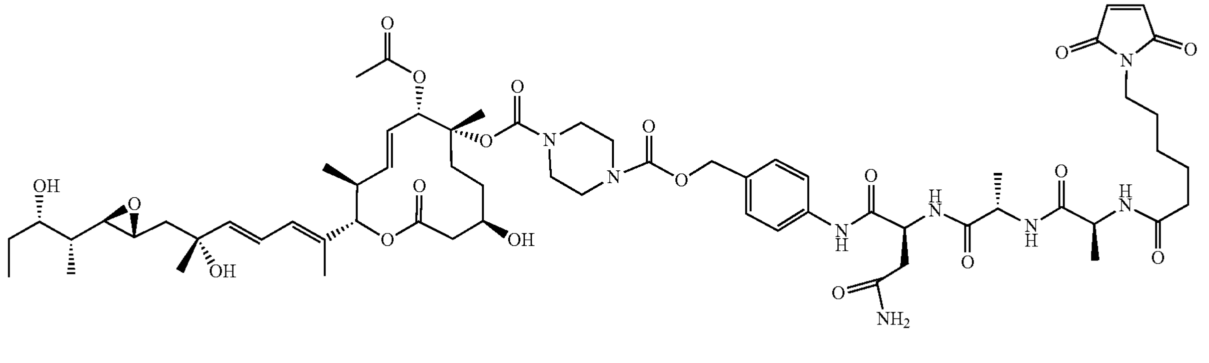 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)[C@@H](OC(C)=O)/C=C/[C@@H]1C]

To a solution of (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate (27.0 mg, 0.041 mmol) in DMF was added (9H-fluoren-9-yl)methyl ((S)-1-(((S)-1-(((S)-4-amino-1-((4((((4nitrophenoxy)carbonyl)oxy)methyl)phenyl)amino)-1,4-dioxobutan-2-yl)amino)-1-oxopropan-2-yl)amino)-1-oxopropan-2-yl)carbamate (40.5 mg, 0.053 mmol) followed Hunig's base (36.2 µl, 0.203 mmol). After stirring for 20 minutes at rt, the mixture was then concentrated in vacuo and the resulting residue was purified by column chromatography (0-20% MeOH/DCM) to afford the desired intermediate. The residue was then combined with DMF (2 mL) and diethylamine (29.7 mg, 0.406 mmol) and stirred for 20 minutes at rt. Subsequently, the mixture was concentrated in vacuo and the resulting residue was re-dissolved in DMF (2 ml) and treated with 2,5-dioxopyrrolidin-1-yl 6-(2,5-dioxo-2,5-dihydro-1H-pyrrol-1-yl)hexanoate (16.28 mg, 0.053 mmol) and Hunig's base (36.2 µl, 0.203 mmol). The resulting mixture was stirred for 20 minutes before concentrating to dryness and purifying the resulting residue by column chromatography with the intermediate eluting in a 0-20% MeOH/DCM gradient. The residue obtained was then subjected to reverese phase HPLC purification to afford 1-((2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl) 4-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) piperazine-1,4-dicarboxylate (3.5 mg, 2.77 µmol, 6.82% yield) isolated as a white solid. 1-((2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl) 4-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) piperazine-1,4-dicarboxylate (3.5 mg, 6.8%) LCMS (ESI, m/z) 1285.60 $[M+Na]^+$ $^1H$ NMR: 0.68-0.90 (m, 11H) 1.03-1.13 (m, 2H) 1.15-1.26 (m, 14H) 1.24-1.38 (m, 4H) 1.40-1.63 (m, 12H), 1.69 (s, 3H) 1.74-1.83 (m, 1H) 2.03 (s, 3H) 2.06-2.12 (m, 2H) 2.24-2.41 (m, 3H) 2.53-2.63 (m, 4H), 3.79-3.80 (m, 1H) 4.13-4.30 (m, 2H) 4.32-4.33 (m, 1H) 4.33-4.47 (m, 1H) 4.44-4.48 (m, 1H) 4.52-4.73 (m, 2H) 4.74-4.97 (m, 2H) 5.03 (s, 3H) 5.47-5.61 (m, 1H) 5.65-5.77 (m, 1H) 5.79-5.92 (m, 1H) 5.98-6.12 (m, 1H) 6.30-6.46 (m, 1H) 6.75-6.85 (m, 1H) 6.90-6.95 (m, 1H) 6.99 (s, 1H) 7.26-7.36 (m, 2H) 7.37-7.46 (m, 1H) 7.56-7.73 (m, 2H) 7.90-8.09 (m, 1H) 8.07-8.22 (m, 2H) 8.46 (s, 1H) 9.59-9.78 (m, 1H)

1.3.7 Preparation of DBCO-Val-Cit-pABC Linker-Payload, ADL25-D4

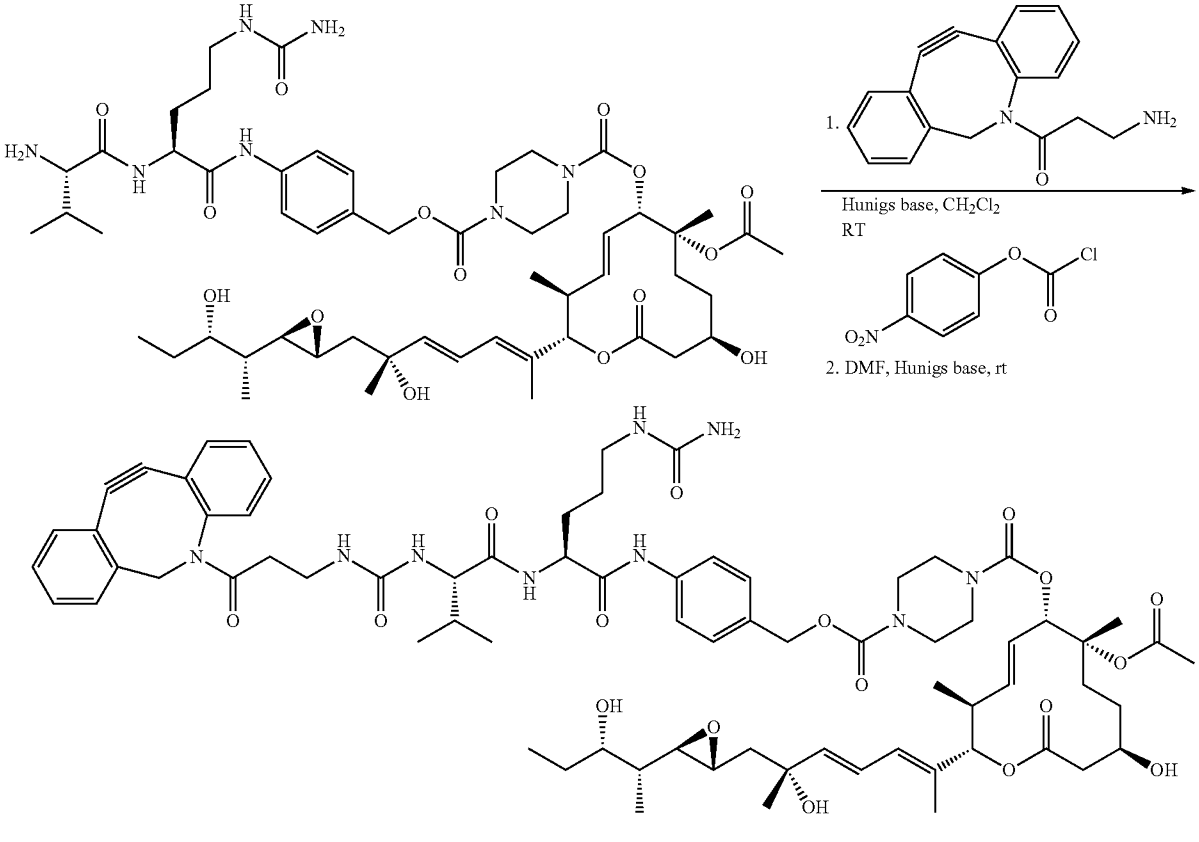

To a solution of 3-amino-1-(11,12-dihydrodibenzo[b,f]azocin-5(6H)-yl)propan-1-one (19.36 mg, 0.07 mmol) in DCM (5 mL) at 0° C. was added Hunig's base (10.26 mg, 0.079 mmol) followed by 4-nitrophenyl carbonochloridate (14.12 mg, 0.07 mmol). The reaction was warmed to 20° C. and stirred for 2 h. The mixture was then concentrated to dryness and diluted with DMF. The resulting mixture was charged Hunig's base (10.26 mg, 0.079 mmol) and 1-((2S, 3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((S)-2-((S)-2-amino-3-methylbutanamido)-5-ureidopentanamido)benzyl) piperazine-1,4-dicarboxylate (50 mg, 0.047 mmol) and stirred for 1 h. The mixture was then concentrated to dryness and purified by column chromatography followed by reverese-phase purification to afford 1-((2S,3S,6S,7R,10R, E)-7-acetoxy-10-hydroxy-2-((R,2E,4E)-6-hydroxy-7-((2R, 3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((9S,12S)-9-isopropyl-3,7,10-trioxo-12-(3-ureidopropyl)-2,6,8,11-tetraazatridecan-13-dibenzenecyclooctyneamido)benzyl) piperazine-1,4-dicarboxylate (5.3 mg, 8.27%) LCMS (ESI, m/z) 1372.7 $[M]^+$

1.3.8. Preparation of Maleimido-Glu-Val-Cit-pABC Linker-Payload

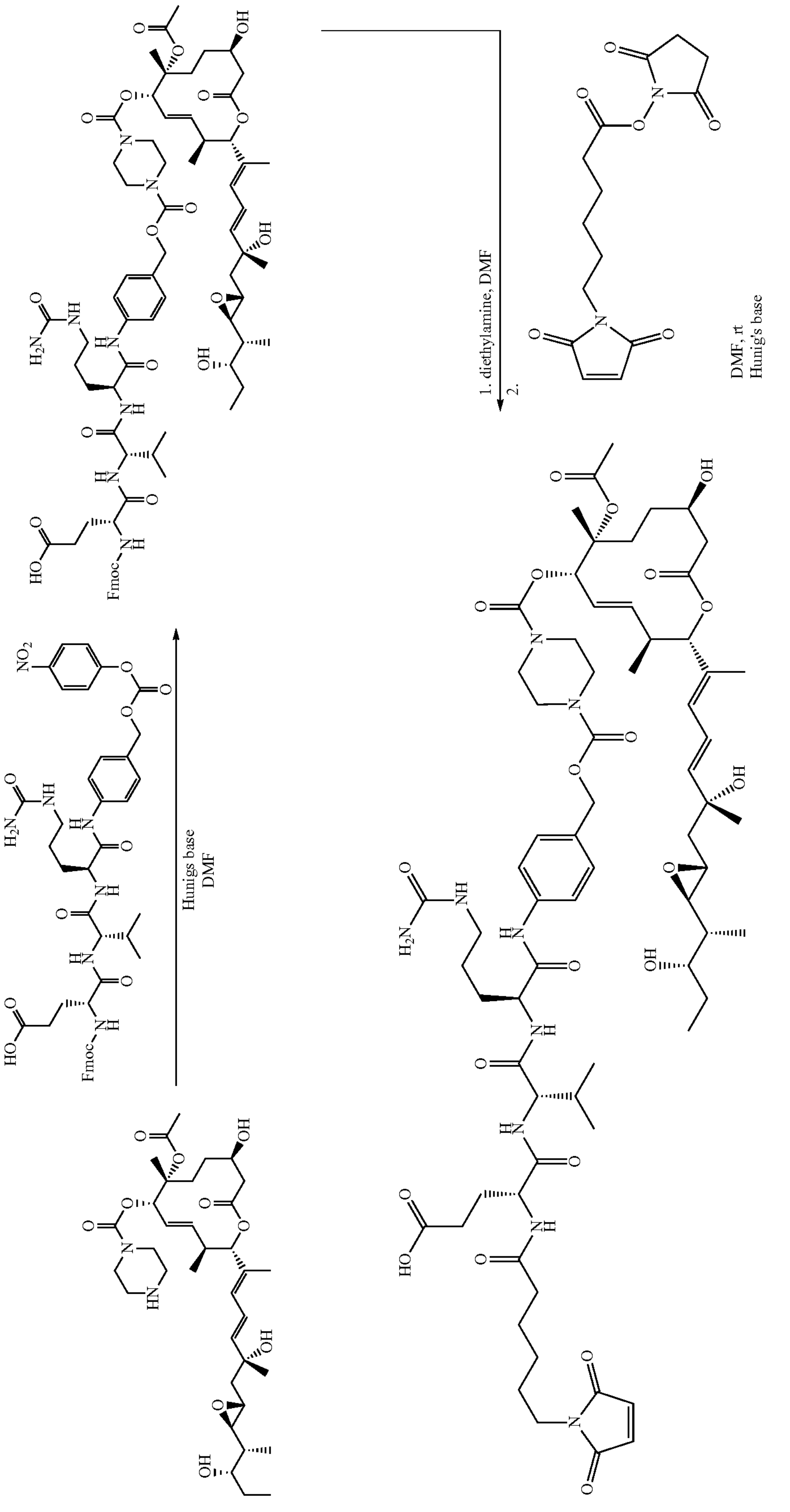
Hunigs base
DMF
1. diethylamine, DMF
2.
DMF, rt
Hunig's base

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (20 mg, 0.03 mmol) in DMF (1 mL) was added (S)-4-((((9H-fluoren-9-yl)methoxy)carbonyl)amino)-5-(((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)amino)-5-oxopentanoic acid (32.3 mg, 0.036 mmol) and Hunig's base (11.66 mg, 0.09 mmol) and stirred 1 h at 20° C. Diethylamine (110 mg, 1.504 mmol) was then added and the mixture was stirred for an additional 30 min at 20° C. The mixture was then diluted with ethyl acetate and concentrated in vacuo. The resulting residue was diluted with DMF (1 mL), 2,5-dioxopyrrolidin-1-yl-6-(2,5-dioxo-2,5-dihydro-1H-pyrrol-1-yl)hexanoate (13.91 mg, 0.045 mmol) and Hunig's base (11.66 mg, 0.09 mmol) and the reaction stirred 50 minutes. The reaction mixture was then diluted with ethyl acetate, concentrated to dryness and purified using reverse-phase HPLC to furnish (S)-5-(((S)-1-(((S)-1-((4-(((4-((((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)piperazine-1-carbonyl)oxy)methyl)phenyl)amino)-1-oxo-5-ureidopentan-2-yl)amino)-3-methyl-1-oxobutan-2-yl)amino)-4-(6-(2,5-dioxo-2,5-dihydro-1H-pyrrol-1-yl)hexanamido)-5-oxopentanoic acid (9.3 mg, 6.68 μmol, 22.20% yield) as a white solid; LCMS (ESI, m/z) 1393.4 $[M+H]^+$ $^1$H NMR (400 MHz, DMSO-d6) δ ppm 0.74-0.89 (m, 16H) 1.03-1.66 (m, 25H) 1.69 (s, 4H) 1.74-1.94 (m, 2H) 2.00 (s, 4H) 2.09 (br d, J=4.39 Hz, 2H) 2.21 (br d, J=7.53 Hz, 3H) 2.31-2.42 (m, 2H) 2.53-2.84 (m, 3H) 2.89-3.09 (m, 2H) 3.34-3.48 (m, 10H) 3.65-3.74 (m, 1H) 4.19, (dd, J=8.47, 6.59 Hz, 1H) 4.26-4.45 (m, 3H) 4.57-4.64 (m, 1H) 4.79-4.85 (m, 1H) 4.90 (br d, J=9.03 Hz, 2H) 5.01 (s, 2H) 5.43 (br s, 2H), 5.47-5.59 (m, 1H) 5.67-5.80 (m, 1H) 5.81-5.93 (m, 1H) 5.94-6.14 (m, 2H) 6.35-6.47 (m, 1H) 6.99 (s, 2H) 7.30 (d, J=8.66 Hz, 2H) 7.58, (d, J=8.53 Hz, 2H) 7.63-7.71 (m, 1H) 7.98-8.06 (m, 1H) 8.15-8.27 (m, 1H) 9.99-10.09 (m, 1H)

1.3.10. ADL1-D3, ADL10-D3

The payload D3 was prepared via the procedure given below

D3

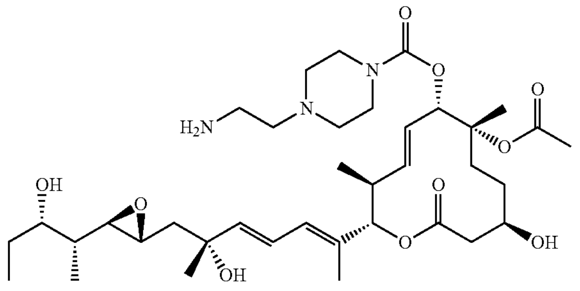 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCN)CC2)/C=C/[C@@H]1C]

To a mixture of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (55 mg, 0.083 mmol) in DCM (3 mL) was added (9H-fluoren-9-yl)methyl (2-oxoethyl)carbamate (46.5 mg, 0.165 mmol) and Sodium triacetoxy borohydride (52.6 mg, 0.248 mmol). The reaction was stirred for 20 minutes at rt. The reaction mixture was then concentrated to dryness and purified by silica gel column chromatography (0-10% MeOH/DCM). The purified material was dissolved in DMF (3 mL). The mixture was then charged with diethylamine (121 mg, 1.655 mmol) and stirred at rt. The mixture was then concentrated in vacuo and purified via reverse phase HPLC purification to afford (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (6 mg, 8.48 μmol, 10.25% yield) as a white solid.

LCMS (ESI, m/z), 708.2 $[M+H]^+$ $^1$H NMR (400 MHz, DMSO-d6) δ ppm 0.74-0.86 (m, 9H) 1.04-1.15 (m, 1H) 1.23 (s, 3H) 1.26-1.40 (m, 3H) 1.45 (s, 4H) 1.47-1.51 (m, 1H), 1.52-1.63 (m, 1H) 1.69 (s, 3H) 1.73-1.82 (m, 1H) 1.99 (s, 3H) 2.13-2.42 (m, 9H) 2.53-2.65 (m, 4H) 2.72-2.80 (m, 1H), 3.35-3.41 (m, 3H) 3.65-3.76 (m, 1H) 4.36-4.46 (m, 1H) 4.57-4.66 (m, 1H) 4.79-4.85 (m, 1H) 4.87-4.95 (m, 2H) 5.43-5.56 (m, 1H) 5.64-5.77 (m, 1H) 5.80-5.91 (m, 1H) 6.01-6.12 (m, 1H) 6.33-6.49 (m, 1H).

1.3.10.1 ADL10-D3

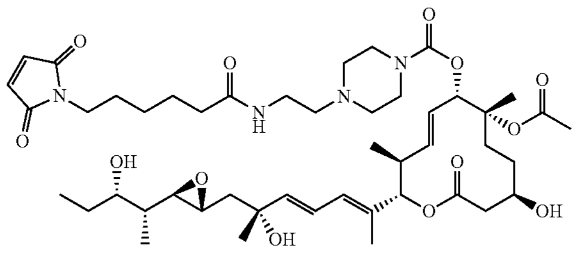 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCNC(=O)CCCCCN3C(=O)C=CC3=O)CC2)/C=C/[C@@H]1C]

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (40 mg, 0.057 mmol) in DMF (2 mL) was added 2,5-dioxopyrrolidin-1-yl 6-(2,5-dioxo-2,5-dihydro-1H-pyrrol-1-yl)hexanoate (27.9 mg, 0.09 mmol) followed by Hunig'a base (36.5 mg, 0.283 mmol) and stirred for 20 minutes. The resulting mixture was then concentrated onto silica gel and purified via column chromatography (0-20% MeOH/DCM) to provide (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-(6-(2,5-dioxo-2,5-dihydro-1H-pyrrol-1-yl)hexanamido)ethyl)piperazine-1-carboxylate (22 mg, 43.2% yield) as a yellowish solid. LCMS (ESI, m/z) 902.1 $[M+H]^+$ $^1$H NMR (400 MHz, DMSO-d6) δ ppm 0.73-0.89 (m, 10H) 0.99-1.29 (m, 10H) 1.30-1.38 (m, 2H) 1.40-1.49 (m, 9H) 1.52-1.64 (m, 1H), 1.69 (s, 3H) 1.74-1.83 (m, 1H) 1.93-2.07 (m, 5H) 2.34 (br d, J=16.94 Hz, 9H) 2.59 (s, 3H) 3.07-3.21 (m, 2H) 3.36 (br d, J=14.05 Hz, 3H) 3.66-3.78 (m, 1H) 4.37-4.45 (m, 1H) 4.57-4.66 (m, 1H) 4.79-4.86 (m, 1H) 4.87-4.97 (m, 2H) 5.46-5.57 (m, 1H) 5.66-5.75 (m, 1H) 5.81-5.91 (m, 1H) 5.99-6.13 (m, 1H) 6.31-6.47 (m, 1H) 7.00 (s, 2H) 7.62-7.71 (m, 1H)

1.3.10.2 ADL1-D3

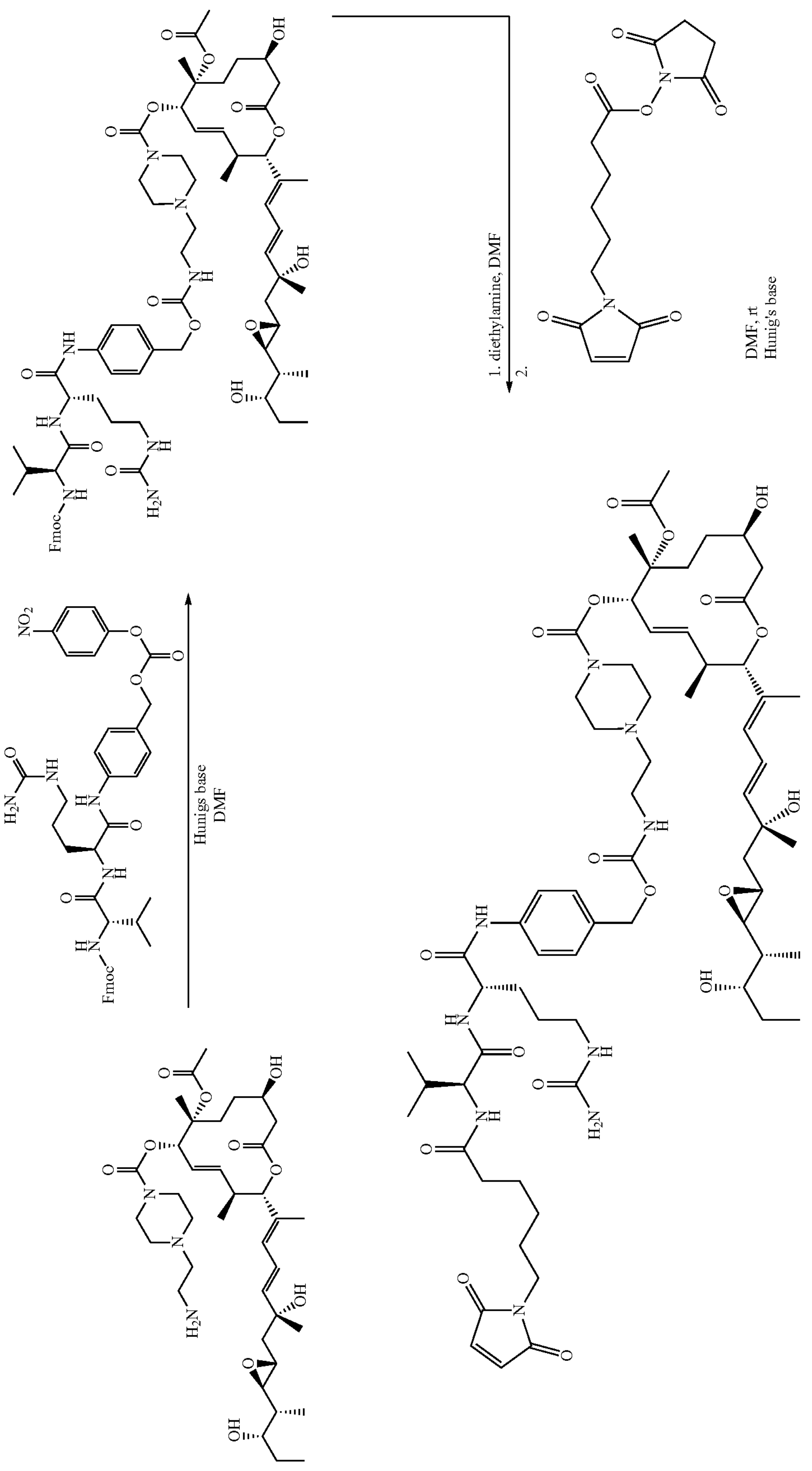
Hunigs base
DMF
1. diethylamine, DMF
2.
DMF, rt
Hunig's base

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (30 mg, 0.042 mmol) in DMF (2 mL) was added (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate (35.7 mg, 0.047 mmol) followed by Hunig's base (16.43 mg, 0.127 mmol) and mixture allowed to stir for 1 h. The resulting mixture was concentrated directly on to silica gel and purified by silica gel column chromatography to provide (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-((((9H-fluoren-9-yl)methoxy)carbonyl)amino)-3-methylbutanamido)-5-ureidopentanamido)benzyl)oxy)carbonyl)amino)ethyl)piperazine-1-carboxylate which was carried on directly to following step directly. To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-((((9H-fluoren-9-yl)methoxy)carbonyl)amino)-3-methylbutanamido)-5-ureidopentanamido)benzyl)oxy)carbonyl)amino)ethyl)piperazine-1-carboxylate (30 mg, 0.022 mmol) in DMF (2 mL) was added diethylamine (82 mg, 1.123 mmol) and mixture allowed to stir 1 h at 20° C. The resulting mixture was diluted with ethyl acetate and concentrated in vacuo. The resulting residue was then re-dissolved in DMF and charged with 2,5-dioxopyrrolidin-1-yl 6-(2,5-dioxo-2,5-dihydro-1H-pyrrol-1-yl)hexanoate (8.31 mg, 0.027 mmol) and Hunig's base (8.71 mg, 0.067 mmol). The resulting mixture stirred 1 h at 20° C. The solution was then concentrated on to silica gel and purified by column chromatography (0-20% MeOH/DCM) to provide (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethyl)piperazine-1-carboxylate (25 mg, 0.019 mmol, 85% yield) as a white solid; LC/MS (ESI, m/z), 1306.2 $[M]^+$.

$^1H$ NMR (400 MHz, DMSO-$d_6$) δ ppm 0.75-0.89 (m, 18H) 1.05-1.12 (m, 1H) 1.15-1.20 (m, 1H) 1.21-1.26 (m, 4H) 1.26-1.39 (m, 5H) 1.40-1.40 (m, 1H) 1.42-1.47 (m, 5H) 1.57 (br s, 3H) 1.69 (s, 4H) 1.73-1.81 (m, 1H) 1.92-1.98 (m, 1H) 1.99 (d, J=4.39 Hz, 4H) 2.14-2.26 (m, 1H) 2.29-2.42 (m, 4H) 2.42-2.47 (m, 1H) 2.53-2.64 (m, 2H) 2.73-2.78 (m, 1H) 2.88-3.08 (m, 2H) 3.35-3.60 (m, 19H) 3.65-3.75 (m, 1H) 4.22 (dd, J=8.47, 6.71 Hz, 1H) 4.32-4.45 (m, 2H) 4.60-4.65 (m, 1H) 4.79-4.85 (m, 1H) 4.90 (br d, J=9.03 Hz, 2H) 5.01 (s, 2H) 5.40 (s, 2H) 5.47-5.58 (m, 1H) 5.66-5.77 (m, 1H) 5.87 (s, 1H) 5.97 (s, 1H) 6.03-6.13 (m, 1H) 6.35-6.45 (m, 1H) 7.02 (s, 2H) 7.30 (d, J=8.53 Hz, 2H) 7.59 (d, J=8.53 Hz, 2H) 7.81-7.88 (m, 1H), 8.09-8.15 (m, 1H) 9.90-10.09 (m, 1H)

1.3.11 ADL1-D6 and ADL1-D7 were Prepared Via the General Procedure Below

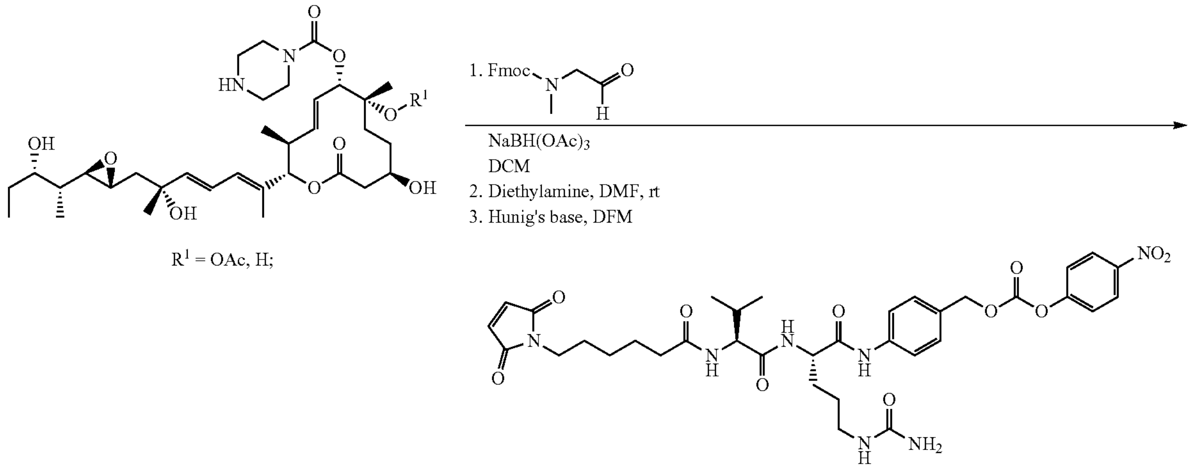

$R^1$ = OAc, H;

-continued

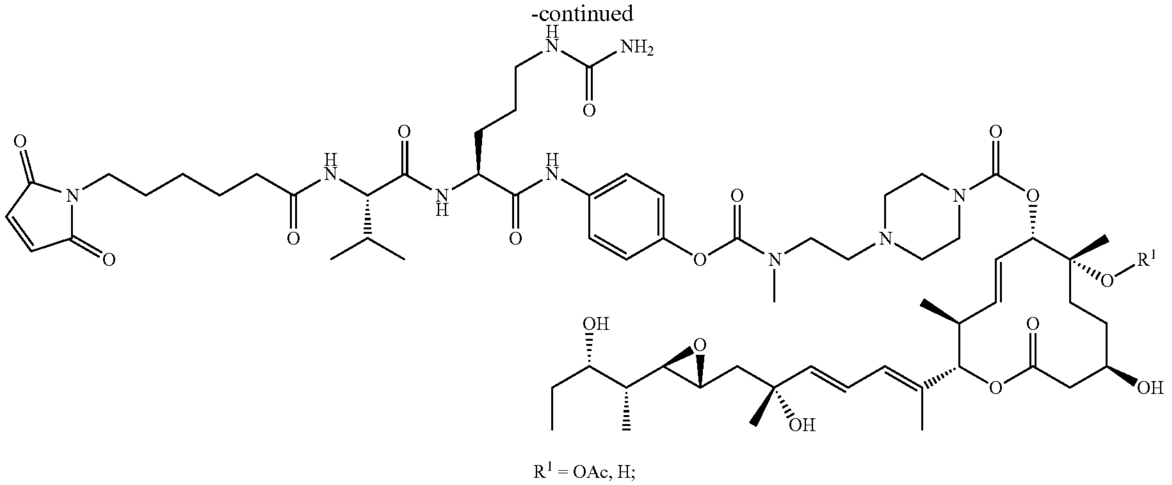

R[1] = OAc, H;

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (30 mg, 0.045 mmol) in DCM (0.1 M) was added (9H-fluoren-9-yl)methyl methyl(2-oxoethyl) carbamate (5 equiv.) and sodium triacetoxy borohydride (10 equiv.) and stirred for 30 minutes. The mixture then diluted with ethyl acetate and washed with water and brine. The organic layer was dried over anhydrous $Na_2SO_4$, concentrated and purified by column chromatography (0-10% MeOH/DCM gradient) to isolate the desired product. The resulting material was then diluted with DMF (0.1M), charged with diethylamine (20 equiv.) and stirred for 20 minutes. The mixture was then concentrated to dryness and diluted again in DMF and charged with 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (1.2 equiv.), then Hunig's base (3.0 equiv.). The mixture was stirred for 30 minutes, concentrated in vacuo, and purified via preparative HPLC purification to afford target product.

1.3.11.2 ADL1-D7

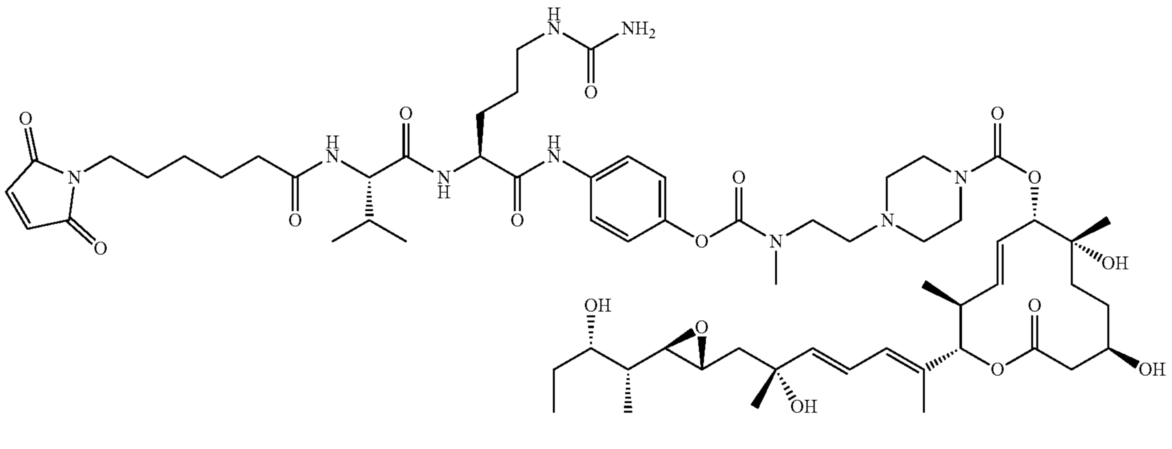 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(CCN(C)C(=O)Oc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

General procedure 1 (1.3.11) afforded (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-(((4-((S)-2-((S)-2-(6-(2,5-dioxo-2,5-dihydro-1H-pyrrol-1-yl)hexanamido)-3-methylbutanamido)-5-ureidopentanamido)phenoxy)carbonyl)(methyl)amino)ethyl)piperazine-1-carboxylate (3.1 mg, 5.03% yield). LC/MS (ESI, m/z), 1278.4 $[M+H]^+$.

1.3.11.2 ADL1-D6

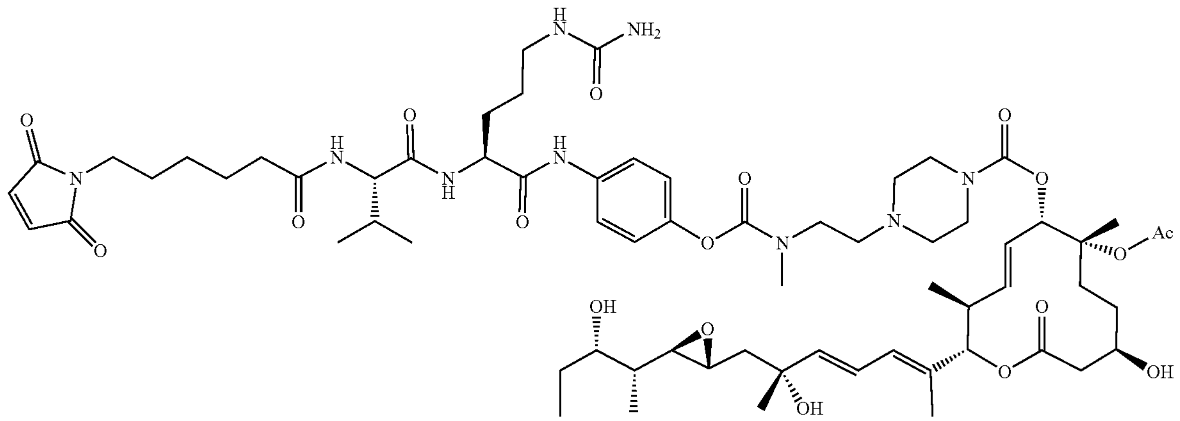 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCN(C)C(=O)Oc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

General procedure 1 (1.3.11) afforded (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-(((4-((S)-2-((S)-2-(6-(2,5-dioxo-2,5-dihydro-1H-pyrrol-1-yl)hexanamido)-3-methylbutanamido)-5-ureidopentanamido)phenoxy)carbonyl)(methyl)amino)ethyl)piperazine-1-carboxylate (2 mg, 3.36% yield LC/MS (ESI, m/z), 1321.37 $[M+H]^+$.

1.3.1.5 ADL1-D9, ADL6-D9, & ADL1-D13

D9 & D13

D9 and D13 were synthesized as a 3:1 mixture of isomers employing procedures outlined in the synthesis of D4 (Scheme 4) utilizing tri-TES Pladienolide B.

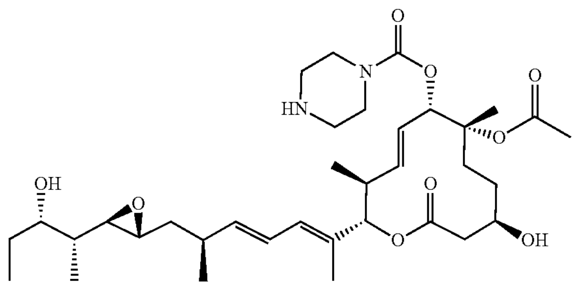 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCNCC2)/C=C/[C@@H]1C]

Payload (D9): LC/MS (ESI, m/z), 649.7 $[M+H]^+$.

$^1$H-NMR (400 MHz, $CHCl_3$-d): δ ppm 0.87-1.01 (m, 10H) 1.08 (d, J=6.78 Hz, 3H) 1.27-1.63 (m, 12H) 1.66-1.74 (m, 1H) 1.76 (s, 3H) 1.97-2.10 (m, 3H) 2.35-2.57 (m, 5H) 2.58-2.65 (m, 1H) 2.65-2.71 (m, 1H) 2.77 (td, J=5.93, 2.32 Hz, 1H) 2.89-3.05 (m, 4H) 3.07-3.34 (m, 8H) 3.50-3.68 (m, 5H) 3.72-3.88 (m, 1H) 4.88-5.09 (m, 1H) 5.18 (d, J=10.67 Hz, 1H) 5.50-5.84 (m, 3H) 6.01-6.13 (m, 1H) 6.19-6.36 (m, 1H).

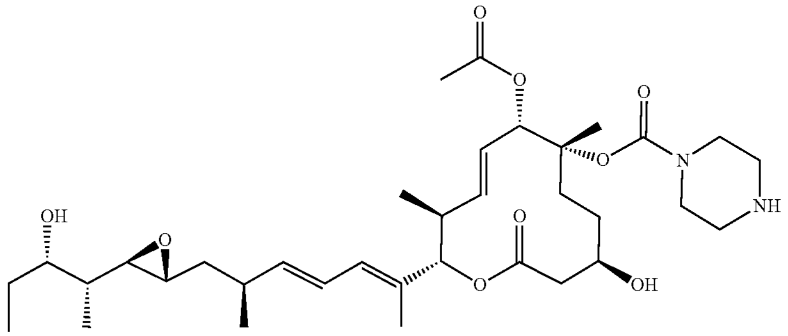 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCNCC2)[C@@H](OC(C)=O)/C=C/[C@@H]1C]

Payload (D13): LC/MS (ESI, m/z), 649.6 $[M+H]^+$.

$^1H$ NMR (400 MHz, $CHCl_3$-d) δ ppm 0.84-1.01 (m, 11H) 1.08 (d, J=6.78 Hz, 3H) 1.29-1.64 (m, 10H) 1.63-1.73 (m, 1H) 1.76 (s, 3H) 1.94-2.12 (m, 4H) 2.37-2.58 (m, 4H) 2.59-2.65 (m, 1H) 2.68 (dd, J=7.40, 2.26 Hz, 1H) 2.77 (td, J=5.93, 2.32 Hz, 1H) 3.01-3.30 (m, 4H) 3.49 (s, 1H) 3.54-3.67 (m, 2H) 3.69-3.92 (m, 5H) 4.13-4.78 (m, 11H) 5.13-5.24 (m, 2H) 5.48-5.61 (m, 1H) 5.62-5.74 (m, 2H) 6.04-6.13 (m, 1H) 6.18-6.32 (m, 1H).

ADL1-D9

General procedure 1 (outlined in section 1.3.1) was employed to synthesize ADL1-D9.

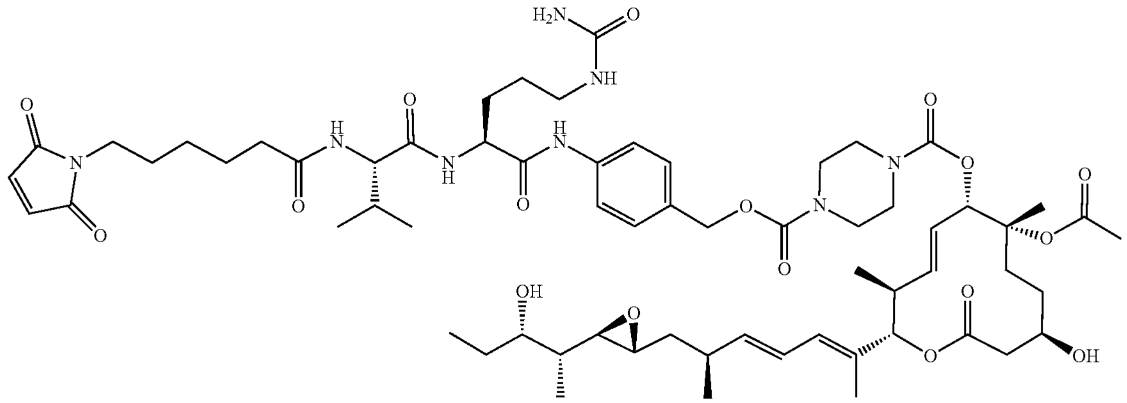 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

Linker-Payload (ADL1-D9): (30.5 mg, 0.024 mmol, 77% yield). LC/MS (ESI, m/z), 1263.8 $[M+H]^+$.

$^1H$-NMR (400 MHz, MeOH-$d_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

ADL6-D9

General procedure 1 (outlined in section 1.3.1) was employed to synthesize ADL6-D9.

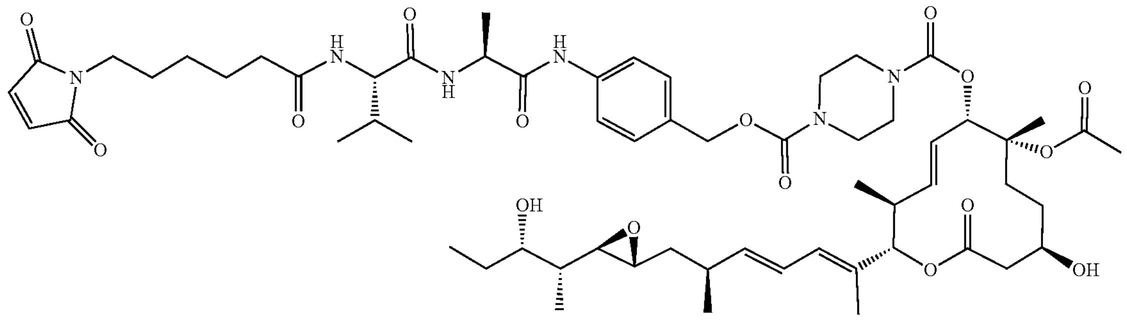 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Linker-Payload (ADL6-D9): To diluted 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (16.5 mg, 0.025 mmol) in DMF (784 μL) was added Hunig's Base (13.27 μL, 0.076 mmol). The reaction mixture was cooled to 0° C., and D9 was added. The reaction mixture was stirred at RT until LC/MS showed the reaction complete. The reaction mixture was concentrated in vacuo. Flash chromatography of the residue on silica gel with DCM/MeOH gave the titled compound (16.7 mg, 57% yield). LC/MS (ESI, m/z), 1184.6 $[M+Na]^+$.

$^1$H-NMR (400 MHz, MeOH-$d_4$): δ ppm 0.80-1.02 (m, 16H) 1.05-1.12 (m, 4H) 1.13-1.34 (m, 5H) 1.38-1.51 (m, 7H) 1.53-1.68 (m, 11H) 1.71-1.80 (m, 4H) 1.97-2.16 (m, 4H) 2.24-2.32 (m, 2H) 2.32-2.42 (m, 1H) 2.43-2.55 (m, 3H) 2.56-2.69 (m, 3H) 2.73 (br d, J=2.13 Hz, 1H) 3.07-3.18 (m, 1H) 3.42-3.61 (m, 17H) 3.75-3.91 (m, 1H) 4.11-4.24 (m, 1H) 4.43 (s, 2H) 5.59-5.88 (m, 4H) 6.06-6.17 (m, 1H) 6.29-6.39 (m, 1H) 7.24-7.39 (m, 2H) 7.52-7.64 (m, 2H).

ADL1-D13

Linker-Payload (AD1-D13): 4-((S)-2-((S)-2-(6-(2,5-dioxo-2,5-dihydro-1H-pyrrol-1-yl)hexanamido)-3-methylbutanamido)-5ureidopentanamido)benzyl (4-nitrophenyl) carbonate (4.2 mg, 5.693 μmol) in DMF (176 μL, 2.277 mmol) was added Hunig's base (2.98 μL, 0.017 mmol). The reaction mixture was cooled to 0° C., and D13 was added (4.06 mg, 6.262 μmol). The reaction mixture was stirred at RT until LC/MS showed the reaction was complete. The reaction mixture was concentrated in vacuo. Flash chromatography of the residue on silica gel with DCM/MeOH gave the titled compound (4.8 mg, 68% yield). LC/MS (ESI, m/z), 1248.0 $[M+H]^+$.

$^1$H-NMR (400 MHz, $CHCl_3$-d): δ ppm 0.58-0.98 (m, 10H) 0.99-1.06 (m, 2H) 1.11-1.31 (m, 6H) 1.57-1.75 (m, 3H) 2.11-2.26 (m, 1H) 2.30-2.73 (m, 2H) 3.28-3.80 (m, 7H) 4.14-4.33 (m, 1H) 4.44-4.55 (m, 1H) 4.63-4.81 (m, 1H) 4.92-5.06 (m, 1H) 5.09 (s, 1H) 5.49-5.74 (m, 1H) 5.88-6.09 (m, 1H) 6.14-6.36 (m, 1H) 6.99-7.08 (m, 1H) 7.21-7.38 (m, 2H) 7.53-7.67 (m, 1H) 7.95 (s, 1H).

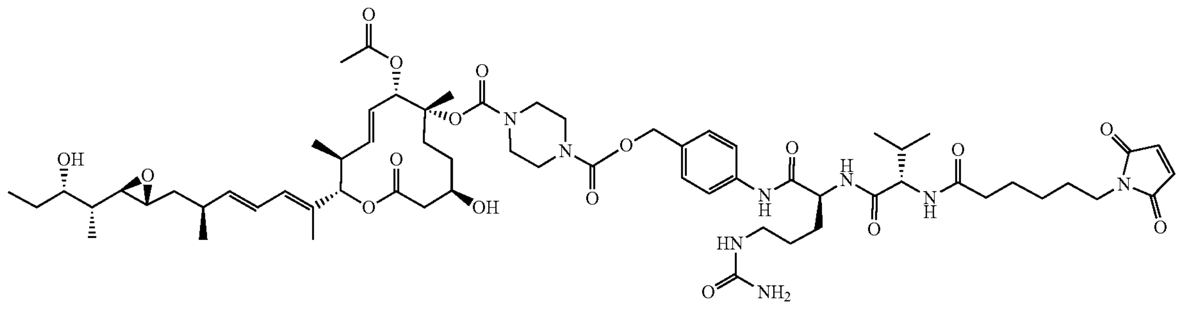 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]

1.3.1.6 ADL1-D14

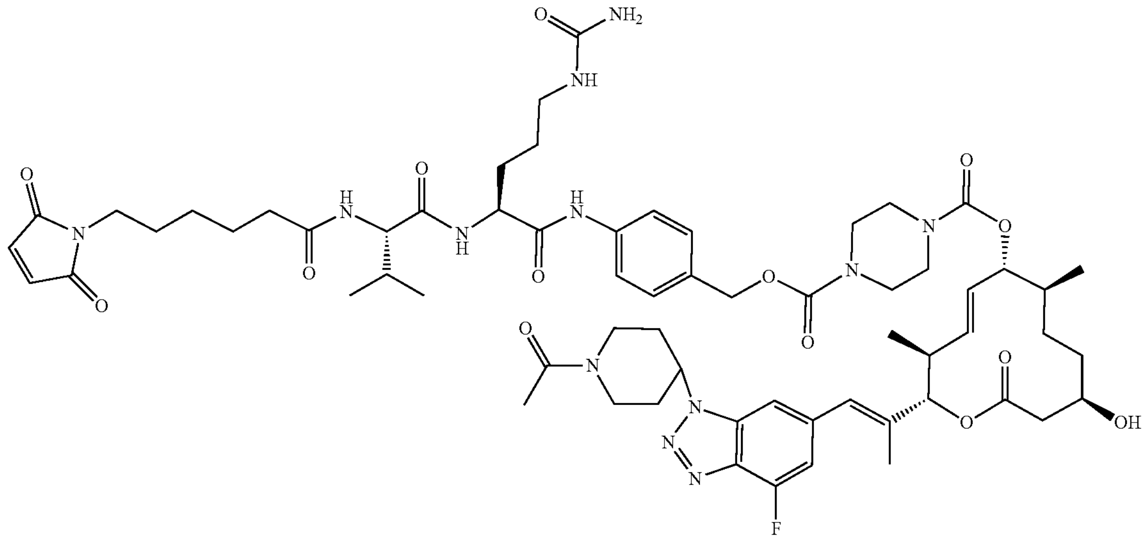 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]

General procedure 1 (outlined in section 1.3.1) was employed to synthesize 1-((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)-5-ureidopentanamido)benzyl) piperazine-1,4-dicarboxylate (30 mg, 0.024 mmol, 39.2% yield). LC/MS (ESI, m/z), 1254.5 $[M+H]^+$.

$^1$H-NMR (400 MHz, DMSO-$d_6$): δ ppm 0.75-1.00 (m, 12H), 1.06-1.26 (m, 4H), 1.26-1.77 (m, 13H), 1.75-2.02 (m, 7H), 2.08 (s, 8H), 2.23-2.35 (m, 2H), 2.54-2.70 (m, 2H), 2.78-3.10 (m, 4H), 3.36 (br s, 13H), 3.66-3.79 (m, 1H), 3.95-4.08 (m, 1H), 4.11-4.25 (m, 1H), 4.28-4.46 (m, 1H), 4.46-4.58 (m, 1H), 4.58-4.66 (m, 1H), 4.66-4.77 (m, 1H), 5.01 (s, 3H), 5.14-5.27 (m, 1H), 5.39 (s, 4H), 5.71-5.79 (m, 1H), 5.87-6.00 (m, 1H), 6.63-6.75 (m, 1H), 6.99 (s, 2H), 7.13-7.24 (m, 1H), 7.24-7.34 (m, 2H), 7.52-7.62 (m, 2H), 7.65-7.74 (m, 1H), 7.75-7.82 (m, 1H), 7.98-8.13 (m, 1H).

1.3.1.7 ADL1-D33

D33

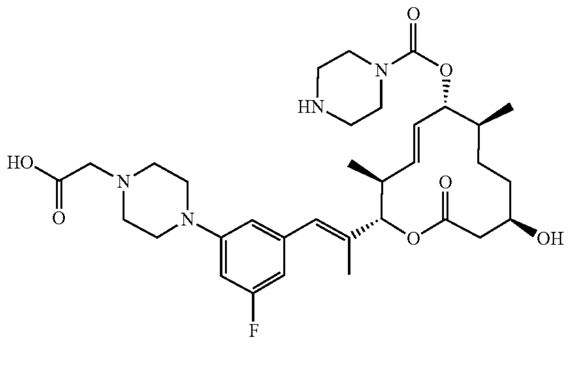 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCNCC2)/C=C/[C@@H]1C]

To a stirred solution of (2S,3S,6R,7S,10R,E)-2-((E)-1-(3-fluoro-5-(4-(2-methoxy-2-oxoethyl)piperazin-1-yl)phenyl) prop-1-en-2-yl)-10-hydroxy-3,7-dimethyl-12-oxooxacyclododec-4-en-6-yl piperazine-1-carboxylate (27 mg, 0.042 mmol) in $THF/H_2O$ (3 mL/1 mL) at 0° C. was added LiOH, and the reaction mixture was allowed to slowly warm to 25° C. (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate was synthesized using procedures outlined in International Application No. PCT/US2019/026992 (see, e.g., Procedures 17 and 19), which is incorporated herein by reference. After 6 hours, the reaction mixture was neutralized with phosphate buffer ($NaH_2PO_4$, 1.0 M, 3 mL) and the phases were separated. The aqueous layer was extracted with ethyl acetate (3×2 mL), and the combined organic layers were dried with anhydrous sodium sulfate and concentrated in vacuo. Reversed phase column chromatography afforded the titled compound (19.4 mg, 0.031 mmol, 73.4% yield). LC/MS (ESI, m/z), 631.4 $[M+H]^+$.

$^1$H-NMR (400 MHz, $CHCl_3$-d): δ ppm 0.85-1.16 (m, 2H) 1.23-1.52 (m, 1H) 1.57-1.77 (m, 1H) 1.87 (s, 1H) 1.92-2.13 (m, 1H) 2.35-2.55 (m, 1H) 2.50-2.74 (m, 1H) 3.11 (br s, 1H) 3.36-3.54 (m, 2H) 3.64 (br d, J=10.42 Hz, 2H) 3.77-3.90 (m, 1H) 4.76 (br s, 4H) 5.07-5.19 (m, 1H) 5.38-5.68 (m, 1H) 6.40-6.76 (m, 1H) 8.02-8.66 (m, 1H).

ADL1-D33

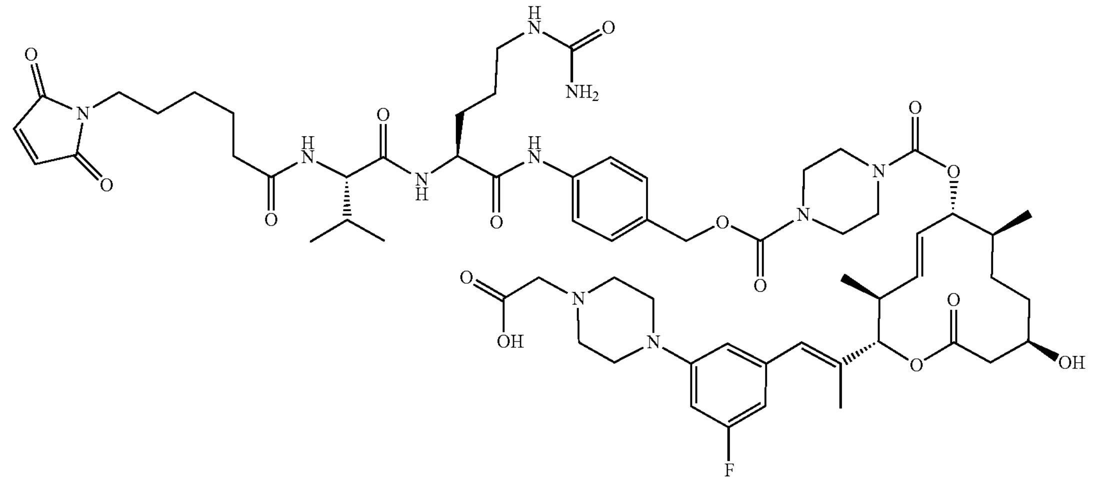 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

Linker-Payload (ADL1-D33): To 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (17 mg, 0.023 mmol) in DMF (714 μL, 9.217 mmol) was added Hunig's base (12.07 μL, 0.069 mmol). The reaction mixture was cooled to 0° C., and added 2-(4-(3-fluoro-5-((E)-2-((2S,3S,6R,7S,10R,E)-10-hydroxy-3,7-dimethyl-12-oxo-6-((piperazine-1-carbonyl)oxy)oxacyclododec-4-en-2-yl)prop-1-en-1-yl)phenyl)piperazin-1-yl) acetic acid (16.71 mg, 0.026 mmol). The reaction mixture was stirred at RT until LC/MS showed the reaction was complete. The reaction mixture was then concentrated in vacuo. Flash chromatography on silica gel and further HPLC purification gave the titled compound (13.5 mg, 10.98 μmol, 47.7% yield). LC/MS (ESI, m/z), 1229.5 $[M+H]^+$.

$^1$H-NMR (400 MHz, MeOH-$d_4$): δ ppm 0.92-0.99 (m, 10H) 1.01 (d, J=6.78 Hz, 3 H) 1.24-1.46 (m, 9H) 1.52-1.70 (m, 10H) 1.70-1.82 (m, 1H) 1.87 (d, J=1.00 Hz, 4H) 1.89-2.00 (m, 2H) 2.01-2.23 (m, 2H) 2.27 (t, J=7.40 Hz, 2H) 2.46 (dd, J=14.31, 5.27 Hz, 1H) 2.57-2.71 (m, 2H) 2.86 (d, J=0.63 Hz, 1H) 3.00 (s, 1H) 3.06-3.27 (m, 4H) 3.35 (s, 5H) 3.41-3.53 (m, 19H) 3.66 (s, 2H) 3.76-3.90 (m, 1H) 4.07-4.21 (m, 1H) 4.39-4.69 (m, 37H) 5.09 (s, 3H) 5.13 (d, J=10.54 Hz, 1H) 5.52 (dd, J=14.56, 9.03 Hz, 2H) 6.55 (br s, 2H) 6.69 (d, J=1.38 Hz, 2H) 7.33 (d, J=8.66 Hz, 2H) 7.59 (d, J=8.53 Hz, 2H) 7.88-8.04 (m, 1H) 8.16-8.33 (m, 1H).

ADL1-D28

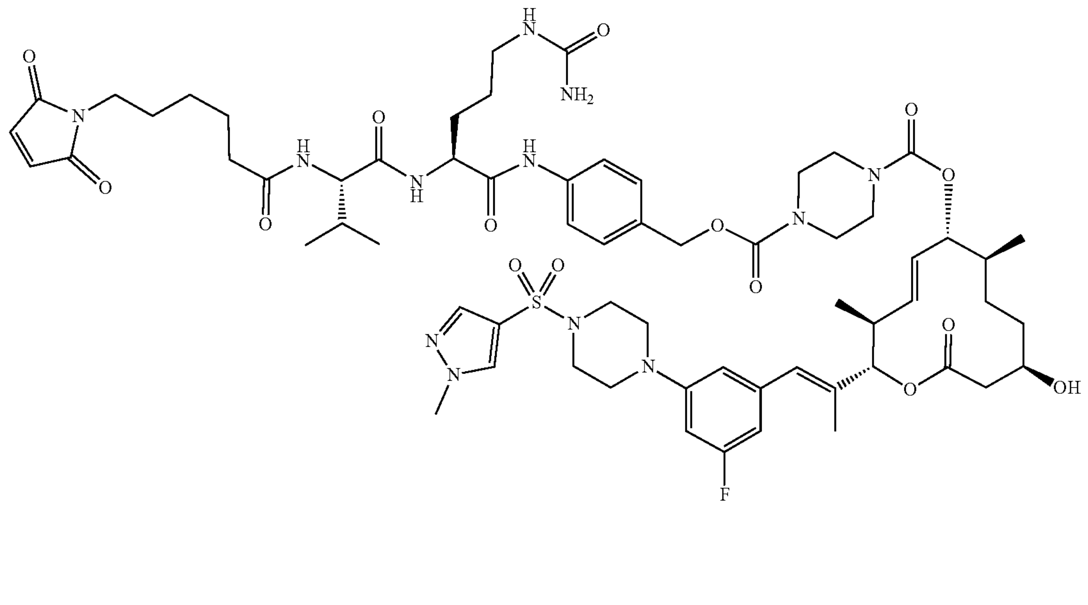 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (6.17 mg, 8.37 μmol) and (2S,3S,6R,7S,10R,E)-2-((E)-1-(3-fluoro-5-(4-((1-methyl-1H-imidazol-4-yl)sulfonyl)piperazin-1-yl)phenyl)prop-1-en-2-yl)-10-hydroxy-3,7-dimethyl-12-oxooxacyclododec-4-en-6-yl piperazine-1-carboxylate (6 mg, 8.37 μmol) were dissolved in DMF (0.3 ml) and Hunig's Base (4.39 μL, 0.025 mmol) was added. The reaction mixture was stirred at rt overnight. The solvent was evaporated and subjected to reverse-phase HPLC purification to afford (4-((S)-2-((S)-2-(6-(2,5-dioxo-2,5-dihydro-1H-pyrrol-1-yl)hexanamido)-3-methylbutanamido)-5-ureidopentanamido)benzyl) 4-((2S,3S,6R,7S,10R,E)-2-((E)-1-(3-fluoro-5-(4-((1-methyl-1H-imidazol-4-yl)sulfonyl)piperazin-1-yl)phenyl)prop-1-en-2-yl)-10-hydroxy-3,7-dimethyl-12-oxooxacyclododec-4-en-6-yl) piperazine-1,4-dicarboxylate (1.5 mg, 13.6%). LC/MS (ESI, m/z), 1315.66 $[M+H]^+$.

$^1$H NMR (400 MHz, METHANOL-d4) δ ppm 0.85-0.93 (m, 12H) 1.16-1.31 (m, 6H) 1.43-1.57 (m, 9H) 1.62-1.70 (m, 1H) 1.75 (s, 3H) 1.77-1.90 (m, 2H) 1.96-2.03 (m, 1H) 2.13-2.20 (m, 2H) 2.31-2.40 (m, 1H) 2.46-2.55 (m, 2H) 2.97-3.06 (m, 2H) 3.08-3.10 (m, 1H) 3.15 (br d, J=6.27 Hz, 9H) 3.33-3.43 (m, 10H) 3.71 (s, 4H) 4.03-4.09 (m, 1H) 4.37-4.44 (m, 1H) 4.44-4.53 (m, 1H) 4.96-5.06 (m, 3H) 5.33-5.51 (m, 2H) 6.36-6.44 (m, 2H) 6.45-6.53 (m, 2H) 6.69 (s, 2H) 7.19-7.25 (m, 2H) 7.47-7.52 (m, 2H) 7.63-7.70 (m, 2H)

ADL1-D31

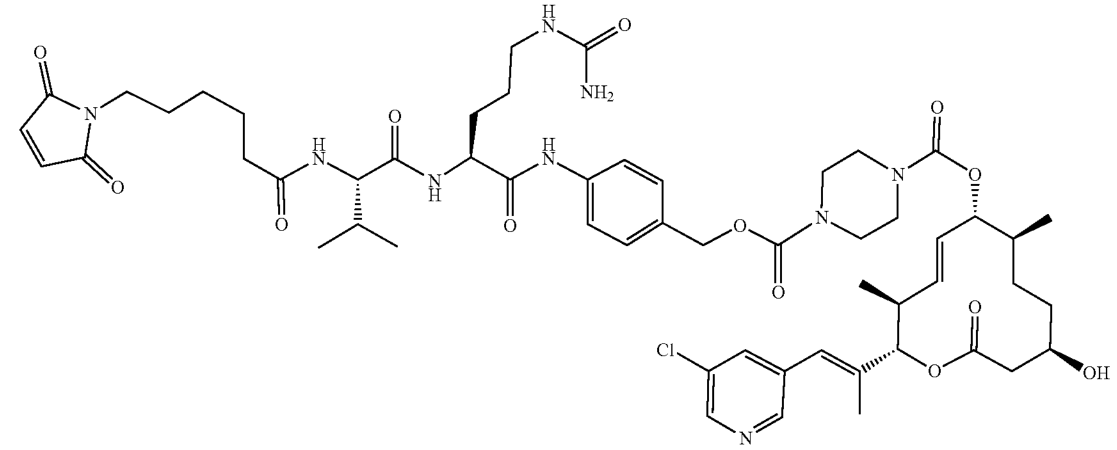 [SMILES: C/C(=C\c1cncc(Cl)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (13.12 mg, 0.018 mmol) and (2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl piperazine-1-carboxylate (9 mg, 0.018 mmol) were dissolved in DMF (179 μl, 2.312 mmol) and Hunig's Base (9.32 μl, 0.053 mmol) was added. The reaction mixture was stirred at rt overnight. The solvent was evaporated and purified via reverse-phase HPLC to afford 1-((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)-5-ureidopentanamido)benzyl) piperazine-1,4-dicarboxylate (6.9 mg, 34.09%). LC/MS (ESI, m/z), 1105.59 $[M+H]^+$.

$^1$H NMR (400 MHz, METHANOL-d4) δ ppm 0.88 (s, 12H) 1.17-1.31 (m, 4H) 1.43-1.57 (m, 8H) 1.61-1.70 (m, 1H) 1.80 (d, J=1.25 Hz, 5H), 1.92-2.01 (m, 1H) 2.14-2.20 (m, 2H) 2.32-2.42 (m, 1H) 2.48-2.59 (m, 2H) 2.96-3.14 (m, 3H) 3.38 (s, 10H) 3.36-3.36 (m, 1H) 3.38-3.40 (m, 3H) 3.67-3.75 (m, 1H) 4.03-4.07 (m, 1H) 4.37-4.42 (m, 1H) 4.97-5.01 (m, 2H) 5.04-5.11 (m, 1H) 5.35-5.51 (m, 2H) 6.46-6.52, (m, 1H) 6.69 (s, 2H) 7.18-7.26 (m, 2H) 7.45-7.54 (m, 2H) 7.68-7.74 (m, 1H) 8.29-8.34 (m, 2H).

ADL1-D29

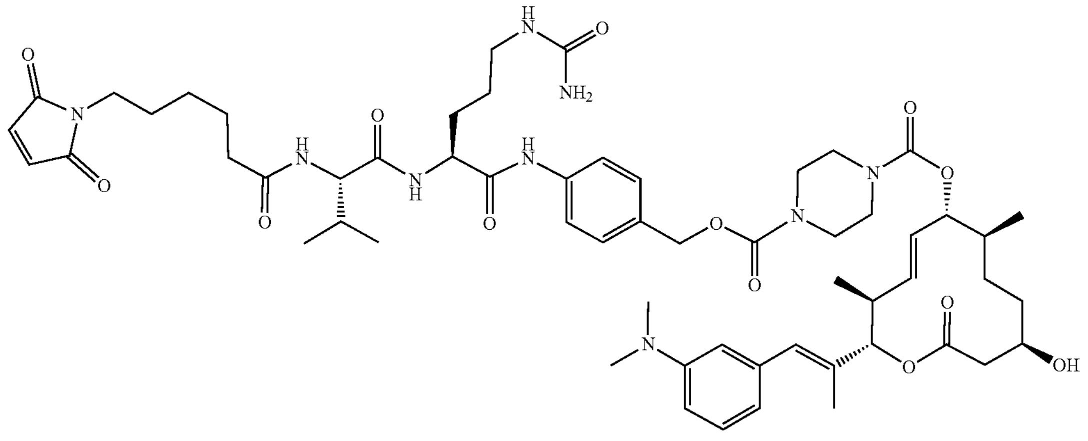 [SMILES: C/C(=C\c1cccc(N(C)C)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (8.62 mg, 0.012 mmol) and (2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl piperazine-1-carboxylate (6 mg, 0.012 mmol) were dissolved in DMF (118 μl, 1.518 mmol) and Hunig'sBase (6.12 μl, 0.035 mmol). The reaction mixture was stirred at rt overnight. The solvent was evaporated and purified via reverse-phase HPLC to afford 1-((2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)-5-ureidopentanamido)benzyl) piperazine-1,4-dicarboxylate (4.0 mg, 30.79%). LC/MS (ESI, m/z), 1112.59 $[M+H]^+$.

$^1H$ NMR (400 MHz, METHANOL-$d_4$) δ ppm 0.87 (s, 12H) 1.17-1.23 (m, 3H) 1.26-1.32 (m, 1H) 1.44-1.57 (m, 8H) 1.63-1.69 (m, 1H) 1.74-1.81 (m, 4H) 1.83-1.88 (m, 1H) 1.93-2.03 (m, 1H) 2.13-2.20 (m, 2H) 2.34-2.42 (m, 1H) 2.48-2.57 (m, 2H) 2.81 (s, 5H) 2.98-3.05 (m, 2H) 3.08-3.14 (m, 1H) 3.38 (br s, 9H) 3.65-3.75 (m, 1H) 4.03-4.07 (m, 1H) 4.35-4.43 (m, 1H) 4.44-4.52 (m, 1H) 4.96-5.01 (m, 2H) 5.02-5.08 (m, 1H) 5.34-5.51 (m, 2H) 6.43-6.48 (m, 1H) 6.51-6.61 (m, 3H) 6.69 (s, 2H) 7.03-7.10 (m, 1H) 7.20-7.26 (m, 2H) 7.46-7.51 (m, 2H).

ADL1-D35

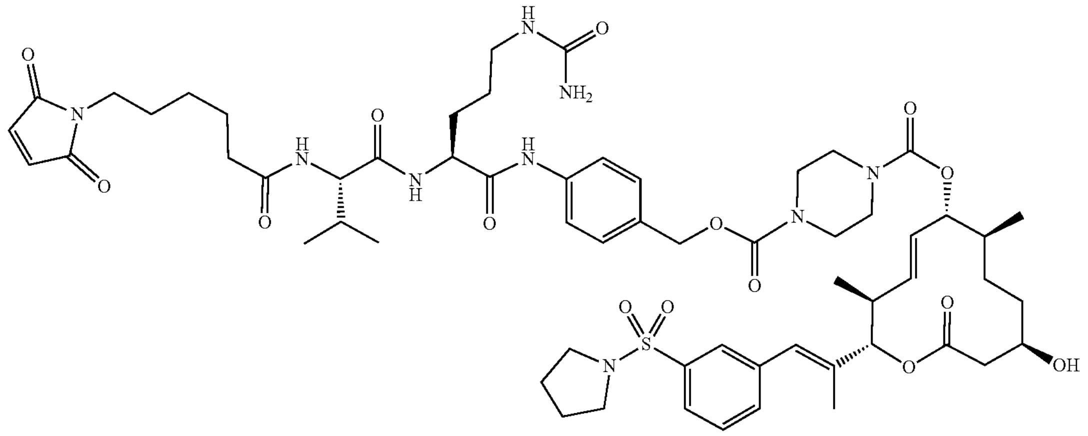 [SMILES: C/C(=C\c1cccc(S(=O)(=O)N2CCCC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (9.78 mg, 0.013 mmol) and (2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl piperazine-1-carboxylate (8 mg, 0.013 mmol) were dissolved in DMF (133 µl, 1.722 mmol) and Hunig's Base (6.94 µl, 0.04 mmol) [two drops] was added. The resulting mixture was stirred at rt overnight, concentrated in vacuo, and purified via reverse-phase HPLC to afford product 1-(4-((S)-2-((S)-2-(6-(2,5-dioxo-2,5-dihydro-1H-pyrrol-1-yl)hexanamido)-3-methylbutanamido)-5-ureidopentanamido)benzyl) 4-((2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl) piperazine-1,4-dicarboxylate (8.2 mg, 51.47%). LC/MS (ESI, m/z), 1203.53 $[M+H]^+$.

1H NMR (400 MHz, METHANOL-d4) δ ppm 0.85-0.93 (m, 12H) 1.17-1.34 (m, 4H) 1.42-1.57 (m, 8H) 1.61-1.69 (m, 5H) 1.79 (s, 4H) 1.83-1.90 (m, 1H) 1.94-2.03 (m, 1H) 2.12-2.20 (m, 2H) 2.33-2.43 (m, 1H) 2.48-2.59 (m, 2H) 2.96-3.05 (m, 2H) 3.06-3.17 (m, 6H) 3.31-3.41 (m, 10H) 3.67-3.77 (m, 1H) 4.02-4.10 (m, 1H) 4.36-4.43 (m, 1H) 4.96-5.02 (m, 2H) 5.04-5.11 (m, 1H) 5.35-5.51 (m, 2H) 6.59 (s, 1H) 6.69 (s, 2H) 7.20-7.27 (m, 2H) 7.45-7.52 (m, 4H) 7.58-7.65 (m, 2H).

1.4 Preparation of MC-Val-Ala-pABC Linker-Payloads 1.4.1 Overview

Scheme 5

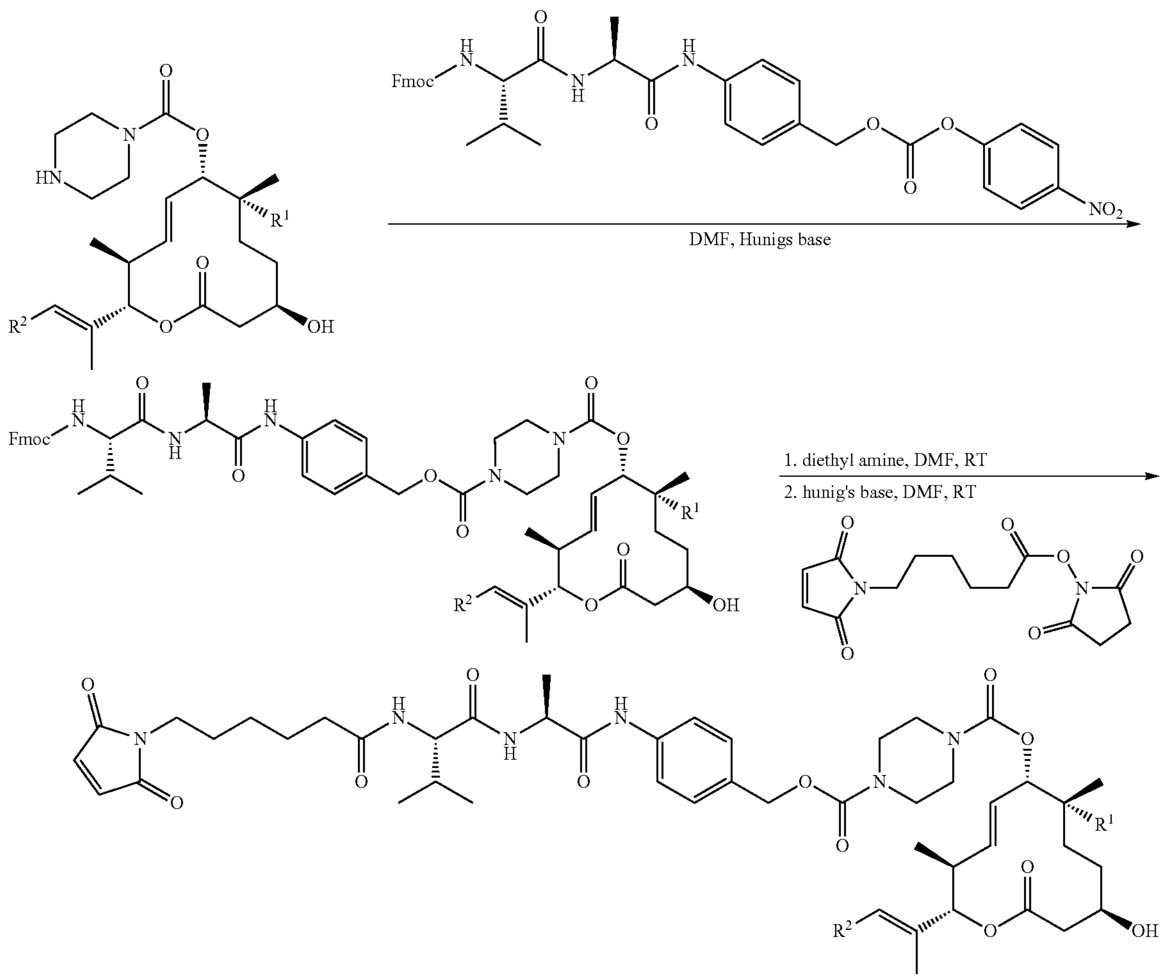

Step 1: Macrocycle payload (1.0 equiv.), DMF (0.1 M), (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (1.5 equiv.; prepared using the procedure described in WO 2012/153193), and Hunig's base (3.0 equiv.) were combined and stirred overnight. The reaction mix was concentrated to dryness and chromatographed to afford fmocVal-Ala-pABC-payload.

Step 2: Ammonium fmoc-Val-Ala-pABC payload (1.0 equiv.), dissolved in DMF (0.1 M), and diethylamine (10 equiv.) were combined and stirred for 30 min. The reaction mix was concentrated to dryness under high vacuum. The crude product was dissolved in DMF (0.1 M), and Hunig's base (2 equiv.) was added, after which 2,5-dioxopyrrolidin-1-yl 6-(2,5-dioxo-2,5-dihydro-1H-pyrrol-1-yl)hexanoate (3 equiv.) was added and stirred overnight. The reaction mix was then concentrated to dryness and chromatographed (0-30% MeOH in DCM) to afford the desired MC-Val-Ala-pABC-payload.

1.4.1.1 ADL6-D1

Scheme 5—Step 1: General procedure outlined above (section 1.4.1) was followed to afford 1-(4-((S)-2-((S)-2-((((9H-fluoren-9-yl)methoxy)carbonyl)amino)-3-methylbutanamido)propanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (32 mg, 0.027 mmol, 27.9% yield). LC/MS (ESI, m/z), $[M+Na]^+$1200.5.

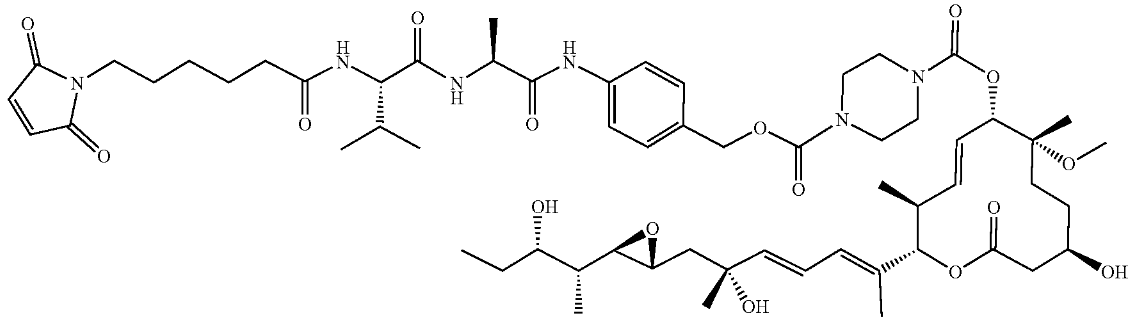 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Scheme 5—Step 2: General procedure outlined above (section 1.4.1) was followed to afford 1-(4-((S)-2-((S)-2-(6-(2,5-dioxo-2,5-dihydro-1H-pyrrol-1-yl)hexanamido)-3-methylbutanamido)propanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (24 mg, 0.021 mmol, 77% yield). LC/MS (ESI, m/z), 1149.2 $[M+H]^+$.

$^1$H-NMR (400 MHz, MeOH-d4): δ ppm 0.85-1.02 (m, 16H), 1.20-1.23 (m, 3H) 1.23-1.32 (m, 3H) 1.34 (s, 3H) 1.41-1.46 (m, 4H) 1.46-1.72 (m, 11H) 1.78 (s, 3H) 1.87 (dd, J=14.05, 5.40 Hz, 1H) 2.08 (dq, J=13.77, 6.83 Hz, 1H) 2.27 (t, J=7.40 Hz, 2H) 2.43-2.63 (m, 3H) 2.64-2.70 (m, 1H) 2.90 (td, J=5.83, 2.26 Hz, 1H) 3.32-3.33 (m, 4H) 3.42-3.57 (m, 11H) 3.82 (br dd, J=8.66, 3.89 Hz, 1H) 4.15 (d, J=7.15 Hz, 1H), 4.47 (q, J=7.15 Hz, 1H) 4.99-5.12 (m, 4H) 5.57 (dd, J=15.18, 9.79 Hz, 1H) 5.69-5.78 (m, 1H) 5.87 (d, J=15.18 Hz, 1H) 6.13 (d, J=10.92 Hz, 1H), 6.53 (dd, J=15.31, 10.92 Hz, 1H) 6.78 (s, 2H) 7.32 (d, J=8.53 Hz, 2H) 7.58 (d, J=8.53 Hz, 2H).

1.4.1.2 ADL6-D16

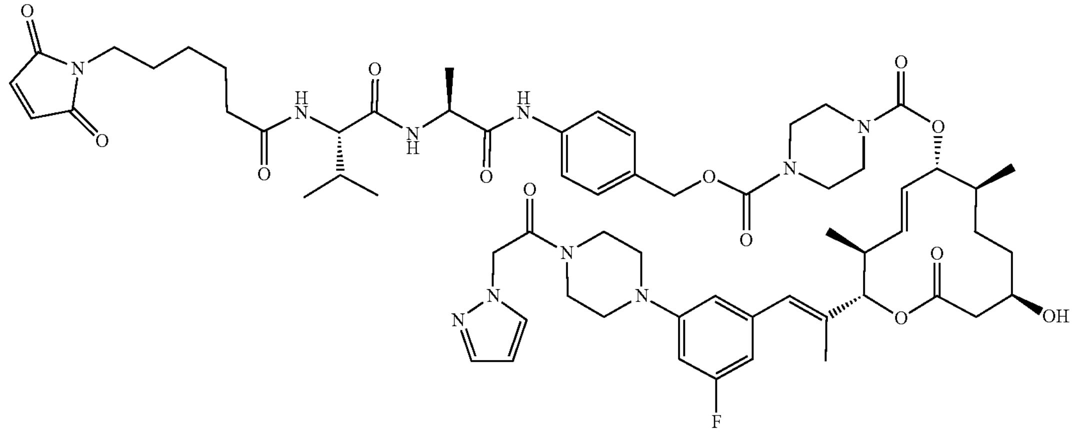 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Scheme 5—Step 1: General procedure outlined above (section 1.4.1) was followed to afford 1-((2S,3S,6R,7S,10R,E)-2-((E)-1-(3-(4-(2-(1H-pyrazol-1-yl)acetyl)piperazin-1-yl)-5-fluorophenyl)prop-1-en-2-yl)-10-hydroxy-3,7-dimethyl-12-oxooxacyclododec-4-en-6-yl) 4-(4-((S)-2-((S)-2-((((9H-fluoren-9-yl)methoxy)carbonyl)amino)-3-methylbutanamido)propanamido)benzyl) piperazine-1,4-dicarboxylate (0.060 g, 0.049 mmol, 60.8% yield). LC/MS (ESI, m/z), 1223.68 [M+H].

Scheme 5—Step 2: General procedure outlined above (section 1.4.1) was followed to afford 1-((2S,3S,6R,7S,10R,E)-2-((E)-1-(3-(4-(2-(1H-pyrazol-1-yl)acetyl)piperazin-1-yl)-5-fluorophenyl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)propanamido)benzyl) piperazine-1,4-dicarboxylate (11.50 mg, 9.64 μmol, 12.05% yield). LC/MS (ESI, m/z),1194.82 $[M+H]^+$.

$^1$H-NMR (400 MHz, $CHCl_3$-d): δ ppm 0.97 (br d, J=1.25 Hz, 12H), 1.24-1.41 (m, 5H), 1.41-1.47 (m, 3H), 1.52-1.69 (m, 6H), 1.84-1.90 (m, 3H), 1.92-2.01 (m, 1H), 2.02-2.16 (m, 1H), 2.23-2.30 (m, 2H), 2.42-2.51 (m, 1H), 2.57-2.65 (m, 2H), 3.19-3.28 (m, 4H), 3.35 (s, 4H), 3.40-3.54 (m, 11H), 3.69-3.77 (m, 4H), 3.78-3.85 (m, 1H), 4.12-4.18 (m, 1H), 4.43-4.51 (m, 1H), 5.07-5.16 (m, 3H), 5.20 (s, 2H), 5.42-5.62 (m, 2H), 6.29-6.38 (m, 1H), 6.46-6.58 (m, 2H), 6.59-6.68 (m, 2H), 7.28-7.37 (m, 2H), 7.50-7.67 (m, 4H).

1.5 Preparation of MC-Val-Ala-pAB Linker-Payloads

1.5.1 Overview

Scheme 6

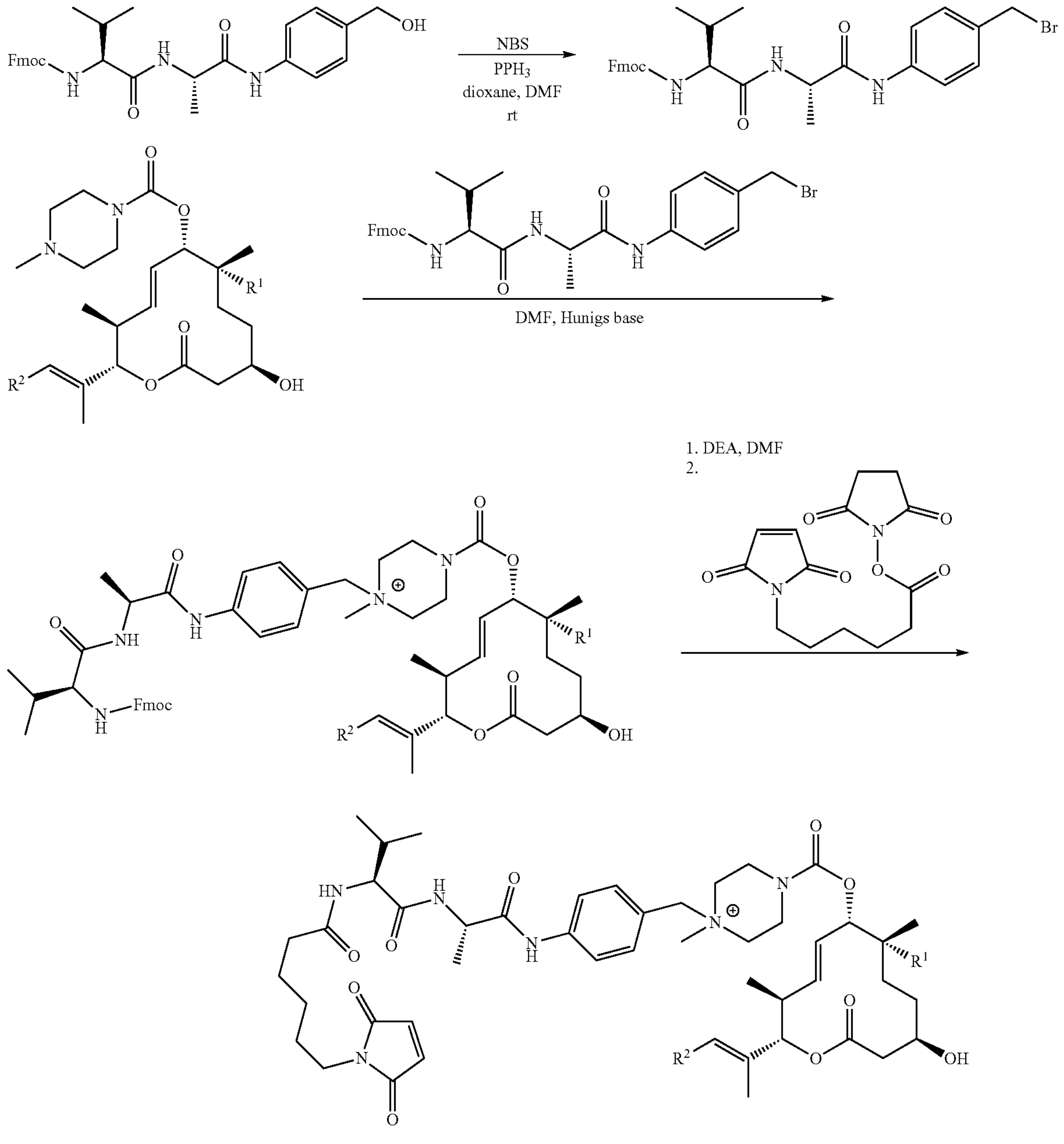

Step 1: (9H-fluoren-9-yl)methyl ((S)-1-(((S)-1-((4-(hydroxymethyl)phenyl)amino)-1-oxopropan-2-yl)amino)-3-methyl-1-oxobutan-2-yl)carbamate (0.5 g, 0.97 mmol), 1,4-dioxane (9.70 mL, 0.97 mmol), triphenylphosphine (0.509 g, 1.939 mmol), N-bromosuccinimide (0.345 g, 1.939 mmol), and DMF (2.424 mL, 0.97 mmol) were combined and stirred for 3 hours at RT. The reaction mix was concentrated and chromatographed to afford (9H-fluoren-9-yl) methyl ((S)-1-(((S)-1-((4-(bromomethyl)phenyl)amino)-1-oxopropan-2-yl)amino)-3-methyl-1-oxobutan-2-yl) carbamate (116 mg, 0.201 mmol, 20.68% yield). LC/MS (ESI, m/z), 580.14 [M+H].

Step 2: The payload (1.0 equiv.), (9H-fluoren-9-yl)methyl ((S)-1-(((S)-1-((4-(bromomethyl)phenyl)amino)-1-oxopropan-2-yl)amino)-3-methyl-1-oxobutan-2-yl)carbamate (0.069 g, 0.12 mmol), N,N-dimethylformamide (0.1 M), and Hunig's base (1.5 equiv.) were combined and stirred overnight. The reaction mix was concentrated to dryness and chromatographed (0-10% MeOH in DCM) to afford the quaternary ammonium fmoc-Val-Ala-pAB payload.

Step 3: Quaternary ammonium fmoc-Val-Ala-pAB payload (1.0 equiv.), dissolved in DMF (0.1 M), and diethylamine (10 equiv.) were combined and stirred for 30 min. The reaction mix was concentrated to dryness under high vacuum. The crude product was dissolved in DMF (0.1 M) and Hunig's base (2 equiv.) was added, after which 2,5-dioxopyrrolidin-1-yl 6-(2,5-dioxo-2,5-dihydro-1H-pyrrol-1-yl)hexanoate (3 equiv.) was added and stirred overnight. The reaction mix was then concentrated to dryness and chromatographed (0-30% MeOH in DCM) to afford the desired quaternary ammonium linker-payload.

1.5.1.1 ADL5-D2

4-en-6-yl)oxy)carbonyl)-1-methylpiperazin-1-ium-2-ylium) monobromide (4.8 mg, 15.33% yield). LC/MS (ESI, m/z), 1120.99 $[M+H]^+$.

$^1$H-NMR (400 MHz, MeOH-d4): δ ppm 0.88 (s, 15H), 1.09-1.26 (m, 9H), 1.31-1.58 (m, 14H), 1.42-1.44 (m, 1H), 1.68 (s, 3H), 1.73-1.81 (m, 1H), 1.91-2.03 (m, 1H), 2.14-2.22 (m, 2H), 2.35-2.52 (m, 3H), 2.53-2.60 (m, 1H), 2.74-2.83 (m, 1H), 2.97 (s, 3H), 3.25 (s, 1H), 3.28-3.46 (m, 8H), 3.52-3.66 (m, 2H), 3.70-3.78 (m, 1H), 3.97-4.11 (m, 3H), 4.32-4.41 (m, 1H), 4.45-4.54 (m, 2H), 4.91-5.01 (m, 2H), 5.44-5.55 (m, 1H), 5.57-5.70 (m, 1H), 5.72-5.82 (m, 1H), 6.00-6.08 (m, 1H), 6.43 (dd, J=15.25, 10.98 Hz, 1H), 6.69 (s, 2H), 7.36-7.47 (m, 2H), 7.67-7.75 (m, 2H).

1.5.1.2 ADL5-D19

General procedure outlined above (section 1.5.1) was employed to synthesize ADL5-D19. The payload D19 was synthesized using procedures outlined in section 1.2.1.

D19

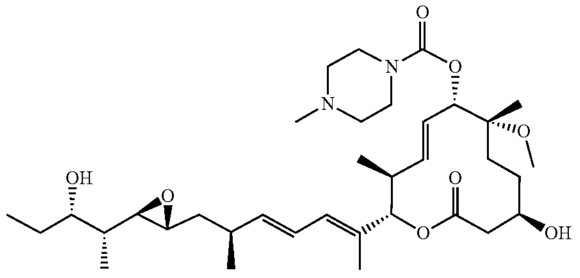

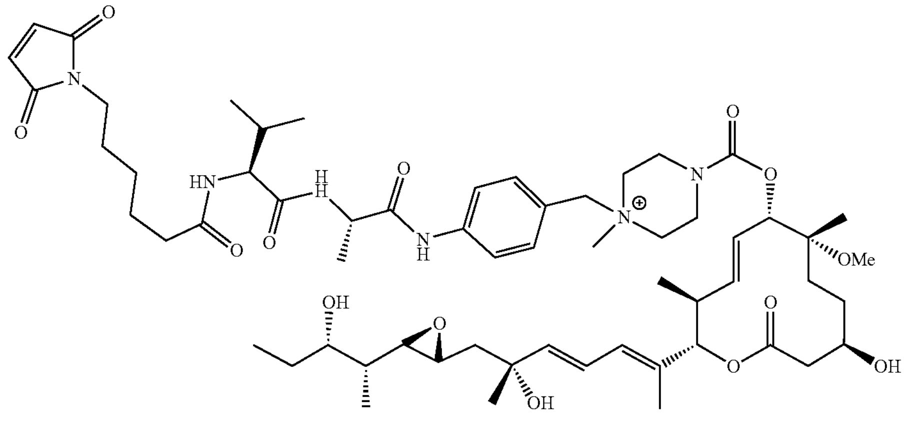

Scheme 6—Step 2: 1-(4-((S)-2-((S)-2-((((9H-fluoren-9-yl)methoxy)carbonyl)amino)-3-methylbutanamido)propanamido)benzyl)-4-((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium bromide (30 mg, 0.024 mmol, 26.5% yield). LC/MS (ESI, m/z), 1149.77 $[M+H]^+$.

Scheme 6—Step 3: mono(1-(4-((S)-2-((S)-2-(6-(2,5-dioxo-2,5-dihydro-1H-pyrrol-1-yl)hexanamido)-3-methylbutanamido)propanamido)benzyl)-4-((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec- (2S,3S,6S,7R,10R,E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-methylpiperazine-1-carboxylate (114.2 mg, 0.180 mmol, 82% yield). LC/MS (ESI, m/z), 635.8 [M+H].

$^1$H-NMR (400 MHz, MeOH-d4): δ ppm 0.88-1.00 (m, 9H) 1.10 (d, J=6.65 Hz, 3H) 1.16-1.27 (m, 4H) 1.40-1.70 (m, 8H) 1.77 (d, J=0.88 Hz, 3H) 2.28-2.36 (m, 3H) 2.42 (br t, J=5.08 Hz, 3H) 2.47-2.61 (m, 4H) 2.68 (dd, J=8.22, 2.20 Hz, 1H) 2.74 (td, J=5.99, 2.20 Hz, 1H) 3.13-3.17 (m, 1H) 3.34-3.38 (m, 3H) 3.47-3.58 (m, 5H) 3.81-3.87 (m, 1H) 5.01-5.10 (m, 2H) 5.54-5.81 (m, 3H) 6.06-6.15 (m, 1H) 6.34 (dd, J=15.00, 10.98 Hz, 1H).

1-(4-((S)-2-((S)-2-((((9H-fluoren-9-yl)methoxy)carbonyl)amino)-3-methylbutanamido)propanamido)benzyl)-4-

((((2S,3S,6S,7R,10R,E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium (25 mg, 45.6%). LC/MS (ESI, m/z), 1133.1 [M+]$^+$.

$^1$H-NMR (400 MHz, MeOH-d4): δ ppm 0.94 (br dd, J=18.45, 7.15 Hz, 18H) 1.10 (d, J=6.78 Hz, 3H) 1.25 (s, 4H) 1.28-1.35 (m, 1H) 1.46 (br d, J=7.03 Hz, 9H) 1.59-1.70 (m, 2H) 1.77 (s, 3H) 2.05-2.12 (m, 1H) 2.44-2.60 (m, 4H) 2.63-2.72 (m, 1H) 2.70-2.77 (m, 1H) 3.06 (s, 3H) 3.40-3.44 (m, 1H) 3.50 (br d, J=1.63 Hz, 4H) 3.64-3.75 (m, 1H) 3.80-3.88 (m, 1H) 3.91-3.99 (m, 1H) 4.04-4.20 (m, 1H) 4.21-4.28 (m, 1H) 4.37-4.43 (m, 1H) 4.59 (br s, 2H) 4.93-4.95 (m, 2H) 5.06-5.08 (m, 2H) 5.57-5.80 (m, 4H) 6.05-6.16 (m, 1H) 6.27-6.41 (m, 1H) 7.28-7.37 (m, 2H) 7.38-7.45 (m, 2H) 7.47-7.53 (m, 2H) 7.65-7.72 (m, 2H) 7.74-7.86 (m, 4H).

ADL5-D19 hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium (19.4 mg, 0.018 mmol, 80% yield). LC/MS (ESI, m/z), 1105.9 [M+H].

$^1$H NMR (400 MHz, MeOH-d4): δ ppm 0.85-1.03 (m, 16H) 1.10 (d, J=6.78 Hz, 3H) 1.17-1.27 (m, 4H) 1.29-1.37 (m, 3H) 1.44-1.70, (m, 15H) 1.74-1.80 (m, 3H) 2.04-2.14 (m, 1H) 2.30 (t, J=7.47 Hz, 2H) 2.44-2.61 (m, 4H) 2.64-2.69 (m, 1H) 2.72-2.78 (m, 1H) 3.09 (s, 3H) 3.40-3.59 (m, 9H) 3.62-3.77 (m, 2H) 3.82-3.89 (m, 1H) 4.12-4.21 (m, 3H) 4.40-4.55 (m, 1H) 4.56-4.66 (m, 3H) 5.03-5.12 (m, 2H) 5.55-5.81 (m, 3H) 6.06-6.16 (m, 1H) 6.26-6.41 (m, 1H) 6.81 (s, 2H) 7.48-7.57 (m, 2H) 7.78-7.86 (m, 2H).

1.5.1.3 ADL5-D17

General procedure outlined above (section 1.5.1) was employed to synthesize ADL5-D17. The payload D17 was synthesized using procedures outlined in International Application No. PCT/US2019/026992 (see, e.g., Procedure 2, Procedure 3, and Procedure 4 or 5), which is incorporated herein by reference.

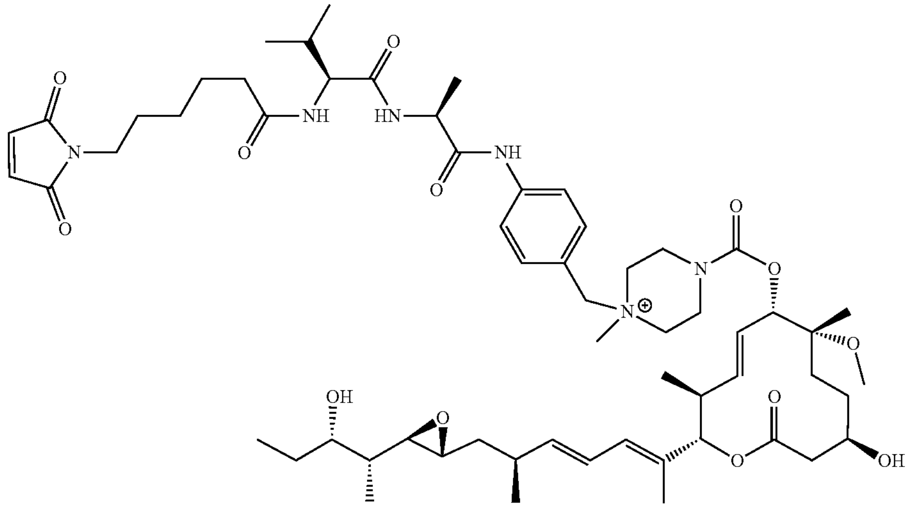 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

Linker-Payload (ADL5-D19): 1-(4-((S)-2-((S)-2-(6-(2,5-dioxo-2,5-dihydro-1H-pyrrol-1-yl)hexanamido)-3-methylbutanamido)propanamido)benzyl)-4-((((2S,3S,6S,7R,10R,E)-10-hydroxy-2-((S,2E,4E)-7-((2R,3R)-3-((2R,3S)-3-

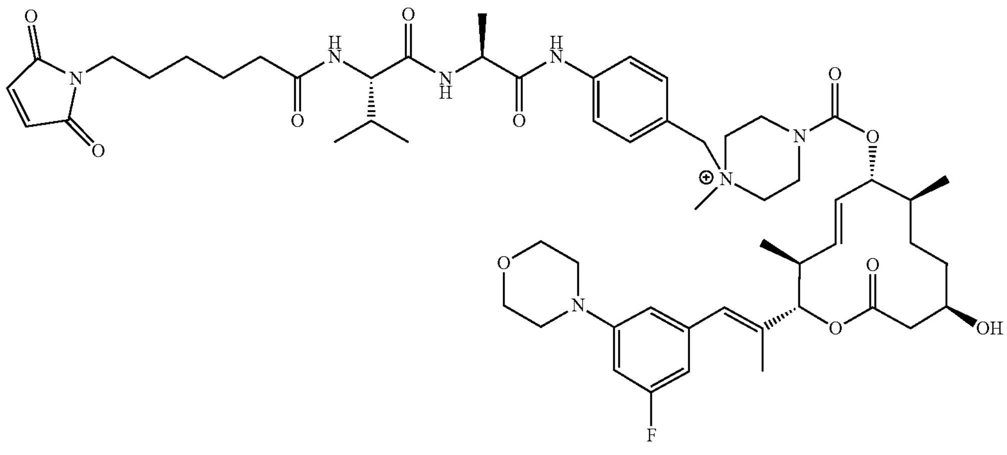 [SMILES: C/C(=C\c1cc(F)cc(N2CCOCC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

Step 1: 1-(4-((S)-2-((S)-2-((((9H-fluoren-9-yl)methoxy)carbonyl)amino)-3-methylbutanamido)propanamido)benzyl)-4-((((2S,3S,6R,7S,10R,E)-2-((E)-1-(3-fluoro-5-morpholinophenyl)prop-1-en-2-yl)-10-hydroxy-3,7-dimethyl-12-oxooxacyclododec-4-en-6-yl)oxy)carbonyl)-1-methylpiperazin-1-ium (12.9 mg, 69.8%). LC/MS (ESI, m/z), 1086.43 [M+H].

$^1$H-NMR (400 MHz, MeOH-d4): δ ppm 0.96-1.07 (m, 12H), 1.27-1.42 (m, 3H), 1.46 (d, J=7.15 Hz, 3H), 1.62-1.72 (m, 2H), 1.88 (d, J=1.13 Hz, 3H), 1.97-2.06 (m, 1H), 2.04-2.14 (m, 1H), 2.44-2.53 (m, 1H), 2.58-2.69 (m, 2H), 3.08 (s, 3H), 3.13-3.19 (m, 4H), 3.38-3.56 (m, 4H), 3.61-3.75 (m, 2H), 3.79-3.88 (m, 5H), 3.90-3.98 (m, 1H), 4.07-4.18 (m, 2H), 4.20-4.29 (m, 1H), 4.35-4.45 (m, 2H), 4.45-4.54 (m, 1H), 4.61 (s, 2H), 4.86-4.92 (m, 2H), 5.15 (d, J=10.67 Hz, 1H), 5.46-5.65 (m, 2H), 6.46-6.67 (m, 4H), 7.28-7.37 (m, 2H), 7.37-7.45 (m, 2H), 7.47-7.53 (m, 2H), 7.66-7.71 (m, 2H), 7.74-7.84 (m, 4H).

Step 2: 1-(4-((R)-2-((R)-2-(6-(2,5-dioxo-2,5-dihydro-1H-pyrrol-1-yl)hexanamido)-3-methylbutanamido)propanamido)benzyl)-4-((((2S,3S,6R,7S,10R,E)-2-((E)-1-(3-fluoro-5-morpholinophenyl)prop-1-en-2-yl)-10-hydroxy-3,7-dimethyl-12-oxooxacyclododec-4-en-6-yl)oxy)carbonyl)-1-methylpiperazin-1-ium bromide (7.6 mg, 60.5% yield). LC/MS (ESI, m/z), 1057.62 [M+H].

$^1$H-NMR (400 MHz, MeOH-d4): δ ppm 0.95-1.08 (m, 12H), 1.24-1.42 (m, 5H), 1.47 (d, J=7.15 Hz, 3H), 1.52-1.71 (m, 6H), 1.89 (d, J=1.13 Hz, 3H), 1.95-2.05 (m, 1H), 2.05-2.15 (m, 1H), 2.26-2.34 (m, 2H), 2.46-2.53 (m, 1H), 2.58-2.69 (m, 2H), 3.07-3.12 (m, 3H), 3.14-3.19 (m, 4H), 3.39-3.58 (m, 6H), 3.61-3.76 (m, 2H), 3.80-3.86 (m, 5H), 4.09-4.18 (m, 3H), 4.43-4.51 (m, 1H), 4.62 (s, 2H), 4.87-4.93 (m, 2H), 5.12-5.19 (m, 1H), 5.46-5.65 (m, 2H), 6.47-6.66 (m, 4H), 6.80 (s, 2H), 7.53 (d, J=8.66 Hz, 2H), 7.82 (d, J=8.66 Hz, 2H).

1.5.1.4 ADL5-D10

General procedure outlined above (section 1.5.1) was employed to synthesize ADL5-D10. The payload D10 was synthesized using procedures outlined in section 1.2.1.

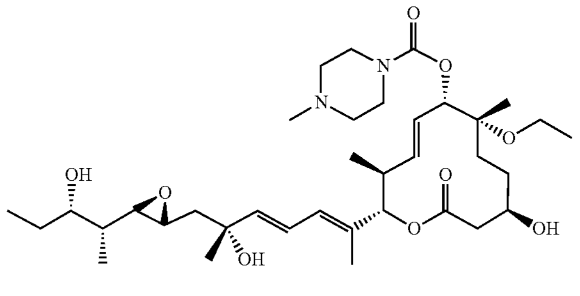

(2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-methylpiperazine-1-carboxylate (16.6 mg, 0.025 mmol, 38.7% yield). LC/MS (ESI, m/z), 665.7 [M+H]$^+$.

$^1$H-NMR (400 MHz, METHANOL-d): δ ppm 0.76-0.87 (m, 9H), 1.03-1.09 (m, 3H), 1.10-1.13 (m, 3H) 1.13-1.19 (m, 1H) 1.20-1.27 (m, 3H), 1.29-1.48 (m, 6H) 1.51-1.59 (m, 1H) 1.65-1.71 (m, 3H) 1.73-1.81 (m, 1H) 2.20 (s, 3H), 2.27-2.34 (m, 4H) 2.34-2.44 (m, 2H) 2.44-2.53 (m, 1H) 2.53-2.59 (m, 1H) 2.76-2.83 (m, 1H) 3.23-3.26 (m, 1H) 3.34-3.52 (m, 7H) 3.67-3.75 (m, 1H) 4.86-4.92 (m, 1H) 4.92-4.99 (m, 1H), 5.41-5.51 (m, 1H), 5.60-5.71 (m, 1H), 5.72-5.82 (m, 1H), 6.00-6.07 (m, 1H), 6.37-6.48 (m, 1H)

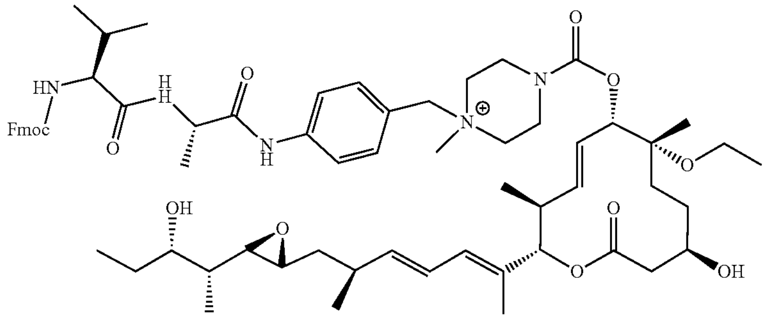

Step 1: 1-(4-((S)-2-((S)-2-((((9H-fluoren-9-yl)methoxy)carbonyl)amino)-3-methylbutanamido)propanamido)benzyl)-4-((((2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)-1-methylpiperazin-1-ium (18.6 mg, 0.016 mmol, 87% yield) as a colorless glaze. LC/MS (ESI, m/z), 1163.01 [M]$^+$.

$^1$H-NMR (400 MHz, MeOH-d4): δ ppm 0.86-1.03 (m, 16H), 1.20 (s, 3H), 1.25 (s, 4H), 1.36 (s, 3H), 1.43-1.72 (m, 10H), 1.81 (s, 3H), 1.84-1.92 (m, 1H), 2.06-2.14 (m, 1H), 2.46-2.63 (m, 3H), 2.67-2.72 (m, 1H), 2.88-2.94 (m, 1H), 3.03-3.09 (m, 3H), 3.38-3.45 (m, 3H), 3.54 (s, 6H), 3.63-3.79 (m, 2H), 3.81-3.88 (m, 1H), 3.92-3.98 (m, 1H), 4.07-4.18 (m, 2H), 4.21-4.28 (m, 1H), 4.36-4.44 (m, 2H), 4.47-4.53 (m, 1H), 4.55-4.63 (m, 3H), 5.02-5.11 (m, 3H), 5.56-5.66 (m, 1H), 5.75-5.84 (m, 1H), 5.86-5.92 (m, 1H), 6.12-6.19 (m, 1H), 6.49-6.61 (m, 1H), 7.29-7.36 (m, 2H), 7.38-7.44 (m, 2H), 7.47-7.53 (m, 2H), 7.64-7.71 (m, 2H), 7.80 (dd, J=15.06, 7.91 Hz, 4H).

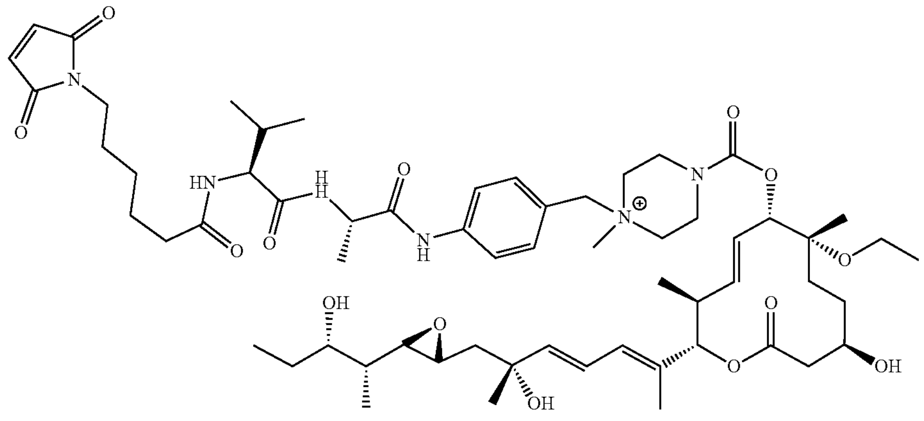

Step 2: 1-(4-((S)-2-((S)-2-(6-(2,5-dioxo-2,5-dihydro-1H-pyrrol-1-yl)hexanamido)-3-methylbutanamido)propanamido)benzyl)-4-((((2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)-1-methylpiperazin-1-ium (14.09 mg, 82% yield). LC/MS (ESI, m/z), 1057.62 $[M+H]^+$.

$^1$H-NMR (400 MHz, MeOH-d4): δ ppm 0.87-1.03 (m, 15H), 1.20 (s, 3H), 1.22-1.29 (m, 4H), 1.37 (s, 6H), 1.45-1.72 (m, 14H), 1.81 (s, 3H), 1.84-1.95 (m, 1H), 2.05-2.16 (m, 1H), 2.26-2.36 (m, 2H), 2.47-2.62 (m, 3H), 2.66-2.74 (m, 1H), 2.86-2.95 (m, 1H), 3.11 (s, 3H), 3.42-3.51 (m, 4H), 3.51-3.62 (m, 5H), 3.64-3.78 (m, 2H), 3.81-3.89 (m, 1H), 4.09-4.20 (m, 3H), 4.43-4.52 (m, 1H), 4.54-4.59 (m, 1H), 4.55-4.67 (m, 2H), 4.60-4.68 (m, 2H), 5.01-5.12 (m, 2H), 5.54-5.65 (m, 1H), 5.75-5.86 (m, 1H), 5.86-5.94 (m, 1H), 6.10-6.21 (m, 1H), 6.47-6.62 (m, 1H), 6.81 (s, 2H), 7.49-7.60 (m, 2H) 7.76-7.89 (m, 2H).

1.5.1.5 ADL5-D15

General procedure outlined above (section 1.5.1) was employed to synthesize ADL5-D15. The payload D15 was synthesized using procedures outlined in International Application No. PCT/US2019/026992, which is incorporated herein by reference.

Step 1: 1-(4-((S)-2-((S)-2-((((9H-fluoren-9-yl)methoxy)carbonyl)amino)-3-methylbutanamido)propanamido)benzyl)-4-((((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl)oxy)carbonyl)-1-methylpiperazin-1-ium (100 mg, 0.086 mmol, 57.3% yield). LC/MS (ESI, m/z), 1167.76 [M+H].

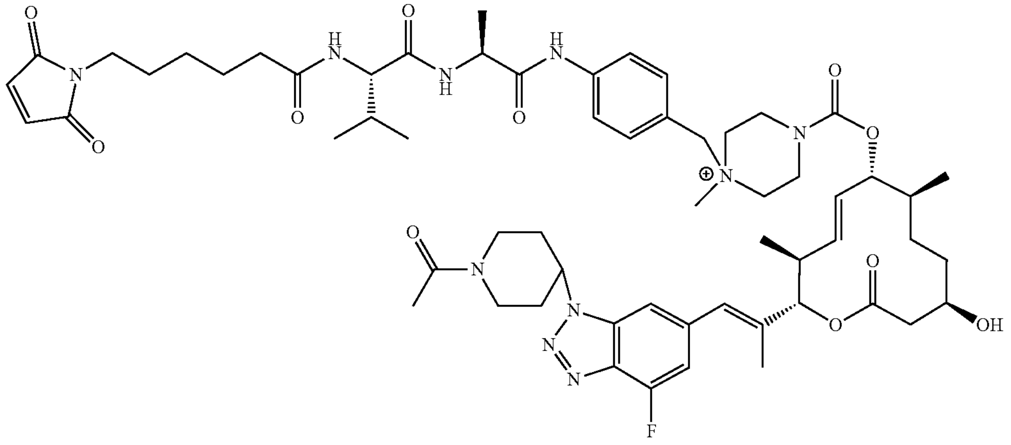 [SMILES: CC(=O)N1CCC(n2nnc3c(F)cc(/C=C(\C)[C@H]4OC(=O)C[C@H](O)CC[C@H](C)[C@@H](OC(=O)N5CC[N+](C)(Cc6ccc(NC(=O)[C@H](C)NC(=O)[C@@H](NC(=O)CCCCCN7C(=O)C=CC7=O)C(C)C)cc6)CC5)/C=C/[C@@H]4C)cc32)CC1]

Step 2: 4-((((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl)hexanamido)-3-methylbutanamido)propanamido)benzyl)-1-methylpiperazin-1-ium (32 mg, 0.028 mmol, 32.8% yield). LC/MS (ESI, m/z), 1138.64 [M+H].

$^1$H-NMR (400 MHz, MeOH-d4): δ ppm 0.99 (s, 10H), 1.26-1.40 (m, 5H), 1.42-1.49 (m, 3H), 1.67 (br s, 6H), 1.96 (d, J=1.00 Hz, 3H), 2.00-2.13 (m, 2H), 2.16-2.42 (m, 7H), 2.44-2.55 (m, 1H), 2.59-2.76 (m, 2H), 2.98-3.26 (m, 4H), 3.38-3.59 (m, 7H), 3.60-3.76 (m, 2H), 3.78-3.90 (m, 1H), 4.13 (br d, J=7.15 Hz, 3H), 4.41-4.52 (m, 1H), 4.53-4.71 (m, 3H), 4.89-4.97 (m, 1H), 5.10-5.27 (m, 2H), 5.48-5.67 (m, 2H), 6.79 (s, 2H) 7.07-7.17 (m, 1H), 7.48-7.61 (m, 3H), 7.78-7.84 (m, 2H).

1.5.1.5 ADL5-D32

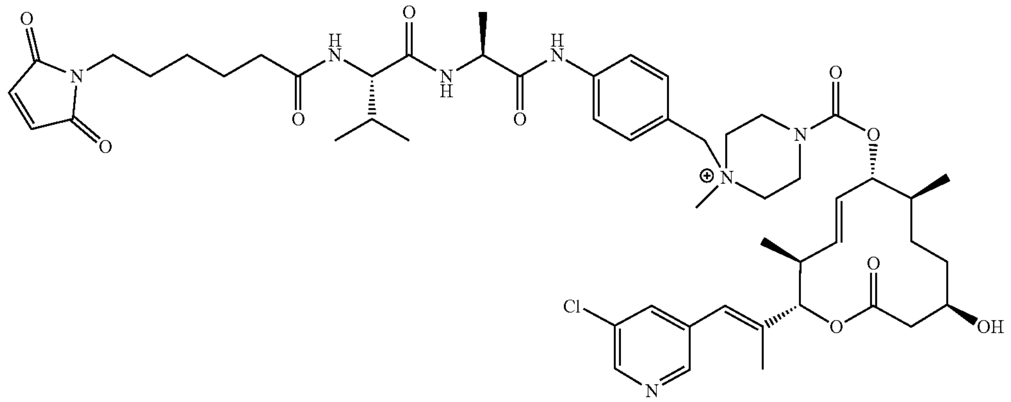 [SMILES: C/C(=C\c1cncc(Cl)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D32. The payload D15 was synthesized using procedures outlined in International Application No. PCT/US2019/026992, which is incorporated herein by reference.

Step 1: 1-(4-((S)-2-((S)-2-((((9H-fluoren-9-yl)methoxy) carbonyl)amino)-3-methylbutanamido)propanamido)benzyl)-4-((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-methylpiperazin-1-ium (15 mg, 0.015 mmol, 69.6% yield) LC/MS (ESI, m/z), 1018.4 $[M]^+$ $^1$H NMR (400 MHz, METHANOL-d4) δ ppm 0.99 (s, 14H) 1.29-1.41 (m, 3H) 1.44-1.49 (m, 3H) 1.61-1.71 (m, 2H) 1.92 (d, J=1.25 Hz, 3H), 1.95-2.13 (m, 2H) 2.45-2.53 (m, 1H) 2.60-2.70 (m, 2H) 3.04-3.09 (m, 3H) 3.37 (s, 3H) 3.39-3.47 (m, 1H) 3.47-3.54 (m, 2H) 3.61-3.75, (m, 2H) 3.78-3.87 (m, 1H) 3.93-3.99 (m, 1H) 4.08-4.18 (m, 2H) 4.22-4.29 (m, 1H) 4.39-4.45 (m, 2H) 4.45-4.53 (m, 1H) 4.56-4.63 (m, 3H) 5.17-5.23 (m, 1H) 5.48-5.64 (m, 2H) 6.57-6.64 (m, 1H) 7.28-7.36 (m, 2H) 7.37-7.45 (m, 2H) 7.47-7.54 (m, 2H) 7.64-7.70 (m, 2H) 7.75-7.84 (m, 5H) 8.41-8.48 (m, 2H)

Step 2: 4-((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl) hexanamido)-3-methylbutanamido)propanamido)benzyl)-1-methylpiperazin-1-ium (6.2 mg, 42.5% yield). LC/MS (ESI, m/z), 990.34 [M+H].

$^1$H NMR (400 MHz, METHANOL-d4) δ ppm 0.97-1.09 (m, 12H) 1.24-1.41 (m, 5H) 1.47 (d, J=7.15 Hz, 3H) 1.55-1.71 (m, 6H) 1.92 (d, J=1.13 Hz, 3H) 1.98-2.15 (m, 2H) 2.27-2.36 (m, 2H) 2.46-2.53 (m, 1H) 2.60-2.71 (m, 2H) 3.06-3.13 (m, 3H) 3.35-3.38 (m, 1H) 3.41-3.58 (m, 6H) 3.62-3.76 (m, 2H) 3.80-3.88 (m, 1H) 4.08-4.19 (m, 3H) 4.43-4.52 (m, 1H) 4.57-4.66 (m, 2H) 5.16-5.24 (m, 1H) 5.49-5.68, (m, 2H) 6.62 (s, 1H) 6.81 (s, 2H) 7.49-7.57 (m, 2H) 7.76-7.87 (m, 3H) 8.39-8.49 (m, 2H)

1.5.1.5 ADL5-D30

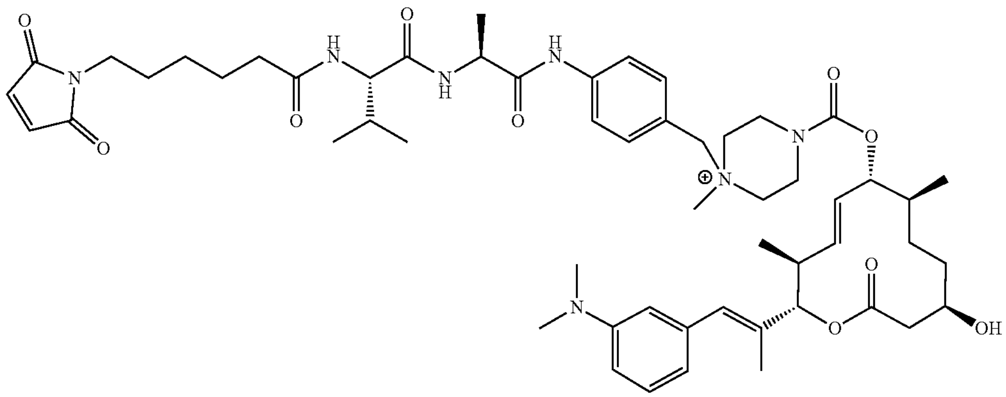 [SMILES: C/C(=C\c1cccc(N(C)C)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D30. The payload D30 was synthesized using procedures outlined in International Application No. PCT/US2019/026992, which is incorporated herein by reference.

Step 1: 1-(4-((S)-2-((S)-2-((((9H-fluoren-9-yl)methoxy) carbonyl)amino)-3-methylbutanamido)propanamido)benzyl)-4-((((2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl)oxy)carbonyl)-1-methylpiperazin-1-ium (16 mg, 0.016 mmol, 51.4% yield) LC/MS (ESI, m/z), 1027.50 $[M+H]^+$ $^1$H NMR (400 MHz, METHANOL-$d_4$) δ ppm 0.95-1.07 (m, 13H) 1.31-1.42 (m, 2H) 1.44-1.50 (m, 3H) 1.63-1.71 (m, 2H) 1.84-1.92 (m, 3H) 1.98-2.14 (m, 2H) 2.47-2.56 (m, 1H) 2.60-2.67 (m, 2H) 2.93 (s, 6H) 3.03-3.09 (m, 3H) 3.37 (s, 4H) 3.47-3.56 (m, 2H) 3.63-3.75 (m, 2H) 3.79-3.88 (m, 1H) 3.92-3.98 (m, 1H) 4.08-4.19 (m, 2H) 4.21-4.27 (m, 1H) 4.37-4.44 (m, 2H) 4.45-4.54 (m, 1H) 4.57-4.62 (m, 2H) 4.91-4.94 (m, 2H) 5.15-5.20 (m, 1H) 5.47-5.55 (m, 1H) 5.56-5.65 (m, 1H) 6.58 (s, 1H) 6.67 (d, J=1.51 Hz, 3H) 7.15-7.24 (m, 1H), 7.28-7.36 (m, 2H) 7.38-7.45 (m, 2H) 7.47-7.54 (m, 2H) 7.64-7.73 (m, 2H) 7.75-7.85 (m, 4H)

Step 2: 4-((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl)hexanamido)-3-methylbutanamido)propanamido)benzyl)-1-methylpiperazin-1-ium (6.2 mg, 42.5% yield). LC/MS (ESI, m/z), 990.34 [M+H].

$^1$H NMR (400 MHz, METHANOL-d4) δ ppm 0.88 (d, J=6.65 Hz, 12H) 1.16-1.30 (m, 4H) 1.32-1.38 (m, 3H) 1.43-1.58 (m, 6H) 1.75-1.80, (m, 3H) 1.84-1.92 (m, 1H) 1.93-2.02 (m, 1H) 2.14-2.21 (m, 2H) 2.35-2.42 (m, 1H) 2.48-2.57 (m, 2H) 2.82 (s, 6H) 2.94-3.02 (m, 3H), 3.27-3.32 (m, 1H) 3.35-3.45 (m, 4H) 3.50-3.64 (m, 2H) 3.68-3.76 (m, 1H) 3.97-4.07 (m, 3H) 4.31-4.40 (m, 1H) 4.47-4.53 (m, 2H) 5.03-5.09 (m, 1H) 5.35-5.44 (m, 1H) 5.45-5.55 (m, 1H) 6.42-6.50 (m, 1H) 6.51-6.62 (m, 3H) 6.69 (s, 2H) 7.03-7.12 (m, 1H) 7.38-7.44 (m, 2H) 7.66-7.75 (m, 2H) 8.42-8.47 (m, 1H).

1.5.1.5 ADL5-D27

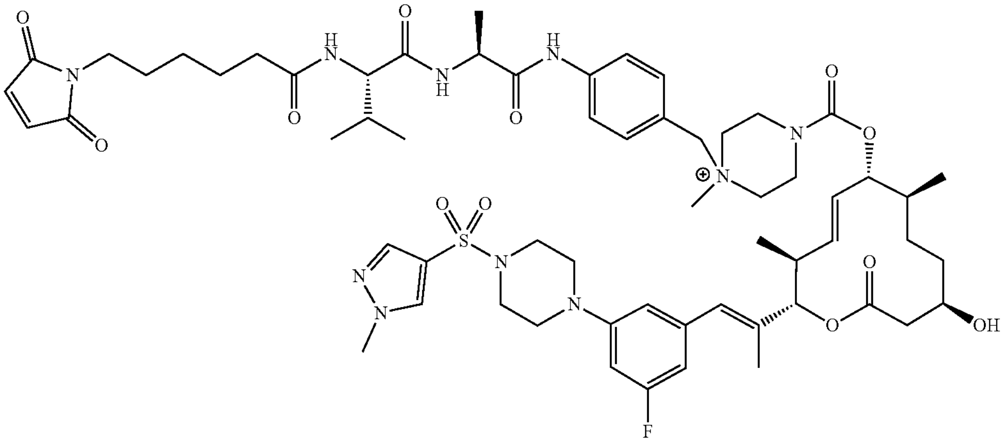 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D27. The payload D27 was synthesized using procedures outlined in International Application No. PCT/US2019/026992, which is incorporated herein by reference.

Step 1: 1-(4-((S)-2-((S)-2-((((9H-fluoren-9-yl)methoxy)carbonyl)amino)-3-methylbutanamido)propanamido)benzyl)-4-((((2S,3S,6R,7S,10R,E)-2-((E)-1-(3-fluoro-5-(4-((1-methyl-1H-pyrazol-4-yl)sulfonyl)piperazin-1-yl)phenyl)prop-1-en-2-yl)-10-hydroxy-3,7-dimethyl-12-oxooxacyclododec-4-en-6-yl)oxy)carbonyl)-1-methylpiperazin-1-ium (25.2 mg, 0.020 mmol, 83% yield). LC/MS (ESI, m/z), 1230.54 $[M+H]^+$ Step 2: 1-(4-((S)-2-((S)-2-(6-(2,5-dioxo-2,5-dihydro-1H-pyrrol-1-yl)hexanamido)-3-methylbutanamido)propanamido)benzyl)-4-((((2S,3S,6R,7S,10R,E)-2-((E)-1-(3-fluoro-5-(4-((1-methyl-1H-pyrazol-4-yl)sulfonyl)piperazin-1-yl)phenyl)prop-1-en-2-yl)-10-hydroxy-3,7-dimethyl-12-oxooxacyclododec-4-en-6-yl)oxy)carbonyl)-1-methylpiperazin-1-ium (5.2 mg, 4.33 μmol, 21.13% yield). LC/MS (ESI, m/z), 1201.68 $[M+H]^+$ $^1$H NMR (400 MHz, METHANOL-$d_4$) δ ppm 0.87 (d, J=6.78 Hz, 12H) 1.13-1.29 (m, 4H) 1.31-1.38 (m, 3H) 1.43-1.59 (m, 6H) 1.71-1.79, (m, 3H) 1.83-2.02 (m, 2H) 2.14-2.21 (m, 2H) 2.34-2.41 (m, 1H) 2.56 (s, 8H) 2.94-3.01 (m, 3H) 3.12-3.18 (m, 8H) 3.28-3.45 (m, 5H), 3.48-3.63 (m, 2H) 3.70 (s, 4H) 3.97-4.07 (m, 3H) 4.29-4.41 (m, 1H) 4.49 (s, 2H) 4.98-5.06 (m, 1H) 5.34-5.54 (m, 2H) 6.37-6.45 (m, 2H) 6.51 (s, 2H) 6.69 (s, 2H) 7.37-7.43 (m, 2H) 7.63-7.73 (m, 4H)

1.5.1.6 ADL10-D1

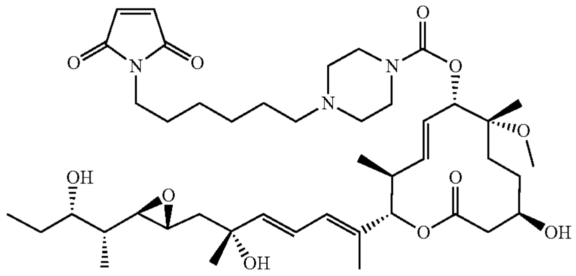 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)CC2)/C=C/[C@@H]1C]

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (0.012 g, 0.019 mmol), 2,5-dioxopyrrolidin-1-yl 6-(2,5-dioxo-2,5-dihydro-1H-pyrrol-1-yl)hexanoate (0.012 g, 0.038 mmol), and DCM (0.188 ml, 0.019 mmol) were combined and stirred overnight. The mixture was directly loaded onto a silica gel column and chromatographed to afford (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(6-(2,5-dioxo-2,5-dihydro-1H-pyrrol-1-yl)hexanoyl)piperazine-1-carboxylate (8.4 mg, 10.12 μmol, 53.7% yield). LC/MS [M+Na]853.5.

$^1$H-NMR (400 MHz, MeOH-d4): δ ppm 0.89 (s, 9H) 1.21-1.39 (m, 9H) 1.41-1.56 (m, 5H) 1.57-1.71 (m, 6H) 1.69-1.71 (m, 1H) 1.79, (d, J=0.88 Hz, 3H) 1.82-1.90 (m, 1H) 2.34-2.43 (m, 1H) 2.41-2.41 (m, 1H) 2.46-2.63 (m, 3H) 2.65-2.68 (m, 2H) 2.68 (s, 3H) 2.86-2.92 (m, 1H) 3.33 (s, 3H) 3.51 (br d, J=7.03 Hz, 6H) 3.54-3.60 (m, 5H) 3.77-3.88

(m, 1H) 5.06 (s, 2H) 5.53-5.63 (m, 1H) 5.70-5.80 (m, 1H), 5.83-5.94 (m, 1H) 6.08-6.19 (m, 1H) 6.47-6.59 (m, 1H) 6.80 (s, 2H).

1.6 Preparation of ADL12-D1, ADL14-D1, and ADL15-D1

1.6.1 Overview—General Procedure 1

Scheme 7

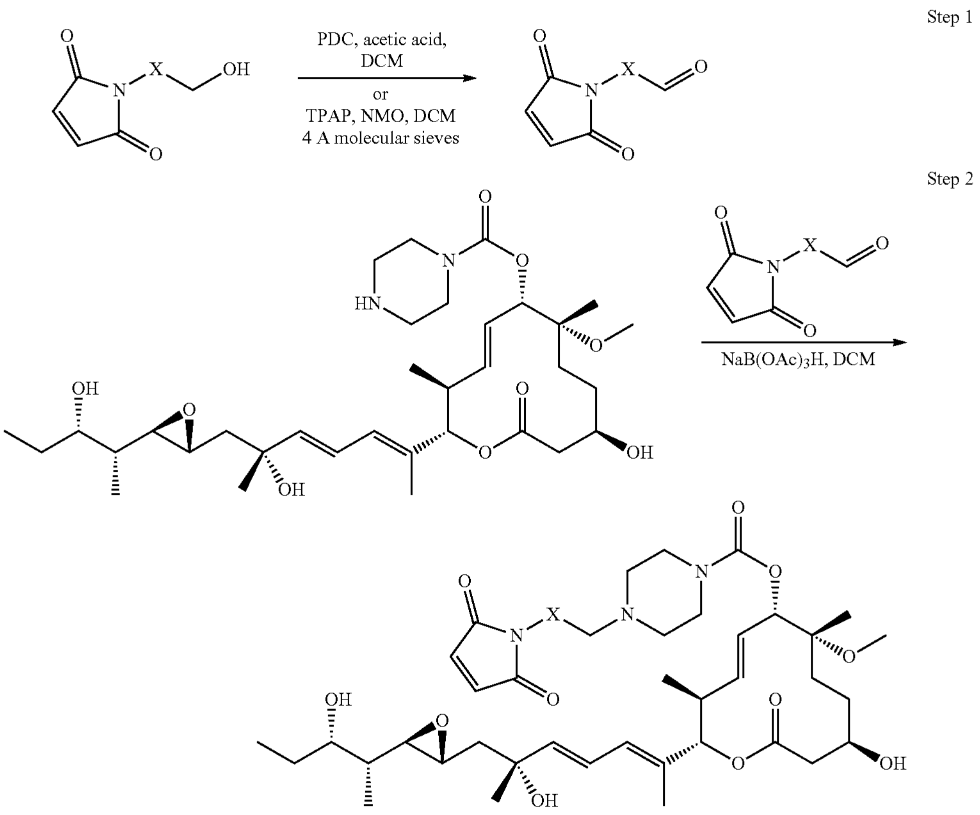

For ADL12-D1—Step 1: To a stirred solution of 1-(6-hydroxyhexyl)-1H-pyrrole-2,5-dione (0.200 g, 1.014 mmol) in DCM (20.28 mL, 1.014 mmol) was added PDC (3.81 g, 10.14 mmol) and acetic acid (0.1 mL). The reaction mixture was stirred for 3 hours at RT. The reaction mixture was then filtered through a silica pad and concentrated to dryness to afford 6-(2,5-dioxo-2,5-dihydro-1H-pyrrol-1-yl)hexanal (40 mg, 0.205 mmol, 20.21% yield).

For ADL14-D1 and ADL15-D1—Step 1: To a stirred solution of maleimide alcohol (1.0 equiv.) in DCM (0.05 M) was added pre-activated powdered MS-4A 2.6 mg per 1 mg of alcohol, N-methylmorpholine-N-oxide (1.2 equiv.), and TPAP (0.1 equiv.) in that order. The reaction mixture was stirred for 60 min at RT. The reaction mixture was then filtered through a silica gel pad and concentrated to dryness. Unpurified product was taken forward to the next step (Step 2).

Step 2: (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (1.0 equiv.), 2-(2,5-dioxo-2,5-dihydro-1H-pyrrol-1-yl)acetaldehyde (2.0-3.0 equiv.), DCM (0.1 M), sodium triacetoxyborohydride (3.0 equiv.) were mixed and stirred for 10 min. The reaction mixture was then loaded directly onto a silica gel column and chromatographed to afford the desired linker-payload.

1.6.1.1 ADL12-D1

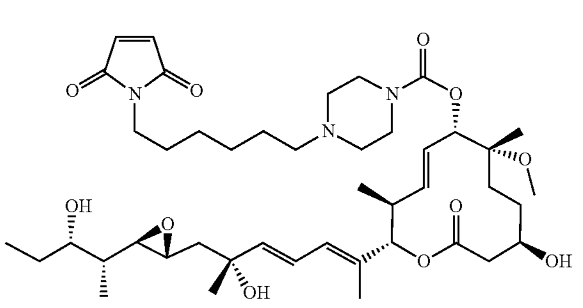 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)CC2)/C=C/[C@@H]1C]

Linker-Payload (ADL12-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (41 mg, 0.050 mmol, 80% yield). LC/MS $[M+]^+$ 816.75.

$^1$H-NMR (400 MHz, MeOH-d4): δ ppm 0.86-0.98 (m, 9H) 1.20-1.23 (m, 3H) 1.23-1.40 (m, 8H) 1.41-1.70 (m, 12H) 1.79 (d, J=0.63 Hz, 3H) 1.83-1.91 (m, 1H) 2.33-2.40 (m, 2H) 2.43 (br t, J=4.77 Hz, 4H) 2.48-2.64 (m, 3H) 2.65-2.69 (m, 1H) 2.87-2.92 (m, 1H) 3.32 (s, 3H) 3.41-3.60 (m, 7H) 3.79-3.87 (m, 1H) 5.04 (dd, J=19.39, 10.23 Hz, 2H) 5.57 (dd, J=15.18, 9.79 Hz, 1H) 5.69-5.79 (m, 1H) 5.87 (d, J=15.31 Hz, 1H) 6.11-6.17 (m, 1H) 6.49-6.58 (m, 1H) 6.80 (s, 2H).

1.6.1.X ADL12-D28

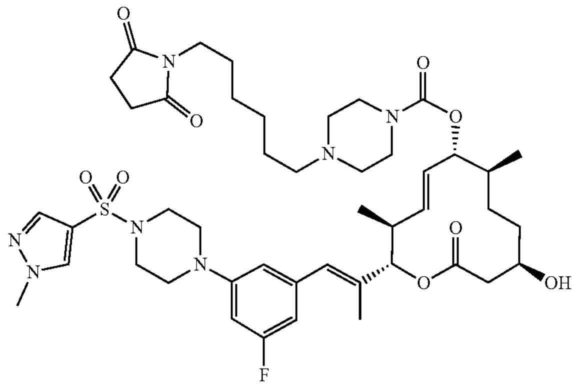 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(CCCCCCN3C(=O)CCC3=O)CC2)/C=C/[C@@H]1C]

Linker-Payload (ADL12-D28): General procedure outlined in section 1.6.1 was employed to synthesize (2S,3S,6R,7S,10R,E)-2-((E)-1-(3-fluoro-5-(4-((1-methyl-1H-pyrazol-4-yl)sulfonyl)piperazin-1-yl)phenyl)prop-1-en-2-yl)-10-hydroxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (2.3 mg, 30.7%). LC/MS $[M+]^+$ 897.32

$^1$H NMR (400 MHz, METHANOL-$d_4$) δ ppm 0.85-0.93 (m, 6H) 1.16-1.34 (m, 6H) 1.37-1.58 (m, 6H) 1.72-1.77 (m, 3H) 1.80-1.88 (m, 1H), 2.23-2.41 (m, 7H) 2.47-2.57 (m, 2H) 3.08-3.19 (m, 9H) 3.33-3.42 (m, 5H) 3.70 (s, 4H) 4.67-4.72 (m, 1H) 4.98-5.07 (m, 1H) 5.33-5.50 (m, 2H) 6.36-6.43 (m, 2H) 6.44-6.53 (m, 2H) 6.70 (s, 2H) 7.62-7.69 (m, 2H)

1.6.1.X ADL12-D35

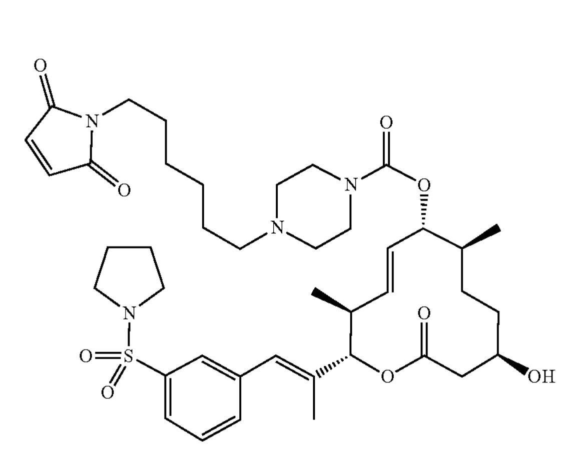 [SMILES: C/C(=C\c1cccc(S(=O)(=O)N2CCCC2)c1)[C@H]1OC(=O)C[C@H](O)CC[C@H](C)[C@@H](OC(=O)N2CCN(CCCCCCN3C(=O)C=CC3=O)CC2)/C=C/[C@@H]1C]

Linker-Payload (ADL12-D35): General procedure outlined in section 1.6.1 was employed to synthesize (2S,3S,6R,7S,10R,E)-10-hydroxy-3,7-dimethyl-12-oxo-2-((E)-1-(3-(pyrrolidin-1-ylsulfonyl)phenyl)prop-1-en-2-yl) oxacyclododec-4-en-6-yl 4-(6-(2,5-dioxo-2,5-dihydro-1H-pyrrol-1-yl)hexyl)piperazine-1-carboxylate (4.0 mg, 5.11 μmol, 28.8% yield). LC/MS $[M+H]^+$ 783.5

$^1$H NMR (400 MHz, METHANOL-d4) δ ppm 0.91 (dd, J=6.78, 2.51 Hz, 6H) 1.17-1.33 (m, 6H) 1.38-1.59 (m, 6H) 1.65 (s, 4H) 1.80 (s, 3H), 1.82-1.91 (m, 1H) 2.23-2.41 (m, 7H) 2.49-2.61 (m, 2H) 3.14 (s, 4H) 3.38 (br d, J=7.15 Hz, 6H) 3.67-3.76 (m, 1H) 4.68-4.73 (m, 1H) 5.03-5.11 (m, 1H) 5.34-5.52 (m, 2H) 6.55-6.62 (m, 1H) 6.70 (s, 2H) 7.46-7.54 (m, 2H) 7.58-7.65 (m, 2H)

1.6.1.X ADL12-D22 (R)

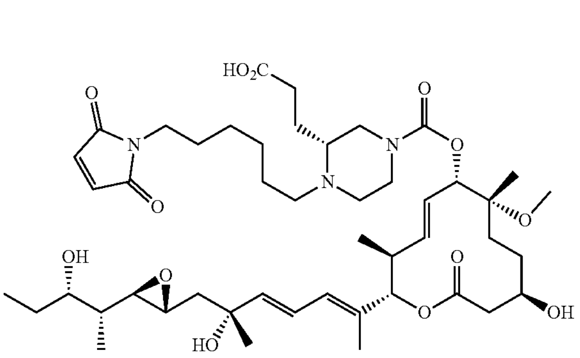

Linker-Payload (ADL12-D28): General procedure outlined in section 1.6.1 was employed to synthesize 3-((R)-1-(6-(2,5-dioxo-2,5-dihydro-1H-pyrrol-1-yl)hexyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl) propanoic acid (3.2 mg, 3.60 μmol, 15.39% yield). LC/MS $[M+]^+$ 888.5

1.6.1.X ADL12-D22 (S)

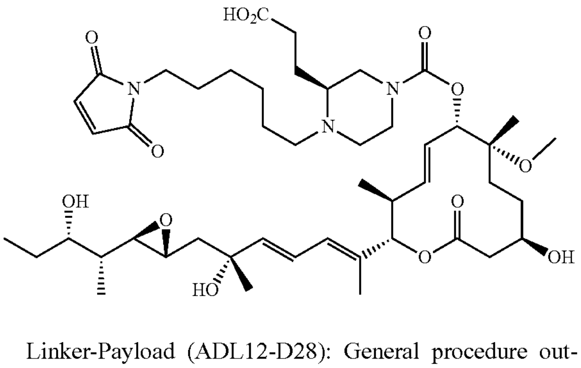

Linker-Payload (ADL12-D28): General procedure outlined in section 1.6.1 was employed to synthesize 3-((S)-1-(6-(2,5-dioxo-2,5-dihydro-1H-pyrrol-1-yl)hexyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl) propanoic acid (3.6 mg, 3.60 μmol, 28.7% yield). LC/MS $[M+]^+$ 888.56

1.6.1.2 ADL14-D1

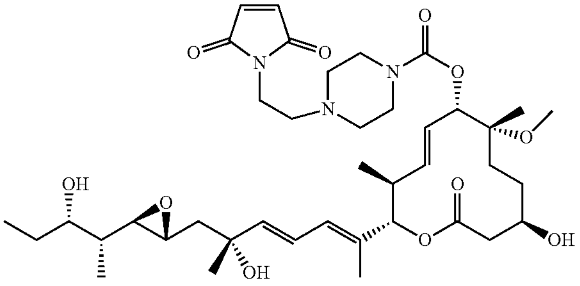 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCN3C(=O)C=CC3=O)CC2)/C=C/[C@@H]1C]

Linker-Payload (ADL14-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2,5-dioxo-2,5-dihydro-1H-pyrrol-1-yl)ethyl)piperazine-1-carboxylate (8 mg, 10.53 μmol, 33.5% yield). LC/MS [M+H] 760.3.

$^1$H-NMR (400 MHz, MeOH-d4): δ ppm 0.85-1.01 (m, 9H), 1.17-1.33 (m, 5H), 1.36 (s, 3H), 1.41-1.71 (m, 7H), 1.80 (s, 3H), 1.83-1.95 (m, 1H), 2.48 (br s, 10H), 2.89-2.98 (m, 1H), 3.40-3.57 (m, 5H), 3.61-3.72 (m, 2H), 3.78-3.91 (m, 1H), 4.98-5.14 (m, 2H), 5.50-5.52 (m, 1H), 5.52-5.65 (m, 1H), 5.69-5.82 (m, 1H), 5.86-5.96 (m, 1H), 6.09-6.21 (m, 1H), 6.47-6.60 (m, 1H), 6.79-6.90 (m, 2H).

1.6.1.3 ADL15-D1

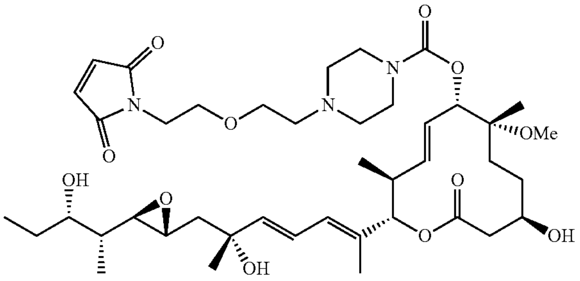 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCOCCN3C(=O)C=CC3=O)CC2)/C=C/[C@@H]1C]

Linker-Payload (ADL15-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)piperazine-1-carboxylate (7 mg, 8.71 μmol, 23.10% yield). LC/MS [M=+H] 804.1.

$^1$H-NMR (400 MHz, MeOH-d4): δ ppm 0.85-1.02 (m, 9H), 1.18-1.32 (m, 4H), 1.36 (s, 3H), 1.40-1.72 (m, 7H), 1.78-1.83 (m, 3H), 1.85-1.93 (m, 1H), 2.42-2.65 (m, 9H), 2.67-2.73 (m, 1H), 2.89-2.96 (m, 1H), 3.37 (s, 5H), 3.41-3.58 (m, 5H), 3.59-3.67 (m, 4H), 3.68-3.75 (m, 2H), 3.81-3.89 (m, 1H), 4.94-5.15 (m, 2H), 5.61 (br d, J=10.04 Hz, 1H), 5.69-5.82 (m, 1H), 5.89 (br d, J=15.18 Hz, 1H), 6.16 (br d, J=10.92 Hz, 1H), 6.56 (br s, 1H), 6.77-6.91 (m, 2H).

1.7 ADL12-D2

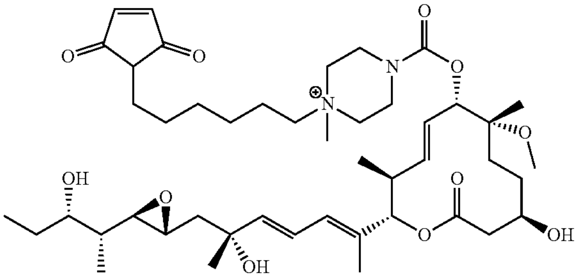 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCCCCCC3C(=O)C=CC3=O)CC2)/C=C/[C@@H]1C]

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (26 mg, 0.032 mmol), acetonitrile (319 μL, 0.032 mmol), iodomethane (19.92 μL, 0.319 mmol) were combined and stirred overnight. The reaction mix was concentrated to dryness and chromatographed (0-30% MeOH in DCM) to afford 1-(6-(2,5-dioxo-2,5-dihydro-1H-pyrrol-1-yl)hexyl)-4-((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium (14 mg, 0.017 mmol, 52.9% yield). LC/MS [M+] 831.6.

$^1$H-NMR (400 MHz, MeOH-d4): δ ppm 0.86-0.98 (m, 9H) 1.26 (s, 4H) 1.36 (s, 3H) 1.40-1.58 (m, 9H) 1.60-1.71 (m, 4H) 1.80 (d, J=0.88 Hz, 4H) 1.85-1.91 (m, 1H) 1.87-1.88 (m, 1H) 2.48-2.63 (m, 3H) 2.65-2.72 (m, 1H) 2.88-2.94 (m, 1H) 3.18 (s, 3H) 3.34-3.41 (m, 3H) 3.53 (s, 10H) 3.73-3.90 (m, 3H) 3.90-4.06 (m, 2H) 5.02-5.11 (m, 2H) 5.56-5.66 (m, 1H) 5.70-5.81 (m, 1H) 5.84-5.94 (m, 1H) 6.11-6.20 (m, 1H) 6.50-6.60 (m, 1H) 6.83 (s, 2H).

1.8 ADL15-D2

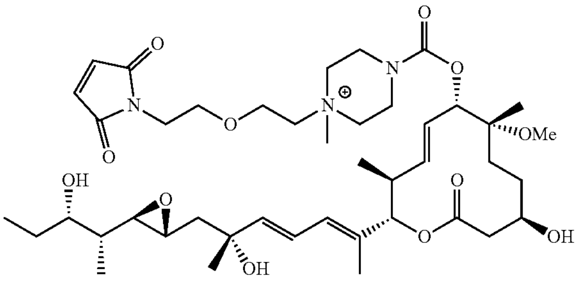 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCOCCN3C(=O)C=CC3=O)CC2)/C=C/[C@@H]1C]

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)piperazine-1-carboxylate (6 mg, 7.463 μmol), iodomethane (0.467 μL, 7.463 μmol), and acetonitrile (0.390 μL, 7.463 μmol) were combined and stirred at RT. The reaction mixture was concentrated to dryness to afford (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)-4-methyl-414-piperazine-1-carboxylate (6 mg, 7.33 μmol, 98% yield). LC/MS [M+]$^+$ 819.28.

$^1$H-NMR (400 MHz, MeOH-d4): δ ppm 0.74-0.88 (m, 9H) 1.18 (br d, J=4.27 Hz, 5H) 1.23-1.27 (m, 3H) 1.28-1.49 (m, 5H) 1.51-1.61 (m, 2H) 1.66-1.71 (m, 3H) 1.73-1.80 (m, 1H) 2.36-2.53 (m, 3H) 2.55-2.60 (m, 1H) 2.78-2.83 (m, 1H) 3.10-3.14 (m, 3H) 3.23-3.25 (m, 3H) 3.32-3.51 (m, 5H) 3.52-3.67 (m, 6H) 3.67-3.87 (m, 7H) 4.93-5.01 (m, 2H) 5.44-5.55 (m, 1H) 5.61-5.70 (m, 1H) 6.00-6.07 (m, 1H) 6.38-6.48 (m, 1H) 6.75 (s, 2H).
1.9 ADL5-D25
Scheme 8
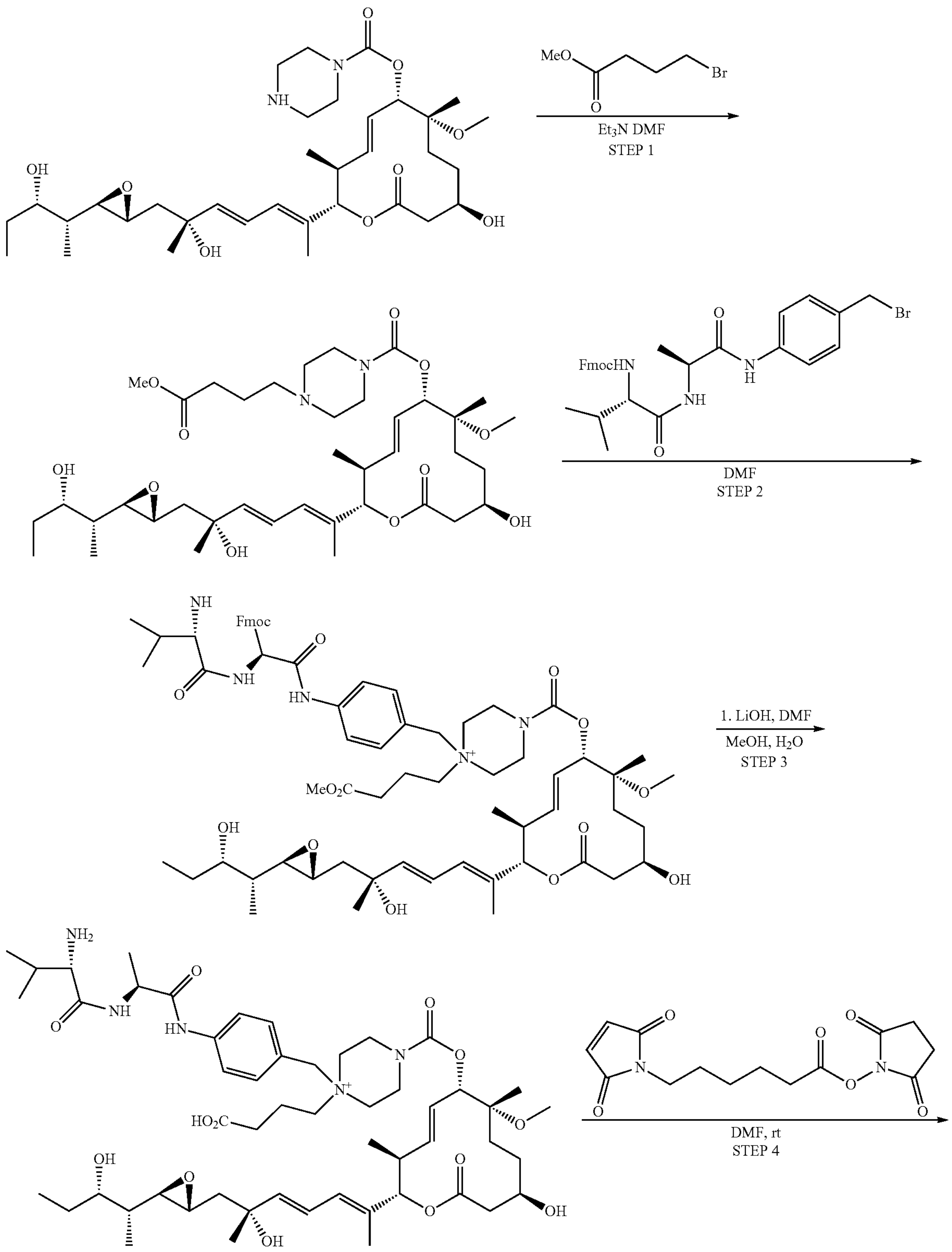

-continued

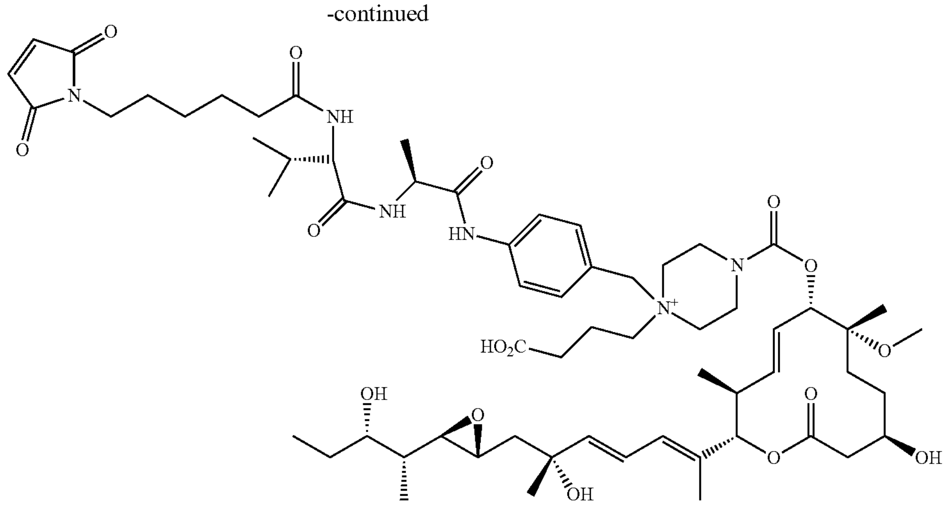

Step 1: D1 (40 mg, 0.063 mmol) was dissolved in N,N-dimethylformamide (730 μl, 9.422 mmol) and methylbromobutarate (23.69 μL, 0.188 mmol) was added followed by triethylamine (35.0 μL, 0.251 mmol). The solution was stirred at RT for 2 days. The solvent was evaporated. Purification by column chromatography afforded (2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(4-methoxy-4-oxobutyl)piperazine-1-carboxylate (51 mg, 0.069 mmol, ~100% yield) as a colorless oil. LC/MS (ESI, m/z), 737.4 $[M+H]^+$. $^1$H-NMR (400 MHz, MeOH-d4): δ ppm 0.76-0.86 (m, 9H), 1.12 (s, 3H), 1.14-1.19 (m, 1H), 1.24 (s, 3H), 1.34-1.50 (m, 5H), 1.52-1.60 (m, 1H), 1.69 (s, 6H), 2.27 (s, 8H), 2.37-2.49 (m, 3H), 2.54-2.61 (m, 1H), 2.77-2.83 (m, 1H), 3.35-3.47 (m, 5H), 3.56 (s, 3H), 3.67-3.76 (m, 1H), 4.46 (s, 3H), 4.89-5.00 (m, 3H), 5.42-5.52 (m, 1H), 5.57-5.70 (m, 1H), 5.73-5.81 (m, 1H), 5.98-6.08 (m, 1H), 6.43 (dd, J=15.25, 10.98 Hz, 1H).

Step 2: Fmoc-ValAla-PAB bromide (88 mg, 0.152 mmol) and (2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(4-methoxy-4-oxobutyl)piperazine-1-carboxylate (51 mg, 0.069 mmol) were suspended in N,N-dimethylformamide (670 μL, 8.651 mmol).

The reaction was stirred at RT overnight. The solvent was evaporated. Purification by column chromatography afforded 1-(4-((S)-2-((S)-2-((((9H-fluoren-9-yl)methoxy)carbonyl)amino)-3-methylbutanamido)propanamido)benzyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-(4-methoxy-4-oxobutyl)piperazin-1-ium (42 mg, 0.034 mmol, 49.1% yield) as a waxy solid. LC/MS (ESI, m/z), 1235.4 $[M]^+$.

Step 3: 1-(4-((S)-2-((S)-2-((((9H-fluoren-9-yl)methoxy)carbonyl)amino)-3-methylbutanamido)propanamido)benzyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-(4-methoxy-4-oxobutyl)piperazin-1-ium (42 mg, 0.034 mmol) was dissolved in a 5:2:1 ratio of THF (600 μL, 7.322 mmol), MeOH (250 μL, 6.179 mmol), water (125 μL, 6.939 mmol), and lithium hydroxide (1.221 mg, 0.051 mmol) was added. The mixture was stirred at RT for 1 hour. The mixture was quenched with acetic acid (5.84 μL, 0.102 mmol) and the solvent was evaporated and purified by RP HPLC to afford 1-(4-((S)-2-((S)-2-amino-3-methylbutanamido)propanamido)benzyl)-1-(3-carboxypropyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium as a waxy solid (18.4 mg, 0.018 mmol, 54.2% yield). LC/MS (ESI, m/z), 998.5 $[M]^+$.

Step 4: 1-(4-((S)-2-((S)-2-amino-3-methylbutanamido)propanamido)benzyl)-1-(3-carboxypropyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium (18.4 mg, 0.018 mmol) was dissolved in N,N-dimethylformamide (356 μL, 4.603 mmol) and 2,5-dioxopyrrolidin-1-yl 6-(2,5-dioxo-2,5-dihydro-1H-pyrrol-1-yl)hexanoate (6.81 mg, 0.022 mmol) was added followed by Hunig's base (8.04 μL, 0.046 mmol). The reaction solution was stirred at RT for 30 min. The solvent was evaporated and the crude residue was purified by RP HPLC to afford (1-(3-carboxypropyl)-1-(4-((S)-2-((R)-2-(6-(2,5-dioxo-2,5-dihydro-1H-pyrrol-1-yl)hexanamido)-3-methylbutanamido)propanamido)benzyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium (8.8 mg, 7.38 μmol, 40.1% yield) as a white lyophilized solid. LC/MS (ESI, m/z), 1191.5 $[M]^+$.

$^1$H-NMR (400 MHz, DMSO-d6): δ ppm 0.68-0.81 (m, 18H), 0.98-1.07 (m, 4H), 1.07-1.14 (m, 3H), 1.16 (br d, J=3.89 Hz, 5H), 1.22-1.33 (m, 8H), 1.36-1.47 (m, 7H), 1.62 (s, 3H) 1.66-1.73 (m, 1H), 1.83-1.92 (m, 5H), 1.98-2.13 (m, 2H), 2.26 (dt, J=3.54, 1.80 Hz, 1H), 2.27-2.33 (m, 1H), 2.47-2.51 (m, 2H), 2.58-2.62 (m, 1H), 2.66-2.72 (m, 1H), 3.15 (s, 3H) 3.45-3.58 (m, 3H), 3.60-3.68 (m, 2H) 3.77-3.86 (m, 2H), 4.06-4.13 (m, 1H), 4.27-4.37 (m, 2H), 4.46-4.54 (m, 3H), 4.72-4.78 (m, 1H), 4.80-4.87 (m, 2H), 5.32-5.48

(m, 1H), 5.53-5.67 (m, 1H), 5.73-5.86 (m, 1H), 5.93-6.05 (m, 1H), 6.16-6.26 (m, 1H), 6.20 (s, 1H), 6.23-6.41 (m, 1H), 6.27-6.38 (m, 1H), 6.93 (s, 2H), 6.98-7.06 (m, 2H), 7.43-7.50 (m, 2H), 7.62-7.69 (m, 2H), 7.74-7.80 (m, 1H), 8.22-8.27 (m, 1H), 8.44-8.49 (m, 4H), 10.15-10.22 (m, 1H).

1.10 ADL12-D20 & ADL12-D21

General procedure 1 outlined in section 1.2.1 was employed to synthesize D20.

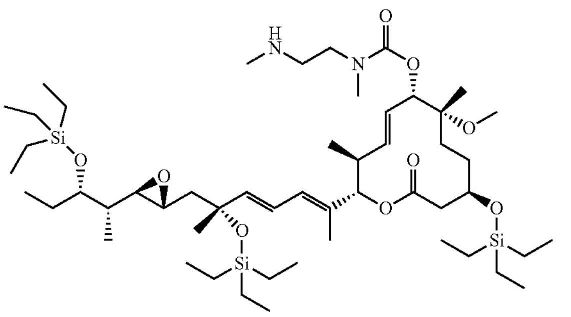 [SMILES: CC[C@H](O[Si](CC)(CC)CC)[C@@H](C)[C@H]1O[C@@H]1C[C@](C)(/C=C/C=C(\C)[C@H]1OC(=O)C[C@H](O[Si](CC)(CC)CC)CC[C@@](C)(OC)[C@@H](OC(=O)N(C)CCNC)/C=C/[C@@H]1C)O[Si](CC)(CC)CC]

(2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl methyl(2-(methylamino)ethyl)carbamate (43 mg, 0.044 mmol, 90% yield) as a colorless oil. LC/MS (ESI, m/z), 981.4 $[M+H]^+$.

$^1$H-NMR (400 MHz, MeOH-d4): δ ppm 0.62-0.73 (m, 18H), 0.82-0.93 (m, 9H), 0.95-1.06 (m, 27H), 1.24 (br s, 4H), 1.45 (br s, 10H), 1.78 (br s, 3H), 1.92-2.00 (m, 1H), 2.46 (br s, 4H), 2.51-2.67 (m, 3H), 2.76-2.84 (m, 2H), 2.86-2.93 (m, 1H), 2.93-3.02 (m, 3H), 3.34-3.38 (m, 3H), 3.43-3.49 (m, 2H), 3.72-3.82 (m, 1H), 3.93-4.04 (m, 1H), 4.94-5.07 (m, 2H), 5.53-5.64 (m, 1H), 5.72-5.89 (m, 2H), 6.07-6.21 (m, 1H), 6.44-6.61 (m, 1H).

D20

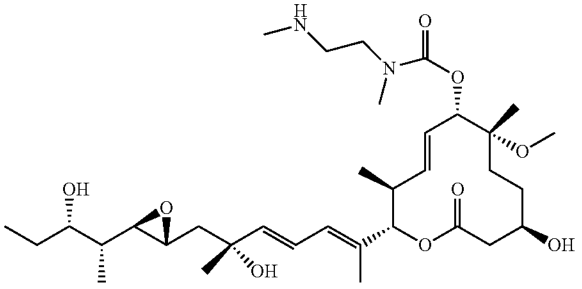 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N(C)CCNC)/C=C/[C@@H]1C]

(2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl methyl(2-(methylamino)ethyl)carbamate (16.4 mg, 0.026 mmol, 58.6% yield) as a colorless oil. LC/MS (ESI, m/z), 639.7 $[M+H]^+$.

$^1$H-NMR (400 MHz, MeOH-d4): δ ppm 0.92 (br d, J=6.53 Hz, 9H), 1.25 (br s, 4H), 1.36 (s, 3H), 1.41-1.74 (m, 6H), 1.45-1.59 (m, 1H), 1.64-1.72 (m, 1H), 1.80 (s, 3H), 1.85-1.94 (m, 1H), 2.42 (s, 3H), 2.50-2.63 (m, 3H), 2.65-2.73 (m, 1H), 2.73-2.80 (m, 2H), 2.88-3.01 (m, 4H), 3.35-3.38 (m, 3H), 3.35-3.40 (m, 3H), 3.41-3.48 (m, 2H), 3.52-3.57 (m, 1H), 3.78-3.89 (m, 1H), 5.00-5.13 (m, 2H), 5.53-5.64 (m, 1H), 5.71-5.82 (m, 1H), 5.84-5.94 (m, 1H), 6.12-6.19 (m, 1H), 6.49-6.61 (m, 1H).

ADL12-D20

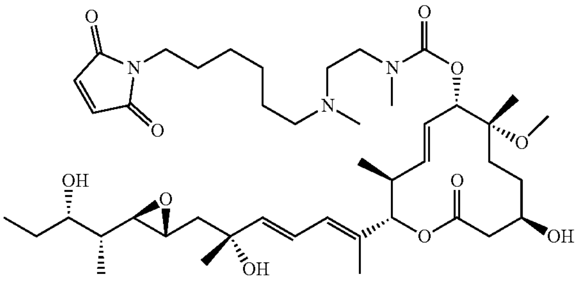 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N(C)CCN(C)CCCCCCN2C(=O)C=CC2=O)/C=C/[C@@H]1C]

General procedure outlined in section 1.6.1 was employed to synthesize ALD12-D20 and afforded (13.0 mg, 0.016 mmol, 67.7%) as a colorless oil. LC/MS (ESI, m/z), 818.3 $[M+H]^+$.

$^1$H-NMR (400 MHz, MeOH-d4): δ ppm 0.91 (br s, 9H), 1.21-1.31 (m, 4H), 1.36 (br s, 7H), 1.46-1.73 (m, 11H), 1.80 (s, 3H), 1.84-1.93 (m, 1H), 2.50-2.72 (m, 7H), 2.75-2.85 (m, 1H), 2.87-3.09 (m, 7H), 3.48-3.68 (m, 6H) 3.80-3.89 (m, 1H), 5.02-5.13 (m, 2H), 5.55-5.66 (m, 1H), 5.71-5.82 (m, 1H), 5.85-5.94 (m, 1H), 6.11-6.22 (m, 1H), 6.49-6.61 (m, 1H), 6.83 (br d, J=1.13 Hz, 2H).

ADL12-D21

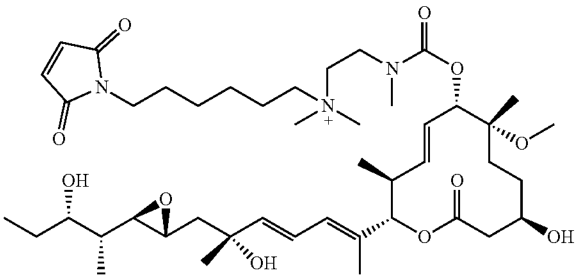

((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl (2-((6-(2,5-dioxo-2,5-dihydro-1H-pyrrol-1-yl)hexyl)(methyl)amino)ethyl)(methyl)carbamate (7 mg, 8.557 μmol) was dissolved in N,N-dimethylformamide (99 μl, 1.284 mmol) and methyl iodide (2.68 μL, 0.043 mmol) was added. The solution was stirred at rt o/n. The solvent was evaporated. Purification by column chromatography afforded 6-(2,5-dioxo-2,5-dihydro-1H-pyrrol-1-yl)-N-(2-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)(methyl)amino)ethyl)-N,N-dimethylhexan-1-aminium (7 mg, 8.40 μmol, 98% yield). LC/MS (ESI, m/z), 832.7 $[M+H]^+$.

$^1$H-NMR (400 MHz, MeOH-d4): δ ppm 0.75-0.87 (m, 9H), 1.14 (s, 4H), 1.25 (s, 3H), 1.27-1.45 (m, 9H), 1.48-1.61 (m, 4H), 1.69 (s, 4H), 1.72-1.79 (m, 2H), 2.35-2.53 (m, 3H), 2.53-2.60 (m, 1H), 2.75-2.83 (m, 1H), 2.85-2.95 (m, 3H), 3.06 (br d, J=10.42 Hz, 6H), 3.15-3.20 (m, 2H), 3.25 (br d, J=2.38 Hz, 3H), 3.42 (br d, J=6.90 Hz, 5H), 3.53-3.69 (m, 2H), 3.69-3.78 (m, 1H), 4.88-5.01 (m, 2H), 5.44-5.56 (m, 1H), 5.59-5.72 (m, 1H), 5.73-5.83 (m, 1H), 5.99-6.10 (m, 1H), 6.40 (s, 1H), 6.72 (s, 2H).

1.11 ADL12-D22

General procedure 1 outlined in section 1.2.1 was employed to synthesize D22.

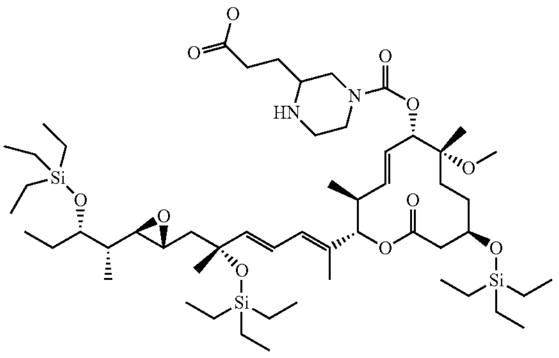 [SMILES: CC[C@H](O[Si](CC)(CC)CC)[C@@H](C)[C@H]1O[C@@H]1C[C@](C)(/C=C/C=C(\C)[C@H]1OC(=O)C[C@H](O[Si](CC)(CC)CC)CC[C@@](C)(OC)[C@@H](OC(=O)N2CCNC(CCC(=O)O)C2)/C=C/[C@@H]1C)O[Si](CC)(CC)CC]

3-(4-((((2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl)oxy)carbonyl)piperazin-2-yl)propanoic acid (48 mg, 0.046 mmol, 34.4% yield) as a colorless oil. LC/MS (ESI, m/z), 1051.4 $[M+H]^+$.

$^1$H-NMR (400 MHz, MeOH-d4): δ ppm 0.62-0.70 (m, 18H), 0.82-0.94 (m, 9H), 1.01 (tt, J=7.92, 3.18 Hz, 27H), 1.22-1.28 (m, 4H), 1.45 (s, 3H), 1.47-1.66 (m, 7H), 1.76-1.87 (m, 5H), 1.92-1.99 (m, 1H), 2.36-2.47 (m, 3H), 2.50-2.68 (m, 3H), 2.86-2.93 (m, 1H), 2.98-3.08 (m, 2H), 3.10-3.18 (m, 1H), 3.18-3.26 (m, 2H), 3.27-3.31 (m, 1H), 3.34-3.36 (m, 3H), 3.36-3.37 (m, 1H) 3.72-3.81 (m, 1H), 3.95-4.19 (m, 3H), 4.93-5.00 (m, 1H), 5.01-5.07 (m, 1H), 5.54-5.66 (m, 1H) 5.72-5.81 (m, 1H) 5.81-5.90 (m, 1H), 6.12-6.19 (m, 1H), 6.47-6.58 (m, 1H).

D22

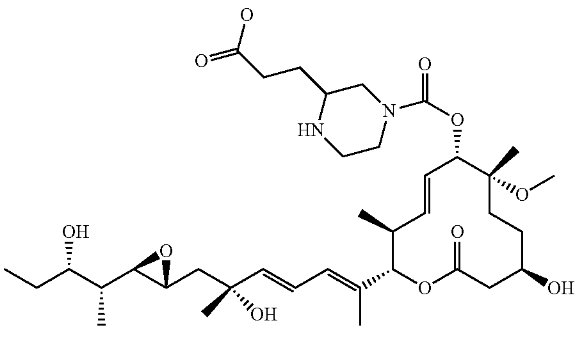 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCNC(CCC(=O)O)C2)/C=C/[C@@H]1C]

N-ethyl-N-isopropylpropan-3-(4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (23.5 mg, 0.031 mmol, 68.2% yield). LC/MS (ESI, m/z), 709.5 $[M+H]^+$.

$^1$H-NMR (400 MHz, DMSO-d6): δ ppm 0.71-0.77 (m, 9H), 1.03 (s, 5H), 1.14-1.20 (m, 6H), 1.23-1.33 (m, 5H), 1.36-1.48 (m, 5H), 1.63 (s, 3H), 1.67-1.75 (m, 1H), 2.13-2.24 (m, 4H), 2.58-2.64 (m, 1H), 2.68-2.81 (m, 2H), 3.20-3.20 (m, 3H), 3.61-3.77 (m, 4H), 4.28-4.39 (m, 1H), 4.44-4.53 (m, 1H), 4.79-4.88 (m, 2H), 5.28-5.43 (m, 1H), 5.52-5.66 (m, 1H), 5.73-5.85 (m, 1H), 5.94-6.04 (m, 1H), 6.27-6.41 (m, 1H), 6.43-6.53 (m, 2H), 8.19-8.29 (m, 1H).

ADL12-D22

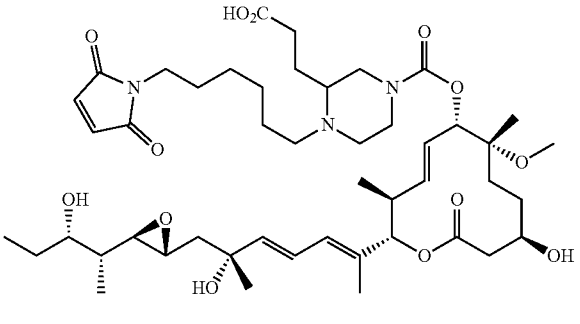 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)C(CCC(=O)O)C2)/C=C/[C@@H]1C]

General procedure outlined in section 1.6.1 was employed to synthesize ADL12-D22 (3.6 mg, 4.05 μmol, 34.4% yield). LC/MS (ESI, m/z), 888.7 $[M+H]^+$.

$^1$H-NMR (400 MHz, MeOH-d4): δ ppm 0.77-0.89 (m, 9H), 1.08-1.31 (m, 13H), 1.35-1.60 (m, 12H), 1.69 (s, 3H), 1.73-1.83 (m, 1H), 1.85-1.97 (m, 1H), 2.15-2.27 (m, 1H), 2.27-2.83 (m, 11H), 2.84-2.98 (m, 1H), 3.39 (s, 7H), 3.67-3.77 (m, 1H), 4.89-5.01 (m, 2H), 5.40-5.53 (m, 1H), 5.59-5.69 (m, 1H), 5.72-5.83 (m, 1H), 5.99-6.11 (m, 1H), 6.37-6.49 (m, 1H), 6.69 (s, 2H).

ADL1-D22

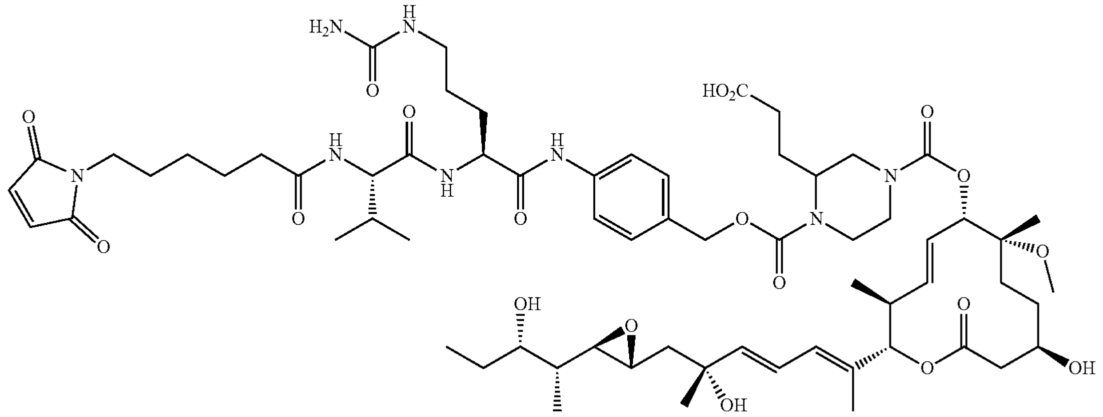 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)C(CCC(=O)O)C2)/C=C/[C@@H]1C]

General procedure 1 outlined in section 1.2.1 was employed to synthesize ADL1-D22 (4.7 mg, 3.59 μmol, 38.6% yield) as a white lyophilized solid. LC/MS (ESI, m/z), 1307.6 $[M+H]^+$.

$^1$H NMR (400 MHz, DMSO-d6): δ ppm 0.68-0.79 (m, 16H), 1.03 (s, 3H), 1.16 (s, 5H), 1.23-1.44 (m, 13H), 1.48-1.55 (m, 1H), 1.62 (s, 4H), 1.68-1.74 (m, 1H), 1.86-1.93 (m, 1H), 2.02 (s, 4H), 2.24-2.37 (m, 3H), 2.46-2.51 (m, 2H), 2.66-2.73 (m, 1H), 2.79-2.99 (m, 4H), 3.15 (s, 3H), 3.21-3.22 (m, 2H), 3.30 (s, 4H), 3.61-3.67 (m, 1H), 3.73-3.88 (m, 3H), 4.01-4.08 (m, 1H), 4.09-4.16 (m, 1H), 4.29-4.38 (m, 2H), 4.43-4.51 (m, 1H), 4.73-4.78 (m, 1H), 4.79-4.88 (m, 2H), 4.91-4.98 (m, 2H), 5.29-5.43 (m, 3H), 5.54-5.67 (m, 1H), 5.74-5.83 (m, 1H), 5.95-6.07 (m, 1H), 6.28-6.40 (m, 1H), 6.54-6.62 (m, 1H), 6.93 (s, 2H), 7.17-7.26 (m, 2H), 7.44-7.57 (m, 2H), 7.66-7.76 (m, 1H), 7.95-8.03 (m, 1H), 8.42-8.49 (m, 1H), 9.89-9.96 (m, 1H).

ADL1-D23

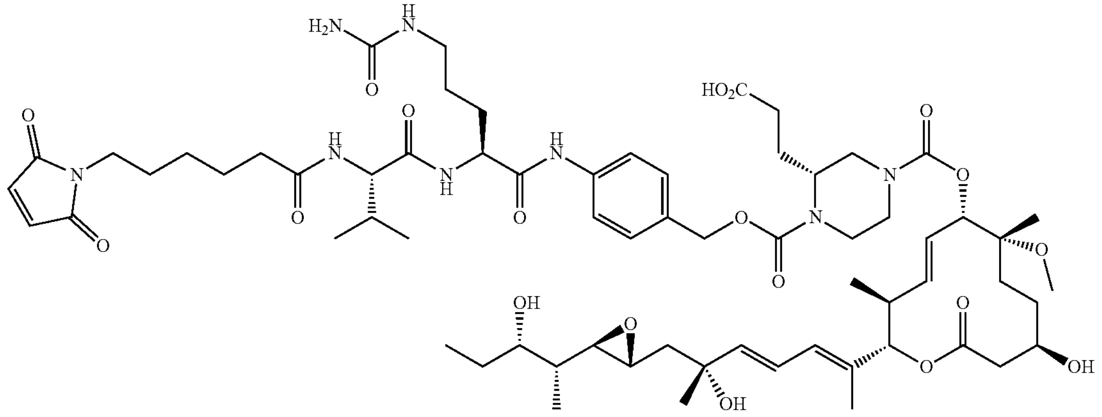 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)[C@H](CCC(=O)O)C2)/C=C/[C@@H]1C]

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (16.76 mg, 0.023 mmol) and 3-((R)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (16.1 mg, 0.023 mmol) were dissolved in DMF (229 μl, 2.953 mmol) and Hunig's Base (11.90 μl, 0.068 mmol) was added. The reaction mixture was stirred overnight at rt. The solvent was then evaporated and subjected to reverse-phase HPLC purification to afford 3-((R)-1-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (3.9 mg, 2.98 μmol, 13.13% yield). LC/MS (ESI, m/z), 1308.6 $[M+H]^+$.

ADL1-D24 (S)

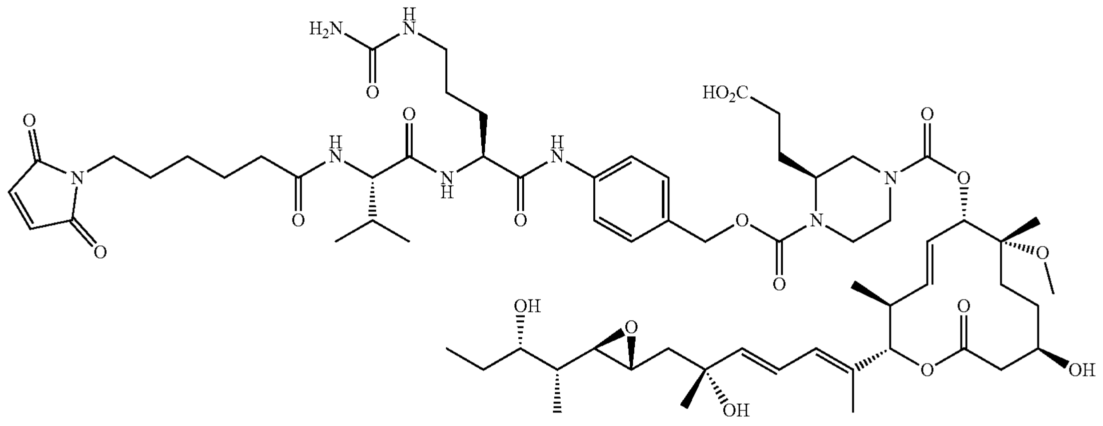 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)[C@@H](CCC(=O)O)C2)/C=C/[C@@H]1C]

3-((S)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (10 mg, 0.014 mmol), N,N-dimethylformamide (141 μl, 0.014 mmol), Hunig's base (5 μl, 0.028 mmol), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (20.8 mg, 0.028 mmol) were combined and stirred for 2 hours. chromatograoged ($MeOH/CH_2Cl_2$) to afford 3-((S)-1-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (5 mg, 3.82 μmol, 27.1% yield). LC/MS (ESI, m/z), 1308.4 $[M+H]^+$.

Example 2

Exemplary spliceosome modulator payloads used in the preparation of ADCs were profiled. Payloads were evaluated for binding to the SF3b complex, in vitro splicing activity, and ability to inhibit cell growth. 2.1 SF3B1 Binding/Scintillation Proximity Assay (SPA)

A scintillation proximity assay was performed to measure the binding affinity of compounds ("payloads") to the SF3b complex. Batch immobilization of anti-SF3B1 antibody (MBL) to anti-mouse PVT SPA scintillation beads (PerkinElmer) was prepared as follows: for every 2.5 mg of nuclear extracts, 5 μg of anti-SF3B1 antibody and 1.5 mg of beads were mixed in 150 μL PBS. The antibody-bead mixture was incubated for 30 min at RT and centrifuged at 18,000 g for 5 min. 150 μL PBS was used to resuspend every 1.5 mg antibody-bead mixture. The beads were suspended and added to the prepared nuclear extracts. The slurry was incubated for 2 hours at 4° C. with gentle mixing. The beads were then collected by centrifuging at 18,000 g for 5 min, and washed twice with PBS+0.1% Triton X-100. After a final centrifugation step, every 1.5 mg of beads was suspended with 150 μL of PBS. SF3b complexes were tested for $[^3H]$-labeled pladienolide B probe binding ($[^3H]$-PB), synthesized as previously described (Kotake et al. (2007) Nat Chem Biol. 3(9):570-5). 100 μL binding reactions were prepared with 50 μL bead slurry and by adding varying concentrations of PB or PB—OH, and after 30 min preincubation, 2.5 nM of $[^3H]$—PB was added. The mixture was incubated for 30 min, and luminescence signals were read using a MicroBeta2 Plate Counter (PerkinElmer). Prism 7 (Graphpad) was used for non-linear regression curve fitting of the data.

Similar binding profiles were observed for all tested payloads (FIG. 1). In general, specific binding was in the low nanomolar range, suggesting that all tested payloads are potent SF3b complex binders and promising candidate compounds for use in ADCs.

2.2 In Vitro Splicing (IVS)

To evaluate payload activity in a cell-free system, an in vitro splicing assay was performed. The payloads were incubated with nuclear extracts and pre-mRNA substrate minigenes.

HeLa nuclear extract preparation: HeLa S3 cell pellets were resuspended in hypotonic buffer (10 mM HEPES pH 7.9, 1.5 mM $MgCl_2$, 10 mM KCl, 0.2 mM PMSF, 0.5 mM DTT) and the suspension was brought up to a total of 5 packed cell volume (PCV). After centrifugation, the supernatant was discarded, and the cells were brought up to 3 PCV with hypotonic buffer and incubated on ice for 10 min. Cells were lysed using a dounce homogenizer and then centrifuged. The supernatant was discarded, and the pellet was resuspended with % packed nuclear volume (PNV) of low salt buffer (20 mM HEPES pH 7.9, 1.5 mM $MgCl_2$, 20 mM KCl, 0.2 mM EDTA, 25% glycerol, 0.2 mM PMSF, 0.5 mM DTT), followed by % PNV of high salt buffer (same as low salt buffer except 1.4 M KCl). The nuclei were gently mixed for 30 min before centrifuging. The supernatant (nuclear extract) was then dialyzed into storage buffer (20 mM HEPES pH 7.9, 100 mM KCl, 0.2 mM EDTA, 20% glycerol, 0.2 mM PMSF, 0.5 mM DTT). Protein concentration was determined using NanoDrop 8000 UV-Vis spectrophotometer (ThermoFisher Scientific).

Figure 2:
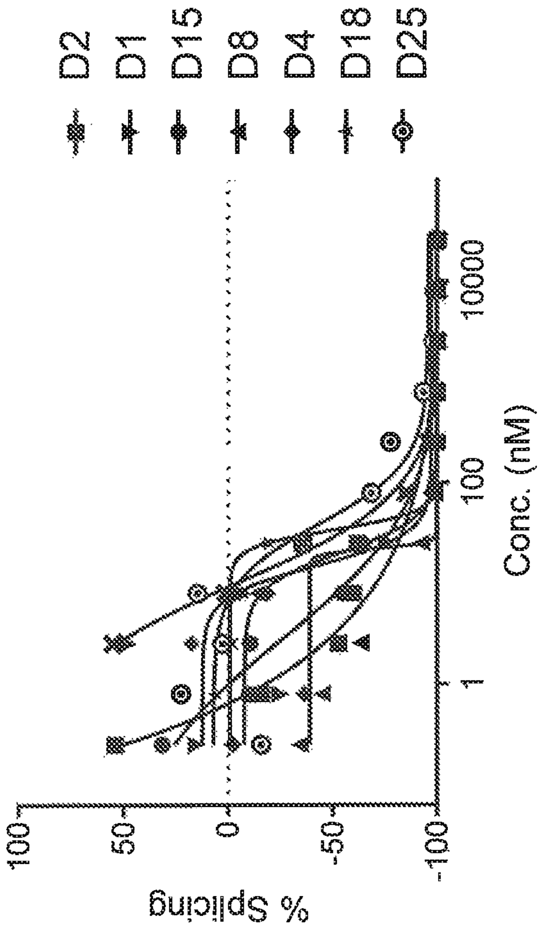
FIG. 2 shows modulation of splicing by exemplary payload compounds in an in vitro splicing assay. Nuclear extracts from HeLa S3 cells were incubated with Ad2.2 pre-mRNA and increasing concentrations of compound, followed by quantification of splicing modulation via RT-PCR. The Ad2.2 sequence is derived from the adenoviral Ad2 pre-mRNA substrate with modifications around the branch point sequence. The y-axis represents the percent change (% response) of splicing relative to the DMSO control (0%). Data are represented as mean±SD.

IVS: All Ad2-derived sequences (Pellizzoni et al. (1998) Cell 95(5):615-24) were cloned into pcDNA3.1(+) vector (Promega) using 5' EcoRI and 3' XbaI restriction sites. The plasmids were linearized using XbaI and used as DNA templates in in vitro transcription reactions. The FtzAi intron-less plasmid (Luo and Reed (1999) 96(26):14937-42) was linearized using EcoRI. All RNAs were in vitro transcribed and then purified using MEGAScript T7 (Invitrogen)

and MegaClear (Invitrogen) kits, respectively. For splicing reactions using Ad2 variant pre-mRNAs, 1 μL reactions were prepared using 8 μg nuclear extracts prepared from HeLa S3, 2 ng pre-mRNA, 0.2 ng FTZAi, and varying concentrations of compounds or DMSO. After a 15 min pre-incubation at 30° C., 1 μL splicing activation buffer (0.5 mM ATP, 20 mM creatine phosphate, 1.6 mM $MgCl_2$) was added, and the reactions were incubated for 90 min at 30° C. The reactions were then quenched with 13 μL DMSO, and 25 nL was used for RT-qPCR. RT-qPCR reactions were prepared using TaqMan RNA-to-$C_T$ 1-step kit (Life Technologies), RNA from splicing reactions, Ad2 (forward: ACTCTCTTCCGCATCGCTGT; reverse: CCGACGGG-TTTCCGATCCAA; probe: CTGTTGGGCTCGCGGTTG) and Ftz (forward: TGGCATCAGATTGCAAAGAC; reverse: ACGCCGGGTGATGTATCTAT; probe: CGAAACGCACCCGTCAGACG) mRNA primer-probe sets. Prism 7 (Graphpad) was used for non-linear regression curve fitting of the formed spliced product and normalized to the control (DMSO) sample. Given that all tested payloads specifically bind to the SF3b complex and demonstrate similar binding profiles (FIG. 1), it was hypothesized that all payloads should also modulate splicing to a comparable degree. All payloads significantly modulated splicing of Ad2.2 pre-mRNA (FIG. 2). In the presence of payload, a decrease in the amount of spliced product was observed.

2.3 Cell Viability

HCC1954 (American Type Culture Collection (ATCC)) breast ductal carcinoma cells were plated at 2000 cells/well in flat bottom 96-well tissue culture plates (Corning) in a total volume of 90 μL tissue culture medium supplemented with 10% fetal bovine serum (ThermoFisher Scientific). Cells were treated with a 3-fold serial dilution of compound from 200 nM to 0.03 nM. Each concentration was tested in triplicate. At the time of treatment, a plate of untreated cells was evaluated using CellTiter-Glo®2.0 Luminescent Cell Viability Assay according to the manufacturer's recommendations (Promega; #G9241). CellTiter-Glo® 2.0 reagent was added to the medium, incubated, and assayed on an EnVision Multilabel Reader (PerkinElmer). Values represent time zero (TO). The number of viable cells following 144 hours (T144) of compound treatment was also determined using the CellTiter-Glo®2.0 Luminescent Cell Viability Assay. Using the luminescence value at time zero (TO), DMSO control growth (C), and test growth in the presence of compound (T144), the percentage growth was calculated at each of the compound concentrations levels. Percentage growth inhibition was calculated as: [(T144−T0)/(C−T0)]×100 for concentrations for which T144>/=T0 or [(T144−T0)/T0]×100 for concentrations for which T144<T0. The dose response curve plots were generated using Prism 7 (Graphpad) and fit using nonlinear regression analysis and the log(inhibitor) versus response-variable slope (four parameters).

Figure 3:
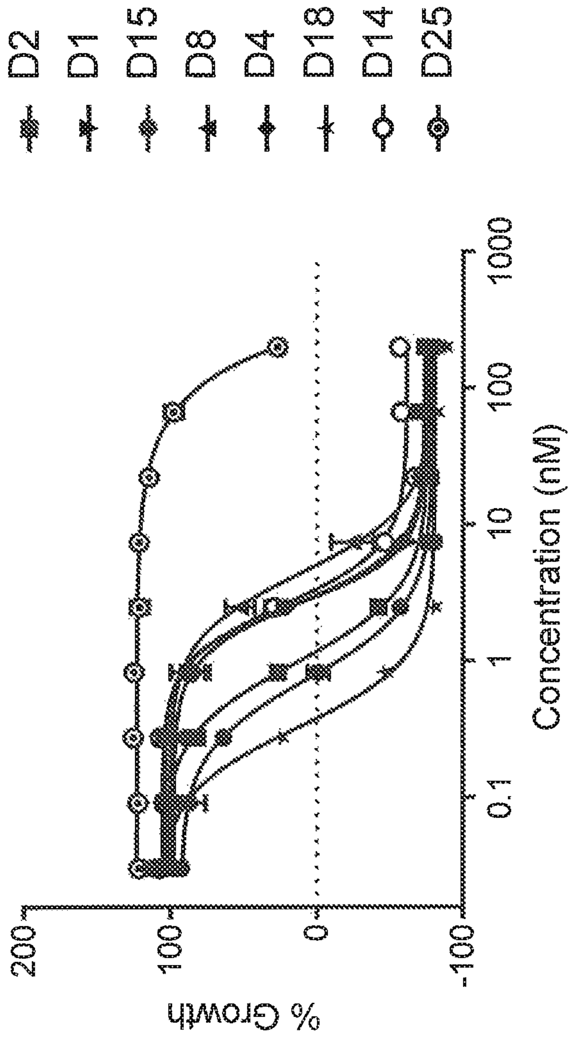
FIG. 3 shows viability dose response of exemplary payload compounds in HER2-amplified breast cancer cells (HCC1954). Cells were incubated with compound for 144 hours (6 days) and viability was read in CellTiter-Glo® reagent. Data are represented as mean±SD.

Cell viability dose response was determined for all payloads in HER2-amplified HCC1954 breast cancer cells. Most of the tested payloads exhibited $GI_{50}$ values (i.e., concentration of compound to cause 50% reduction in cell proliferation) in the single digit nanomolar range, with the exception of poorly permeable payloads such as D25 (FIG. 3). Exemplary permeability data is shown in Table 14.

Example 3

Exemplary payloads evaluated in Example 2 were conjugated to an exemplary anti-HER2 antibody (trastuzumab) via cysteine residues on the antibody. The preparation and evaluation of exemplary anti-HER2 ADCs is described below.

3.1 Antibody

Trastuzumab antibody ("AB185") (Molina et al. (2001) Cancer Res. 61(12):4744-9) was used for the preparation of anti-HER2 ADCs (also referred to herein as SMLAs).

3.2 Bioconjugation

Antibody (trastuzumab) at 10 mg/mL in PBS buffer (pH 7.0) was mixed with 5 mM TCEP (2-4 molar equivalents) (ThermoFisher Scientific; #77720) to break interchain disulfide bonds. The reaction was gently mixed at 22° C. for 3 hours. Propylene glycol (15% v/v) was then added followed by 8 molar equivalents of linker-payload (6 mM stock in DMSO), and the solution was mixed thoroughly. The reaction was placed onto a rotary plate in an incubator at 22° C. After a 2-hour conjugation, the reaction mixture was purified to remove unconjugated payload by AKTA GE M150 (HiTrap™ 26/10 desalting column; flow rate: 3 mL/min) (GE Healthcare Bio-Sciences) into DPBS (pH 7.5). The resulting conjugate was concentrated via Amicon ultrafiltration (30 kDa, Ultra-4) (EMD Millipore) and submitted to sterile filtration through a 0.22 m PVDF disposable filter (EMD Millipore). The final clear solution was measured by UV-VIS to determine antibody concentration ([mAb]; mole/L) and conjugated payload concentration ([LD]; mole/L) according to the Beer-Lambert law (A=E*c*I) and the following equations:

$$A_{280\ nm}=E^{mAb}{}_{280\ nm}*[\mathrm{mAb}]*l+E^{LD}{}_{280\ nm}*[LD]*l$$

$$A_{252\ nm}=E^{mAb}{}_{252\ nm}*[\mathrm{mAb}]*l+E^{LD}{}_{252\ nm}*[LD]*l$$

$$E^{mAb}{}_{280\ nm}\text{:trastuzumab}=213{,}380\ \mathrm{cm}^{-1}\mathrm{M}^{-1}$$

$$E^{mAb}{}_{252\ nm}\text{:trastuzumab}=79{,}112\ \mathrm{cm}^{-1}\mathrm{M}^{-1}$$

$$E^{LD}{}_{280\ nm}=800\ \mathrm{cm}^{-1}\mathrm{M}^{-1}$$

$$E^{LD}{}_{252\ nm}=31{,}000\ \mathrm{cm}^{-1}\mathrm{M}^{-1}$$

Abbreviations: c—molar concentration; I—light path length (Nanodrop: 0.1 cm); E—molar extinction coefficient; A—absorbance.

3.3 Biophysical Characterization

The drug-to-antibody ratio (DAR), percent aggregation, and percent unconjugated payload was analyzed for exemplary anti-HER2 ADCs by liquid chromatography-mass spectrometry (LC/MS), size exclusion chromatography (SEC), and reverse-phase high-performance liquid chromatography (HPLC), respectively. In general, conjugates contained less than 2% free drug and contained less than 10% aggregate.

3.3.1 LC/MS Analysis—DAR

LC/MS analysis was performed using an Agilent 1290 UPLC system interfaced to an Agilent G6224A Accurate Mass TOF mass spectrometer. Conjugate was deglycosylated with PNGase F (New England Biolabs; #P0705L) for 4 hours at 37° C., denatured with 8 M Gdn-HCl (Sigma; #G9284), and finally separated into light and heavy chain domains using DTT (5 mM final concentration) (Promega; #V3151). The prepared sample was injected onto an Agilent PLRP-S column (2.1×150 mm, 8 μm) and eluted with a gradient of 25% B to 50% B over 28 min at room temperature (RT). Mobile phase A was water with 0.05% TFA, mobile phase B was acetonitrile with 0.04% TFA, and the flow rate was 1 mL/min. DAR was calculated from the deconvoluted mass spectrum by weighted averaging the intensities of the unconjugated and drug conjugated peaks for the light chain (L0 or L1) and heavy chain (H0, H1, H2, and H3). The total DAR of the intact conjugate was calculated using the equation: $(DAR_{LC}*2)+(DAR_{HC}*2)$=total DAR. DAR values for exemplary anti-HER2 ADCs are reported in Tables 10-14.

3.3.2 SEC Analysis—Aggregation

Size exclusion chromatography was performed using a TOSON-G3000SWXL (#008541) column in 0.2 M potassium phosphate (pH 7) with 0.25 mM potassium chloride and 15% (v/v) IPA at a flow rate of 0.75 mL/min. The peak area absorbance at 280 nm was determined for the high molecular weight and monomeric conjugate components by area under the curve integration. Percent monomer for exemplary anti-HER2 ADCs is reported in Table 10.

3.3.3 HPLC Analysis—Free Drug

Conjugate was precipitated with 10 volumes of acetonitrile on ice for 2 hours and spun down. Supernatants containing residual unconjugated payload were then injected onto an Agilent Poroshell 120 SB-C18 120A column (4.6×100 mm, 2.7 μm) and eluted with a gradient of 45% B to 70% B over 10 min at RT. Mobile phase A was 100% water, mobile phase B was 100% acetonitrile, and the flow rate was 0.6 mL/min with detection at 252 nm. The amount of residual free drug was quantified via UV detection with comparison to the external standard curve of unconjugated linker-payload. Percent free drug for exemplary anti-HER2 ADCs is reported in Table 10.

3.4 Binding Characterization 3.4.1 FACS Binding to Target-positive Cells

Binding of unconjugated anti-HER2 antibody and anti-HER2 ADCs to target-positive cells was evaluated by flow-cytometry using indirect immunofluorescence. JIMT1 cells (DSMZ), a breast cancer cell line that endogenously expresses HER2, were plated ($5\times10^4$ cells/well) in a v-bottom 96-well plate (Greiner Bio-One) and incubated for 2 hours at 4° C. with the test compounds diluted to various concentrations in assay medium (RPMI-1640 supplemented with 10% (w/v) fetal bovine serum albumin (Thermo Fisher Scientific)). The cells were then washed with PBS+2% FBS (FACS buffer), and stained with phycoerythrin-labeled (PE) goat anti-human immunoglobulin G (IgG) antibody (Invitrogen) for 40 min at 4° C. in the dark. Cells were washed with cold FACS buffer and fixed with FluroFix buffer (Biolegend) for 30 min at room temperature. Fixative was washed off with FACS buffer. Fixed cells were analyzed for the geometric mean fluorescence of PE using an LSR-Fortessa flow cytometer (BD Bioscience). Trastuzumab and T-DM1 (DM1 conjugated to trastuzumab) were included as controls.

Figure 4:
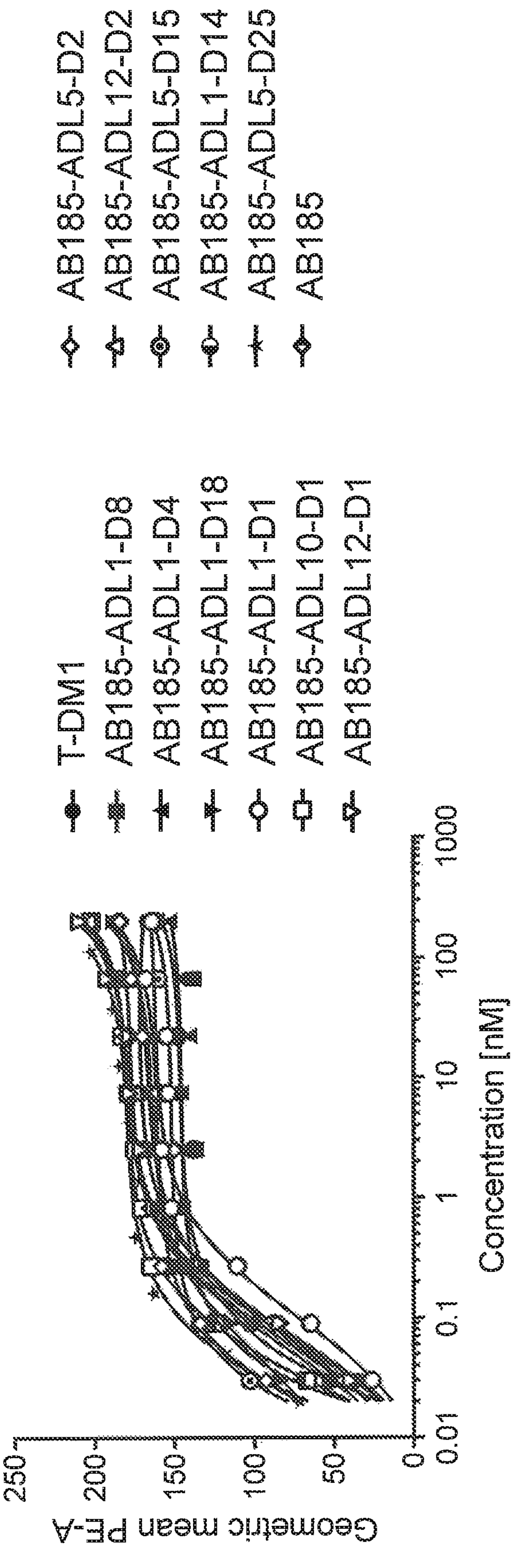
FIG. 4 shows the results of a cell binding assay. Binding of exemplary HER2-ADCs to JIMT1 cells was assessed by flow cytometry. Mean fluorescence intensity values were measured to determine binding of conjugates, followed by PE-labelled secondary. Data are represented as mean±SD.

All anti-HER2 ADCs demonstrated robust binding to HER2 in JIMT1 cells. ADC binding was comparable to binding of trastuzumab and T-DM1 (FIG. 4). This suggests that conjugation to payload does not affect antigen binding affinity of the antibody.

3.5 In Vitro Analysis 3.5.1 Cell Viability

Anti-HER2 ADCs were tested in several HER2-amplified cell lines for their ability to inhibit cell growth. HCC1954 (ATCC), 2000 cells/well), N87 (ATCC, 4000 cells/well), SKBR3 (ATCC, 3000 cells/well), and MCF7 (ATCC, 1500 cells/well) cell lines were used. Cell viability analysis was performed as described in section 2.3.

Figure 5A:
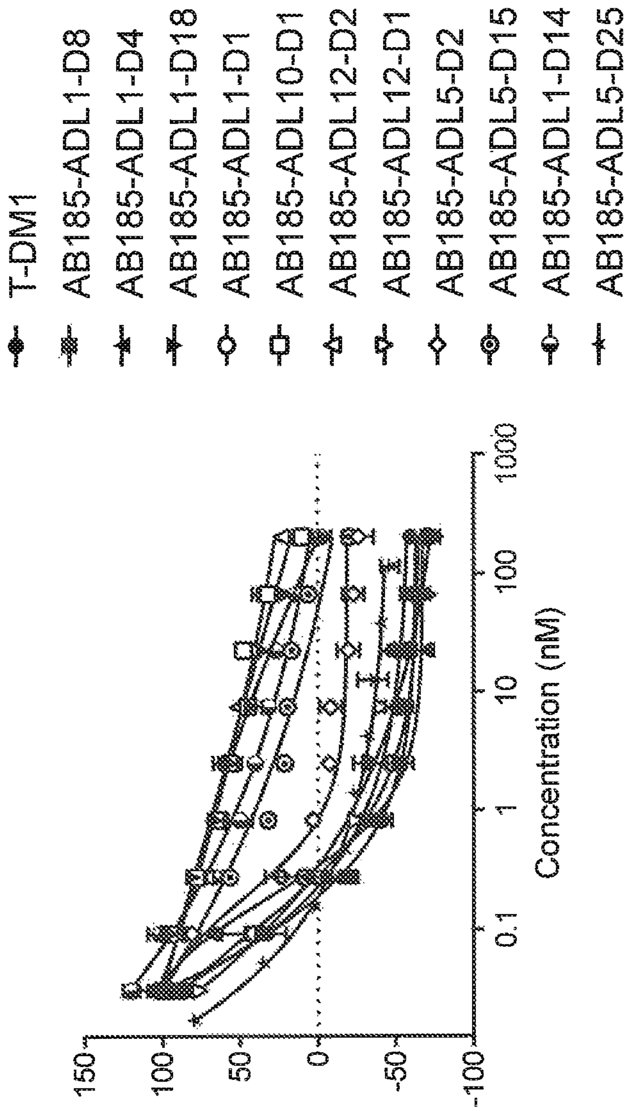
FIG. 5A shows viability dose response of exemplary HER2-ADCs in HER2-amplified breast cancer cells (HCC1954).
Figure 5B:
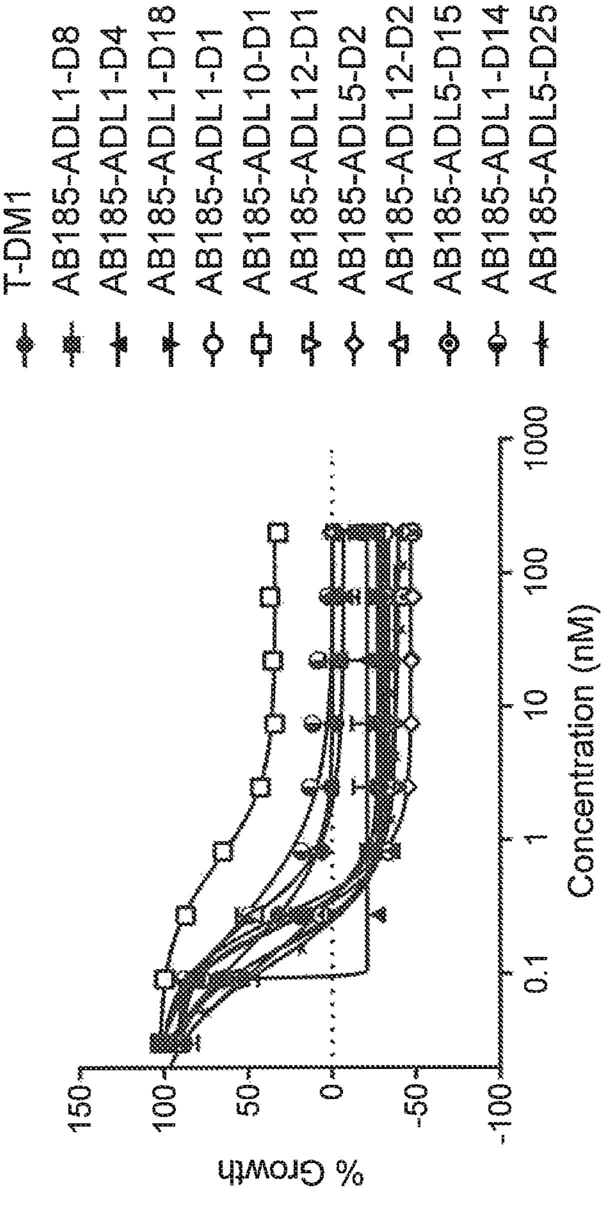
FIG. 5B shows viability dose response of exemplary HER2-ADCs in HER2-amplified gastric cancer cells (N87).
Figure 5C:
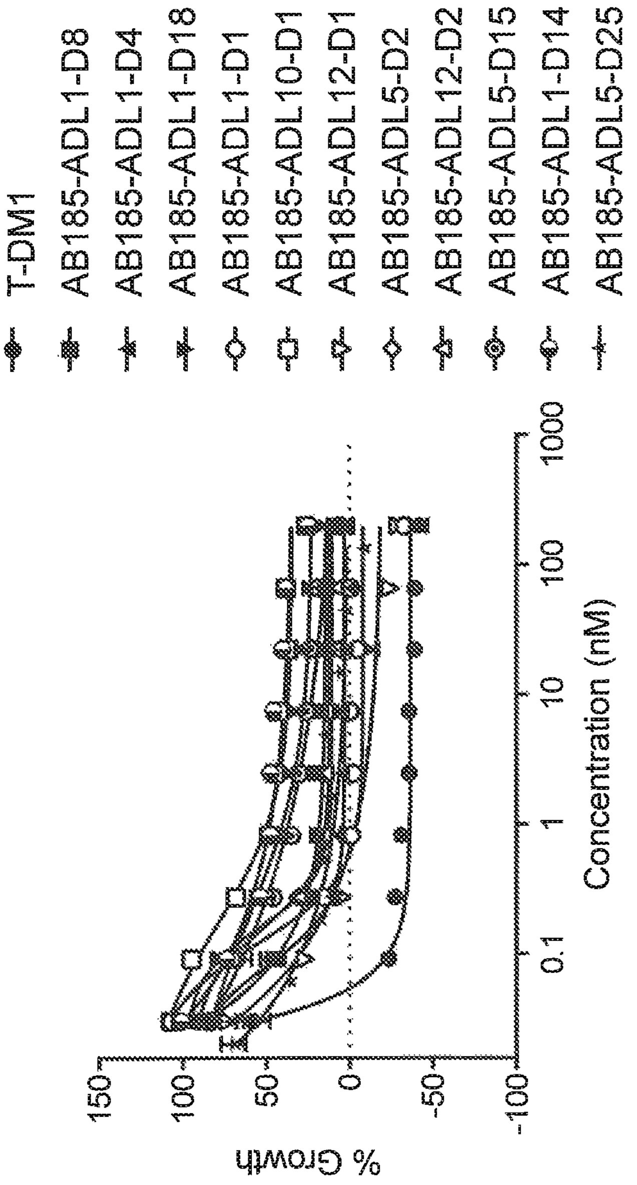
FIG. 5C shows viability dose response of exemplary HER2-ADCs in HER2-amplified breast cancer cells (SKBR3). Cells were incubated with conjugates for 144 hours (6 days) and viability was read in CellTiter-Glo® reagent. Data are represented as mean±SD.

Surprisingly, not all ADCs were active in HCC1954 cells, despite having similar binding profiles (FIG. 1) and payloads with similar biochemical properties. ADCs with certain linkers (e.g., ADL10) and/or certain payloads (e.g., D14) were less capable of inhibiting cell growth, whereas ADCs with alternate linkers (ADL1, ADL5, ADL12) and/or payloads (e.g., D1, D25, D2, D4) were more potent in HCC1954 cells (FIG. 5A and Tables 10, 11, and 14). These trends were generally observed across cell lines (HCC1954, N87, and SKBR3) and indications (HCC1954 and SKBR3 are high HER2 breast cancer lines; N87 is a high HER2 gastric cancer line) (FIGS. 5B-C and Tables 11 and 12). Moreover, in general, traditional non-cleavable linkers such as ADL10 did not deliver splicing modulator payloads efficiently. However, small modifications in length to the same linkers rendered ADCs much more potent, e.g., compare cell viability dose response of AB185-ADL10-D1 to AB185-ADL12-D1 (FIGS. 5A-C).

Figure 6:
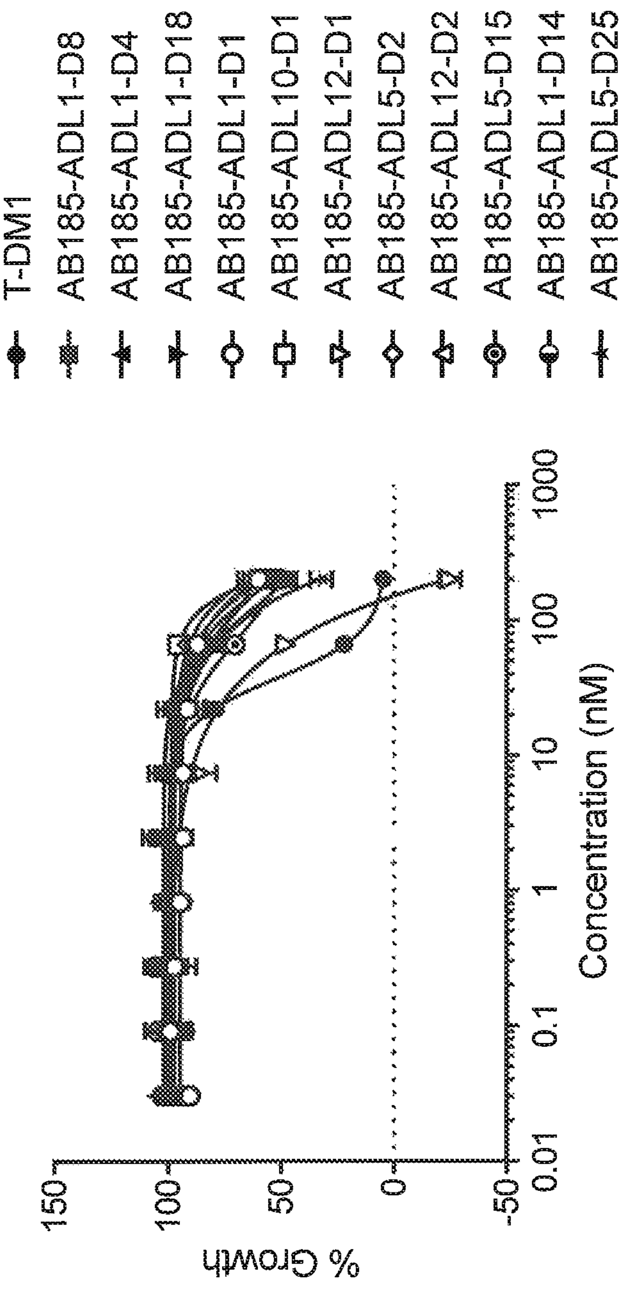
FIG. 6 shows viability dose response of exemplary HER2-ADCs in non-HER2 expressing breast cancer cells (MCF7). Cells were incubated with conjugates for 144 hours (6 days) and viability was read in CellTiter-Glo® reagent. Data are represented as mean±SD.

To ensure activity of anti-HER2 ADCs is antigen-dependent, HER2-negative MCF7 cells were treated. None of the tested ADCs were active at the same concentrations that robustly targeted HER2-positive cells (FIG. 6 and Table 13). This suggests that anti-HER2 ADC activity is antigen-dependent.

TABLE 10

Characterization of exemplary anti-HER2 ADCs

| SMLA Batch ID | Payload Class | Linker | Linker Name | DAR | Percent Monomer | Free Drug (%) | Concentration (mg/ml) | CTGlo GMean GI50 (nM) HCC1954.1 | CTGlo GMean LD50 (nM) HCC1954.1 | CTGlo Mean MinResponse % HCC1954.1 |
|---|---|---|---|---|---|---|---|---|---|---|
| AB185-ADL10-D8 | Plad D | ADL0010-01 | maleimido caproyl | 2.000 | 99.000 | <1 | 0.730 | >200.000 | >200.000 | 58.601 |
| AB185-ADL10-D1 | Plad D | ADL0010-01 | maleimido caproyl | 3.600 | 97.000 | <1 | 3.600 | 25.502 | >200.000 | 23.963 |
| AB185-ADL5-D17 | ArylPlad | ADL0005-01 | mc-Val-Ala-PAB (Qamine) | 3.960 | 98.000 | <1 | 1.400 | 2.668 | >160.000 | 14.873 |
| AB185-ADL1-D16 | ArylPlad | ADL0001-01 | mc-Val-Cit-PABC | 4.400 | 95.000 | <1 | 0.550 | 2.086 | 158.245 | |
| AB185-ADL5-D26 | ArylPlad | ADL0005-01 | mc-Val-Ala-PAB (Qamine) | 4.400 | 98.000 | <1 | 1.200 | 0.943 | >200.000 | |
| AB185-ADL1-D14 | ArylPlad | ADL0001-01 | mc-Val-Cit-PABC | 4.340 | 88.000 | <1 | 4.200 | 0.925 | >200.000 | 1.271 |
| AB185-ADL5-D15 | ArylPlad | ADL0005-01 | mc-Val-Ala-PAB (Qamine) | 4.000 | 98.000 | <1 | 0.780 | 0.912 | >200.000 | −46.388 |
| AB185-ADL5-D11 | Plad D | ADL0005-01 | mc-Val-Ala-PAB (Qamine) | 3.700 | 96.000 | <1 | 0.880 | 0.806 | >93.000 | −30.929 |
| AB185-ADL1-D33 | ArylPlad | ADL0001-01 | mc-Val-Cit-PABC | 8.000 | 95.000 | <1 | 0.570 | 0.466 | >200.000 | −25.859 |

TABLE 10-continued

| Characterization of exemplary anti-HER2 ADCs | | | | | | | | | | |
|---|---|---|---|---|---|---|---|---|---|---|
| SMLA Batch ID | Payload Class | Linker | Linker Name | DAR | Percent Monomer | Free Drug (%) | Concentration (mg/ml) | CTGlo GMean GI50 (nM) HCC1954.1 | CTGlo GMean LD50 (nM) HCC1954.1 | CTGlo Mean MinResponse % HCC1954.1 |
| AB185-ADL1-D22 | Plad D | ADL0001-01 | mc-Val-Cit-PABC | 3.000 | 99.000 | <1 | 0.840 | 0.443 | >200.000 | −7.520 |
| AB185-ADL12-D2 | Plad D | ADL0012-01 | mal-(CH2)6-(non-cleavable) | 3.600 | 98.600 | <1 | 1.060 | 0.432 | >200.000 | 18.569 |
| AB185-ADL1-D13 | Plad B | ADL0001-01 | mc-Val-Cit-PABC | 5.000 | 98.000 | <1 | 1.200 | 0.289 | 18.948 | −94.860 |
| AB185-ADL5-D19 | Plad B | ADL0005-01 | mc-Val-Ala-PAB (Qamine) | 6.600 | 97.000 | <1 | 3.230 | 0.278 | >200.000 | −47.381 |
| AB185-ADL5-D10 | Plad D | ADL0005-01 | mc-Val-Ala-PAB (Qamine) | 4.020 | 97.000 | <1 | 0.650 | 0.254 | >200.000 | −2.273 |
| AB185-ADL6-D9 | Plad D | ADL0006-01 | mc-Val-Ala-PABC | 5.200 | 98.000 | <1 | 0.500 | 0.244 | 4.206 | −94.511 |
| AB185-ADL5-D2 | Plad D | ADL0005-01 | mc-Val-Ala-PAB (Qamine) | 4.140 | 99 | <1 | 4.5 | 0.206 | >200.000 | −12.239 |
| AB185-ADL1-D8 | Plad D | ADL0001-01 | mc-Val-Cit-PABC | 7.200 | 97.000 | <1 | 3.410 | 0.188 | >200.000 | −55.079 |
| AB185-ADL5-D2 | Plad D | ADL0005-01 | mc-Val-Ala-PAB (Qamine) | 4.300 | 99.000 | <1 | 5.440 | 0.179 | >200.000 | −18.586 |
| AB185-ADL15-D2 | Plad D | ADL0015-01 | mal-CH2CH2—O—CH2CH2-(non-cleavable) | 3.300 | 98.800 | <1 | 1.600 | 0.170 | >200.000 | −23.513 |
| AB185-ADL12-D20 | Plad D | ADL0012-01 | mal-(CH2)6-(non-cleavable) | 3.200 | 98.600 | <1 | 1.390 | 0.142 | >200.000 | −57.399 |
| AB185-ADL12-D1 | Plad D | ADL0012-01 | mal-(CH2)6-(non-cleavable) | 3.300 | 98.800 | <1 | 1.620 | 0.126 | >200.000 | −34.649 |
| T-DM1 | DM1 | ADL0019-01 | SMCC | 3.300 | 98.000 | <1 | 3.300 | 0.118 | 2.759 | −47.952 |
| AB185-ADL5-D2 | Plad D | ADL0005-01 | mc-Val-Ala-PAB (Qamine) | 8.500 | 98 | <1 | 5.1 | 0.086 | 2.918 | −63.909 |
| AB185-ADL6-D1 | Plad D | ADL0006-01 | mc-Val-Ala-PABC | 8.000 | 97.000 | <1 | 1.200 | 0.081 | 2.877 | −85.692 |
| AB185-ADL12-D1 | Plad D | ADL0012-01 | mal-(CH2)6-(non-cleavable) | 3.000 | 98.000 | <1 | 2.860 | 0.081 | 2.148 | −68.999 |
| AB185-ADL12-D22 | Plad D | ADL0012-01 | mal-(CH2)6-(non-cleavable) | 4.300 | 97.000 | <1 | 0.120 | 0.078 | >80.000 | 28.071 |
| AB185-ADL1-D4 | Plad D | ADL0001-01 | mc-Val-Cit-PABC | 8.000 | 98.000 | <1 | 3.600 | 0.073 | 1.949 | −67.199 |
| AB185-ADL15-D1 | Plad D | ADL0015-01 | mal-CH2CH2—O—CH2CH2-(non-cleavable) | 3.200 | 98.800 | <1 | 0.950 | 0.062 | >200.000 | −57.829 |
| AB185-ADL14-D1 | Plad D | ADL0014-01 | mal-CH2CH2-(non-cleavable) | 3.500 | 98.600 | <1 | 0.740 | 0.055 | >200.000 | −56.889 |
| AB185-ADL1-D4 | Plad D | ADL0001-01 | mc-Val-Cit-PABC | 2.800 | 98.000 | <1 | 1.200 | 0.050 | >200.000 | −57.212 |
| AB185-ADL1-D1 | Plad D | ADL0001-01 | mc-Val-Cit-PABC | 3.900 | 99 | <1 | 5.2 | 0.046 | 0.374 | −78.519 |
| AB185-ADL1-D1 | Plad D | ADL0001-01 | mc-Val-Cit-PABC | 4.000 | 98.000 | <1 | 3.500 | 0.042 | 0.447 | −77.970 |
| AB185-ADL5-D25 | Plad D Zwitt | ADL0005-01 | mc-Val-Ala-PAB (Qamine) | 6.000 | 98.000 | <1 | 0.170 | 0.038 | >113.000 | −46.265 |
| AB185-ADL1-D1 | Plad D | ADL0001-01 | mc-Val-Cit-PABC | 7.700 | 98.000 | <1 | 4.200 | 0.034 | 0.120 | −87.001 |

TABLE 11

| Exemplary anti-HER2 ADCs-HCC1954 cells | | | | | | | |
|---|---|---|---|---|---|---|---|
| | ADC | | | | Payload | | |
| Sample | DAR | GI50 (nM) | LD50 (nM) | Rmin (%) | GI50 (nM) | LD50 (nM) | Rmin (%) |
| AB185-ADL12-D1 | 3.1 | 0.064 | 4.86 | −78.393 | 1.853 | 5.485 | −75.579 |
| AB185-ADL1-D8 | 7.2 | 0.075 | 1.01 | −72.765 | 2.638 | 11.175 | −80.463 |
| T-DM1 | 3.3 | 0.063 | >200 | −64.227 | | | |
| AB185-ADL1-D1 | 4.04 | 0.089 | 2.078 | −74.165 | 1.853 | 5.485 | −75.579 |
| AB185-ADL1-D4 | 4.9 | 0.145 | 1.217 | −75.638 | 1.699 | 6.374 | −81.34 |
| AB185-ADL5-D2 | 4.1 | 0.18 | >200 | −36.513 | 0.6 | 2.758 | −78.732 |
| AB185-ADL5-D15 | 4 | 0.503 | >200 | −20.387 | 0.358 | 2.037 | −84.412 |
| AB185-ADL1-D18 | 3.8 | 5.994 | >200 | −8.011 | 0.208 | 0.787 | −90.055 |

TABLE 11-continued

Exemplary anti-HER2 ADCs-HCC1954 cells

| | ADC | | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| AB185-ADL12-D2 | 3.6 | 6.129 | >200 | 18.763 | 0.6 | 2.758 | −78.732 |
| AB185-ADL10-D1 | 3.5 | 6.642 | >200 | 8.138 | 1.853 | 5.485 | −75.579 |
| AB185-ADL5-D26 | 6.3 | 0.038 | >113.000 | −51.503 | 167.54 | >200 | 26.882 |
| AB185 | N/A | >200 | >200 | 76.916 | | | |

TABLE 12

Exemplary anti-HER2 ADCs-N87 cells

| | SMLA | | | | Payload | | |
|---|---|---|---|---|---|---|---|
| | DAR | GI50 (nM) | LD50 (nM) | Rmin (%) | GI50 (nM) | LD50 (nM) | Rmin (%) |
| AB185-ADL1-D4 | 4.9 | 0.093 | >200 | −40.056 | 3.241 | 38.774 | −81.775 |
| AB185-ADL5-D15 | 4 | 0.106 | >200 | −50.886 | 0.41 | >200 | −68.045 |
| AB185-ADL5-D25 | 6.3 | 0.11 | 133 | −43.398 | >200 | >200 | 40.364 |
| AB185-ADL12-D1 | 3.1 | 0.111 | >200 | −41.228 | 7.041 | >200 | −40.041 |
| AB185-ADL1-D18 | 3.8 | 0.113 | >200 | −39.509 | 0.275 | 2.993 | −92.127 |
| AB185-ADL1-D1 | 4.04 | 0.163 | >200 | −41.075 | 7.041 | >200 | −40.041 |
| T-DM1 | 3.3 | 0.168 | >200 | −20.785 | | | |
| AB185-ADL1-D8 | 7.2 | 0.172 | >200 | −31.708 | 8.844 | >200 | −34.052 |
| AB185-ADL5-D2 | 4.1 | 0.206 | >200 | −51.328 | 0.749 | >200 | −72.706 |
| AB185-ADL12-D2 | 3.6 | 0.243 | >200 | −9.79 | 0.749 | >200 | −72.706 |
| AB185-ADL1-D14 | 4.3 | 0.296 | >200 | −26.143 | 2.925 | >200 | −52.662 |
| AB185-ADL10-D1 | 3.5 | 1.531 | >200 | 30.759 | 7.041 | >200 | −40.041 |
| AB185 | N/A | >200 | >200 | 77.029 | | | |

TABLE 13

Exemplary anti-HER2 ADCs-MCF7 cells

| | SMLA | | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| T-DM1 | 3.3 | 38.503 | >200 | 3.876 | | | |
| AB185-ADL12-D1 | 3.1 | 57.818 | >200 | −30.172 | 16.998 | 135.42 | −63.414 |
| AB185-ADL5-D25 | 6.3 | 80.856 | 113 | 28.12 | >200 | >200 | 65.639 |
| AB185-ADL1-D4 | 4.9 | 189.392 | >200 | 43.848 | 11.416 | 96.46 | −60.923 |
| AB185-ADL5-D2 | 4.1 | >200 | >200 | 56.182 | 2.851 | 30.318 | −66.915 |
| AB185-ADL1-D8 | 7.2 | >200 | >200 | 61.169 | 29.614 | 181.521 | −62.957 |
| AB185-ADL1-D18 | 3.8 | >200 | >200 | 48.851 | 0.883 | 7.697 | −68.226 |
| AB185-ADL5-D15 | 4 | >200 | >200 | 49.619 | 0.961 | 130.398 | −68.503 |
| AB185-ADL12-D2 | 3.6 | >200 | >200 | 48.868 | 2.851 | 30.318 | −66.915 |
| AB185-ADL10-D1 | 3.5 | >200 | >200 | 52.699 | 16.998 | 135.42 | −63.414 |
| AB185-ADL1-D14 | 4.3 | >200 | >200 | 49.325 | 5.288 | 77.198 | −61.886 |
| AB185-ADL1-D1 | 4.04 | >200 | >200 | 59.181 | 16.998 | 135.42 | −63.414 |
| AB185 | N/A | >200 | >200 | 72.747 | | | |

3.5.2 Caco-2 Permeability of ADC Payload

Caco-2 cells were cultured for 21 days in transwell 24-well plates at 37° C., 95% humidity, 5% $CO_2$. Integrity of cell monolayer was confirmed by TEER (transepithelial electrical resistance) and Lucifer yellow. Payloads were spiked in duplicate at 10 μM, separately, on both sides of the cell monolayer. Permeability rates from the apical to basolateral (A-B) direction and the basolateral to apical (B-A) direction were determined by sampling aliquots from both chambers immediately after treatment (t=0) and following incubation for 2 hours. Samples were protein precipitated with organic solvent containing internal standard and analyzed by LC-MS/MS (SCIEX; API 5500). The area ratio responses of payload/internal standard over time in both directions were used to generate permeability (cm/sec) values. Efflux ratio was calculated by dividing B-A/A-B. Control compounds for low and high permeability and efflux behaved as expected. Permeability values are reported in Table 14.

3.5.3 Chemical Stability of ADC Payload

Payloads were incubated in Mcilvane (Citrate-Phosphate) buffer, pH 5.5 (Boston Bioproducts; #BB-2466) at a final concentration of 20 μM (less than 0.5% DMSO from stock solution). The payload solution and the internal standard were pipetted into 96-well plates, ran on UPLC (Waters Aquity H class), and analyzed for initial chromatographic signal (t=0). The column was a Waters UPLC HSS T3 1.8 μm 2.1×50 mm column (#186003538). A gradient of mobile phase A from 95% to 10% was employed over 1 min, where A was 0.1% formic acid in water and mobile phase B was 0.1% formic acid in acetonitrile (flow rate 0.9 mL/min). The remainder of the payload solution was kept in a plate shaker at 37° C. (Eppendorf ThermoMixer). Sample analyses by UPLC were repeated at 24, 72, and 96 hours post-incubation at 37° C. The area ratio response of the payload and internal standard was determined for three time points: time 0, day 1, and either day 3 or day 4. Time 0 was set to 100. The area ratio responses of the later time points were compared to time 0. Percent remaining was calculated as follows: (Area Ratio day X/Area Ratio time 0)*100=% remaining. The slope of the line was calculated in Excel comparing the log of % remaining and time point. Half-lives were calculated in Excel by In(2)/slope and are reported in Table 14.

TABLE 14

Characterization of exemplary anti-HER2 ADCs and corresponding payloads

| | | | SMLA activity | | | | |
|---|---|---|---|---|---|---|---|
| SMLA Batch ID | Linker | DAR | CT Glo GMean G150 (nM) HCC1954.1 | CTGlo GMean LD50 (nM) HCC1954.1 | Rmin (%) (max lethality) | Payload Class | Mass |
| AB185-ADL5-D25 | ADL0005-01 | 6.3 | 0.038 | >113.000 | −51.503 | Plad D Zwitt | 722.917 |
| AB185-ADL1-D1 | ADL0001-01 | 4 | 0.042 | 0.447 | −78.554 | Plad D | 636.827 |
| AB185-ADL14-D4 | ADL0001-01 | 2.8 | 0.05 | >200.000 | −75.774 | Plad D | 664.837 |
| AB185-ADL14-D1 | ADL0014-01 | 3.5 | 0.055 | >200.000 | −60.34 | Plad D | 636.827 |
| AB185-ADL15-D1 | ADL0015-01 | 3.2 | 0.062 | >200.000 | −60.34 | Plad D | 636.827 |
| AB185-ADL1-D8 | ADL0001-01 | 7.2 | 0.075 | 1.01 | −72.765 | Plad D | 664.83 |
| AB185-ADL12-D22 | ADL0012-01 | 4.3 | 0.078 | >80.000 | 27.157 | Plad D Zwitt | 708.89 |
| AB185-ADL12-D1 | ADL0012-01 | 3.1 | 0.081 | 2.148 | −85.136 | Plad D | 636.827 |
| AB185-ADL6-D1 | ADL0006-01 | 3.8 | 0.081 | 2.877 | −86.59 | Plad D | 636.827 |
| T-DM1 | SMCC | 3.3 | 0.118 | 2.759 | −56 | DM1 | 738.29 |
| AB185-ADL12-D21 | ADL0012-01 | 3.3 | 0.126 | >200.000 | −39.556 | Plad D | 652.87 |
| AB185-ADL12-D20 | ADL0012-01 | 3.2 | 0.142 | >200.000 | −61.497 | Plad D | 638.843 |
| AB185-ADL15-D2 | ADL0015-01 | 3.3 | 0.17 | >200.000 | −25.778 | Plad D | 650.854 |
| AB185-ADL5-D2 | ADL0005-01 | 4.1 | 0.179 | >200.000 | −19.945 | Plad D | 650.854 |
| AB185-ADL6-D9 | ADL0006-01 | 5.2 | 0.244 | 4.206 | −95.509 | Plad B | 648.838 |
| AB185-ADL5-D10 | ADL0005-01 | 4 | 0.254 | >200.000 | −7.125 | Plad D | 664.881 |
| AB185-ADL1-D13 | ADL0001-01 | 5 | 0.289 | 18.948 | −95.484 | Plad B | 648.838 |
| AB185-ADL12-D2 | ADL0012-01 | 3.6 | 0.432 | >200.000 | 17.824 | Plad D | 650.854 |
| AB185-ADL1-D22 | ADL0001-01 | 2.9 | 0.443 | >200.000 | 27.157 | Plad D Zwitt | 708.89 |
| AB185-ADL1-D33 | ADL0001-01 | 8 | 0.466 | >200.000 | −34.274 | ArPlad Zwitt | 630.758 |
| AB185-ADL5-D11 | ADL0005-01 | 3.7 | 0.806 | >93.000 | −57.844 | Plad D | 718.973 |
| AB185-ADL5-D15 | ADL0005-01 | 4 | 0.912 | >200.000 | −50.337 | ArPlad | 668.811 |
| AB185-ADL1-D14 | ADL0001-01 | 4.3 | 0.925 | >200.000 | 3.753 | ArPlad | 654.784 |
| AB185-ADL5-D26 | ADL0005-01 | 4.3 | 0.943 | >200.000 | −29 | ArPlad | 694.849 |
| AB185-ADL1-D16 | ADL0001-01 | 4.3 | 2.086 | 158.245 | −55 | ArPlAD | 680.822 |
| AB185-ADL5-D17 | ADL0005-01 | 4 | 2.668 | >100.000 | 12.42 | ArPlad | 587.733 |
| AB185-ADL1-D18 | ADL0001-01 | 3.8 | 5.994 | >200 | −8.011 | Plad B | 620.828 |
| AB185-ADL10-D1 | ADL0010-01 | 3.5 | 6.642 | >200 | 8.138 | Plad D | 636.827 |

| | Payload SF381 binding and mRNA splice modulation | | | Payload cell potency and lethality | | | Payload cell permeability | | | Payload chemical stability |
|---|---|---|---|---|---|---|---|---|---|---|
| SMLA Batch ID | SPA-AT S GMean IC50 (nM) SF381 (WT) HELA.2 | qPCR-IVS-AT S Gmean IC50 (nm) Ad2.1 HELA.2 | qPCR-IVS-AT S GMean IC50 (nM) Ad2.2 HELA.2 | CTGlo-AT S GMean GI50 (nM) Ad2.2 HELA.2 | CTGlo-AT S GMean LD50 (nM) 72 h THP1.1 | CTGlo-AT S Mean Min-Response % 72 h THP1.1 | Perme-abllity Mean Caco-2 A-B Perm (10e−6 cm/s) | Perme-ability Mean Caco-2 B-A Perm (10e−G cm/s) | Efflux ratio | Stability Mean Stability t1/2 pH5.5 (d) |
| AB185-ADL5-D25 | 14.567 | 243.749 | 50.858 | 348.114 | 2076.811 | −77.246 | 0.137 | 0.349 | 2.547 | 5 |
| AB185-ADL1-D1 | 6.085 | 17.568 | 15.853 | 11.085 | 41.408 | −100.615 | 0.14 | 2.05 | 14.643 | 3.95 |
| AB185-ADL14-D4 | 8.778 | 20.887 | 17.321 | 10.943 | 33.329 | −99.957 | 0.1 | 1.79 | 17.9 | 4.4 |
| AB185-ADL14-D1 | 6.085 | 17.568 | 15.853 | 11.085 | 41.408 | −100.615 | 0.14 | 2.05 | 14.643 | 3.95 |
| AB185-ADL15-D1 | 6.085 | 17.568 | 15.853 | 11.085 | 41.408 | −100.615 | 0.14 | 2.05 | 14.643 | 3.95 |
| AB185-ADL1-D8 | 5.92'1 | 11.403 | 9.034 | 8.745 | 38.969 | −99.92 | 0.128 | 2.027 | 15.875 | 3.525 |
| AB185-ADL12-D22 | 29.188 | 66.293 | 49.131 | 223.348 | 1594.636 | −78.119 | 0.14 | 0.18 | 1.143 | |
| AB185-ADL12-D1 | 6.085 | 17.568 | 15.853 | 11.085 | 41.408 | −100.615 | 0.14 | 2.05 | 14.643 | 3.95 |
| AB185-ADL6-D1 | 6.085 | 17.568 | 15.853 | 11.085 | 41.408 | −100.615 | 0.14 | 2.05 | 14.643 | 3.95 |
| T-DM1 | >1200.000 | >25000.000 | <25000.000 | 0.503 | 3.287 | −93.785 | 0.38 | 28.6 | 75.263 | 1.3 |
| AB185-ADL12-D21 | | | | | | | | | | |
| AB185-ADL12-D20 | 18.251 | 10.929 | 8.748 | 28.336 | 113.557 | −100.664 | 0.16 | 0.38 | 2.375 | >7.000 |
| AB185-ADL15-D2 | 15.533 | 19.133 | 15.342 | 2015 | 11.708 | −100.218 | 0.624 | 14.2 | 22.756 | 4 |
| AB185-ADL5-D2 | 15.533 | 19.'33 | 15.342 | 2015 | 11.708 | −100.218 | 0.624 | 14.2 | 22.756 | 4 |
| AB185-ADL6-D9 | 2.177 | 20.224 | 18.121 | 0.87 | 3.56 | −99.938 | 1.15 | 16.11 | 14.009 | <1.000 |
| AB185-ADL5-D10 | 9.228 | 16.317 | 14.658 | 1.819 | 8.454 | −99.951 | 1.81 | 23.5 | 12.983 | >7.000 |
| AB185-ADL1-D13 | 2.085 | 11.287 | 8.816 | 0.892 | 3.358 | −99.941 | 0.9 | 17.17 | 19.078 | <1.000 |

TABLE 14-continued

Characterization of exemplary anti-HER2 ADCs and corresponding payloads

| | | | | | | | | | | |
|---|---|---|---|---|---|---|---|---|---|---|
| AB185-ADL12-D2 | 15.533 | 19.133 | 15.342 | 2.015 | 11.708 | −100.218 | 0.624 | 14.2 | 22.756 | 4 |
| AB185-ADL1-D22 | 29.188 | 66.293 | 49.131 | 223.348 | 1594.636 | −78.119 | 0.14 | 0.16 | 1.143 | |
| AB185-ADL1-D33 | 35.694 | 33.402 | 72.404 | 195.752 | 5202.992 | −53.128 | 0.13 | 0.53 | 4.077 | |
| AB185-ADL5-D11 | 5.99 | 10.545 | 9.364 | 1.352 | 8.086 | −100.481 | 0.87 | 10.56 | 12.138 | 3.75 |
| AB185-ADL5-D15 | 1.648 | 4.632 | 4.928 | 1.017 | 11.038 | −99.595 | 3.43 | 26.9 | 7.843 | >7.000 |
| AB185-ADL1-D14 | 1.924 | 10.022 | 8.586 | 3.584 | 25.594 | −99.209 | 0.06 | 12.13 | 202.167 | >7.000 |
| AB185-ADL5-D26 | 5.505 | 18.838 | 14.314 | 3.719 | 28.483 | −99.401 | 15.955 | 41.125 | 2.578 | >7.000 |
| AB185-ADL1-D16 | 5.564 | 16.01 | 15.144 | 2.975 | 21.46 | −99.681 | 0.72 | 23.3 | 32.361 | >7.000 |
| AB185-ADL5-D17 | 1.82 | 17.943 | 9.44 | 2.827 | 24.908 | −99.033 | 20.25 | 18.18 | 0.896 | |
| AB185-ADL1-D18 | 0.99 | 12.686 | 12.709 | 0.863 | 4.355 | −99.621 | 1.19 | 27.4 | 23.025 | |
| AB185-ADL10-D1 | 6.085 | 17.568 | 15.853 | 11.085 | 41.408 | −100.615 | 0.14 | 2.05 | 14.643 | 3.95 |

3.5.4 In-Cell Splicing PD Assay

To interrogate the mechanism of action of exemplary anti-HER2 ADCs, splicing of the SLC25A19 mature transcript was examined in HCC1954 cells treated with increasing concentrations of ADC.

HCC1954 cells (ATCC) were plated in phenol-red free RPMI+10% FBS media (ATCC) at $1\times10^5$ cells per well at 90 μL per well. Cells were treated with conjugates in a 3-fold dilution dose-response. After 24 hours or 6 hours, respectively, cells were lysed with 50 μL of CL buffer (IgePal CA-630, 5M NaCl, 1M Tris HCl 1M pH 7.4 in water) containing 25 μL/mL of RNAsin (Promega) and incubated for 45 min at RT on a rocker. Resulting mixture (0.5 μL) was used to assess splicing modulation in a Taqman Fast Virus 1-Step MasterMix (Applied Biosystems) reverse transcription PCR reaction with the following Taqman primers according to the manufacturer's recommendations: SLC25A19 (Invitrogen, Hs00222265_m1); RPLPO (Invitrogen, Hs99999902_m1); 18S (Invitrogen, Hs99999901_s1).

Figure 7:
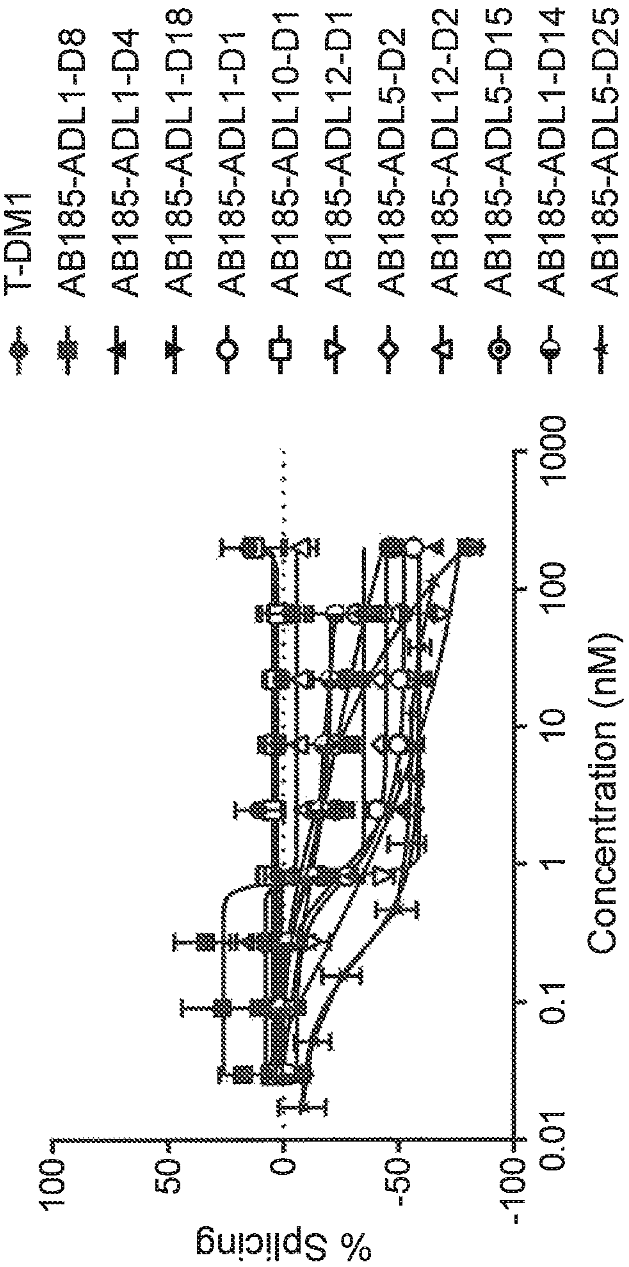
FIG. 7 shows the results of a SLC25A19 splicing assay in HER2-amplified breast cancer cells (HCC1954). Cells were incubated with conjugates for 24 hours and splicing of SLC25A19 transcript was measured in a real time qPCR reaction with a specific Taqman primer-probe set. The y-axis represents the percent (%) response relative to the DMSO control (0%). Data are represented as mean±SD.

T-DM1 control (trastuzumab with a microtubule disrupting agent as payload) did not affect SLC25A19 splicing (FIG. 7). In contrast, anti-HER2 ADCs that demonstrated potent growth inhibition activity in different tested cell lines (FIG. 5) also demonstrated potent splicing modulation, indicating an on-target mechanism of action (FIG. 7). Likewise, anti-HER2 ADCs that exhibited lower potency in cell viability assays were less potent in terms of splicing modulation.

3.5.5 Bystander Cell Killing Assay

The ability of exemplary anti-HER2 conjugates to kill both target-positive cells and neighboring target-negative cells was measured in a bystander cell killing assay. NCI-H1568, non-small cell lung cancer cells (ATCC) were engineered to express luciferase. cDNA was synthesized at GeneArt (ThermoFisher Scientific) and cloned into a pLVX-EF1a destination vector (ThermoFisher Scientific). Separately, NCI-H1568 were engineered to express human HER2 (cloned into pLenti6.3N5-DEST, ThermoFisher Scientific) utilizing the TranslT® viral transfection system according to manufacturer's instructions (Mirus Bio LLC; #MIR6003). To assess the bystander activity of conjugates, 2000 target-positive (HER2-transduced) NCI-H1568 cells and 2000 target-negative (luc-tagged) NCI-H1568 cells were plated together in clear 96-well round bottom plates (Corning) and incubated with conjugates dosed at a 3-fold serial dilution in triplicate, 30-0.005 nM. At the time of treatment, a plate of untreated cells was assayed using OneGlo® Luciferase Assay System (Promega) and CellTiter-Glo®2.0 Luminescent Cell Viability Assay System (Promega) according to the manufacturer's recommendations, to establish a time zero (T0). After 6 days in culture, the remaining cell population was analyzed by OneGlo® Luciferase Assay System (Promega) to measure the fraction of target-negative cells surviving. Overall viability was measured by CellTiter-Glo®2.0 Luminescent Cell Viability Assay System (T144). Dose response curves were calculated as described in section 2.3.

The design of the bystander killing assay allows tracking of only target-negative cells, the elimination of which relies on uptake of the catabolite released by neighboring target-positive cells. As discussed above, cells are plated under three conditions: (1) target-negative (luc-tagged) cells alone; (2) target-positive cells alone; and (3) co-culture of target-negative and target-positive cells. When the plates are read with CellTiter-Glo® reagent, viability of all cell populations can be tracked to confirm antigen-dependent ADC activity. In contrast, when OneGlo® reagent is used, only the target-negative (luc-tagged) cells will have a signal.

Figure 8:
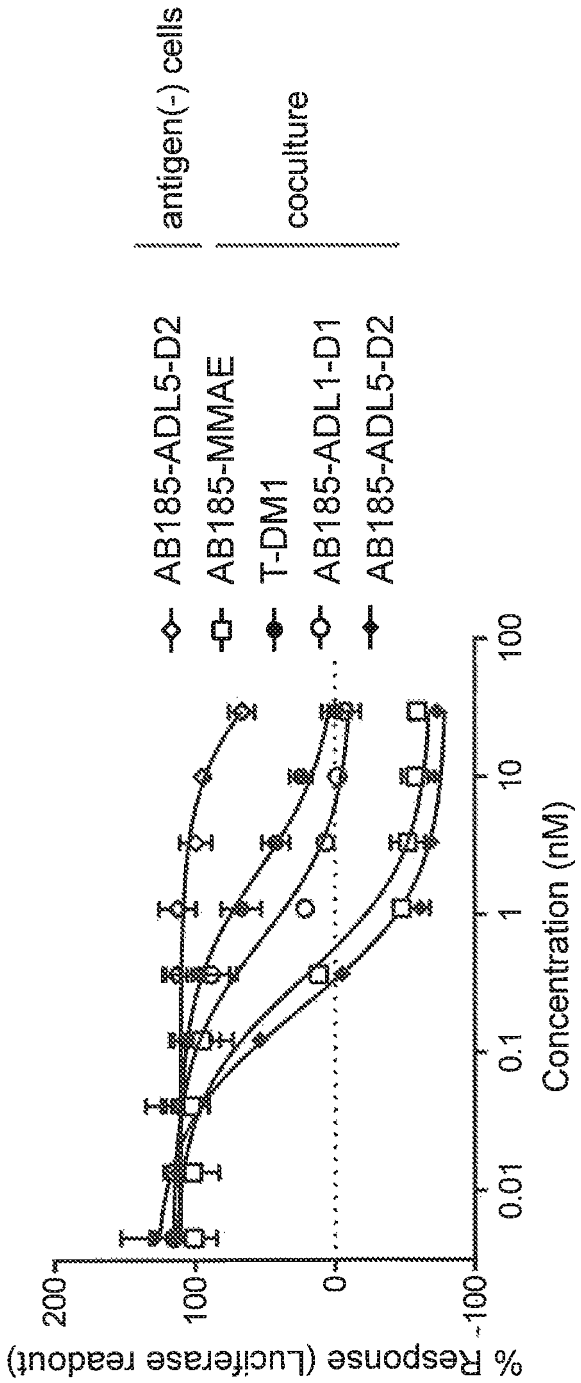
FIG. 8 shows the results of a bystander killing assay. H1568 cells overexpressing HER2 (target-positive) or H1568 cells tagged with luciferase (target-negative) plated either alone or incubated together in co-culture for 144 hours (6 days) were treated with exemplary HER2-ADCs. Plates were read with OneGlo® reagent. The y-axis represents the percent (%) response relative to the PBS control (100%). Data are represented as mean±SD.

Target-negative (luc-tagged) cells were not sensitive to treatment with anti-HER2 ADCs when cultured on their own (FIG. 8). However, when target-negative cells were cultured with target-positive cells, treatment with anti-HER2 ADCs resulted in increased killing of target-negative cells. These data suggest that target-negative cells are killed more effectively by anti-HER2 ADCs when co-cultured with target-positive cells, referred to herein as bystander killing. Bystander killing is distinguishable from off-target killing, which is defined as the killing of target (antigen)-negative cells on their own, in the absence of and independent of co-culturing with target-positive cells.

In this experiment, AB185-ADL5-D2 demonstrated an increased ability to kill an antigen heterogenous cancer cell population as compared to AB185-ADL1-D1. Without wishing to be bound by theory, this difference in potency may be due to the addition of one methyl group in D2, which gives a three-fold increase in payload cell potency and permeability as compared to D1 (see Table 14). The D2 ADC treated an antigen heterogenous cancer cell population as effectively as the AB185-MC-Val-Cit-MMAE control ADC.

3.6 In Vivo Analysis

Exemplary anti-HER2 ADCs that exhibited potent splicing modulation and cell growth inhibition were assessed in vivo.

3.6.1 HCC1954 Xenograft Efficacy Study

To investigate the efficacy of exemplary anti-HER2 ADCs in a mouse xenograft model, HCC1954 (ATCC) breast ductal carcinoma cells ($10\times10^6$ cells/100 μL/1:1 RPMI:Matrigel volume) were subcutaneously implanted into the flank of female CB17-SCID mice. Mice were treated with single bolus IV doses of conjugates (formulated in DPBS, pH 7.4) or vehicle control. The animals were dosed at the amounts indicated in FIG. 9. All animals were monitored for tumor growth and body weight twice weekly until they reached either of the following endpoints: (1) excessive tumor volume (calculated by using the ellipsoid formula: (length×width$^2$)/2); or (2) development of any health problems such as excessive body weight loss. All animal studies were carried out according to the H3 Biomedicine Guide for the Care and Use of Laboratory Animals.

Figure 9:
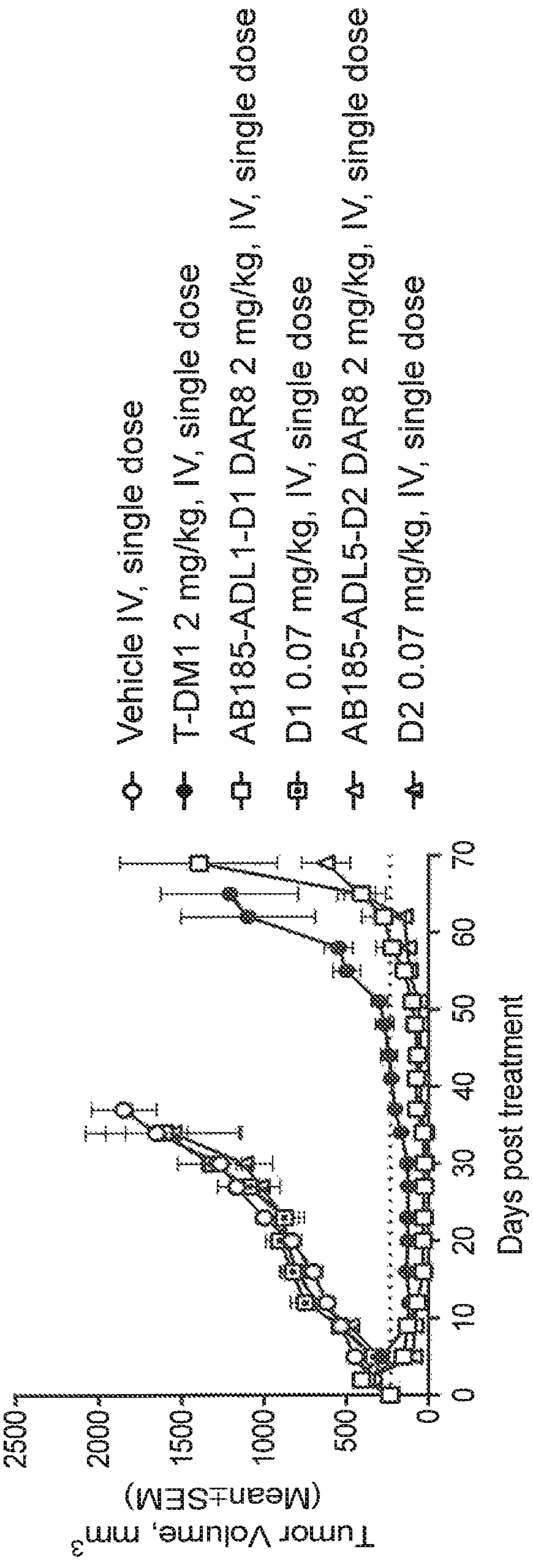
FIG. 9 shows tumor growth kinetics for each group of HCC1954-implanted CB17-SCID mice treated with a single intravenous dose of an exemplary HER2-ADC or corresponding dose-matched payload (6-10 animals per group). Tumor volumes were measured twice weekly after treatment. Data are represented as mean±standard error of the mean (SEM).

Treatment with anti-HER2 ADC (AB185-ADL5-D2 or AB185-ADL1-D1) at a single dose as low as 2 mg/kg resulted in significant tumor regression (FIG. 9). A dose response for the conjugated payload was also observed, such that anti-HER2 ADCs with higher DAR values (DAR ~4) demonstrated increased efficacy and slower tumor regrowth relative to dose-matched antibody T-DM1 control. Additionally, payload targeted to the tumor via an ADC was more potent relative to the corresponding unconjugated payload.

Example 4

To determine whether the properties of the exemplary anti-HER2 ADCs described in Example 3 could be extrapolated to other ADCs targeting alternate antigens and/or indications, select payloads were conjugated to an exemplary anti-CD138 antibody (B-B4) and an exemplary anti-EPH2A antibody (1C1). CD138 is expressed on malignant plasma cells, e.g., in multiple myeloma, while EPH2A is more generally expressed in a variety of malignancies. The preparation and evaluation of exemplary anti-CD138 and anti-EPH2A ADCs is described below.

4.1 Antibodies

B-B4 antibody ("AB205") (Tassone et al. (2004) Blood 104:3688-96) and 1C1 antibody ("AB206") (Jackson et al. (2008) Cancer Res. 68(22):9367-74) were used for the preparation of anti-CD138 ADCs and anti-EPH2A ADCs, respectively.

4.2 Bioconjugation

Antibody (B-B4 or 1C1) at 10 mg/mL in PBS buffer (pH 7.0) was mixed with 5 mM TCEP (2-4 molar equivalents) (ThermoFisher Scientific; #77720) to break interchain disulfide bonds. The reaction was gently mixed at 22° C. for 3 hours. Propylene glycol (15% v/v) was then added followed by 8 molar equivalents of linker-payload (6 mM stock in DMSO), and the solution was mixed thoroughly. The reaction was placed onto a rotary plate in an incubator at 22° C. After a 2-hour conjugation, the reaction mixture was purified to remove unconjugated payload by AKTA GE M150 (HiTrap™ 26/10 desalting column; flow rate: 3 mL/min) (GE Healthcare Bio-Sciences) into DPBS (pH 7.5). The resulting conjugate was concentrated via Amicon ultrafiltration (30 kDa, Ultra-4) (EMD Millipore) and submitted to sterile filtration through a 0.22 m PVDF disposable filter (EMD Millipore). The final clear solution was measured by UV-VIS to determine antibody concentration ([mAb]; mole/L) and conjugated payload concentration ([LD]; mole/L) according to the Beer-Lambert law (A=E*c*I) and the following equations:

$$A_{280\ nm}=E^{mAb}_{280\ nm}*[\mathrm{mAb}]*l+E^{LD}_{280\ nm}*[LD]*l$$

$$A_{252\ nm}=E^{mAb}_{252\ nm}*[\mathrm{mAb}]*l+E^{LD}_{252\ nm}*[LD]*l$$

$$E^{mAb}_{280\ nm}:B\text{-}B4=224{,}320\ \mathrm{cm}^{-1}\mathrm{M}^{-1}$$

$$1C1=215{,}380\ \mathrm{cm}^{-1}\mathrm{M}^{-1}$$

$$E^{mAb}_{252\ nm}:B\text{-}B4=83{,}670\ \mathrm{cm}^{-1}\mathrm{M}^{-1}$$

$$1C1=80{,}337\ \mathrm{cm}^{-1}\mathrm{M}^{-1};$$

$$E^{LD}_{280\ nm}=800\ \mathrm{cm}^{-1}\mathrm{M}^{-1}$$

$$E^{LD}_{252\ nm}=31{,}000\ \mathrm{cm}^{-1}\mathrm{M}^{-1}$$

Abbreviations: c—molar concentration; l—light path length (Nanodrop: 0.1 cm); E—molar extinction coefficient; A—absorbance.

4.3 Biophysical Characterization

DAR, percent aggregation, and percent unconjugated payload was analyzed for exemplary anti-CD138 and anti-EPHA2 ADCs by liquid chromatography-mass spectrometry (LC/MS), size exclusion chromatography (SEC), and reverse-phase high-performance liquid chromatography (HPLC), respectively. All conjugates described herein contained less than 2% free drug and contained less than 10% aggregate.

4.3.1 LC/MS Analysis—DAR

LC/MS analysis was performed as described in section 3.3.1. DAR values for exemplary anti-CD138 and anti-EPHA2 ADCs are reported in Tables 15-18.

4.3.2 SEC Analysis—Aggregation

SEC analysis was performed as described in section 3.3.2. Percent monomer for exemplary anti-CD138 and anti-EPHA2 ADCs is reported in Tables 15 and 17.

4.3.3 HPLC Analysis—Free Drug

HPLC analysis was performed as described in section 3.3.3. Percent free drug for exemplary anti-CD138 and anti-EPHA2 ADCs is reported in Tables 15 and 17.

4.4 In Vitro Analysis 4.4.1 Cell Viability

Anti-CD138 ADCs were tested in the CD138-expressing MOLP8 multiple myeloma cell line. Similarly, anti-EPHA2 ADCs were tested in the EPHA2-expressing PC3 prostate cancer cell line. Cell viability analysis was performed as described in section 2.3.

Figure 10:
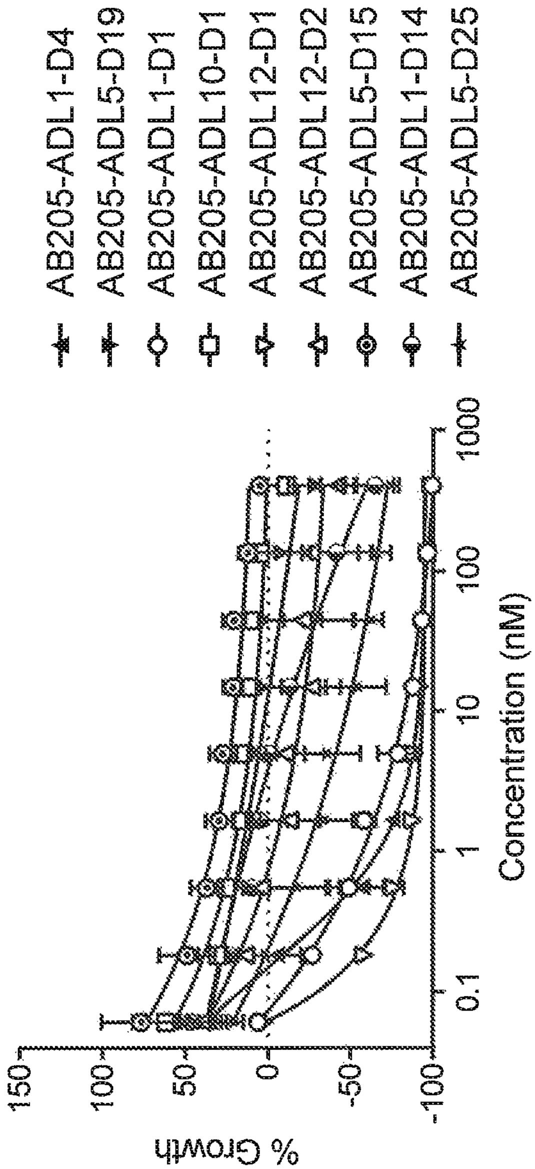
FIG. 10 shows viability dose response of exemplary CD138-ADCs in a CD138-expressing multiple myeloma cell line. MOLP8 cells were incubated with conjugates for 144 hours (6 days) and viability was read in CellTiter-Glo® reagent. Data are represented as mean±SD.
Figure 11:
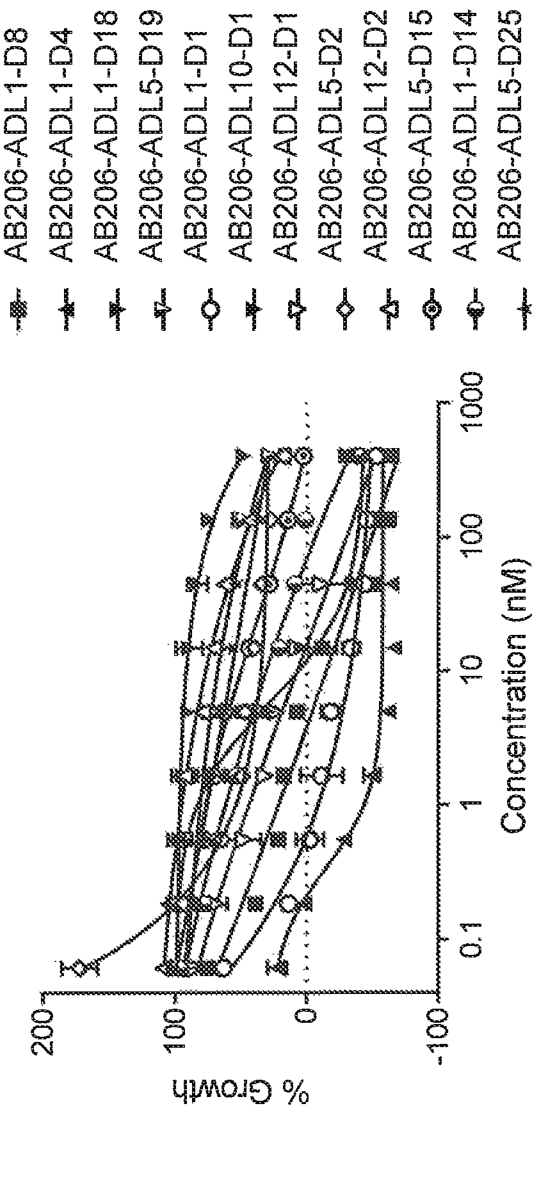
FIG. 11 shows viability dose response of exemplary EPH2A-ADCs in an EPHA2-expressing prostate cancer cell line. PC3 cells were incubated with conjugates for 144 hours (6 days) and viability was read in CellTiter-Glo® reagent. Data are represented as mean±SD.

Payload conjugation to anti-CD138 antibody (FIG. 10 and Table 16) and anti-EPHA2 antibody (FIG. 11 and Table 18) resulted in similar trends as those discussed in section 3.5.1 for anti-HER2 ADCs. In particular, ADCs with certain linkers (e.g., ADL12) and/or payloads (e.g., D1, D25, D4) demonstrated the highest potency in antigen-expressing cells. Consistently, alternate payloads (e.g., D14) were less capable of inhibiting cell growth via antibody-mediated delivery, despite being potent small molecules.

TABLE 15

Characterization of exemplary anti-CD138 ADCs

| SMLA Batch ID | Payload Class | Linker | DAR | Percent Monomer | Free Drug (%) | Concentration (mg/ml) |
|---|---|---|---|---|---|---|
| AB205-ADL1-D14 | ArylPlad | ADL0001 | 2.900 | 92.000 | <2 | 1.010 |
| AB205-ADL5-D15 | ArylPlad | ADL0005 | 2.800 | 95.000 | <2 | 1.060 |
| AB205-ADL5-D19 | Plad B | ADL0005 | 4.900 | 95.000 | <2 | 0.880 |
| AB205-ADL1-D1 | Plad D | ADL0001 | 5.000 | 98.000 | <2 | 0.620 |

TABLE 15-continued

| Characterization of exemplary anti-CD138 ADCs | | | | | | |
|---|---|---|---|---|---|---|
| SMLA Batch ID | Payload Class | Linker | DAR | Percent Monomer | Free Drug (%) | Concentration (mg/ml) |
| AB205-ADL1-D4 | Plad D | ADL0001 | 4.800 | 98.000 | <2 | 1.010 |
| AB205-ADL5-D25 | Plad D Zwitt | ADL0005 | 6.400 | 98.000 | <2 | 0.890 |
| AB205-ADL10-D1 | Plad D | ADL0010 | 3.400 | 96.000 | <2 | 0.750 |
| AB205-ADL12-D1 | Plad D | ADL0012 | 3.800 | 97.000 | <2 | 0.830 |
| AB205-ADL12-D2 | Plad D | ADL0012 | 3.300 | 97.000 | <2 | 0.970 |

TABLE 16

| Exemplary anti-CD138 ADCs-MOLP8 cells | | | | | | | |
|---|---|---|---|---|---|---|---|
| | SMLA | | | | Payload | | |
| Sample | DAR | GI50 (nM) | LD50 (nM) | Rmin (%) | GI50 (nM) | LD50 (nM) | Rmin (%) |
| AB205-ADL1-D1 | 5 | <0.061 | 0.656 | −100.099 | 6.885 | 25.712 | −100.248 |
| AB205-ADL5-D15 | 2.8 | 0.268 | >400 | 2.419 | 0.776 | 9.178 | −100.198 |
| AB205-ADL5-D19 | 4.9 | <0.061 | >400 | −46.23 | 0.84 | 4.58 | −62.2 |
| AB205-ADL10-D1 | 3.4 | 0.08 | >400 | −25.099 | 6.885 | 25.712 | −100.248 |
| AB205-ADL12-D1 | 3.8 | <0.061 | 0.168 | −99.851 | 6.885 | 25.712 | −100.248 |
| AB205-ADL12-D2 | 3.3 | <0.061 | >400 | −53.125 | 0.316 | 5.035 | −100.198 |
| AB205-ADL1-D14 | 3 | <0.061 | >400 | −74.008 | 1.9 | 8.5 | −61 |
| AB205-ADL1-D4 | 4.8 | <0.061 | 0.535 | −99.306 | 1.151 | 12.99 | −101.935 |
| AB205-ADL5-D25 | 6.4 | <0.061 | 11.669 | −76.736 | 149.874 | >400 | 5.94 |

TABLE 17

| Characterization of exemplary anti-EPHA2 ADCs | | | | | | |
|---|---|---|---|---|---|---|
| SMLA Batch ID | Payload Class | Linker | DAR | Percent Monomer | Free Drug (%) | Concentration (mg/ml) |
| AB206-ADL1-D1 | Plad D | ADL0001 | 5.600 | 99.000 | <2 | 2.060 |
| AB206-ADL5-D2 | Plad D | ADL0005 | 6.300 | 99.000 | <2 | 1.900 |
| AB206-ADL1-D4 | Plad D | ADL0001 | 6.000 | 95.000 | <2 | 1.140 |
| AB206-ADL1-D8 | Plad D | ADL0001 | 6.500 | 95.000 | <2 | 1.660 |
| AB206-ADL1-D14 | Aryl Plad | ADL0001 | 3.600 | 80.000 | <2 | 1.620 |
| AB206-ADL5-D19 | Plad B | ADL0006 | 4.600 | 97.000 | <2 | 0.960 |
| AB206-ADL5-D15 | Aryl Plad | ADL0005 | 4.200 | 95.000 | <2 | 0.820 |
| AB206-ADL5-D25 | Plad D Zwitt | ADL0005 | 5.000 | 96.000 | <2 | 1.130 |
| AB206-ADL10-D1 | Plad D | ADL0010 | 2.700 | 97.000 | <2 | 1.620 |
| AB206-ADL12-D1 | Plad D | ADL0012 | 6.400 | 90.000 | <2 | 0.670 |
| AB206-ADL12-D2 | Plad D | ADL0012 | 6.300 | 90.000 | <2 | 0.850 |

TABLE 18

| Exemplary anti-EPHA2 ADCs-PC3 cells | | | | | | | |
|---|---|---|---|---|---|---|---|
| | SMLA | | | | Payload | | |
| | DAR | GI50 (nM) | LD50 (nM) | Rmin (%) | GI50 (nM) | LD50 (nM) | Rmin (%) |
| AB206-ADL1-D8 | 6.5 | 0.175 | 95.51 | −68.678 | 16.622 | 177.783 | −68.37 |
| AB206-ADL1-D4 | 6 | <0.051 | 2.732 | −69.096 | 11.057 | >400 | −55.97 |
| AB206-ADL1-D14 | 3.6 | 3.046 | >400 | −49.267 | 3.877 | >400 | −79.835 |
| AB206-ADL12-D1 | 6.4 | 0.808 | >400 | −64.516 | 13.291 | >400 | −71.987 |
| AB206-ADL12-D2 | 6.3 | 78.977 | >400 | 17.376 | 2.391 | >400 | −68.803 |
| AB206-ADL5-D19 | 4.6 | 71.73 | >400 | 19.765 | 1.41 | >400 | −29.33 |
| AB206-ADL10-D1 | 2.7 | >400 | >400 | 43.796 | 13.291 | >400 | −71.987 |
| AB206-ADL5-D15 | 4.2 | 9.959 | >400 | 2.441 | 3.877 | >400 | −79.855 |
| AB206-ADL5-D25 | 5 | 28.078 | >400 | 20.041 | >400 | >400 | 77.524 |

TABLE 18-continued

| Exemplary anti-EPHA2 ADCs-PC3 cells | | | | | | | |
|---|---|---|---|---|---|---|---|
| | | SMLA | | | Payload | | |
| | DAR | GI50 (nM) | LD50 (nM) | Rmin (%) | GI50 (nM) | LD50 (nM) | Rmin (%) |
| AB206-ADL1-D1 | 5.6 | <0.061 | >400 | −59.643 | 13.291 | >400 | −71.987 |
| AB206-ADL5-D2 | 6.3 | 1.003 | >400 | 16.465 | 2.391 | >400 | −68.803 |

Example 5

The in vitro and/or in vivo stability of exemplary anti-HER2 ADCs was assessed as described below.

5.1 Total Antibody and Conjugated Payload of AB185-ADL1-D1 in Plasma

Following in vitro treatment (section 5.1.1) or in vivo treatment (section 5.1.2) with AB185-ADL1-D1, levels of total antibody (TAb) and conjugated payload (CP) were quantified in plasma by immunoprecipitation LC/MS/MS technique. Quantitation fit was linear with $1/x^2$ weighting from 0.5-100 μg/mL, and 0.5-500 ng/mL, in mouse plasma for TAb and CP, respectively. Plasma samples were mixed with stable-isotope labeled universal monoclonal human antibody internal standard (Slu™ MAB, Sigma, St. Louis, MO) and 10 mM PBS, pH 7.4 and incubated at room temperature for one hour. Dynabeads$^R$ MyOne™ Streptavidin Ti magnetic beads (ThermoFisher Scientific) were added to the mixture and incubated for an additional 30 min at room temperature. A magnetic stand was used to bind beads, which were sequentially washed with CHAPS buffer and then PBS buffer. Analytes of interest were eluted from the beads with 30 mM HCl. Separate eluent aliquots were used to quantify TAb or OP. For TAb, Tris-HCl, pH 8.3 was added, followed by trypsin and allowed to incubate overnight at 37° C. For the CP, 1M ammonium acetate was added, followed by deuterated payload internal standard, and cathepsin B, and allowed to incubate overnight at 25° C. Samples were analyzed by LC/MS/MS and quantified using area ratio of analyte to internal standard and compared against respective calibration curve. To calculate CP concentration, the concentration of TAb was corrected for molecular weights of payload, molecular weight of AB185-ADL1-D1 and DAR (drug-to-antibody ratio).

5.1.1 In Vitro Stability of AB185-ADL1-D1 in Mouse, Rat, and Monkey Plasma

Pooled plasma (Bioreclamation) from mouse, rat, and monkey, and PBS were spiked with AB185-ADL1-D1 (4.81 mg/mL) to achieve a final concentration of 50 μg/mL. Samples were incubated at 37° C., 95% humidity, 5% $CO_2$ for 4 days in a manner to stabilize pH and minimize non-specific binding and evaporation. Aliquots were removed at 4, 24, 48, 72, and 96 hours and stored at −70° C. until processing. Samples were thawed and processed for bioanalysis using methods described above (section 5.1) for total antibody and conjugated payload. Time 0 was set to 100% for each matrix. The area ratio responses of the later time points were compared to time 0 separately for each matrix. Percent remaining was calculated as follows: (Area Ratio day X/Area Ratio time 0)*100=% remaining. The slope of the line was calculated in Excel comparing the log of % remaining and time point. Half-life was calculated in Excel by In(2)/slope.

Figure 12A:
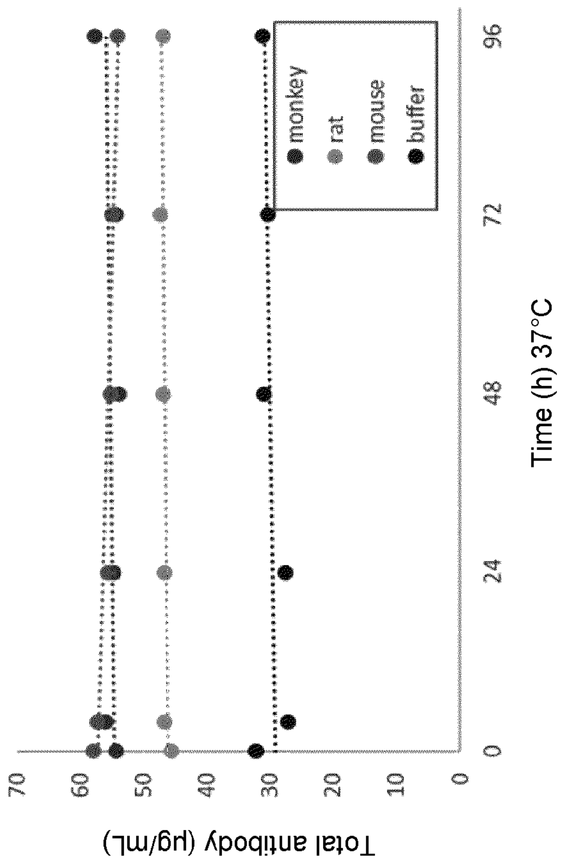
FIG. 12A and FIG. 12B show the results of an in vitro stability assay for an exemplary anti-HER2 ADC, AB185-ADL1-D1. The y-axis represents concentration of total antibody (FIG. 12A) and conjugated (intact) payload (FIG. 12B); the x-axis represents time as measured in hours at 37° C.
Figure 12B:
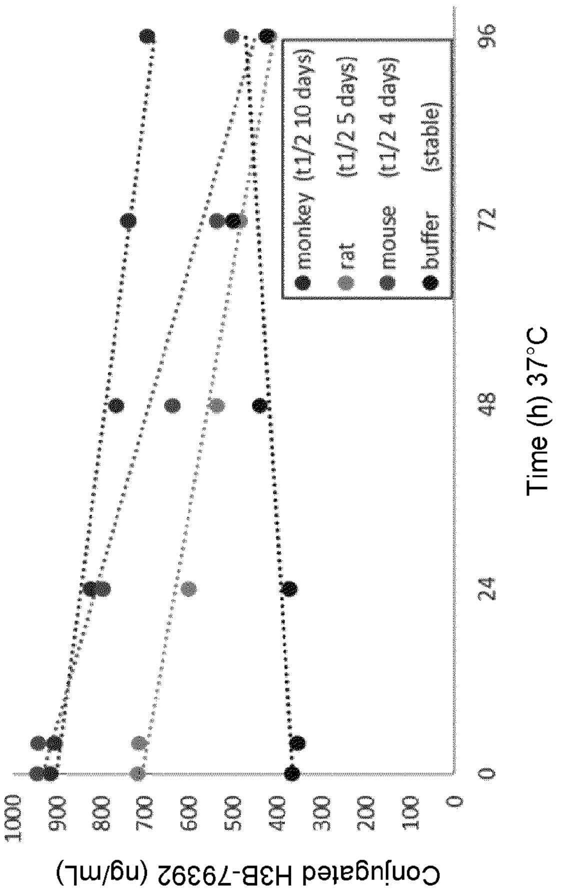

Total antibody from AB185-ADL1-D1 was found to be stable in buffer and in all species of plasma, exhibiting only modest precipitation over 4 days (FIG. 12A). Conjugated (intact) payload D1 levels were maintained over 4 days (FIG. 12B).

5.1.2 Snapshot Pharmacokinetics (PK) in Mouse Plasma Following Single IV Dose of AB185-ADL1-D1

Mice (CB17-SCID) were treated with a single IV dose of AB185-ADL1-D1 at 10 mg/kg or 20 mg/kg, followed by terminal collections (cardiac puncture) in Lithium-Heparin tubes (n=3 per time point per dose group) at 24, 48, and 72 hours post dose. Blood was centrifuged for 5 min at 5000 rpm at 4° C. to remove red blood cells and the plasma was stored at −80° C. until processing. Samples were thawed and processed for bioanalysis using methods described above (section 5.1) for total antibody and conjugated payload.

Figure 13:
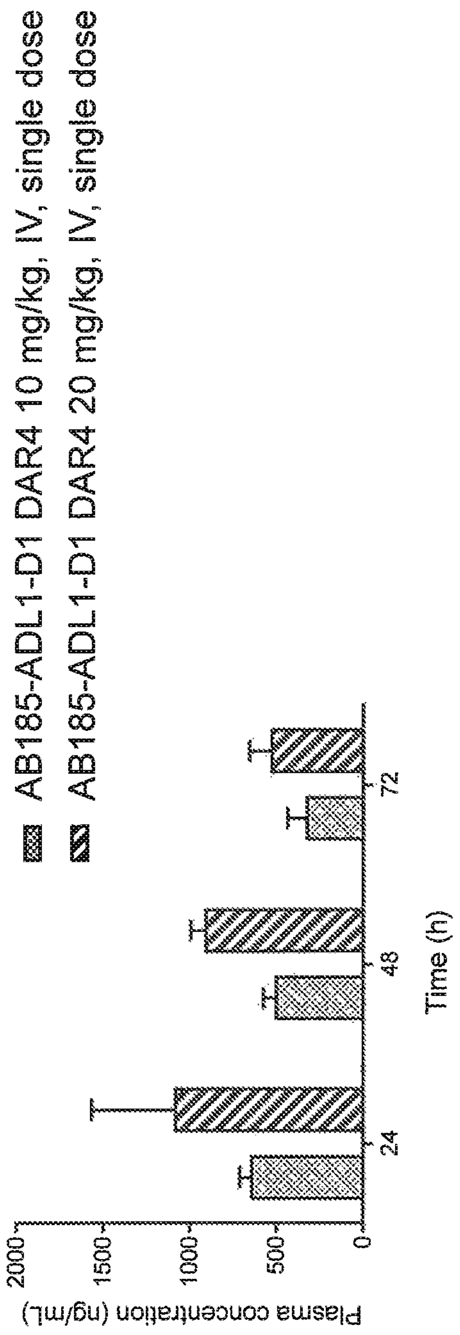
FIG. 13 shows plasma concentrations of an exemplary anti-HER2 ADC, AB185-ADL1-D1, following a single intravenous dose in CD17-SCID N87 tumor-bearing mice.

Following a single IV dose of AB185-ADL1-D1, more than 400 ng/mL of intact D1 payload remained conjugated to AB185 antibody at 72 hours post dose (FIG. 13). The AB185-ADL1-D1 ADC demonstrated improved stability as compared to an alternate ADC carrying a payload with a similar mechanism of action. The thailanstatin A-based ADC reported in Puthenveetil et al. (Bioconjugate Chem. (2016) 27:1880-8) is relatively less stable, and shows complete bioconversion of payload by 72 hours (i.e., acetate is completely hydrolyzed).

5.2 Accelerated Stability Testing of AB185-ADL14-D1 and AB185-ADL5-D25

Freshly produced SMLAs (~1 mg each in Eppendorf tubes, 4-5 mg/mL) were centrifuged and measured by UV absorption (NanoDrop) at 280 nm to determine the protein concentrations. Samples were then incubated in a 37° C. waterbath and sampled at four time points, 0 (freshly prepared), 1 day, 2 days, and 4 days. Samples taken at different time points were stored at −80° C. until the last sampling was completed. After thawing at 22° C., samples were analyzed with SEC, hydrophobic interaction chromatography (HIC), and reverse-phase-MS (RP-HPLC) for quantification of antibody aggregation/fragments, and DAR. Percent aggregation, concentration, and DAR values (HIC and RP-HPLC) for AB185-ADL14-D1 and AB185-ADL5-D25 at four time points are shown in Table 19.

TABLE 19

| Accelerated stability testing of select anti-HER2 ADCs | | | | | | |
|---|---|---|---|---|---|---|
| | | | | | DAR | |
| ADC | Storage Buffer | Days @ 37C | Aggregation (%) | Concentration (mg/mL) | HIC | RP-HPLC |
| AB185-ADL14-D1 | DPBS (pH 7.5) | 0 | 0.68 | 4.99 | 4.3 | 4.32 |
| | | 1 | 1.18 | 4.98 | 4.29 | 4.31 |
| | | 2 | 1.31 | 5.12 | 4.33 | 4.32 |
| | | 4 | 2.08 | 5.02 | 4.28 | 4.27 |
| AB185-ADL5-D25 | DPBS (pH 7.5) | 0 | 0.84 | 5.05 | 4.54 | 4.22 |
| | | 1 | 1.14 | 4.16 | 4.44 | 4.19 |
| | | 2 | 1.41 | 4.52 | 4.74 | 4.19 |
| | | 4 | 2.43 | 3.98 | 4.64 | 4.12 |

Example 6

To determine whether cells treated with splicing modulator-based ADCs (i.e. the exemplary ADCs described herein) could produce neoantigens suitable to prime naïve T-cells to transition to effector cells (i.e., effector cells capable of targeting such neoantigens), the following experiments were performed.

6.1 RNA Sequencing and Protein Ligandome Experiment

6.1.1 Overview

Changes in the transcriptome were interrogated following ADC treatment. Two HER2-overexpressing cell lines, one engineered non-small-cell lung cancer line (NCI-H1568) and one HER2-amplified breast cancer line (HCC1954) were treated with ADC (AB185-ADL1-D1) at concentrations intended to trigger robust aberrant mRNA splicing (4 nM and 1.3 nM, respectively). RNAseq experiments were performed at 24 hours post treatment. These experiments demonstrated that multiple mRNA transcripts exhibited altered splicing patterns.

To then interrogate whether the identified transcripts could be translated and presented as neoantigens on tumor cell MHC1 complexes, a timepoint that would allow for translation of the mRNA transcripts, but that would precede extensive cytotoxicity effects (as those may impair collection of cell material for analysis) was selected. NCI-H1568 and HCC1954 cell lines were then treated with ADC at 3 nM for 48 hours and the MHC1-bound peptidome was analyzed by LC-MS/MS. Peptidome data was filtered by primary peptide size to 8-14 amino acid fragments (defined as the size limit criteria for binding to MHC1) and then filtered against known human proteins. The identified peptides were characterized as self antigens, regardless of under which conditions and in which cell line they were detected. All remaining peptide sequences were mapped against 3-frame translations of the RNAseq data. Using stringent criteria for evaluating the peptide sequences (including exclusion of: any peptide identified in any untreated sample, any peptide that was not encoded in the canonical open reading frame, and any peptide that was not encoded by an exon-junction-spanning portion of the mRNA where the exon junctions were altered by treatment with AB185-ADL1-D1), four MHC1-bound neopeptides were identified. For a schematic of an exemplary RNA sequencing and protein ligandome experiment, see FIG. 14.

6.1.2 Detailed Methods 6.1.2.1 RNA Sequencing of ADC-Treated Cells

HCC1954 and HER2 overexpressing NCI-H1568 (ATCC) cells were plated at $1\times10^5$ cells per individual well of a 6-well tissue culture plate (Corning). Cells were treated with phosphate-buffered saline or AB185-ADL1-D1 at 1.3 nM and 4 nM, respectively, for 24 hours. Total RNA was extracted from cells using an RNAeasy Mini kit (Qiagen), and assessed for quality and quantity (RNA 6000 Nano LabChip kit on a 2100 Bioanalyzer, both from Agilent). Poly-A selected RNA-Seq libraries were prepared according to standard Illumina protocols. cDNA libraries were checked for quality and quantified using the DNA-1000 kit on a 2100 Bioanalyzer (both from Agilent). Libraries were pooled and sequenced on a HiSeq2000 (Illumina) to obtain 101-base paired-end reads.

Raw sequence reads were aligned to the human reference sequence hg19 by STAR 2.4.2a using two-pass alignment35, and isoform quantification was performed using Kallisto 0.42.4 (Bray et al. (2016) Nat Biotechnol. 34(5):525-7) against GENCODE annotation v 25 mapped to GRCh37. Estimation of the retained intron count was performed by defining 6 nt (−3 nt from the splice site and +3 following the splice site) exon-intron boundary regions and counting alignments, which fully overlapped the regions. All raw junction counts, including those from exon-intron boundaries, were pooled over all technical replicates per cohort. Differential junction usage was assessed using a binomial z test for differences in proportion between treated and untreated sample pools. Proportions were calculated on the basis of all splice junctions (and exon-intron boundaries) which shared a splice site, similar to the percent spliced in (PSI) measurement. In order to preserve Gaussian assumptions, only those shared splice sites with total junction count (sum raw count over all junctions sharing that splice site) greater than or equal to 10 reads in both treated and untreated cohorts were considered for analysis. z-scores corresponding to a false discovery rate (FDR)-corrected q value of ≤0.05 for treated ('aberrant') junctions and 50.20 for untreated ('canonical') junctions were considered significant.

Two or more splice junctions that share a splice site and have at least one junction that is significantly upregulated in treated samples or at least one junction significantly upregulated in untreated samples were considered aberrant or canonical junctions, respectively. Both aberrant and canonical junctions were required to be present in an event for it to be considered differential splicing. In the case of intron-retention events, both exon-intron boundaries (5' and 3' splice sites) as well as the junction bridging the two were required to be significant.

6.1.2.2 MHC1-Bound Peptidome of ADC-Treated Cells

Figure 14:
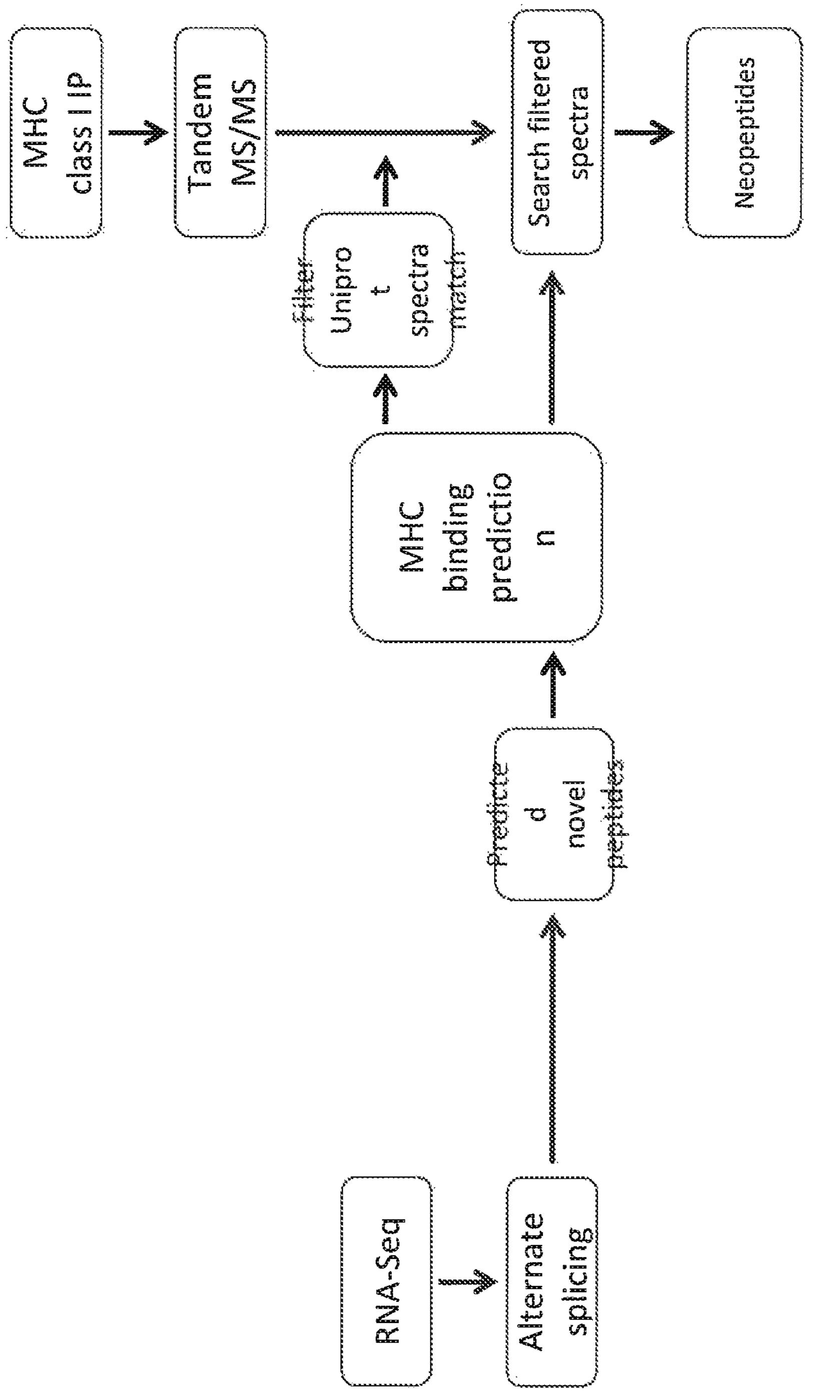
FIG. 14 shows a schematic diagram of an exemplary RNA sequencing and protein ligandome experiment.

HCC1954 and HER2 overexpressing NCI-H1568 (ATCC) cells were plated at $1\times10^8$ cells on 15 $cm^2$ tissue culture plates (Corning). Cells were treated with phosphate-buffered saline or AB185-ADL1-D1 at 3 nM for 48 hours. Cells were mechanically removed from the plates and processed as per Bassani-Sternberg et al. ((2015) Mol Cell Proteomics 14(3):658-73). Briefly, the procedure involved solubilization of the MHC-1 protein complexes from cellular membranes, enrichment of MHC-1 protein together with its bound peptides by immunoprecipitation, selective elution and purification of bound peptides, and identification and quantification of peptides by LC/MS/MS analysis. For immunoprecipitation the monoclonal antibody W6/32 purified from its hybridoma cell line HB-95TM was used. Mass spectrometric analyses were performed on a Q Exactive HF instrument. Raw files acquired in this study were processed with the MaxQuant software suite (version 1.5.7.13) for peptide and protein identification and quantification using a human protein sequence database (version 22017). In addition to this database, predicted transcript variants based on RNAseq experiments of AB185-ADL1-D1-treated HCC1954 and NCI-H1568 cells were included. MaxQuant performs 6-frame translation and integrates obtained peptide sequences for matching with $MS^2$ spectra. Data were further manually filtered for peptide sequences unique to AB185-ADL1-D1-treated samples as well as for peptides encoded by mRNA splice junctions modulated by AB185-ADL1-D1 treatment (FIG. 14). Four neopeptides were identified by a high-stringency filtering of the RNAseq and MHC-1-bound ligandome data. These were encoded by four genes. The protein sequences of the four neopeptides, referred to herein as Neoantigen 1, Neoantigen 2, Neoantigen 3, and Neoantigen 4, were extended for the following experiments on triggering immune cell priming. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes.

6.2 T-Cell Priming Experiment

PS 6.2.1 Overview

This experiment was an in vitro reconstitution of the interactions that occur in normal human secondary lymphatic organs (e.g., tumor draining lymph nodes). In this experiment, monocytes were isolated from peripheral blood mononuclear cells (PBMC) and were induced to differentiate into dendritic cells (DC) through culturing in a cytokine cocktail. Following differentiation to mature DC, the mature DC were cultured with extended neopeptide sequences. During culturing, the mature DC take up the peptides, process them into fragments, and present them on MHC1 for priming of CD8 T-cells. The DC were then mixed with additional PBMC from the same donor and incubated for approximately 2 weeks in a cocktail of cytokines to stimulate the activation of CD8 T-cells. Following incubation, the cells were transferred to an ELISpot plate that had been re-coated with the peptides used for priming and re-stimulation of CD8 T-cells was monitored by secretion of IFNγ. The ELISpot plate was then processed and imaged, and the IFNγ spots were counted to estimate the number of active CD8 T-cells. For a schematic of an exemplary T-cell priming experiment, see FIG. 15.

Figure 15:
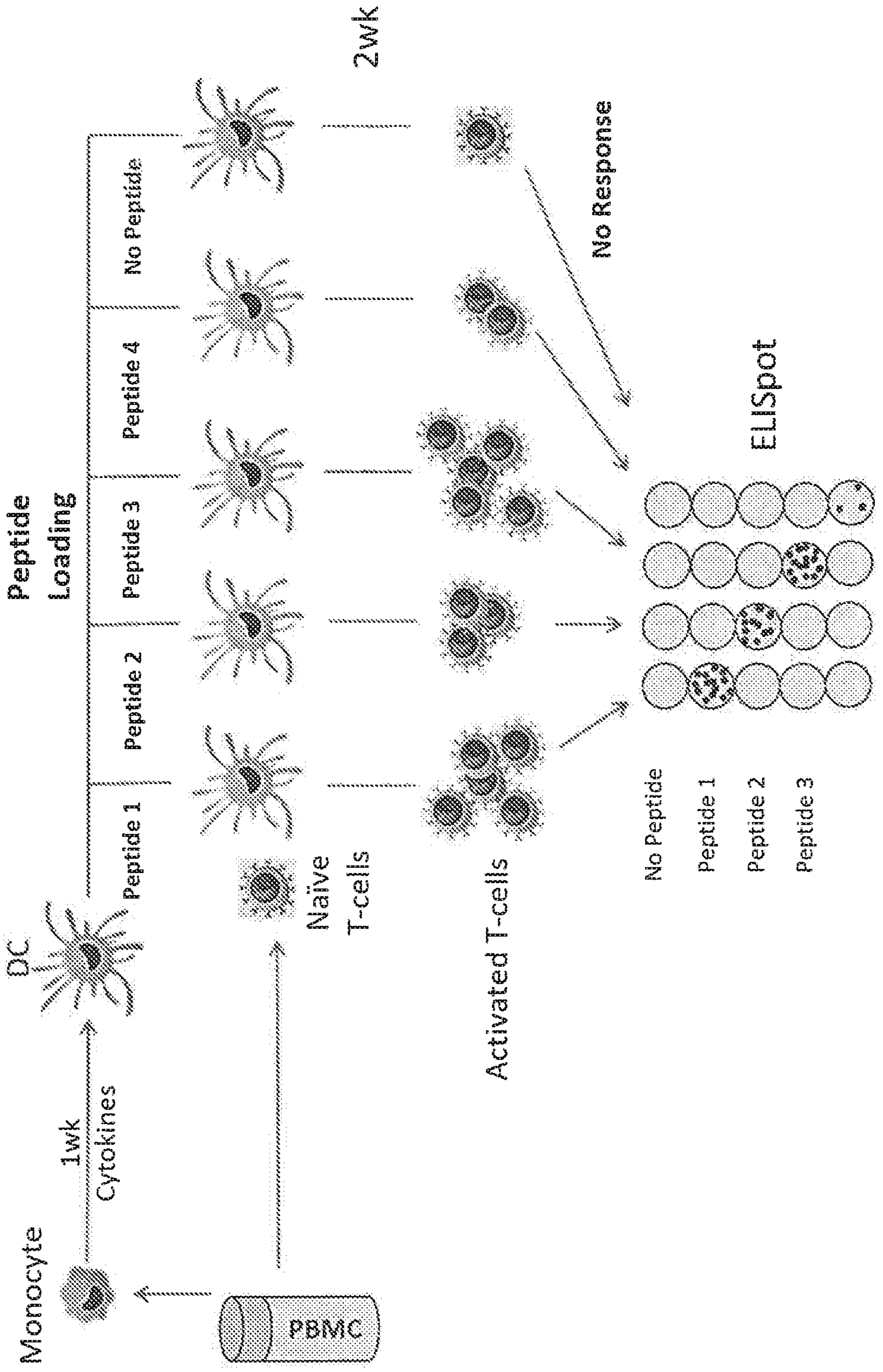
FIG. 15 shows a schematic diagram of an exemplary T-cell priming experiment.
Figure 16:
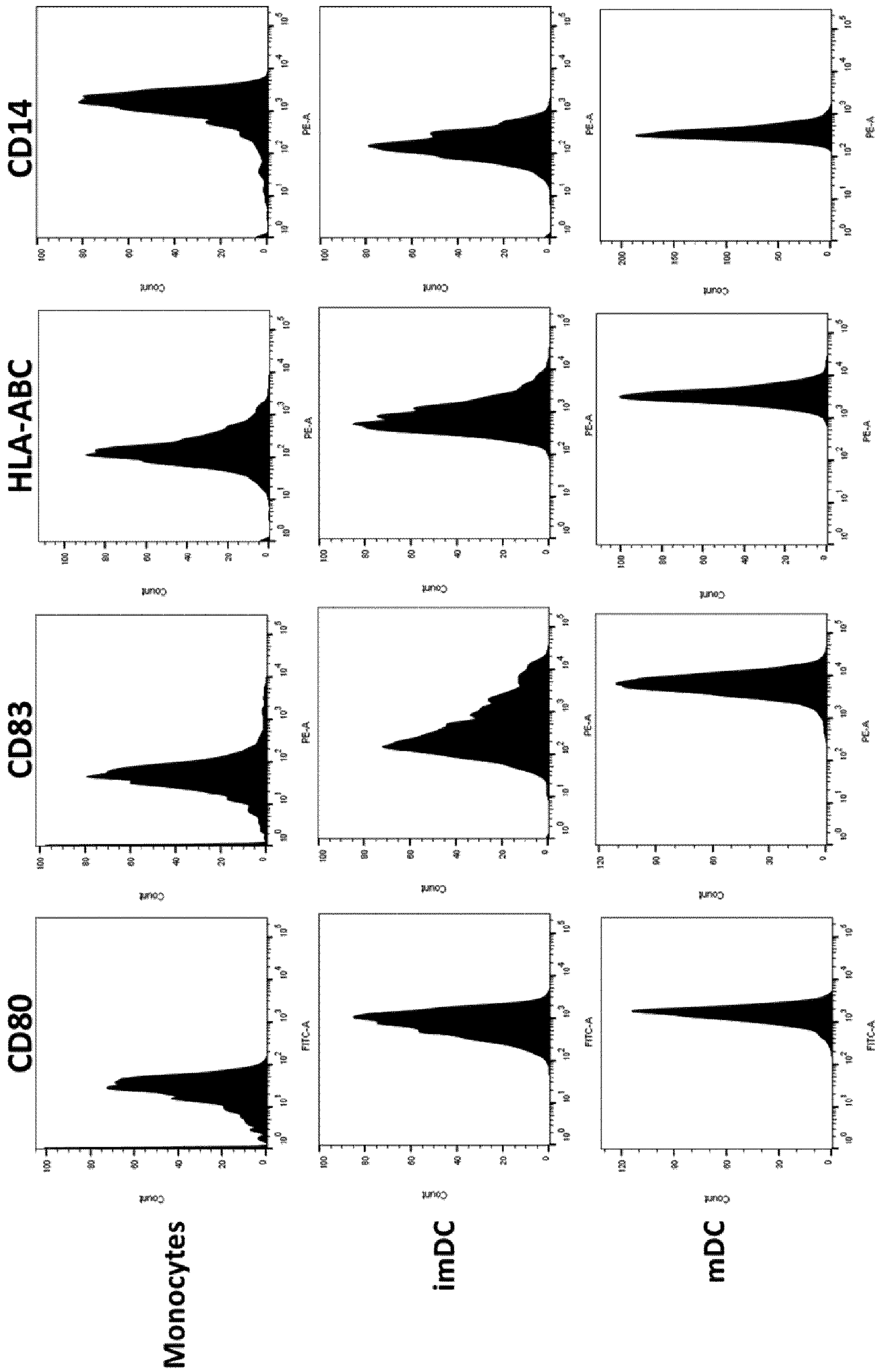
FIG. 16 shows the results of a FACS analysis. Monocytes were isolated from peripheral blood mononuclear cells (PBMC) and were induced to differentiate into dendritic cells (DC) through culturing in a cytokine cocktail. FACS was performed to validate the maturation of DC from monocytes.
Figure 17A:
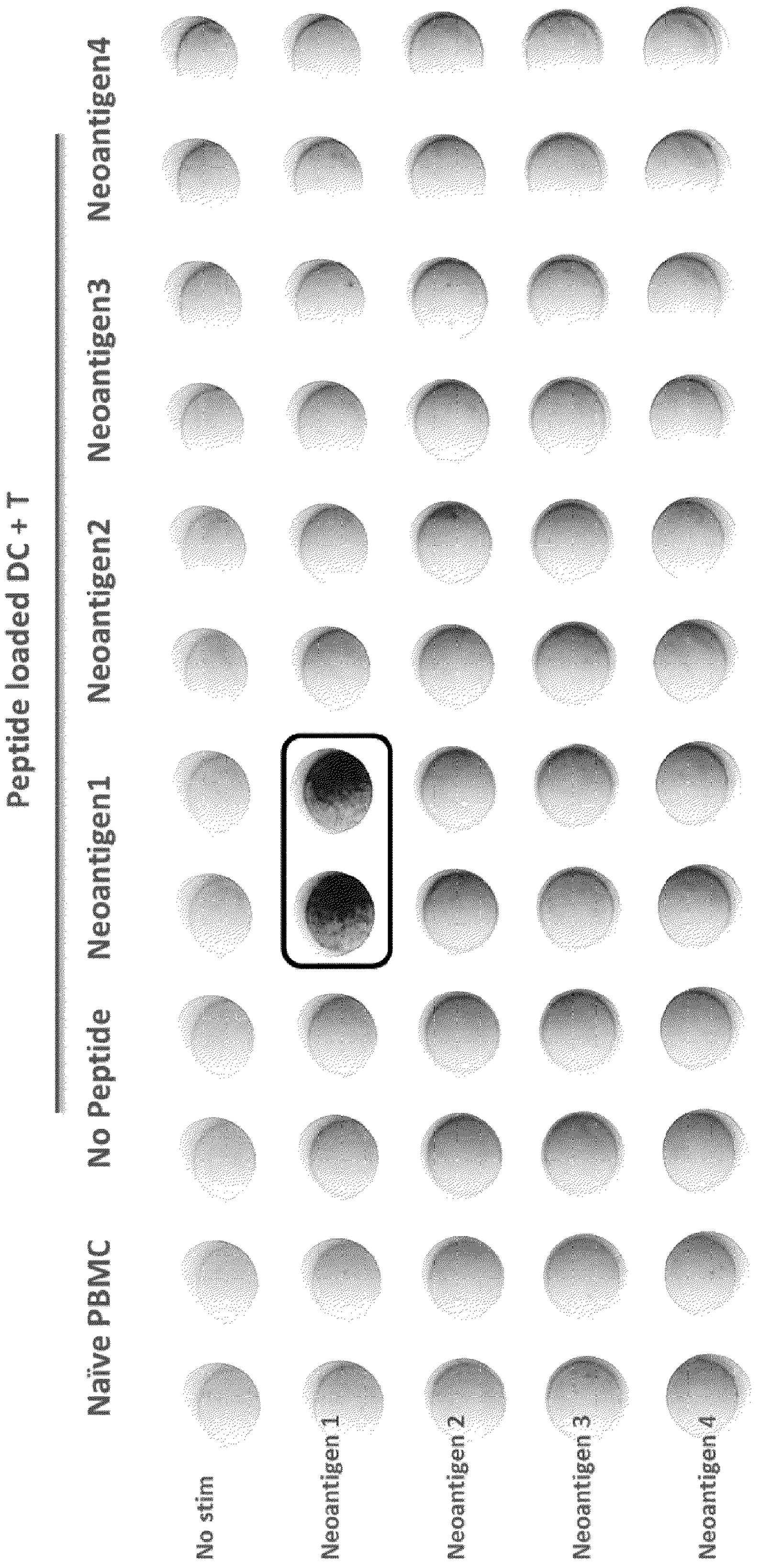
FIG. 17A-D show the results of an ELISpot assay.
Figure 17B:
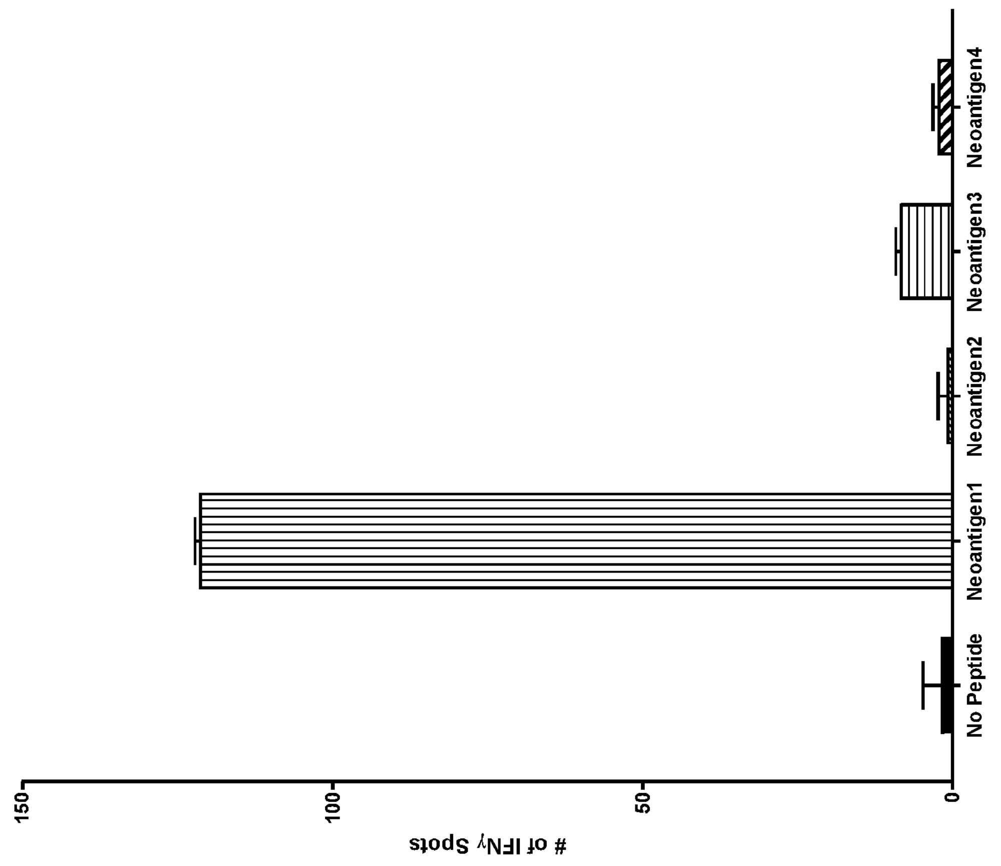
Figure 17C:
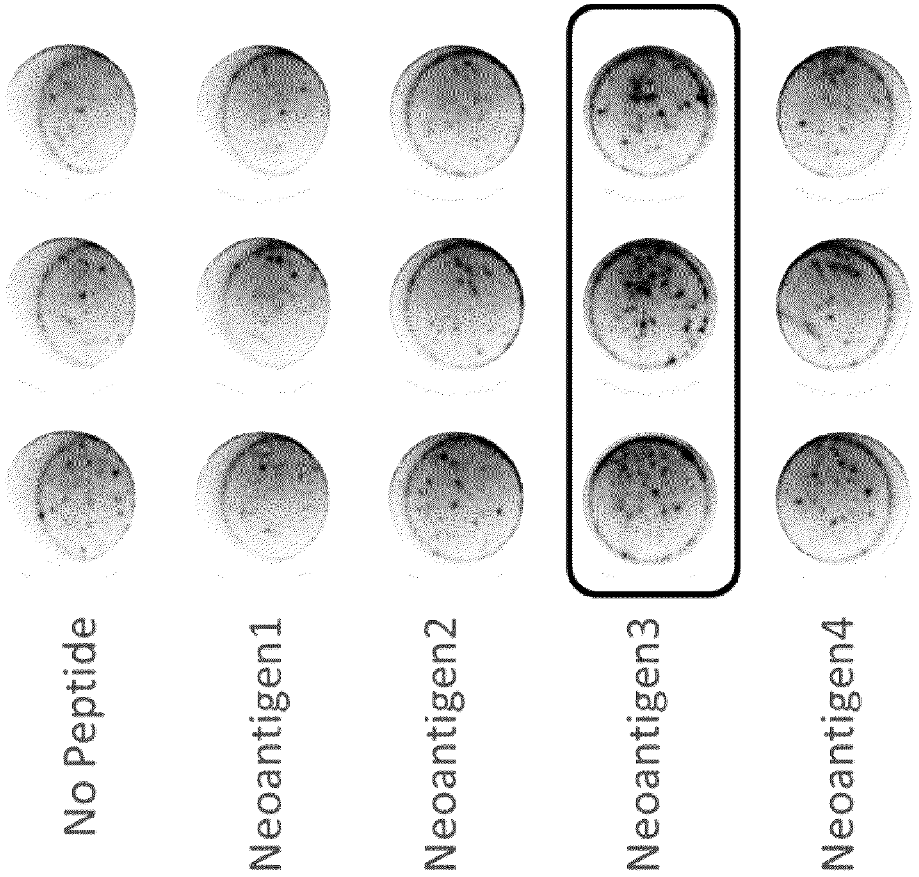
Figure 17D:
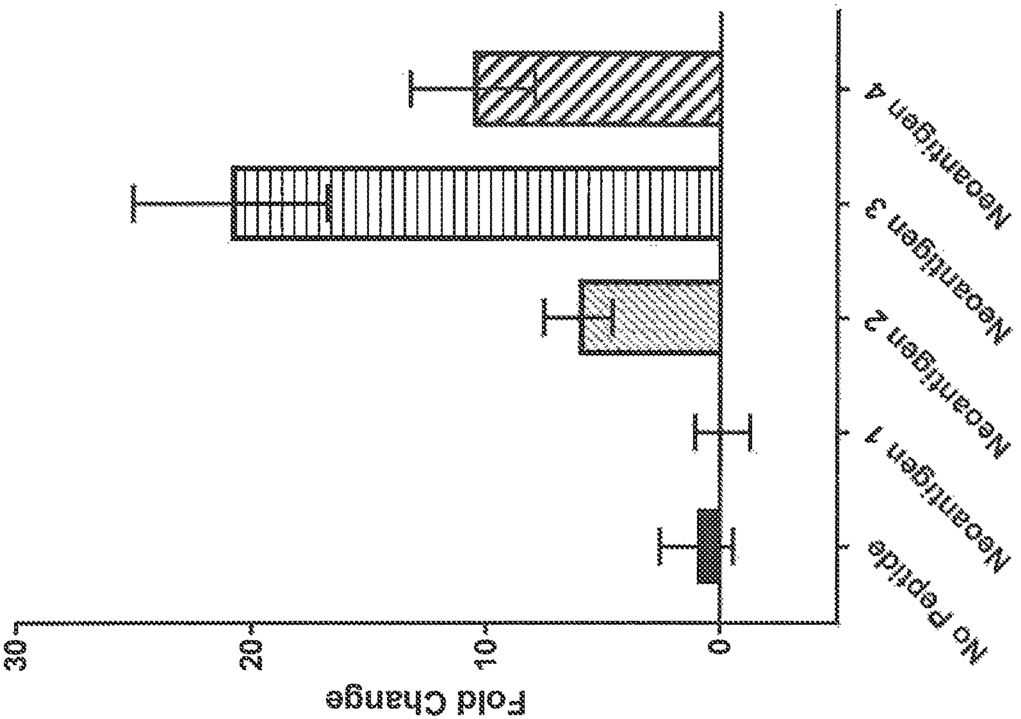

6.2.2 Detailed Methods 6.2.2.1 Neoantigen-Mediated T-Cell Priming and Activation ELISpot Bulk peripheral blood mononuclear cells (PBMC) were purchased from multiple vendors (StemExpress, HemaCare, Precision Medicine) and were used to generate antigen-reactive CD8+ T-cells as per Wöfl and Greenberg ((2014) Nat Prot. 9(4):950-66; FIG. 15). Briefly, frozen PBMC ($5\times10^7$ cells) were thawed and plated on T-75 tissue culture plastic (Corning) in RPM11640, supplemented with 5% human AB serum and 1% penicillin/streptomycin for 2-3 hours. Non-adherent cells were removed and discarded, and adherent cells were cultured in RPM11640/5% human serum, supplemented with 20 ng/mL GM-CSF and 20 ng/mL IL-4 for 5 days. On day 6, media was further supplemented with 20 ng/mL TNF-α. On day 7, mature DC were collected, counted, and loaded with neopeptides that were identified from MHC1-peptidome experiments (FIG. 16). Cells were separated and loaded with each peptide at a final concentration of 10 μg/$10^6$ cells/mL and incubated for 1 day. On day 8, DCs were treated with mitomycin C at 20 μg/mL for 30 min and washed extensively. Concurrent with the treatment of the DC, $10^8$ matched PBMC were thawed and washed with RPM11640. PBMC were then mixed with DC at a ratio of 10:1 in 10 mL RPM11640/5% human AB serum, supplemented with IL-21 at 30 ng/mL in T25 flasks. After 3 days of co-culture (day 11), an additional 10 mL of fresh media was added and supplemented with IL-7 and IL-15 at a final concentration of 5 ng/mL. Following an additional 3 days of co-culture (day 14), an additional 10 mL of fresh media, supplemented with IL-7 and IL-15 at a final concentration of 5 ng/mL, was added and the co-culture was moved to a T-75 flask. On day 17, an additional 20 mL of media, supplemented IL-7 and IL-15 at a final concentration of 10 ng/mL, was added and cells were transferred to a T-175 flask. On day 20, cells were collected, and ELISpot assay was performed as per manufacturer's instructions (R&D Systems). Wells were pre-loaded using peptide at 10 μg/mL final concentration per well, cell density at $2\times10^5$ cells per well, duplicate seeding, and overnight incubation. IFNγ spots were developed and read on an AID ELISpot reader as per manufacturer's instructions (FIG. 17A-D).

Exemplary data from antigen priming experiments are shown in FIG. 17A-D. Donor-derived PBMC lots were differentiated into DC and primed with neopeptides as outlined in FIG. 15. Analysis of ELISpot data shows that, in healthy donor PBMC, priming of naïve T-cells by DC presenting neopeptides can result in antigen-specific expansion and maturation of effector (CD8) T-cell populations. These T-cell populations exhibit antigen-specific re-activation, as evidenced by IFNγ secretion only in the presence of the antigenic peptide and not in the presence of non-priming peptides.

RT-qPCR

RNA was purified from cell lines using RNeasy Mini with DNaseI treatment (Qiagen) and 1-2 μg of RNA reverse transcribed using Superscript VILO reverse transcriptase (ThermoFisher Scientific) in 20 μL according to manufacturer's instructions. RNA lysates were isolated and reverse transcribed using TaqMan Gene Expression Cells-to-CT Kit (ThermoFisher Scientific) according to manufacturer's instructions. Quantitative PCR was performed using TaqMan Gene Expression Master Mix (ThermoFisher Scientific) with transcript probes targeting neoantigen junctions duplexed with GAPDH RNA VIC-PL (ThermoFisher Scientific) and quantified using the AACt method.

Example 7

7.1 RNA Sequencing and Protein Ligandome Experiment 7.1.1 Methods

RNA sequencing and protein ligandome experiment was performed as described in Example 6 (Section 6.1). For a schematic of an exemplary RNA sequencing and MHC1 ligandome experiment, see FIG. 14.

7.1.2 Results

Twenty nine neopeptides were identified by a high-stringency filtering of the RNAseq and MHC1-bound ligandome data (Table 20). Four neopeptides were selected and extended for the following experiments on triggering immune cell priming. The four selected neopeptides are shown in bold in Table 20.

TABLE 20

Neopeptides

| | Neopeptide | SEQ ID NO | Junction (HG19) | Gene | Event type | Observed in |
|---|---|---|---|---|---|---|
| 1 | SPTLPPRSL | 37 | chr12: 49663470-49663610: + | TUBA1C | Intron retention | H1568 |
| 2 | HPSIKRGLSSL | 38 | chr12: 42729776-42781257: + | PPHLN1 | Exon skipping | H1568 |

TABLE 20-continued

| Neopeptides | | | | | |
|---|---|---|---|---|---|
| Neopeptide | SEQ ID NO | Junction (HG19) | Gene | Event type | Observed in |
| 3 LLLPHHVL | 39 | chr12: 49663470-49663610: + | TUBA1C | Intron retention | H1568 |
| 4 RTAPGVRPPF | 40 | chr14: 35182767-35183743: − | CFL2 | Intron retention | H1568 |
| 5 RPQKSIQAL | 41 | chr10: 28822963-28823162: + | WAC | Intron retention | H1568 |
| 6 APAPPPLPA | 42 | chr17: 80009840-80011149: + | GPS1 | Intron retention | H1568 |
| 7 RPRPSFPVSL | 43 | chr7: 55087058-55134942: + | EGFR | Intron retention | H1568 |
| 8 RPKHGDGFSL | 44 | chr11: 57472287-57472444: − | MED19 | Intron retention | H1568 |
| 9 GPAPGKTGL | 45 | chr7: 75932393-75933118: + | HSBP1 | Intron retention | H1568 |
| 10 **EAARKGNSL** | 46 | chr1: 53480715-53504588: + | SCP2 | Exon skipping | H1568 |
| 11 **RIKEKIEEL** | 47 | chr9: 72897499-72912881: + | SMC5 | Exon skipping | H1568 |
| 12 **EIKKRFRQF** | 48 | chr1: 28531860-28541450: − | DNAJC8 | Exon skipping | H1568 |
| 13 **HESAAMAET** | 49 | chr11: 10227293 7-102323254: − | TMEM123 | Exon skipping | HCC1954 |
| 14 ALKLKQVGV | 50 | chr1: 153610924-153617539: + | CHTOP | Exon skipping | H1568 |
| 15 DLKKRHITF | 51 | chr13: 41323417-41331008: − | MRPS31 | Exon skipping | H1568 |
| 16 DVKRNDIAM | 52 | chr1: 41213277-41218822: + | NFYC | Exon skipping | H1568 |
| 17 IPSDHILTPA | 53 | chr6: 149718900-149720239: + | TAB2 | Exon skipping | H1568 |
| 18 TVFSTSSLK | 54 | chr11: 61197654-61213412: + | SDHAF2 | Exon skipping | H1568 |
| 19 ITSCLLNF | 55 | chr5: 137892555-137893090: − | HSPA9 | Intron retention | H1568 |
| 20 RASPVRGQL | 56 | chr7: 75677544-75677893: + | MDH2 | Intron retention | H1568 |
| 21 VVRKPVIAL | 57 | chr1: 36923582-36929406: − | MRPS15 | Exon skipping | H1568 |
| 22 LLSEKKKIS | 58 | chr6: 31750622-31750872: − | VARS | Intron retention | H1568 |
| 23 APASKPRPRL | 59 | chr19: 3573798-3574380: + | HMG20B | Intron retention | H1568 |
| 24 RYGQLSEKF | 60 | chr19: 33076813-33078158: + | PDCD5 | Exon skipping | HCC1954 |
| 25 VYISNVSKL | 61 | chr3: 53920961-53925796: − | SELK | Exon skipping | HCC1954 |
| 26 LPTKETPSF | 62 | chr2: 85133241-85133394: + | TMSB10 | Alt 3'ss | HCC1954 |
| 27 GEAPPPPPA | 63 | chr17: 80223672-80231181: − | CSNK1D | Intron retention | HCC1954 |

TABLE 20-continued

| Neopeptides | | | | | |
|---|---|---|---|---|---|
| Neopeptide | SEQ ID NO | Junction (HG19) | Gene | Event type | Observed in |
| 28 LEEISKQEI | 64 | chr17: 27804724-27807385: + | TAOK1 | Exon skipping | HCC1954 |
| 29 IYNHITVKI | 65 | chr4: 2886393-2896308: + | ADD1 | Exon skipping | HCC1954 |

The protein sequences of the twenty nine neopeptides were extended. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes. Amino acid sequences of the twenty nine extended neopeptides are set forth in Table 21.

TABLE 21

| Amino acid sequences of extended neopeptides | | |
|---|---|---|
| Gene | SEQ ID NO | Extended neopeptide amino acid sequence* |
| TUBA1C | 66 | VDLEPTVIGELTSVTQVRSQGAGTGGLSWGGSAGHSPTLPPRSLSLLLL PHHVLQMKFALALTASSSTLSNSSQARKMLPITMPEGTTPLARRSLTSC WTEFASWLTSAPVFRASWFSTALVGELVLGSPRCSWNVSQLIMARSPSW SSPFTRRPRFPQL |
| PPHLN1 | 67 | APPRSHPSIKRGLSSL |
| CFL2 | 68 | MVRRARWPGGRGEARKAPRTAPGVRPPF |
| WAC | 69 | WVNCLFVSGRAAAGGGGGGAVPPYLELAGPPFLLLTLIRIGLGRRSGRA GGRAGTQCGGERGPGFAAFRPLRPFRRLRVCAVCVRGSALGRSVGLPRG GAAGAPFSSSPAPHPRRVLCRCLLFLFFSCHDRRGDSQPYQVPAEAGVE GLEGAGGGREGLLLERRPQKSIQALRCNTSETSTADPLKIPGLVPLALS SKV |
| GPS1 | 70 | MPLPVQVFNLQVTSRGRPGPPRPRAPRHWGRAEVEQGRGACARSRSGTL RAGPPRAARVGGCRAEGASPPWLRAAIGGRRAAPAPPPLPAAHGRGSRP PRR |
| EGFR | 71 | QPAQPRTGAPARRPRPRPSFPVSLRSAAPPTGTAGGTGRFVLRPGESGA GGGGDAWDTGLQARRGTAAGTSGAPNRSQLSSLTFPAQLRRIGVSGRKP GAGGRLGPGSRTCAPRCLPRARRGPGAHPRGGRCPPAETALFREAEEGT QKYSLPSDPAGQAAF |
| MED19 | 72 | FRLHTGPVSPVGGRRQMGRPKHGDGFSLQVCSFIMEQNG |
| HSBP1 | 73 | GVVEITGEPPCSCRGEEEASRAGRAGGVRLKRGSRGPGELNVGPAPGKT GLLIPLLRNWECGSLLRALSAL |
| SCP2 | 74 | KMGFPEAARKGNSL |
| SMC5 | 75 | LEARIKEKIEELQQALI |
| DNAJC8 | 76 | EIKKRFRQFKQAVYKQ |
| TMEM123 | 77 | AHESAAMAETLQHVPS |
| CHTOP | 78 | NRPSVQAALKLKQVGV |
| MRPS31 | 79 | KTDDLKKRHITFTLGCGIC |
| NFYC | 80 | MKLDEDVKRNDIAMAI |
| TAB2 | 81 | NSISQIPSDHILTPALFITFMTILDL |
| SDHAF2 | 82 | TVFSTSSLKLNQPQKYLKMKSWPC |
| HSPA9 | 83 | AEEDRRKKVITSCLLNFNLSKAQS |
| MDH2 | 84 | RSFSTSAQVGQTRGGLQAEAPRPGPRASPVRGQL |
| MRPS15 | 85 | RGYVVRKPVIALSVKI |

TABLE 21-continued

Amino acid sequences of extended neopeptides

| Gene | SEQ ID NO | Extended neopeptide amino acid sequence* |
|---|---|---|
| VARS | 86 | VDMDFGTGGQGAGPVGRGKDWSCTLAVHLLSEKKKISFSQIDRAWGGSQ GTVLDKWGPGVVSELHPSAKEVSVGRNSVESLMTWAS |
| HMG20B | 87 | EKGSHEEEVRVPALSWGRPRAPAPASKPRPRLDLNCLWLRPQPIFLWKL RPRPVPAATPLTGPLPL |
| PDCD5 | 88 | RYGQLSEKFNRRKVMDS |
| SELK | 89 | MVYISNVSKLCFSKM |
| TMSB10 | 90 | NTLPTKETPSFLLNPHTSWVPRPHREAPRLRVGVAAPLQRPLPALHSH |
| CSNK1D | 91 | FGDIYLGEAPPPPPAARRPGPCGCQDQARSRKEVVAPAGSPRKSRHRRI VARTQRPLG |
| TAOK1 | 92 | GSASDLLEEISKQEISF |
| ADD1 | 93 | QLIYNHITVKINLQGD |

*Underline indicates amino acids derived from the canonical transcript open reading frame (i.e., the canonical peptide sequence).

7.2 T-Cell Priming Experiment 7.2.1 Overview

For a schematic of an exemplary T-cell priming experiment, see FIG. 15.

7.2.2 Materials

Materials used for T-cell priming:
- RPMI 1640 Medium (Thermo Fisher Scientific, Cat. No. A10491-01)
- Penicillin/Streptomycin (100×, Thermo Fisher Scientific, Cat. No. 15140122)
- Human Serum Type AB (Sigma, Cat. No. H3667-100 ML)
- Recombinant Human IL-4 (Peprotech, Cat. No. 200-04)
- Recombinant Human GM-CSF (Peprotech, Cat. No. 300-03)
- Recombinant Human TNF-α (Peprotech, Cat. No. 300-01A)
- Human IL-7 (Peprotech, Cat. No. 200-07)
- Human IL-15 (Peprotech, Cat. No. 200-15)
- Human IL-21 (Peprotech, Cat. No. 200-21)
- Peptides (New England Peptide—95% purity, dissolved in DMSO to a 1000× stock at a concentration of 10 μg/μL)
- ELISpot kit for Human IFN-γ (R&D Systems, Cat. No. EL285)

7.2.3 Methods 7.2.3.1 Generation and Maturation of Human Monocyte-Derived Dendritic Cells and Loading of Neopeptides Frozen or fresh PBMC were thawed and washed in pre-warmed RPMI media once, and an aliquot of non-adherent cells was reserved for baseline TCR sequencing. PBMC were resuspended in 10 mL of dendritic cells (DC) medium (RPM11640, supplemented with 5% human AB serum and 1% penicillin/streptomycin) at $5\times10^6$ cells per mL, for a total of 50 million cells. Cells were transferred to T-75 tissue culture plastic and incubated at 37° C., 5% $CO_2$ for 2-3 hours. After gentle shaking, non-adherent cells were removed and discarded, and adherent (monocyte-enriched) cells were washed three times with pre-warmed DC medium. 10 mL of DC medium supplemented with a final concentration of 20 ng/mL GM-CSF and 20 ng/mL IL-4 was added to adherent cells. Adherent cells were incubated at 37° C., 5% $CO_2$, at 100% humidity for 5 days. On day 6, recombinant TNF-α was added to a final concentration of 20 ng/mL for another 48 hours. On day 7, DC were collected and counted, then loaded with neopeptides (each at 10 μg/$1\times10^6$ cells/mL) or no neopeptide control. On day 8, cells were harvested as mature DC. Mature DC were treated with mitomycin C at a final concentration of 20 μg/mL for 30 min at 37° C. followed by extensive washing before co-incubation with T-cells for priming.

7.2.3.2 Start of Co-Culture with Autologous T-Cells

On day 0, frozen or fresh were thawed and washed in pre-warmed media once. PBMC were then resuspended and mixed with DC at a ratio of 10:1 ($10\times10^6$:$1\times10^6$ cells) in 10 mL RPMI1640/5% human AB serum, supplemented with IL-21 at 30 ng/mL in T25 flasks. After 3 days of co-culture (day 3), an additional 10 mL of fresh media was added and supplemented with IL-7 and IL-15 at a final concentration of 5 ng/mL. Following an additional 3 days of co-culture (day 6), an additional 10 mL of fresh media, supplemented with IL-7 and IL-15 at a final concentration of 5 ng/mL, was added and the co-culture was moved to a T-75 flask. On day 9, an additional 20 mL of media, supplemented IL-7 and IL-15 at a final concentration of 10 ng/mL, was added and cells were transferred to a T-175 flask. On days 11-12, cells were collected, ELISpot assay was performed as per manufacturer's instructions (R&D Systems), and TCR sequencing was performed ($1\times10^6$ cells). Wells were pre-loaded using peptide at 10 μg/mL final concentration per well, cell density at $2\times10^5$ cells per well, duplicate seeding, and overnight incubation. IFNγ spots were developed and read on an AID ELISpot reader as per manufacturer's instructions.

7.2.4 Results

Exemplary data from antigen priming experiments are provided in Table 22.

TABLE 22

| T-cell priming data | | | | |
|---|---|---|---|---|
| Donor | ELISpot response | Gene | SEQ ID NO | HLA (predicted binding) |
| 1 | +++ | DNAJC8 | 76 | A*31:01/B*40:13 |
| 1 | + | TMEM123 | 77 | A*02:01 |
| 2 | +++ | TMEM123 | 77 | A*02:01 |
| 2 | + | SCP2 | 74 | B*39:06 |
| 6 | + | DNAJC8 | 76 | C*07:01/B*27 |
| 7 | +++ | DNAJC8 | 76 | C*07:02/C*06:02 |
| 8 | +++ | DNAJC8 | 76 | C*07:01 |
| 8 | + | SMC5 | 75 | C*07:01/B*08:02 |
| 8 | +++ | SCP2 | 74 | C*03:03 |

Donor-derived PBMC lots were differentiated into DC and primed with neopeptides as outlined in FIG. 15. Analysis of ELISpot data shows that, in healthy donor PBMC, priming of naïve T-cells by DC presenting neopeptides can result in antigen-specific expansion and maturation of effector (CD8) T-cell populations. These T-cell populations exhibit antigen-specific re-activation, as evidenced by IFNγ secretion only in the presence of the antigenic peptide and not in the presence of non-priming peptides. The data also suggest that response to neopeptides cannot necessarily be predicted based on HLA.

Example 8

8.1 Identification of Neopeptides 8.1.1 Overview

To identify neopeptides resulting from splicing modulation, peptides 8 to 11 amino acids in length and predicted to bind to MHC class I from the canonical and splicing-modulated proteome were matched separately against tandem mass spectra using a standard target-decoy approach. First, alternatively-spliced mRNA transcripts were translated and compared against a reference proteome. Next, spectra that did not match the reference proteome were searched for matching novel peptides. For a schematic diagram of an exemplary process for identifying novel peptides resulting from splicing modulation, see FIG. 14.

8.1.2 Methods 8.1.2.1 Creating A Database of Potential Neopeptides

To generate a database of potential neopeptides, junction-spanning or intron-containing peptides not found in a reference proteome were identified (see Li et al. (2011) Mol. Cell Proteomics 10(5):M110.006536). Peptides derived from the reference proteome were selected from manually reviewed protein sequences and downloaded. In addition, the proteins were filtered for junctions that are found in normal tissues. As an alternative approach, complete proteins may be translated from splicing events, searched for junction-spanning or intron-containing peptides, and then matched by BLAST against the reference proteome.

To avoid unnecessary statistical tests, only peptides predicted as likely to bind to MHC were used. Protein sequences (both from the reference proteome and from predicted translation of exon-skipped or intron-retained transcripts) were evaluated for high affinity binding to MHC1 alleles using NetMHCPan and/or MHCnuggets software. For both software packages, hits with with strong or weak binding were chosen (i) by raw affinity binding prediction strength (500 nM threshold for weak binding), or (ii) by selecting a large number of random real peptides and identifying the distribution of predicted binding strengths for the peptides. The predicted binding strength for any novel peptides were then matched against this distribution. The thresholds for strong and weak binding measured by the latter method (method (ii)) were predicted binding strengths within the top 0.5% or the top 2.0% of the random real peptides, respectively (see Nielsen and Andreatta (2016) Genome Med. 8(1):33). Currently, MHC prediction is restricted to peptide sequences 8 to 11 amino acids in length and contained in the Immune Epitope Database (IEDB).

8.1.2.2 Identifying Splicing Modulation-Derived Transcripts by RNAseq and RiboSeq Several neopeptides are derived from larger peptide domains (e.g., TUBA1C), while peptide fragments from the remainder of the translated region may risk going undetected. This may be a consequence of either enhanced degradation of the undetected regions, MHC1 binding affinity, or technical challenges associated with detection by mass spectrometry (MS). Generally, RNAseq analysis will overestimate the number of predicted neopeptides (since not all alternatively-spliced transcripts will be translated), while the MHC1-ligandome will underestimate the number of predicted neopeptides.

To establish a list of neopeptides, available splicing modulation-derived variant splice junctions with bound ribosomes were identified, as a marker of translation to proteins (Andreev et al. (2017) Nucleic Acids Res. 45(2): 513-26). RiboSeq or ribosomal profiling allowed for detection of mRNA sequences (and variant domains) that were undergoing active translation, as evidenced by the presence of ribosomes bound to the transcript, as well as specific exon junction domains.

Example 9

9.1 In Vitro Analysis of Exemplary Anti-HER2 ADCs 9.1.1 Methods

HCC1954, NCI-N87, or MCF7 cells (ATCC) were plated in phenol-red free RPMI+10% FBS (ATCC) or EMEM+10% FBS+insulin (0.01 mg/mL) (for MCF7) at $2.5\times10^3$ cells per well at 90 μL per well. Cells (n=3 wells per condition) were treated with conjugates in a 3-fold dilution dose-response. After 24 hours, cells were lysed with 50 μL of CL buffer (IgePal CA-630, 5M NaCl, 1M Tris HCl 1M pH 7.4 in water) containing 25 μL/mL of RNAsin (Promega) and incubated for 45 min at RT on a rocker. Resulting mixture (1 μL) was used to assess splicing modulation in a Taqman Fast Virus 1-Step MasterMix (Applied Biosystems) reverse transcription PCR reaction with the following Taqman primers according to the manufacturer's recommendations: SLC25A19 (Invitrogen, Hs00222265_ml); FBXW5 (IDT, forward primer: CACACCAGATCGGCATCAA (SEQ ID NO:37), reverse primer: CGATGATGTGTCCGTGTATGT (SEQ ID NO:38), probe: ATCCTGCCACACCAGATGAC-CAC (SEQ ID NO:39), dye: FAM, quencher: ZEN/Iowa Black FQ); TAOK1 (IDT, forward primer: CTGCTTCG-GATTTACTAGAAGAGATA (SEQ ID NO:40), reverse primer: GCGTTCCCACAAAGGAATTG (SEQ ID NO:41), probe: TGCTGACTTTGGCTCTGCTTCCAT (SEQ ID NO:42), dye: FAM, quencher: ZEN/Iowa Black FQ); RPLPO (Invitrogen, Hs99999902_m1).

9.2 In Vivo Efficacy and Pharmacodyamics (PD) of Exemplary Anti-HER2 ADCs

9.2.1 Methods—In Vivo Efficacy in NCI-N87 Xenograft Model

CB17-SCID mice (Charles River Laboratories) were kept in accordance with federal, state, city, & AAALAC-accreditation policies on animal research in the city of Cambridge, Massachusetts. NCI-N87 human gastric carcinoma cell line was purchased from American Type Culture Collection (ATCC No. CRL-5822). Passage 14 cells were used for tumor experiments. Cells were last tested for murine pathogens in September 2016 and *mycoplasma* in December 2018.

Single cell suspension of 5 million cells per 0.1 mL (50% ATCC-modification-RPMI-1640-medium, Cat. No. A10491-01 (Thermo-Fisher Scientific); and 50% Corning Matrigel, Cat No. 356254 (VWR Scientific)) was injected subcutaneously on the right lateral flank with a syringe with a 25 Ga needle. Mice were randomized on day 0 at a mean tumor volume of 180-183 $mm^3$, n=8 per group for efficacy and n=4 per group for pharmacodynamics (PD). On day 1, test articles were administered (10 mg/kg) at a volume of 5 mL/kg intravenously every 7 days for 2 cycles for efficacy; a single course of treatment was used for PD assessment. Animals in the PD cohorts were euthanized at 24, 48, 72, and/or 96 hours post-dosing of a single dose, depending on the test article. Tumor volume and body weight were measured one or two times weekly until the termination (day 61) of the study. Tumor volume was calculated using the formula length×width$^2$/2. During the study, mice that reached endpoint (tumor size 20 $mm^3$ in any direction or tumor volume starting body weight×100), or had a tumor ulceration or eye infection, were removed.

Compounds were formulated in biological safety cabinets. Test article vehicle was phosphate buffered saline pH 7.4 (Cat No. A10010-049 (Thermo-Fisher Scientific)). Groups were as set forth in Table 23.

Anti-tumor activity was calculated as follows:

$$\%\ T/C \text{ formula} = \text{treated/control} * 100$$

$$\%\ TGI \text{ formula} = (\text{vehicle average}_{day\ X} - \text{treated average}_{day\ X})/\text{vehicle average}_{day\ X} * 100,$$

wherein day X is day 22.

9.2.2 Methods—In Vivo PD (RT-qPCR)

RNA was purified from tumor samples using MagMAX-96 for Microarrays kit and MagMAX Express-96 Deep Well Magnetic Particle Processor (ThermoFisher Scientific). Tumor samples (size 50-100 mg) were collected in RNAlater buffer and kept at −80° C. until RNA isolation. Tissue homogenization was performed by adding 2-3 ceramic beads and 1 mL of Tri-reagent into a tube containing tumors, followed by disruption on an Omni Bead Ruptor 24 instrument (Omni International). RNA isolation was done according to the manufacturer's instructions.

RNA lysates were isolated and reverse transcribed using TaqMan Fast Virus 1-Step Master Mixt (ThermoFisher Scientific) according to the manufacturer's instructions.

Quantitative PCR from cDNA was performed using TaqMan Gene Expression Master Mix (ThermoFisher Scientific) with transcript probes targeting FBXW5 or TAOK1 junctions duplexed with RPLPO RNA VIC-PL (ThermoFisher Scientific) and quantified using the AACt method.

TABLE 23

| Groups | |
|---|---|
| Test Articles (efficacy) | Test Articles (PD) |
| Vehicle (PBS) | Vehicle (PBS) |
| TDM1 | TDM1 |
| trastuzumab (AB185) | trastuzumab (AB185) |
| AB185-ADL5-D2 | AB185-ADL5-D2 |
| AB185-ADL1-D4 | AB185-ADL1-D4 |
| AB185-ADL5-D15 | AB185-ADL5-D15 |
| AB185-ADL14-D1 | AB185-ADL14-D1 |

9.3 Results

In Vitro Analysis:

Exemplary anti-HER2 ADCs were measured for antiproliferative activity in two HER2-positive cell lines of different lineage (HCC1954 breast cancer and N87 gastric cancer) and a HER2-negative cell line (MCF7). The efficiency of growth inhibition was measured (GI50 potency), as well as the depth of response (R min compared to control). Alternative splicing in a representative house keeping gene SLC25A19 was measured by qPCR after treatment of the ADCs on the specified cell lines. G150 and depth of splicing response were measured. The results of the in vitro analysis are shown in Table 25.

In general, the tested anti-HER2 ADCs showed favorable potency on the antigen positive cell lines and minimal response for viability and splicing in the antigen negative cell line. The ADCs differed in depth of response in cell killing and completeness of alternative junction splicing of SLC25A19. The ADCs fell into one of four categories on each of the antigen positive cell lines: 1) high depth of response/lethality and high splicing response; 2) high depth of response/lethality and low splicing response; 3) low depth of response/lethality and high splicing response; or 4) low cell lethality and low splicing response. Several ADCs showed favorable, category 3 behavior on the N87 gastric cancer cell line. AB185-ADL13-D4 was consistently lethal and showed strong depth of splicing response in both HCC1954 and N87 cells. This consistent antigen specific lethality is generally desirable for ADCs and the water soluble linker would allow for even higher drug loading with good conjugate specifications. Switching the linker to ADL23 (EVC tripeptide) surprisingly changed the profile in both cell lines. AB185-ADL1-D12 was also unique in that it is highly lethal on HCC1954, but the cellular potency of the payload is consistently low on a number of solid and heme tumor lines. D12 is also the only payload in this series with a low efflux ratio. Thus, ADCs releasing this payload may be active against multiple drug resistant cancers that express a target antigen.

Figure 18:
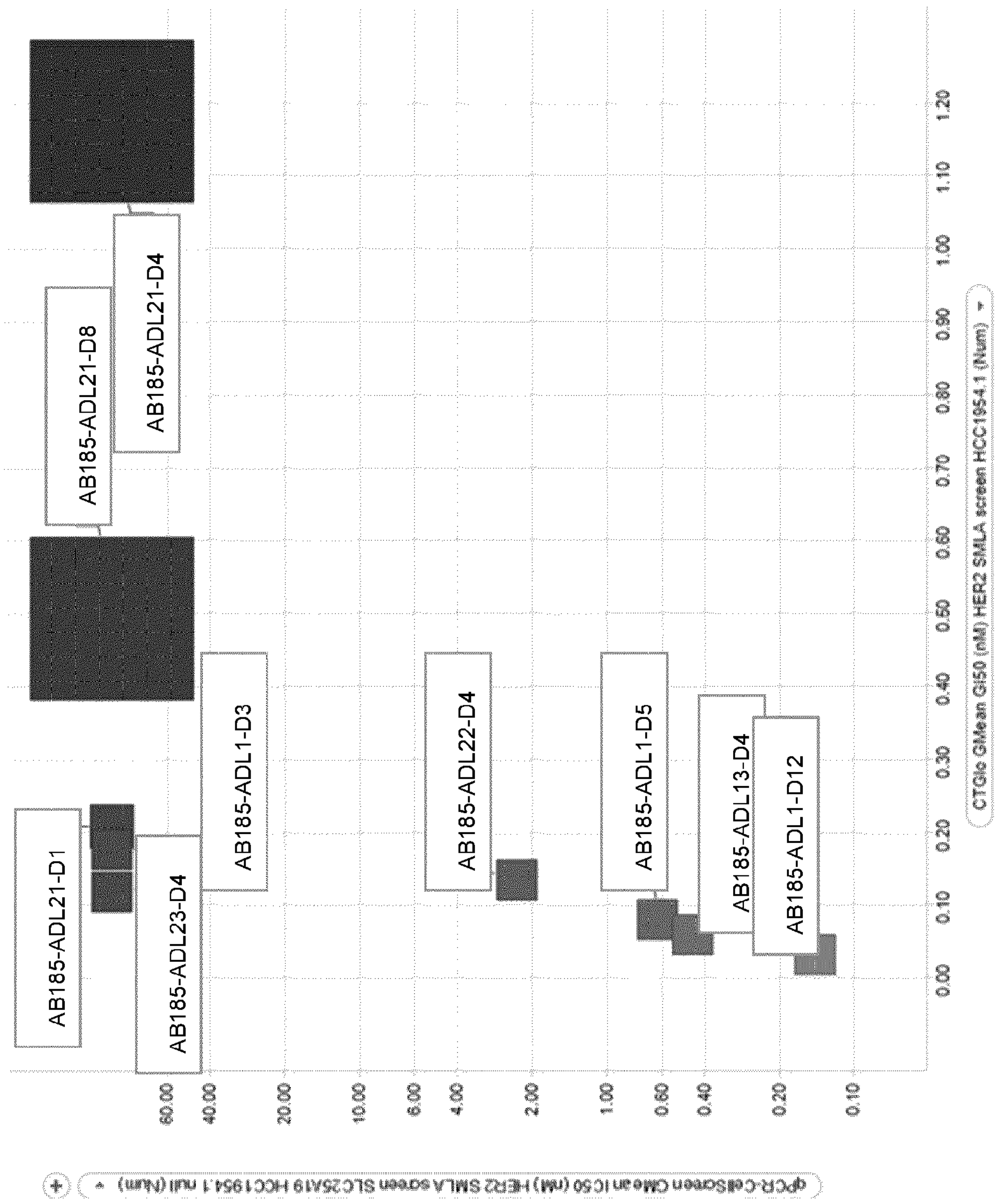
FIG. 18 shows a plot comparing splicing potency (IC50 qPCR) against cellular potency (G150 CTG) for exemplary anti-HER2 ADCs in HCC1954 breast cancer cells. Values shown are sized by cell lethality and shaded by depth of alternative splicing response.

When splicing potency (IC50 qPCR) is compared against cellular potency (G150 CTG) in HCC1954 breast cancer cells, the glucuronide linker and the D12 payload showed favorable properties. The $C_6/C_7$ carbamate switch (D8) payload and the dibasic payload (D5) showed cellular potency but did not demonstrate the most efficient alternative splicing. Switching from a dipeptide to a tripeptide linker with the D4 or the D1 payload reduced alternative splicing efficiency yet cellular activity remained high. See FIG. 18 (sized by cell lethality, shaded by depth of alternative splicing response).

Figure 19:
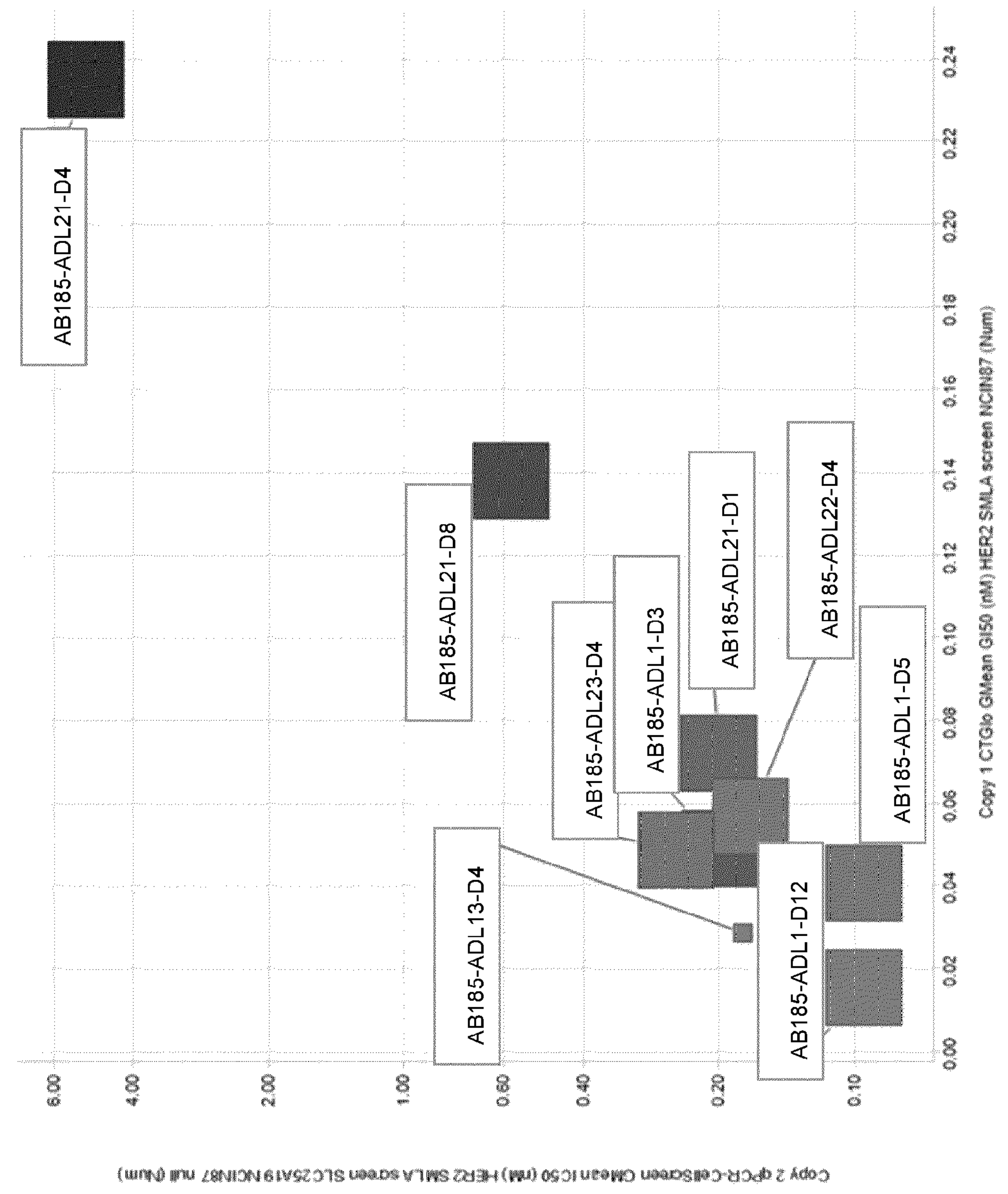
FIG. 19 shows a plot comparing splicing potency (IC50 qPCR) against cellular potency (G150 CTG) for exemplary anti-HER2 ADCs in N87 gastric cancer cells. Values shown are sized by cell lethality and shaded by depth of alternative splicing response.

When splicing potency (IC50 qPCR) is compared against cellular potency (G150 CTG) in N87 gastric cancer cells, the glucuronide linker (with D4) and the D12 payload showed favorable properties, as in HCC1954. Overall, all ADCs showed minimal splicing and potency on the HER2-negative cell line MCF7. Despite the relatively low cellular potency of the D12 payload, the activity of anti-HER2 ADCs with this payload was high and the payload showed a low efflux ratio. These properties could potentially translate to better efficacy in a multiple drug resistant cancer setting. See FIG. 19 (sized by cell lethality, shaded by depth of alternative splicing response).

Figure 20:
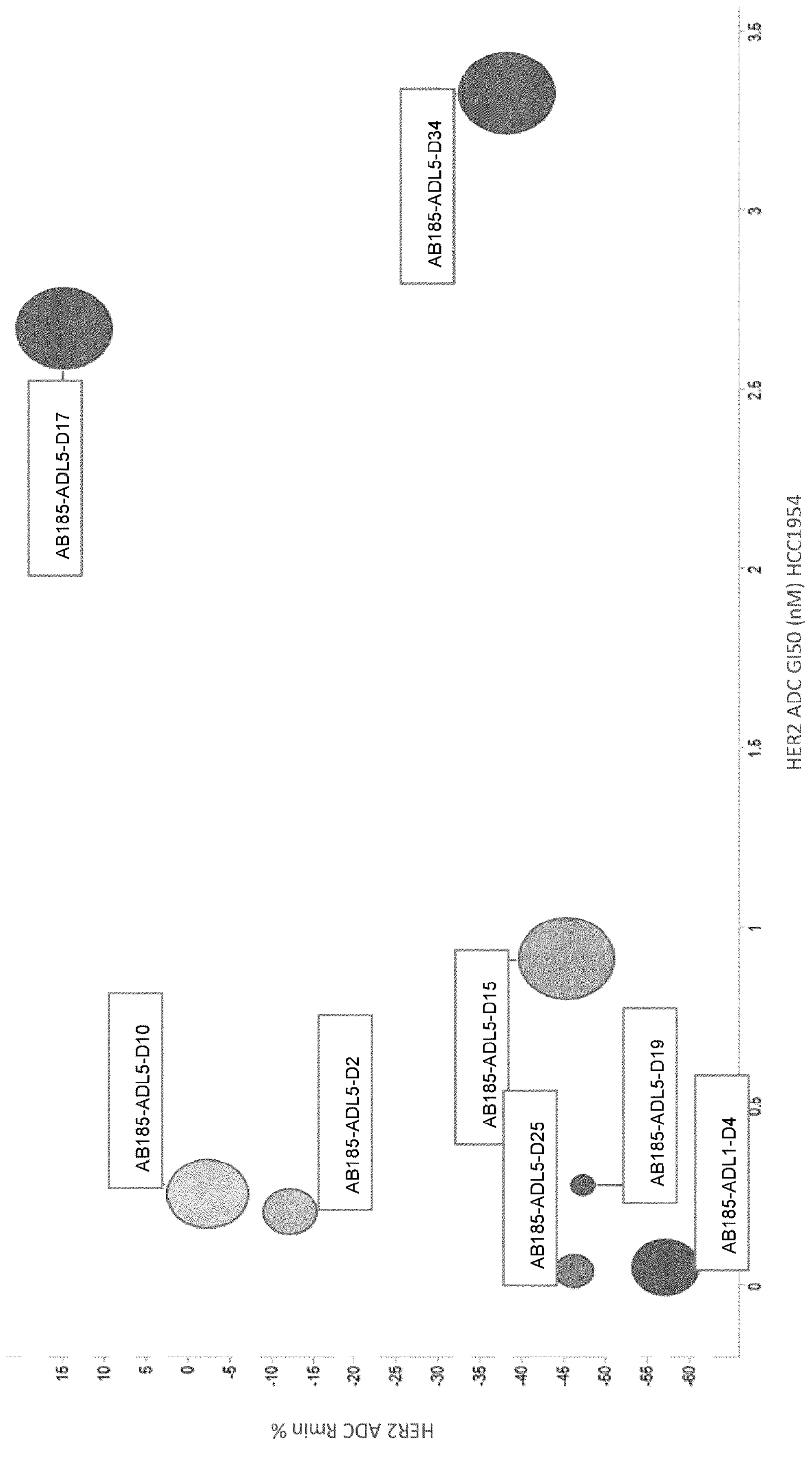
FIG. 20 shows a plot comparing potency and lethality of exemplary anti-HER2 ADCs (in HCC1954 breast cancer cells) against stability and permeability of corresponding payloads. Values shown are sized by payload stability and shaded by payload permeability.

In vitro analysis was performed on additional anti-HER2 ADCs. A comparison between anti-HER2 ADCs and corresponding payloads is shown in Table 26. When potency and lethality of anti-HER2 ADCs is compared against stability and permeability of corresponding payloads (FIG. 20), AB185-ADL5-D15 demonstrated a favorable balance of potency, lethality, chemical stability, and catabolite permeability (e.g., for putative bystander killing). As described below, AB185-ADL5-D15 was also active in vivo and demonstrated potent anti-tumor activity in a NCI-N87 xenograft model.

In Vivo Efficacy:

The human HER2-expressing NCI-N87 gastric cancer cell line and its xenograft model was generated by inoculating NCI-N87 cells into SCID mice to evaluate anti-tumor activity of exemplary anti-HER2 ADCs. Trastuzumab and TDM1 were used as comparators.

Figure 21:
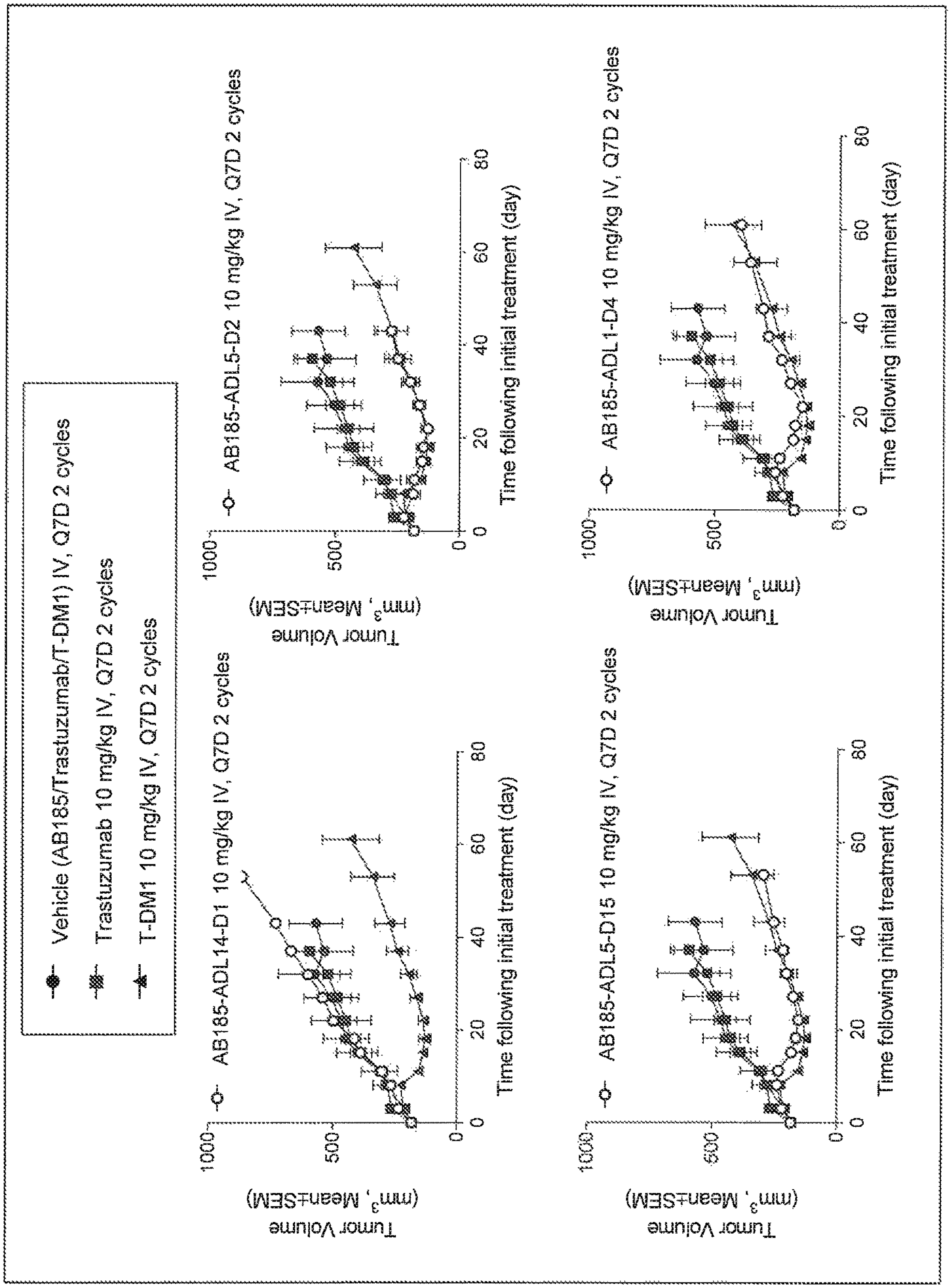
FIG. 21 shows tumor growth kinetics for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±standard error of the mean (SEM) ($mm^3$).
Figure 22:
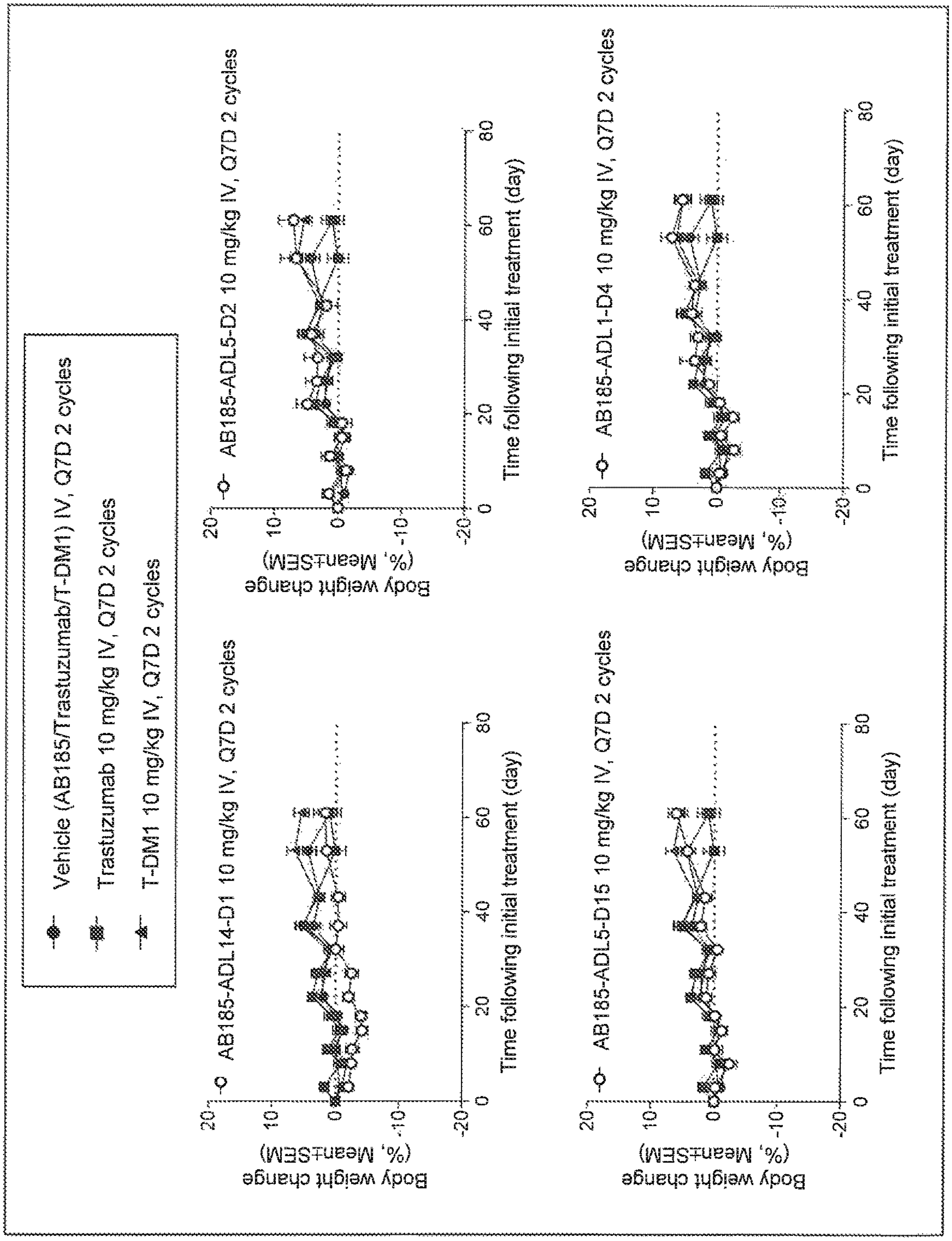
FIG. 22 shows body weight change for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±standard error of the mean (SEM) (%).
Figure 23:
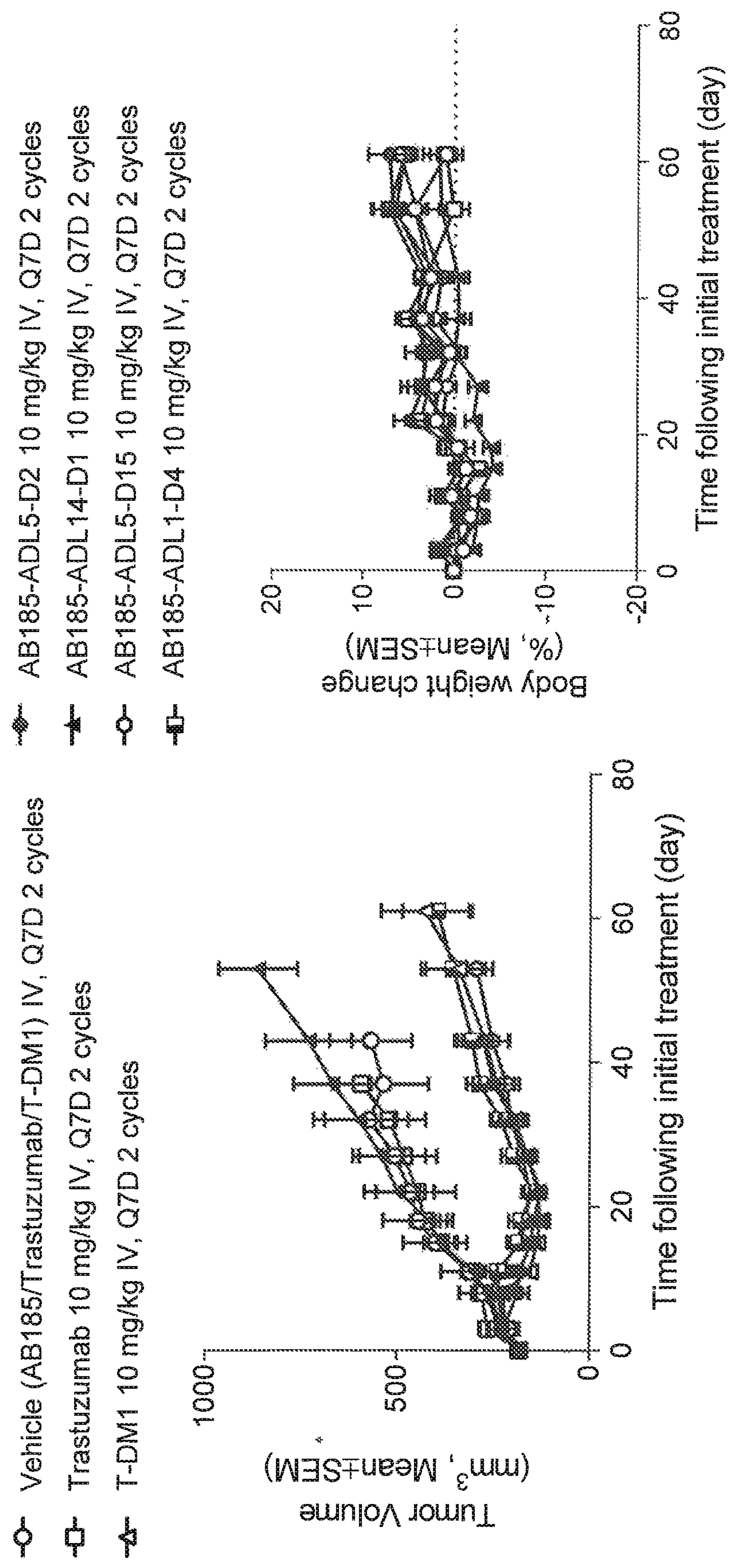
FIG. 23 shows tumor growth kinetics (left) and body weight change (right) for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±SEM (tumor volume, $mm^3$) or mean±SEM (body weight, %).

Anti-tumor effects of intravenous trastuzumab, TDM1, and four HER2 ADCs in NCI-N87 xenograft model of gastric carcinoma are shown in FIG. 21 and FIG. 23. Body weight effects are shown in FIG. 22 and FIG. 23. Test article or vehicle was given intravenously (IV) Q7D for 2 cycles. Data represent the mean±SEM (tumor volume, $mm^3$) or ±SEM (body weight, %) (N=8). *p<0.0001 versus vehicle group on Day 22 using one-way ANOVA test.

Tabular data for in vitro and in vivo efficacy in NCI-N87 is provided in Table 24. Tabular data represent percent (%) Tumor Growth Inhibition (TGI of Tumor Volume) or % T/C (Tumor Volume) (N=8). AB185-ADL5-D2 was surprisingly active in vivo despite little lethality in vitro, and demonstrated improved in vivo efficacy as compared to, e.g., AB185-ADL14-D1.

TABLE 24

Efficacy of exemplary anti-HER2 ADCs in NCI-N87

| | Day 22 (in vivo) | | NCI-N87 (in vitro) | | |
|---|---|---|---|---|---|
| | TGI (%) | T/C (%) | $GI_{50}$ (nM) | $LD_{50}$ (nM) | $R_{min}$ % |
| Vehicle/IV/Q7D × 2 | — | — | — | — | — |
| TDM1/10 mg/kg/IV/Q7D × 2 | 71 | 29 | 0.1 | 40 | −37 |
| trastuzumab/10 mg/kg/IV/Q7D × 2 | 4 | 96 | >200 | >200 | 98 |
| AB185-ADL5-D2/10 mg/kg/IV/Q7D × 2 | 73 | 27 | 0.2 | >200 | 0 |
| AB185-ADL1-D4/10 mg/kg/IV/Q7D × 2 | 68 | 32 | 0.1 | >200 | −22 |
| AB185-ADL5-D15/10 mg/kg/IV/Q7D × 2 | 67 | 33 | 0.1 | >200 | −37 |
| AB185-ADL14-D1/10 mg/kg/IV/Q7D × 2 | −7 | 107 | 0.1 | >200 | −40 |

Trastuzumab, an anti-human HER2 antibody and a standard of care therapy for HER2-positive breast cancer, did not demonstrate anti-tumor activity in this model. However, TDM1, a second-line treatment containing trastuzumab plus covalently linked DM1 (a cytotoxic agent) showed significantly better anti-tumor activity (TGI 71%) than trastuzumab alone (TGI 4%). Among the four ADCs tested, ABL185-ADL5-D2, AB185-ADL5-D15, and AB185-ADL1-D4 showed potent anti-tumor activity with Tumor Growth Inhibition (TGI) of 73%, 67%, and 68%, respectively. Tumors of all responding groups eventually started to grow again. No complete response was observed in any group, and one of eight animals in each of the following groups showed a partial response: TDM1, ABL185-ADL5-D2, and AB185-ADL5-D15. All reagents and test articles were well tolerated by mice and minimal body weight loss was observed. Overall, 3 out of the 4 tested anti-HER2 ADCs demonstrated similarly potent anti-tumor activity in comparison with TDM1 in the NCI-N87 tumor model without significant body weight loss.

Figure 24A:
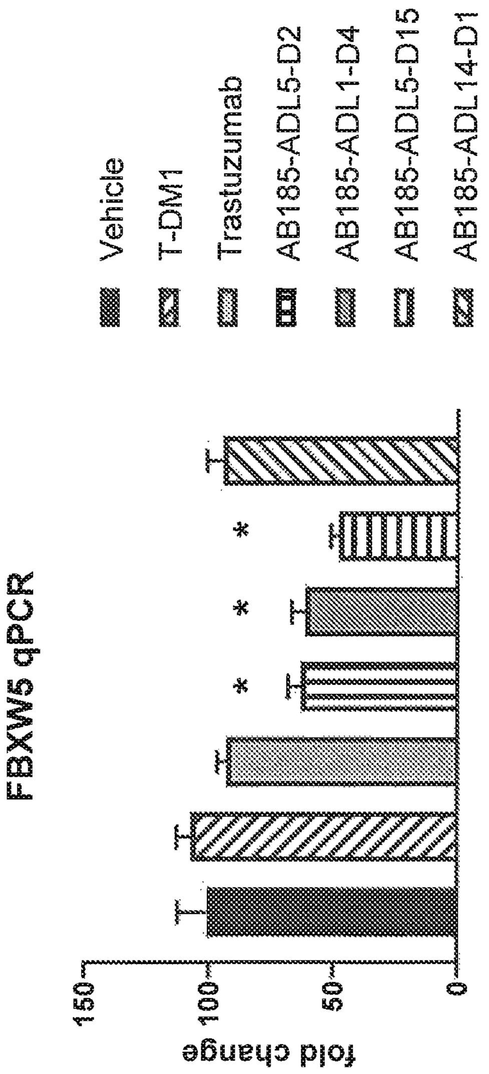
FIG. 24A-24D show pharmacodynamics (PD) modulation of mRNA junctions in N87-implanted CB17-SCID mice treated intravenously with vehicle or 10 mg/kg trastuzumab, TDM1, or an exemplary HER2-ADC Q7D for 2 cycles. RT-qPCR of FBXW5 (mature mRNA transcript) was monitored and is shown in FIG. 24A and FIG. 24C. RT-qPCR of TAOK1 (neojunction transcript) was monitored and is shown in FIG. 24B and FIG. 24D. Animals (N=4 per group) were collected at either 48 hours (FIG. 24A and FIG. 24B) or at the times indicated (FIG. 24C and FIG. 24D). Tumors were isolated for RNA extraction and RT-qPCR.
Figure 24B:
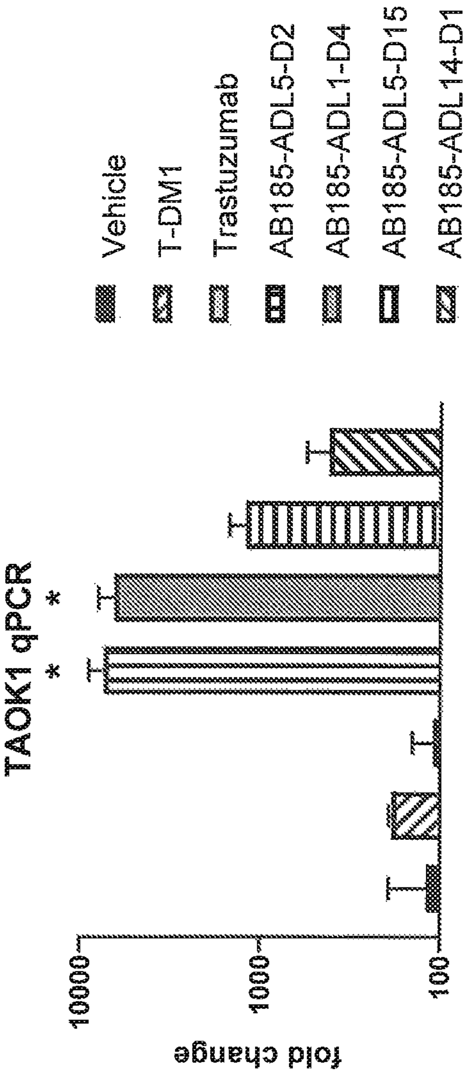
Figure 24C:
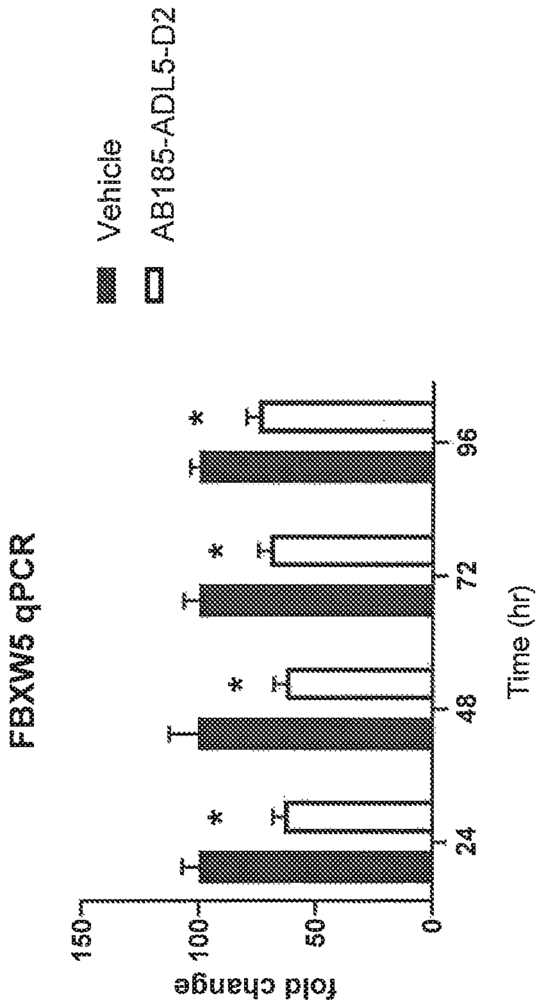
Figure 24D:
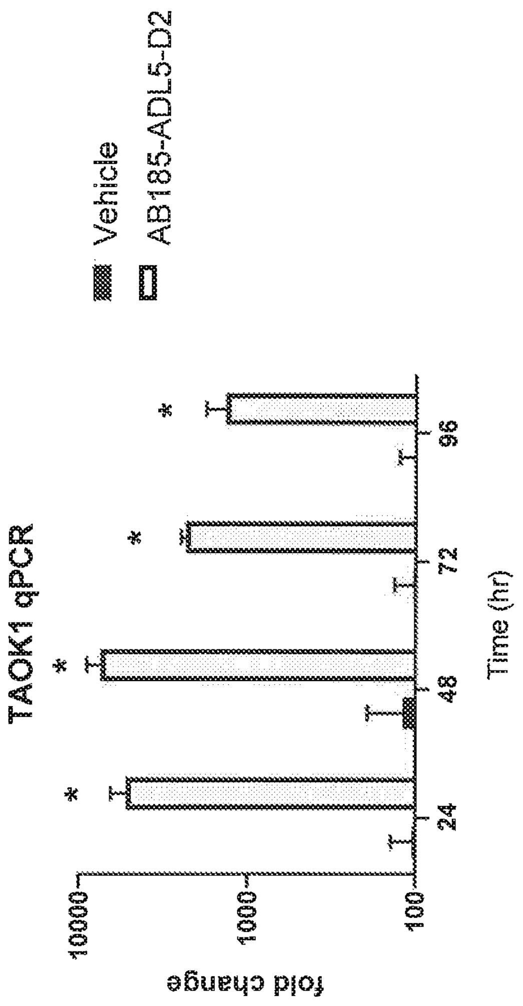

In Vivo PD:

PD modulation of mRNA junctions by intravenous trastuzumab, TDM1, and four anti-HER2 ADCs in NCI-N87 xenograft model of gastric carcinoma is shown in FIG. 24A-24D. RT-qPCR of FBXW5 (mature mRNA transcript) and TAOK1 (neojunction transcript) were monitored. Test article or vehicle was given intravenously (IV) at 10 mg/kg. Animals (N=4 per group) were collected at either 48 hours (FIG. 24A and FIG. 24B) or at the times indicated (FIG. 24C and FIG. 24D). Tumors were isolated for RNA extraction and RT-qPCR. *p<0.05 versus vehicle using one-way ANOVA (FIG. 24A and FIG. 24B) or two-way ANOVA (FIG. 24C and FIG. 24D).

Neither trastuzumab nor TDM1 exhibited significant changes in the observed splicing of either FBXW5 or TAOK1. AB185 conjugates ADL5-D2/ADL1-D4/ADL5-D15 all exhibited significant depletion of FBXW5, and AB185 conjugates ADL5-D2/ADL1-D4 exhibited significant increases in TAOK1. ADL5-D15 showed an increase in TAOK1, but did not reach statistical significance. ADL14-D1 did not exhibit statistically significant changes in abundance of either mRNA transcript.

TABLE 25

Characterization of exemplary anti-HER2 ADCs and corresponding payloads

| | | | | | | | Properties-HER2 ADCs | | | | | | | | |
|---|---|---|---|---|---|---|---|---|---|---|---|---|---|---|---|
| | | | | | | | antiproliferative activity antigen (+) cell #1 | | | antiproliferative activity antigen (+) cell #2 | | | antiproliferative activity antigen (−) cell | | |
| ADC Batch Id | Linker | Lethality/Splicing Category (HCC-1954, N87) | DAR | Percent Monomer | Free Drug | Conc. | CTGlo GMean GI50 (nM) HER2 SMLA screen HCC-1954.1 | CTGlo GMean LD50 (nM) HER2 SMLA screen HCC-1954.1 | CTGlo Mean MinResp % HER2 SMLA screen HCC-1954.1 | CTGlo GMean GI50 (nM) HER2 SMLA screen NCIN87 | CTGlo GMean LD50 (nM) HER2 SMLA screen NCIN87 | CTGlo Mean MinResp % HER2 SMLA screen NCIN87 | CTGlo GMean GI50 (nM) HER2 SMLA screen MCF7 | CTGlo GMean LD50 (nM) HER2 SMLA screen MCF7 | CTGlo Mean MinResp % HER2 SMLA screen MCF7 |
| AB185-ADL1-D12 | mc-Val-Cit-PABC | 1, 3 | 6.25 | 99% | <1% | 0.82 | 0.032 | 0.09 | −78.471 | <0.015 | >100.000 | −35.162 | >100.000 | >100.000 | 53.606 |
| AB185-ADL13-D4 | b-glucuronide | 1, 1 | 4.47 | 99% | <1% | 0.78 | 0.059 | 0.275 | −80.145 | 0.029 | 3.436 | −55.322 | >100.000 | >100.000 | 87.451 |
| AB185-ADL1-D5 | mc-Val-Cit-PABC | 1, 3 | 6.14 | 99% | <1% | 1.1 | 0.079 | 0.298 | −81.189 | 0.04 | >100.000 | −32.663 | >100.000 | >100.000 | 93.099 |
| AB185-ADL23-D4 | mc-Glu-Val-Cit-PABC | 2, 3 | 5.84 | 99% | <1% | 1.03 | 0.175 | 1.526 | −68.762 | 0.049 | >100.000 | −49.316 | >100.000 | >100.000 | 91.248 |
| AB185-ADL1-D3 | mc-Val-Cit-PABC | 2, 3 | 6.75 | 99% | <1% | 1.13 | 0.117 | 0.741 | −77.982 | 0.049 | >100.000 | −15.629 | >100.000 | >100.000 | 91.495 |
| AB185-ADL22-D4 | mal-PEG2-Val-Cit-PABC | 1, 3 | 6.12 | 99% | <1% | 1.01 | 0.134 | 0.797 | −75.134 | 0.057 | >100.000 | −25.808 | >100.000 | >100.000 | 79.996 |
| AB185-ADL21-D1 | mc-Ala-Ala-Asn-PABC | 2, 3 | 5.51 | 99% | <1% | 1.35 | 0.207 | 2.65 | −72.894 | 0.072 | >100.000 | −46.965 | >100.000 | >100.000 | 74.018 |
| AB185-ADL21-D8 | mc-Ala-Ala-Asn-PABC | 4, 3 | 6.4 | 99% | <1% | 1.67 | 0.493 | >100.000 | −37.547 | 0.138 | >100.000 | −40.873 | >100.000 | >100.000 | 94.772 |
| AB185-ADL21-D4 | mc-Ala-Ala-Asn-PABC | | 1.55 | 99% | <1% | 1.11 | 1.174 | >100.000 | 14.652 | 0.235 | >100.000 | −36.848 | >100.000 | >100.000 | 96.18 |
| AB185-ADL15-D2 | mal-CH2CH2—O—CH2CH2-(non-cleavable) | 3, ND | 3.25 | 98.80% | <1% | 1.6 | 0.24 | >200.000 | −13.023 | 0.115 | >100.000 | −15.056 | | | |

TABLE 25-continued

| Characterization of exemplary anti-HER2 ADCs and corresponding payloads | | | | | | | | | | | |
|---|---|---|---|---|---|---|---|---|---|---|---|
| | | | | | | Properties-HER2 ADCs | | | | | |
| | | | | | | splicing PD antigen (+) cell #1 | | splicing PD antigen (+) cell #2 | | splicing PD antigen (−) cell | |
| ADC Batch Id | Linker | Lethality/Splicing Category (HCC-1954, N87) | DAR | Percent Monomer | Free Drug | Conc. | qPCR-CellScreen GMean IC50 (nM) HER2 SMLA screen SLC25A19 HCC1954.1 null | qPCR-CellScreen Mean MinResp % HER2 SMLA screen SLC25A19 HCC1954.1 null | qPCR-CellScreen GMean IC50 (nM) HER2 SMLA screen SLC25A19 NCIN87 null | qPCR-CellScreen Mean MinResp % HER2 SMLA screen SLC25A19 NCIN87 null | qPCR-CellScreen GMean IC50 (nM) HER2 SMLA screen SLC25A19 MCF7 null | qPCR-CellScreen Mean MinResp % HER2 SMLA screen SLC25A19 MCF7 null |
| AB185-ADL1-D12 | mc-Val-Cit-PABC | 1, 3 | 6.25 | 99% | <1% | 0.82 | 0.144 | −85.744 | 0.095 | −93.185 | >100.000 | −12.254 |
| AB185-ADL13-D4 | b-glucuronide | 1, 1 | 4.47 | 99% | <1% | 0.78 | 0.45 | −72.455 | 0.177 | −93.984 | >100.000 | −28.389 |
| AB185-ADL1-D5 | mc-Val-Cit-PABC | 1, 3 | 6.14 | 99% | <1% | 1.1 | 0.624 | −65.799 | 0.095 | −91.243 | >100.000 | −10.455 |
| AB185-ADL23-D4 | mc-Glu-Val-Cit-PABC | 2, 3 | 5.84 | 99% | <1% | 1.03 | >100.000 | −40.549 | 0.249 | −89.841 | >100.000 | −16.033 |
| AB185-ADL1-D3 | mc-Val-Cit-PABC | 2, 3 | 6.75 | 99% | <1% | 1.13 | >100.000 | −38.621 | 0.199 | −78.218 | >100.000 | −24.342 |
| AB185-ADL22-D4 | mal-PEG2-Val-Cit-PABC | 1, 3 | 6.12 | 99% | <1% | 1.01 | 2.302 | −58.063 | 0.17 | −91.266 | >100.000 | −23.433 |
| AB185-ADL21-D1 | mc-Ala-Ala-Asn-PABC | 2, 3 | 5.51 | 99% | <1% | 1.35 | >100.000 | −37.396 | 0.201 | −84.588 | >100.000 | −15.463 |
| AB185-ADL21-D8 | mc-Ala-Ala-Asn-PABC | 4 ,3 | 6.4 | 99% | <1% | 1.67 | >100.000 | −27.319 | 0.577 | −70.144 | >100.000 | −12.798 |
| AB185-ADL21-D4 | mc-Ala-Ala-Asn-PABC | | 1.55 | 99% | <1% | 1.11 | >100.000 | −16.088 | 5.097 | −54.535 | >100.000 | −12.096 |
| AB185-ADL15-D2 | mal-CH2CH2—O—CH2CH2-(non-cleavable) | 3, ND | 3.25 | 98.80% | <1% | 1.6 | | | 0.296 | −83.148 | | |

TABLE 25-continued

Characterization of exemplary anti-HER2 ADCs and corresponding payloads

| ADC Batch Id | Linker | Lethality/ Splicing Category (HCC-1954, N87) | DAR | Percent Monomer | Free Drug | Conc. | Properties-Corresponding Free Payloads: target binding SPA-ATS GMean IC50 (nM) SF3B1 (WT) HELA.2 | biochemical splicing assay qPCR-IVS-ATS GMean IC50 (nM) Ad2.1 HELA.2 | biochemical splicing assay qPCR-IVS-ATS GMean IC50 (nM) Ad2.2 HELA.2 | biochemical splicing assay Ratio Ad2.1/2.2 | cellular potency cell line #1 CTGlo-ATS GMean GI50 (nM) 72 h NCIH-1650.1 | cellular potency cell line #1 CTGlo-ATS GMean LD50 (nM) 72 h NCIH-1650.1 | cellular potency cell line #2 CTGlo-ATS GMean GI50 (nM) 72 h NCIH-1568.1 | cellular potency cell line #2 CTGlo-ATS GMean LD50 (nM) 72 h NCIH-1568.1 | cellular potency cell line #3 CTGlo-ATS GMean GI50 (nM) 72 h THP-1.1 | cellular potency cell line #3 CTGlo-ATS GMean LD50 (nM) 72 h THP-1.1 | cellular permeability Perm. Mean Caco-2 A-B Perm (10e−6 cm/s) | cellular permeability Perm. Mean Caco-2 B-A Perm (10e−6 cm/s) | cellular permeability ER |
|---|---|---|---|---|---|---|---|---|---|---|---|---|---|---|---|---|---|---|---|
| AB185-ADL1-D12 | mc-Val-Cit-PABC | 1, 3 | 6.25 | 99% | <1% | 0.82 | | 16.528 | 25.09 | 0.659 | 257.925 | >10000.00 | 163.604 | 1193.037 | 202.487 | 900.227 | 0.17 | 0.23 | 1.353 |
| AB185-ADL13-D4 | b-glucuronide | 1, 1 | 4.47 | 99% | <1% | 0.78 | 8.778 | 20.887 | 17.321 | 1.206 | 11.941 | 1960.398 | 6.369 | 45.485 | 10.943 | 33.329 | 0.1 | 1.79 | 17.9 |
| AB185-ADL1-D5 | mc-Val-Cit-PABC | 1, 3 | 6.14 | 99% | <1% | 1.1 | | 17.392 | 23.943 | 0.726 | | | | | | | | | |
| AB185-ADL23-D4 | mc-Glu-Val-Cit-PABC | 2, 3 | 5.84 | 99% | <1% | 1.03 | 8.778 | 20.887 | 17.321 | 1.206 | 11.941 | 1960.398 | 6.369 | 45.485 | 10.943 | 33.329 | 0.1 | 1.79 | 17.9 |
| AB185-ADL1-D3 | mc-Val-Cit-PABC | 2, 3 | 6.75 | 99% | <1% | 1.13 | | 9.326 | 10.928 | 0.853 | | | | | | | | | |
| AB185-ADL22-D4 | mal-PEG2-Val-Cit-PABC | 1, 3 | 6.12 | 99% | <1% | 1.01 | 8.778 | 20.887 | 17.321 | 1.206 | 11.941 | 1960.398 | 6.369 | 45.485 | 10.943 | 33.329 | 0.1 | 1.79 | 17.9 |
| AB185-ADL21-D1 | mc-Ala-Ala-Asn-PABC | 2, 3 | 5.51 | 99% | <1% | 1.35 | 6.085 | 17.568 | 15.853 | 1.108 | 12.121 | >10000.00 | 7.363 | 65.737 | 11.085 | 41.408 | 0.14 | 2.05 | 14.64 |
| AB185-ADL21-D8 | mc-Ala-Ala-Asn-PABC | 4, 3 | 6.4 | 99% | <1% | 1.67 | 5.921 | 11.403 | 9.034 | 1.262 | 19.15 | >10000.00 | 6.568 | 68.125 | 8.745 | 38.969 | 0.128 | 2.027 | 15.88 |
| AB185-ADL21-D4 | mc-Ala-Ala-Asn-PABC | | 1.55 | 99% | <1% | 1.11 | 8.778 | 20.887 | 17.321 | 1.206 | 11.941 | 1960.398 | 6.369 | 45.485 | 10.943 | 33.329 | 0.1 | 1.79 | 17.9 |
| AB185-ADL15-D2 | mal-CH2CH2—O—CH2CH2-(non-cleavable) | 3, ND | 3.25 | 98.80% | <1% | 1.6 | | | | | | | | | | | | | |

TABLE 26

Exemplary anti-HER2 ADCs-HCC1954 cells

| | | | | | Properties-HER2 ADCs antiproliferative activity antigen (+) cell #1 | |
|---|---|---|---|---|---|---|
| ADC Batch Id | Linker | DAR | Permeability Caco-2 A-B (10e−6 cm/s) | pH 5.5 Stability (t1/2, 37C) | CTGlo GMean GI50 (nM) HER2 SMLA screen HCC1954.1 | CTGlo Mean MinResp % HER2 SMLA screen HCC1954.1 |
| AB185-ADL5-D19 | QVal-Ala | 6.600 | 16 | 0.8 | 0.278 | −47.381 |
| AB185-ADL5-D25 | QVal-Ala | 6.000 | 0.14 | 3.4 | 0.038 | −46.265 |
| AB185-ADL5-D2 | QVal-Ala | 4.140 | 0.6 | 4 | 0.206 | −12.239 |
| AB185-ADL1-04 | Val-Cit | 2.800 | 0.1 | 4.5 | 0.050 | −57.212 |
| AB185-ADL5-D10 | QVal-Ala | 4.020 | 1.8 | 5 | 0.254 | −2.273 |
| AB185-ADL1-D16 | Val-Cit | 4.400 | 0.72 | 7 | 2.086 | |
| AB185-ADL5-D17 | QVal-Ala | 3.960 | 20 | 7 | 2.668 | 14.873 |
| AB185-ADL5-D34 | QVal-Ala | | 26 | 7 | 3.325 | −38.285 |
| AB185-ADL5-D15 | QVal-Ala | 4.000 | 3.4 | 7 | 0.912 | −45.388 |

Example 10

10.1 Bioinformatics-Driven Indication/Target Selection

Figure 25:
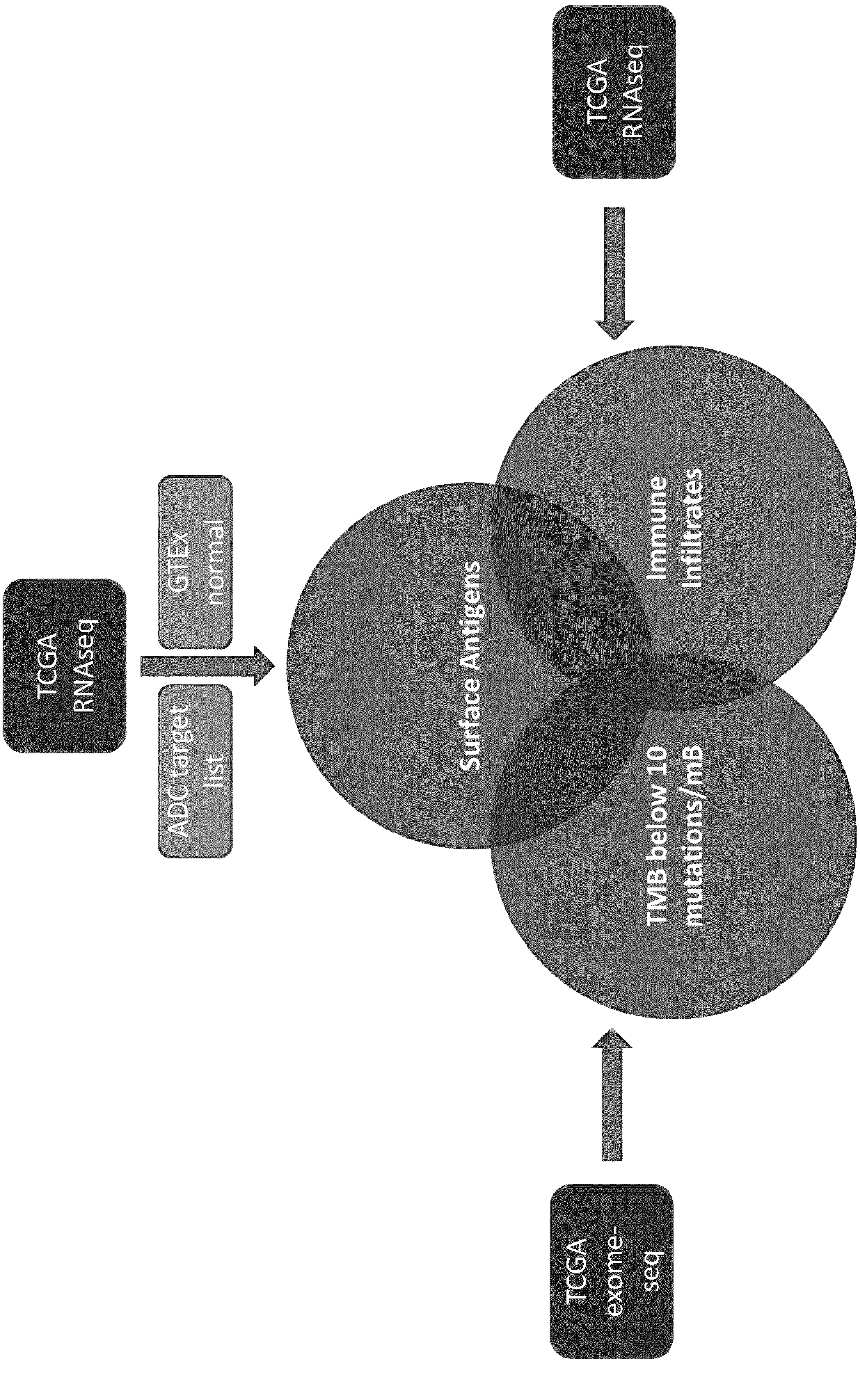
FIG. 25 shows a schematic diagram of an exemplary target indication analysis.

To identify target antigens highly expressed in low tumor mutation burden (TMB) tumors, as compared to normal tissue, a bioinformatics predictive analysis was performed. This example explains 1) how each filter was defined; and 2) how to use the antigen/indication table to identify suitable target/tumor pairs. For a schematic diagram of an exemplary target indication analysis, see FIG. 25.

10.1.1 Overview

Target antigens and indications were identified using a bioinformatics predictive analysis. Data from TCGA was processed for tumor mutation burden (TMB), expression of target antigens for ADC delivery, and tumor immune infiltration. Analyses, using published cutoffs of TMB and infiltration to stratify predicted responders vs. non-responders to immune checkpoint inhibitors (ICI), were performed to identify indications and matching antigens. Surface antigen expression was further filtered to assess a probabilistic population with antigen expression at least 2-fold higher than any normal tissue (as evaluated from the GTEx tissue expression database). Indications (or subsets of a TCGA lineage) with a suitable percentage of patients having one or more target antigens were further analyzed for mutation and immune metrics. Percentages of antigen positive patients having a tumor mutation burden below an aggregate of 10 mutations/megabase and with a T-cell infiltration score above 0.5 were assessed Indications with an estimate of ~50% of patients meeting these criteria are listed in Table 27. Patients in these cohorts (but not limited to these cohorts) may respond to treatment with a splicing modulator ADC (e.g., a splicing modulator ADC described herein).

10.1.2 Methods

Indication Prediction for Annals of Oncology Antigen Table Annotation:

Antigen: antigen gene name, only 59 genes likely to be good ADC targets from Annals of Oncology literature review (see Moek et al. (2017) Annals of Oncology, 28: 3083-3091) were included in the table (initial full analysis included all in silico surfaceome genes)

Cohort: TCGA cohort name

SUBTYPE: TCGA tumor subtype information

Cases_Total: The total number of cases

Cases.by.subtype: The number of cases by subtype

LTPM_median: Expression median value by Log 2(TPM+1)

LTPM_median_LowTMB: Expression median value by Log 2(TPM+1) for the cases with low TMB (<350)

LTMB_Median: Median value of Log 10(TMB)

LTMB_MAD: Robust measurement of standard deviation by MAD value of Log 10(TMB)

Infil_Median: Median value of infiltration score according to PLoS One T-cell signature Infil_MAD: Robust measurement of standard deviation by MAD value of infiltration score according to PLoS One Tcell signature Cor.with.Purity: Expression correlation with tumor purity GTEX_Tissue: The GTEx tissue name with the highest median value of expression GTEX_LTPM_Median: The median expression value of antigen in the GTEx tissue with the highest median value of expression Surfaceome.Filter*: Patient population after applying surfaceome filter: expression >2 fold of GTEx normal tissue with the highest median LowTMB.Filter: Patient population after applying low TMB filter: <350 per exome-seq (10 per mega bases2)

LowTMB.Surfaceome.Filter: Patient population after applying both surfaceome and tmb filters Hilnfil.LowTMB.Surfaceome.Filter: Patient population after applying three filters: surfaceome expression filter, low tmb filter and high infiltration filter Surfaceome.Filter.Perc: Percentage of population after applying surfaceome filter: expression >2 fold of GTEx normal tissue with the highest median LowTMB.Filter.Perc: Percentage of population after applying low TMB filter: <350

LowTMB.Surfaceome.Filter.Perc: Percentage of population after applying both surfaceome and tmb filters Hilnfil.LowTMB.Surfaceome.Filter.Perc: Percentage of population after applying three filters: surfaceome expression filter, low tmb filter, and high infiltration filter Probabilistic Estimation of Patient Population:

Resources compiled:

1. Pan-can immune landscape paper (Ready et al. (2019) Journal of Clinical Oncology, 37:992-1000)
2. TCGA RNA-seq/Exome-seq data bundle from Omicsoft
3. Immune gene signatures (Thorsson et al. (2018) Immunity, 48, 812-830)
4. GTEx data v7

Tumor mutation burden was calculated from the TCGA exome-seq mutation calling using Omicsoft data. PLoS One T-cell signature (CD3D, CD3E, CD2) was used to quantify sample immune infiltration. Z score was generated using log 2(TPM+1) value from TCGA RNA-seq data.

Surfaceome.Filter: Probability of individual patient to have >2 fold expression (log 2(TPM+1)) value comparing to the GTEx normal tissue with the highest median was calculated as follows:

1. Identify the GTEx normal tissue that has the highest median value for this gene among all GTEx normal tissues, assume it is $T_h$
2. Synthesize GTEx data for this gene with 1000 patients for each tissue using Synthetic Minority Over-sampling Technique (SMOTE (Siemers et al. (2017) PLoS One, 12(7):e0179726) maintaining the data distribution by tissue
3. Count the number of times (n times) this patient will be >2 fold of the GTEx synthesized data for the tissue $T_h$, the probability for this patient to be >2 fold of the GTEx normal is n/1000
4. Calculate this probability for every patient
5. The sum of the individual probability is the probabilistic estimation of the cohort population with >2 fold higher than the GTEx normal
6. When applying other filters together, the sum of individual probability will be only for the patients that pass the other filters 10.1.3 Examples Target antigens and indications identified using the exemplary bioinformatics predictive analysis described above are set forth in Table 27.

TABLE 27

Exemplary target antigens and indications

| Target Antigen | Indication(s) |
|---|---|
| MSLN | ovarian cancer |
| | cervical cancer |
| | pancreatic cancer |
| | lung adenocarcinoma |
| EPHA2 | esophageal cancer |
| FOLH1 | prostate cancer |
| CDH6 | kidney cancer |
| CEACAM5 | colorectal cancer |
| CFC1B | pancreatic cancer |
| ENPP3 | kidney cancer |
| FOLR1 | ovarian cancer |
| HAVCR1 | kidney cancer |
| | esophageal cancer |
| KIT | kidney cancer |
| MET | kidney cancer |
| | esophageal cancer |
| MUC16 | ovarian cancer |
| | cervical cancer |
| | breast cancer |
| SLC39A6 | breast cancer |
| | prostate cancer |
| SLC44A4 | prostate cancer |
| STEAP1 | prostate cancer |

The invention claimed is:

1. A compound of Formula (VI-A):

(VI-A)

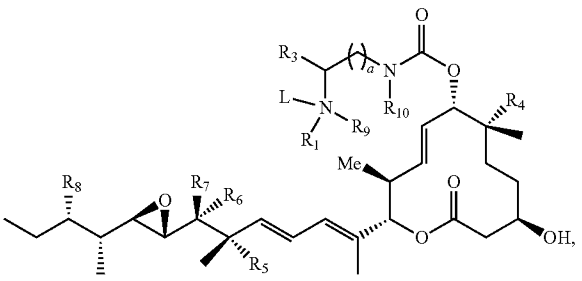

or a pharmaceutically acceptable salt thereof, wherein:

$R^1$ and $R^9$ are each independently chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$, $R^5$, and $R^8$ are each independently chosen from hydrogen, hydroxyl, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$ alkyl groups, and —$NR^{15}R^{16}$;

$R^{10}$ is chosen from hydrogen, $C_1$-$C_6$ alkyl groups, —C(=O)—($C_1$-$C_6$ alkyl) groups, and —$CD_3$;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and a is 1, 2, 3, 4, 5, 6, 7, 8, 9, or 10;

wherein $R^1$, $R^3$, $R^4$, $R^5$, $R^6$, $R^7$, $R^8$, $R^9$, and $R^{10}$ are each independently substituted with 0 to 3 groups independently chosen from halogens, hydroxyl, $C_1$-$C_6$alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen;

wherein $R^1$ and $R^9$ cannot both be absent; and

L is a linker.

2. The compound or pharmaceutically acceptable salt of claim 1, wherein the compound is:

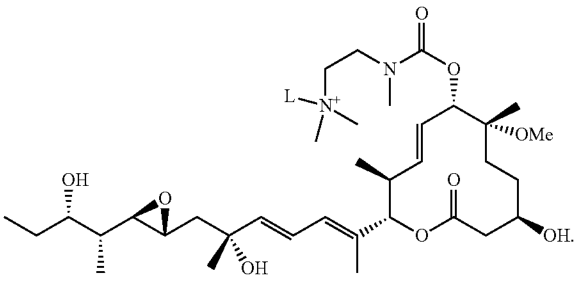

3. The compound or pharmaceutically acceptable salt of claim 1, wherein the compound is:

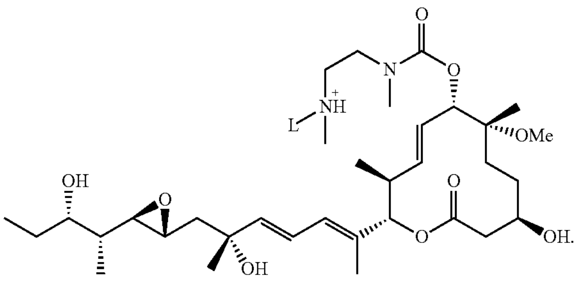

4. The compound or pharmaceutically acceptable salt of claim 1, wherein the linker L comprises a cleavable peptide moiety.

5. The compound or pharmaceutically acceptable salt of claim 4, wherein the cleavable peptide moiety comprises valine-citrulline (Val-Cit), valine-alanine (Val-Ala), glutamic acid-valine-citrulline (Glu-Val-Cit), or alanine-alanine-asparagine (Ala-Ala-Asn).

6. The compound or pharmaceutically acceptable salt of claim 4, wherein the linker L comprises at least one spacer unit comprising: (i) a polyethylene glycol moiety, (ii) an alkyl moiety, or (iii) a combination of (i) and (ii).

7. The compound or pharmaceutically acceptable salt of claim 4, wherein the linker L comprises a maleimide (Mal) moiety.

8. The compound or pharmaceutically acceptable salt of claim 4, wherein the linker L comprises maleimidocaproyl (MC).

9. The compound or pharmaceutically acceptable salt of claim 4, wherein the linker L comprises p-aminobenzyl (pAB) or p-aminobenzyloxycarbonyl (pABC).

10. The compound or pharmaceutically acceptable salt of claim 4, wherein the linker L comprises MC-Val-Cit-pAB, MC-Val-Ala-pAB, MC-Glu-Val-Cit-pAB, MC-Ala-Ala-Asn-pAB, MC-Val-Cit-pABC, MC-Val-Ala-pABC, MC-Glu-Val-Cit-pABC, or MC-Ala-Ala-Asn-pABC.

11. The compound or pharmaceutically acceptable salt of claim 1, wherein the linker L comprises a cleavable glucuronide moiety.

12. The compound or pharmaceutically acceptable salt of claim 11, wherein the cleavable glucuronide moiety is cleavable by a glucuronidase.

13. The compound or pharmaceutically acceptable salt of claim 11, wherein the linker L comprises MC-β-glucuronide-pAB or MC-β-glucuronide-pABC.

14. The compound or pharmaceutically acceptable salt of claim 1, wherein the linker L is a non-cleavable linker comprising at least one spacer unit.

15. The compound or pharmaceutically acceptable salt of claim 14, wherein the linker L comprises a maleimide moiety.

16. The compound or pharmaceutically acceptable salt of claim 15, wherein the at least one spacer unit comprises (i) a polyethylene glycol moiety, (ii) an alkyl moiety, or (iii) a combination of (i) and (ii).

17. The compound or pharmaceutically acceptable salt of claim 16, wherein the linker L is chosen from:

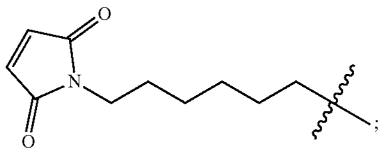 [SMILES: *CCCCCCN1C(=O)C=CC1=O]

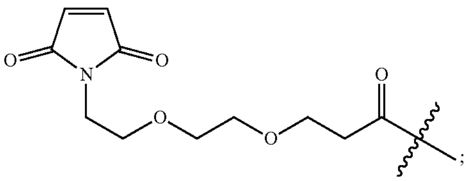 [SMILES: *C(=O)CCOCCOCCN1C(=O)C=CC1=O]

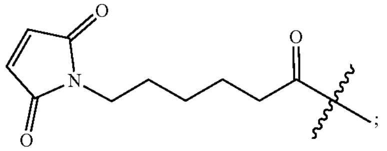 [SMILES: *C(=O)CCCCCN1C(=O)C=CC1=O]

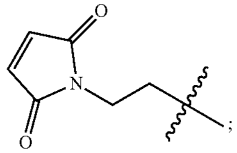 [SMILES: *CCN1C(=O)C=CC1=O]

and

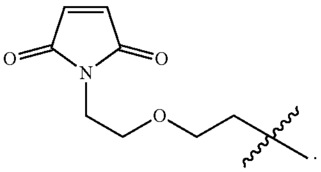 [SMILES: *CCOCCN1C(=O)C=CC1=O]

18. An antibody-drug conjugate of Formula (I):

$$\text{Ab-(L-D)}_p \quad \text{(I)}$$

wherein:

Ab is an antibody or antigen binding fragment which targets a neoplastic cell;

L-D is a compound or pharmaceutically acceptable salt of claim 1; and p is an integer from 1 to 15.

19. The antibody-drug conjugate of claim 18, wherein L-D is a compound of formula:

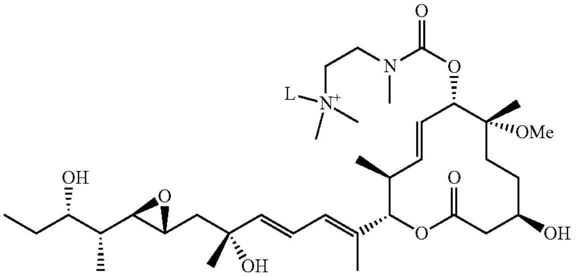

or a pharmaceutically acceptable salt thereof.

20. The antibody-drug conjugate of claim 18, wherein L-D is a compound of formula:

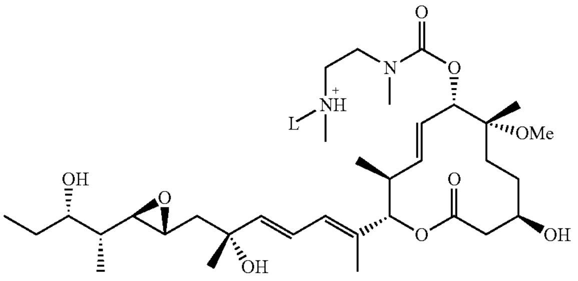

or a pharmaceutically acceptable salt thereof.

21. The antibody-drug conjugate of claim 18, wherein the linker L comprises a cleavable peptide moiety.

22. The antibody-drug conjugate of claim 21, wherein the cleavable peptide moiety comprises valine-citrulline (Val-Cit), valine-alanine (Val-Ala), glutamic acid-valine-citrulline (Glu-Val-Cit), or alanine-alanine-asparagine (Ala-Ala-Asn).

23. The antibody-drug conjugate of claim 21, wherein the linker L comprises at least one spacer unit comprising: (i) a polyethylene glycol moiety, (ii) an alkyl moiety, or (iii) a combination of (i) and (ii).

24. The antibody-drug conjugate of claim 21, wherein the linker L comprises a maleimide (Mal) moiety.

25. The antibody-drug conjugate of claim 21, wherein the linker L comprises maleimidocaproyl (MC).

26. The antibody-drug conjugate of claim 21, wherein the linker L comprises p-aminobenzyl (pAB) or p-aminobenzyloxycarbonyl (pABC).

27. The antibody-drug conjugate of claim 21, wherein the linker L comprises MC-Val-Cit-pAB, MC-Val-Ala-pAB, MC-Glu-Val-Cit-pAB, MC-Ala-Ala-Asn-pAB, MC-Val-Cit-pABC, MC-Val-Ala-pABC, MC-Glu-Val-Cit-pABC, or MC-Ala-Ala-Asn-pABC.

28. The antibody-drug conjugate of claim 18, wherein the linker L comprises a cleavable glucuronide moiety.

29. The antibody-drug conjugate of claim 28, wherein the linker L comprises MC-β-glucuronide-pAB or MC-β-glucuronide-pABC.

30. The antibody-drug conjugate of claim 21, wherein p is an integer from 2 to 8.

31. A pharmaceutical composition comprising the antibody-drug conjugate of claim 18 and a pharmaceutical acceptable carrier.

32. A method of treating a subject having, or suspected of having, a neoplastic disorder, comprising administering a therapeutically effective amount of the antibody-drug conjugate of claim 18.

33. The method of claim 32, wherein the neoplastic disorder is a leukemia, a lymphoma, or a myeloma.

34. The method of claim 33, wherein the myeloma is multiple myeloma.

35. A method of reducing or inhibiting growth of a tumor in a subject having, or suspected of having, a neoplastic disorder, comprising administering to the subject a therapeutically effective amount of the antibody-drug conjugate of claim 18.

* * * * *

SEQUENCE LISTING

```
Sequence total quantity: 119
SEQ ID NO: 1          moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 1
GFNIKDTYIH                                                  10

SEQ ID NO: 2          moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 2
RIYPTNGYTR YADSVKG                                          17

SEQ ID NO: 3          moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 3
WGGDGFYAMD V                                                11
```

-continued

```
SEQ ID NO: 4            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 4
RASQDVNTAV AW                                                       12

SEQ ID NO: 5            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 5
SASFLES                                                             7

SEQ ID NO: 6            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
QQHYTTPPT                                                           9

SEQ ID NO: 7            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 7
NYWIE                                                               5

SEQ ID NO: 8            moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 8
ILPGTGRTIY NEKFKGKA                                                 18

SEQ ID NO: 9            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 9
RDYYGNFYYA MDY                                                      13

SEQ ID NO: 10           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 10
ASQGINNYLN                                                          10

SEQ ID NO: 11           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 11
TSTLQS                                                              6
```

```
SEQ ID NO: 12           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 12
QQYSKLPRT                                                                  9

SEQ ID NO: 13           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 13
HYMMA                                                                      5

SEQ ID NO: 14           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 14
RIGPSGGPTH YADSVKG                                                         17

SEQ ID NO: 15           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 15
YDSGYDYVAV AGPAEYFQH                                                       19

SEQ ID NO: 16           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 16
RASWSISTWL A                                                               11

SEQ ID NO: 17           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 17
KASNLHT                                                                    7

SEQ ID NO: 18           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 18
QQYNSYSRT                                                                  9

SEQ ID NO: 19           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
```

-continued

```
SEQUENCE: 19
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120

SEQ ID NO: 20          moltype = AA  length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 20
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRT              109

SEQ ID NO: 21          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 21
QVQLQQSGSE LMMPGASVKI SCKATGYTFS NYWIQRPGHG LEWIGEILPG TGRTIYNEKF  60
KGKATFTADI SSNTVQMQLS SLTSEDSAVY YCARRDYYGN FYYAMDYWGQ GTSVTVSS    118

SEQ ID NO: 22          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 22
DIQMTQSTSS LSASLGDRVT ISCSASQGIN NYLNWYQQKP DGTVELLIYY TSTLQSGVPS  60
RFSGSGSGTD YSLTISNLEP EDIGTYYCQQ YSKLPRTFGG GTKLEIK                107

SEQ ID NO: 23          moltype = AA  length = 128
FEATURE                Location/Qualifiers
REGION                 1..128
                       note = Description of Artificial Sequence: Synthetic
                        polypeptide
source                 1..128
                       mol_type = protein
                       organism = synthetic construct
SEQUENCE: 23
EVQLLESGGG LVQPGGSLRL SCAASGFTFS HYMMAWVRQA PGKGLEWVSR IGPSGGPTHY  60
ADSVKGRFTI SRDNSKNTLY LQMNSLRAED TAVYYCAGYD SGYDYVAVAG PAEYFQHWGQ  120
GTLVTVSS                                                           128

SEQ ID NO: 24          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 24
DIQMTQSPSS LSASVGDRVT ITCRASQSIS TWLAWYQQKP GKAPKLLIYK ASNLHTGVPS  60
RFSGSGSGTE FSLTISGLQP DDFATYYCQQ YNSYSRTFGQ GTKVEIK                107

SEQ ID NO: 25          moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 25
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP PKSCDKTHTC PPCPAPELLG  240
GPSVFLFPPK PKDTLMISRT PEVTCVVVDV SHEDPEVKFN WYVDGVEVHN AKTKPREEQY  300
```

```
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 26          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 26
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 27          moltype = AA  length = 441
FEATURE                Location/Qualifiers
REGION                 1..441
                       note = Description of Artificial Sequence: Synthetic
                        polypeptide
source                 1..441
                       mol_type = protein
                       organism = synthetic construct
SEQUENCE: 27
QVQLQQSGSE LMMPGASVKI SCKATGYTFS NYWIQRPGHG LEWIGEILPG TGRTIYNEKF  60
KGKATFTADI SSNTVQMQLS SLTSEDSAVY YCARRDYYGN FYYAMDYWGQ GTSVTVSSAK  120
TTPPSVYPLA PGSAAQTNSM VTLGCLVKGY FPEPVTVTWN SGSLSSGVHT FPAVLQSDLY  180
TLSSSVTVPS STWPSETVTC NVAHPASSTK VDKKIVPRDC GCKPCICTVP EVSSVFIFPP  240
KPKDVLTITL TPKVTCVVVD ISKDDPEVQF SWFVDDVEVH TAQTQPREEQ FNSTFRSVSE  300
LPIMHQDWLN GKEFKCRVNS AAFPAPIEKT ISKTKGRPKA PQVYTIPPPK EQMAKDKVSL  360
TCMITDFFPE DITVEWQWNG QPAENYKNTQ PIMDTDGSYF VYSKLNVQKS NWEAGNTFTC  420
SVLHEGLHNH HTEKSLSHSP G                                            441

SEQ ID NO: 28          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 28
DIQMTQSTSS LSASLGDRVT ISCSASQGIN NYLNWYQQKP DGTVELLIYY TSTLQSGVPS  60
RFSGSGSGTD YSLTISNLEP EDIGTYYCQQ YSKLPRTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 29          moltype = AA  length = 457
FEATURE                Location/Qualifiers
REGION                 1..457
                       note = Description of Artificial Sequence: Synthetic
                        polypeptide
source                 1..457
                       mol_type = protein
                       organism = synthetic construct
SEQUENCE: 29
EVQLLESGGG LVQPGGSLRL SCAASGFTFS HYMMAWVRQA PGKGLEWVSR IGPSGGPTHY  60
ADSVKGRFTI SRDNSKNTLY LQMNSLRAED TAVYYCAGYD SGYDYVAVAG PAEYFQHWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKKVEPKS CDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSRDELT KNQVSLTCLV KGFYPSDIAV EWESNGQPEN NYKTTPPVLD SDGSFFLYSK  420
LTVDKSRWQQ GNVFSCSVMH EALHNHYTQK SLSLSPG                           457

SEQ ID NO: 30          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 30
DIQMTQSPSS LSASVGDRVT ITCRASQSIS TWLAWYQQKP GKAPKLLIYK ASNLHTGVPS  60
RFSGSGSGTE FSLTISGLQP DDFATYYCQQ YNSYSRTFGQ GTKVEIKRTV AAPSVFIFPP  120
```

-continued

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 31          moltype = AA  length = 1255
FEATURE                Location/Qualifiers
source                 1..1255
                       mol_type = protein
                       organism = Homo sapiens
SEQUENCE: 31
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 32          moltype = AA  length = 310
FEATURE                Location/Qualifiers
source                 1..310
                       mol_type = protein
                       organism = Homo sapiens
SEQUENCE: 32
MRRAALWLWL CALALSLQPA LPQIVATNLP PEDQDGSGDD SDNFSGSGAG ALQDITLSQQ  60
TPSTWKDTQL LTAIPTSPEP TGLEATAAST STLPAGEGPK EGEAVVLPEV EPGLTAREQE  120
ATPRPRETTQ LPTTHLASTT TATTAQEPAT SHPHRDMQPG HHETSTPAGP SQADLHTPHT  180
EDGGPSATER AAEDGASSQL PAAEGSGEQD FTFETSGENT AVVAVEPDRR NQSPVDQGAT  240
GASQGLLDRK EVLGGVIAGG LVGLIFAVCL VGFMLYRMKK KDEGSYSLEE PKQANGGAYQ  300
KPTKQEEFYA                                                         310

SEQ ID NO: 33          moltype = AA  length = 976
FEATURE                Location/Qualifiers
source                 1..976
                       mol_type = protein
                       organism = Homo sapiens
SEQUENCE: 33
MELQAARACF ALLWGCALAA AAAAQGKEVV LLDFAAAGGE LGWLTHPYGK GWDLMQNIMN  60
DMPIYMYSVC NVMSGDQDNW LRTNWVYRGE AERIFIELKF TVRDCNSFPG GASSCKETFN  120
LYYAESDLDY GTNFQKRLFT KIDTIAPDEI TVSSDFEARH VKLNVEERSV GPLTRKGFYL  180
AFQDIGACVA LLSVRVYYKK CPELLQGLAH FPETIAGSDA PSLATVAGTC VDHAVVPPGG  240
EEPRMHCAVD GEWLVPIGQC LCQAGYEKVE DACQACSPGF FKFEASESPC LECPEHTLPS  300
PEGATSCECE EGFFRAPQDP ASMPCTRPPS APHYLTAVGM GAKVELRWTP PQDSGGREDI  360
VYSVTCEQCW PESGECGPCE ASVRYSEPPH GLTRTSVTVS DLEPHMNYTF TVEARNGVSG  420
LVTSRSFRTA SVSINQTEPP KVRLEGRSTT SLSVSWSIPP PQQSRVWKYE VTYRKKGDSN  480
SYNVRRTEGF SVTLDDLAPD TTYLVQVQAL TQEGQGAGSK VHEFQTLSPE GSGNLAVIGG  540
VAVGVVLLLV LAGVGFFIHR RRKNQRARQS PEDVYFSKSE QLKPLKTYVD PHTYEDPNQA  600
VLKFTTEIHP SCVTRQKVIG AGEFGEVYKG MLKTSSGKKE VPVAIKTLKA GYTEKQRVDF  660
LGEAGIMGQF SHHNIIRLEG VISKYKPMMI ITEYMENGAL DKFLREKDGE FSVLQLVGML  720
RGIAAGMKYL ANMNYVHRDL AARNILVNSN LVCKVSDFGL SRVLEDDPEA TYTTSGGKIP  780
IRWTAPEAIS YRKFTSASDV WSFGIVMWEV MTYGERPYWE LSNHEVMKAI NDGFRLPTPM  840
DCPSAIYQLM MQCWQQERAR RPKFADIVSI LDKLIRAPDS LKTLADFDPR VSIRLPSTSG  900
SEGVPFRTVS EWLESIKMQQ YTEHFMAAGY TAIEKVVQMT NDDIKRIGVR LPGHQKRIAY  960
SLLGLKDQVN TVGIPI                                                  976

SEQ ID NO: 34          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 34
GFGG                                                               4

SEQ ID NO: 35          moltype = AA  length = 4
```

-continued

```
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 35
GFLG                                                                       4

SEQ ID NO: 36           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 36
ALAL                                                                       4

SEQ ID NO: 37           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 37
SPTLPPRSL                                                                  9

SEQ ID NO: 38           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 38
HPSIKRGLSS L                                                               11

SEQ ID NO: 39           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 39
LLLPHHVL                                                                   8

SEQ ID NO: 40           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 40
RTAPGVRPPF                                                                 10

SEQ ID NO: 41           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 41
RPQKSIQAL                                                                  9

SEQ ID NO: 42           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 42
APAPPPLPA                                                                  9
```

```
SEQ ID NO: 43          moltype = AA  length = 630
FEATURE                Location/Qualifiers
source                 1..630
                       mol_type = protein
                       organism = Homo sapiens
SEQUENCE: 43
MALPTARPLL GSCGTPALGS LLFLLFSLGW VQPSRTLAGE TGQEAAPLDG VLANPPNISS  60
LSPRQLLGFP CAEVSGLSTE RVRELAVALA QKNVKLSTEQ LRCLAHRLSE PPEDLDALPL  120
DLLLFLNPDA FSGPQACTRF FSRITKANVD LLPRGAPERQ RLLPAALACW GVRGSLLSEA  180
DVRALGGLAC DLPGRFVAES AEVLLPRLVS CPGPLDQDQQ EAARAALQGG GPPYGPPSTW  240
SVSTMDALRG LLPVLGQPII RSIPQGIVAA WRQRSSRDPS WRQPERTILR PRFRREVEKT  300
ACPSGKKARE IDESLIFYKK WELEACVDAA LLATQMDRVN AIPFTYEQLD VLKHKLDELY  360
PQGYPESVIQ HLGYLFLKMS PEDIRKWNVT SLETLKALLE VNKGHEMSPQ APRRPLPQVA  420
TLIDRFVKGR GQLDKDTLDT LTAFYPGYLC SLSPEELSSV PPSSIWAVRP QDLDTCDPRQ  480
LDVLYPKARL AFQNMNGSEY FVKIQSFLGG APTEDLKALS QQNVSMDLAT FMKLRTDAVL  540
PLTVAEVQKL LGPHVEGLKA EERHRPVRDW ILRQRQDDLD TLGLGLQGGI PNGYLVLDLS  600
MQEALSGTPC LLGPGPVLTV LALLLASTLA                                 630

SEQ ID NO: 44          moltype = AA  length = 750
FEATURE                Location/Qualifiers
source                 1..750
                       mol_type = protein
                       organism = Homo sapiens
SEQUENCE: 44
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP  120
NKTHPNYISI INEDGNEIFN TSLFEPPPPG YENVSDIVPP FSAFSPQGMP EGDLVYVNYA  180
RTEDFFKLER DMKINCSGKI VIARYGKVFR GNKVKNAQLA GAKGVILYSD PADYFAPGVK  240
SYPDGWNLPG GGVQRGNILN LNGAGDPLTP GYPANEYAYR RGIAEAVGLP SIPVHPIGYY  300
DAQKLLEKMG GSAPPDSSWR GSLKVPYNVG PGFTGNFSTQ KVKMHIHSTN EVTRIYNVIG  360
TLRGAVEPDR YVILGGHRDS WVFGGIDPQS GAAVVHEIVR SFGTLKKEGW RPRRTILFAS  420
WDAEEFGLLG STEWAEENSR LLQERGVAYI NADSSIEGNY TLRVDCTPLM YSLVHNLTKE  480
LKSPDEGFEG KSLYESWTKK SPSPEFSGMP RISKLGSGND FEVFFQRLGI ASGRARYTKN  540
WETNKFSGYP LYHSVYETYE LVEKFYDPMF KYHLTVAQVR GGMVFELANS IVLPFDCRDY  600
AVVLRKYADK IYSISMKHPQ EMKTYSVSFD SLFSAVKNFT EIASKFSERL QDFDKSNPIV  660
LRMMNDQLMF LERAFIDPLG LPDRPFYRHV IYAPSSHNKY AGESFPGIYD ALFDIESKVD  720
PSKAWGEVKR QIYVAAFTVQ AAAETLSEVA                                 750

SEQ ID NO: 45          moltype = AA  length = 790
FEATURE                Location/Qualifiers
source                 1..790
                       mol_type = protein
                       organism = Homo sapiens
SEQUENCE: 45
MRTYRYFLLL FWVGQPYPTL STPLSKRTSG FPAKKRALEL SGNSKNELNR SKRSWMWNQF  60
FLLEEYTGSD YQYVGKLHSD QDRGDGSLKY ILSGDGAGDL FIINENTGDI QATKRLDREE  120
KPVYILRAQA INRRTGRPVE PESEFIIKIH DINDNEPIFT KEVYTATVPE MSDVGTFVVQ  180
VTATDADDPT YGNSAKVVYS ILQGQPYFSV ESETGIIKTA LLNMDRENRE QYQVVIQAKD  240
MGGQMGGLSG TTTVNITLTD VNDNPPRFPQ STYQFKTPES SPPGTPIGRI KASDADVGEN  300
AEIEYSITDG EGLDMFDVIT DQETQEGIIT VKKLLDFEKK KVYTLKVEAS NPYVEPRFLY  360
LGPFKDSATV RIVVEDVDEP PVFSKLAYIL QIREDAQINT TIGSVTAQDP DAARNPVKYS  420
VDRHTDMDRI FNIDSGNGSI FTSKLLDRET LLWHNITVIA TEINNPKQSS RVPLYIKVLD  480
VNDNAPEFAE FYETFVCEKA KADQLIQTLH AVDKDDPYSG HQFSFSLAPE AASGSNFTIQ  540
DNKDNTAGIL TRKNGYNRHE MSTYLLPVVI SDNDYPVQSS TGTVTVRVCA CDHHGNMQSC  600
HAEALIHPTG LSTGALVAIL LCIVILLVTV VLFAALRRQR KKEPLIISKE DIRDNIVSYN  660
DEGGGEEDTQ AFDIGTLRNP EAIEDNKLRR DIVPEALFLP RRTPTARDNT DVRDFINQRL  720
KENDTDPTAP PYDSLATYAY EGTGSVADSL SSLESVTTDA DQDYDYLSDW GPRFKKLADM  780
YGGVDSDKDS                                                       790

SEQ ID NO: 46          moltype = AA  length = 702
FEATURE                Location/Qualifiers
source                 1..702
                       mol_type = protein
                       organism = Homo sapiens
SEQUENCE: 46
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDT ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYA EPPKPFITSN NSNPVEDEDA VALTCEPEIQ NTTYLWWVNN  360
QSLPVSPRLQ LSNDNRTLTL LSVTRNDVGP YECGIQNKLS VDHSDPVILN VLYGPDDPTI  420
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAN LNLSCHSASN PSPQYSWRIN GIPQQHTQVL FIAKITPNNN GTYACFVSNL  660
ATGRNNSIVK SITVSASGTS PGLSAGATVG IMIGVLVGVA LI                   702

SEQ ID NO: 47          moltype = AA  length = 223
```

-continued

```
FEATURE                Location/Qualifiers
source                 1..223
                       mol_type = protein
                       organism = Homo sapiens
SEQUENCE: 47
MTWRHHVRLL FTVSLALQII NLGNSYQREK HNGGREEVTK VATQKHRQSP LNWTSSHFGE  60
VTGSAEGWGP EEPLPYSWAF GEGASARPRC CRNGGTCVLG SFCVCPAHFT GRYCEHDQRR  120
SECGALEHGA WTLRACHLCR CIFGALHCLP LQTPDRCDPK DFLASHAHGP SAGGAPSLLL  180
LLPCALLHRL LRPDAPAHPR SLVPSVLQRE RRPCGRPGLG HRL                   223

SEQ ID NO: 48          moltype = AA  length = 875
FEATURE                Location/Qualifiers
source                 1..875
                       mol_type = protein
                       organism = Homo sapiens
SEQUENCE: 48
MESTLTLATE QPVKKNTLKK YKIACIVLLA LLVIMSLGLG LGLGLRKLEK QGSCRKKCFD  60
ASFRGLENCR CDVACKDRGD CCWDFEDTCV ESTRIWMCNK FRCGETRLEA SLCSCSDDCL  120
QRKDCCADYK SVCQGETSWL EENCDTAQQS QCPEGFDLPP VILFSMDGFR AEYLYTWDTL  180
MPNINKLKTC GIHSKYMRAM YPTKTFPNHY TIVTGLYPES HGIIDNNMYD VNLNKNFSLS  240
SKEQNNPAWW HGQPMWLTAM YQGLKAATYF WPGSEVAING SFPSIYMPYN GSVPFEERIS  300
TLLKWLDLPK AERPRFYTMY FEEPDSSGHA GGPVSARVIK ALQVVDHAFG MLMEGLKQRN  360
LHNCVNIILL ADHGMDQTYC NKMEYMTDYF PRINFFYMYE GPAPRIRAHN IPHDFFSFNS  420
EEIVRNLSCR KPDQHFKPYL TPDLPKRLHY AKNVRIDKVH LFVDQQWLAV RSKSNTNCGG  480
GNHGYNNEFR SMEAIFLAHG PSFKEKTEVE PFENIEVYNL MCDLLRIQPA PNNGTHGSLN  540
HLLKVPFYEP SHAEEVSKFS VCGFANPLPT ESLDCFCPHL QNSTQLEQVN QMLNLTQEEI  600
TATVKVNLPF GRPRVLQKNV DHCLLYHREY VSGFGKAMRM PMWSSYTVPQ LGDTSPLPPT  660
VPDCLRADVR VPPSESQKCS FYLADKNITH GFLYPPASNR TSDSQYDALI TSNLVPMYEE  720
FRKMWDYFHS VLLIKHATER NGVNVVSGPI FDYNYDGHFD APDEITKHLA NTDVPIPTHY  780
FVVLTSCKNK SHTPENCPGW LDVLPFIIPH RPTNVESCPE GKPEALWVEE RFTAHIARVR  840
DVELLTGLDF YQDKVQPVSE ILQLKTYLPT FETTI                            875

SEQ ID NO: 49          moltype = AA  length = 257
FEATURE                Location/Qualifiers
source                 1..257
                       mol_type = protein
                       organism = Homo sapiens
SEQUENCE: 49
MAQRMTTQLL LLLVWVAVVG EAQTRIAWAR TELLNVCMNA KHHKEKPGPE DKLHEQCRPW  60
RKNACCSTNT SQEAHKDVSY LYRFNWNHCG EMAPACKRHF IQDTCLYECS PNLGPWIQQV  120
DQSWRKERVL NVPLCKEDCE QWWEDCRTSY TCKSNWHKGW NWTSGFNKCA VGAACQPFHF  180
YFPTPTVLCN EIWTHSYKVS NYSRGSGRCI QMWFDPAQGN PNEEVARFYA AAMSGAGPWA  240
AWPFLLSLAL MLLWLLS                                                257

SEQ ID NO: 50          moltype = AA  length = 364
FEATURE                Location/Qualifiers
source                 1..364
                       mol_type = protein
                       organism = Homo sapiens
SEQUENCE: 50
MHPQVVILSL ILHLADSVAG SVKVGGEAGP SVTLPCHYSG AVTSMCWNRG SCSLFTCQNG  60
IVWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIAKKYF FKKEVQQLSV SFSSLQIKAL QNAVEKEVQA EDNIYIENSL  360
YATD                                                              364

SEQ ID NO: 51          moltype = AA  length = 976
FEATURE                Location/Qualifiers
source                 1..976
                       mol_type = protein
                       organism = Homo sapiens
SEQUENCE: 51
MRGARGAWDF LCVLLLLLRV QTGSSQPSVS PGEPSPPSIH PGKSDLIVRV GDEIRLLCTD  60
PGFVKWTFEI LDETNENKQN EWITEKAEAT NTGKYTCTNK HGLSNSIYVF VRDPAKLFLV  120
DRSLYGKEDN DTLVRCPLTD PEVTNYSLKG CQGKPLPKDL RFIPDPKAGI MIKSVKRAYH  180
RLCLHCSVDQ EGKSVLSEKF ILKVRPAFKA VPVVSVSKAS YLLREGEEFT VTCTIKDVSS  240
SVYSTWKREN SQTKLQEKYN SWHHGDFNYE RQATLTISSA RVNDSGVFMC YANNTFGSAN  300
VTTTLEVVDK GFINIFPMIN TTVFVNDGEN VDLIVEYEAF PKPEHQQWIY MNRTFTDKWE  360
DYPKSENESN IRYVSELHLT RLKGTEGGTY TFLVSNSDVN AAIAFNVYVN TKPEILTYDR  420
LVNGMLQCVA AGFPEPTIDW YFCPGTEQRC SASVLPVDVQ TLNSSGPPFG KLVVQSSIDS  480
SAFKHNGTVE CKAYNDVGKT SAYFNFAFKG NNKEQIHPHT LFTPLLIGFV IVAGMMCIIV  540
MILTYKYLQK PMYEVQWKVV EEINGNNYVY IDPTQLPYDH KWEFPRNRLS FGKTLGAGAF  600
GKVVEATAYG LIKSDAAMTV AVKMLKPSAH LTEREALMSE LKVLSYLGNH MNIVNLLGAC  660
TIGGPTLVIT EYCCYGDLLN FLRRKRDSFI CSKQEDHAEA ALYKNLLHSK ESSCSDSTNE  720
YMDMKPGVSY VVPTKADKRR SVRIGSYIER DVTPAIMEDD ELALDLEDLL SFSYQVAKGM  780
AFLASKNCIH RDLAARNILL THGRITKICD FGLARDIKND SNYVVKGNAR LPVKWMAPES  840
IFNCVYTFES DVWSYGIFLW ELFSLGSSPY PGMPVDSKFY KMIKEGFRML SPEHAPAEMY  900
```

```
DIMKTCWDAD PLKRPTFKQI VQLIEKQISE STNHIYSNLA NCSPNRQKPV VDHSVRINSV  960
GSTASSSQPL LVHDDV                                                  976

SEQ ID NO: 52          moltype = AA  length = 1390
FEATURE                Location/Qualifiers
source                 1..1390
                       mol_type = protein
                       organism = Homo sapiens
SEQUENCE: 52
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD ILFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFISGGSTI TGVGKNLNSV SVPRMVINVH  780
EAGRNFTVAC QHRSNSEIIC CTTPSLQQLN LQLPLKTKAF FMLDGILSKY FDLIYVHNPV  840
FKPFEKPVMI SMGNENVLEI KGNDIDPEAV KGEVLKVGNK SCENIHLHSE AVLCTVPNDL  900
LKLNSELNIE WKQAISSTVL GKVIVQPDQN FTGLIAGVVS ISTALLLLLG FFLWLKKRKQ  960
IKDLGSELVR YDARVHTPHL DRLVSARSVS PTTEMVSNES VDYRATFPED QFPNSSQNGS  1020
CRQVQYPLTD MSPILTSGDS DISSPLLQNT VHIDLSALNP ELVQAVQHVV IGPSSLIVHF  1080
NEVIGRGHFG CVYHGTLLDN DGKKIHCAVK SLNRITDIGE VSQFLTEGII MKDFSHPNVL  1140
SLLGICLRSE GSPLVVLPYM KHGDLRNFIR NETHNPTVKD LIGFGLQVAK GMKYLASKKF  1200
VHRDLAARNC MLDEKFTVKV ADFGLARDMY DKEYYSVHNK TGAKLPVKWM ALESLQTQKF  1260
TTKSDVWSFG VLLWELMTRG APPYPDVNTF DITVYLLQGR RLLQPEYCPD PLYEVMLKCW  1320
HPKAEMRPSF SELVSRISAI FSTFIGEHYV HVNATYVNVK CVAPYPSLLS SEDNADDEVD  1380
TRPASFWETS                                                         1390

SEQ ID NO: 53          moltype = AA  length = 14507
FEATURE                Location/Qualifiers
source                 1..14507
                       mol_type = protein
                       organism = Homo sapiens
SEQUENCE: 53
MLKPSGLPGS SSPTRSLMTG SRSTKATPEM DSGLTGATLS PKTSTGAIVV TEHTLPFTSP  60
DKTLASPTSS VVGRTTQSLG VMSSALPEST SRGMTHSEQR TSPSLSPQVN GTPSRNYPAT  120
SMVSGLSSPR TRTSSTEGNF TKEASTYTLT VETTSGPVTE KYTVPTETST TEGDSTETPW  180
DTRYIPVKIT SPMKTFADST ASKENAPVSM TPAETTVTDS HTPGRTNPSF GTLYSSFLDL  240
SPKGTPNSRG ETSLELILST TGYPFSSPEP GSAGHSRIST SAPLSSSASV LDNKISETSI  300
FSGQSLTSPL SPGVPEARAS TMPNSAIPFS MTLSNAETSA ERVRSTISSL GTPSISTKQT  360
AETILTFHAF AETMDIPSTH IAKTLASEWL GSPGTLGGTS TSALTTTSPS TTLVSEETNT  420
HHSTSGKETE GTLNTSMTPL ETSAPGEESE MTATLVPTLG FTTLDSKIRS PSQVSSSHPT  480
RELRTTGSTS GRQSSSTAAH GSSDILRATT SSTSKASSWT SESTAQQFSE PQHTQWVETS  540
PSMKTERPPA STSVAAPITT SVPSVVSGFT TLKTSSTKGI WLEETSADTL IGESTAGPTT  600
HQFAVPTGIS MTGGSSTRGS QGTTHLLTRA TASSETSADL TLATNGVPVS VSPAVSKTAA  660
GSSPPGGTKP SYTMVSSVIP ETSSLQSSAF REGTSLGLTP LNTRHPFSSP EPDSAGHTKI  720
STSIPLLSSA SVLEDKVSAT STFSHHKATS SITTGTPEIS TKTKPSSAVL SSMTLSNAAT  780
SPERVRNATS PLTHPSPSGE ETAGSVLTLS TSAETTDSPN IHPTGTLTSE SSESPSTLSL  840
PSVSGVKTTF SSSTPSTHLF TSGEETEETS NPSVSQPETS VSRVRTTLAS TSVPTPVFPT  900
MDTWPTRSAQ FSSSHLVSEL RATSSTSVTN STGSALPKIS HLTGTATMSQ TNRDTFNDSA  960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTYTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
```

-continued

VSLDNETTVK TSDILDARKT NELPSDSSSS SDLINTSIAS STMDVTKTAS ISPTSISGMT 2400
ASSSPSLFSS DRPQVPTSTT ETNTATSPSV SSNTYSLDGG SNVGGTPSTL PPFTITHPVE 2460
TSSALLAWSR PVRTFSTMVS TDTASGENPT SSNSVVTSVP APGTWTSVGS TTDLPAMGFL 2520
KTSPAGEAHS LLASTIEPAT AFTPHLSAAV VTGSSATSEA SLLTTSESKA IHSSPQTPTT 2580
PTSGANWETS ATPESLLVVT ETSDTTLTSK ILVTDTILFS TVSTPPSKFP STGTLSGASF 2640
PTLLPDTPAI PLTATEPTSS LATSFDSTPL VTIASDSLGT VPETTLTMSE TSNGDALVLK 2700
TVSNPDRSIP GITIQGVTES PLHPSSTSPS KIVAPRNTTY EGSITVALST LPAGTTGSLV 2760
FSQSSENSET TALVDSSAGL ERASVMPLTT GSQGMASSGG IRSGSTHSTG TKTFSSLPLT 2820
MNPGEVTAMS EITTNRLTAT QSTAPKGIPV KPTSAESGLL TPVSASSSPS KAFASLTTAP 2880
PTWGIPQSTL TFEFSEVPSL DTKSASLPTP GQSLNTIPDS DASTASSSLS KSPEKNPRAR 2940
MMTSTKAISA SSFQSTGFTE TPEGSASPSM AGHEPRVPTS GTGDPRYASE SMSYPDPSKA 3000
SSAMTSTSLA SKLTTLFSTG QAARSGSSSS PISLSTEKET SFLSPTASTS RKTSLFLGPS 3060
MARQPNILVH LQTSALTLSP TSTLNMSQEE PPELTSSQTI AEEEGTTAET QTLTFTPSET 3120
PTSLLPVSSP TEPTARRKSS PETWASSISV PAKTSLVETT DGTLVTTIKM SSQAAQGNST 3180
WPAPAEETGS SPAGTSPGSP EMSTTLKIMS SKEPSISPEI RSTVRNSPWK TPETTVPMET 3240
TVEPVTLQST ALGSGSTSIS HLPTGTTSPT KSPTENMLAT ERVSLSPSPP EAWTNLYSGT 3300
PGGTRQSLAT MSSVSLESPT ARSITGTGQQ SSPELVSKTT GMEFSMWHGS TGGTTGDTHV 3360
SLSTSSNILE DPVTSPNSVS SLTDKSKHKT ETWVSTTAIP STVLNNKIMA AEQQTSRSVD 3420
EAYSSTSSWS DQTSGSDITL GASPDVTNTL YITSTAQTTS LVSLPSGDQG ITSLTNPSGG 3480
KTSSASSVTS PSIGLETLRA NVSAVKSDIA PTAGHLSQTS SPAEVSILDV TTAPTPGIST 3540
TITTMGTNSI STTTPNPEVG MSTMDSTPAT ERRTTSTEHP STWSSTAASD SWTVTDMTSN 3600
LKVARSPGTI STMHTTSFLA SSTELDSMST PHGRITVIGT SLVTPSSDAS AVKTETSTSE 3660
RTLSPSDTTA STPISTFSRV QRMSISVPDI LSTSWTPSST EAEDVPVSMV STDHASTKTD 3720
PNTPLSTFLF DSLSTLDWDT GRSLSSATAT TSAPQGATTP QELTLETMIS PATSQLPFSI 3780
GHITSAVTPA AMARSSGVTF SRPDPTSKKA EQTSTQLPTT TSAHPGQVPR SAATTLDVIP 3840
HTAKTPDATF QRQGQTALTT EARATSDSWN EKEKSTPSAP WITEMMNSVS EDTIKEVTSS 3900
SSVLRTLNTL DINLESGTTS SPSWKSSPYE RIAPSESTTD KEAIHPSTNT VETTGWVTSS 3960
EHASHSTIPA HSASSKLTSP VVTTSTREQA IVSMSTTTWP ESTRARTEPN SFLTIELRDV 4020
SPYMDTSSTT QTSIISSPGS TAITKGPRTE ITSSKRISSS FLAQSMRSSD SPSEAITRLS 4080
NFPAMTESGG MILAMQTSPP GATSLSAPTL DTSATASWTG TPLATTQRFT YSEKTTLFSK 4140
GPEDTSQPSP PSVEETSSSS SLVPIHATTS PSNILLTSQG HSPSSTPPVT SVFLSETSGL 4200
GKTTDMSRIS LEPGTSLPPN LSSTAGEALS TYEASRDTKA IHHSADTAVT NMEATSSEYS 4260
PIPGHTKPSK ATSPLVTSHI MGDITSSTSV FGSSETTEIE TVSSVNQGLQ ERSTSQVASS 4320
ATETSTVITH VSSGDATTHV TKTQATFSSG TSISSPHQFI TSTNTFTDVS TNPSTSLIMT 4380
ESSGVTITTQ TGPTGAATQG PYLLDTSTMP YLTETPLAVT PDFMQSEKTT LISKGPKDVS 4440
WTSPPSVAET SYPSSLTPFL VTTIPPATST LQGQHTSSPV SATSVLTSGL VKTTDMLNTS 4500
MEPVTNSPQN LNNPSNEILA TLAATTDIET IHPSINKAVT NMGTASSAHV LHSTLPVSSE 4560
PSTATSPMVP ASSMGDALAS ISIPGSETTD IEGEPTSSLT AGRKENSTLQ EMNSTTESNI 4620
ILSNVSVGAI TEATKMEVPS FDATFIPTPA QSTKFPDIFS VASSRLSNSP PMTISTHMTT 4680
TQTGSSGATS KIPLALDTST LETSAGTPSV VTEGFAHSKI TTAMNNDVKD VSQTNPPFQD 4740
EASSPSSQAP VLVTTLPSSV AFTPQWHSTS SPVSMSSVLT SSLVKTAGKV DTSLETVTSS 4800
PQSMSNTLDD ISVTSAATTD IETTHPSINT VVTNVGTTGS AFESHSTVSA YPEPSKVTSP 4860
NVTTSTMEDT TISRSIPKSS KTTRTETETT SSLTPKLRET SISQEITSST ETSTVPYKEL 4920
TGATTEVSRT DVTSSSSTSF PGPDQSTVSL DISTETNTRL STSPIMTESA EITITTQTGP 4980
HGATSQDTFT MDPSNTTPQA GIHSAMTHGF SQLDVTTLMS RIPQDVSWTS PPSVDKTSSP 5040
SSFLSSPAMT TPSLISSTLP EDKLSSPMTS LLTSGLVKIT DILRTRLEPV TSSLPNFSST 5100
SDKILATSKD SKDTKEIFPS INTEETNVKA NNSGHESHSP ALADSETPKA TTQMVITTTV 5160
GDPAPSTSMP VHGSSETTNI KREPTYFLTP RLRETSTSQE SSFPTDTSFL LSKVPTGTIT 5220
EVSSTGVNSS SKISTPDHDK STVPPDTFTG EIPRVFTSSI KTKSAEMTIT TQASPPESAS 5280
HSTLPLDTST TLSQGGTHST VTQGFPYSEV TTLMGMGPGN VSWMTTPPVE ETSSVSSLMS 5340
SPAMTSPSPV SSTSPQSIPS SPLPVTALPT SVLVTTTDVL GTTSPESVTS SPPNLSSITH 5400
ERPATYKDTA HTEAAMHHST NTAVTNVGTS GSGHKSQSSV LADSETSKAT PLMSTTSTLG 5460
DTSVSTSTPN ISQTNQIQTE PTASLSPRLR ESSTSEKTSS TTETNTAFSY VPTGAITQAS 5520
RTEISSSRTS ISDLDRPTIA PDISTGMITR LFTSPIMTKS AEMTVTTQTT TPGATSQGIL 5580
PWDTSTTLFQ GGTHSTVSQG FPHSEITTLR SRTPGDVSWM TTPPVEETSS GFSLMSPSMT 5640
SPSPVSSTSP ESIPSSPLPV TALLTSVLVT TTNVLGTTSP EPVTSSPPNL SSPTQERLTT 5700
YKDTAHTEAM HASMHTNTAV ANVGTSISGH ESQSSVPADS HTSKATSPMG ITFAMGDTSV 5760
STSTPAFFET RIQTESTSSL IPGLRDTRTS EEINTVTETS TVLSEVPTTT TTEVSRTEVI 5820
TSSRTTISGP DHSKMSPYIS TETITRLSTF PFVTGSTEMA ITNQTGPIGT ISQATLTLDT 5880
SSTASWEGTH SPVTQRFPHS EETTTMSRST KGVSWQSPPS VEETSSPSSP VPLPAITSHS 5940
SLYSAVSGSS PTSALPVTSL LTSGRRKTID MLDTHSELVT SSLPSASSFS GEILTSEAST 6000
NTETIHFSEN TAETNMGTTN SMHKLHSSVS IHSQPSGHTP PKVTGSMMED AIVSTSTPGS 6060
PETKNVDRDS TSPLTPELKE DSTALVMNST TESNTVFSSV SLDAATEVSR AEVTYYDPTF 6120
MPASAQSTKS PDISPEASSS HSNSPPLTIS THKTIATQTG PSGVTSLGQL TLDTSTIATS 6180
AGTPSARTQD FVDSETTSVM NNDLNDVLKT SPFSAEEANS LSSQAPLLVT TSPSPVTSTL 6240
QEHSTSSLVS VTSVPTPTLA KITDMDTNLE PVTRSPQNLR NTLATSEATT DTHTMHPSIN 6300
TAVANVGTTS SPNEFYFTVS PDSDPYKATS AVVITSTSGD SIVSTSMPRS SAMKKIESET 6360
TFSLIFRLRE TSTSQKIGSS SDTSTVFDKA FTAATTEVSR TELTSSSRTS IQGTEKPTMS 6420
PDTSTRSVTM LSTFAGLTKS EERTIATQTG PHRATSQGTL TWDTSITTSQ AGTHSAMTHG 6480
FSQLDLSTLT SRVPEYISGT SPPSVEKTSS SSSLLSLPAI TSPSPVPTTL PESRPSSPVH 6540
LTSLPTSGLV KTTDMLASVA SLPPNLGSTS HKIPTTSEDI KDTEKMYPST NIAVTNVGTT 6600
TSEKESYSSV PAYSEPPKVT SPMVTSFNIR DTIVSTSMPG SSEITRIEME STFSLAHGLK 6660
GTSTSQDPIV STEKSAVLHK LTTGATETSR TEVASSRRTS IPGPDHSTES PDISTEVIPS 6720
LPISLGITES SNMTIITRTG PPLGSTSQGT FTLDTPTTSS RAGTHSMATQ EFPHSEMTTV 6780
MNKDPEILSW TIPPSIEKTS FSSSLMPSPA MTSPPVSSTL PKTIHTTPSP MTSLLTPSLV 6840
MTTDTLGTSP EPTTSSPPNL SSTSHEILTT DEDTTAIEAM HPSTSTAATN VETTSSGHGS 6900
QSSVLADSEK TKATAPMDTT STMGHTTVST SMSVSSETTK IKRESTYSLT PGLRETSISQ 6960
NASFSTDTSI VLSEVPTGTT AEVSRTEVTS SGRTSIPGPS QSTVLPEIST RTMTRLFASP 7020
TMTESAEMTI PTQTGPSGST SQDTLTLDTS TTKSQAKTHS TLTQRFPHSE MTTLMSRGPG 7080

-continued

```
DMSWQSSPSL ENPSSLPSLL SLPATTSPPP ISSTLPVTIS SSPLPVTSLL TSSPVTTTDM  7140
LHTSPELVTS SPPKLSHTSD ERLTTGKDTT NTEAVHPSTN TAASNVEIPS SGHESPSSAL  7200
ADSETSKATS PMFITSTQED TTVAISTPHF LETSRIQKES ISSLSPKLRE TGSSVETSSA  7260
IETSAVLSEV SIGATTEISR TEVTSSSRTS ISGSAESTML PEISTTRKII KFPTSPILAE  7320
SSEMTIKTQT SPPGSTSEST FTLDTSTTPS LVITHSTMTQ RLPHSEITTL VSRGAGDVPR  7380
PSSLPVEETS PPSSQLSLSA MISPSPVSST LPASSHSSSA SVTSLLTPGQ VKTTEVLDAS  7440
AEPETSSPPS LSSTSVEILA TSEVTTDTEK IHPFSNTAVT KVGTSSSGHE SPSSVLPDSE  7500
TTKATSAMGT ISIMGDTSVS TLTPALSNTR KIQSEPASSL TTRLRETSTS EETSLATEAN  7560
TVLSKVSTGA TTEVSRTEAI SFSRTSMSGP EQSTMSQDIS IGTIPRISAS SVLTESAKMT  7620
ITTQTGPSES TLESTLNLNT ATTPSWVETH SIVIQGFPHP EMTTSMGRGP GGVSWPSPPF  7680
VKETSPPSSP LSLPAVTSPH PVSTTFLAHI PPSPLPVTSL LTSGPATTTD ILGTSTEPGT  7740
SSSSSLSTTS HERLTTYKDT AHTEAVHPST NTGGTNVATT SSGYKSQSSV LADSSPMCTT  7800
STMGDTSVLT STPAFLETRR IQTELASSLT PGLRESSGSE GTSSGTKMST VLSKVPTGAT  7860
TEISKEDVTS IPGPAQSTIS PDISTRTVSW FSTSPVMTES AEITMNTHTS PLGATTQGTS  7920
TLDTSSTTSL TMTHSTISQG FSHSQMSTLM RRGPEDVSWM SPPLLEKTRP SFSLMSSPAT  7980
TSPSPVSSTL PESISSSPLP VTSLLTSGLA KTTDMLHKSS EPVTNSPANL SSTSVEILAT  8040
SEVTTDTEKT HPSSNRTVTD VGTSSSGHES TSFVLADSQT SKVTSPMVIT STMEDTSVST  8100
STPGFFETSR IQTEPTSSLT LGLRKTSSSE GTSLATEMST VLSGVPTGAT AEVSRTEVTS  8160
SSRTSISGFA QLTVSPETST ETITRLPTSS IMTESAEMMI KTQTDPPGST PESTHTVDIS  8220
TTPNWVETHS TVTQRFSHSE MTTLVSRSPG DMLWPSQSSV EETSSASSLL SLPATTSPSP  8280
VSSTLVEDFP SASLPVTSLL NPGLVITTDR MGISREPGTS STSNLSSTSH ERLTTLEDTV  8340
DTEDMQPSTH TAVTNVRTSI SGHESQSSVL SDSETPKATS PMGTTYTMGE TSVSISTSDF  8400
FETSRIQIEP TSSLTSGLRE TSSSERISSA TEGSTVLSEV PSGATTEVSR TEVISSRGTS  8460
MSGPDQFTIS PDISTEAITR LSTSPIMTES AESAITIETG SPGATSEGTL TLDTSTTTFW  8520
SGTHSTASPG FSHSEMTTLM SRTPGDVPWP SLPSVEEASS VSSSLSSPAM TSTSFFSTLP  8580
ESISSSPHPV TALLTLGPVK TTDMLRTSSE PETSSPPNLS STSAEILATS EVTKDREKIH  8640
PSSNTPVVNV GTVIYKHLSP SSVLADLVTT KPTSPMATTS TLGNTSVSTS TPAFPETMMT  8700
QPTSSLTSGL REISTSQETS SATERSASLS GMPTGATTKV SRTEALSLGR TSTPGPAQST  8760
ISPEISTETI TRISTPLTTT GSAEMTITPK TGHSGASSQG TFTLDTSSRA SWPGTHSAAT  8820
HRSPHSGMTT PMSRGPEDVS WPSRPSVEKT SPPSSLVSLS AVTSPSPLYS TPSESSHSSP  8880
LRVTSLFTPV MMKTTDMLDT SLEPVTTSPP SMNITSDESL ATSKATMETE AIQLSENTAV  8940
TQMGTISARQ EFYSSYPGLP EPSKVTSPVV TSSTIKDIVS TTIPASSEIT RIEMESTSTL  9000
TPTPRETSTS QEIHSATKPS TVPYKALTSA TIEDSMTQVM SSSRGPSPDQ STMSQDISTE  9060
VITRLSTSPI KTESTEMTIT TQTGSPGATS RGTLTLDTST TFMSGTHSTA SQGFSHSQMT  9120
ALMSRTPGDV PWLSHPSVEE ASSASFSLSS PVMTSSSPVS STLPDSIHSS SLPVTSLLTS  9180
GLVKTTELLG TSSEPETSSP PNLSSTSAEI LAITEVTTDT EKLEMTNVVT SGYTHESPSS  9240
VLADSVTTKA TSSMGITYPT GDTNVLTSTP AFSDTSRIQT KSKLSLTPGL METSISEETS  9300
SATEKSTVLS SVPTGATTEV SRTEAISSSR TSIPGPAQST MSSDTSMETI TRISTPLTRK  9360
ESTDMAITPK TGPSGATSQG TFTLDSSSTA SWPGTHSATT QRFPQSVVTT PMSRGPEDVS  9420
WPSPLSVEKN SPPSSLVSSS SVTSPSPLYS TPSGSSHSSP VPVTSLFTSI MMKATDMLDA  9480
SLEPETTSAP NMNITSDESL AASKATTETE AIHVFENTAA SHVETTSATE ELYSSSPGFS  9540
EPTKVISPVV TSSSIRDNMV STTMPGSSGI TRIEIESMSS LTPGLRETRT SQDITSSTET  9600
STVLYKMPSG ATPEVSRTEV MPSSRTSIPG PAQSTMSLDI SDEVVTRLST SPIMTESAEI  9660
TITTQTGYSL ATSQVTLPLG TSMTFLSGTH STMSQGLSHS EMTNLMSRGP ESLSWTSPRF  9720
VETTRSSSSL TSLPLTTSLS PVSSTLLDSS PSSPLPVTSL ILPGLVKTTE VLDTSSEPKT  9780
SSSPNLSSTS VEIPATSEIM TDTEKIHPSS NTAVAKVRTS SSVHESHSSV LADSETTITI  9840
PSMGITSAVD DTTVFTSNPA FSETRRIPTE PTFSLTPGFR ETSTSEETTS ITETSAVLYG  9900
VPTSATTEVS MTEIMSSNRI HIPDSDQSTM SPDIITEVIT RLSSSSMMSE STQMTITTQK  9960
SSPGATAQST LTLATTTAPL ARTHSTVPPR FLHSEMTTLM SRSPENPSWK SSLFVEKTSS  10020
SSSLLSLPVT TSPSVSSTLP QSIPSSSFSV TSLLTPGMVK TTDTSTEPGT SLSPNLSGTS  10080
VEILAASEVT TDTEKIHPSS SMAVTNVGTT SSGHELYSSV SIHSEPSKAT YPVGTPSSMA  10140
ETSISTSMPA NFETTGFEAE PFSHLTSGFR KTNMSLDTSS VTPTNTPSSP GSTHLLQSSK  10200
TDFTSSAKTS SPDWPPASQY TEIPVDIITP FNASPSITES TGITSFPESR FTMSVTESTH  10260
HLSTDLLPSA ETISTGTVMP SLSEAMTSFA TTGVPRAISG SGSPFSRTES GPGDATLSTI  10320
AESLPSSTPV PFSSSTFTTT DSSTIPALHE ITSSSATPYR VDTSLGTESS TTEGRLVMVS  10380
TLDTSSQPGR TSSSPILDTR MTESVELGTV TSAYQVPSLS TRLTRTDGIM EHITKIPNEA  10440
AHRGTIRPVK GPQTSTSPAS PKGLHTGGTK RMETTTTALK TTTTALKTTS RATLTTSVYT  10500
PTLGTLTPLN ASMQMASTIP TEMMITTPYV FPDVPETTSS LATSLGAETS TALPRTTPSV  10560
FNRESETTAS LVSRSGAERS PVIQTLDVSS SEPDTTASWV IHPAETIPTV SKTTPNFFHS  10620
ELDTVSSTAT SHGADVSSAI PTNISPSELD ALTPLVTISG TDTSTTFPTL TKSPHETETR  10680
TTWLTHPAET SSTIPRTIPN FSHHESDATP SIATSPGAET SSAIPIMTVS PGAEDLVTSQ  10740
VTSSGTDRNM TIPTLTLSPG EPKTIASLVT HPEAQTSSAI PTSTISPAVS RLVTSMVTSL  10800
AAKTSTTNRA LTNSPGEPAT TVSLVTHPAQ TSPTVPWTTS IFFHSKSDTT PSMTTSHGAE  10860
SSSAVPTPTV STEVPGVVTP LVTSSRAVIS TTIPILTLSP GEPETTPSMA TSHGEEASSA  10920
IPTPTVSPGV PGVVTSLVTS SRAVTSTTIP ILTFSLGEPE TTPSMATSHG TEAGSAVPTV  10980
LPEVPGMVTS LVASSRAVTS TTLPTLTLSP GEPETTPSMA TSHGAEASST VPTVSPEVPG  11040
VVTSLVTSSS GVNSTSIPTL ILSPGELETT PSMATSHGAE ASSAVPTPTV SPGVSGVVTP  11100
LVTSSRAVTS TTIPILTLSS SEPETTPSMA TSHGVEASSA VLTVSPEVPG MVTSLVTSSR  11160
AVTSTTIPTL TISSDEPETT TSLVTHSEAK MISAIPTLAV SPTVQGLVTS LVTSSGSETS  11220
AFSNLTVASS QPETIDSWVA HPGTEASSVV PTLTVSTGEP FTNISLVTHP AESSSTLPRT  11280
TSRFSHSELD TMPSTVTSPE AESSSAISTT ISPGIPGVLT SLVTSSGRDI SATFPTVPES  11340
PHESEATASW VTHPAVTSTT VPRTTPNYSH SEPDTTPSIA TSPGAEATSD FPTITVSPDV  11400
PDMVTSQVTS SGTDTSITIP TLTLSSGEPE TTTSFITYSE THTSSAIPTL PVSPGASKML  11460
TSLVISSGTD STTTFPTLTE TPYEPETTAI QLIHPAETNT MVPRTTPKFS HSKSDTTLPV  11520
AITSPGPEAS SAVSTTTISP DMSDLVTSLV PSSGTDTSTT FPTLSETPYE PETTATWLTH  11580
PAETSTTVSG TIPNFSHRGS DTAPSMVTSP GVDTRSGVPT TTIPPSIPGV VTSQVTSSAT  11640
DTSTAIPTLT PSPGEPETTA SSATHPGTQT GFTVPIRTVP SSEPDTMASW VTHPPQTSTP  11700
VSRTTSSFSH SSPDATPVMA TSPRTEASSA VLTTISPGAP EMVTSQITSS GAATSTTVPT  11760
LTHSPGMPET TALLSTHPRT ETSKTFPAST VFPQVSETTA SLTIRPGAET STALPTQTTS  11820
```

-continued

```
SLFTLLVTGT SRVDLSPTAS PGVSAKTAPL STHPGTETST MIPTSTLSLG LLETTGLLAT  11880
SSSAETSTST LTLTVSPAVS GLSSASITTD KPQTVTSWNT ETSPSVTSVG PPEFSRTVTG  11940
TTMTLIPSEM PTPPKTSHGE GVSPTTILRT TMVEATNLAT TGSSPTVAKT TTTFNTLAGS  12000
LFTPLTTPGM STLASESVTS RTSYNHRSWI STTSSYNRRY WTPATSTPVT STFSPGISTS  12060
SIPSSTAATV PFMVPFTLNF TITNLQYEED MRHPGSRKFN ATERELQGLL KPLFRNSSLE  12120
YLYSGCRLAS LRPEKDSSAT AVDAICTHRP DPEDLGLDRE RLYWELSNLT NGIQELGPYT  12180
LDRNSLYVNG FTHRSSMPTT STPGTSTVDV GTSGTPSSSP SPTTAGPLLM PFTLNFTITN  12240
LQYEEDMRRT GSRKFNTMES VLQGLLKPLF KNTSVGPLYS GCRLTLLRPE KDGAATGVDA  12300
ICTHRLDPKS PGLNREQLYW ELSKLTNDIE ELGPYTLDRN SLYVNGFTHQ SSVSTTSTPG  12360
TSTVDLRTSG TPSSLSSPTI MAAGPLLVPF TLNFTITNLQ YGEDMGHPGS RKFNTTERVL  12420
QGLLGPIFKN TSVGPLYSGC RLTSLRSEKD GAATGVDAIC IHHLDPKSPG LNRERLYWEL  12480
SQLTNGIKEL GPYTLDRNSL YVNGFTHRTS VPTSSTPGTS TVDLGTSGTP FSLPSPATAG  12540
PLLVLFTLNF TITNLKYEED MHRPGSRKFN TTERVLQTLL GPMFKNTSVG LLYSGCRLTL  12600
LRSEKDGAAT GVDAICTHRL DPKSPGVDRE QLYWELSQLT NGIKELGPYT LDRNSLYVNG  12660
FTHWIPVPTS STPGTSTVDL GSGTPSSLPS PTTAGPLLVP FTLNFTITNL KYEEDMHCPG  12720
SRKFNTTERV LQSLLGPMFK NTSVGPLYSG CRLTLLRSEK DGAATGVDAI CTHRLDPKSP  12780
GVDREQLYWE LSQLTNGIKE LGPYTLDRNS LYVNGFTHQT SAPNTSTPGT STVDLGTSGT  12840
PSSLPSPTSA GPLLVPFTLN FTITNLQYEE DMHHPGSRKF NTTERVLQGL LGPMFKNTSV  12900
GLLYSGCRLT LLRPEKNGAA TGMDAICSHR LDPKSPGLNR EQLYWELSQL THGIKELGPY  12960
TLDRNSLYVN GFTHRSSVAP TSTPGTSTVD LGTSGTPSSL PSPTTAVPLL VPFTLNFTIT  13020
NLQYGEDMRH PGSRKFNTTE RVLQGLLGPL FKNSSVGPLY SGCRLISLRS EKDGAATGVD  13080
AICTHHLNPQ SPGLDREQLY WQLSQMTNGI KELGPYTLDR NSLYVNGFTH RSSGLTTSTP  13140
WTSTVDLGTS GTPSPVPSPT TTGPLLVPFT LNFTITNLQY EENMGHPGSR KFNITESVLQ  13200
GLLKPLFKST SVGPLYSGCR LTLLRPEKDG VATRVDAICT HRPDPKIPGL DRQQLYWELS  13260
QLTHSITELG PYTLDRDSLY VNGFTQRSSV PTTSTPGTFT VQPETSETPS SLPGPTATGP  13320
VLLPFTLNFT ITNLQYEEDM RRPGSRKFNT TERVLQGLLM PLFKNTSVSS LYSGCRLTLL  13380
RPEKDGAATR VDAVCTHRPD PKSPGLDRER LYWKLSQLTH GITELGPYTL DRHSLYVNGF  13440
THQSSMTTTR TPDTSTMHLA TSRTPASLSG PMTASPLLVL FTINFTITNL RYEENMHHPG  13500
SRKFNTTERV LQGLLRPVFK NTSVGPLYSG CRLTLLRPKK DGAATKVDAI CTYRPDPKSP  13560
GLDREQLYWE LSQLTHSITE LGPYTLDRDS LYVNGFTQRS SVPTTSIPGT PTVDLGTSGT  13620
PVSKPGPSAA SPLLVLFTLN FTITNLRYEE NMQHPGSRKF NTTERVLQGL LRSLFKSTSV  13680
GPLYSGCRLT LLRPEKDGTA TGVDAICTHH PDPKSPRLDR EQLYWELSQL THNITELGPY  13740
ALDNDSLFVN GFTHRSSVST TSTPGTPTVY LGASKTPASI FGPSAASHLL ILFTLNFTIT  13800
NLRYEENMWP GSRKFNTTER VLQGLLRPLF KNTSVGPLYS GCRLTLLRPE KDGEATGVDA  13860
ICTHRPDPTG PGLDREQLYL ELSQLTHSIT ELGPYTLDRD SLYVNGFTHR SSVPTTSTGV  13920
VSEEPFTLNF TINNLRYMAD MGQPGSLKFN ITDNVMQHLL SPLFQRSSLG ARYTGCRVIA  13980
LRSVKNGAET RVDLLCTYLQ PLSGPGLPIK QVFHELSQQT HGITRLGPYS LDKDSLYLNG  14040
YNEPGPDEPP TTPKPATTFL PPLSEATTAM GYHLKTLTLN FTISNLQYSP DMGKGSATFN  14100
STEGVLQHLL RPLFQKSSMG PFYLGCQLIS LRPEKDGAAT GVDTTCTYHP DPVGPGLDIQ  14160
QLYWELSQLT HGVTQLGFYV LDRDSLFING YAPQNLSIRG EYQINFHIVN WNLSNPDPTS  14220
SEYITLLRDI QDKVTTLYKG SQLHDTFRFC LVTNLTMDSV LVTVKALFSS NLDPSLVEQV  14280
FLDKTLNASF HWLGSTYQLV DIHVTEMESS VYQPTSSSST QHFYLNFTIT NLPYSQDKAQ  14340
PGTTNYQRNK RNIEDALNQL FRNSSIKSYF SDCQVSTFRS VPNRHHTGVD SLCNFSPLAR  14400
RVDRVAIYEE FLRMTRNGTQ LQNFTLDRSS VLVDGYSPNR NEPLTGNSDL PFWAVILIGL  14460
AGLLGVITCL ICGVLVTTRR RKKEGEYNVQ QQCPGYYQSH LDLEDLQ                14507
```

```
SEQ ID NO: 54          moltype = AA  length = 755
FEATURE                Location/Qualifiers
source                 1..755
                       mol_type = protein
                       organism = Homo sapiens
SEQUENCE: 54
MARKLSVILI LTFALSVTNP LHELKAAAFP QTTEKISPNW ESGINVDLAI STRQYHLQQL  60
FYRYGENNSL SVEGFRKLLQ NIGIDKIKRI HIHHDHDHHS DHEHHSDHER HSDHEHHSEH  120
EHHSDHDHHS HHNHAASGKN KRKALCPDHD SDSSGKDPRN SQGKGAHRPE HASGRRNVKD  180
SVSASEVTST VYNTVSEGTH FLETIETPRP GKLFPKDVSS STPPSVTSKS RVSRLAGRKT  240
NESVSEPRKG FMYSRNTNEN PQECFNASKL LTSHGMGIQV PLNATEFNYL CPAIINQIDA  300
RSCLIHTSEK KAEIPPKTYS LQIAWVGGFI AISIISFLSL LGVILVPLMN RVFFKFLLSF  360
LVALAVGTLS GDAFLHLLPH SHASHHHSHS HEEPAMEMKR GPLFSHLSSQ NIEESAYFDS  420
TWKGLTALGG LYFMFLVEHV LTLIKQFKDK KKKNQKKPEN DDDVEIKKQL SKYESQLSTN  480
EEKVDTDDRT EGYLRADSQE PSHFDSQQPA VLEEEEVMIA HAHPQEVYNE YVPRGCKNKC  540
HSHFHDTLGQ SDDLIHHHHD YHHILHHHHH QNHHPHSHSQ RYSREELKDA GVATLAWMVI  600
MGDGLHNFSD GLAIGAAFTE GLSSGLSTSV AVFCHELPHE LGDFAVLLKA GMTVKQAVLY  660
NALSAMLAYL GMATGIFIGH YAENVSMWIF ALTAGLFMYV ALVDMVPEML HNDASDHGCS  720
RWGYFFLQNA GMLLGFGIML LISIFEHKIV FRINF                             755
```

```
SEQ ID NO: 55          moltype = AA  length = 710
FEATURE                Location/Qualifiers
source                 1..710
                       mol_type = protein
                       organism = Homo sapiens
SEQUENCE: 55
MGGKQRDEDD EAYGKPVKYD PSFRGPIKNR SCTDVICCVL FLLFILGYIV VGIVAWLYGD  60
PRQVLYPRNS TGAYCGMGEN KDKPYLLYFN IFSCILSSNI ISVAENGLQC PTPQVCVSSC  120
PEDPWTVGKN EFSQTVGEVF YTKNRNFCLP GVPWNMTVIT SLQQELCPSF LLPSAPALGR  180
CFPWTNVTPP ALPGITNDTT IQQGISGLID SLNARDISVK IFEDFAQSWY WILVALGVAL  240
VLSLLFILLL RLVAGPLVLV LILGVLGVLA YGIYYCWEEY RVLRDKGASI SQLGFTTNLS  300
AYQSVQETWL AALIVLAVLE AILLLMLIFL RQRIRIAIAL LKEASKAVGQ MMSTMFYPLV  360
TFVLLLICIA YWAMTALYLA TSGQPQYVLW ASNISSPGCE KVPINTSCNP TAHLVNSSCP  420
```

-continued

```
GLMCVFQGYS SKGLIQRSVF NLQIYGVLGL FWTLNWVLAL GQCVLAGAFA SFYWAFHKPQ  480
DIPTFPLISA FIRTLRYHTG SLAFGALILT LVQIARVILE YIDHKLRGVQ NPVARCIMCC  540
FKCCLWCLEK FIKFLNRNAY IMIAIYGKNF CVSAKNAFML LMRNIVRVVV LDKVTDLLLF  600
FGKLLVVGGV GVLSFFFFSG RIPGLGKDFK SPHLNYYWLP IMTSILGAYV IASGFFSVFG  660
MCVDTLFLCF LEDLERNNGS LDRPYYMSKS LLKILGKKNE APPDNKKRKK             710

SEQ ID NO: 56           moltype = AA  length = 339
FEATURE                 Location/Qualifiers
source                  1..339
                        mol_type = protein
                        organism = Homo sapiens
SEQUENCE: 56
MESRKDITNQ EELWKMKPRR NLEEDDYLHK DTGETSMLKR PVLLHLHQTA HADEFDCPSE  60
LQHTQELFPQ WHLPIKIAAI IASLTFLYTL LREVIHPLAT SHQQYFYKIP ILVINKVLPM  120
VSITLLALVY LPGVIAAIVQ LHNGTKYKKF PHWLDKWMLT RKQFGLLSFF FAVLHAIYSL  180
SYPMRRSYRY KLLNWAYQQV QQNKEDAWIE HDVWRMEIYV SLGIVGLAIL ALLAVTSIPS  240
VSDSLTWREF HYIQSKLGIV SLLLGTIHAL IFAWNKWIDI KQFVWYTPPT FMIAVFLPIV  300
VLIFKSILFL PCLRKKILKI RHGWEDVTKI NKTEICSQL                         339

SEQ ID NO: 57           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 57
VVRKPVIAL                                                          9

SEQ ID NO: 58           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 58
LLSEKKKIS                                                          9

SEQ ID NO: 59           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 59
APASKPRPRL                                                         10

SEQ ID NO: 60           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 60
RYGQLSEKF                                                          9

SEQ ID NO: 61           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 61
VYISNVSKL                                                          9

SEQ ID NO: 62           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 62
LPTKETPSF                                                          9
```

```
SEQ ID NO: 63           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 63
GEAPPPPPA                                                         9

SEQ ID NO: 64           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 64
LEEISKQEI                                                         9

SEQ ID NO: 65           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 65
IYNHITVKI                                                         9

SEQ ID NO: 66           moltype = AA  length = 160
FEATURE                 Location/Qualifiers
REGION                  1..160
                        note = Description of Artificial Sequence: Synthetic
                         polypeptide
source                  1..160
                        mol_type = protein
                        organism = synthetic construct
SEQUENCE: 66
VDLEPTVIGE LTSVTQVRSQ GAGTGGLSWG GSAGHSPTLP PRSLSLLLLP HHVLQMKFAL  60
ALTASSSTLS NSSQARKMLP ITMPEGTTPL ARRSLTSCWT EFASWLTSAP VFRASWFSTA  120
LVGELVLGSP RCSWNVSQLI MARSPSWSSP FTRRPRFPQL                       160

SEQ ID NO: 67           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 67
APPRSHPSIK RGLSSL                                                 16

SEQ ID NO: 68           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 68
MVRRARWPGG RGEARKAPRT APGVRPPF                                    28

SEQ ID NO: 69           moltype = AA  length = 199
FEATURE                 Location/Qualifiers
REGION                  1..199
                        note = Description of Artificial Sequence: Synthetic
                         polypeptide
source                  1..199
                        mol_type = protein
                        organism = synthetic construct
SEQUENCE: 69
WVNCLFVSGR AAAGGGGGGA VPPYLELAGP PFLLLTLIRI GLGRRSGRAG GRAGTQCGGE  60
RGPGFAAFRP LRPFRRLRVC AVCVRGSALG RSVGLPRGGA AGAPFSSSPA PHPRRVLCRC  120
LLFLFFSCHD RRGDSQPYQV PAEAGVEGLE GAGGGREGLL LERRPQKSIQ ALRCNTSETS  180
TADPLKIPGL VPLALSSKV                                              199

SEQ ID NO: 70           moltype = AA  length = 101
FEATURE                 Location/Qualifiers
```

```
REGION                  1..101
                        note = Description of Artificial Sequence: Synthetic
                         polypeptide
source                  1..101
                        mol_type = protein
                        organism = synthetic construct
SEQUENCE: 70
MPLPVQVFNL QVTSRGRPGP PRPRAPRHWG RAEVEQGRGA CARSRSGTLR AGPPRAARVG  60
GCRAEGASPP WLRAAIGGRR AAPAPPPLPA AHGRGSRPPR R                      101

SEQ ID NO: 71           moltype = AA  length = 162
FEATURE                 Location/Qualifiers
REGION                  1..162
                        note = Description of Artificial Sequence: Synthetic
                         polypeptide
source                  1..162
                        mol_type = protein
                        organism = synthetic construct
SEQUENCE: 71
QPAQPRTGAP ARRPRPRPSF PVSLRSAAPP TGTAGGTGRF VLRPGESGAG GGGDAWDTGL  60
QARRGTAAGT SGAPNRSQLS SLTFPAQLRR IGVSGRKPGA GGRLGPGSRT CAPRCLPRAR  120
RGPGAHPRGG RCPPAETALF REAEEGTQKY SLPSDPAGQA AF                     162

SEQ ID NO: 72           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 72
FRLHTGPVSP VGGRRQMGRP KHGDGFSLQV CSFIMEQNG                         39

SEQ ID NO: 73           moltype = AA  length = 71
FEATURE                 Location/Qualifiers
REGION                  1..71
                        note = Description of Artificial Sequence: Synthetic
                         polypeptide
source                  1..71
                        mol_type = protein
                        organism = synthetic construct
SEQUENCE: 73
GVVEITGEPP CSCRGEEEAS RAGRAGGVRL KRGSRGPGEL NVGPAPGKTG LLIPLLRNWE  60
CGSLLRALSA L                                                       71

SEQ ID NO: 74           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 74
KMGFPEAARK GNSL                                                    14

SEQ ID NO: 75           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 75
LEARIKEKIE ELQQALI                                                 17

SEQ ID NO: 76           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 76
EIKKRFRQFK QAVYKQ                                                  16

SEQ ID NO: 77           moltype = AA  length = 16
FEATURE                 Location/Qualifiers
REGION                  1..16
```

```
                       note = Description of Artificial Sequence: Synthetic peptide
source                 1..16
                       mol_type = protein
                       organism = synthetic construct
SEQUENCE: 77
AHESAAMAET LQHVPS                                                 16

SEQ ID NO: 78          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 78
NRPSVQAALK LKQVGV                                                 16

SEQ ID NO: 79          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 79
KTDDLKKRHI TFTLGCGIC                                              19

SEQ ID NO: 80          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 80
MKLDEDVKRN DIAMAI                                                 16

SEQ ID NO: 81          moltype = AA  length = 26
FEATURE                Location/Qualifiers
REGION                 1..26
                       note = Description of Artificial Sequence: Synthetic peptide
source                 1..26
                       mol_type = protein
                       organism = synthetic construct
SEQUENCE: 81
NSISQIPSDH ILTPALFITF MTILDL                                      26

SEQ ID NO: 82          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 82
TVFSTSSLKL NQPQKYLKMK SWPC                                        24

SEQ ID NO: 83          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 83
AEEDRRKKVI TSCLLNFNLS KAQS                                        24

SEQ ID NO: 84          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 84
RSFSTSAQVG QTRGGLQAEA PRPGPRASPV RGQL                             34

SEQ ID NO: 85          moltype = AA  length = 16
```

-continued

```
FEATURE                Location/Qualifiers
REGION                 1..16
                       note = Description of Artificial Sequence: Synthetic peptide
source                 1..16
                       mol_type = protein
                       organism = synthetic construct
SEQUENCE: 85
RGYVVRKPVI ALSVKI                                                16

SEQ ID NO: 86          moltype = AA  length = 86
FEATURE                Location/Qualifiers
REGION                 1..86
                       note = Description of Artificial Sequence: Synthetic
                        polypeptide
source                 1..86
                       mol_type = protein
                       organism = synthetic construct
SEQUENCE: 86
VDMDFGTGGQ GAGPVGRGKD WSCTLAVHLL SEKKKISFSQ IDRAWGGSQG TVLDKWGPGV  60
VSELHPSAKE VSVGRNSVES LMTWAS                                     86

SEQ ID NO: 87          moltype = AA  length = 66
FEATURE                Location/Qualifiers
REGION                 1..66
                       note = Description of Artificial Sequence: Synthetic
                        polypeptide
source                 1..66
                       mol_type = protein
                       organism = synthetic construct
SEQUENCE: 87
EKGSHEEEVR VPALSWGRPR APAPASKPRP RLDLNCLWLR PQPIFLWKLR PRPVPAATPL  60
TGPLPL                                                           66

SEQ ID NO: 88          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 88
RYGQLSEKFN RRKVMDS                                               17

SEQ ID NO: 89          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 89
MVYISNVSKL CFSKM                                                 15

SEQ ID NO: 90          moltype = AA  length = 48
FEATURE                Location/Qualifiers
REGION                 1..48
                       note = Description of Artificial Sequence: Synthetic
                        polypeptide
source                 1..48
                       mol_type = protein
                       organism = synthetic construct
SEQUENCE: 90
NTLPTKETPS FLLNPHTSWV PRPHREAPRL RVGVAAPLQR PLPALHSH             48

SEQ ID NO: 91          moltype = AA  length = 58
FEATURE                Location/Qualifiers
REGION                 1..58
                       note = Description of Artificial Sequence: Synthetic
                        polypeptide
source                 1..58
                       mol_type = protein
                       organism = synthetic construct
SEQUENCE: 91
FGDIYLGEAP PPPPAARRPG PCGCQDQARS RKEVVAPAGS PRKSRHRRIV ARTQRPLG   58

SEQ ID NO: 92          moltype = AA  length = 17
FEATURE                Location/Qualifiers
REGION                 1..17
                       note = Description of Artificial Sequence: Synthetic peptide
```

```
source                1..17
                      mol_type = protein
                      organism = synthetic construct
SEQUENCE: 92
GSASDLLEEI SKQEISF                                                17

SEQ ID NO: 93         moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 93
QLIYNHITVK INLQGD                                                 16

SEQ ID NO: 94         moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 94
RPRPSFPVSL                                                        10

SEQ ID NO: 95         moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 95
RPKHGDGFSL                                                        10

SEQ ID NO: 96         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 96
GPAPGKTGL                                                         9

SEQ ID NO: 97         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 97
EAARKGNSL                                                         9

SEQ ID NO: 98         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 98
RIKEKIEEL                                                         9

SEQ ID NO: 99         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 99
EIKKRFRQF                                                         9

SEQ ID NO: 100        moltype = AA  length = 9
FEATURE               Location/Qualifiers
REGION                1..9
```

```
                        note = Description of Artificial Sequence: Synthetic peptide
source                  1..9
                        mol_type = protein
                        organism = synthetic construct
SEQUENCE: 100
HESAAMAET                                                                   9

SEQ ID NO: 101          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 101
ALKLKQVGV                                                                   9

SEQ ID NO: 102          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 102
DLKKRHITF                                                                   9

SEQ ID NO: 103          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 103
DVKRNDIAM                                                                   9

SEQ ID NO: 104          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 104
IPSDHILTPA                                                                  10

SEQ ID NO: 105          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 105
TVFSTSSLK                                                                   9

SEQ ID NO: 106          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 106
ITSCLLNF                                                                    8

SEQ ID NO: 107          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 107
RASPVRGQL                                                                   9

SEQ ID NO: 108          moltype = DNA  length = 19
FEATURE                 Location/Qualifiers
```

```
misc_feature           1..19
                       note = Description of Artificial Sequence: Synthetic primer
source                 1..19
                       mol_type = other DNA
                       organism = synthetic construct
SEQUENCE: 108
cacaccagat cggcatcaa                                               19

SEQ ID NO: 109         moltype = DNA  length = 21
FEATURE                Location/Qualifiers
misc_feature           1..21
                       note = Description of Artificial Sequence: Synthetic primer
source                 1..21
                       mol_type = other DNA
                       organism = synthetic construct
SEQUENCE: 109
cgatgatgtg tccgtgtatg t                                            21

SEQ ID NO: 110         moltype = DNA  length = 23
FEATURE                Location/Qualifiers
misc_feature           1..23
                       note = Description of Artificial Sequence: Synthetic probe
source                 1..23
                       mol_type = other DNA
                       organism = synthetic construct
SEQUENCE: 110
atcctgccac accagatgac cac                                          23

SEQ ID NO: 111         moltype = DNA  length = 26
FEATURE                Location/Qualifiers
misc_feature           1..26
                       note = Description of Artificial Sequence: Synthetic primer
source                 1..26
                       mol_type = other DNA
                       organism = synthetic construct
SEQUENCE: 111
ctgcttcgga tttactagaa gagata                                       26

SEQ ID NO: 112         moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 112
gcgttcccac aaaggaattg                                              20

SEQ ID NO: 113         moltype = DNA  length = 24
FEATURE                Location/Qualifiers
misc_feature           1..24
                       note = Description of Artificial Sequence: Synthetic probe
source                 1..24
                       mol_type = other DNA
                       organism = synthetic construct
SEQUENCE: 113
tgctgacttt ggctctgctt ccat                                         24

SEQ ID NO: 114         moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 114
actctcttcc gcatcgctgt                                              20

SEQ ID NO: 115         moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 115
ccgacgggtt tccgatccaa                                              20

SEQ ID NO: 116         moltype = DNA  length = 18
```

-continued

```
FEATURE                 Location/Qualifiers
misc_feature            1..18
                        note = Description of Artificial Sequence: Synthetic probe
source                  1..18
                        mol_type = other DNA
                        organism = synthetic construct
SEQUENCE: 116
ctgttgggct cgcggttg                                                  18

SEQ ID NO: 117          moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 117
tggcatcaga ttgcaaagac                                                20

SEQ ID NO: 118          moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 118
acgccgggtg atgtatctat                                                20

SEQ ID NO: 119          moltype = DNA  length = 20
FEATURE                 Location/Qualifiers
misc_feature            1..20
                        note = Description of Artificial Sequence: Synthetic probe
source                  1..20
                        mol_type = other DNA
                        organism = synthetic construct
SEQUENCE: 119
cgaaacgcac ccgtcagacg                                                20
```